US012729223B2

(12) United States Patent
Fernandez Rodriguez

(10) Patent No.: US 12,729,223 B2
(45) **Date of Patent: *Sep. 8, 2026**

(54) CHIMERIC RECEPTOR BINDING PROTEINS FOR USE IN BACTERIAL DELIVERY VEHICLES

(71) Applicant: Eligo Bioscience, Paris (FR)

(72) Inventor: Jesus Fernandez Rodriguez, Paris (FR)

(73) Assignee: Eligo Bioscience, Paris (FR)

( * ) Notice: Subject to any disclaimer, the term of this patent is extended or adjusted under 35 U.S.C. 154(b) by 750 days.

This patent is subject to a terminal disclaimer.

(21) Appl. No.: 18/301,667

(22) Filed: Apr. 17, 2023

(65) Prior Publication Data

US 2023/0279058 A1 Sep. 7, 2023

Related U.S. Application Data

(63) Continuation of application No. 16/696,769, filed on Nov. 26, 2019, now Pat. No. 11,661,443.

(60) Provisional application No. 62/802,777, filed on Feb. 8, 2019, provisional application No. 62/771,761, filed on Nov. 27, 2018.

(51) Int. Cl.

*C07K 14/005* (2006.01)
*A61K 38/46* (2006.01)
*A61K 48/00* (2006.01)
*C12N 9/22* (2006.01)
*C12N 15/71* (2006.01)

(52) U.S. Cl.

CPC .......... *C07K 14/005* (2013.01); *A61K 38/465* (2013.01); *C12N 9/22* (2013.01); *C12N 15/71* (2013.01); *A61K 48/00* (2013.01); *C07K 2319/00* (2013.01)

(58) Field of Classification Search

None

See application file for complete search history.

(56) References Cited

U.S. PATENT DOCUMENTS

| | | | | |
|---|---|---|---|---|
| 8,673,553 | B2 | 3/2014 | Scholl et al. | |
| 11,208,437 | B2 | 12/2021 | Fernandez Rodriguez | |
| 11,236,133 | B2 | 2/2022 | Fernandez Rodriguez | |
| 11,512,116 | B2 * | 11/2022 | Fernandez Rodriguez ................. | C12N 15/73 |
| 11,661,433 | B2 * | 5/2023 | Hartman .............. | A61K 31/282 424/649 |

FOREIGN PATENT DOCUMENTS

| | | |
|---|---|---|
| WO | 2016100389 A1 | 6/2016 |

OTHER PUBLICATIONS

Landry, et al. (2017) "Engineering Diagnostic and Therapeutic Gut Bacteria", 5(5): article 10.1128, 30 pages long. (Year: 2017).*

Jiang, et al. (2013) "RNA-guided editing of bacterial genomes using CRISPR-Cas systems", Nature Biotechnology, 31(3): 233-41. (Year: 2013).*

Salmond et al. "A century of the phage: past, present and future," Nat. Rev. Microbiol., (Dec. 2015), vol. 13, No. 12; pp. 777-786.

Hyman et al., "Bacteriophage host range and bacterial resistance," Adv. Appl. Microbiol., (2010), vol. 70; pp. 217-248.

Chatterjee et al., "Interaction of Bacteriophage I with Its *E. coli* Receptor, LamB," Viruses, (Nov. 2012), vol. 4, No. 11; pp. 3162-3178.

Nobrega et al, "Targeting mechanisms of tailed bacteriophages," Natural Reviews, Microbiology, (Dec. 2018), vol. 16; pp. 760-773.

Flayhan, et al., "New insights into pb5, the receptor binding protein of bacteriophage T5, and its interaction with its *Escherichia coli* receptor Fhu A," Biochimie, (2012), vol. 94, No. 9; pp. 1982-1989.

Rossmann, et al., "The bacteriophage T4 Dna injection machine," Curr. Opin. Struct. Biol, (Apr. 2004), vol. 14, No. 2; pp. 171-180.

Zivanovic et al., "Insights into Bacteriophage T5 Structure from Analysis of Its Morphogenesis Genes and Protein Components," J. Virol., (Jan. 2014), vol. 88, No. 2; pp. 1162-1174.

Hendrix et al., "Bacteriophage lambda PaPa: not the mother of all lambda phages," Science, (Nov. 1992), vol. 258, No. 5085; pp. 1145-1148.

Speed et al., "Conformation of P22 tailspike folding and aggregation intermediates probed by monoclonal antibodies," Protein Sci. Publ. Protein Soc., (Jan. 1997), vol. 6, No. 1; pp. 99-108.

Abrie et al., "Bacteriophage resistance mechanisms," Nat. Rev. Microbiol., (Mar. 2010), vol. 8, No. 5; pp. 317-327.

Whitfield, "Biosynthesis and assembly of capsular polysaccharides in *Escherichia coli*," Annu. Rev. Biochem., (2006), vol. 75; pp. 39-68.

Meyer et al., "Repeatability and contingency in the evolution of a key innovation in phage lambda," Science, (Jan. 2012), vol. 335, No. 6067; pp. 428-432.

Gupta et al., "Coliphage K5, specific for *E. coli* exhibiting the capsular K5 antigen," FEMS Microbiol. Lett., (May 1982), vol. 14, No. 1; pp. 75-78.

Gross, et al., "Isolation of bacteriophages specific for the K1 polysaccharide antigen of *Escherichia coli*," J. Clin. Microbiol., (Dec. 1977), vol. 6, No. 6; pp. 548-550.

Schwarzer et al., "A Multivalent Adsorption Apparatus Explains the Broad Host Range of Phage phi92: a Comprehensive Genomic and Structural Analysis," J. Virol., (Oct. 2012), vol. 86, No. 19; pp. 10384-10398.

(Continued)

*Primary Examiner* — Robert M Kelly

(74) *Attorney, Agent, or Firm* — Arrigo, Lee, Guttman & Mouta-Bellum LLP

(57) ABSTRACT

The present disclosure relates generally to bacterial delivery vehicles for use in efficient transfer of a desired payload into a target bacterial cell. More specifically, the present disclosure relates to bacterial delivery vehicles with desired host ranges based on the presence of a chimeric receptor binding protein (RBP) composed of a fusion between the N-terminal region of a RBP derived from a lambda-like bacteriophage and the C-terminal region of a different RBP.

14 Claims, 15 Drawing Sheets

Specification includes a Sequence Listing.

(56) References Cited

OTHER PUBLICATIONS

Tétart et al., "Bacteriophage T4 host range is expanded by duplications of a small domain of the tail fiber adhesin," J. Mol. Biol., (May 1996), vol. 258, No. 5; pp. 726-731.
Haggård-Ljungquist, et al., "DNA sequences of the tail fiber genes of bacteriophage P2: evidence for horizontal transfer of tail fiber genes among unrelated bacteriophages.," J. Bacteriol., (Mar. 1992), vol. 174, No. 5; pp. 1462-1477.
Wu, et al., "Characterization of Extended-Host-Range Pseudo-T-Even Bacteriophage Kpp95 Isolated on Klebsiella pneumoniae," Appl. Environ. Microbiol., (Apr. 2007), vol. 73, No. 8; pp. 2532-2540.
Montag et al., "A component of the side tail fiber of *Escherichia coli* bacteriophage lambda can functionally replace the receptor-recognizing part of a long tail fiber protein of the unrelated bacteriophage T4," J. Bacteriol., (Aug. 1989), vol. 171, No. 8; pp. 4378-4384.
Vimr, et al., "Use of prokaryotic-derived probes to identify poly(sialic acid) in neonatal neuronal membranes," Proc. Natl. Acad. Sci., (Apr. 1984), vol. 81, No. 7; pp. 1971-1975.
Stummeyer, et al., "Crystal structure of the polysialic acid-degrading endosialidase of bacteriophage K1F," Nat. Struct. Mol. Biol., (Jan. 2005), vol. 12, No. 1; pp. 90-96.
Scholl et al., "*Escherichia coli* K1's Capsule Is a Barrier to Bacteriophage T7," Appl. Environ. Microbiol., (Aug. 2005), vol. 71, No. 8; pp. 4872-4874.
Jiang et al. "Multigene Editing in the Escherichia coli Genome via the CRISPR-Cas9 System," Appl. Environ. Microbiol., (Apr. 2015), vol. 81, No. 7; pp. 2506-2514.
Cronan, "Improved Plasmid-Based System for Fully Regulated Off-To-On Gene Expression in *Escherichia coli*: Application to Production of Toxic Proteins," Plasmid, (Jan. 2013), vol. 69, No. 1; pp. 81-89.
Thompson et al., "The K5 Lyase KflA Combines a Viral Tail Spike Structure with a Bacterial Polysaccharide Lyase Mechanism," J. Biol. Chem., (Jul. 2010), vol. 285, No. 31; pp. 23963-23969.
Potter et al., "HMMER web server: 2018 update," Nucleic Acids Res., (Jul. 2018), vol. 46, No. W1; pp. W200-W204.
Xu et al., "Chaperone-protein interactions that mediate assembly of the bacteriophage lambda tail to the correct length," J. Mol. Biol., (Mar. 2014), vol. 426, No. 5; pp. 1004-1018.
Schwarzer et al., "Proteolytic Release of the Intramolecular Chaperone Domain Confers Processivity to Endosialidase F," J. Biol. Chem., (Apr. 2009), vol. 284, No. 14; pp. 9465-9474.
Gilbert et al., "Current understanding of the human microbiome," Nat. Med., (Apr. 2018), vol. 24, No. 4; pp. 392-400.
Nkamga et al., "Archaea: Essential inhabitants of the human digestive microbiota," Hum. Microbiome J., (Mar. 2017), vol. 3; pp. 1-8.
Scholl et al., "The Genome of Bacteriophage K1F, a T7-Like Phage That Has Acquired the Ability To Replicate on K1 Strains of *Escherichia coli*," J. Bacteriol (Dec. 2005), vol. 187, No. 24; pp. 8499-8503.
Keen, "Tradeoffs in bacteriophage life histories," Bacteriophage, (Apr. 2014), vol. 4, No. 2; p. e28365.
Mirzaei et al., "Isolation of Phages for Phage Therapy: A Comparison of Spot Tests and Efficiency of Plating Analyses for Determination of Host Range and Efficacy," PLOS ONE, (Mar. 2015), vol. 10, No. 3, p. e0118557.
Goodridge et al., "Morphological, Host Range, and Genetic Characterization of Two Coliphages," Appl. Environ. Microbiol. (Sep. 2003), vol. 69, No. 9; pp. 5364-5371.
Ochman et al., "Standard reference strains of *Escherichia coli* from natural populations," J. Bacteriol, (Feb. 1984), vol. 157, No. 2; pp. 690-693.
McBurney et al., "Establishing What Constitutes a Healthy Human Gut Microbiome: State of the Science, Regulatory Considerations, and Future Directions," J. Nutr. (Nov. 2019), vol. 149, No. 11; pp. 1882-1895.
Nagpal et al., "Gut microbiome and aging: Physiological and mechanistic insights," Nutr. Healthy Aging (2018), vol. 4, No. 4; pp. 267-285.
Singh et al., "Influence of diet on the gut microbiome and implications for human health," J. Transl. Med. (Apr. 2017), vol. 15; pp. 1-17.
Tenaillon et al., "The population genetics of commensal *Escherichia coli*," Nat. Rev. Microbiol., (Mar. 2010), vol. 8, No. 3; pp. 207-217.
Nowrouzian et al., "*Escherichia coli* strains belonging to phylogenetic group B2 have superior capacity to persist in the intestinal microflora of infants," J. Infect. Dis., (Apr. 2005), vol. 191, No. 7; pp. 1078-1083.
Smati et al., "Quantitative analysis of commensal *Escherichia coli* populations reveals host-specific enterotypes at the intra-species level," MicrobiologyOpen (Aug. 2015), vol. 4, No. 4; pp. 604-615.
Hyman, "Phages for Phage Therapy: Isolation, Characterization, and Host Range Breadth," Pharmaceuticals, (Mar. 2019), vol. 12, No. 1; pp. 1-23.
Pantucek et al., "The polyvalent staphylococcal phage phi 812: its host-range mutants and related phages," Virology (Jul. 1998), vol. 246, No. 2; pp. 241-252.
Ross et al., "More Is Better: Selecting for Broad Host Range Bacteriophages," Front. Microbiol. (Sep. 2016), vol. 7; Article 1352; pp. 1-6.
Marusich et al., "Chaperones in bacteriophage T4 assembly," Biochem. Biokhimiia, (Apr. 1998), vol. 63, No. 4; pp. 399-406 (Abstract Only).
Golomidova et al., "Branched Lateral Tail Fiber Organization in T5-Like Bacteriophages DT57C and DT571/2 is Revealed by Genetic and Functional Analysis, " Viruses, (Jan. 2016), vol. 8, No. 26; pp. 1-21.
Chen et al., "Crystal structure of ORF210 from *E. coli* O157:H1 phage CBA120 (TSP1), a putative tailspike protein," PloS One, (2014), vol. 9, No. 3; pp. e93156, 2014.
Kutter et al., "Characterization of a Vil-like phage specific to *Escherichia coli* O157:H7," Virology Journal (2011), vol. 8, No. 430; pp. 1-14 (PubMed—NCBI. [Online]. Available: https://www.ncbi.nlm.nih.gov/pubmed/21899740).
Arumugam et al., Enterotypes of the human gut microbiom, Nature (May 2011), vol. 473, No. 7346; pp. 174-180.
Kapitan et al. , "Fungi as Part of the Microbiota and Interactions with Intestinal Bacteria," Current Topics in Microbiology and Immunology, (2019), vol. 422; pp. 265-301.
Siponen, Marina, et al., "Crystal structure of a chimeric receptor binding protein constructed from two lactococcal phages," Journal of bacteriology, May 2009, pp. 3220-3225, 191.10.
Anonymous, "Short-chain Dehydrogenase," Database: UniProt, Nov. 2018, A0A167SZV7 A0A167SZV7_ECOLX, 7 pages.
European Office Action for related application No. 19 812 752.4, Sep. 1, 2022, 7 pages.
https://en.wikipedia.org/wiki/Lambdavirus, author unknown, published by Wikipedia, San Francisco, CA, downloaded as PDF on Mar. 1, 2021, 3 pages as printed. (Year: 2021).
Author(s) known, https://en.wikipedia.org/wiki/Bacteriophage, Wikimedia Foundation, Inc., San Francisco, CA, downloaded Nov. 5, 2020, 16 pages as printed.
Mobley, et al. (2009) Binding of Small-Molecule Ligands to Proteins: 'What You See' Is Not Always 'What You Get', Structure, 17:489-98.
Scholl et al. *Escherichia coli* K1's Capsule Is a Barrier to Bacteriophage T7. Applied and Environmental Microbiology, 2005, 71(8), 4872-4874.
English Translation of Japanese Office Action for application No. 2021-529822, Nov. 20, 2023, 8 pages.
Ando, H., et al., "Engineering modular viral scaffolds for targeted bacterial population editing," Cell Syst 1, Sep. 2015, pp. 187-196.
Wang, Jiang, Maurice Hofnung, and Alain Charbit, "The C-terminal portion of the tail fiber protein of bacteriophage lambda is responsible for binding to LamB, its receptor at the surface of *Escherichia coli* K-12," Journal of bacteriology, Jan. 2000, pp. 508-512, 182.2.
Tetart, F., C. Desplats, and H. M. Krisch, "Genome plasticity in the distal tail fiber locus of the T-even bacteriophage: recombination

(56) References Cited

OTHER PUBLICATIONS between conserved motifs swaps adhesin specificity," Journal of molecular biology, Sep. 1998, pp. 543-556, 282.3.
De Jonge, Patrick A., et al., "Molecular and evolutionary determinants of bacteriophage host range," Trends in microbiology, Jan. 2019, pp. 51-63, 27.1.
International Search Report and Written Opinion for application No. PCT/EP/2019/082640, Feb. 4, 2020, 15 pages.

* cited by examiner

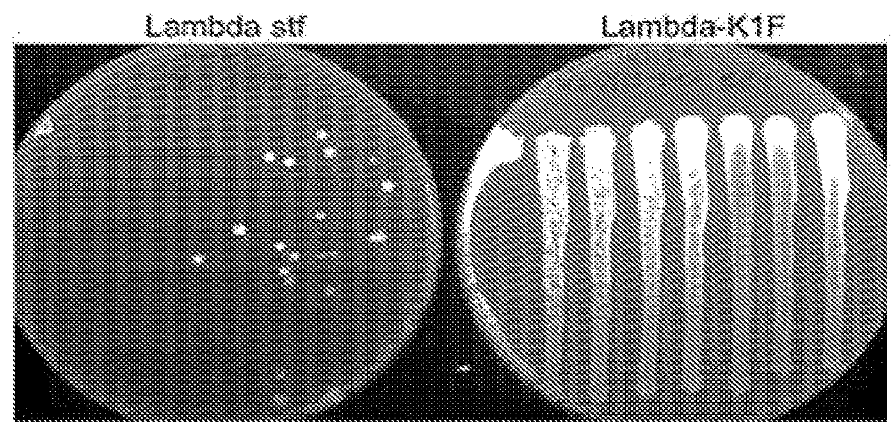
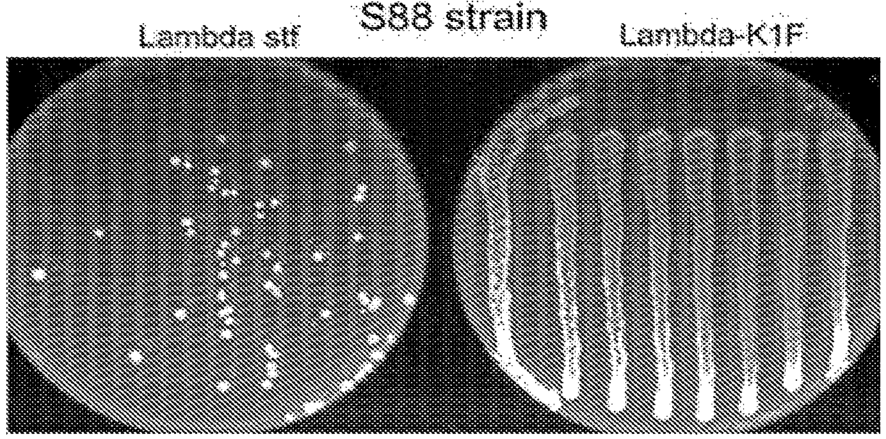
FIG. 2

FIG. 5A-C

CHIMERIC RECEPTOR BINDING PROTEINS FOR USE IN BACTERIAL DELIVERY VEHICLES

CROSS-REFERENCE TO RELATED APPLICATION

This application claims benefit and priority to U.S. application Ser. No. 16/696,769, filed on Nov. 26, 2019, which claims benefit and priority to U.S. Provisional Application No. 62/771,761, filed Nov. 27, 2018; and U.S. Provisional Application No. 62/802,777, filed Feb. 8, 2019, which are both incorporated herein by reference in their entireties.

REFERENCE TO ELECTRONIC SEQUENCE LISTING SUBMITTED VIA EFS-WEB

This application includes an electronically submitted sequence listing in .XLM format. The XLM file contains a sequence listing entitled 2643-3 CONB.xlm created on Apr. 21, 2023. The sequence listing contained in this XLM file is part of the specification and is hereby incorporated by reference herein in its entirety.

TECHNICAL FIELD

The present disclosure relates generally to bacterial delivery vehicles for use in efficient transfer of a desired payload into a target bacterial cell. More specifically, the present disclosure relates to bacterial delivery vehicles with desired host ranges based on the presence of a chimeric receptor binding protein (RBP) composed of a fusion between the N-terminal region of a RBP derived from a lambda-like, or lambda bacteriophage and the C-terminal region of a different RBP.

BACKGROUND

Bacteriophages are parasites that infect and multiply in bacteria. In general, the infection process can be divided in several stages: (i) adsorption corresponding to recognition and binding to the bacterial cell; (ii) injection of the DNA genome into the bacterial cell cytoplasm; (iii) production of a set of viral proteins that can lead to insertion in the host target genome (lysogenic phages) or to the production of infective particles (lytic phages) and (iv) release of mature virions from the infected cell, usually by controlled lysis [1].

Being the first step necessary for a successful infection, recognition and binding to the target cell is an essential process in the bacteriophage life cycle. Bacteriophages can in some cases recognize several strains of the same species, having a "broad host range", but very commonly are able to recognize a specific antigen present only on some strains of the same species [2]. It is thus not surprising that this step of the infection process is central in the competition between bacteriophage and bacteria for successful infection.

As a general mechanism, a bacteriophage encodes two main sets of proteins that are involved in the recognition process. The first set is able to attach to the bacteriophage's primary receptor on the cell surface, an event that triggers DNA ejection into the cytoplasm and is usually viewed as an "irreversible" binding process [3]. Different bacteriophage genera differ in the organization of this set of proteins, and hence the naming can be different. In some Siphovirus, for example, they are called the "central tail fiber" or "tail tip", which binds irreversibly to the LamB receptor in *Escherichia coli*. In the siphoviridae lambda, the "central tail fiber" or "tail tip" is composed of the protein gpJ [4]. In some other Siphovirus, like T5, a protein located at the very tip of the tail mediates this process. In the case of T5, a protein called pb5 recognizes the FhuA receptor [5]. This type of protein can be found in many other bacteriophages. In Myoviruses, like T4, the irreversible binding to the primary receptor or to the cell surface in general is mediated by the "short tail fibers", which are also located at the end of the tail tube [5].

The second set of proteins in the bacteriophage (herein referred to as "receptor binding proteins") encodes recognition and binding activities to the so-called "secondary receptor" on the bacterium. This secondary receptor allows for transient binding of the phage particle on the cell surface in order to scan the surface and position the first set of proteins in contact with the primary receptor. Since this binding is reversible, it allows the phage to "walk" on the cell surface until a primary receptor is found and the infection process starts. These protein complexes are sometimes referred to as "L-shape fibers", such as in T5, "side tail fibers" such as in lambda, "long tail fibers" as in T4, or tailspikes such as in phage P22 [5]-[8]. For some phages, the presence of this second set of proteins is necessary for the infection process to occur, such as T4 [5]. In some other phages, like lambda, this second set of proteins is not strictly necessary for the infection process to happen, but it may allow for a more efficient binding to the target cell [7].

Since the adsorption process is strictly necessary for a successful infection to happen, bacteria can develop multiple ways to avoid being recognized by a bacteriophage. For example, they can mutate the primary or secondary receptor to which the bacteriophage binds; they can mask this receptor by attaching proteins to it (receptor masking); or they can grow physical barriers around them in the form of bacterial capsules, thus blocking any access to the cell surface [9]. Bacteria can produce many different types of extracellular polymeric capsules [10]. In turn, bacteriophages have evolved different strategies to bypass these defense mechanisms. For instance, mutating the tail tip proteins allows them to use a different receptor [11]. However, the presence of a polymeric capsule around the bacterium requires a different approach, as it blocks all contact to any receptors on the cell surface. In these cases, bacteriophages have evolved specific proteins that can enzymatically degrade this capsule to gain access to the cells. These depolymerase activities are encoded in protein complexes that are distinct to the primary receptor recognition machinery, in the form of side tail fibers, long tail fibers or tailspikes [12], [13], [14].

The concept of a bacteriophage's host range needs to be redefined when only the adsorption and injection processes are taken into account. Since all incompatibilities or defense mechanisms related to the phage replication cycle are left out of the picture, the "adsorption host range" of a given phage is usually larger than the "classical host range" in which the infectious cycle leads to newly produced mature virions. The concept of host range becomes even more different to the classical definition when packaged phagemids based on a given bacteriophage capsid is used. Packaged phagemids do not contain the information necessary to replicate the viral particles, because they do not package their cognate viral genome. Thus, the host range of a packaged phagemid tends to be larger than that of the parental bacteriophage it derives from. Therefore, for development of novel bacterial delivery vehicles, designed for the efficient delivery of exogenous DNA payload into target strains, it is of utmost importance to be able to engineer delivery vehicles with desired host ranges as well as the ability to bypass bacterial mechanisms that can lead to unsuccessful binding of the packaged phagemid to the bacterial cell surface.

SUMMARY

As a general mechanism, a bacteriophage encodes sets of proteins that are involved in the bacterial cell recognition process. Described herein are novel approaches to engineering synthetic bacterial delivery vehicles with desired target host ranges. In some aspects, synthetic bacterial delivery vehicles are provided that are characterized by a chimeric receptor binding protein (RBP), wherein the chimeric RBP comprises a fusion between an N-terminal domain of a RBP from a lambda-like bacteriophage, or lambda bacteriophage, and a C-terminal domain of a different bacteriophage RBP. Such bacteriophage RBPs, from which the chimeric RBP are derived, include, for example, and depending on phages families, "L-shape fibers", "side tail fibers (stfs)", "long tail fibers" or "tailspikes." As disclosed herein, it has been demonstrated that a significant portion of a lambda-like bacteriophage receptor binding protein (RBP), such as a stf protein, can be exchanged with a portion of a different RBP. Moreover, specific fusion positions in the RBPs have been identified which allow one to obtain functional chimeric RBPs.

The chimeric receptor binding protein (RBP) is one wherein the chimeric RBP comprises a fusion between an N-terminal domain of a RBP derived from a lambda-like bacteriophage, or lambda bacteriophage, and a C-terminal domain of a different RBP wherein said N-terminal domain of the RBP is fused to said C-terminal domain of a different RBP within one of the amino acids regions selected from positions 1-150, 320-460, or 495-560 of the N-terminal RBP with reference to the lambda stf sequence (SEQ ID NO: 1) or a similar region of a RBP having homology with one or more of three amino acid regions ranging from positions 1-150, 320-460, and 495-560 of the RBP with reference to the lambda stf sequence. In one specific aspect of the invention, the different RBP domain of the chimeric receptor binding protein (RBP) is derived from any bacteriophage or from any bacteriocin.

In one specific aspect, the RBP from the lambda-like bacteriophage, or the lambda bacteriophage, or the different RBP contains homology in one or more of three amino acid regions ranging from positions 1-150, 320-460, and 495-560 of the RBP with reference to the lambda bacteriophage stf sequence (SEQ ID NO: 1). In certain aspects, the homology between the lambda-like bacteriophage, the lambda bacteriophage, or the different RBP and the one or more of three amino acids regions is around 35% identity for 45 amino acids or more, around 50% identify for 30 amino acids or more, and around 90% identity for 18 amino acids or more with reference to the lambda bacteriophage stf sequence (SEQ ID NO:1). Determination of homology can be performed using alignment tools such as the Smith-Waterman algorithm (Smith et al., 1981, J. Mol. Biol 147:195-197) or EMBOSS Matcher (Rice, Longden, Bleasby 2000 EMBOSS Trends in Genetics 16: 276-277).

In one aspect of the invention, the chimeric RBP comprises the N-terminal domain of a RBP fused to the C-terminal domain of a different RBP within one of the amino acid regions selected from positions 80-150, 320-460, or 495-560 of the N-terminal RBP with reference to the lambda bacteriophage stf sequence (SEQ ID NO:1). In another embodiment of the invention, the chimeric RBP comprises an N-terminal domain and a C-terminal domain fused within one of the amino acids regions selected from positions 1-150, 320-460 or 495-560 at an insertion site having at least 80% identity with an insertion site selected from the group consisting of amino acids SAGDAS (SEQ ID NO: 248), ADAKKS (SEQ ID NO: 249), MDETNR (SEQ ID NO: 250), SASAAA (SEQ ID NO: 251) and, GAGENS (SEQ ID NO: 252).

In another aspect, the chimeric RBP comprises the N-terminal domain of a RBP fused to the C-terminal domain of different RBP wherein the different RBP is a protein or group a different proteins that confers an altered host range. In one embodiment, the different RBP is a T4-like or T4 long tail fiber composed of a proximal tail fiber and a distal tail fiber (DTF), and the C-terminal domain of a T4-like or T4 RBP is the distal tail fiber (DTF). In another embodiment, the N-terminal domain of a RBP is fused to the T4-like or T4 distal tail fiber at an insertion site within the T4-like or T4 DTF having at least 80% identity with an insertion site selected from the group consisting of amino acids ATLKQI (SEQ ID NO: 253), IIQLED (SEQ ID NO: 254), GNIIDL (SEQ ID NO: 255), IATRV (SEQ ID NO: 256), TPGEL (SEQ ID NO: 257), GAIIN (SEQ ID NO: 258), NQIID (SEQ ID NO: 259), GQIVN (SEQ ID NO: 260) and, VDRAV (SEQ ID NO: 261). In a specific embodiment, the N-terminal domain of a RBP is fused to the T4-like or T4 distal tail fiber within a region from amino acid 1 to 90, with a preferred region from amino acid 40 to 50 of the DTF.

In specific embodiments, the disclosure provides specific chimeric RBPs. SEQ ID NOS 2-61, 123-153, 216-244 and 246-247 disclose the amino acid sequences of such chimeric RBPs as well as, in some instances, their corresponding natural chaperone proteins (designated "AP"). Such AP proteins assist in the folding of the chimeric RBPs. In a specific embodiment, the RBP comprises the amino acid sequence of SEQ ID NO: 2, 4, 7, 9, 12, 15, 17, 20, 23, 24, 25, 27, 29, 31, 33, 35, 37, 39, 41, 42, 44, 46, 47, 48, 49, 50, 51, 52, 53, 56, 59, 123-129, 130, 131, 132, 135, 138, 139, 142, 145, 148, 151, 216, 219, 221, 223, 227, 230, 232, 234, 236, 238, 240, 243, 245 or 246.

In another aspect, the present disclosure provides nucleotide sequences encoding for the chimeric RBPs disclosed herein. In a specific embodiment, nucleic acids encoding such chimeric RBPs, as well as their corresponding AP proteins, are depicted in SEQ ID NOS 62-120, 122, 154-177, 182-210 and 212-213. In a specific embodiment, the nucleic acids encoding such chimeric RBPs comprise the nucleotide sequence of SEQ ID NO: 62, 64, 67, 69, 72, 75, 77, 80, 83, 84, 85, 87, 89, 91, 93, 95, 97, 99, 101, 102, 104, 106, 107, 108, 109, 110, 111, 112, 113, 116, 119, 154, 155, 156, 159, 162, 163, 166, 169, 172 175, 182, 187, 189, 193, 196, 198, 200, 202, 204, 206, 209 or 212.

In one specific non-limiting aspect of the invention, it has been demonstrated that engineering the chimeric RBP to encode depolymerase activity can dramatically increases the delivery efficiency of the provided bacterial delivery vehicles comprising the chimeric RBP disclosed herein. In an embodiment of the invention, the different RBP domain of the chimeric RPB comprises depolymerase activity against an encapsulated bacterial strain. In a specific embodiment, the depolymerase is an endosialidase such as, for example, a K1F or K5 endosialidase.

In an embodiment of the invention, nucleic acid molecules encoding the chimeric RBPs disclosed herein are provided. Such nucleic acids may be included in vectors such as bacteriophages, plasmids, phagemids, viruses, and other vehicles which enable transfer and expression of the chimeric RBP encoding nucleic acids.

Bacterial delivery vehicles are provided which enable transfer of a nucleic acid payload, encoding a protein or nucleic acid of interest, into a desired target bacterial host cell. Such bacterial delivery vehicles are characterized by having a chimeric RBP comprising a fusion between the N-terminal domain of a RBP from a lambda-like bacteriophage, or lambda bacteriophage, and the C-terminal domain of a different RBP. In an embodiment of the invention, the bacterial delivery vehicles contain a chimeric RBP comprising a fusion between an N-terminal domain of a RBP derived from a lambda-like bacteriophage, or lambda bacteriophage, and a C-terminal domain of a different RBP wherein said N-terminal domain of the chimeric RBP is fused to said C-terminal domain of a different RBP within one of the amino acids regions selected from positions 1-150, 320-460, or 495-560 of the N-terminal domain with reference to the lambda stf sequence (SEQ ID NO: 1). In one aspect, the RBP from the lambda-like bacteriophage, the lambda bacteriophage, and the different RBP contain homology in one or more of three amino acids regions ranging from positions 1-150, 320-460, and 495-560 of the RBP with reference to the lambda bacteriophage stf sequence (SEQ ID NO: 1). In certain aspects, the homology is around 35% identity for 45 amino acids or more, around 50% identify for 30 amino acids or more, or around 90% identity for 18 amino acids or more within the one or more of three amino acids regions ranging from positions 1-150, 320-460, and 495-560 of the RBP with reference to the lambda bacteriophage stf sequence. In one specific aspect of the invention, the different RBP domain of the chimeric receptor binding protein (RBP) is derived from a bacteriophage or a bacteriocin. In one aspect of the invention, the chimeric RBP comprises an N-terminal domain of a RBP fused to a C-terminal domain of a RBP within one of the amino acids regions selected from positions 80-150, 320-460, or 495-560 of the N-terminal RBP domain with reference to the lambda stf sequence. In another embodiment of the invention, the chimeric RBP comprises an N-terminal domain of a RBP and a C-terminal domain of a RBP fused within a site of the N-terminal RBP domain having at least 80% identity with a site selected from the group consisting of amino acids SAGDAS (SEQ ID NO: 248), ADAKKS (SEQ ID NO: 249), MDETNR (SEQ ID NO: 250), SASAAA (SEQ ID NO: 251), and GAGENS (SEQ ID NO: 252).

In specific embodiments, the disclosure provides a bacterial delivery vehicle comprising a chimeric RBP. SEQ ID NOS 2-61, 123-153, 216-244 and 246-247 disclose the amino acid sequences of such chimeric RBPs and in addition, in some instances, their corresponding natural chaperone proteins (designated “AP”). Such AP proteins assist in the folding of the chimeric RBPs. In a specific embodiment, the RBP comprises the amino acid sequence of SEQ ID NO: 2, 4, 7, 9, 12, 15, 17, 20, 23, 24, 25, 27, 29, 31, 33, 35, 37, 39, 41, 42, 44, 46, 47, 48, 49, 50, 51, 52, 53, 56, 59, 130, 131, 132, 135, 138, 139, 142, 145, 148,151, 216, 219, 221, 223, 227, 230, 232, 234, 236, 238, 240, 243, 245 or 246.

In one aspect, the present disclosure also provides nucleotide sequences encoding for the chimeric RBPs disclosed herein. In a specific embodiment, nucleic acids encoding such chimeric RBPs, as well as corresponding AP proteins, are depicted in SEQ ID NOS 62-120, 122, 154-177, 182-210 and 212-213. In a specific embodiment, the nucleic acids encoding such chimeric RBPs comprise the nucleotide sequence of SEQ ID NO: 62, 64, 67, 69, 72, 75, 77, 80, 83, 84, 85, 87, 89, 91, 93, 95, 97, 99, 101, 102, 104, 106, 107, 108, 109, 110, 111, 112, 113, 116, 119, 154, 155, 156, 159, 162, 163, 166, 169, 172, 175, 182, 185, 187, 189, 193, 196, 198, 200, 202, 204, 206, 209 or 212.

In other specific embodiments and to increase the delivery efficiency of the bacterial delivery vehicles disclosed herein the different RBP domain of the chimeric RBP comprises a domain having depolymerase activity against an encapsulated bacterial strain. In a specific embodiment, the depolymerase is an endosialidase, such as for example, a K1F or K5 endosialidase.

The bacterial delivery vehicles provided herein enable transfer of a nucleic acid payload, encoding one or more protein or nucleic acid of interest, into a desired target bacterial host cell. In certain embodiments of the invention, the nucleic acid of interest is selected from the group consisting of a Cas nuclease gene, a Cas9 nuclease gene, a guide RNA, a CRISPR locus, a toxin gene, a gene expressing an enzyme such as a nuclease or a kinase, a TALEN, a ZFN, a meganuclease, a recombinase, a bacterial receptor, a membrane protein, a structural protein, a secreted protein, a gene expressing resistance to an antibiotic or to a drug in general, a gene expressing a toxic protein or a toxic factor, and a gene expressing a virulence protein or a virulence factor, or any of their combination. In an embodiment of the invention, the nucleic acid payload encodes a therapeutic protein. In another embodiment, the nucleic acid payload encodes an anti-sense nucleic acid molecule. In some embodiment, the nucleic acid payload encodes 2 nucleic acid of interest, one being a nuclease gene, for instance a Cas nuclease gene, and one being any other nucleic acid of interest. In one aspect, the bacterial delivery vehicle enables the transfer of a nucleic acid payload that encodes a nuclease that targets cleavage of a host bacterial cell genome or a host bacterial cell plasmid. In some aspects, the cleavage occurs in an antibiotic resistant gene. In another embodiment of the invention, the nuclease mediated cleavage of the host bacterial cell genome is designed to stimulate a homologous recombination event for insertion of a nucleic acid of interest into the genome of the bacterial cell.

The present invention also provides pharmaceutical or veterinary compositions comprising one or more of the bacterial delivery vehicles disclosed herein and a pharmaceutically-acceptable carrier. Also provided is a method for treating a bacterial infection comprising administering to a subject having a bacterial infection in need of treatment the provided pharmaceutical or veterinary composition. A method for reducing the amount of virulent and/or antibiotic resistant bacteria in a bacterial population is provided comprising contacting the bacterial population with the bacterial delivery vehicles disclosed herein.

BRIEF DESCRIPTION OF FIGURES

In order to better understand the subject matter that is disclosed herein and to exemplify how it may be carried out in practice, embodiments will now be described, by way of non-limiting example, with reference to the accompanying drawings. With specific reference to the drawings, it is stressed that the particulars shown are by way of example and for purposes of illustrative discussion of embodiments of the invention FIG. 1 demonstrates delivery in wild-type *E. coli* strains with lambda and OMPF-lambda packaged phagemids. Lambda packaged phagemids were diluted 1:5 in LB plus 5 mM $CaCl_2$) and 10 uL added in each well. 90 uL of cells grown to an OD600 of around 0.5 were then added to each phagemid-containing well, incubated for 30 min at 37° C. and 10 uL spotted on LB-agar supplemented with chloramphenicol. Left panel, wild type lambda packaged phagemids; right panel, OMPF-lambda variant. Circles show strains with modified delivery as compared to lambda wild-type.

DETAILED DESCRIPTION

Figure 1:
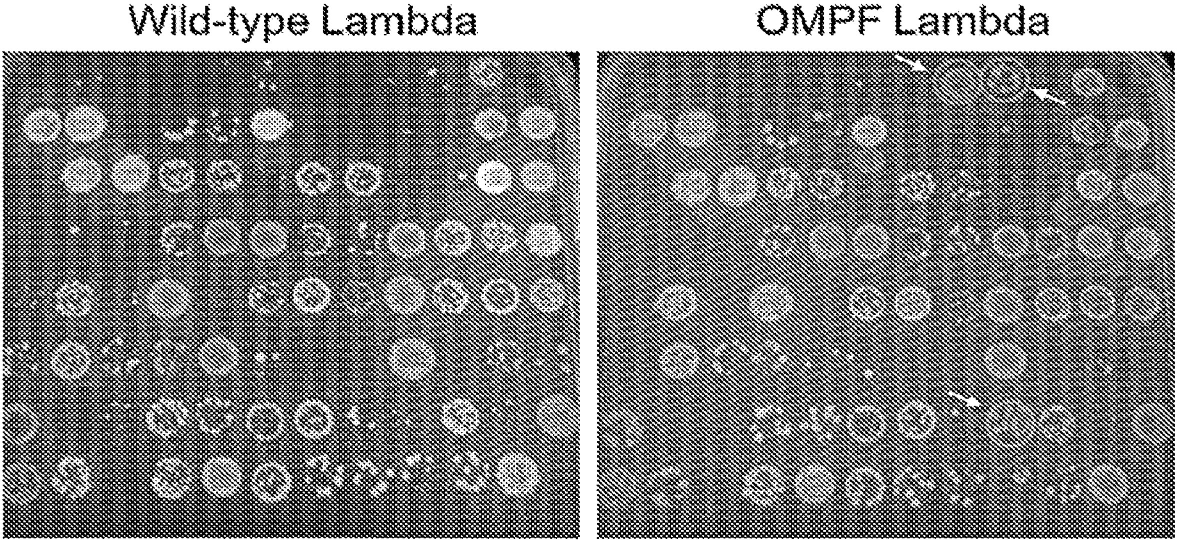

Disclosed herein are novel approaches to engineering synthetic bacterial delivery vehicles with desired target host ranges. The synthetic bacterial delivery vehicles are characterized by a chimeric receptor binding protein (RBP), wherein the chimeric RBP comprises a fusion between the N-terminal domain of a RBP from a lambda-like bacteriophage, or lambda bacteriophage, and the C-terminal domain of a different RBP. It has been demonstrated herein that a significant portion of a lambda-like RBP, such as a stf protein, can be exchanged with a portion of a different RBP. Moreover, specific fusion positions of the receptor binding protein have been identified which allow one to obtain a functional chimeric RBP.

As used herein, a receptor binding protein or RBP is a polypeptide that recognizes, and optionally binds and/or modifies or degrades a substrate located on the bacterial outer envelope, such as, without limitation, bacterial outer membrane, LPS, capsule, protein receptor, channel, structure such as the flagellum, pili, secretion system. The substrate can be, without limitation, any carbohydrate or modified carbohydrate, any lipid or modified lipid, any protein or modified protein, any amino acid sequence, and any combination thereof. As used herein, a lambda-like bacteriophage refers to any bacteriophage encoding a RBP having amino acids sequence homology of around 35% identity for 45 amino acids or more, around 50% identify for 30 amino acids or more, or around 90% identity for 18 amino acids or more in one or more of three amino acids regions ranging from positions 1-150, 320-460, and 495-560 with reference to the lambda bacteriophage stf sequence of SEQ ID NO: 1, independently of other amino acids sequences encoded by said bacteriophage.

The present disclosure provides a chimeric receptor binding protein (RBP), wherein the chimeric RBP comprises a fusion between an N-terminal domain of a RBP from a lambda-like bacteriophage, or lambda bacteriophage, and a C-terminal domain of a different bacteriophage RBP. Such bacteriophage RBPs, from which the chimeric RBP are derived, include, for example, "L-shape fibers", "side tail fibers (stfs)", "long tail fibers" or "tailspikes." As disclosed herein, it has been demonstrated that a significant portion of a lambda-like bacteriophage receptor binding protein (RBP), such as a stf protein, can be exchanged with a portion of a different RBP. Moreover, specific fusion positions in the RBPs have been identified which allow one to obtain a functional chimeric RBP. Such chimeric RBPs include those having an altered host range and/or biological activity such as, for example, depolymerase activity.

The chimeric receptor binding protein (RBP) is one wherein the chimeric RBP comprises a fusion between an N-terminal domain of a RBP derived from a lambda-like bacteriophage, or lambda bacteriophage, and a C-terminal domain of a different RBP wherein said N-terminal domain of the RBP is fused to said C-terminal domain of a different RBP within one of the amino acids regions selected from positions 1-150, 320-460, or 495-560 of the N-terminal RBP with reference to the lambda stf sequence (SEQ ID NO: 1) or a similar region of a RBP having homology with one or more of three amino acids regions ranging from positions 1-150, 320-460, and 495-560 of the RBP with reference to the lambda stf sequence. In one specific aspect of the invention, the different RBP of the chimeric receptor binding protein (RBP) is derived from any bacteriophage or from any bacteriocin.

In one specific aspect, the RBP from the lambda-like bacteriophage, the lambda bacteriophage, or the different RBP contain homology with one or more of three amino acids regions ranging from positions 1-150, 320-460, and 495-560 of the RBP with reference to the lambda bacteriophage stf sequence (SEQ ID NO:1). In certain aspects, the homology between the lambda-like bacteriophage, the lambda bacteriophage, or the different RBP and the one or more amino acids regions is around 35% identity for 45 amino acids or more, around 50% identify for 30 amino acids or more, and around 90% identity for 18 amino acids or more. Determination of homology can be performed using alignment tools such as the Smith-Waterman algorithm (Smith et al., 1981, J. Mol. Biol 147:195-197) or EMBOSS Matcher (Rice, Longden, Bleasby 2000 EMBOSS Trends in Genetics 16: 276-277). In one aspect of the invention, the chimeric RBP comprises the N-terminal domain of the chimeric RBP fused to the C-terminal domain of the chimeric RBP within one of the amino acids regions selected from positions 80-150, 320-460, or 495-560 with reference to the lambda bacteriophage stf sequence (SEQ ID NO: 1). In another embodiment of the invention, the chimeric RBP comprises an N-terminal domain and a C-terminal domain fused within one the three amino acids regions at an insertion site having at least 80% identity with an insertion site selected from the group consisting of amino acids SAGDAS (SEQ ID NO: 248), ADAKKS (SEQ ID NO: 249), MDETNR (SEQ ID NO: 250), SASAAA (SEQ ID NO: 251), and GAGENS (SEQ ID NO: 252).

In specific embodiments, the invention provides chimeric RBPs. SEQ ID NOS 2-61, 123-153, 216-244 and 246-247 disclose the amino acid sequences of such chimeric RBPs and in addition, in some instances, their corresponding natural chaperone proteins (designated "AP"). Such AP proteins assist in the folding of the chimeric RBPs. In a specific embodiment, the RBP comprises the amino acid sequence of SEQ ID NO: 2, 4, 7, 9, 12, 15, 17, 20, 23, 24, 25, 27, 29, 31, 33, 35, 37, 39, 41, 42, 44, 46, 47, 48, 49, 50, 51, 52, 53, 56, 59, 130, 131, 132, 135, 138, 139, 142, 145, 148, 151, 216, 219, 221, 223, 227, 230, 232, 234,236, 238, 240, 243, 245 or 246

In one aspect, the present disclosure also provides nucleotide sequences encoding for the chimeric RPBs disclosed herein. In a specific embodiment, nucleic acids encoding such chimeric RBPs, as well as corresponding AP proteins, are depicted in SEQ ID NOS 62-120, 122, 154-177, 182-210, 212-213. In a specific embodiment, the nucleic acids encoding the chimeric RBP comprise the nucleotide sequence of SEQ ID NO: 62, 64, 67, 69, 72, 75, 77, 80, 83, 84, 85, 87, 89, 91, 93, 95, 97, 99, 101, 102, 104, 106, 107, 108, 109, 110, 111, 112, 113, 116, 119, 154, 155, 156, 159, 162, 163, 166, 169, 172,175 182, 185, 187, 189, 193, 196, 198, 200, 202, 204, 206, 209 or 212.

In one specific non-limiting aspect of the invention, it has been demonstrated that engineering the chimeric RBP to encode depolymerase activity can dramatically increases the delivery efficiency of the provided bacterial delivery vehicles comprising the chimeric RBP disclosed herein. In an embodiment of the invention, the different RBP domain of the chimeric RPB comprises depolymerase activity against an encapsulated bacterial strain. In a specific embodiment, the depolymerase is an endosialidase such as, for example, a K1F or K5 endosialidase.

Nucleic acid molecules encoding the chimeric RBPs disclosed herein are provided. Such nucleic acids may be included in vectors such as bacteriophages, plasmids, phagemids, viruses, and other vehicles which enable transfer and expression of the chimeric RBP encoding nucleic acids.

Bacterial delivery vehicles are provided which enable transfer of a nucleic acid payload, encoding a protein or nucleic acid of interest, into a desired target bacterial host cell. Such bacterial delivery vehicles are characterized by having a chimeric RBP comprising a fusion between the N-terminal domain of a RBP from a lambda-like bacteriophage, or lambda bacteriophage, and the C-terminal domain of a different RBP. In an embodiment of the invention, the bacterial delivery vehicles contain a chimeric RBP comprising a fusion between an N-terminal domain of a RBP derived from a lambda-like bacteriophage, or lambda bacteriophage, and a C-terminal domain of a different RBP wherein said N-terminal domain of the chimeric RBP is fused to said C-terminal domain of a different RBP within one of the amino acids regions selected from positions 1-150, 320-460, or 495-560 of the N-terminal domain RBP with reference to the lambda stf sequence (SEQ ID NO: 1). In one aspect, the RBP from the lambda-like bacteriophage, the lambda bacteriophage, and the different RBP contain homology in one or more of three amino acids regions ranging from positions 1-150, 320-460, and 495-560 of the N-terminal RBP with reference to the lambda bacteriophage stf sequence (SEQ ID NO: 1). In certain aspects, the homology is around 35% identity for 45 amino acids or more, around 50% identify for 30 amino acids or more, or around 90% identity for 18 amino acids or more within the one or more of three amino acids regions ranging from positions 1-150, 320-460, and 495-560 of the N-terminal RBP with reference to the lambda bacteriophage stf sequence (SEQ ID NO: 1). In one specific aspect of the invention, the different RBP domain of the chimeric receptor binding protein (RBP) is derived from a bacteriophage or a bacteriocin. In one aspect of the invention, the chimeric RBP comprises an N-terminal domain of a RBP fused to a C-terminal domain of a RBP within one of the amino acids regions selected from 80-150, 320-460, or 495-560 of the RBPs with reference to the lambda stf sequence (SEQ ID NO: 1). In another embodiment of the invention, the chimeric RBP comprises an N-terminal domain of a RBP and a C-terminal domain of a RBP fused within a site of the N-terminal RBPs having at least 80% identity with a site selected from the group consisting of amino acids SAGDAS (SEQ ID NO. 248), ADAKKS (SEQ ID NO. 249), MDETNR (SEQ ID NO. 250), SASAAA (SEQ ID NO. 251), and GAGENS (SEQ ID NO. 252).

In specific embodiments, the disclosure provides a bacterial delivery vehicle comprising a chimeric RBP. SEQ ID NOS 2-61, 123-153, 216-244 and 246-247 disclose the amino acid sequences of such chimeric RBPs and in addition, in some instances, their corresponding natural chaperone proteins (designated "AP"). Such AP proteins assist in the folding of the chimeric RBPs. In a specific embodiment, the RBP comprises the amino acid sequence of SEQ ID NO: 2, 4, 7, 9, 12, 15, 17, 20, 23, 24, 25, 27, 29, 31, 33, 35, 37, 39, 41, 42, 44, 46, 47, 48, 49, 50, 51, 52, 53, 56, 59, 130, 131, 132, 135, 138, 139, 142, 145, 148 151, 216, 219, 221, 223, 227, 230, 232, 234, 236, 238, 240, 243, 245 or 246

In one aspect, the present disclosure also provides nucleotide sequences encoding for the chimeric RPBs disclosed herein. In a specific embodiment, nucleic acids encoding such chimeric RBPs, as well as corresponding AP proteins, are depicted in SEQ ID NOS 62-120, 122, 154-177, 182-210, 212-213. In a specific embodiment, the nucleic acids encoding the chimeric RBPs comprise the nucleotide sequence of SEQ ID NO: 62, 64, 67, 69, 72, 75, 77, 80, 83, 84, 85, 87, 89, 91, 93, 95, 97, 99, 101, 102, 104, 106, 107, 108, 109, 110, 111, 112, 113, 116, 119, 154, 155, 156, 159, 162, 163, 166, 169, 172,175, 182, 185, 187, 189, 193, 196, 198, 200, 202, 204, 206, 209 or 212.

In other specific embodiments and to increase the delivery efficiency of the bacterial delivery vehicles disclosed herein the different RBP domain of the chimeric comprises a domain having depolymerase activity against an encapsulated bacterial strain. In a specific embodiment, the depolymerase is an endosialidase, such as for example, a K1F or K5 endosialidase.

The bacterial delivery vehicles provided herein enable transfer of a nucleic acid payload, encoding a protein or nucleic acid of interest, into a desired target bacterial host cell. As used herein, the term "delivery vehicle" refers to any means that allows the transfer of a payload into a bacterium. There are several types of delivery vehicles encompassed by the present invention including, without limitation, bacteriophage scaffold, virus scaffold, chemical based delivery vehicle (e.g., cyclodextrin, calcium phosphate, cationic polymers, cationic liposomes), protein-based or peptide-based delivery vehicle, lipid-based delivery vehicle, nanoparticle-based delivery vehicles, non-chemical-based delivery vehicles (e.g., transformation, electroporation, sonoporation, optical transfection), particle-based delivery vehicles (e.g., gene gun, magnetofection, impalefection, particle bombardment, cell-penetrating peptides) or donor bacteria (conjugation).

Any combination of delivery vehicles is also encompassed by the present invention. The delivery vehicle can refer to a bacteriophage derived scaffold and can be obtained from a natural, evolved or engineered capsid. In some embodiments, the delivery vehicle is the payload as bacteria are naturally competent to take up a payload from the environment on their own.

As used herein, the term "payload" refers to any one or more nucleic acid sequence and/or amino acid sequence, or a combination of both (such as, without limitation, peptide nucleic acid or peptide-oligonucleotide conjugate) transferred into a bacterium with a delivery vehicle. The term "payload" may also refer to a plasmid, a vector or a cargo. The payload can be a phagemid or phasmid obtained from natural, evolved or engineered bacteriophage genome. The payload can also be composed only in part of phagemid or phasmid obtained from natural, evolved or engineered bacteriophage genome.

As used herein, the term "nucleic acid" refers to a sequence of at least two nucleotides covalently linked together which can be single-stranded or double-stranded or contains portion of both single-stranded and double-stranded sequence. Nucleic acids of the present invention can be naturally occurring, recombinant or synthetic. The nucleic acid can be in the form of a circular sequence or a linear sequence or a combination of both forms. The nucleic acid can be DNA, both genomic or cDNA, or RNA or a combination of both. The nucleic acid may contain any combination of deoxyribonucleotides and ribonucleotides, and any combination of bases, including uracil, adenine, thymine, cytosine, guanine, inosine, xathanine, hypoxathanine, isocytosine, 5-hydroxymethylcytosine and isoguanine. Other examples of modified bases that can be used in the present invention are detailed in Chemical Reviews 2016, 116 (20) 12655-12687. The term "nucleic acid" also encompasses any nucleic acid analogs which may contain other backbones comprising, without limitation, phosphoramide, phosphorothioate, phosphorodithioate, O-methylphophoroamidite linkage and/or deoxyribonucleotides and ribonucleotides nucleic acids. Any combination of the above features of a nucleic acid is also encompassed by the present invention.

Origins of replication known in the art have been identified from species-specific plasmid DNAs (e.g. ColE1, R1, pT181, pSC101, pMB1, R6K, RK2, p15a and the like), from bacterial virus (e.g. φX174, M13, F1 and P4) and from bacterial chromosomal origins of replication (e.g. oriC). In one embodiment, the phagemid according to the disclosure comprises a bacterial origin of replication that is functional in the targeted bacteria.

Alternatively, the plasmid according to the disclosure does not comprise any functional bacterial origin of replication or contain an origin of replication that is inactive in the targeted bacteria. Thus, the plasmid of the disclosure cannot replicate by itself once it has been introduced into a bacterium by the bacterial virus particle.

In one embodiment, the origin of replication on the plasmid to be packaged is inactive in the targeted bacteria, meaning that this origin of replication is not functional in the bacteria targeted by the bacterial virus particles, thus preventing unwanted plasmid replication.

In one embodiment, the plasmid comprises a bacterial origin of replication that is functional in the bacteria used for the production of the bacterial virus particles.

Plasmid replication depends on host enzymes and on plasmid-controlled cis and trans determinants. For example, some plasmids have determinants that are recognized in almost all gram-negative bacteria and act correctly in each host during replication initiation and regulation. Other plasmids possess this ability only in some bacteria (Kues, U and Stahl, U 1989 Microbiol Rev 53:491-516).

Plasmids are replicated by three general mechanisms, namely theta type, strand displacement, and rolling circle (reviewed by Del Solar et al. 1998 Microhio and Molec Biol.

Rev 62:434-464) that start at the origin of replication. These replication origins contain sites that are required for interactions of plasmid and/or host encoded proteins.

Origins of replication used on the plasmid of the disclosure may be of moderate copy number, such as colE1 ori from pBR322 (15-20 copies per cell) or the R6K plasmid (15-20 copies per cell) or may be high copy number, e.g. pUC oris (500-700 copies per cell), pGEM oris (300-400 copies per cell), pTZ oris (>1000 copies per cell) or pBluescript oris (300-500 copies per cell).

In one embodiment, the bacterial origin of replication is selected in the group consisting of ColE1, pMB1 and variants (pBR322, pET, pUC, etc), p15a, ColA, ColE2, pOSAK, pSC101, R6K, IncW (pSa etc), IncFII, pT181, P1, F IncP, IncC, IncJ, IncN, IncP1, IncP4, IncQ, IncH11, RSF1010, CloDF13, NTP16, R1, f5, pPS10, pC194, pE194, BBR1, pBC1, pEP2, pWVO1, pLF1311, pAP1, pWKS1, pLS1, pLS11, pUB6060, pJD4, pIJ101, pSN22, pAMbeta1, pIP501, pIP407, ZM6100(Sa), pCU1, RA3, pMOL98, RK2/RP4/RP1/R68, pB10, R300B, pRO1614, pRO1600, pECB2, pCM1, pFA3, RepFIA, RepFIB, RepFIC, pYVE439-80, R387, phasyl, RA1, TF-FC2, pMV158 and pUB113.

More preferably, the bacterial origin of replication is a *E. coli* origin of replication selected in the group consisting of ColE1, pMB1 and variants (pBR322, pET, pUC, etc), p15a, ColA, ColE2, pOSAK, pSC101, R6K, IncW (pSa etc), IncFII, pT181, P1, F IncP, IncC, IncJ, IncN, IncP1, IncP4, IncQ, IncH11, RSF1010, CloDF13, NTP16, R1, f5 and pPS10.

More preferably, the bacterial origin of replication is selected in the group consisting of pC194, pE194, BBR1, pBC1, pEP2, pWVO1, pLF1311, pAP1, pWKS1, pLS1, pLS11, pUB6060, pJD4, pIJ101, pSN22, pAMbeta1, pIP501, pIP407, ZM6100(Sa), pCU1, RA3, pMOL98, RK2/RP4/RP1/R68, pB10, R300B, pRO1614, pRO1600, pECB2, pCM1, pFA3, RepFIA, RepFIB, RepFIC, pYVE439-80, R387, phasyl, RA1, TF-FC2, pMV158 and pUB113.

Even more preferably, the bacterial origin of replication is ColEl.

The delivered nucleic acid sequence according to the disclosure may comprise a phage replication origin which can initiate, with complementation of a complete phage genome, the replication of the delivered nucleic acid sequence for later encapsulation into the different capsids.

A phage origin of replication comprised in the delivered nucleic acid sequence of the disclosure can be any origin of replication found in a phage.

Preferably, the phage origin of replication can be the wild-type or non-wildtype sequence of the M13, f1, φX174, P4, lambda, P2, lambda-like, HK022, mEP237, HK97, HK629, HK630, mEP043, mEP213, mEP234, mEP390, mEP460, mEPx1, mEPx2, phi80, mEP234, T2, T4, T5, T7, RB49, phiX174, R17, PRD1 P1-like, P2-like, P22, P22-like, N15 and N15-like bacteriophages.

More preferably, the phage origin of replication is selected in the group consisting of phage origins of replication of M13, f1, φX174, P4, and lambda.

In a particular embodiment, the phage origin of replication is the lambda or P4 origin of replication.

The delivered nucleic acid of interest comprises a nucleic acid sequence under the control of a promoter. In certain embodiments of the invention, the nucleic acid of interest is selected from the group consisting of a Cas nuclease gene, a Cas9 nuclease gene, a guide RNA, a CRISPR locus, a toxin gene, a gene expressing an enzyme such as a nuclease or a kinase, a TALEN, a ZFN, a meganuclease, a recombinase, a bacterial receptor, a membrane protein, a structural protein, a secreted protein, a gene expressing resistance to an antibiotic or to a drug in general, a gene expressing a toxic protein or a toxic factor, and a gene expressing a virulence protein or a virulence factor, or any of their combination. In an embodiment of the invention, the nucleic acid payload encodes a therapeutic protein. In another embodiment, the nucleic acid payload encodes an anti-sense nucleic acid molecule. In some embodiment, the nucleic acid payload encodes 2 nucleic acids of interest, one being a nuclease gene, for instance a Cas nuclease gene, and one being any other nucleic acid of interest.

In one embodiment, the sequence of interest is a programmable nuclease circuit to be delivered to the targeted bacteria. This programmable nuclease circuit is able to mediate in vivo sequence-specific elimination of bacteria that contain a target gene of interest (e.g. a gene that is harmful to humans). Some embodiments of the present disclosure relate to engineered variants of the Type II CRISPR-Cas (Clustered Regularly Interspaced Short Palindromic Repeats-CRISPR-associated) system of *Streptococcus pyogenes*. Other programmable nucleases that can be used include other CRISPR-Cas systems, engineered TALEN (Transcription Activator-Like Effector Nuclease) variants, engineered zinc finger nuclease (ZFN) variants, natural, evolved or engineered meganuclease or recombinase variants, and any combination or hybrids of programmable nucleases. Thus, the engineered autonomously distributed nuclease circuits provided herein may be used to selectively cleave DNA encoding a gene of interest such as, for example, a toxin gene, a virulence factor gene, an antibiotic resistance gene, a remodeling gene or a modulatory gene (cf. WO2014124226).

Other sequences of interest, preferably programmable, can be added to the delivered nucleic acid sequence so as to be delivered to targeted bacteria. Preferably, the sequence of interest added to the delivered nucleic acid sequence leads to cell death of the targeted bacteria. For example, the nucleic acid sequence of interest added to the plasmid may encode holins or toxins.

Alternatively, the sequence of interest circuit added to the delivered nucleic acid sequence does not lead to bacteria death. For example, the sequence of interest may encode reporter genes leading to a luminescence or fluorescence signal. Alternatively, the sequence of interest may comprise proteins and enzymes achieving a useful function such as modifying the metabolism of the bacteria or the composition of its environment.

In a particular embodiment, the nucleic sequence of interest is selected in the group consisting of Cas9, a single guide RNA (sgRNA), a CRISPR locus, a gene expressing an enzyme such as a nuclease or a kinase, a TALEN, a ZFN, a meganuclease, a recombinase, a bacterial receptor, a membrane protein, a structural protein, a secreted protein, resistance to an antibiotic or to a drug in general, a gene expressing a toxic protein or a toxic factor and a gene expressing a virulence protein or a virulence factor.

In a particular embodiment, the delivered nucleic acid sequence according to the disclosure comprises a nucleic acid sequence of interest that encodes a bacteriocin, which can be a proteinaceous toxin produced by bacteria to kill or inhibit growth of other bacteria. Bacteriocins are categorized in several ways, including producing strain, common resistance mechanisms, and mechanism of killing. Such bacteriocin had been described from gram negative bacteria (e.g. microcins, colicin-like bacteriocins and tailocins) and from gram positive bacteria (e.g. Class I, Class II, Class III or Class IV bacteriocins).

In one embodiment, the delivered nucleic acid sequence according to the disclosure further comprises a sequence of interest encoding a toxin selected in the group consisting of microcins, colicin-like bacteriocins, tailocins, Class I, Class II, Class III and Class IV bacteriocins.

In a particular embodiment, the corresponding immunity polypeptide (i.e. anti-toxin) may be used to protect bacterial cells (Cotter et al., Nature Reviews Microbiology 11: 95, 2013, which is hereby incorporated by reference in its entirety) for delivered nucleic acid sequence production and encapsidation purpose but is absent in the pharmaceutical composition and in the targeted bacteria in which the delivered nucleic acid sequence of the disclosure is delivered.

In one aspect of the disclosure, the CRISPR system is included in the delivered nucleic acid sequence. The CRISPR system contains two distinct elements, i.e. i) an endonuclease, in this case the CRISPR associated nuclease (Cas or "CRISPR associated protein") and ii) a guide RNA. The guide RNA is in the form of a chimeric RNA which consists of the combination of a CRISPR (RNAcr) bacterial RNA and a RNAtracr (trans-activating RNA CRISPR) (Jinek et al., Science 2012). The guide RNA combines the targeting specificity of the RNAcr corresponding to the "spacing sequences" that serve as guides to the Cas proteins, and the conformational properties of the RNAtracr in a single transcript. When the guide RNA and the Cas protein are expressed simultaneously in the cell, the target genomic sequence can be permanently modified or interrupted. The modification is advantageously guided by a repair matrix. In general, the CRISPR system includes two main classes depending on the nuclease mechanism of action. Class 1 is made of multi-subunit effector complexes and includes type I, III and IV. Class 2 is made of single-unit effector modules, like Cas9 nuclease, and includes type II (II-A, II-B, II-C, II-C variant), V (V-A, V-B, V-C, V-D, V-E, V-U1, V-U2, V-U3, V-U4, V-U5) and VI (VI-A, VI-B1, VI-B2, VI-C, VI-D)

The sequence of interest according to the present disclosure comprises a nucleic acid sequence encoding Cas protein. A variety of CRISPR enzymes are available for use as a sequence of interest on the plasmid. In some embodiments, the CRISPR enzyme is a Type II CRISPR enzyme. In some embodiments, the CRISPR enzyme catalyzes DNA cleavage. In some other embodiments, the CRISPR enzyme catalyzes RNA cleavage. In one embodiment, the CRISPR enzymes may be coupled to a sgRNA. In certain embodiments, the sgRNA targets a gene selected in the group consisting of an antibiotic resistance gene, virulence protein or factor gene, toxin protein or factor gene, a bacterial receptor gene, a membrane protein gene, a structural protein gene, a secreted protein gene and a gene expressing resistance to a drug in general.

Non-limiting examples of Cas proteins as part of a multi-subunit effector or as a single-unit effector include Cas1, Cas1B, Cas2, Cas3, Cas4, Cas5, Cash, Cas7, Cas8, Cas9 (also known as Csn1 and Csx12), Cas10, Cas11 (SS), Cas12a (Cpf1), Cas12b (C2c1), Cas12c (C2c3), Cas12d (CasY), Cas12e (CasX), C2c4, C2c8, C2c5, C2c10, C2c9, Cas13a (C2c2), Cas13b (C2c6), Cas13c (C2c7), Cas13d, Csa5, Csc1, Csc2, Cse1, Cse2, Csy1, Csy2, Csy3, Csf1, Csf2, Csf3, Csf4, Csm2, Csm3, Csm4, Csm5, Csm6, Cmr1, Cmr3, Cmr4, Cmr5, Cmr6, Csn2, Csb1, Csb2, Csb3, Csx17, Csx14, Csx10, Csx16, CsaX, Csx13, Csx1, Csx15, SdCpf1, CmtCpf1, TsCpf1, CmaCpf1, PcCpf1, ErCpf1, FbCpf1, UbcCpf1, AsCpf1, LbCpf1, homologues thereof, orthologues thereof, variants thereof, or modified versions thereof. In some embodiments, the CRISPR enzyme cleaves both strands of the target nucleic acid at the Protospacer Adjacent Motif (PAM) site.

In a particular embodiment, the CRISPR enzyme is any Cas9 protein, for instance any naturally-occurring bacterial Cas9 as well as any variants, homologs or orthologs thereof.

By "Cas9" is meant a protein Cas9 (also called Csn1 or Csx12) or a functional protein, peptide or polypeptide fragment thereof, i.e. capable of interacting with the guide RNA(s) and of exerting the enzymatic activity (nuclease) which allows it to perform the double-strand cleavage of the DNA of the target genome. "Cas9" can thus denote a modified protein, for example truncated to remove domains of the protein that are not essential for the predefined functions of the protein, in particular the domains that are not necessary for interaction with the gRNA (s).

The sequence encoding Cas9 (the entire protein or a fragment thereof) as used in the context of the disclosure can be obtained from any known Cas9 protein (Fonfara et al., Nucleic Acids Res 42 (4), 2014; Koonin et al., Nat Rev Microbiol 15(3), 2017). Examples of Cas9 proteins useful in the present disclosure include, but are not limited to, Cas9 proteins of *Streptococcus pyogenes* (SpCas9), *Streptococcus thermophiles* (St1Cas9, St3Cas9), *Streptococcus mutans, Staphylococcus aureus* (SaCas9), *Campylobacter jejuni* (CjCas9), *Francisella novicida* (FnCas9) and *Neisseria meningitides* (NmCas9).

The sequence encoding Cpf1 (Cas12a) (the entire protein or a fragment thereof) as used in the context of the disclosure can be obtained from any known Cpf1 (Cas12a) protein (Koonin et al., 2017). Examples of Cpf1(Cas12a) proteins useful in the present disclosure include, but are not limited to, Cpf1(Cas12a) proteins of *Acidaminococcus* sp, *Lachnospiraceae bacteriu* and *Francisella novicida.*

The sequence encoding Cas13a (the entire protein or a fragment thereof) can be obtained from any known Cas13a (C2c2) protein (Abudayyeh et al., 2017). Examples of Cas13a (C2c2) proteins useful in the present disclosure include, but are not limited to, Cas13a (C2c2) proteins of *Leptotrichia wadei* (LwaCas13a).

The sequence encoding Cas13d (the entire protein or a fragment thereof) can be obtained from any known Cas13d protein (Yan et al., 2018). Examples of Cas13d proteins useful in the present disclosure include, but are not limited to, Cas13d proteins of *Eubacterium siraeum* and *Ruminococcus* sp.

In a particular embodiment, the nucleic sequence of interest is a CRISPR/Cas9 system for the reduction of gene expression or inactivation a gene selected in the group consisting of an antibiotic resistance gene, virulence factor or protein gene, toxin factor or protein gene, a gene expressing a bacterial receptor, a membrane protein, a structural protein, a secreted protein, and a gene expressing resistance to a drug in general.

In one embodiment, the CRISPR system is used to target and inactivate a virulence factor. A virulence factor can be any substance produced by a pathogen that alter host-pathogen interaction by increasing the degree of damage done to the host. Virulence factors are used by pathogens in many ways, including, for example, in cell adhesion or colonization of a niche in the host, to evade the host's immune response, to facilitate entry to and egress from host cells, to obtain nutrition from the host, or to inhibit other physiological processes in the host. Virulence factors can include enzymes, endotoxins, adhesion factors, motility factors, factors involved in complement evasion, and factors that promote biofilm formation. For example, such targeted virulence factor gene can be *E. coli* virulence factor gene such as, without limitation, EHEC-HlyA, Stx1 (VT1), Stx2 (VT2), Stx2a (VT2a), Stx2b (VT2b), Stx2c (VT2c), Stx2d (VT2d), Stx2e (VT2e) and Stx2f (VT2f), Stx2h (VT2h), fimA, fimF, fimH, neuC, kpsE, sfa, foc, iroN, aer, iha, papC, papGl, papGll, papGIII, hlyC, cnfl, hra, sat, ireA, usp ompT, ibeA, malX, fyuA, irp2, traT, afaD, ipaH, eltB, estA, bfpA, eaeA, espA, aaiC, aatA, TEM, CTX, SHV, csgA, csgB, csgC, csgD, csgE, csgF, csgG, csgH, T1SS, T2SS, T3SS, T4SS, T5SS, T6SS (secretion systems). For example, such targeted virulence factor gene can be *Shigella dysenteriae* virulence factor gene such as, without limitation, stx1 and stx2. For example, such targeted virulence factor gene can be *Yersinia pestis* virulence factor gene such as, without limitation, yscF (plasmid-borne (pCD1) T3SS external needle subunit). For example, such targeted virulence factor gene can be *Francisella tularensis* virulence factor gene such as, without limitation, fs1A. For example, such targeted virulence factor gene can be *Bacillus anthracis* virulence factor gene such as, without limitation, pag (Anthrax toxin, cell-binding protective antigen). For example, such targeted virulence factor gene can be *Vibrio cholera* virulence factor gene such as, without limitation, ctxA and ctxB (cholera toxin), tcpA (toxin co-regulated pilus), and toxT (master virulence regulator). For example, such targeted virulence factor gene can be *Pseudomonas aeruginosa* virulence factor genes such as, without limitation, pyoverdine (e.g., sigma factor pvdS, biosynthetic genes pvdL, pvdl, pvdJ, pvdH, pvdA, pvdF, pvdQ, pvdN, pvdM, pvdO, pvdP, transporter genes pvdE, pvdR, pvdT, opmQ), siderophore pyochelin (e.g., pchD, pchC, pchB, pchA, pchE, pchF and pchG, and toxins (e.g., exoU, exoS and exoT). For example, such targeted virulence factor gene can be *Klebsiella pneumoniae* virulence factor genes such as, without limitation, fimA (adherence, type I fimbriae major subunit), and cps (capsular polysaccharide). For example, such targeted virulence factor gene can be *Acinetobacter baumannii* virulence factor genes such as, without limitation, ptk (capsule polymerization) and epsA (assembly). For example, such targeted virulence factor gene can be *Salmonella enterica Typhi* virulence factor genes such as, without limitation, MIA (invasion, SPI-1 regulator), ssrB (SPI-2 regulator), and those associated with bile tolerance, including efflux pump genes acrA, acrB and tolC. For example, such targeted virulence factor gene can be *Fusobacterium nucleatum* virulence factor genes such as, without limitation, FadA and TIGIT. For example, such targeted virulence factor gene can be *Bacteroides fragilis* virulence factor genes such as, without limitation, bft.

In another embodiment, the CRISPR/Cas9 system is used to target and inactivate an antibiotic resistance gene such as, without limitation, GyrB, ParE, ParY, AAC(1), AAC(2'), AAC(3), AAC(6'), ANT(2"), ANT(3"), ANT(4'), ANT(6), ANT(9), APH(2"), APH(3"), APH(3'), APH(4), APH(6), APH(7"), APH(9), ArmA, RmtA, RmtB, RmtC, Sgm, AER, BLA1, CTX-M, KPC, SHV, TEM, BlaB, CcrA, IMP, NDM, VIM, ACT, AmpC, CMY, LAT, PDC, OXA β-lactamase, mecA, Omp36, OmpF, PIB, bla (blaI, blaR1) and mec (mecI, mecR1) operons, Chloramphenicol acetyltransferase (CAT), Chloramphenicol phosphotransferase, Ethambutol-resistant arabinosyltransferase (EmbB), MupA, MupB, Integral membrane protein MprF, Cfr 23S rRNA methyltransferase, Rifampin ADP-ribosyltransferase (Arr), Rifampin glycosyltransferase, Rifampin monooxygenase, Rifampin phosphotransferase, DnaA, RbpA, Rifampin-resistant beta-subunit of RNA polymerase (RpoB), Erm 23S rRNA methyltransferases, Lsa, MsrA, Vga, VgaB, Streptogramin Vgb lyase, Vat acetyltransferase, Fluoroquinolone acetyltransferase, Fluoroquinolone-resistant DNA topoisomerases, Fluoroquinolone-resistant GyrA, GyrB, ParC, Quinolone resistance protein (Qnr), FomA, FomB, FosC, FosA, FosB, FosX, VanA, VanB, VanD, VanR, VanS, Lincosamide nucleotidyltransferase (Lin), EreA, EreB, GimA, Mgt, Ole, Macrolide phosphotransferases (MPH), MefA, MefE, Mel, Streptothricin acetyltransferase (sat), Sul1, Sul2, Sul3, sulfonamide-resistant FolP, Tetracycline inactivation enzyme TetX, TetA, TetB, TetC, Tet30, Tet31, TetM, TetO, TetQ, Tet32, Tet36, MacAB-TolC, MsbA, MsrA, VgaB, EmrD, EmrAB-TolC, NorB, GepA, MepA, AdeABC, AcrD, MexAB-OprM, mtrCDE, EmrE, adeR, acrR, baeSR, mexR, phoPQ, mtrR, or any antibiotic resistance gene described in the Comprehensive Antibiotic Resistance Database (CARD https://card.mcmaster.cal).

In another embodiment, the CRISPR/Cas9 system is used to target and inactivate a bacterial toxin gene. Bacterial toxin can be classified as either exotoxins or endotoxins. Exotoxins are generated and actively secreted; endotoxins remain part of the bacteria. The response to a bacterial toxin can involve severe inflammation and can lead to sepsis. Such toxin can be for example Botulinum neurotoxin, Tetanus toxin, Staphylococcus toxins, Diphteria toxin, Anthrax toxin, Alpha toxin, Pertussis toxin, Shiga toxin, Heat-stable enterotoxin (*E. coli* ST), colibactin, BFT (*B. fragilis* toxin) or any toxin described in Henkel et al., (Toxins from Bacteria in EXS. 2010; 100: 1-29).

The bacteria targeted by bacterial delivery vehicles disclosed herein can be any bacteria present in a mammal organism. In a certain aspect, the bacteria are targeted through interaction of the chimeric RBPs expressed by the delivery vehicles with the bacterial cell. It can be any commensal, symbiotic or pathogenic bacteria of the microbiota or microbiome.

A microbiome may comprise of a variety of endogenous bacterial species, any of which may be targeted in accordance with the present disclosure. In some embodiments, the genus and/or species of targeted endogenous bacterial cells may depend on the type of bacteriophages being used for preparing the bacterial delivery vehicles. For example, some bacteriophages exhibit tropism for, or preferentially target, specific host species of bacteria. Other bacteriophages do not exhibit such tropism and may be used to target a number of different genus and/or species of endogenous bacterial cells.

Examples of bacterial cells include, without limitation, cells from bacteria of the genus *Yersinia* spp., *Escherichia* spp., *Klebsiella* spp., *Acinetobacter* spp., *Bordetella* spp., *Neisseria* spp., *Aeromonas* spp., *Franciesella* spp., *Corynebacterium* spp., *Citrobacter* spp., *Chlamydia* spp., Hemophilus spp., *Brucella* spp., *Mycobacterium* spp., *Legionella* spp., *Rhodococcus* spp., *Pseudomonas* spp., *Helicobacter* spp., *Vibrio* spp., *Bacillus* spp., Erysipelothrix spp., *Salmonella* spp., *Streptomyces* spp., *Streptococcus* spp., *Staphylococcus* spp., *Bacteroides* spp., *Prevotella* spp., *Clostridium* spp., *Bifidobacterium* spp., *Clostridium* spp., *Brevibacterium* spp., *Lactococcus* spp., *Leuconostoc* spp., *Actinobacillus* spp., *Selnomonas* spp., *Shigella* spp., *Zymonas* spp., *Mycoplasma* spp., *Treponema* spp., *Leuconostoc* spp., *Corynebacterium* spp., *Enterococcus* spp., *Enterobacter* spp., *Pyrococcus* spp., *Serratia* spp., *Morganella* spp., *Parvimonas* spp., *Fusobacterium* spp., *Actinomyces* spp., *Porphyromonas* spp., *Micrococcus* spp., *Bartonella* spp., *Borrelia* spp., *Brucelia* spp., *Campylobacter* spp., *Chlamydophilia* spp., *Cutibacterium* spp., *Propionibacterium* spp., *Gardnerella* spp., *Ehrlichia* spp., *Haemophilus* spp., *Leptospira* spp., *Listeria* spp., *Mycoplasma* spp.,

*Nocardia* spp., *Rickettsia* spp., *Ureaplasma* spp., and *Lactobacillus* spp, and a mixture thereof.

Thus, bacterial delivery vehicles may target (e.g., specifically target) a bacterial cell from any one or more of the foregoing genus of bacteria to specifically deliver the payload of interest according to the disclosure.

Preferably, the targeted bacteria can be selected from the group consisting of *Yersinia* spp., *Escherichia* spp., *Klebsiella* spp., *Acinetobacter* spp., *Pseudomonas* spp., *Helicobacter* spp., *Vibrio* spp, *Salmonella* spp., *Streptococcus* spp., *Staphylococcus* spp., *Bacteroides* spp., *Clostridium* spp., *Shigella* spp., *Enterococcus* spp., *Enterobacter* spp., *Listeria* spp., *Cutibacterium* spp., *Propionibacterium* spp., *Fusobacterium* spp., *Porphyromonas* spp. and *Gardnerella* spp.

In some embodiments, bacterial cells of the present disclosure are anaerobic bacterial cells (e.g., cells that do not require oxygen for growth). Anaerobic bacterial cells include facultative anaerobic cells such as but not limited to *Escherichia coli, Shewanella oneidensis, Gardnerella vaginalis* and *Listeria*. Anaerobic bacterial cells also include obligate anaerobic cells such as, for example, *Bacteroides, Clostridium, Cutibacterium, Propionibacterium, Fusobacterium* and *Porphyromona* species. In humans, anaerobic bacteria are most commonly found in the gastrointestinal tract. In some particular embodiment, the targeted bacteria are thus bacteria most commonly found in the gastrointestinal tract. Bacteriophages used for preparing the bacterial virus particles, and then the bacterial virus particles, may target (e.g., to specifically target) anaerobic bacterial cells according to their specific spectra known by the person skilled in the art to specifically deliver the plasmid.

In some embodiments, the targeted bacterial cells are, without limitation, *Bacteroides* thetaiotaomicron, *Bacteroides fragilis, Bacteroides distasonis, Bacteroides vulgatus, Clostridium leptum, Clostridium coccoides, Staphylococcus aureus, Bacillus subtilis, Clostridium butyricum, Brevibacterium lactofermentum, Streptococcus agalactiae, Lactococcus lactis, Leuconostoc lactis, Actinobacillus actinobycetemcomitans, cyanobacteria, Escherichia coli, Helicobacter pylori, Selnomonas ruminatium, Shigella sonnei, Zymomonas mobilis, Mycoplasma mycoides, Treponema denticola, Bacillus thuringiensis, Staphilococcus lugdunensis, Leuconostoc oenos, Corynebacterium xerosis, Lactobacillus plantarum, Lactobacillus rhamnosus, Lactobacillus casei, Lactobacillus acidophilus, Enterococcus faecalis, Bacillus coagulans, Bacillus cereus, Bacillus popillae, Synechocystis* strain PCC6803, *Bacillus liquefaciens, Pyrococcus abyssi, Selenomonas nominantium, Lactobacillus hilgardii, Streptococcus ferus, Lactobacillus pentosus, Bacteroides fragilis, Staphylococcus epidermidis, Streptomyces phaechromogenes, Streptomyces ghanaenis, Klebsiella pneumoniae, Enterobacter cloacae, Enterobacter aerogenes, Serratia marcescens, Morganella morganii, Citrobacter freundii, Propionibacterium freudenreichii, Pseudomonas aerigunosa, Parvimonas micra, Prevotella intermedia, Fusobacterium nucleatum, Prevotella nigrescens, Actinomyces israelii, Porphyromonas endodontalis, Porphyromonas gingivalis Micrococcus luteus, Bacillus megaterium, Aeromonas hydrophila, Aeromonas caviae, Bacillus anthracis, Bartonella henselae, Bartonella Quintana, Bordetella pertussis, Borrelia burgdorferi, Borrelia garinii, Borrelia afzelii, Borrelia recurrentis, Brucella abortus, Brucella canis, Brucella melitensis, Brucella suis, Campylobacter jejuni, Campylobacter coli, Campylobacter fetus, Chlamydia pneumoniae, Chlamydia trachomatis, Chlamydophila psittaci, Clostridium botulinum, Clostridium difficile, Clostridium perfringens, Clostridium tetani, Corynebacterium diphtheria, Cutibacterium acnes* (formerly *Propionibacterium acnes*), *Ehrlichia canis, Ehrlichia chaffeensis, Enterococcus faecium, Francisella tularensis, Haemophilus influenza, Legionella pneumophila, Leptospira interrogans, Leptospira santarosai, Leptospira weilii, Leptospira noguchii, Listeria monocytogenes, Mycobacterium leprae, Mycobacterium tuberculosis, Mycobacterium ulcerans, Mycoplasma pneumonia, Neisseria gonorrhoeae, Neisseria meningitides, Nocardia asteroids, Rickettsia rickettsia, Salmonella enteritidis, Salmonella typhi, Salmonella paratyphi, Salmonella typhimurium, Shigella flexnerii, Shigella dysenteriae, Staphylococcus saprophyticus, Streptococcus pneumoniae, Streptococcus pyogenes, Gardnerella vaginalis, Streptococcus viridans, Treponema pallidum, Ureaplasma urealyticum, Vibrio cholera, Vibrio parahaemolyticus, Yersinia pestis, Yersinia enterocolitica, Yersinia pseudotuberculosis, Actinobacter baumanii, Pseudomonas aerigunosa*, and a mixture thereof, preferably the bacteria of interest are selected from the group consisting of *Escherichia coli, Enterococcus faecium, Staphylococcus aureus, Klebsiella pneumoniae, Acinetobacter baumanii, Pseudomonas aeruginosa, Enterobacter cloacae*, and *Enterobacter aerogenes*, and a mixture thereof.

In one embodiment, the targeted bacteria are *Escherichia coli.*

Thus, bacteriophages used for preparing the bacterial delivery vehicles, and then the bacterial delivery vehicles, may target (e.g., specifically target) a bacterial cell from any one or more of the foregoing genus and/or species of bacteria to specifically deliver the plasmid.

In one embodiment, the targeted bacteria are pathogenic bacteria. The targeted bacteria can be virulent bacteria.

The targeted bacteria can be antibacterial resistance bacteria, preferably selected from the group consisting of extended-spectrum beta-lactamase-producing (ESBL) *Escherichia coli*, ESBL *Klebsiella pneumoniae*, vancomycin-resistant *Enterococcus* (VRE), methicillin-resistant *Staphylococcus aureus* (MRSA), multidrug-resistant (MDR) *Acinetobacter baumannii*, MDR *Enterobacter* spp., and a combination thereof. Preferably, the targeted bacteria can be selected from the group consisting of extended-spectrum beta-lactamase-producing (ESBL) *Escherichia coli* strains.

Alternatively, the targeted bacterium can be a bacterium of the microbiome of a given species, preferably a bacterium of the human microbiota.

The present disclosure is directed to bacterial delivery vehicle containing the payload as described herein. The bacterial delivery vehicles are prepared from bacterial virus. The bacterial delivery vehicles are chosen in order to be able to introduce the payload into the targeted bacteria.

Bacterial viruses, from which the bacterial delivery vehicles having chimeric receptor binding proteins may be derived, are preferably bacteriophages. Optionally, the bacteriophage is selected from the Order Caudovirales consisting of, based on the taxonomy of Krupovic et al, Arch Virol, 2015:

Bacteriophages may be selected from the family Myoviridae (such as, without limitation, genus Cp220virus, Cp8virus, Ea214virus, Felixo1virus, Mooglevirus, Suspvirus, Hp1virus, P2virus, Kayvirus, P100virus, Silviavirus, Spo1virus, Tsarbombavirus, Twortvirus, Cc31virus, Jd18virus, Js98virus, Kp15virus, Moonvirus, Rb49virus, Rb69virus, S16virus, Schizot4virus, Sp18virus, T4virus, Cr3virus, Se1virus, V5virus, Abouovirus, Agatevirus, Agrican357virus, Ap22virus, Arv1virus, B4virus, Bastillevirus, Bc431virus, Bcep78virus, Bcepmuvirus, Biquartavirus, Bxz1virus, Cd119virus, Cp51virus, Cvm10virus, Eah2virus, Elvirus, Hapunavirus, Jimmervirus, Kpp10virus, M12virus, Machinavirus, Marthavirus, Msw3virus, Muvirus, Myohalovirus, Nit1virus, P1virus, Pakpunavirus, Pbunavirus, Phikzvirus, Rheph4virus, Rsl2virus, Rslunavirus, Secunda5virus, Sep1virus, Spn3virus, Svunavirus, Tg1virus, Vhmlvirus and Wphvirus)

Bacteriophages may be selected from the family Podoviridae (such as, without limitation, genus Fri1virus, Kp32virus, Kp34virus, Phikmvvirus, Pradovirus, Sp6virus, T7virus, Cp8virus, P68virus, Phi29virus, Nona33virus, Pocjvirus, T12011virus, Bcep22virus, Bpp1virus, Cba41virus, Dfl12virus, Ea92virus, Epsilon15virus, F116virus, G7cvirus, Jwalphavirus, Kf1virus, Kpp25virus, Lit1virus, Luz24virus, Luz7virus, N4virus, Nonanavirus, P22virus, Pagevirus, Phieco32virus, Prtbvirus, Sp58virus, Una961virus and Vp5virus)

Bacteriophages may be selected from the family Siphoviridae (such as, without limitation, genus Camvirus, Likavirus, R4virus, Acadianvirus, Coopervirus, Pg1virus, Pipefishvirus, Rosebushvirus, Brujitavirus, Che9cvirus, Hawkeyevirus, Plotvirus, Jerseyvirus, K1gvirus, Sp31virus, Lmd1virus, Una4virus, Bongovirus, Reyvirus, Buttersvirus, Charlievirus, Redivirus, Baxtervirus, Nymphadoravirus, Bignuzvirus, Fishburnevirus, Phayoncevirus, Kp36virus, Rogue1virus, Rtpvirus, T1virus, T1svirus, Ab18virus, Amigovirus, Anatolevirus, Andromedavirus, Attisvirus, Barnyardvirus, Bernal13virus, Biseptimavirus, Bronvirus, C2virus, C5virus, Cba181virus, Cbastvirus, Cecivirus, Che8virus, Chivirus, Cjwlvirus, Corndogvirus, Cronusvirus, D3112virus, D3virus, Decurrovirus, Demosthenesvirus, Doucettevirus, E125virus, Eiauvirus, Ff47virus, Gaiavirus, Gilesvirus, Gordonvirus, Gordtnkvirus, Harrisonvirus, Hk578virus, Hk97virus, Jenstvirus, Jwxvirus, Kelleziovirus, Korravirus, L5virus, lambdavirus, Laroyevirus, Liefievirus, Marvinvirus, Mudcatvirus, N15virus, Nonagvirus, Np1virus, Omegavirus, P12002virus, P12024virus, P23virus, P70virus, Pa6virus, Pamx74virus, Patiencevirus, Pbi1virus, Pepy6virus, Pfr1virus, Phic31virus, Phicbkvirus, Phietavirus, Phifelvirus, Phijl1virus, Pis4avirus, Psavirus, Psimunavirus, Rdjlvirus, Rer2virus, Sap6virus, Send513virus, Septima3virus, Seuratvirus, Sextaecvirus, Sfi11virus, Sfi21dtivirus, Sitaravirus, Sk1virus, Slashvirus, Smoothievirus, Soupsvirus, Spbetavirus, Ssp2virus, T5virus, Tankvirus, Tin2virus, Titanvirus, Tm4virus, Tp21virus, Tp84virus, Triavirus, Trigintaduovirus, Vegasvirus, Vendettavirus, Wbetavirus, Wildcatvirus, Wizardvirus, Woesvirus, Xp10virus, Ydn12virus and Yuavirus)

Bacteriophages may be selected from the family Ackermannviridae (such as, without limitation, genus Ag3virus, Limestonevirus, Cba120virus and Vi1virus)

Optionally, the bacteriophage is not part of the order Caudovirales but from families with unassigned order such as, without limitation, family Tectiviridae (such as genus Alphatectivirus, Betatectivirus), family Corticoviridae (such as genus Corticovirus), family Inoviridae (such as genus Fibrovirus, Habenivirus, Inovirus, Lineavirus, Plectrovirus, Saetivirus, Vespertiliovirus), family Cystoviridae (such as genus Cystovirus), family Leviviridae (such as genus Allolevivirus, Levivirus), family Microviridae (such as genus Alpha3microvirus, G4microvirus, Phix174microvirus, Bdellomicrovirus, Chlamydiamicrovirus, Spiromicrovirus) and family Plasmaviridae (such as genus Plasmavirus).

Optionally, the bacteriophage is targeting Archea not part of the Order Caudovirales but from families with Unassigned order such as, without limitation, Ampullaviridae, FuselloViridae, Globuloviridae, Guttaviridae, Lipothrixviridae, Pleolipoviridae, Rudiviridae, Salterprovirus and Bicaudaviridae.

A non-exhaustive listing of bacterial genera and their known host-specific bacteria viruses is presented in the following paragraphs. The chimeric RBPs and the bacterial delivery vehicles disclosed herein may be engineered, as non-limiting examples, from the following phages. Synonyms and spelling variants are indicated in parentheses. Homonyms are repeated as often as they occur (e.g., D, D, d). Unnamed phages are indicated by “NN” beside their genus and their numbers are given in parentheses.

Bacteria of the genus *Actinomyces* can be infected by the following phages: Av-I, Av-2, Av-3, BF307, CT1, CT2, CT3, CT4, CT6, CT7, CT8 and 1281.

Bacteria of the genus *Aeromonas* can be infected by the following phages: AA-I, Aeh2, N, PMl, TP446, 3, 4, 11, 13, 29, 31, 32, 37, 43, 43-10T, 51, 54, 55R.1, 56, 56RR2, 57, 58, 59.1, 60, 63, Aehl, F, PM2, 1, 25, 31, 40RR2.8t, (syn=44R), (syn=44RR2.8t), 65, PM3, PM4, PM5 and PM6.

Bacteria of the genus *Bacillus* can be infected by the following phages: A, aizl, Al-K-I, B, BCJA1, BC1, BC2, BLL1, BL1, BP142, BSL1, BSL2, BS1, BS3, BS8, BS15, BS18, BS22, BS26, BS28, BS31, BS104, BS105, BS106, BTB, B1715V1, C, CK-I, Coll, Corl, CP-53, CS-I, CSi, D, D, D, D5, entl, FPB, FP9, FSi, FS2, FS3, FS5, FS8, FS9, G, GH8, GT8, GV-I, GV-2, GT-4, g3, g12, g13, g14, g16, g17, g21, g23, g24, g29, H2, kenl, KK-88, Kuml, Kyul, J7W-1, LP52, (syn=LP-52), L7, Mexl, MJ-I, mor2, MP-7, MP1O, MP12, MP14, MP15, Neol, No2, N5, N6P, PBCl, PBLA, PBPl, P2, S-a, SF2, SF6, Shal, Sill, SP02, (syn=ΦSPP1), SPβ, STI, STi, SU-Il, t, TbI, Tb2, Tb5, TbIO, Tb26, Tb51, Tb53, Tb55, Tb77, Tb97, Tb99, Tb560, Tb595, Td8, Td6, Td15, TgI, Tg4, Tg6, Tg7, Tg9, TgIO, TgI1, Tg13, Tg15, Tg21, Tin1, Tin7, Ting, Tin13, Tm3, Toc1, Tog1, tol1, TP-I, TP-10vir, TP-15c, TP-16c, TP-17c, TP-19, TP35, TP51, TP-84, Tt4, Tt6, type A, type B, type C, type D, type E, Tφ3, VA-9, W, wx23, wx26, Yun1, α, γ, pl 1, φmed-2, φT, φμ-4, φ3T, φ75, φ1O5, (syn=φ1O5), IA, IB, 1-97A, 1-97B, 2, 2, 3, 3, 3, 5, 12, 14, 20, 30, 35, 36, 37, 38, 41C, 51, 63, 64, 138D, I, II, IV, NN-*Bacillus* (13), ale1, AR1, AR2, AR3, AR7, AR9, Bace-11, (syn=11), Bastille, BL1, BL2, BL3, BL4, BL5, BL6, BL8, BL9, BP124, BS28, BS80, Ch, CP-51, CP-54, D-5, darl, denl, DP-7, entl, FoSi, FoS2, FS4, FS6, FS7, G, gall, gamma, GE1, GF-2, GSi, GT-I, GT-2, GT-3, GT-4, GT-5, GT-6, GT-7, GV-6, g15, 19, 110, ISi, K, MP9, MP13, MP21, MP23, MP24, MP28, MP29, MP30, MP32, MP34, MP36, MP37, MP39, MP40, MP41, MP43, MP44, MP45, MP47, MP50, NLP-I, No. 1, N17, N19, PBS1, PK1, PMB1, PMB12, PMJ1, S, SPOl, SP3, SP5, SP6, SP7, SP8, SP9, SPlO, SP-15, SP50, (syn=SP-50), SP82, SST, subl, SW, Tg8, Tg12, Tg13, Tg14, thul, thuΛ, thuS, Tin4, Tin23, TP-13, TP33, TP50, TSP-I, type V, type VI, V, Vx, β22, φe, φNR2, φ25, φ63, 1, 1, 2, 2C, 3NT, 4, 5, 6, 7, 8, 9, 10, 12, 12, 17, 18, 19, 21, 138, III, 4 (*B. megateriwn*), 4 (*B. sphaericus*), AR13, BPP-IO, BS32, BS107, B1, B2, GA-I, GP-IO, GV-3, GV-5, g8, MP20, MP27, MP49, Nf, PP5, PP6, SFS, Tg18, TP-I, Versailles, φ15, φ29, 1-97, 837/IV, mï-*Bacillus* (1), BatlO, BSLlO, BSLI1, BS6, BSI1, BS16, BS23, BSlOl, BS102, g18, morl, PBL1, SN45, thu2, thu3, TmI, Tm2, TP-20, TP21, TP52, type F, type G, type IV, HN-BacMus (3), BLE, (syn=θc), BS2, BS4, BS5, BS7, B10, B12, BS20, BS21, F, MJ-4, PBA12, AP50, AP50-04, AP50-11, AP50-23, AP50-26, AP50-27 and Bam35. The following

*Bacillus*-specific phages are defective: DLP10716, DLP-11946, DPB5, DPB12, DPB21, DPB22, DPB23, GA-2, M, No. IM, PBLB, PBSH, PBSV, PBSW, PBSX, PBSY, PBSZ, phi, SPa, type 1 and μ.

Bacteria of the genus *Bacteroides* can be infected by the following phages: ad I2, Baf-44, Baf-48B, Baf-64, Bf-I, Bf-52, B40-8, Fl, β1, φA1, BrOl, φBrO2, 11, 67.1, 67.3, 68.1, mt-*Bacteroides* (3), Bf42, Bf71, HN-Bdellovibrio (1) and BF-41.

Bacteria of the genus *Bordetella* can be infected by the following phages: 134 and NN-*Bordetella* (3).

Bacteria of the genus *Borrellia* can be infected by the following phages: NN-*Borrelia* (1) and NN-*Borrelia* (2).

Bacteria of the genus *Brucella* can be infected by the following phages: A422, Bk, (syn=Berkeley), BM29, FOi, (syn=FOl), (syn=FQl), D, FP2, (syn=FP2), (syn=FD2), Fz, (syn=Fz75/13), (syn=Firenze 75/13), (syn=Fi), Fi, (syn=Fl), Fim, (syn=FIm), (syn=Fim), FiU, (syn=FlU), (syn=FiU), F2, (syn=F2), F3, (syn=F3), F4, (syn=F4), F5, (syn=F5), F6, F7, (syn=F7), F25, (syn=F25), (syn=£25), F25U, (syn=F25u), (syn=F25U), (syn=F25V), F44, (syn-F44), F45, (syn=F45), F48, (syn=F48), I, Im, M, MC/75, M51, (syn=M85), P, (syn=D), S708, R, Tb, (syn=TB), (syn=Tbilisi), W, (syn=Wb), (syn=Weybridge), X, 3, 6, 7, 10/1, (syn=10), (syn=F8), (syn=F8), 12m, 24/11, (syn=24), (syn=F9), (syn=F9), 45/111, (syn=45), 75, 84, 212/XV, (syn=212), (syn=Fi0), (syn=F10), 371/XXIX, (syn=371), (syn=Fn), (syn=Fll) and 513.

Bacteria of the genus *Burkholderia* can be infected by the following phages: CP75, NN-*Burkholderia* (1) and 42.

Bacteria of the genus *Campylobacter* can be infected by the following phages: C type, NTCC12669, NTCC12670, NTCC12671, NTCC12672, NTCC12673, NTCC12674, NTCC12675, NTCC12676, NTCC12677, NTCC12678, NTCC12679, NTCC12680, NTCC12681, NTCC12682, NTCC12683, NTCC12684, 32f, 111c, 191, NN-*Campylobacter* (2), Vfi-6, (syn=V19), VfV-3, V2, V3, V8, V16, (syn=Vfi-1), V19, V20(V45), V45, (syn=V-45) and NN-*Campylobacter* (1).

Bacteria of the genus *Chlamydia* can be infected by the following phage: Chp1.

Bacteria of the genus *Clostridium* can be infected by the following phages: CAK1, CA5, Ca7, CEβ, (syn=1C), CEγ, Cldl, c-n71, c-203 Tox-, DEP, (syn=ID), (syn=lDt0X+), HM3, KM1, KT, Ms, NA1, (syn=Naltox+), PA135Oe, Pfő, PL73, PL78, PL81, P1, P50, P5771, P19402, 1Ct0X+, 2Ct0X\2D3 (syn=2Dt0X+), 3C, (syn=3Ctox+), 4C, (syn=4Ct0X+), 56, III-1, NN-*Clostridium* (61), NB1t0X+, α1, CA1, HMT, HM2, PF15 P-23, P-46, Q-05, Q-oe, Q-16, Q-21, Q-26, Q-40, Q-46, S111, SA02, WA01, WA03, Wm, W523, 80, C, CA2, CA3, CPT1, CPT4, cl, c4, c5, HM7, H11/A1, H18/Ax, FWS23, Hi58ZA1, K2ZA1, K21ZS23, ML, NA2t0X; Pf2, Pf3, Pf4, S9ZS3, S41ZA1, S44ZS23, α2, 41, 112ZS23, 214/S23, 233/Ai, 234/S23, 235/S23, II-1, II-2, II-3, NN-*Clostridium* (12), CA1, Fl, K, S2, 1, 5 and NN-*Clostridium* (8).

Bacteria of the genus *Corynebacterium* can be infected by the following phages: CGK1 (defective), A, A2, A3, A101, A128, A133, A137, A139, A155, A182, B, BF, B17, B18, B51, B271, B275, B276, B277, B279, B282, C, capi, CC1, CG1, CG2, CG33, CL31, Cog, (syn=CG5), D, E, F, H, H-I, hqi, hq2, 11ZH33, Ii/31, J, K, K, (syn=Ktox"), L, L, (syn=Ltox+), M, MC-I, MC-2, MC-3, MC-4, MLMa, N, O, ovi, ov2, ov3, P, P, R, RP6, RS29, S, T, U, UB1, ub2, UH1, UH3, uh3, uh5, uh6, β, (syn=βtox+), βhv64, βvir, γ, (syn=γtoχ−), γ19, 6, (syn=δ'ox+), p, (syn=ptoχ−), Φ9, φ984, ω, IA, 1/1180, 2, 2/1180, 5/1180, 5ad/9717, 7/4465, 8/4465, 8ad/10269, 10/9253, 13Z9253, 15/3148, 21/9253, 28, 29, 55, 2747, 2893, 4498 and 5848.

Bacteria of the genus *Enterococcus* are infected by the following phage: DF78, F1, F2, 1, 2, 4, 14, 41, 867, Dl, SB24, 2BV, 182, 225, C2, C2F, E3, E62, DS96, H24, M35, P3, P9, SBlOl, S2, 2BII, 5, 182a, 705, 873, 881, 940, 1051, 1057, 21096C, NN-*Enterococcus* (1), PE1, F1, F3, F4, VD13, 1, 200, 235 and 341.

Bacteria of the genus Erysipelothrix can be infected by the following phage: NN-Eiysipelothrix (1).

Bacteria of the genus *Escherichia* can be infected by the following phages: BW73, B278, D6, D108, E, El, E24, E41, FI-2, FI-4, FI-5, HI8A, Ffl8B, i, MINI, Mu, (syn=mu), (syn=MuI), (syn=Mu-I), (syn=MU-I), (syn=MuI), (syn=μ), 025, PhI-5, Pk, PSP3, P1, P1D, P2, P4 (defective), Sl, Wφ, φK13, φR73 (defective), φ1, φ2 , φ7 , φ92, ψ (defective), 7 A, 8φ, 9φ, 15 (defective), 18, 28-1, 186, 299, HH-*Escherichia* (2), AB48, CM, C4, C16, DD-VI, (syn=Dd-Vi), (syn=DDVI), (syn=DDVi), E4, E7, E28, FI1, FI3, H, H1, H3, H8, K3, M, N, ND-2, ND-3, ND4, ND-5, ND6, ND-7, Ox-I (syn=OXl), (syn=HF), Ox-2 (syn=0x2), (syn=0X2), Ox-3, Ox-4, Ox-5, (syn=0X5), Ox-6, (syn=66F), (syn=φ66t), (syn=φ66t−)5 0111, PhI-I, RB42, RB43, RB49, RB69, S, SaI-I, Sal-2, Sal-3, Sal-4, Sal-5, Sal-6, TC23, TC45, TuII*-6, (syn=TuII*), TuIP-24, TuII*46, TuIP-60, T2, (syn=ganuTia), (syn=γ), (syn=PC), (syn=P.C.), (syn=T-2), (syn=T2), (syn=P4), T4, (syn=T-4), (syn=T4), T6, T35, αl, 1, IA, 3, (syn=Ac3), 3A, 3T+, (syn=3), (syn=M1), 5φ, (syn=φ5), 9266Q, CFO103, HK620, J, K, KlF, m59, no. A, no. E, no. 3, no. 9, N4, sd, (syn=Sd), (syn=SD), (syn=Sa)3 (syn=sd), (syn=SD), (syn=CD), T3, (syn=T-3), (syn=T3), T7, (syn=T-7), (syn=T7), WPK, W31, ΔH, φC3888, φK3, φK7, φK12, φV-1, Φ04-CF, Φ05, Φ06 , Φ07 , φ1 , φ1.2, φ20 , φ95, φ263, φlO92, (syn=φW), Ω8, 1, 3, 7, 8, 26, 27, 28-2, 29, 30, 31, 32, 38, 39, 42, 933W, NN-*Escherichia* (1), Esc-7-11, AC30, CVX-5, Cl, DDUP, EC1, EC2, E21, E29, F1, F26S, F27S, Hi, HK022, HK97, (syn=ΦHK97), HK139, HK253, HK256, K7, ND-I, no. D, PA-2, q, S2, T1, (syn=α), (syn=P28), (syn=T-I), (syn=Tx), T3C, T5, (syn=T-5), (syn=T5), UC-I, w, β4, γ2, λ (syn=lambda), (syn=Φλ), ΦD326, φγ, Φ06, 17, Φ10 , φ80, χ, (syn=χi), (syn=φχ), (syn=φχi), 2, 4, 4A, 6, 8A, 102, 150, 168, 174, 3000, AC6, AC7, AC28, AC43, AC50, AC57, AC81, AC95, HK243, KlO, ZG/3A, 5, 5A, 21EL, H19-J and 933H.

Bacteria of the genus *Fusobacterium* are infected by the following phage: NN-*Fusobacterium* (2), fv83-554/3, fv88-531/2, 227, fv2377, fv2527 and fv8501.

Bacteria of the genus *Haemophilus* are infected by the following phage: HP1, S2 and N3.

Bacteria of the genus *Helicobacter* are infected by the following phage: HP1 and ^^-*Helicobacter* (1).

Bacteria of the genus *Klebsiella* are infected by the following phage: AIO-2, KI4B, K16B, K19, (syn=K19), K114, K115, K121, K128, K129, KI32, K133, K135, K1106B, K1171B, K1181B, K1832B, AIO-I, AO-I, AO-2, AO-3, FC3-10, K, K11, (syn=KII), K12, (syn=K12), K13, (syn=K13), (syn=K1 70/11), K14, (syn=K14), K15, (syn=K15), K16, (syn=K16), K17, (syn=K17), K18, (syn=K18), K119, (syn=K19), K127, (syn=K127), K131, (syn=K131), K135, K1171B, II, VI, IX, CI-I, K14B, K18, K111, K112, K113, K116, K117, K118, K120, K122, K123, K124, K126, K130, K134, K1106B, KIi65B, K1328B, KLXI, K328, P5046, 11, 380, III, IV, VII, VIII, FC3-11, K12B, (syn=K12B), K125, (syn=K125), K142B, (syn=K142), (syn=K142B), K1181B, (syn=KII 81), (syn=K1181B), K1765/!, (syn=K1765/1), K1842B, (syn=K1832B), K1937B, (syn=K1937B), L1, φ28, 7, 231, 483, 490, 632 and 864/100.

Bacteria of the genus Lepitospira are infected by the following phage: LE1, LE3, LE4 and ~NN-*Leptospira* (1).

Bacteria of the genus *Listeria* are infected by the following phage: A511, 01761, 4211, 4286, (syn=BO54), A005, A006, A020, A500, A502, A511, A118, A620, A640, B012, B021, B024, B025, B035, B051, B053, B054, B055, B056, B101, BlOl, B545, B604, B653, C707, D441, HSO47, HlOG, H8/73, H19, H21, H43, H46, H107, H108, HI lO, H163/84, H312, H340, H387, H391/73, H684/74, H924A, PSA, U153, φMLUP5, (syn=P35), 00241, 00611, 02971A, 02971C, 5/476, 5/911, 5/939, 5/11302, 5/11605, 5/11704, 184, 575, 633, 699/694, 744, 900, 1090, 1317, 1444, 1652, 1806, 1807, 1921/959, 1921/11367, 1921/11500, 1921/11566, 1921/12460, 1921/12582, 1967, 2389, 2425, 2671, 2685, 3274, 3550, 3551, 3552, 4276, 4277, 4292, 4477, 5337, 5348/11363, 5348/11646, 5348/12430, 5348/12434, 10072, 11355C, 11711A, 12029, 12981, 13441, 90666, 90816, 93253, 907515, 910716 and NN-Lisferia (15).

Bacteria of the genus *Morganella* are infected by the following phage: 47.

Bacteria of the genus *Mycobacterium* are infected by the following phage: 13, AGl, ALi, ATCC 11759, A2, B.C3, BG2, BK1, BK5, *butyricum*, B-I, B5, B7, B30, B35, Clark, C1, C2, DNAIII, DSP1, D4, D29, GS4E, (syn=GS4E), GS7, (syn=GS-7), (syn=GS7), IPa, lacticola, Legendre, Leo, L5, (syn=ΦL-5), MC-I, MC-3, MC-4, minetti, MTPHI 1, Mx4, MyF3P/59a, phlei, (syn=phlei 1), phlei 4, Polonus II, rabinovitschi, smegmatis, TM4, TM9, TMlO, TM20, Y7, YlO, φ630, IB, IF, IH, 1/1, 67, 106, 1430, Bl, (syn=Bol), B24, D, D29, F-K, F-S, HP, Polonus I, Roy, Rl, (syn=Rl-Myb), (syn=Ri), 11, 31, 40, 50, 103a, 103b, 128, 3111-D, 3215-D and NN-*Mycobacterium* (1).

Bacteria of the genus *Neisseria* are infected by the following phage: Group I, group II and NPl.

Bacteria of the genus *Nocardia* are infected by the following phage: MNP8, NJ-L, NS-8, N5 and TtiN-*Nocardia*.

Bacteria of the genus *Proteus* are infected by the following phage: Pm5, 13vir, 2/44, 4/545, 6/1004, 13/807, 20/826, 57, 67b, 78, 107/69, 121, 9/0, 22/608, 30/680, PmI, Pm3, Pm4, Pm6, Pm7, Pm9, PmIO, PmI 1, Pv2, πl, φm, 7/549, 9B/2, 10A/31, 12/55, 14, 15, 16/789, 17/971, 19A/653, 23/532, 25/909, 26/219, 27/953, 32A/909, 33/971, 34/13, 65, 5006M, 7480b, VI, 13/3a, Clichy 12, π2600, φχ7, 1/1004, 5/742, 9, 12, 14, 22, 24/860, 2600/D52, Pm8 and 24/2514.

Bacteria of the genus *Providencia* are infected by the following phage: PL25, PL26, PL37, 9211/9295, 9213/921 Ib, 9248, 7/R49, 7476/322, 7478/325, 7479, 7480, 9000/9402 and 9213/921 Ia.

Bacteria of the genus *Pseudomonas* are infected by the following phage: PfI, (syn=Pf-I), Pf2, Pf3, PP7, PRR1, 7s, im-*Pseudomonas* (1), AI-I, AI-2, B 17, B89, CB3, Col 2, Col 11, Col 18, Col 21, C154, C163, C167, C2121, E79, F8, ga, gb, H22, K1, M4, N2, Nu, PB-I, (syn=PBl), pfl6, PMN17, PP1, PP8, Psal, PsP1, PsP2, PsP3, PsP4, PsP5, PS3, PS17, PTB80, PX4, PX7, PYO1, PYO2, PYO5, PYO6, PYO9, PYO1O, PYO13, PYO14, PYO16, PYO18, PYO19, PYO20, PYO29, PYO32, PYO33, PYO35, PYO36, PYO37, PYO38, PYO39, PYO41, PYO42, PYO45, PYO47, PYO48, PYO64, PYO69, PYO103, PlK, SLPl, SL2, S2, UNL-I, wy, Yai, Ya4, Yan, φBE, φCTX, φC17, φKZ, (syn=ΦKZ), φ-LT, Φmu78, φNZ, φPLS-1, φST-1, φW-14, φ-2, 1/72, 2/79, 3, 3/DO, 4/237, 5/406, 6C, 6/6660, 7, 7v, 7/184, 8/280, 9/95, 10/502, 11/DE, 12/100, 12S, 16, 21, 24, 25F, 27, 31, 44, 68, 71, 95, 109, 188, 337, 352, 1214, HN-*Pseudomonas* (23), A856, B26, CI-I, CI-2, C5, D, gh-1, Fl 16, HF, H90, K5, K6, K1 04, K109, K166, K267, N4, N5, O6N-25P, PE69, Pf, PPN25, PPN35, PPN89, PPN91, PP2, PP3, PP4, PP6, PP7, PP8, PP56, PP87, PP1 14, PP206, PP207, PP306, PP651, Psp231a, Pssy401, Pssy9220, psi, PTB2, PTB20, PTB42, PX1, PX3, PX1O, PX12, PX14, PYO70, PYO71, R, SH6, SH133, tf, Ya5, Ya7, φBS, ΦKf77, φ-MC, ΦmnF82, φPLS27, φPLS743, φS-1, 1, 2, 2, 3, 4, 5, 6, 7, 7, 8, 9, 10, 11, 12, 12B, 13, 14, 15, 14, 15, 16, 17, 18, 19, 20, 20, 21, 21, 22, 23, 23, 24, 25, 31, 53, 73, 119x, 145, 147, 170, 267, 284, 308, 525, NN-*Pseudomonas* (5), af, A7, B3, B33, B39, BI-I, C22, D3, D37, D40, D62, D3112, F7, F1O, g, gd, ge, gξ Hw12, Jb 19, KF1, L°, OXN-32P, O6N-52P, PCH-I, PC13-1, PC35-1, PH2, PH51, PH93, PH132, PMW, PM13, PM57, PM61, PM62, PM63, PM69, PM105, PM1 13, PM681, PM682, PO4, PP1, PP4, PP5, PP64, PP65, PP66, PP71, PP86, PP88, PP92, PP401, PP711, PP891, Pssy41, Pssy42, Pssy403, Pssy404, Pssy420, Pssy923, PS4, PS-IO, Pz, SD1, SL1, SL3, SL5, SM, φC5, φC11, φC11-1, φC13, φC15, φMO, φO4, φ11, φ240, 2, 2F, 5, 7m, 11, 13, 13/441, 14, 20, 24, 40, 45, 49, 61, 73, 148, 160, 198, 218, 222, 236, 242, 246, 249, 258, 269, 295, 297, 309, 318, 342, 350, 351, 357-1, 400-1, HN-*Pseudomonas* (6), G1O1, M6, M6a, L1, PB2, Pssy15, Pssy4210, Pssy4220, PYO12, PYO34, PYO49, PYO50, PYO51, PYO52, PYO53, PYO57, PYO59, PYO200, PX2, PX5, SL4, p03, p06 and 1214.

Bacteria of the genus *Rickettsia* are infected by the following phage: NN-*Rickettsia*.

Bacteria of the genus *Salmonella* are infected by the following phage: b, Beccles, C T, d, Dundee, f, FeIs 2, GI, GUI, GVI, GVIII, k, K, i, j, L, 01, (syn=0-1), (syn=O1), (syn=O-I), (syn=7), 02, 03, P3, P9a, PlO, Sab3, Sab5, SanlS, Sanl7, SI, Taunton, ViI, (syn=ViI), 9, imSalmonella (1), N-I, N-5, N-IO, N-17, N-22, 11, 12, 16-19, 20.2, 36, 449C/C178, 966A/C259, a, B.A.O.R., e, G4, GUI, L, LP7, M, MG40, N-18, PSA68, P4, P9c, P22, (syn=P22), (syn=PLT22), (syn=PLT22), P22al, P22-4, P22-7, P22-11, SNT-I, SNT-2, SP6, Villi, ViIV, ViV, ViVI, ViVII, Worksop, Sj5, ε34, 1,37, 1(40), (syn=φ1[40]), 1, 422, 2, 2.5, 3b, 4, 5, 6, 14(18), 8, 14(6, 7), 10, 27, 28B, 30, 31, 32, 33, 34, 36, 37, 39, 1412, SNT-3, 7-11, 40.3, c, C236, C557, C625, C966N, g, GV, G5, Gl 73, h, IRA, Jersey, MB78, P22-1, P22-3, P22-12, Sabl, Sab2, Sab2, Sab4, Sanl, San2, San3, San4, San6, San7, Sang, San9, San13, San14, San16, San18, San19, San20, San21, San22, San23, San24, San25, San26, SasL1, SasL2, SasL3, SasL4, SasL5, SlBL, SII, ViIl, φl, 1, 2, 3a, 3al, 1010, Ym-*Salmonella* (1), N-4, SasL6 and 27.

Bacteria of the genus *Serratia* are infected by the following phage: A2P, PS20, SMB3, SMP, SMP5, SM2, V40, V56, ic, ΦCP-3, ΦCP-6, 3M, 10/la, 20A, 34CC, 34H, 38T, 345G, 345P, 501B, SMB2, SMP2, BC, BT, CW2, CW3, CW4, CW5, Lt232, L2232, L34, L.228, SLP, SMPA, V.43, σ, φCWl, ΦCP6-1, ΦCP6-2, ΦCP6-5, 3T, 5, 8, 9F, 10/1, 2OE, 32/6, 34B, 34CT, 34P, 37, 41, 56, 56D, 56P, 6OP, 61/6, 74/6, 76/4, 101/8900, 226, 227, 228, 229F, 286, 289, 290F, 512, 764a, 2847/10, 2847/1Oa, L.359 and SMBl.

Bacteria of the genus *Shigella* are infected by the following phage: Fsa, (syn=a), FSD2d, (syn=D2d), (syn=W2d), FSD2E, (syn=W2e), fv, F6, f7.8, H-Sh, PES, P90, SfII, Sh, SHm, SHrv, (syn=HIV), SHvi, (syn=HVI), SHVvm, (syn=HVIII), SKγ66, (syn=gamma 66), (syn=yββ), (syn=γ66b), SKm, (syn=SIIIb)5 (syn=UI), SKw, (syn=Siva), (syn=IV), SIC™, (syn=SIVA.), (syn=IVA), SKvi, (syn=KVI), (syn=Svi), (syn=VI), SKvm, (syn=Svm), (syn=VIII), SKVTIIA, (syn=SvmA), (syn=VIIIA), STvi, STK, STx1, STxn, S66, W2, (syn=D2c), (syn=D20), φl, φIVb 3-SO-R, 8368-SO-R, F7, (syn=FS7), (syn=K29), FlO, (syn=FSlO), (syn=K31), I1, (syn=alfa), (syn=FSa), (syn=Kl 8), (syn=α), I2, (syn=a), (syn=K19), SG33, (syn=G35), (syn=SO-35/G), SG35, (syn=SO-55/G), SG3201, (syn=SO-3201/G), SHn, (syn=HII), SHv, (syn=SHV), SHx, SHX, SKn, (syn=K2), (syn=KII), (syn=Sn), (syn=SsII), (syn=II), SKrv, (syn=Sm), (syn=SsIV), (syn=IV), SK1Va, (syn=Swab), (syn=SsIVa), (syn=IVa), SKV, (syn=K4), (syn=KV), (syn=SV), (syn=SsV), (syn=V), SKx, (syn=K9), (syn=KX), (syn=SX), (syn=SsX), (syn=X), STV, (syn=T35), (syn=35-50-R), STvm, (syn=T8345), (syn=8345-SO-S-R), W1, (syn=D8), (syn=FSD8), W2a, (syn=D2A), (syn=FS2a), DD-2, Sf6, FSi, (syn=Fl), SF6, (syn=F6), SG42, (syn=SO-42/G), SG3203, (syn=SO-3203/G), SKF12, (syn=SsF12), (syn=F12), (syn=F12), STn, (syn=1881-SO-R), γ66, (syn=gamma 66a), (syn=Ssy66), φ2, BIl, DDVII, (syn=DD7), FSD2b, (syn=W2B), FS2, (syn=F2), (syn=F2), FS4, (syn=F4), (syn=F4), FS5, (syn=F5), (syn=F5), FS9, (syn=F9), (syn=F9), FI 1, P2-S0-S, SG36, (syn=SO-36/G), (syn=G36), SG3204, (syn=SO-3204/G), SG3244, (syn=SO-3244/G), SHi, (syn=HI), SHvπ, (syn=HVII), SHK, (syn=HIX), SHx1, SHxπ, (syn=HXn), SKI, KI, (syn=S1), (syn=SsI), SKVII, (syn=KVII), (syn=Svπ), (syn=SsVII), SKIX, (syn=KIX), (syn=S1x), (syn=SsIX), SKXII, (syn=KXII), (syn=Sxn), (syn=SsXII), STi, STffl, STrv, STVi, STvπ, S70, S206, U2-S0-S, 3210-SO-S, 3859-SO-S, 4020-SO-S, φ3, φ5 , φ7 , φ8 , φ9, φlO, φl 1, φ13, φ14, φ18, SHm, (syn=Hπi), SHχi, (syn=HXt) and SKxI, (syn=KXI), (syn=Sχi), (syn=SsXI), (syn=XI).

Bacteria of the genus *Staphylococcus* are infected by the following phage: A, EW, K, Ph5, Ph9, PhIO, Phl3, Pl, P2, P3, P4, P8, P9, PlO, RG, SB-i, (syn=Sb-I), S3K, Twort, ΦSK311, φ812, 06, 40, 58, 119, 130, 131, 200, 1623, STCl, (syn=stcl), STC2, (syn=stc2), 44AHJD, 68, ACl, AC2, A6"C", A9"C", b581, CA-I, CA-2, CA-3, CA-4, CA-5, DI1, L39x35, L54a, M42, Nl, N2, N3, N4, N5, N7, N8, N10, Ni 1, N12, N13, N14, N16, Ph6, Ph12, Ph14, UC-18, U4, U15, Sl, S2, S3, S4, S5, X2, Z1, φB5-2, φD, ω, 11, (syn=φl 1), (syn=P11-M15), 15, 28, 28A, 29, 31, 31B, 37, 42D, (syn=P42D), 44A, 48, 51, 52, 52A, (syn=P52A), 52B, 53, 55, 69, 71, (syn=P71), 71A, 72, 75, 76, 77, 79, 80, 80a, 82, 82A, 83 A, 84, 85, 86, 88, 88A, 89, 90, 92, 95, 96, 102, 107, 108, 111, 129-26, 130, 130A, 155, 157, 157A, 165, 187, 275, 275A, 275B, 356, 456, 459, 471, 471A, 489, 581, 676, 898, 1139, 1154A, 1259, 1314, 1380, 1405, 1563, 2148, 2638A, 2638B, 2638C, 2731, 2792A, 2792B, 2818, 2835, 2848A, 3619, 5841, 12100, AC3, A8, A10, A13, b594n, D, HK2, N9, N15, P52, P87, 51, S6, Z4, φRE, 3A, 3B, 3C, 6, 7, 16, 21, 42B, 42C, 42E, 44, 47, 47A5 47C, 51, 54, 54x1, 70, 73, 75, 78, 81, 82, 88, 93, 94, 101, 105, 110, 115, 129/16, 174, 594n, 1363/14, 2460 and mS-*Staphylococcus* (1).

Bacteria of the genus *Streptococcus* are infected by the following phage: EJ-I, NN-Streptococais (1), a, Cl, FL0Ths, H39, Cp-I, Cp-5, Cp-7, Cp-9, Cp-IO, AT298, A5, alO/Jl, alO/J2, alO/J5, alO/J9, A25, BTI1, b6, CAI, c20-1, c20-2, DP-I, Dp-4, DTl, ET42, elO, FA101, FEThs, Fκ, FKKIOI, FKLIO, FKP74, FKH, FLOThs, FyIOl, fl, F10, F20140/76, g, GT-234, HB3, (syn=HB-3), HB-623, HB-746, M102, O1205, φO1205, PST, PO, Pl, P2, P3, P5, P6, P8, P9, P9, P12, P13, P14, P49, P50, P51, P52, P53, P54, P55, P56, P57, P58, P59, P64, P67, P69, P71, P73, P75, P76, P77, P82, P83, P88, sc, sch, sf, SfIl 1, (syn=SFiI 1), (syn=φSFill), (syn=ΦSfil 1), (syn=φSfil 1), sfi19, (syn=SFil9), (syn=φSFil9), (syn=φSfil9), Sfi21, (syn=SFi21), (syn=φSFi21), (syn=φSfi21), ST0, STX, st2, ST2, ST4, S3, (syn=φS3), s265, Φ17 , φ42, Φ57 , φ80 , φ81, φ82, φ83, φ84, φ85, φ86 , φ87 , φ88 , φ89 , φ90 , φ91, φ92, φ93, φ94, φ95, φ96 , φ97 , φ98 , φ99, φlOO, φlOl, φlO2, φ227 , φ7201, ω1 , ω2 , ω3 , ω4 , ω5 , ω6 , ω8, ωlO, 1, 6, 9, lOF, 12/12, 14, 17SR, 19S, 24, 50/33, 50/34, 55/14, 55/15, 70/35, 70/36, 71/5T15, 71/45, 71/46, 74F, 79/37, 79/38, 80/J4, 80/J9, 80/5T16, 80/15, 80/47, 80/48, 101, 103/39, 103/40, 121/41, 121/42, 123/43, 123/44, 124/44, 337/ST17 and m *Streptococcus* (34).

Bacteria of the genus *Treponema* are infected by the following phage: NN-*Treponema* (1).

Bacteria of the genus *Vibrio* are infected by the following phage: CTXΦ, fs, (syn=si), fs2, Ivpf5, Vfl2, Vf33, VPIΦ, VSK, v6, 493, CP-T1, ET25, kappa, K139, Labol, XN-69P, OXN-86, O6N-21P, PB-I, P147, rp-1, SE3, VA-I, (syn=VcA-I), VcA-2, VPl, VP2, VP4, VP7, VP8, VP9, VPlO, VP17, VP18, VP19, X29, (syn=29 d'Herelle), t, ΦHAWI-1, ΦHAWI-2, ΦHAWI-3, ΦHAWI-4, ΦHAWI-5, ΦHAWI-6, ΦHAWI-7, XHAWI-8, ΦHAWI-9, ΦHAWI-10, ΦHCl-1, ΦHC1-2, ΦHC1-3, ΦHC1-4, ΦHC2-1, >HC2-2, ΦHC2-3, ΦHC2-4, ΦHC3-1, ΦHC3-2, ΦHC3-3, ΦHD1S-1, ΦHD1S-2, ΦHD2S-1, ΦHD2S-2, ΦHD2S-3, ΦHD2S-4, ΦHD2S-5, ΦHDO-1, ΦHDO-2, ΦHDO-3, ΦHDO-4, ΦHDO-5, ΦHDO-6, ΦKL-33, ΦKL-34, ΦKL-35, ΦKL-36, ΦKWH-2, ΦKWH-3, ΦKWH-4, ΦMARQ-1, ΦMARQ-2, ΦMARQ-3, ΦMOAT-1, ΦO139, ΦPEL1A-1, ΦPEL1A-2, ΦPEL8A-1, ΦPEL8A-2, ΦPEL8A-3, ΦPEL8C-1, ΦPEL8C-2, ΦPEL13A-1, ΦPEL13B-1, ΦPEL13B-2, ΦPEL13B-3, ΦPEL13B-4, ΦPEL13B-5, ΦPEL13B-6, ΦPEL13B-7, ΦPEL13B-8, ΦPEL13B-9, ΦPEL13B-10, φVP143, φVP253, Φ16 , φ138, 1-II, 5, 13, 14, 16, 24, 32, 493, 6214, 7050, 7227, II, (syn=group II), (syn=φ2), V, VIII, ~m-*Vibrio* (13), KVP20, KVP40, nt-1, O6N-22P, P68, e1, e2, e3, e4, e5, FK, G, I, K, nt-6, N1, N2, N3, N4, N5, O6N-34P, OXN-72P, OXN-85P, OXN-100P, P, Ph-I, PL163/10, Q, S, T, φ92, 1-9, 37, 51, 57, 70A-8, 72A-4, 72A-10, 110A-4, 333, 4996, I (syn=group I), III (syn=group III), VI, (syn=A-Saratov), VII, IX, X, HN-*Vibrio* (6), pAl, 7, 7-8, 70A-2, 71A-6, 72A-5, 72A-8, 108A-10, 109A-6, 109A-8, 110A-1, 110A-5, 110A-7, by-1, OXN-52P, P13, P38, P53, P65, P108, Pill, TP13 VP3, VP6, VP12, VP13, 70A-3, 70A-4, 70A-10, 72A-1, 108A-3, 109-B1, 110A-2, 149, (syn=φ149), IV, (syn=group IV), NN-*Vibrio* (22), VPS, VPIl, VP15, VP16, α1, α2, α3a, α3b, 353B and HN-*Vibrio* (7).

Bacteria of the genus *Yersinia* are infected by the following phage: H, H-1, H-2, H-3, H-4, Lucas 110, Lucas 303, Lucas 404, YerA3, YerA7, YerA20, YerA41, 3/M64-76, 5/G394-76, 6/C753-76, 8/C239-76, 9/F18167, 1701, 1710, PST, 1/F2852-76, D'Herelle, E V, H, Kotljarova, PTB, R, Y, YerA41, φYerO3-12, 3, 4/C1324-76, 7/F783-76, 903, 1/M6176 and Yer2AT.

More preferably, the bacteriophage is selected in the group consisting of Salmonella virus SKML39, Shigella virus AG3, Dickeya virus Limestone, Dickeya virus RC2014, Escherichia virus CBA120, Escherichia virus PhaxI, Salmonella virus 38, Salmonella virus Det7, Salmonella virus GG32, Salmonella virus PM10, Salmonella virus SFP10, Salmonella virus SH19, Salmonella virus 5J3, Escherichia virus ECML4, Salmonella virus Marshall, Salmonella virus Maynard, Salmonella virus 5J2, Salmonella virus STML131, Salmonella virus ViI, Erwinia virus Ea2809, Klebsiella virus 0507KN21, Serratia virus IME250, Serratia virus MAM1, Campylobacter virus CP21, Campylobacter virus CP220, Campylobacter virus CPt10, Campylobacter virus IBB35, Campylobacter virus CP81, Campylobacter virus CP30A, Campylobacter virus CPX, Campylobacter virus NCTC12673, Erwinia virus Ea214, Erwinia virus M7, Escherichia virus AYO145A, Escherichia virus EC6, Escherichia virus HY02, Escherichia virus JH2, Escherichia virus TP1, Escherichia virus VpaE1, Escherichia virus wV8, Salmonella virus FelixO1, Salmonella virus HB2014, Salmonella virus Mushroom, Salmonella virus UAB87, Citrobacter virus Moogle, Citrobacter virus Mordin, Escherichia virus SUSP1, Escherichia virus SUSP2, Aeromonas virus phiO18P, Haemophilus virus HP1, Haemophilus virus HP2, Pasteurella virus F108, Vibrio virus K139, Vibrio virus Kappa, Burkholderia virus phi52237, Burkholderia virus phiE122, Burkholderia virus phiE202, Escherichia virus 186, Escherichia virus P4, Escherichia virus P2, Escherichia virus Wphi, Mannheimia virus PHL101, Pseudomonas virus phiCTX, Ralstonia virus RSA1, Salmonella virus Fels2, Salmonella virus PsP3, Salmonella virus SopEphi, Yersinia virus L413C, Staphylococcus virus G1, Staphylococcus virus G15, Staphylococcus virus JD7, Staphylococcus virus K, Staphylococcus virus MCE2014, Staphylococcus virus P108, Staphylococcus virus Rodi, Staphylococcus virus S253, Staphylococcus virus S25-4, Staphylococcus virus SA12, Listeria virus A511, Listeria virus P100, Staphylococcus virus Remus, Staphylococcus virus SA11, Staphylococcus virus Stau2, Bacillus virus Camphawk, Bacillus virus SPO1, Bacillus virus BCP78, Bacillus virus TsarBomba, Staphylococcus virus Twort, Enterococcus virus phiEC24C, Lactobacillus virus Lb338-1, Lactobacillus virus LP65, Enterobacter virus PG7, Escherichia virus CC31, Klebsiella virus JD18, Klebsiella virus PKO111, Escherichia virus Bp7, Escherichia virus IME08, Escherichia virus JS10, Escherichia virus J598, Escherichia virus QL01, Escherichia virus VR5, Enterobacter virus Eap3, Klebsiella virus KP15, Klebsiella virus KP27, Klebsiella virus Matisse, Klebsiella virus Miro, Citrobacter virus Merlin, Citrobacter virus Moon, Escherichia virus JSE, Escherichia virus phi1, Escherichia virus RB49, Escherichia virus HX01, Escherichia virus JS09, Escherichia virus RB69, Shigella virus UTAM, Salmonella virus S16, Salmonella virus STML198, Vibrio virus KVP40, Vibrio virus ntl, Vibrio virus ValKK3, Escherichia virus VR7, Escherichia virus VR20, Escherichia virus VR25, Escherichia virus VR26, Shigella virus SP18, Escherichia virus AR1, Escherichia virus C40, Escherichia virus E112, Escherichia virus ECML134, Escherichia virus HY01, Escherichia virus Ime09, Escherichia virus RB3, Escherichia virus RB14, Escherichia virus T4, Shigella virus Pssl, Shigella virus Shf12, Yersinia virus D1, Yersinia virus PST, Acinetobacter virus 133, Aeromonas virus 65, Aeromonas virus Aeh1, Escherichia virus RB16, Escherichia virus RB32, Escherichia virus RB43, Pseudomonas virus 42, Cronobacter virus CR3, Cronobacter virus CR8, Cronobacter virus CR9, Cronobacter virus PBES02, Pectobacterium virus phiTE, Cronobacter virus GAP31, Escherichia virus 4MG, Salmonella virus SE1, Salmonella virus SSE121, Escherichia virus FFH2, Escherichia virus FV3, Escherichia virus JES2013, Escherichia virus V5, Brevibacillus virus Abouo, Brevibacillus virus Davies, Bacillus virus Agate, Bacillus virus Bobb, Bacillus virus Bp8pC, Erwinia virus Deimos, Erwinia virus Ea35-70, Erwinia virus RAY, Erwinia virus Simmy50, Erwinia virus SpecialG, Acinetobacter virus AB1, Acinetobacter virus AB2, Acinetobacter virus AbC62, Acinetobacter virus AP22, Arthrobacter virus ArV1, Arthrobacter virus Trina, Bacillus virus AvesoBmore, Bacillus virus B4, Bacillus virus Bigbertha, Bacillus virus Riley, Bacillus virus Spock, Bacillus virus Troll, Bacillus virus Bastille, Bacillus virus CAM003, Bacillus virus Bc431, Bacillus virus Bcp1, Bacillus virus BCP82, Bacillus virus BM15, Bacillus virus Deepblue, Bacillus virus JBP901, Burkholderia virus Bcep1, Burkholderia virus Bcep43, Burkholderia virus Bcep781, Burkholderia virus BcepNY3, Xanthomonas virus OP2, Burkholderia virus BcepMu, Burkholderia virus phiE255, Aeromonas virus 44RR2, Mycobacterium virus Alice, Mycobacterium virus Bxzl, Mycobacterium virus Dandelion, Mycobacterium virus HyRo, Mycobacterium virus 13, Mycobacterium virus Nappy, Mycobacterium virus Sebata, Clostridium virus phiC2, Clostridium virus phiCD27, Clostridium virus phiCD119, Bacillus virus CP51, Bacillus virus JL, Bacillus virus Shanette, Escherichia virus CVM10, Escherichia virus ep3, Erwinia virus Asesino, Erwinia virus EaH2, Pseudomonas virus EL, Halomonas virus HAP1, Vibrio virus VP882, Brevibacillus virus Jimmer, Brevibacillus virus Osiris, Pseudomonas virus Ab03, Pseudomonas virus KPP10, Pseudomonas virus PAKP3, Sinorhizobium virus M7, Sinorhizobium virus M12, Sinorhizobium virus N3, Erwinia virus Machina, Arthrobacter virus Brent, Arthrobacter virus Jawnski, Arthrobacter virus Martha, Arthrobacter virus Sonny, Edwardsiella virus MSW3, Edwardsiella virus PEi21, Escherichia virus Mu, Shigella virus SfMu, Halobacterium virus phiH, Bacillus virus Grass, Bacillus virus NIT1, Bacillus virus SPG24, Aeromonas virus 43, Escherichia virus P1, Pseudomonas virus CAb1, Pseudomonas virus CAb02, Pseudomonas virus JG004, Pseudomonas virus PAKP1, Pseudomonas virus PAKP4, Pseudomonas virus PaP1, Burkholderia virus BcepF1, Pseudomonas virus 141, Pseudomonas virus Ab28, Pseudomonas virus DL60, Pseudomonas virus DL68, Pseudomonas virus F8, Pseudomonas virus JG024, Pseudomonas virus KPP12, Pseudomonas virus LBL3, Pseudomonas virus LMA2, Pseudomonas virus PB1, Pseudomonas virus SN, Pseudomonas virus PA7, Pseudomonas virus phiKZ, Rhizobium virus RHEph4, Ralstonia virus RSF1, Ralstonia virus RSL2, Ralstonia virus RSL1, Aeromonas virus 25, Aeromonas virus 31, Aeromonas virus Aes12, Aeromonas virus Aes508, Aeromonas virus AS4, Stenotrophomonas virus IME13, Staphylococcus virus IPLAC1C, Staphylococcus virus SEP1, Salmonella virus SPN3US, Bacillus virus 1, Geobacillus virus GBSV1, Yersinia virus R1RT, Yersinia virus TG1, Bacillus virus G, Bacillus virus PBS1, Microcystis virus Ma-LMM01, Vibrio virus MAR, Vibrio virus VHML, Vibrio virus VP585, Bacillus virus BPS13, Bacillus virus Hakuna, Bacillus virus Megatron, Bacillus virus WPh, Acinetobacter virus AB3, Acinetobacter virus Abp1, Acinetobacter virus Fri1, Acinetobacter virus IME200, Acinetobacter virus PD6A3, Acinetobacter virus PDAB9, Acinetobacter virus phiAB1, Escherichia virus K30, Klebsiella virus K5, Klebsiella virus K11, Klebsiella virus Kp1, Klebsiella virus KP32, Klebsiella virus KpV289, Klebsiella virus F19, Klebsiella virus K244, Klebsiella virus Kp2, Klebsiella virus KP34, Klebsiella virus KpV41, Klebsiella virus KpV71, Klebsiella virus KpV475, Klebsiella virus SU503, Klebsiella virus SU552A, Pantoea virus Limelight, Pantoea virus Limezero, Pseudomonas virus LKA1, Pseudomonas virus phiKMV, Xanthomonas virus f20, Xanthomonas virus f30, Xylella virus Prado, Erwinia virus Era103, Escherichia virus K5, Escherichia virus K1-5, Escherichia virus K1E, Salmonella virus SP6, Escherichia virus T7, Kluyvera virus Kvp1, Pseudomonas virus gh1, Prochlorococcus virus PSSP7, Synechococcus virus P60, Synechococcus virus Syn5, Streptococcus virus Cp1, Streptococcus virus Cp1, Staphylococcus virus 44AHJD, Streptococcus virus C1, Bacillus virus B103, Bacillus virus GA1, Bacillus virus phi29, Kurthia virus 6, Actinomyces virus Av1, Mycoplasma virus P1, Escherichia virus 24B, Escherichia virus 933W, Escherichia virus Min27, Escherichia virus PA28, Escherichia virus Stx2 II, Shigella virus 7502Stx, Shigella virus POCJ13, Escherichia virus 191, Escherichia virus PA2, Escherichia virus TL2011, Shigella virus VASD, Burkholderia virus Bcep22, Burkholderia virus Bcepi102, Burkholderia virus Bcepmigl, Burkholderia virus DC1, Bordetella virus BPP1, Burkholderia virus BcepC6B, Cellulophaga virus Cba41, Cellulophaga virus Cba172, Dinoroseobacter virus DFL12, Erwinia virus Ea9-2, Erwinia virus Frozen, Escherichia virus phiV10, Salmonella virus Epsilon15, Salmonella virus SPN1S, Pseudomonas virus F116, Pseudomonas virus H66, Escherichia virus APECS, Escherichia virus APEC7, Escherichia virus Bp4, Escherichia virus EC1UPM, Escherichia virus ECBP1, Escherichia virus G7C, Escherichia virus IME11, Shigella virus Sb 1, Achromobacter virus Axp3, Achromobacter virus JWAlpha, Edwardsiella virus KF1, Pseudomonas virus KPP25, Pseudomonas virus R18, Pseudomonas virus Ab09, Pseudomonas virus LIT1, Pseudomonas virus PA26, Pseudomonas virus Ab22, Pseudomonas virus CHU, Pseudomonas virus LUZ24, Pseudomonas virus PAA2, Pseudomonas virus PaP3, Pseudomonas virus PaP4, Pseudomonas virus TL, Pseudomonas virus KPP21, Pseudomonas virus LUZ7, Escherichia virus N4, Salmonella virus 9NA, Salmonella virus SP069, Salmonella virus BTP1, Salmonella virus HK620, Salmonella virus P22, Salmonella virus ST64T, Shigella virus Sf6, Bacillus virus Page, Bacillus virus Palmer, Bacillus virus Pascal, Bacillus virus Pony, Bacillus virus Pookie, Escherichia virus 172-1, Escherichia virus ECB2, Escherichia virus NJ01, Escherichia virus phiEco32, Escherichia virus Septima11, Escherichia virus SU10, Brucella virus Pr, Brucella virus Tb, Escherichia virus Pollock, Salmonella virus FSL SP-058, Salmonella virus FSL SP-076, Helicobacter virus 1961P, Helicobacter virus KHP30, Helicobacter virus KHP40, Hamiltonella virus APSE1, Lactococcus virus KSY1, Phormidium virus WMP3, Phormidium virus WMP4, Pseudomonas virus 119X, Roseobacter virus SIO1, Vibrio virus VpV262, Vibrio virus VC8, Vibrio virus VP2, Vibrio virus VPS, Streptomyces virus Amela, Streptomyces virus phiCAM, Streptomyces virus Aaronocolus, Streptomyces virus Caliburn, Streptomyces virus Danzina, Streptomyces virus Hydra, Streptomyces virus Izzy, Streptomyces virus Lannister, Streptomyces virus Lika, Streptomyces virus Sujidade, Streptomyces virus Zemlya, Streptomyces virus ELB20, Streptomyces virus R4, Streptomyces virus phiHau3, Mycobacterium virus Acadian, Mycobacterium virus Baee, Mycobacterium virus Reprobate, Mycobacterium virus Adawi, Mycobacterium virus Bane1, Mycobacterium virus BrownCNA, Mycobacterium virus Chrisnmich, Mycobacterium virus Cooper, Mycobacterium virus JAMaL, Mycobacterium virus Nigel, Mycobacterium virus Stinger, Mycobacterium virus Vincenzo, Mycobacterium virus Zemanar, Mycobacterium virus Apizium, Mycobacterium virus Manad, Mycobacterium virus Oline, Mycobacterium virus Osmaximus, Mycobacterium virus Pg1, Mycobacterium virus Soto, Mycobacterium virus Suffolk, Mycobacterium virus Athena, Mycobacterium virus Bernardo, Mycobacterium virus Gadjet, Mycobacterium virus Pipefish, Mycobacterium virus Godines, Mycobacterium virus Rosebush, Mycobacterium virus Babsiella, Mycobacterium virus Brujita, Mycobacterium virus Che9c, Mycobacterium virus Sbash, Mycobacterium virus Hawkeye, Mycobacterium virus Plot, Salmonella virus AG11, Salmonella virus Entl, Salmonella virus f18SE, Salmonella virus Jersey, Salmonella virus L13, Salmonella virus LSPA1, Salmonella virus SE2, Salmonella virus SETP3, Salmonella virus SETP7, Salmonella virus SETP13, Salmonella virus SP101, Salmonella virus SS3e, Salmonella virus wks13, Escherichia virus K1G, Escherichia virus K1H, Escherichia virus Klind1, Escherichia virus Klind2, Salmonella virus SP31, Leuconostoc virus Lmd1, Leuconostoc virus LN03, Leuconostoc virus LN04, Leuconostoc virus LN12, Leuconostoc virus LN6B, Leuconostoc virus P793, Leuconostoc virus 1A4, Leuconostoc virus Ln8, Leuconostoc virus Ln9, Leuconostoc virus LN25, Leuconostoc virus LN34, Leuconostoc virus LNTR3, Mycobacterium virus Bongo, Mycobacterium virus Rey, Mycobacterium virus Butters, Mycobacterium virus Michelle, Mycobacterium virus Charlie, Mycobacterium virus Pipsqueaks, Mycobacterium virus Xeno, Mycobacterium virus Panchino, Mycobacterium virus Phrann, Mycobacterium virus Redi, Mycobacterium virus Skinnyp, Gordonia virus BaxterFox, Gordonia virus Yeezy, Gordonia virus Kita, Gordonia virus Zirinka, Gorrdonia virus Nymphadora, Mycobacterium virus Bignuz, Mycobacterium virus Brusacoram, Mycobacterium virus Donovan, Mycobacterium virus Fishburne, Mycobacterium virus Jebeks, Mycobacterium virus Malithi, Mycobacterium virus Phayonce, Enterobacter virus F20, Klebsiella virus 1513, Klebsiella virus KLPN1, Klebsiella virus KP36, Klebsiella virus PKP126, Klebsiella virus Sushi, Escherichia virus AHP42, Escherichia virus AHS24, Escherichia virus AKS96, Escherichia virus C119, Escherichia virus E41c, Escherichia virus Eb49, Escherichia virus Jk06, Escherichia virus KP26, Escherichia virus Roguel, Escherichia virus ACGM12, Escherichia virus Rtp, Escherichia virus ADB2, Escherichia virus JMPW1, Escherichia virus JMPW2, Escherichia virus T1, Shigella virus PSf2, Shigella virus Shfl1, Citrobacter virus Stevie, Escherichia virus TLS, Salmonella virus SP126, Cronobacter virus Esp2949-1, Pseudomonas virus Ab18, Pseudomonas virus Ab19, Pseudomonas virus PaMx11, Arthrobacter virus Amigo, Propionibacterium virus Anatole, Propionibacterium virus B3, Bacillus virus Andromeda, Bacillus virus Blastoid, Bacillus virus Curly, Bacillus virus Eoghan, Bacillus virus Finn, Bacillus virus Glittering, Bacillus virus Riggi, Bacillus virus Taylor, Gordonia virus Attis, Mycobacterium virus Barnyard, Mycobacterium virus Konstantine, Mycobacterium virus Predator, Mycobacterium virus Bernal13, Staphylococcus virus 13, Staphylococcus virus 77, Staphylococcus virus 108PVL, Mycobacterium virus Bron, Mycobacterium virus Faith1, Mycobacterium virus Joedirt, Mycobacterium virus Rumpelstiltskin, Lactococcus virus bIL67, Lactococcus virus c2, Lactobacillus virus c5, Lactobacillus virus Ld3, Lactobacillus virus Ld17, Lactobacillus virus Ld25A, Lactobacillus virus LLKu, Lactobacillus virus phiLdb, Cellulophaga virus Cba121, Cellulophaga virus Cba171, Cellulophaga virus Cba181, Cellulophaga virus ST, Bacillus virus 250, Bacillus virus IEBH, Mycobacterium virus Ardmore, Mycobacterium virus Avani, Mycobacterium virus Boomer, Mycobacterium virus Che8, Mycobacterium virus Che9d, Mycobacterium virus Deadp, Mycobacterium virus Dlane, Mycobacterium virus Dorothy, Mycobacterium virus Dotproduct, Mycobacterium virus Drago, Mycobacterium virus Fruitloop, Mycobacterium virus Gumbie, Mycobacterium virus Ibhubesi, Mycobacterium virus Llij, Mycobacterium virus Mozy, Mycobacterium virus Mutaforma13, Mycobacterium virus Pacc40, Mycobacterium virus PMC, Mycobacterium virus Ramsey, Mycobacterium virus Rockyhorror, Mycobacterium virus SG4, Mycobacterium virus Shauna1, Mycobacterium virus Shilan, Mycobacterium virus Spartacus, Mycobacterium virus Taj, Mycobacterium virus Tweety, Mycobacterium virus Wee, Mycobacterium virus Yoshi, Salmonella virus Chi, Salmonella virus FSLSP030, Salmonella virus FSLSP088, Salmonella virus iEPS5, Salmonella virus SPN19, Mycobacterium virus 244, Mycobacterium virus Bask21, Mycobacterium virus CJW1, Mycobacterium virus Eureka, Mycobacterium virus Kostya, Mycobacterium virus Porky, Mycobacterium virus Pumpkin, Mycobacterium virus Sirduracell, Mycobacterium virus Toto, Mycobacterium virus Corndog, Mycobacterium virus Firecracker, Rhodobacter virus RcCronus, Pseudomonas virus D3112, Pseudomonas virus DMS3, Pseudomonas virus FHA0480, Pseudomonas virus LPB1, Pseudomonas virus MP22, Pseudomonas virus 1V11329, Pseudomonas virus MP38, Pseudomonas virus PA1KOR, Pseudomonas virus D3, Pseudomonas virus PMG1, Arthrobacter virus Decurro, Gordonia virus Demosthenes, Gordonia virus Katyusha, Gordonia virus Kvothe, Propionibacterium virus B22, Propionibacterium virus Doucette, Propionibacterium virus E6, Propionibacterium virus G4, Burkholderia virus phi6442, Burkholderia virus phil026b, Burkholderia virus phiE125, Edwardsiella virus eiAU, Mycobacterium virus Ff47, Mycobacterium virus Muddy, Mycobacterium virus Gaia, Mycobacterium virus Giles, Arthrobacter virus Captnmurica, Arthrobacter virus Gordon, Gordonia virus GordTnk2, Paenibacillus virus Harrison, Escherichia virus EK99P1, Escherichia virus HK578, Escherichia virus JL1, Escherichia virus SSL2009a, Escherichia virus YD2008s, Shigella virus EP23, Sodalis virus SO1, Escherichia virus HK022, Escherichia virus HK75, Escherichia virus HK97, Escherichia virus HK106, Escherichia virus HK446, Escherichia virus HK542, Escherichia virus HK544, Escherichia virus HK633, Escherichia virus mEp234, Escherichia virus mEp235, Escherichia virus mEpX1, Escherichia virus mEpX2, Escherichia virus mEp043, Escherichia virus mEp213, Escherichia virus mEp237, Escherichia virus mEp390, Escherichia virus mEp460, Escherichia virus mEp505, Escherichia virus mEp506, Brevibacillus virus Jenst, Achromobacter virus 83-24, Achromobacter virus JWX, Arthrobacter virus Kellezzio, Arthrobacter virus Kitkat, Arthrobacter virus Bennie, Arthrobacter virus DrRobert, Arthrobacter virus Glenn, Arthrobacter virus HunterDalle, Arthrobacter virus Joann, Arthrobacter virus Korra, Arthrobacter virus Preamble, Arthrobacter virus Pumancara, Arthrobacter virus Wayne, Mycobacterium virus Alma, Mycobacterium virus Arturo, Mycobacterium virus Astro, Mycobacterium virus Backyardigan, Mycobacterium virus BBPiebs31, Mycobacterium virus Benedict, Mycobacterium virus Bethlehem, Mycobacterium virus Billknuckles, Mycobacterium virus Bruns, Mycobacterium virus Bxb 1, Mycobacterium virus Bxz2, Mycobacterium virus Che12, Mycobacterium virus Cuco, Mycobacterium virus D29, Mycobacterium virus Doom, Mycobacterium virus Ericb, Mycobacterium virus Euphoria, Mycobacterium virus George, Mycobacterium virus Gladiator, Mycobacterium virus Goose, Mycobacterium virus Hammer, Mycobacterium virus Heldan, Mycobacterium virus Jasper, Mycobacterium virus JC27, Mycobacterium virus Jeffabunny, Mycobacterium virus JHC117, Mycobacterium virus KBG, Mycobacterium virus Kssjeb, Mycobacterium virus Kugel, Mycobacterium virus L5, Mycobacterium virus Lesedi, Mycobacterium virus LHTSCC, Mycobacterium virus lockley, Mycobacterium virus Marcell, Mycobacterium virus Microwolf, Mycobacterium virus Mrgordo, Mycobacterium virus Museum, Mycobacterium virus Nepal, Mycobacterium virus Packman, Mycobacterium virus Peaches, Mycobacterium virus Perseus, Mycobacterium virus Pukovnik, Mycobacterium virus Rebeuca, Mycobacterium virus Redrock, Mycobacterium virus Ridgecb, Mycobacterium virus Rockstar, Mycobacterium virus Saintus, Mycobacterium virus Skipole, Mycobacterium virus Solon, Mycobacterium virus Switzer, Mycobacterium virus SWU1, Mycobacterium virus Ta17a, Mycobacterium virus Tiger, Mycobacterium virus Timshel, Mycobacterium virus Trixie, Mycobacterium virus Turbido, Mycobacterium virus Twister, Mycobacterium virus U2, Mycobacterium virus Violet, Mycobacterium virus Wonder, Escherichia virus DE3, Escherichia virus HK629, Escherichia virus HK630, Escherichia virus lambda, Arthrobacter virus Laroye, Mycobacterium virus Halo, Mycobacterium virus Liefie, Mycobacterium virus Marvin, Mycobacterium virus Mosmoris, Arthrobacter virus Circum, Arthrobacter virus Mudcat, Escherichia virus N15, Escherichia virus 9g, Escherichia virus JenKl, Escherichia virus JenP1, Escherichia virus JenP2, Pseudomonas virus NP1, Pseudomonas virus PaMx25, Mycobacterium virus Baka, Mycobacterium virus Courthouse, Mycobacterium virus Littlee, Mycobacterium virus Omega, Mycobacterium virus Optimus, Mycobacterium virus Thibault, Polaribacter virus P12002L, Polaribacter virus P12002S, Nonlabens virus P12024L, Nonlabens virus P12024S, Thermus virus P23-45, Thermus virus P74-26, Listeria virus LP26, Listeria virus LP37, Listeria virus LP110, Listeria virus LP114, Listeria virus P70, Propionibacterium virus ATCC29399BC, Propionibacterium virus ATCC29399BT, Propionibacterium virus Attacne, Propionibacterium virus Keiki, Propionibacterium virus Kubed, Propionibacterium virus Lauchelly, Propionibacterium virus MrAK, Propionibacterium virus Ouroboros, Propionibacterium virus P91, Propionibacterium virus P105, Propionibacterium virus P144, Propionibacterium virus P1001, Propionibacterium virus P1.1, Propionibacterium virus P100A, Propionibacterium virus P100D, Propionibacterium virus P101A, Propionibacterium virus P104A, Propionibacterium virus PA6, Propionibacterium virus Pacnes201215, Propionibacterium virus PAD20, Propionibacterium virus PAS50, Propionibacterium virus PHLOO9M11, Propionibacterium virus PHL025M00, Propionibacterium virus PHL037M02, Propionibacterium virus PHL041M10, Propionibacterium virus PHL060L00, Propionibacterium virus PHL067M01, Propionibacterium virus PHL070N00, Propionibacterium virus PHL071N05, Propionibacterium virus PHL082M03, Propionibacterium virus PHL092M00, Propionibacterium virus PHL095N00, Propionibacterium virus PHL111M01, Propionibacterium virus PHL112N00, Propionibacterium virus PHL113M01, Propionibacterium virus PHL114L00, Propionibacterium virus PHL116M00, Propionibacterium virus PHL117M00, Propionibacterium virus PHL117M01, Propionibacterium virus PHL132N00, Propionibacterium virus PHL141N00, Propionibacterium virus PHL151M00, Propionibacterium virus PHL151N00, Propionibacterium virus PHL152M00, Propionibacterium virus PHL163M00, Propionibacterium virus PHL171M01, Propionibacterium virus PHL179M00, Propionibacterium virus PHL194M00, Propionibacterium virus PHL199M00, Propionibacterium virus PHL301M00, Propionibacterium virus PHL308M00, Propionibacterium virus Pirate, Propionibacterium virus Procrass1, Propionibacterium virus SKKY, Propionibacterium virus Solid, Propionibacterium virus Stormborn, Propionibacterium virus Wizzo, Pseudomonas virus PaMx28, Pseudomonas virus PaMx74, Mycobacterium virus Patience, Mycobacterium virus PBI1, Rhodococcus virus Pepy6, Rhodococcus virus Poco6, Propionibacterium virus PFR1, Streptomyces virus phiBT1, Streptomyces virus phiC31, Streptomyces virus TG1, Caulobacter virus Karma, Caulobacter virus Magneto, Caulobacter virus phiCbK, Caulobacter virus Rogue, Caulobacter virus Swift, Staphylococcus virus 11, Staphylococcus virus 29, Staphylococcus virus 37, Staphylococcus virus 53, Staphylococcus virus 55, Staphylococcus virus 69, Staphylococcus virus 71, Staphylococcus virus 80, Staphylococcus virus 85, Staphylococcus virus 88, Staphylococcus virus 92, Staphylococcus virus 96, Staphylococcus virus 187, Staphylococcus virus 52a, Staphylococcus virus 80alpha, Staphylococcus virus CNPH82, Staphylococcus virus EW, Staphylococcus virus IPLA5, Staphylococcus virus IPLA7, Staphylococcus virus IPLA88, Staphylococcus virus PH15, Staphylococcus virus phiETA, Staphylococcus virus phiETA2, Staphylococcus virus phiETA3, Staphylococcus virus phiMR11, Staphylococcus virus phiMR25, Staphylococcus virus phiNM1, Staphylococcus virus phiNM2, Staphylococcus virus phiNM4, Staphylococcus virus SAP26, Staphylococcus virus X2, Enterococcus virus FL1, Enterococcus virus FL2, Enterococcus virus FL3, Lactobacillus virus ATCC8014, Lactobacillus virus phiJL1, Pediococcus virus cIP1, Aeromonas virus pIS4A, Listeria virus LP302, Listeria virus PSA, Methanobacterium virus psiM1, Roseobacter virus RDJL1, Roseobacter virus RDJL2, Rhodococcus virus RER2, Enterococcus virus BC611, Enterococcus virus IMEEF1, Enterococcus virus SAP6, Enterococcus virus VD13, Streptococcus virus SPQS1, Mycobacterium virus Papyrus, Mycobacterium virus Send513, Burkholderia virus KL1, Pseudomonas virus 73, Pseudomonas virus Ab26, Pseudomonas virus Kakheti25, Escherichia virus Cajan, Escherichia virus Seurat, Staphylococcus virus SEP9, Staphylococcus virus Sextaec, Streptococcus virus 858, Streptococcus virus 2972, Streptococcus virus ALQ132, Streptococcus virus O1205, Streptococcus virus Sfi11, Streptococcus virus 7201, Streptococcus virus DT1, Streptococcus virus phiAbc2, Streptococcus virus Sfi19, Streptococcus virus Sfi21, Paenibacillus virus Diva, Paenibacillus virus Hb10c2, Paenibacillus virus Rani, Paenibacillus virus Shelly, Paenibacillus virus Sitara, Paenibacillus virus Willow, Lactococcus virus 712, Lactococcus virus ASCC191, Lactococcus virus ASCC273, Lactococcus virus ASCC281, Lactococcus virus ASCC465, Lactococcus virus ASCC532, Lactococcus virus Bibb29, Lactococcus virus 1)11,170, Lactococcus virus CB13, Lactococcus virus CB14, Lactococcus virus CB19, Lactococcus virus CB20, Lactococcus virus jj50, Lactococcus virus P2, Lactococcus virus P008, Lactococcus virus sk1, Lactococcus virus S14, Bacillus virus Slash, Bacillus virus Stahl, Bacillus virus Staley, Bacillus virus Stills, Gordonia virus Bachita, Gordonia virus ClubL, Gordonia virus OneUp, Gordonia virus Smoothie, Gordonia virus Soups, Bacillus virus SPbeta, Vibrio virus MAR10, Vibrio virus SSP002, Escherichia virus AKFV33, Escherichia virus BF23, Escherichia virus DT57C, Escherichia virus EPS7, Escherichia virus FFH1, Escherichia virus H8, Escherichia virus s1ur09, Escherichia virus T5, Salmonella virus 118970sal2, Salmonella virus Shivani, Salmonella virus SPC35, Salmonella virus Stitch, Arthrobacter virus Tank, Tsukamurella virus TIN2, Tsukamurella virus TIN3, Tsukamurella virus TIN4, Rhodobacter virus RcSpartan, Rhodobacter virus RcTitan, Mycobacterium virus Anaya, Mycobacterium virus Angelica, Mycobacterium virus Crimd, Mycobacterium virus Fionnbarth, Mycobacterium virus Jaws, Mycobacterium virus Larva, Mycobacterium virus Macncheese, Mycobacterium virus Pixie, Mycobacterium virus TM4, Bacillus virus BMBtp2, Bacillus virus TP21, Geobacillus virus Tp84, Staphylococcus virus 47, Staphylococcus virus 3a, Staphylococcus virus 42e, Staphylococcus virus IPLA35, Staphylococcus virus phi12, Staphylococcus virus phiSLT, Mycobacterium virus 32HC, Rhodococcus virus RGL3, Paenibacillus virus Vegas, Gordonia virus Vendetta, Bacillus virus Wbeta, Mycobacterium virus Wildcat, Gordonia virus Twister6, Gordonia virus Wizard, Gordonia virus Hotorobo, Gordonia virus Monty, Gordonia virus Woes, Xanthomonas virus CP1, Xanthomonas virus OP1, Xanthomonas virus phi17, Xanthomonas virus Xop411, Xanthomonas virus Xp10, Streptomyces virus TP1604, Streptomyces virus YDN12, Alphaproteobacteria virus phiJ1001, Pseudomonas virus LKO4, Pseudomonas virus M6, Pseudomonas virus MP1412, Pseudomonas virus PAE1, Pseudomonas virus Yua, Pseudoalteromonas virus PM2, Pseudomonas virus phi6, Pseudomonas virus phi8, Pseudomonas virus phi12, Pseudomonas virus phi13, Pseudomonas virus phi2954, Pseudomonas virus phiNN, Pseudomonas virus phiYY, Vibrio virus fs1, Vibrio virus VGJ, Ralstonia virus RS603, Ralstonia virus RSM1, Ralstonia virus RSM3, Escherichia virus M13, Escherichia virus 122, Salmonella virus IKe, Acholeplasma virus L51, Vibrio virus fs2, Vibrio virus VFJ, Escherichia virus If1, Propionibacterium virus B5, Pseudomonas virus Pf1, Pseudomonas virus Pf3, Ralstonia virus PE226, Ralstonia virus RSS1, Spiroplasma virus SVTS2, Stenotrophomonas virus PSH1, Stenotrophomonas virus SMA6, Stenotrophomonas virus SMA7, Stenotrophomonas virus SMA9, Vibrio virus CTXphi, Vibrio virus KSF1, Vibrio virus VCY, Vibrio virus Vf33, Vibrio virus VfO3K6, Xanthomonas virus Cf1c, Spiroplasma virus C74, Spiroplasma virus R8A2B, Spiroplasma virus SkV1CR23x, Escherichia virus FI, Escherichia virus Qbeta, Escherichia virus BZ13, Escherichia virus MS2, Escherichia virus alpha3, Escherichia virus ID21, Escherichia virus ID32, Escherichia virus ID62, Escherichia virus NC28, Escherichia virus NC29, Escherichia virus NC35, Escherichia virus phiK, Escherichia virus St1, Escherichia virus WA45, Escherichia virus G4, Escherichia virus ID52, Escherichia virus Talmos, Escherichia virus phiX174, Bdellovibrio virus MAC1, Bdellovibrio virus MH2K, Chlamydia virus Chp1, Chlamydia virus Chp2, Chlamydia virus CPAR39, Chlamydia virus CPG1, Spiroplasma virus SpV4, Acholeplasma virus L2, Pseudomonas virus PR4, Pseudomonas virus PRD1, Bacillus virus AP50, Bacillus virus Bam35, Bacillus virus GIL16, Bacillus virus Wip1, Escherichia virus phi80, Escherichia virus RB42, Escherichia virus T2, Escherichia virus T3, Escherichia virus T6, Escherichia virus VT2-Sa, Escherichia virus VT1-Sakai, Escherichia virus VT2-Sakai, Escherichia virus CP-933V, Escherichia virus P27, Escherichia virus Stx2phi-I, Escherichia virus Stx1phi, Escherichia virus Stx2phi-II, Escherichia virus CP-1639, based on the Escherichia virus BP-4795, Escherichia virus 86, Escherichia virus Min27, Escherichia virus 2851, Escherichia virus 1717, Escherichia virus YYZ-2008, Escherichia virus EC026_P06, Escherichia virus ECO103_P15, Escherichia virus ECO103_P12, Escherichia virus ECO111_P16, Escherichia virus ECO111_P11, Escherichia virus VT2phi_272, Escherichia virus TL-2011c, Escherichia virus P13374, Escherichia virus Spy.

In one embodiment, the bacterial virus particles target *E. coli* and includes the capsid of a bacteriophage selected in the group consisting of BW73, B278, D6, D108, E, E1, E24, E41, FI-2, FI-4, FI-5, HI8A, Ffl8B, i, MINI, Mu, 025, PhI-5, Pk, PSP3, P1, P1D, P2, P4, S1, Wφ, φK13, φl, φ2, φ7 , φ92, 7 A, 8φ, 9φ, 18, 28-1, 186, 299, HH-*Escherichia* (2), AB48, CM, C4, C16, DD-VI, E4, E7, E28, FIl, FI3, H, H1, H3, H8, K3, M, N, ND-2, ND-3, ND4, ND-5, ND6, ND-7, Ox-I, Ox-2, Ox-3, Ox-4, Ox-5, Ox-6, PhI-I, RB42, RB43, RB49, RB69, S, SaI-I, Sal-2, Sal-3, Sal-4, Sal-5, Sal-6, TC23, TC45, TuII*-6, TuIP-24, TuII*46, TuIP-60, T2, T4, T6, T35, αl, 1, IA, 3, 3A, 3T+, 5φ, 9266Q, CFO103, HK620, J, K, KlF, m59, no. A, no. E, no. 3, no. 9, N4, sd, T3, T7, WPK, W31, ΔH, φC3888, φK3, φK7, φK12, φV-1, Φ04-CF, Φ05, Φ06 , Φ07, φl, φ1.2, φ20 , φ95, φ263, φlO92, φl, φll, Ω8, 1, 3, 7, 8, 26, 27, 28-2, 29, 30, 31, 32, 38, 39, 42, 933W, NN-*Escherichia* (1), Esc-7-11, AC30, CVX-5, Cl, DDUP, ECl, EC2, E21, E29, Fl, F26S, F27S, Hi, HK022, HK97, HK139, HK253, HK256, K7, ND-I, PA-2, q, S2, Tl), T3C, T5, UC-I, w, β4, γ2, λ, ΦD326, φγ, Φ06 , Φ7 , Φ10 , φ80, χ, 2, 4, 4A, 6, 8A, 102, 150, 168, 174, 3000, AC6, AC7, AC28, AC43, AC50, AC57, AC81, AC95, HK243, KlO, ZG/3A, 5, 5A, 21EL, H19-J and 933H.

Prebiotics include, but are not limited to, amino acids, biotin, fructo-oligosaccharide, galacto-oligosaccharides, hemicelluloses (e.g., arabinoxylan, xylan, xyloglucan, and glucomannan), inulin, chitin, lactulose, mannan oligosaccharides, oligofructose-enriched inulin, gums (e.g., guar gum, gum arabic and carregenaan), oligofructose, oligodextrose, tagatose, resistant maltodextrins (e.g., resistant starch), trans-galactooligosaccharide, pectins (e.g., xylogalactouronan, citrus pectin, apple pectin, and rhamnogalacturonan-I), dietary fibers (e.g., soy fiber, sugarbeet fiber, pea fiber, corn bran, and oat fiber) and xylooligosaccharides.

Probiotics include, but are not limited to lactobacilli, bifidobacteria, streptococci, enterococci, propionibacteria, saccaromycetes, lactobacilli, bifidobacteria, or proteobacteria.

The antibiotic can be selected from the group consisting in penicillins such as penicillin G, penicillin K, penicillin N, penicillin O, penicillin V, methicillin, benzylpenicillin, nafcillin, oxacillin, cloxacillin, dicloxacillin, ampicillin, amoxicillin, pivampicillin, hetacillin, bacampicillin, metampicillin, talampicillin, epicillin, carbenicillin, ticarcillin, temocillin, mezlocillin, and piperacillin; cephalosporins such as cefacetrile, cefadroxil, cephalexin, cefaloglycin, cefalonium, cefaloridine, cefalotin, cefapirin, cefatrizine, cefazaflur, cefazedone, cefazolin, cefradine, cefroxadine, ceftezole, cefaclor, cefonicid, cefprozil, cefuroxime, cefuzonam, cefmetazole, cefotetan, cefoxitin, loracarbef, cefbuperazone, cefminox, cefotetan, cefoxitin, cefotiam, cefcapene, cefdaloxime, cefdinir, cefditoren, cefetamet, cefixime, cefmenoxime, cefodizime, cefotaxime, cefovecin, cefpimizole, cefpodoxime, cefteram, ceftamere, ceftibuten, ceftiofur, ceftiolene, ceftizoxime, ceftriaxone, cefoperazone, ceftazidime, latamoxef, cefclidine, cefepime, cefluprenam, cefoselis, cefozopran, cefpirome, cefquinome, flomoxef, ceftobiprole, ceftaroline, ceftolozane, cefaloram, cefaparole, cefcanel, cefedrolor, cefempidone, cefetrizole, cefivitril, cefmatilen, cefmepidium, cefoxazole, cefrotil, cefsumide, ceftioxide, cefuracetime, and nitrocefin; polymyxins such as polysporin, neosporin, polymyxin B, and polymyxin E, rifampicins such as rifampicin, rifapentine, and rifaximin; Fidaxomicin; quinolones such as cinoxacin, nalidixic acid, oxolinic acid, piromidic acid, pipemidic acid, rosoxacin, ciprofloxacin, enoxacin, fleroxacin, lomefloxacin, nadifloxacin, norfloxacin, ofloxacin, pefloxacin, rufloxacin, balofloxacin, grepafloxacin, levofloxacin, pazufloxacin, temafloxacin, tosufloxacin, clinafloxacin, gatifloxacin, gemifloxacin, moxifloxacin, sitafloxacin, trovafloxacin, prulifloxacin, delafloxacin, nemonoxacin, and zabofloxacin; sulfonamides such as sulfafurazole, sulfacetamide, sulfadiazine, sulfadimidine, sulfafurazole, sulfisomidine, sulfadoxine, sulfamethoxazole, sulfamoxole, sulfanitran, sulfadimethoxine, sulfametho-xypyridazine, sulfametoxydiazine, sulfadoxine, sulfametopyrazine, and terephtyl; macrolides such as azithromycin, clarithromycin, erythromycin, fidaxomicin, telithromycin, carbomycin A, josamycin, kitasamycin, midecamycin, oleandomycin, solithromycin, spiramycin, troleandomycin, tylosin, and roxithromycin; ketolides such as telithromycin, and cethromycin; lluoroketolides such as solithromycin; lincosamides such as lincomycin, clindamycin, and pirlimycin; tetracyclines such as demeclocycline, doxycycline, minocycline, oxytetracycline, and tetracycline; aminoglycosides such as amikacin, dibekacin, gentamicin, kanamycin, neomycin, netilmicin, sisomicin, tobramycin, paromomycin, and streptomycin; ansamycins such as geldanamycin, herbimycin, and rifaximin; carbacephems such as loracarbef; carbapenems such as ertapenem, doripenem, imipenem (or cilastatin), and meropenem; glycopeptides such as teicoplanin, vancomycin, telavancin, dalbavancin, and oritavancin; lincosamides such as clindamycin and lincomycin; lipopeptides such as daptomycin; monobactams such as aztreonam; nitrofurans such as furazolidone, and nitrofurantoin; oxazolidinones such as linezolid, posizolid, radezolid, and torezolid; teixobactin, clofazimine, dapsone, capreomycin, cycloserine, ethambutol, ethionamide, isoniazid, pyrazinamide, rifabutin, arsphenamine, chloramphenicol, fosfomycin, fusidic acid, metronidazole, mupirocin, platensimycin, quinupristin (or dalfopristin), thiamphenicol, tigecycline, tinidazole, trimethoprim, alatrofloxacin, fidaxomycin, nalidixice acide, rifampin, derivatives and combination thereof.

The present invention provides pharmaceutical or veterinary compositions comprising one or more of the bacterial delivery vehicles disclosed herein and a pharmaceutically-acceptable carrier. Generally, for pharmaceutical use, the bacterial delivery vehicles may be formulated as a pharmaceutical preparation or compositions comprising at least one bacterial delivery vehicles and at least one pharmaceutically acceptable carrier, diluent or excipient, and optionally one or more further pharmaceutically active compounds. Such a formulation may be in a form suitable for oral administration, for parenteral administration (such as by intravenous, intramuscular or subcutaneous injection or intravenous infusion), for topical administration, for administration by inhalation, by a skin patch, by an implant, by a suppository, etc. Such administration forms may be solid, semi-solid or liquid, depending on the manner and route of administration. For example, formulations for oral administration may be provided with an enteric coating that will allow the synthetic bacterial delivery vehicles in the formulation to resist the gastric environment and pass into the intestines. More generally, synthetic bacterial delivery vehicle formulations for oral administration may be suitably formulated for delivery into any desired part of the gastrointestinal tract. In addition, suitable suppositories may be used for delivery into the gastrointestinal tract. Various pharmaceutically acceptable carriers, diluents and excipients useful in bacterial delivery vehicle compositions are known to the skilled person.

Also provided are methods for treating a bacterial infection using the synthetic bacterial delivery vehicles disclosed herein. The methods include administering the synthetic bacterial delivery vehicles or compositions disclosed herein to a subject having a bacterial infection in need of treatment. In some embodiments, the subject is a mammal. In some embodiments, the subject is a human.

The pharmaceutical or veterinary composition according to the disclosure may further comprise a pharmaceutically acceptable vehicle. A solid pharmaceutically acceptable vehicle may include one or more substances which may also act as flavouring agents, lubricants, solubilisers, suspending agents, dyes, fillers, glidants, compression aids, inert binders, sweeteners, preservatives, dyes, coatings, or tablet-disintegrating agents. Suitable solid vehicles include, for example calcium phosphate, magnesium stearate, talc, sugars, lactose, dextrin, starch, gelatin, cellulose, polyvinylpyrrolidine, low melting waxes and ion exchange resins.

The pharmaceutical or veterinary composition may be prepared as a sterile solid composition that may be suspended at the time of administration using sterile water, saline, or other appropriate sterile injectable medium. The pharmaceutical or veterinary compositions of the disclosure may be administered orally in the form of a sterile solution or suspension containing other solutes or suspending agents (for example, enough saline or glucose to make the solution isotonic), bile salts, acacia, gelatin, sorbitan monoleate, polysorbate 8o (oleate esters of sorbitol and its anhydrides copolymerized with ethylene oxide) and the like. The particles according to the disclosure can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for enteral administration include sterile solutions, emulsions, and suspensions.

The bacterial delivery vehicles according to the disclosure may be dissolved or suspended in a pharmaceutically acceptable liquid vehicle such as water, an organic solvent, a mixture of both or pharmaceutically acceptable oils or fats. The liquid vehicle can contain other suitable pharmaceutical additives such as solubilisers, emulsifiers, buffers, preservatives, sweeteners, flavouring agents, suspending agents, thickening agents, colours, viscosity regulators, stabilizers or osmo-regulators. Suitable examples of liquid vehicles for oral and enteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and *arachis* oil). For parenteral administration, the vehicle can also be an oily ester such as ethyl oleate and isopropyl myristate. Sterile liquid vehicles are useful in sterile liquid form compositions for enteral administration. The liquid vehicle for pressurized compositions can be a halogenated hydrocarbon or other pharmaceutically acceptable propellant.

For transdermal administration, the pharmaceutical or veterinary composition can be formulated into ointment, cream or gel form and appropriate penetrants or detergents could be used to facilitate permeation, such as dimethyl sulfoxide, dimethyl acetamide and dimethylformamide.

For transmucosal administration, nasal sprays, rectal or vaginal suppositories can be used. The active compounds can be incorporated into any of the known suppository bases by methods known in the art. Examples of such bases include cocoa butter, polyethylene glycols (carbowaxes), polyethylene sorbitan monostearate, and mixtures of these with other compatible materials to modify the melting point or dissolution rate.

The diseases or disorders caused by bacteria may be selected from the group consisting of abdominal cramps, acne vulgaris, acute epiglottitis, arthritis, bacteraemia, bloody diarrhea, botulism, Brucellosis, brain abscess, chancroid venereal disease, *Chlamydia*, Crohn's disease, conjunctivitis, cholecystitis, colorectal cancer, polyposis, dysbiosis, Lyme disease, diarrhea, diphtheria, duodenal ulcers, endocarditis, erysipelothricosis, enteric fever, fever, glomerulonephritis, gastroenteritis, gastric ulcers, Guillain-Barre syndrome tetanus, gonorrhoea, gingivitis, inflammatory bowel diseases, irritable bowel syndrome, leptospirosis, leprosy, listeriosis, tuberculosis, Lady Widermere syndrome, Legionaire's disease, meningitis, mucopurulent conjunctivitis, multi-drug resistant bacterial infections, multi-drug resistant bacterial carriage, myonecrosis-gas gangrene, *Mycobacterium avium* complex, neonatal necrotizing enterocolitis, nocardiosis, nosocomial infection, otitis, periodontitis, phalyngitis, pneumonia, peritonitis, purpuric fever, Rocky Mountain spotted fever, shigellosis, syphilis, sinusitis, sigmoiditis, septicaemia, subcutaneous abscesses, tularaemia, tracheobronchitis, tonsillitis, typhoid fever, ulcerative colitis, urinary infection, whooping cough.

The infection caused by bacteria may be selected from the group consisting of skin infections such as acne, intestinal infections such as esophagitis, gastritis, enteritis, colitis, sigmoiditis, rectitis, and peritonitis, urinary tract infections, vaginal infections, female upper genital tract infections such as salpingitis, endometritis, oophoritis, myometritis, parametritis and infection in the pelvic peritoneum, respiratory tract infections such as pneumonia, intra-amniotic infections, odontogenic infections, endodontic infections, fibrosis, meningitis, bloodstream infections, nosocomial infection such as catheter-related infections, hospital acquired pneumonia, post-partum infection, hospital acquired gastroenteritis, hospital acquired urinary tract infections, or a combination thereof. Preferably, the infection according to the disclosure is caused by a bacterium presenting an antibiotic resistance. In a particular embodiment, the infection is caused by a bacterium as listed above in the targeted bacteria.

The disclosure concerns a pharmaceutical or veterinary composition for use in the treatment of metabolic disorder including, for example, obesity and diabetes.

In a particular embodiment, the disclosure concerns a pharmaceutical or veterinary composition for use in the treatment of pathologies involving bacteria of the human microbiome, such as inflammatory and auto-immune diseases, cancers, infections or brain disorders. Indeed, some bacteria of the microbiome, without triggering any infection, can secrete molecules that will induce and/or enhance inflammatory or auto-immune diseases or cancer development. More specifically, the present disclosure relates also to modulating microbiome composition to improve the efficacy of immunotherapies based, for example, on CAR-T (Chimeric Antigen Receptor T) cells, TIL (Tumor Infiltrating Lymphocytes) and Tregs (Regulatory T cells) also known as suppressor T cells. Modulation of the microbiome composition to improve the efficacy of immunotherapies may also include the use of immune checkpoint inhibitors well known in the art such as, without limitation, PD-1 (programmed cell death protein 1) inhibitor, PD-L1 (programmed death ligand 1) inhibitor and CTLA-4 (cytotoxic T lymphocyte associated protein 4).

Some bacteria of the microbiome can also secrete molecules that will affect the brain.

Therefore, a further object of the disclosure is a method for controlling the microbiome of a subject, comprising administering an effective amount of the pharmaceutical composition as disclosed herein in said subject.

In a particular embodiment, the disclosure also relates to a method for personalized treatment for an individual in need of treatment for a bacterial infection comprising: i) obtaining a biological sample from the individual and determining a group of bacterial DNA sequences from the sample; ii) based on the determining of the sequences, identifying one or more pathogenic bacterial strains or species that were in the sample; and iii) administering to the individual a pharmaceutical composition according to the disclosure capable of recognizing each pathogenic bacterial strain or species identified in the sample and to deliver the packaged plasmid.

Preferably, the biological sample comprises pathological and non-pathological bacterial species, and subsequent to administering the pharmaceutical or veterinary composition according to the disclosure to the individual, the amount of pathogenic bacteria on or in the individual are reduced, but the amount of non-pathogenic bacteria is not reduced.

In another particular embodiment, the disclosure concerns a pharmaceutical or veterinary composition according to the disclosure for use in order to improve the effectiveness of drugs. Indeed, some bacteria of the microbiome, without being pathogenic by themselves, are known to be able to metabolize drugs and to modify them in ineffective or harmful molecules.

In another particular embodiment, the disclosure concerns the in-situ bacterial production of any compound of interest, including therapeutic compound such as prophylactic and therapeutic vaccine for mammals. The compound of interest can be produced inside the targeted bacteria, secreted from the targeted bacteria or expressed on the surface of the targeted bacteria. In a more particular embodiment, an antigen is expressed on the surface of the targeted bacteria for prophylactic and/or therapeutic vaccination.

The present disclosure also relates to a non-therapeutic use of the bacterial delivery particles. For instance, the non-therapeutic use can be a cosmetic use or a use for improving the well-being of a subject, in particular a subject who does not suffer from a disease. Accordingly, the present disclosure also relates to a cosmetic composition or a non-therapeutic composition comprising the bacterial delivery particles if the disclosure.

Example 1

The example below demonstrates that a significative portion of a lambda receptor binding protein (RBP), e.g. the stf protein, can be exchanged with a portion of a different RBP. More particularly, specific fusion positions in the lambda RBP have been identified which allow one to obtain a functional chimeric RBP. Specifically, the data demonstrate, in a non-limiting embodiment, that in the case of phagemids derived from bacteriophage lambda, modifying the side tail fiber protein results in an expanded host range. The addition of chimeric stf proteins to lambdoid phagemids, is demonstrated to be a very powerful approach to modify and increase their host range, and in some cases is more efficient than the modification of the gpJ gene. In addition, modification of the side tail fiber protein to encode depolymerase activities can dramatically increase the delivery efficiency. In some cases, the addition of this enzymatic activity allows for 100% delivery efficiency while the wild-type lambda phagemid showed no entry at all. These two approaches can be combined to generate phagemid variants with different specificities and delivery efficiencies to many strains of bacterial species.

Tests were conducted to determine whether the modification of the tail tip gene (gpJ) would have an impact in the host range of lambda phagemids. The lambda tail tip was modified to include the mutations described in [11] to generate OMPF-lambda. This phagemid should now use OmpF instead of LamB as a primary receptor in the cell surface. Next, the delivery efficiency was tested in a collection of *E. coli* strains that spans a variety of O and K serotypes, as shown in FIG. 1.

As can be seen in FIG. 1, using phagemids that recognize a different cell surface receptor has a minimal impact on efficiency delivery and host range. Only 3 strains show a marginal improvement in the number of colonies after treatment with the modified phagemid. This result may be due to the presence of a capsule around the majority of the cells that forms a physical barrier to the phagemids, thus rendering this approach unsuccessful. In view of these results, the lambda stf gene was modified to include enzymatic activities against bacterial capsules.

```
The sequence of lambda stf (SEQ ID NO: 1) is:
MAVKISGVLKDGTGKPVQNCTIQLKARRNSTTVVVNTV
GSENPDEAGRYSMDVEYGQYSVILQVDGFPPSHAGTIT
VYEDSQPGTLNDFLCAMTEDDARPEVLRRLELMVEEVA
RNASVVAQSTADAKKSAGDASASAAQVAALVTDATDSA
RAASTSAGQAASSAQEASSGAEAASAKATEAEKSAAAA
ESSKNAAATSAGAAKTSETNAAASQQSAATSASTAATK
ASEAATSARDAVASKEAAKSSETNASSSAGRAASSATA
AENSARAAKTSETNARSSETAAERSASAAADAKTAAAG
SASTASTKATEAAGSAVSASQSKSAAEAAAIRAKNSAK
RAEDIASAVALEDADTTRKGIVQLSSATNSTSETLAAT
PKAVKVVMDETNRKAPLDSPALTGTPTAPTALRGTNNT
QIANTAFVLAAIADVIDASPDALNTLNELAAALGNDPD
FATTMTNALAGKQPKNATLTALAGLSTAKNKLPYFAEN
DAASLTELTQVGRDILAKNSVADVLEYLGAGENSAFPA
GAPIPWPSDIVPSGYVLMQGQAFDKSAYPKLAVAYPSG
VLPDMRGWTIKGKPASGRAVLSQEQDGIKSHTHSASAS
GTDLGTKTTSSFDYGTKTTGSFDYGTKSTNNTGAHAHS
LSGSTGAAGAHAHTSGLRMNSSGWSQYGTATITGSLST
VKGTSTQGIAYLSKTDSQGSHSHSLSGTAVSAGAHAHT
VGIGAHQHPVVIGAHAHSFSIGSHGHTITVNAAGNAEN
TVKNIAFNYIVRLA
```

The bold and underlined sequence represents the part of the protein that was introduced in the T4 phage [47]. Experiments were conducted to investigate if it was possible to exchange the C-terminus of the lambda stf with a tail fiber from a different phage to yield chimeric side tail fibers with an enzymatic activity against encapsulated *E. coli*. The tail fiber from the K1F phage which has been studied in depth and its structure solved [19], [20] was chosen. K1F encodes an enzyme with endosialidase activity, which is active against polymer of sialic acid secreted by K1-encapsulated *E. coli*. In fact, K1+ strains are immune to T7 infection because the capsule forms a physical barrier that prevents attachment of the phage, but if purified K1F enzyme is added to the cells before infection, T7 is able to lyse them [21], confirming that the presence of bacterial capsules is a powerful mechanism to avoid recognition by bacteriophages. Thus, by testing delivery of modified lambda-stf-K1 phagemids in K1+ strains it was possible to verify whether the lambda-stf chimeric proteins retain its enzymatic activity.

The sequence of KIF tail fiber (SEQ ID NO: 121) is:

MSTITQFPSGNTQYRIEFDYLARTFVVVTLVNSSNPTLNRVLEVGRDYR

FLNPTMIEMLVDQSGFDIVRIHRQTGTDLVVDFRNGSVLTASDLTTAEL

QAIHIAEEGRDQTVDLAKEYADAAGSSAGNAKDSEDEARRIAESIRAAG

LIGYMTRRSFEKGYNVTTWSEVLLWEEDGDYYRWDGTLPKNVPAGSTPE

TSGGIGLGAWVSVGDAALRSQISNPEGAILYPELHRARWLDEKDARGWG

AKGDGVTDDTAALTSALNDTPVGQKINGNGKTYKVTSLPDISRFINTRF

VYERIPGQPLYYASEEFVQGELFKITDTPYYNAWPQDKAFVYENVIYAP

YMGSDRHGVSRLHVSWVKSGDDGQTWSTPEWLTDLHPDYPTVNYHCMSM

GVCRNRLFAMIETRTLAKNALTNCALWDRPMSRSLHLTGGITKAANQRY

ATIHVPDHGLFVGDFVNFSNSAVTGVSGDMTVATVIDKDNFTVLTPNQQ

TSDLNNAGKNWHMGTSFHKSPWRKTDLGLIPSVTEVHSFATIDNNGFAM

GYHQGDVAPREVGLFYFPDAFNSPSNYVRRQIPSEYEPDASEPCIKYYD

GVLYLITRGTRGDRLGSSLHRSRDIGQTWESLRFPHNVHHTTLPFAKVG

DDLIMFGSERAENEWEAGAPDDRYKASYPRTFYARLNVNNWNADDIEWV

NITDQIYQGGIVNSGVGVGSVVVKDNYIYYMFGGEDHFNPWTYGDNSAK

DPFKSDGHPSDLYCYKMKIGPDNRVSRDFRYGAVPNRAVPVFFDTNGVR

TVPAPMEFTGDLGLGHVTIRASTSSNIRSEVLMEGEYGFIGKSIPTDNP

AGQRIIFCGGEGTSSTTGAQITLYGANNTDSRRIVYNGDEHLFQSADVK

PYNDNVTALGGPSNRFTTAYLGSNPIVTSNGERKTEPVVFDDAFLDAWG

DVHYIMYQWLDAVQLKGNDARIHFGVIAQQIRDVFIAHGLMDENSTNCR

YAVLCYDKYPRMTDTVFSHNEIVEHTDEEGNVTTTEEPVYTEVVIHEEG

EEWGVRPDGIFFAEAAYQRRKLERIEARLSALEQK

The bold and underlined sequence represents the part of the protein that has been crystalized and has been shown to retain its endosialidase activity. Since there is no identity between the lambda stf protein and the K1F tail fiber, the insertion point was made based on conclusions extracted from different sources of information, including literature and crystal structures.

Figures 1, 12:
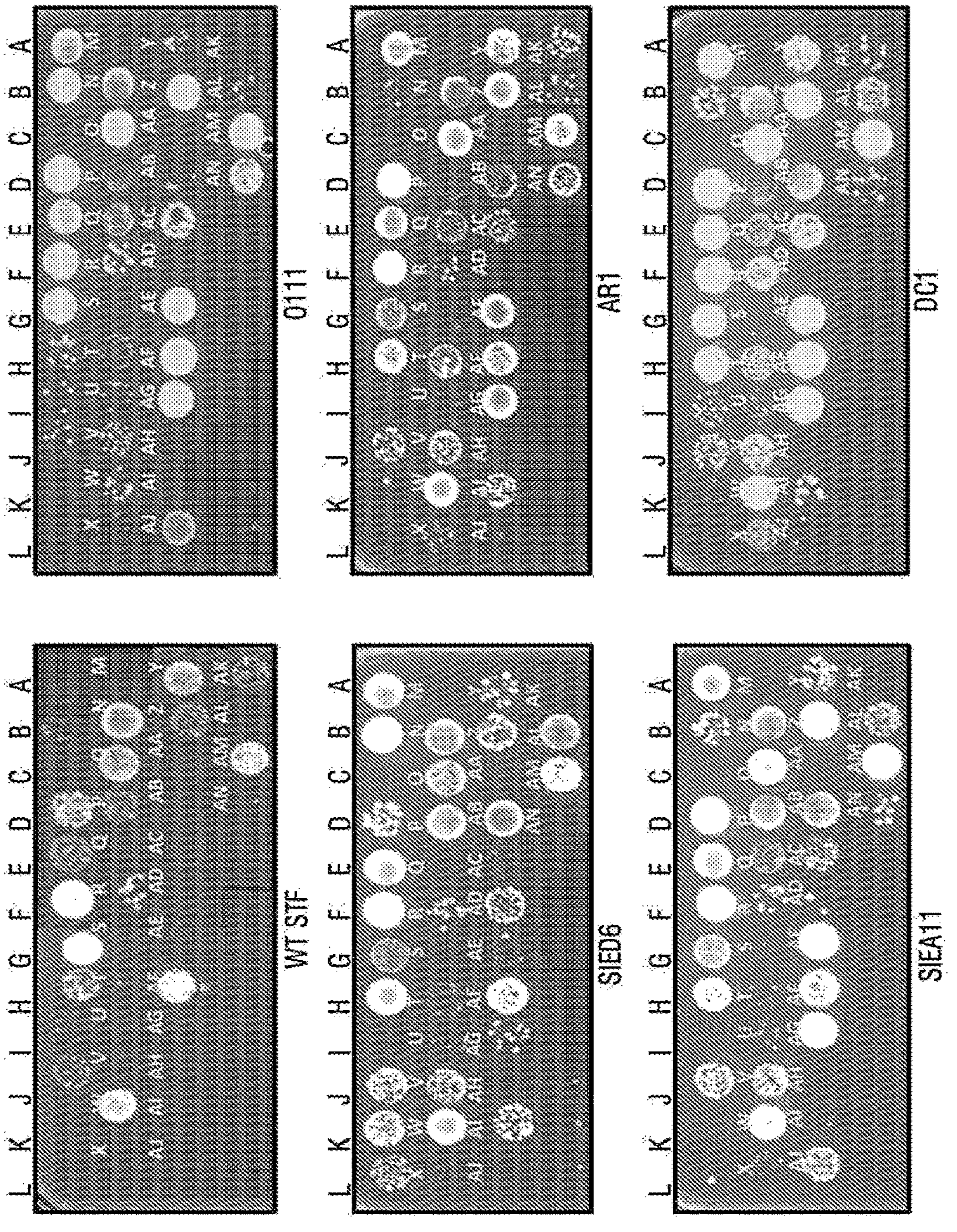
FIG. 12 depicts raw dot titrations of delivery particles with chimeric stf in 40 human strains of the ECOR collection. Below each panel, the name of the chimeric stf. Above each dot, the 1-2 letter code used to identify strains in FIG. 13.
Figures 2, 12:
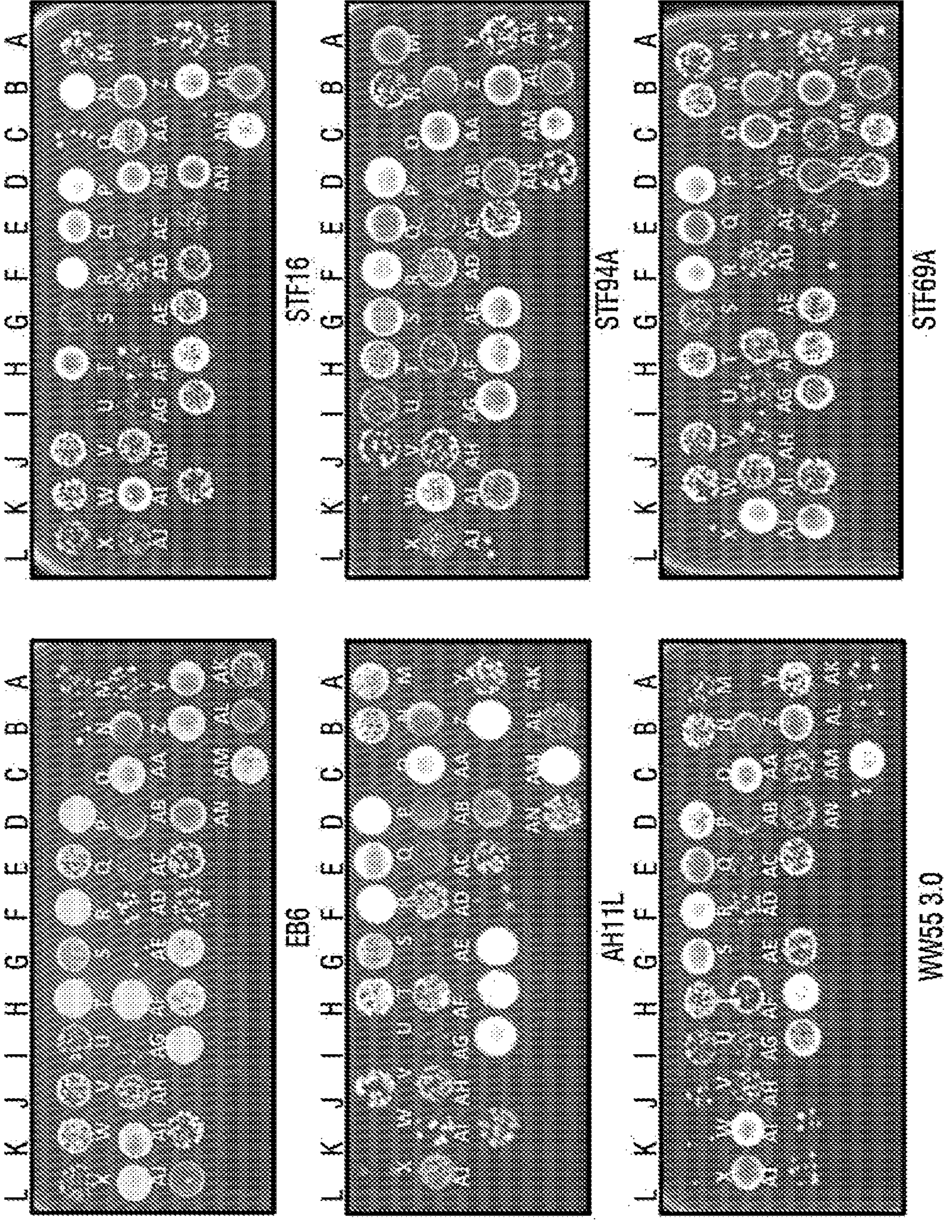
FIG. 2 depicts wild-type lambda and lambda-stf-K1F chimeric delivery vehicles on K1+ strains. Lambda packaged phagemids were sequentially diluted 10× in LB plus 5 mM CaCl2 and 10 uL added in each well. Cells grown to an OD600 of around 0.5 were then added to each phagemid dilution, incubated for 30 min at 37° C. and 10 uL plated on LB supplemented with chloramphenicol. Top panel, strain UTI89; bottom panel, strain S88. Left plates, wild type lambda packaged phagemids; right plates, stf-K1F lambda packaged phagemids.
Figures 3, 12:
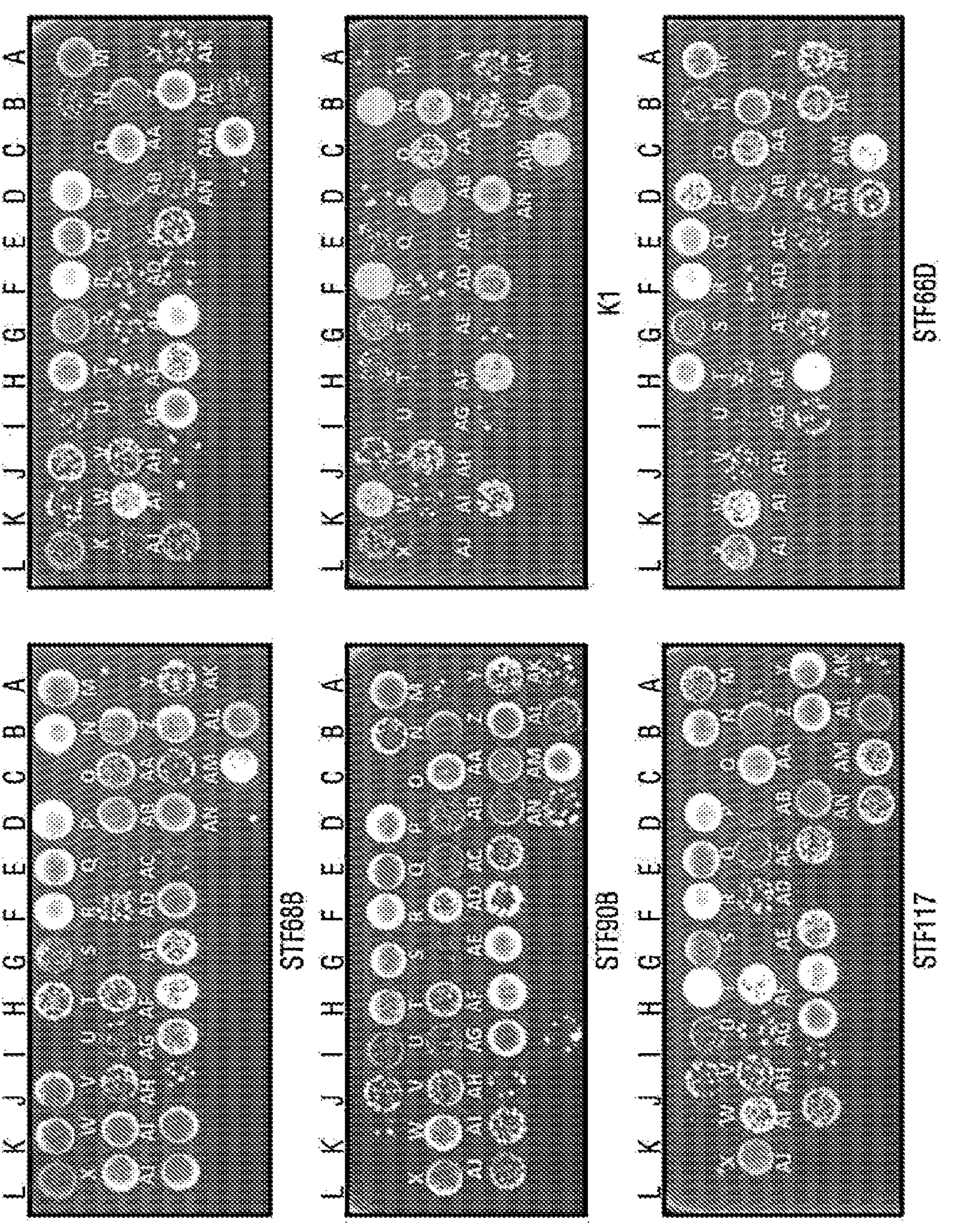

The stf gene was modified to include the K1F endosialidase at its C-terminus using a Cas9-mediated gene exchange protocol [22]. lambda-K1F phagemids were produced as in [23] and titrated against some K1+ strains, specifically *E. coli* UTI89 and S88. The results were striking; in these strains, there is no delivery if lambda wild-type stf is used, but the addition of the K1F variant gives 100% delivery (FIG. 2).

Figure 3:
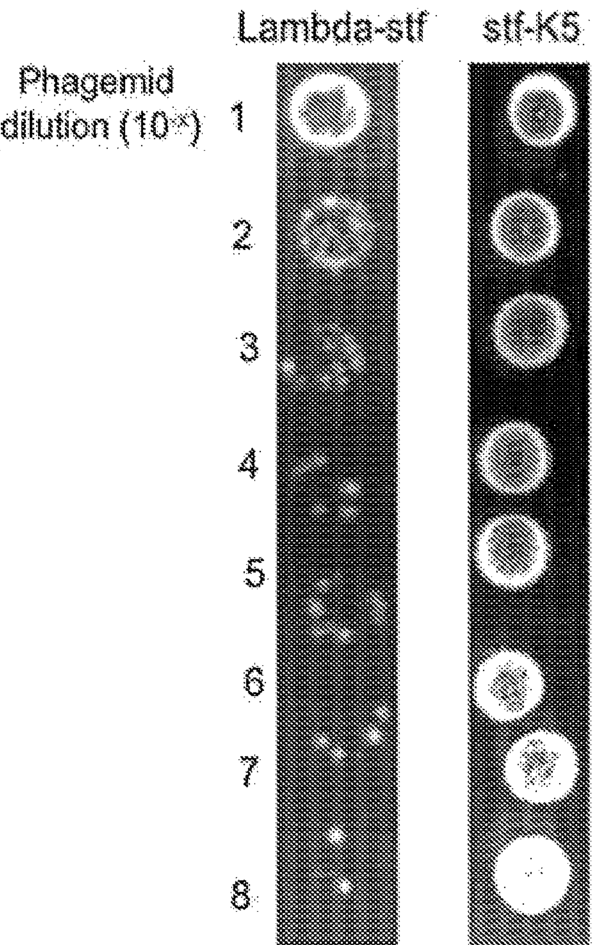
FIG. 3 depicts wild-type lambda and lambda-stf-K5 chimeric delivery vehicles on a K5+ strain. Lambda packaged phagemids were sequentially diluted 10× in LB plus 5 mM CaCl2 and 10 uL added in each well. ECOR55 grown to an OD600 of around 0.5 were then added to each phagemid dilution, incubated for 30 min at 37° C. and 10 uL plated on LB supplemented with chloramphenicol. Left panel, wild type lambda packaged phagemids; right panel, stf-K15 lambda packaged phagemids.

The same principle was followed to create a different variant of lambda-stf, this time with K5-capsule degrading activity (K5 lyase tail fiber from phage K5A). As in the case of K1F, there is no homology between lambda-stf and K5 lyase, but its crystal structure has been published [24]. Hence, the same approach as for K1F was used to generate stf-K5 chimeric side tail fibers and tested the produced phagemids against a K5-encapsulated strain of *E. coli* (ECOR 55). In this case, however, a delta-stf lambda production strain was produced with the stf fusion gene expressed in trans under the control of an inducible promoter. As depicted in FIG. 3, there was some residual delivery using the wild-type lambda-stf, probably due to the presence of some cells with a thinner K5 capsule. However, the addition of lambda-stf-K5 chimeras allows for an improvement in delivery of more than $10^6$ fold.

In some other cases, side tail fibers can be found that have some degree of homology to lambda stf, although no crystal structure is available. In these cases, the insertion point was designed as the last stretch of amino acids with identity to lambda stf. For example, in two in-house sequenced phages, the predicted side tail fiber proteins are as follows:

Phage AG22 stf (SEQ ID NO: 262)

MAIYRQGQASMDAQGYVTGYGTKWREQLTLIRPGATIF

FLAQPLQAAVITEVISDTSIRAITTGGAVVQKTNYLI

LLHDSLTVDGLAQDVAETLRYYQGKESEFAGFIEIIKD

FDWDKLQKIQEDVKTNADAAAASQQAAKTSENNAKTSA

TNAANSKKGADTAKAAAESARDAANTAKTGAEAAKSGA

ESARDAANTAKAGAESARDQAEEYAKQAAEPYKDLLQP

LPDVWIPFNDSLDMITGFSPSYKKIVIGDDEITMPGDK

IVKFKRASTATYINKSGVLTNAAIDEPRFEKDGLLIEG

QRTNLLINSTNPSKWNKSSNMILDRSGVDDFGFQYAKF

TLKPEMVGQTSSINIVTVSGSRGFDVTGNEKYVTISCR

AQSGTPNLRCRLRFENYDGSAYASLGDAYVNLTDLSIE

KTGGAANRITARAVKDEASKWIFFEATIKALDTENMIG

AMVQYAPAKDGGGTGADDYIYIATPQVEGGVCASSFII

TEATPVTRASDMVTIPIKNNLYNLPFTVLCEVHKNWYI

TPNAAPRVFDTGGHQSGAAIILAFGSADGDNDGFPYCD

IGKSNRRVNENAKLKKMIIGMRVKSDYNTCCVSNARIS

SETKTEWRYIVSTATIRIGGQTSTGERHLFGHVRNFRI

WHKALTDHQLGEIV

Its alignment to lambda stf is as follows:

```
Lambda 156 STSAGQAASSAQEASSGAEAASAKATEAEKSAAAAESSENAAATSAGAAKTSETNAAASQ

AG22    92 ETLRYYQGKESEFAGFIEIIKDFDWDKLQKIQEDVKTNADAAAASQQAAKTSENNAKTSA
            *           *               *          *** *  ****** **  *
```

The sequence of the stf of a second in-house phage is as follows:

Phage SIEA11 stf (SEQ ID NO: 263)

MSTKFKTVITTAGAAKLAAATVPGGKKVTLSAMAV

GDGNGKLPVPDAGQTKLVHEVWRHALNKVSVDNKN

KNYIVAELVVPPEVGGFWMRELGLYDDAGTLIAVS

NMAESYKPELAEGSGRAQTCRMVIIVSNVASVELS

IDASTVMATQDYVDDKIAEHEQSRRHPDATLTEKG

-continued

FTQLSSATNSTSESLAATPKAVKAANDNANSRLAK

NQNGADIQDKSAFLDNVGVTSLTFMKNNGEMPVDA

DLNTFGSVKAYSGIWSKATSTNATLEKNFPEDNAV

GVLEVFTGGNFAGTQRYTTRDGNLYIRKLIGTWNG

NDGPWGAWRHVQAVTRALSTTIDLNSLGGAEHLGL

WRNSSSAIASFERHYPEQGGDAQGILEIFEGGLYG

RTQRYTTRNGTMYIRGLTAKWDAENPQWEDWNQIG

YQTSSTFYEDDLDDLMSPGIYSVTGKATHTPIQGQ

SGFLEVIRRKDGVYVLQRYTTTGTSAATKDRLYER

VFLGGSFNAWGEWRQIYNSNSLPLELGIGGAVAKL

TSLDWQTYDFVPGSLITVRLDNMTNIPDGMDWGVI

DGNLINISVGPSDDSGSGRSMHVWRSTVSKANYRF

FMVRISGNPGSRTITTRRVPIIDEAQTWGAKQTFS

AGLSGELSGNAATATKLKTARKINNVSFDGTSDIN

LTPKNIGAFASGKTGDTVANDKAVGWNWSSGAYNA

TIGGASTLILHFNIGEGSCPAAQFRVNYKNGGIFY

RSARDGYGFEADWSEFYTTTRKPTAGDVGALPLSG

GQLNGALGIGTSSALGGNSIVLGDNDTGFKQNGDG

NLDVYANSVHVMRFVSGSVQSNKTINITGRVNPSD

YGNFDSRYVRDVRLGTRVVQTMQKGVMYEKAGHVI

TGLGIVGEVDGDDPAVFRPIQKYINGTWYNVAQV

Its alignment to lambda stf is as follows:

```
Lambda 367 SSATNSTSETLAATPKAVKVVMDETNRKAPLDSPALTGTPTAPTALRGTNNTQIANTAFV

STEA11 180 SSATNSTBESLAATPRAVKAANDNANSRL---AKNQNGADTQDKSAF-LDNVGVTSLTPM
           ********* *********   *  *          *          *      *
```

In these two specific cases, it was unknown which antigen these side tail fibers were able to recognize, so lambda packaged phagemids with the chimeric side tail fibers were produced and their delivery efficiency was tested in a *E. coli* collection that contains a very diverse group of O and K serotypes.

Figure 4:
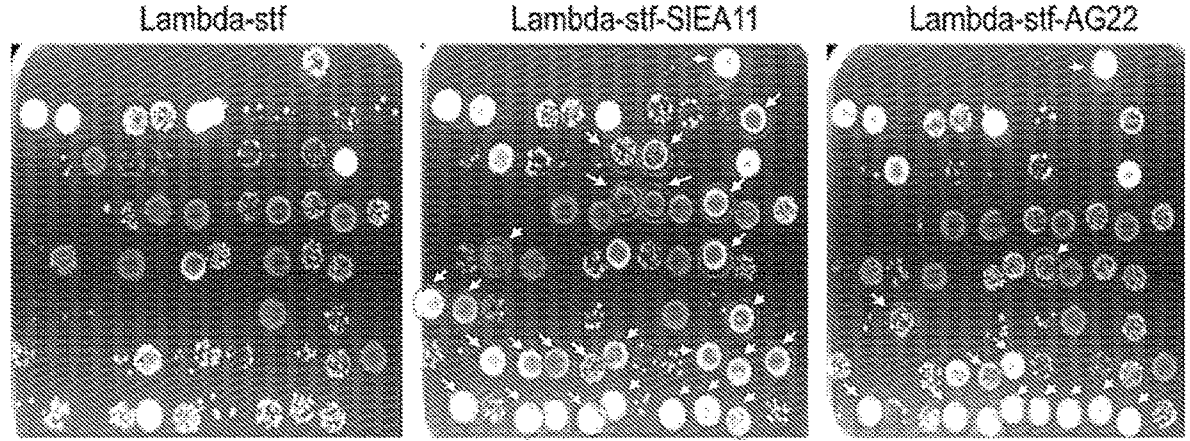
FIG. 4 depicts wild-type lambda, lambda-stf-AG22 and lambda-stf-SIEA11 chimeric delivery vehicles on a variety of encapsulated strains (0 and K capsules). Lambda phagemids were diluted 1:5 in LB plus 5 mM CaCl2 and 10 uL added in each well. 90 uL of cells grown to an OD600 of around 0.5 were then added to each phagemid-containing well, incubated for 30 min at 37° C. and 10 uL spotted on LB-agar supplemented with chloramphenicol. Left panel, wild type lambda phagemids; middle panel, lambda stf-SIEA11 variant; right panel, lambda-stf-AG22 variant. Circles show strains with modified delivery as compared to lambda wild-type.

As shown in FIG. 4, the addition of a chimeric stf allows the lambda-based phagemid to show increased delivery efficiency in 25 out of 96 strains tested (more than 25% of the collection). In some cases, the increase is modest; in others, it allows for very good delivery efficiency in strains that had no or very low entry with wild-type lambda phagemids. It is also worth noting that AG22 belongs to the Siphovirus family, like lambda, but SIEA11 is a P2-like phage. This highlights the significant observation that stf modules can be exchanged across bacteriophage genera.

Other side tail fiber genes have been analyzed as shown in FIG. 4 and several insertion points into the lambda stf gene have been identified that give chimeric variants with differential entry in the *E. coli* collection as shown previously. These insertion points are based on the results for the non-homologous tail fiber variants (such as in the cases for K1F and K5 above) or on varying degrees of homology between lambda stf and the variant to be tested. This homology can be short, about 5-10 aminoacids, or substantially similar. The insertion points tested are shown in bold and underlined below:

Lambda stf (SEQ ID NO: 1)
MAVKISGVLKDGTGKPVQNCTIQLKARRNSTTVVVNTV

GSENPDEAGRYSMDVEYGQYSV

ILQVDGFPPSHAGTITVYEDSQPGTLNDFLCAMTEDDA

RPEVLRRLELMVEEVARNASVVAQSTADAKKSAGDASA

SAAQVAALVTDATDSARAASTSAGQAASSAQEASSGAE

AASAKATEAEKSAAAAESSKNAAATSAGAAKTSETNAA

ASQQSAATSASTAATKASEAATSARDAVASKEAAKSSE

TNASSSAGRAASSATAAENSARAAKTSETNARSSETAA

ERSASAAADAKTAAAGSASTASTKATEAAGSAVSASQS

KSAAEAAAIRAKNSAKRAEDIASAVALEDADTTRKGIV

QLSSATNSTSETLAATPKAVKVVMDETNRKAPLDSPAL

TGTPTAPTALRGTNNTQIANTAFVLAAIADVIDASPDA

LNTLNELAAALGNDPDFATTMTNALAGKQPKNATLTAL

AGLSTAKNKLPYFAENDAASLTELTQVGRDILAKNSVA

DVLEYLGAGENSAFPAGAPIPWPSDIVPSGYVLMQGQA

FDKSAYPKLAVAYPSGVLPDMRGWTIKGKPASGRAVLS

QEQDGIKSHTHSASASGTDLGTKTTSSFDYGTKTTGSF

DYGTKSTNNTGAHAHSLSGSTGAAGAHAHTSGLRMNSS

GWSQYGTATITGSLSTVKGTSTQGIAYLSKTDSQGSHS

-continued

HSLSGTAVSAGAHAHTVGIGAHQHPVVIGAHAHSFSIG

SHGHTITVNAAGNAENTVKNIAFNYIVRLA

Figure 5:
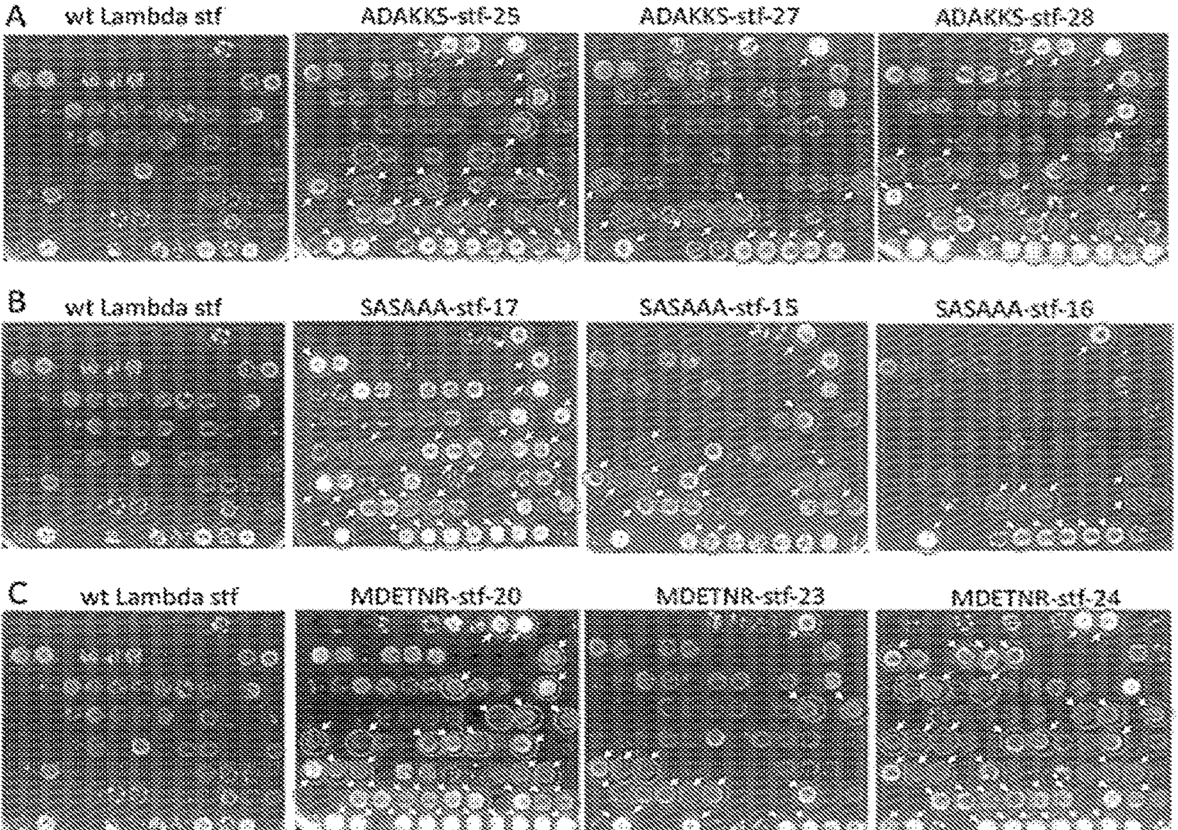
FIG. 5A-C demonstrates delivery of wild-type lambda and stf chimeras with different insertion sites on a variety of encapsulated strains (0 and K capsules). Lambda packaged phagemids were diluted 1:5 in LB plus 5 mM CaCl2 and 10 uL added in each well. 90 uL of cells grown to an OD600 of around 0.5 were then added to each phagemid-containing well, incubated for 30 min at 37° C. and 10 uL spotted on LB-agar supplemented with chloramphenicol. A) Left panel, wild type lambda packaged phagemids; rest of panels, three different ADAKKS-stf variants. B) Left panel, wild type lambda packaged phagemids; rest of panels, three different SASAAA-stf variants. C) Left panel, wild type lambda packaged phagemids; rest of panels, three different MDE-TNR-stf variants. For all panels, circles show strains with improved delivery efficiency as compared to lambda wild-type.

The lambda stf protein consists of 774 aminoacids. The insertion points can be found closer to the N-terminus (amino acid 131, insertion point ADAKKS (SEQ ID NO: 249)) or closer to the C-terminus (amino acid 529, insertion point GAGENS (SEQ ID NO: 252)). FIG. 5 depicts some selected examples for the insertion points ADAKKS (SEQ ID NO: 249), SASAAA (SEQ ID NO: 251) and MDETNR (SEQ ID NO: 250).

Figure 6:
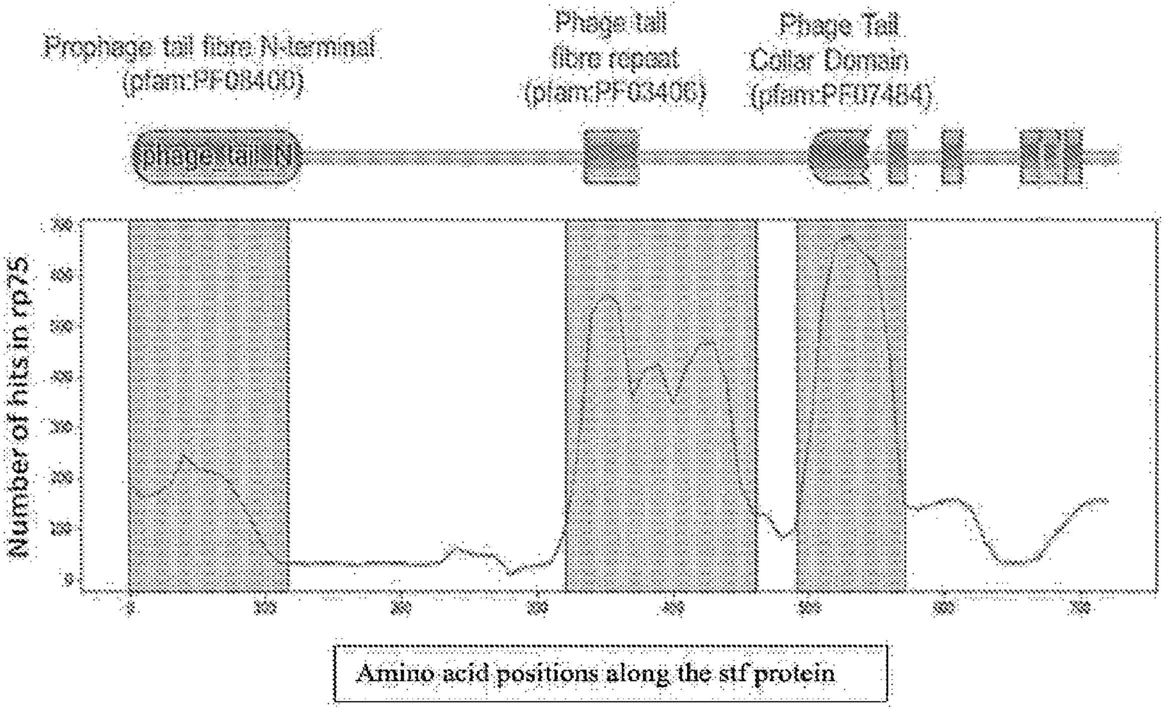
FIG. 6 depicts a phmmer search that was performed with a 50aa sliding window (step 10) on the representative proteome database (rp75). The number of significant hits (E-value <0.01) is reported.

The results described herein show that it is possible to build chimeric tail fibers that combine the part of one tail fiber that attaches to the capsid of one phage (usually the N-terminus of the protein) with the part of another fiber that interacts with the bacterium (usually the C-terminus of the protein). Stretches of homology between the sequence of different tail fibers can be considered as preferable recombination points. In order to identify such points for the stf protein of phage lambda a scan of the stf sequence was performed with a 50aa window and a phmmer search [25]

was performed on each window to identify homologous sequences in the representative proteome 75 database (FIG. 6).

Example 2

T4-like phages are a very diverse family of bacteriophages that share a common long tail fiber architecture: a proximal tail fiber that attaches to the phage particle and a distal tail fiber (DTF) that encodes host specificity linked by proteins acting as "hinge connectors" (Desplats and Krisch, 2003, Res. Microbiol. 154:259-267; Bartual et al. 2010, Proc. Natl. Acad. Sci. 107: 20287-20292). It is thought that the main host range determinants of the tail fiber reside in the distal part. Hence, it is very important to understand if it is possible to translate the host range of a given T4-like phage, which are known to be very broad, to any other phage or phagemid of interest. The distal tail fiber (C-terminal domain of the T4-like long tail fiber) of several T4-like phages were screened for possible functional insertion sites, several fusions with the Lambda stf gene were generated and their host range screened.

Figure 7:
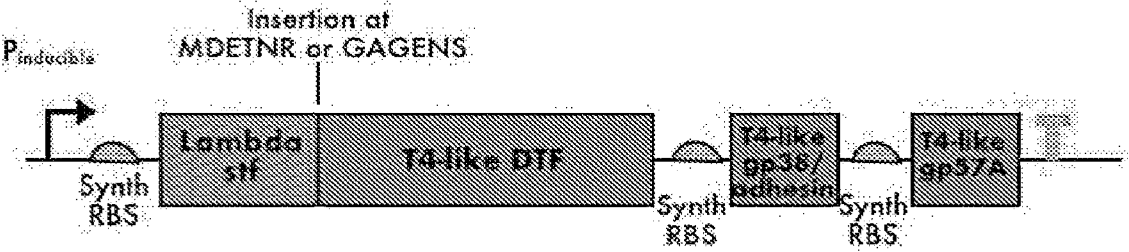
FIG. 7. depicts architecture of the engineered lambda stf-T4-like DTF chimera. The semicircles denote RBS sites; the T sign, a transcriptional terminator; the arrow, a promoter.

Possible insertion sites in the DTF that, when fused to a heterologous tail fiber (the lambda phage stf), will give a functional chimera were searched. The DTF of the phage (WW13) was used as a testbed. This phage possesses a classical T4-like architecture, with a proximal and a distal tail fiber separated by hinge connectors, a gp38 chaperone/adhesin (to assist folding of the tail fiber and recognition of the host (Trojet et al., 2011, Genome Biol. Evol. 3:674-686) and a gp57A chaperone known to be needed for proper folding of the tail fiber (Matsui et al., 1997, J. Bacteriol. 179:1846-1851). Since the endogenous genomic regulation of T4-like phages is complex and may include unknown layers of regulation (Miller et al., 2003, Microbio. Mol. Biol. Rev. 67:86-156), a synthetic linker encoding a RBS was designed to replace the natural DNA linker between the DTF gene and the adhesin; immediately downstream, another synthetic RBS preceding the chaperone gp57A was added, hence creating a polycistronic mRNA encoding for all the functions needed for the proper folding of the DTF (FIG. 7). This construct was built in a plasmid under the control of an inducible promoter and complemented in trans in a strain producing lambda-based phagemids.

Figure 11:
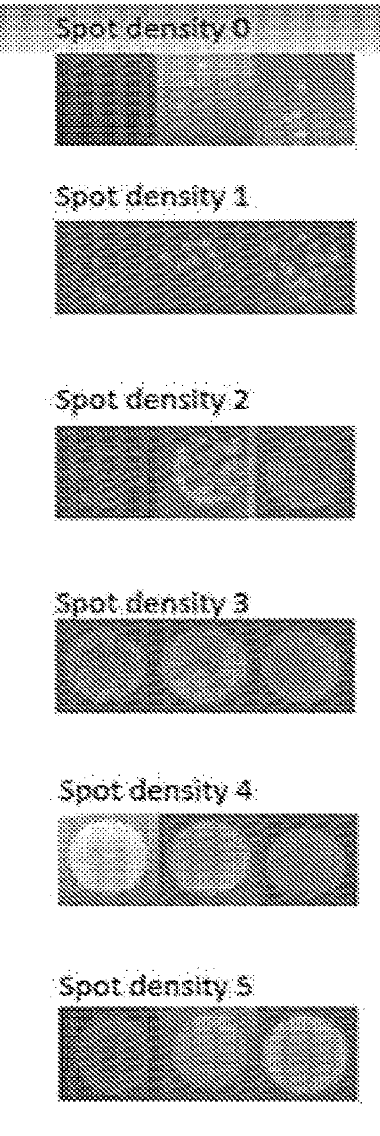
FIG. 11. depicts dot scoring system to quantify delivery efficiency. Density 0, 5 or fewer colonies; density 1, more than 5 colonies but not enough to define a clear circular drop; density 2, several colonies, but the background is clearly visible and some colonies are still separated; density 3, many colonies, the background is still visible but the colonies are hardly discernible as separate; density 4, spot almost completely dense, the background can only be seen faintly in some parts of the drop; density 5, spot looks completely dense, background cannot be seen.

FIG. 7. depicts the architecture of an engineered lambda stf-T4-like DTF chimera. The semicircles denote RBS sites; the T sign, a transcriptional terminator; the arrow, a promoter. Several parts of the C-terminus of the DTF were screened and fused to the lambda stf gene at the GAGENS (SEQ ID NO: 252) insertion site. Several variants of the chimera lambda stf-WW13 were functional, as assessed by production of phagemid particles and transduction of a chloramphenicol marker in a collection of *E. coli* strains. The functional chimeras shown in FIG. 8 were obtained with fusion at the IIQLED (SEQ ID NO: 254) insertion site in WW13. Additional functional chimeras were obtained by fusion at the lambda stf MDETNR (SEQ ID NO: 250) insertion site and at the WW13 DTF GNIIDL (SEQ ID NO: 255), VDRAV (SEQ ID NO: 261) and IIQLED (SEQ ID NO: 254) insertion sites (FIG. 11).

Figure 8:
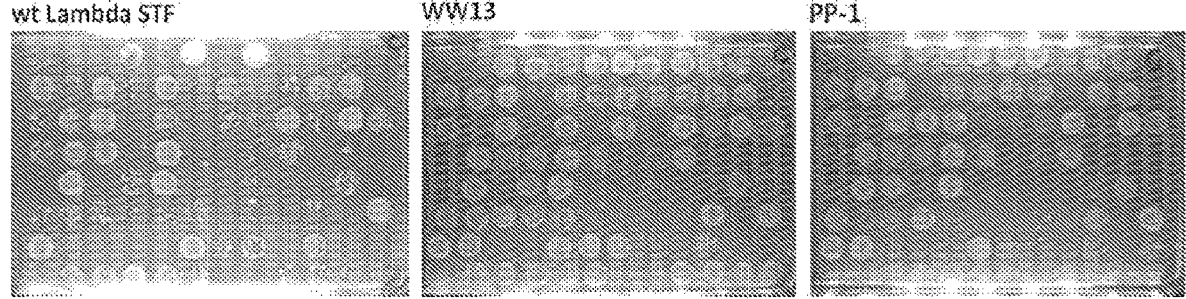
FIG. 8. shows screening of phagemid particles with chimeric lambda stf-T4-like DTFs. A collection of 96 different wild type *E. coli* strains, encompassing different serotypes, was transduced with lambda-based phagemids and plated on Cm LB agar. Left panel, wild-type lambda stf; middle panel, chimeric lambda-stf-WW13; right panel, chimeric lambda-stf-PP-1.

Other T4-like phages, like PP-1, sharing sequence homology with WW13 were also tested and verified to produce functional chimeras (FIG. 8). These functional chimeras show a IATRV insertion site at the beginning of PP-1 DTF part.

FIG. 8 depicts screening of phagemid particles with chimeric lambda stf-T4-like DTFs. A collection of 96 different wild type *E. coli* strains, encompassing different serotypes, was transduced with lambda-based phagemids and plated on Cm LB agar. Left panel represents wild-type lambda stf; the middle panel represents chimeric lambda-stf-WW13; and the right panel, represents chimeric lambda-stf-PP-1.

The insertion sites found for WW13 do not always exist in a given T4-like DTF, thereby complicating the analysis. Another functional insertion site without homology to WW13 was discovered for a second phage (WW55, FIG. 9). The same TPGEL insertion site could be found in a subset of T4-like phages and proven to yield functional chimeras with at least one of them, WW34 (FIG. 9), and at MDETNR (SEQ ID NO: 250) insertion site in lambda stf.

Figure 9:
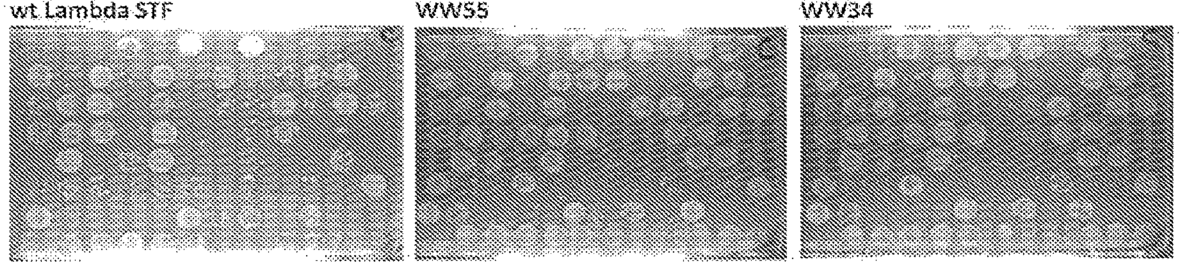
FIG. 9. demonstrates screening of phagemid particles with chimeric lambda stf-T4-like DTFs. A collection of 96 different wild type *E. coli* strains, encompassing different serotypes, was transduced with lambda-based phagemids and plated on Cm LB agar. Left panel, wild-type lambda stf; middle panel, chimeric lambda-stf-WW55; right panel, chimeric lambda-stf-WW34.

FIG. 9. shows screening of phagemid particles with chimeric lambda stf-T4-like DTFs. A collection of 96 different wild type *E. coli* strains, encompassing different serotypes, was transduced with lambda-based phagemids and plated on Cm LB agar. The left panel represents wild-type lambda stf; the middle panel represents chimeric lambda-stf-WW55; and the right panel represents chimeric lambda-stf-WW34.

Since T4-like DTF proteins may or may not share common sites for insertion, attempts were made to identify a universal insertion site that exists in all T4-like DTFs. When several T4-like DTFs are aligned, no homology along the whole DTF gene present in all the sequences exists, except for the N-terminus which is well conserved. The N-terminus of the DTF is thought to interact with the hinge connectors for attachment to the main phage particle.

Figure 10:
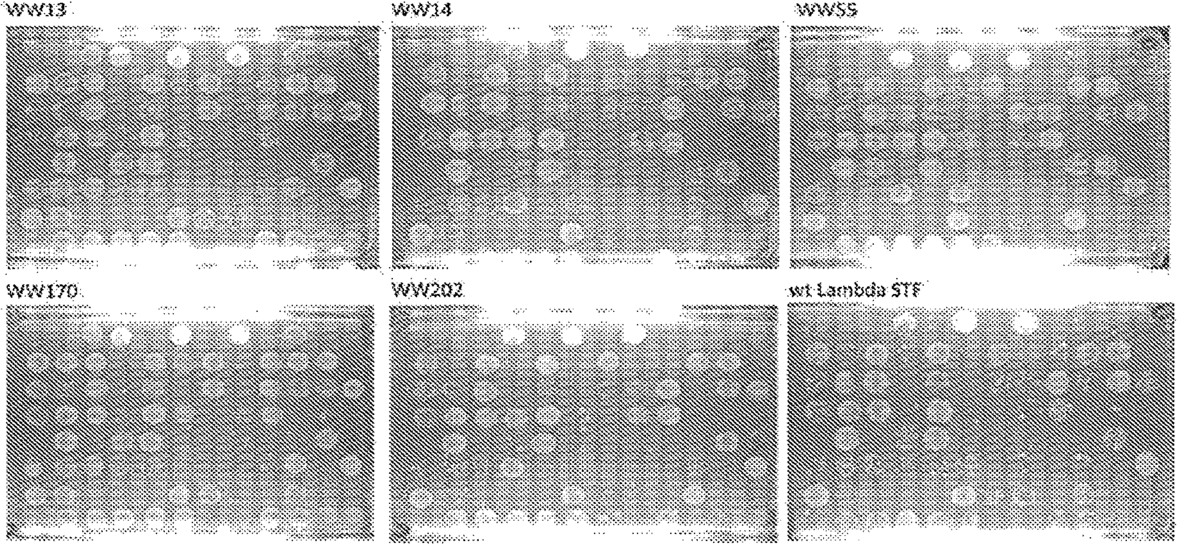
FIG. 10. depicts screening of phagemid particles with chimeric lambda stf-T4-like DTFs. All points shown refer to the universal insertion site of the DTF, located within aminoacid range from position 1 to 90 with reference to WW13 aminoacid sequence. A collection of 96 different wild type *E. coli* strains, encompassing different serotypes, was transduced with lambda-based phagemids and plated on Cm LB agar (names on top).

Although the classic view is that the host range determinants reside in the C-terminal part of the DTF, recent studies have proven that the N-terminus may also be involved in this process (Chen et al., 2017, Appl. Environ. Microbiol. Vl. 83 No. 23). The N-terminus of the DTF was then scanned to look for an insertion site that exists in all T4-like phages and that is able to yield functional chimeras. Phage WW13 DTF and insertion site MDETNR (SEQ ID NO: 250) in lambda stf were used. While the direct fusion of the complete DTF gene (starting at amino acid 2) gives particles with some activity, a region from amino acid 1 to 90, with a preferred region from amino acid 40 to 50 of the DTF, that recapitulates the behavior of the DTF fusion was identified and is shown in FIG. 10. Importantly, this region exists in all T4-like phages screened and could be very rapidly used to generate chimeras with a diverse set of DTFs, including WW55 (FIG. 10).

Accordingly, the present disclosure is useful for the generation of phage and phagemid particles with altered host ranges, since it provides a practical framework for the construction of chimeras using the DTFs from any T4-like phage, highlighting its modularity and translatability.

Example 3

The human microbiome comprises different zones of the body, including gut, skin, vagina and mouth [29]. The microbiota in these areas is composed of different communities of microorganisms, such as bacteria, archaea and fungi [29]-[31]. While numerous studies have been made that try to elucidate the specific composition of these communities, it is becoming clear that while there may exist a "core microbiome", there are many variations in the relative content of each microorganism depending on several factors, such as geographical location, diet or age [32]-[35].

Specifically, in the case of the human gut microbiota, it is not possible to know a priori what are the bacterial species that a given person possesses without running a diagnostic method. In the case of *Escherichia coli*, some studies have been made that point out to the prevalence of some serotypes and phylogenetic groups in the majority of humans; however, there are significant changes in the composition of the samples depending on the geographic distribution as well as the time of sampling: for example, samples isolated from Europe, Africa, Asia and South America in the 1980s show a prevalence for phylogroups A and B1 (55% and 21%, respectively); but samples obtained in the 2000s in Europe, North America, Asia and Australia belong mainly to the B2 group (43%), followed by the A (24%), D (21%), and B1 (12%) [36]. It is also thought that phylogenetic groups B2 and D are usually more commonly associated with pathogenic strains than with commensal strains [37], but there are studies showing a number of human- and non-human-specific strains belonging to phylogenetic group B2 that are commensals and belong to different serotypes [38].

The intrinsic variability of the human microbiome, and specifically that of *Escherichia coli* subtypes, makes it difficult to design targeted therapeutic approaches. In the case of phage therapy aimed at killing a target bacterial population, for instance, two possible approaches are possible: first, the use of narrow host range particles that are able to recognize and target a specific *E. coli* serotype or second the use of broad host range phages that are able to recognize many different strains, sometimes even from different genera [39]. This difficulty is exacerbated if one takes into account strategies that do not aim to kill the target bacterial population, but that seek to add a function to them (i.e. delivery of a factor that will have an effect in the host and that will be expressed by the targeted microbiota). In this specific case, the use of packaged phagemids is of great interest, since they do not kill the host (unless their payload carries genes aimed at killing the host), payload does not replicate and expand and does not contain any endogenous phage genes. However, as in the case of phages, a diagnostic study would be needed to identify the specific serotypes/variants of bacteria that exist in the patient before the treatment in order to find or design a packaged phagemid that allows for delivery of a payload adding a function to the target bacteria without killing them.

By combining these two approaches, it was proposed to use engineered delivery vehicles that are able to recognize a large number of strains belonging to different serotypes and phylogenetic groups (i.e., engineered particles having a "broad host range"), with a focus on *Escherichia coli*. As opposed to a killing-oriented approach, where the targeted bacterial population needs to be as close as possible to 100% to reduce their numbers, a therapeutic delivery approach does not need a priori to reach a large percentage of bacteria; the delivery needs to be high enough for the therapeutic payload to be expressed at the correct levels, which may be highly variable depending on the application. Additionally, the payload can be expressed by different serotypes or phylogenetic groups. This approach increases the chance that the particle will deliver a payload expressed in vivo in the majority of patients.

To achieve the delivery in bacterial communities composed of unknown serotypes/variants of target strains, delivery vehicles were engineered to contain chimeric side tail fibers (stf) that have been selected due to their ability to recognize a large variety of target strains. There are many phages that have been described as having a broad host range in *E. coli* and many of these belong to the T4 family, although in general, phages against *E. coli* and related bacteria have a restricted host range.

However, according to [41], there is no consensus as to how many strains need to be targeted by a phage to be considered as a "broad host range".

In the case of *Escherichia coli*, the ECOR collection is a set of strains isolated from different sources that is thought to represent the variability of this bacterium in Nature [42]. Some phage have been shown to have a broad host range against this collection (for instance, about 53% of the ECOR strains can be lysed with phage AR1 [43] and about 60% with phage SU16 [44]). As opposed to this, a single phage is able to infect 95% of *Staphylococcus aureus* strains [40].

It was decided to use human strains of this collection to test engineered delivery vehicles with chimeric stf and assess their host range in an attempt to identify variants that are able to recognize as many hosts as possible, as has been described in the literature [45]. The difference is that the present assays measure delivery efficiency as opposed to lysis.

Strains from an overnight culture were diluted 1:100 in 600 uL of LB supplemented with 5 mM CaCl2 in deep 96 well plates and grown for 2 hours at 37° C. at 900 rpm. 10 uL of packaged phagemids produced at an average of 106/uL were then added to 90 uL of the bacterial cultures, incubated 30 minutes at 37° C. and 10 uL of the mixtures plated on LB agar supplemented with 24 ug/mL chloramphenicol and incubated overnight at 37° C. The next day, the density of the dots was scored from 0 to 5, with 0 being no transductants and 5 being a spot with very high density [FIG. 11]. The density of the spots is directly related to the delivery efficiency of the packaged phagemids, since it corresponds to the number of bacteria that have received a payload containing a chloramphenicol acetyltransferase gene.

Figure 13:
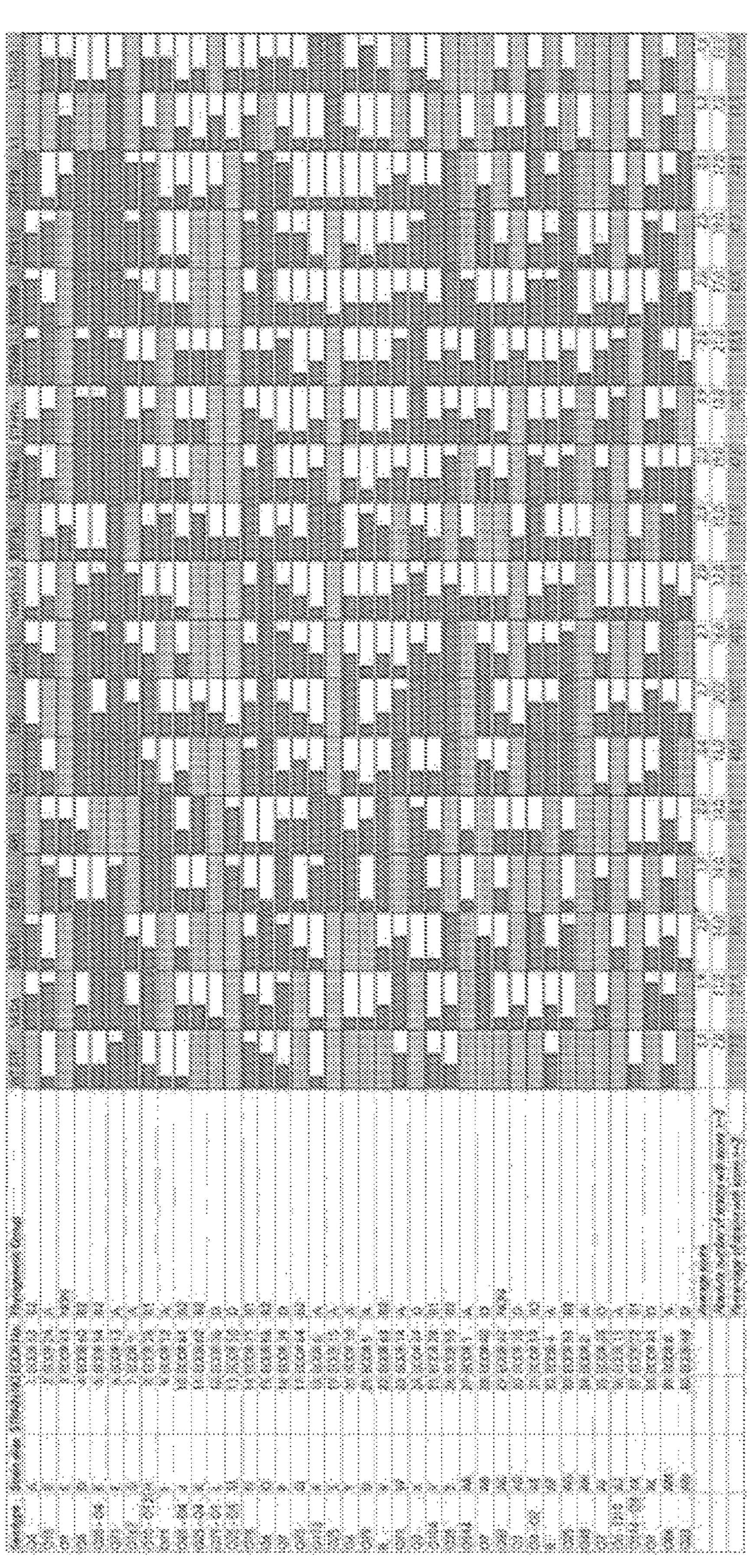
FIG. 13 represents bar-formatted delivery data of FIG. 12. From 0 (no entry, grey background) to 5 (maximum delivery). The bar length is proportional to the entry score from 1 (smallest bars) to 5 (longest bars).

Several stf chimeras were tested and screened in 40 human strains of the ECOR collection. As a control, the delivery efficiency of the wild-type stf was tested. The packaged phagemid variant used for the delivery experiments was modified so that its tail tip gpJ now recognizes a receptor other than LamB (1A2 variant)(SEQ ID NO: 214). In FIG. 12, the raw dot titrations for 18 stf are shown and in FIG. 13 a bar-formatted table is shown with the delivery efficiencies scored by dot density as well as the delivery statistics.

Taking only into account dots with density scores of 3 and higher (considered as medium to high delivery efficiency), some stf s can be considered as broad host range because the delivery efficiency in the selected ECOR strains is significantly higher than when using the wild type stf. For example, for stf EB6 or stf 68B, about 50% of the strains show medium to high delivery efficiencies, as compared to 17.5% of the strains with the wild type stf. These stf are good candidates for in vivo delivery, since they are able to deliver in different phylogenetic groups as well as serotypes. At the bottom of the Table in FIG. 13, a bar-formatted representation for density scores higher than 3 is shown, where the threshold for a broad host range stf is set at an increase of at least 2× compared to the basal line of the wild type stf; this is, stf that are able to deliver with scores of 3 and higher in at least 35% of the strains. Other stf also show an increased delivery as compared to the wild type stf, so a less stringent threshold was set for stf able to deliver with scores 3 or higher with at least a 50% increase compared to the number of strains delivered with the wild-type stf (this is, delivery with scores of 3 and higher in at least 26.25% of the strains). As a comparison, data for stf K1 and stf 66D is shown: these stf seem to be delivering efficiently in a small number of strains (for instance, strains B and AB for stf K1; and strains E and AF for stf 66D), which means that they probably have a narrow host range; this is to be expected, since in the case of the K1 stf the cognate receptor is the K1 capsule [46]. Additionally, data are shown for a chimera with a stf originating in a T4-like phage; as the literature suggests, this chimera shows a broad host range although it does not seem to be the best candidate.

Taken together, these results suggest that the stf of a delivery vehicle can be engineered to recognize a wide number of target *E. coli* strains, hence rendering it "broad host range". This type of particles can be very useful to deliver payloads adding a function to the target bacteria without having to engineer a specific variant that recognizes a given bacterial strain.

LIST OF REFERENCES CITED

Each of the reference cited within the specification and those listed below are hereby incorporated by reference in their entirety.

[1] G. P. C. Salmond and P. C. Fineran, "A century of the phage: past, present and future," Nat. Rev. Microbiol., vol. 13, no. 12, pp. 777-786, December 2015.

[2] P. Hyman and S. T. Abedon, "Bacteriophage host range and bacterial resistance," Adv. Appl. Microbiol., vol. 70, pp. 217-248, 2010.

[3] S. Chatterjee and E. Rothenberg, "Interaction of Bacteriophage λ, with Its *E. coli* Receptor, LamB," Viruses, vol. 4, no. 11, pp. 3162-3178, Nov. 2012.

[4] Nobrega et al, Nat Rev, 2018 "Targeting mechanisms of tailed bacteriophages"

[5] A. Flayhan, F. Wien, M. Paternostre, P. Boulanger, and C. Breyton, "New insights into pb5, the receptor binding protein of bacteriophage T5, and its interaction with its *Escherichia coli* receptor FhuA," Biochimie, vol. 94, no. 9, pp. 1982-1989, Sep. 2012.

[5] M. G. Rossmann, V. V. Mesyanzhinov, F. Arisaka, and P. G. Leiman, "The bacteriophage T4 DNA injection machine," Curr. Opin. Struct. Biol., vol. 14, no. 2, pp. 171-180, Apr. 2004.

[6] Y. Zivanovic et al., "Insights into Bacteriophage T5 Structure from Analysis of Its Morphogenesis Genes and Protein Components," J. Virol., vol. 88, no. 2, pp. 1162-1174, Jan. 2014.

[7] R. W. Hendrix and R. L. Duda, "Bacteriophage lambda PaPa: not the mother of all lambda phages," Science, vol. 258, no. 5085, pp. 1145-1148, Nov. 1992.

[8] M. A. Speed, T. Morshead, D. I. Wang, and J. King, "Conformation of P22 tailspike folding and aggregation intermediates probed by monoclonal antibodies," Protein Sci. Publ. Protein Soc., vol. 6, no. 1, pp. 99-108, Jan. 1997.

[9] S. J. Labrie, J. E. Samson, and S. Moineau, "Bacteriophage resistance mechanisms," Nat. Rev. Microbiol., vol. 8, no. 5, pp. 317-327, Mar. 2010.

[10] C. Whitfield, "Biosynthesis and assembly of capsular polysaccharides in *Escherichia coli*," Annu. Rev. Biochem., vol. 75, pp. 39-68, 2006.

[11] J. R. Meyer, D. T. Dobias, J. S. Weitz, J. E. Barrick, R. T. Quick, and R. E. Lenski, "Repeatability and contingency in the evolution of a key innovation in phage lambda," Science, vol. 335, no. 6067, pp. 428-432, Jan. 2012.

[12] D. S. Gupta et al., "Coliphage K5, specific for *E. coli* exhibiting the capsular K5 antigen," FEMS Microbiol. Lett., vol. 14, no. 1, pp. 75-78, May 1982.

[13] R. J. Gross, T. Cheasty, and B. Rowe, "Isolation of bacteriophages specific for the K1 polysaccharide antigen of *Escherichia coli*," J. Clin. Microbiol., vol. 6, no. 6, pp. 548-550, Dec. 1977.

[14] D. Schwarzer et al., "A Multivalent Adsorption Apparatus Explains the Broad Host Range of Phage phi92: a Comprehensive Genomic and Structural Analysis," J. Virol., vol. 86, no. 19, pp. 10384-10398, Oct. 2012.

[15] F. Tétart, F. Repoila, C. Monod, and H. M. Krisch, "Bacteriophage T4 host range is expanded by duplications of a small domain of the tail fiber adhesin," J. Mol. Biol., vol. 258, no. 5, pp. 726-731, May 1996.

[16] E. Haggard-Ljungquist, C. Halling, and R. Calendar, "DNA sequences of the tail fiber genes of bacteriophage P2: evidence for horizontal transfer of tail fiber genes among unrelated bacteriophages.," J. Bacteriol., vol. 174, no. 5, pp. 1462-1477, Mar. 1992.

[17] L.-T. Wu, S.-Y. Chang, M.-R. Yen, T.-C. Yang, and Y.-H. Tseng, "Characterization of Extended-Host-Range Pseudo-T-Even Bacteriophage Kpp95 Isolated on *Klebsiella pneumoniae*," Appl. Environ. Microbiol., vol. 73, no. 8, pp. 2532-2540, Apr. 2007.

[18] D. Montag, H. Schwarz, and U. Henning, "A component of the side tail fiber of *Escherichia coli* bacteriophage lambda can functionally replace the receptor-recognizing part of a long tail fiber protein of the unrelated bacteriophage T4," J. Bacteriol., vol. 171, no. 8, pp. 4378-4384, Aug. 1989.

[19] E. R. Vimr, R. D. McCoy, H. F. Vollger, N. C. Wilkison, and F. A. Troy, "Use of prokaryotic-derived probes to identify poly(sialic acid) in neonatal neuronal membranes," Proc. Natl. Acad. Sci., vol. 81, no. 7, pp. 1971-1975, Apr. 1984.

[20] K. Stummeyer, A. Dickmanns, M. Mühlenhoff, R. Gerardy-Schahn, and R. Ficner, "Crystal structure of the polysialic acid-degrading endosialidase of bacteriophage K1F," Nat. Struct. Mol. Biol., vol. 12, no. 1, pp. 90-96, Jan. 2005.

[21] D. Scholl, S. Adhya, and C. Merril, "*Escherichia coli* K1's Capsule Is a Barrier to Bacteriophage T7," Appl. Environ. Microbiol., vol. 71, no. 8, pp. 4872-4874, Aug. 2005.

[22] Y. Jiang, B. Chen, C. Duan, B. Sun, J. Yang, and S. Yang, "Multigene Editing in the *Escherichia coli* Genome via the CRISPR-Cas9 System," Appl. Environ. Microbiol., vol. 81, no. 7, pp. 2506-2514, Apr. 2015.

[23] J. E. Cronan, "Improved Plasmid-Based System for Fully Regulated Off-To-On Gene Expression in *Escherichia coli*: Application to Production of Toxic Proteins," Plasmid, vol. 69, no. 1, pp. 81-89, Jan. 2013.

[24] J. E. Thompson et al., "The K5 Lyase KflA Combines a Viral Tail Spike Structure with a Bacterial Polysaccharide Lyase Mechanism," J. Biol. Chem., vol. 285, no. 31, pp. 23963-23969, Jul. 2010.

[25] S. C. Potter, A. Luciani, S. R. Eddy, Y. Park, R. Lopez, and R. D. Finn, "HMMER web server: 2018 update," Nucleic Acids Res., vol. 46, no. W1, pp. W200-W204, Jul. 2018.

[26] E. I. Marusich, L. P. Kurochkina, and V. V. Mesyanzhinov, "Chaperones in bacteriophage T4 assembly," Biochem. Biokhimiia, vol. 63, no. 4, pp. 399-406, Apr. 1998.

[27] J. Xu, R. W. Hendrix, and R. L. Duda, "Chaperone-protein interactions that mediate assembly of the bacteriophage lambda tail to the correct length," J. Mol. Biol., vol. 426, no. 5, pp. 1004-1018, Mar. 2014.

[28] D. Schwarzer et al., "Proteolytic Release of the Intramolecular Chaperone Domain Confers Processivity to Endosialidase F," J. Biol. Chem., vol. 284, no. 14, pp. 9465-9474, Apr. 2009.

[29] J. A. Gilbert, M. J. Blaser, J. G. Caporaso, J. K. Jansson, S. V. Lynch, and R. Knight, "Current understanding of the human microbiome," Nat. Med., vol. 24, no. 4, pp. 392-400, Apr. 2018.

[30] M. Kapitan, M. J. Niemiec, A. Steimle, J. S. Frick, and I. D. Jacobsen, "Fungi as Part of the Microbiota and Interactions with Intestinal Bacteria," Curr. Top. Microbiol. Immunol., vol. 422, pp. 265-301, 2019.

[31] V. D. Nkamga, B. Henrissat, and M. Drancourt, "Archaea: Essential inhabitants of the human digestive microbiota," Hum. Microbiome J., vol. 3, pp. 1-8, Mar. 2017.

[32] M. Arumugam et al., "Enterotypes of the human gut microbiome," Nature, vol. 473, no. 7346, pp. 174-180, May 2011.

[33] M. I. McBurney et al., "Establishing What Constitutes a Healthy Human Gut Microbiome: State of the Science, Regulatory Considerations, and Future Directions," J. Nutr., vol. 149, no. 11, pp. 1882-1895, Nov. 2019.

[34] R. Nagpal et al., "Gut microbiome and aging: Physiological and mechanistic insights," Nutr. Healthy Aging, vol. 4, no. 4, pp. 267-285.

[35] R. K. Singh et al., "Influence of diet on the gut microbiome and implications for human health," J. Transl. Med., vol. 15, Apr. 2017.

[36] O. Tenaillon, D. Skurnik, B. Picard, and E. Denamur, "The population genetics of commensal *Escherichia coli*," Nat. Rev. Microbiol., vol. 8, no. 3, pp. 207-217, Mar. 2010.

[37] F. L. Nowrouzian, A. E. Wold, and I. Adlerberth, "*Escherichia coli* strains belonging to phylogenetic group B2 have superior capacity to persist in the intestinal microflora of infants," J. Infect. Dis., vol. 191, no. 7, pp. 1078-1083, Apr. 2005.

[38] M. Smati et al., "Quantitative analysis of commensal *Escherichia coli* populations reveals host-specific enterotypes at the intra-species level," MicrobiologyOpen, vol. 4, no. 4, pp. 604-615, Aug. 2015.

[39] P. Hyman, "Phages for Phage Therapy: Isolation, Characterization, and Host Range Breadth," Pharmaceuticals, vol. 12, no. 1, Mar. 2019.

[40] R. Pantůcek et al., "The polyvalent staphylococcal phage phi 812: its host-range mutants and related phages," Virology, vol. 246, no. 2, pp. 241-252, Jul. 1998.

[41] A. Ross, S. Ward, and P. Hyman, "More Is Better: Selecting for Broad Host Range Bacteriophages," Front. Microbiol., vol. 7, Sep. 2016.

[42] H. Ochman and R. K. Selander, "Standard reference strains of *Escherichia coli* from natural populations," J. Bacteriol., vol. 157, no. 2, pp. 690-693, Feb. 1984.

[43] L. Goodridge, A. Gallaccio, and M. W. Griffiths, "Morphological, Host Range, and Genetic Characterization of Two Coliphages," Appl. Environ. Microbiol., vol. 69, no. 9, pp. 5364-5371, Sep. 2003.

[44] M. K. Mirzaei and A. S. Nilsson, "Isolation of Phages for Phage Therapy: A Comparison of Spot Tests and Efficiency of Plating Analyses for Determination of Host Range and Efficacy," PLOS ONE, vol. 10, no. 3, p. e0118557, Mar. 2015.

[45] E. C. Keen, "Tradeoffs in bacteriophage life histories," Bacteriophage, vol. 4, no. 2, p. e28365, Apr. 2014.

[46] D. Scholl and C. Merril, "The Genome of Bacteriophage K1F, a T7-Like Phage That Has Acquired the Ability To Replicate on K1 Strains of *Escherichia coli*," J. Bacteriol., vol. 187, no. 24, pp. 8499-8503, December 2005.

[47] D Montag et al, «A component of the side tail fiber of *Escherichia coli* bacteriophage lambda can functionally replace the receptor-recognizing part of a long tail fiber protein of the unrelated bacteriophage T4 » J. Bacteriol., 171(8), pp. 4378-4384, Aug. 1989

---

SEQUENCE LISTING

```
Sequence total quantity: 263
SEQ ID NO: 1           moltype = AA  length = 774
FEATURE                Location/Qualifiers
REGION                 1..774
                       note = Synthetic: lambda stf
source                 1..774
                       mol_type = protein
                       organism = synthetic construct
SEQUENCE: 1
MAVKISGVLK DGTGKPVQNC TIQLKARRNS TTVVVNTVGS ENPDEAGRYS MDVEYGQYSV  60
ILQVDGFPPS HAGTITVYED SQPGTLNDFL CAMTEDDARP EVLRRLELMV EEVARNASVV  120
AQSTADAKKS AGDASASAAQ VAALVTDATD SARAASTSAG QAASSAQEAS SGAEAASAKA  180
TEAEKSAAAA ESSKNAAATS AGAAKTSETN AAASQQSAAT SASTAATKAS EAATSARDAV  240
ASKEAAKSSE TNASSSAGRA ASSATAAENS ARAAKTSETN ARSSETAAER SASAAADAKT  300
AAAGSASTAS TKATEAAGSA VSASQSKSAA EAAAIRAKNS AKRAEDIASA VALEDADTTR  360
KGIVQLSSAT NSTSETLAAT PKAVKVVMDE TNRKAPLDSP ALTGTPTAPT ALRGTNNTQI  420
ANTAFVLAAI ADVIDASPDA LNTLNELAAA LGNDPDFATT MTNALAGKQP KNATLTALAG  480
LSTAKNKLPY FAENDAASLT ELTQVGRDIL AKNSVADVLE YLGAGENSAF PAGAPIPWPS  540
DIVPSGYVLM QGQAFDKSAY PKLAVAYPSG VLPDMRGWTI KGKPASGRAV LSQEQDGIKS  600
HTHSASASGT DLGTKTTSSF DYGTKTTGSF DYGTKSTNNT GAHAHSLSGS TGAAGAHAHT  660
SGLRMNSSGW SQYGTATITG SLSTVKGTST QGIAYLSKTD SQGSHSHSLS GTAVSAGAHA  720
HTVGIGAHQH PVVIGAHAHS FSIGSHGHTI TVNAAGNAEN TVKNIAFNYI VRLA        774

SEQ ID NO: 2           moltype = AA  length = 686
FEATURE                Location/Qualifiers
REGION                 1..686
                       note = Synthetic: STF-25
source                 1..686
```

```
                         mol_type = protein
                         organism = synthetic construct
SEQUENCE: 2
MAVKISGVLK DGTGKPVQNC TIQLKARRNS TTVVVNTVGS ENPDEAGRYS MDVEYGQYSV  60
ILQVDGFPPS HAGTITVYED SQPGTLNDFL CAMTEDDARP EVLRRLELMV EEVARNASVV  120
AQSTADAKKS ETAAASSRNA AKTSETNAGN SAKAAASSKT AAQNAATAAE RSETNARASE  180
EASADSEEAS RRNAESAAEN AGVATTKARE AAADATKAGQ KKDEALSAAT RAEKAADRAE  240
AAAEVTAEPC ANIVPPLPDV WIPFNDSLDM IAGFSPGYKK IAIGDDVVQV ASDKQVNFSR  300
ASTATYINKS GELKTAEINE PRFECDGLLI EGQRTNYMLN SESPASWGKS SNMDVPETGT  360
DSFGFTYGKF VCNDSLVGQT SAINMASIAA TKSVDVSGDN KYVTTSCRFK TERQVRLRIR  420
FDKYDGSATT FLGDAYIDTQ TLEISMTGGA AGRITARVRK DKTTGWIFAE ATIQAIDGEL  480
KIGSQIQYSP GQGGATVSGD YIYLATPQVE NGPCVSSFII SGGSATTRAS DLVSIPTRNN  540
LYKLPFTFLL EIHKNWDIAP NAAPRVWDIA AANTGQSAIA AINRGSGKLY MSLSNPSGSY  600
VNSAATDVFA EKTTFGCIAK ADGHFHVVTN GKAVNEVYCE YNGVTADKNI RFGGQTNTGE  660
RHLFGHIRNF RIWHKELNDR QLKEVV                                      686

SEQ ID NO: 3             moltype = AA  length = 92
FEATURE                  Location/Qualifiers
REGION                   1..92
                         note = Synthetic: STF25-AP1
source                   1..92
                         mol_type = protein
                         organism = synthetic construct
SEQUENCE: 3
MKDLTLKFHD KLQFKAFLSS LGWAEDEDLQ NKLLVDEIGF TYTETGVTEE GEPVCIRNDG  60
YFVNIRILDD LFDVSVFSDY VVELETPLRE WS                               92

SEQ ID NO: 4             moltype = AA  length = 687
FEATURE                  Location/Qualifiers
REGION                   1..687
                         note = Synthetic: STF-27
source                   1..687
                         mol_type = protein
                         organism = synthetic construct
SEQUENCE: 4
MAVKISGVLK DGTGKPVQNC TIQLKARRNS TTVVVNTVGS ENPDEAGRYS MDVEYGQYSV  60
ILQVDGFPPS HAGTITVYED SQPGTLNDFL CAMTEDDARP EVLRRLELMV EEVARNASVV  120
AQSTADAKKS ETAAASSKNA AKTSETNAAN SAQAAAASQT ASANSATAAK KSETSAKNSE  180
TATKASEKNA KSSQTAAKTS ETNAKDSEAN AKVSETAAAN SAKASAASQT AAKASEDAAR  240
EYANQTAEPY RYVLQPLPDV WIPFNDSLDM ITGYSPGYKK VKIGDNVVQV ASDKQVNFSR  300
ASTATYINKS GELKTAEINE PRFECDGLLI EGQRTNFFQN STDPSKWNKS TSLDVTETGT  360
DSFGFNYGRF VVQDSIVGTS KAHTIIGLYS STGGVDTSGD EKHVTISCRV KSEVDNIAVR  420
ILFEHYDGEV RTSIGAANLN LTTRIISKTG QTSRVTARSV KDDATGWIFF EATLKADTTE  480
NTVGGFVQYS PDTGQMVTSG DYLDVTTPQI EAGTGASSFI VTGTAPATRA SDMVTVPIKN  540
NLYNLPFTVL CEVHKNWYKT PNVAPRVFDT GGHQTGAGIV MGFGSSGGYD GFPYCDIGGS  600
DRRINENAGL EKMLIGMRVK SERSTCVVSN GKLSSETKTK WEYIRSTATI RIGGQTTAGL  660
RHLFGHVRNF RLWHKELTDA QLGEVVE                                     687

SEQ ID NO: 5             moltype = AA  length = 92
FEATURE                  Location/Qualifiers
REGION                   1..92
                         note = Synthetic: STF27-AP1
source                   1..92
                         mol_type = protein
                         organism = synthetic construct
SEQUENCE: 5
VRDFTLRFSD KADFRAFLRK LNWEEDEELQ NAVLVDEIGF TFRETDVSDD GEPEYTRNEG  60
YFVNIRLLDD GFEDSVFREW VVTPERPLRE WF                               92

SEQ ID NO: 6             moltype = AA  length = 88
FEATURE                  Location/Qualifiers
REGION                   1..88
                         note = Synthetic: STF27-AP2
source                   1..88
                         mol_type = protein
                         organism = synthetic construct
SEQUENCE: 6
MLPQHSDIEI AWYASIQQEP NGWKTVTTQF YIQEFSEYIA PLQDAVDLEI ATEEERSLLE  60
AWNKYRVLLN RVDTSTAPDI EWPTSPAE                                    88

SEQ ID NO: 7             moltype = AA  length = 673
FEATURE                  Location/Qualifiers
REGION                   1..673
                         note = Synthetic: STF-28
source                   1..673
                         mol_type = protein
                         organism = synthetic construct
SEQUENCE: 7
MAVKISGVLK DGTGKPVQNC TIQLKARRNS TTVVVNTVGS ENPDEAGRYS MDVEYGQYSV  60
```

```
ILQVDGFPPS HAGTITVYED SQPGTLNDFL CAMTEDDARP EVLRRLELMV EEVARNASVV  120
AQSTADAKKS ETAAASSRNA AKTSETNAGN SAKAAASSKT AAQNAATAAE RSETNARASE  180
EASADSEEAS RRNAESAAEN AGVATTKARE AAADATKAGQ KKDEALSAAT RAEKAADRAE  240
SAAEVTAEPC ANIVPPLPDV WIPFNDSLDM ITGFSPSYKK IVIGDDEITM PGDKIVKFKR  300
ASTATYINKS GQLKLAEVDE PRFERDGLLI EGQRTNYLRN SNKPDSWTVH SALNKTFGTD  360
KQGFNYATVT PTESIVGTTG GYTVHGVVAA DRFPLASGEC FTFSCRVKGA KARCRLRVSV  420
IIGGTDTFSA DSYLDLDTRI ATVSGNTSLI TAKAEQQGEW TYYEATYTAN TDIDTVNCAF  480
YMTNKISNEP FYDDSTLTMT TPQIELGNTA SSFIVTTMPT TRASDVVTIP SANNLSTRPF  540
TVLCEVRRNW STPPNVAPRI FDVGGHSIDD NYLSLGFVST GKISANVGMV QPQISSDGER  600
FIVGVRAKSD LSVNAICNGN YTTNLNGKIF GVTATSYRFG GQTAAGTRHL FGHIRNFRVW  660
FKELNDRQIK EAV                                                     673

SEQ ID NO: 8           moltype = AA  length = 92
FEATURE                Location/Qualifiers
REGION                 1..92
                       note = Synthetic: STF28-AP1
source                 1..92
                       mol_type = protein
                       organism = synthetic construct
SEQUENCE: 8
MKDLTLKFPG NREFKSFLSS LDWEEDEDLQ NKLLVDEIGF TYTETGVTEE GEPVCIRNNG  60
YFVNIRILDD LFDVSVFSDY VVELETPLRE WS                               92

SEQ ID NO: 9           moltype = AA  length = 798
FEATURE                Location/Qualifiers
REGION                 1..798
                       note = Synthetic: STF-15
source                 1..798
                       mol_type = protein
                       organism = synthetic construct
SEQUENCE: 9
MAVKISGVLK DGTGKPVQNC TIQLKARRNS TTVVVNTVGS ENPDEAGRYS MDVEYGQYSV  60
ILQVDGFPPS HAGTITVYED SQPGTLNDFL CAMTEDDARP EVLRRLELMV EEVARNASVV  120
AQSTADAKKS AGDASASAAQ VAALVTDATD SARAASTSAG QAASSAQEAS SGAEAASAKA  180
TEAEKSAAAA ESSKNAAATS AGAAKTSETN AAASQQSAAT SASTAATKAS EAATSARDAV  240
ASKEAAKSSE TNASSSAGRA ASSATAAENS ARAAKTSETN ARSSETAAER SASAAAASAT  300
ASANSQKAAK TSETNAKVSE TAAANSAKAS AASQTAAKAS EDAAREYASQ AAEPYKYVLQ  360
PLPDVWIPFN DSLDMITGFS PSYKKIVIGD DEITMPGDKV VKFKRASTAT YINKSGVFSV  420
AKIDEPRFEK EGLLIEGQRT NYFVKSNTPA EWTSTSNIDK TNNGVDEFGF SYAKMRTKDN  480
MTGQSSALSL HRCSASRGID VSGDNKYCTV SCRVKAPDGL RCRLRFEKYD GSVYTFLGDA  540
YLTFGTLIIE KTGGAANRIA ATATKDPVTG WIFYEATIEA VEGETLIGAM IQYAPKKGGI  600
TEAGDYIYLA TPQFENGGCA SSFVITTTAP ATRSSDMVTI PTKNNIYNRP LTCLVEVNRI  660
WGDIPPNVAP RIFDFSGVPP IESITYAFNT TEKYYGQLYM QTYKASTSTY VSSVFAGRAD  720
VRKFIGGFNI YSDGTKRVVS NGEATKTMKT EWTGVKTRTF IRIGGQATSG TRHLFGHLRN  780
LRLWHKELTD AQMGESIK                                                798

SEQ ID NO: 10          moltype = AA  length = 93
FEATURE                Location/Qualifiers
REGION                 1..93
                       note = Synthetic: STF15-AP1
source                 1..93
                       mol_type = protein
                       organism = synthetic construct
SEQUENCE: 10
MKDLTLKFAD RADFSAFMES IGYYDDESMQ DDILIDVIGN VYKETGELTE DGEPACVKED  60
GYFVNVRIIN DSQISSLFDE HAVAVEHQLR SWM                              93

SEQ ID NO: 11          moltype = AA  length = 234
FEATURE                Location/Qualifiers
REGION                 1..234
                       note = Synthetic: STF15-AP2
source                 1..234
                       mol_type = protein
                       organism = synthetic construct
SEQUENCE: 11
MATSTVIPDD IKTLKGDVSK AKEDISSINV KVSTLQTDMD SAKQDISTRY TKTEVDNKLK  60
NKVEVNDLES GRYGGDFYPL TGREAFYLWG LGTTTAAANL YLNPDPAISS VLRSTSSIRY  120
KHSVETIDSE HADLIFRMRP VWYRSQCEND RRDWGFYGLI AEEVGEIAPQ FVHWRPANED  180
DAPETISSNG LVAEGVMYER LVVPLIHHIQ KLTERVDELE SELKLLSTSQ SDIG       234

SEQ ID NO: 12          moltype = AA  length = 791
FEATURE                Location/Qualifiers
REGION                 1..791
                       note = Synthetic: STF-16
source                 1..791
                       mol_type = protein
                       organism = synthetic construct
SEQUENCE: 12
MAVKISGVLK DGTGKPVQNC TIQLKARRNS TTVVVNTVGS ENPDEAGRYS MDVEYGQYSV  60
```

```
ILQVDGFPPS HAGTITVYED SQPGTLNDFL CAMTEDDARP EVLRRLELMV EEVARNASVV  120
AQSTADAKKS AGDASASAAQ VAALVTDATD SARAASTSAG QAASSAQEAS SGAEAASAKA  180
TEAEKSAAAA ESSKNAAATS AGAAKTSETN AAASQQSAAT SASTAATKAS EAATSARDAV  240
ASKEAAKSSE TNASSSAGRA ASSATAAENS ARAAKTSETN ARSSETAAER SASAAAASAT  300
ASANSQKAAK TSETNAKTSE TAAANSAKAS AASQTAAKAS EDAAREYASQ AADPYKYVLQ  360
PLPDVWIPFN DSLDMITGFS PSYKKIVIGD DEITMPGDKI VKFKRASKAT YINKSGVLTE  420
AAIDEPRFER DGLLIEGQRT NLLLNSTNPS KWNKSGNLEL TEISTDSFNF TYGRFTVKDT  480
LIGQTSAINI VTISGSKGFD VTGDEKYVTI SCRVRSDVEN IRCRLRFEHH DGYTYTFLGD  540
AYLNLSTLVI DKTGTAADRI IAKAVKDEVT GWIFYQATIN ALDTESMIGA MVQYAPVKGS  600
GTASGDYLDI ATPQVEGGSS ASSFIVTDIT ASTRASDMVT VPIKNNLYNL PFTVLCEVHK  660
NWYKTPNAAP RVFDTGGHQT GAAIILGFGR STDYDGFPYC DIGLANRRVN ENASLEKMVM  720
GMRVKSDQST CSVSNGRISS EKKATWSYIQ NSAIIRIGGQ TTAGLRHLFG HVRNFRIWHK  780
ALTDAQMGES I                                                       791

SEQ ID NO: 13          moltype = AA  length = 93
FEATURE                Location/Qualifiers
REGION                 1..93
                       note = Synthetic: STF16-AP1
source                 1..93
                       mol_type = protein
                       organism = synthetic construct
SEQUENCE: 13
MKDLTLKFAD RADFSAFMDS IGYYDDESMQ DDILIDVIGN VYKETGELTE DGEPVCVKED  60
GYYVNVRIIN DAKKSSIFDE YAVVVEHQLR GWM                              93

SEQ ID NO: 14          moltype = AA  length = 234
FEATURE                Location/Qualifiers
REGION                 1..234
                       note = Synthetic: STF16-AP2
source                 1..234
                       mol_type = protein
                       organism = synthetic construct
SEQUENCE: 14
MATSTVIPGD ITTLKGDVSK AKEDISSING KVSTLQADMT SAKQDISTRY TKTEVDNKLK  60
NKLEVNALES GRYGGDFYPL TGREAFYLWG LGTTTAAANL YLNPDPAISS VLRSTSSIRY  120
KHSVETIDSE HADLIFRMRP VWYRSQCEND RRDWGFYGLI AEEVGEIAPQ FVHWRPANED  180
DAPEAISSNG LVAEGVMYER LVVPLIHHIQ KLTERVDELE SELKLLSVSR SDIG        234

SEQ ID NO: 15          moltype = AA  length = 941
FEATURE                Location/Qualifiers
REGION                 1..941
                       note = Synthetic: STF-17
source                 1..941
                       mol_type = protein
                       organism = synthetic construct
SEQUENCE: 15
MAVKISGVLK DGTGKPVQNC TIQLKARRNS TTVVVNTVGS ENPDEAGRYS MDVEYGQYSV  60
ILQVDGFPPS HAGTITVYED SQPGTLNDFL CAMTEDDARP EVLRRLELMV EEVARNASVV  120
AQSTADAKKS AGDASASAAQ VAALVTDATD SARAASTSAG QAASSAQEAS SGAEAASAKA  180
TEAEKSAAAA ESSKNAAATS AGAAKTSETN AAASQQSAAT SASTAATKAS EAATSARDAV  240
ASKEAAKSSE TNASSSAGRA ASSATAAENS ARAAKTSETN ARSSETAAER SASAAAGSKT  300
AAALSASAAS TSAGQASASA TAAGKSAESA ASSASTATTK AGKATEQATA AARSASAAKT  360
SETNAKTSAD NAASSKAAAA SSASSAASSA SSASASKDEA TRQASAAKGS ATTASTKATE  420
AAGSATAAAQ SKSTAESAAT RAETAAKRAE DIASAVALED ASTTKKGIVQ LSSATNSTSE  480
SLAATPKAVK AVMGETNKKA PLNSPALTGT PTTPTARQGT NNTQIASTAY VMAAIAALVD  540
SSPDALNTLN ELAAALGNDP NFATTMTSAL AGKQPKDATL TALAGLATAA DRFPYFTGND  600
VASLATLTKV GRDILAKSTV AAVIEYLGLR ELGTSGEKIP LLSTANTWTN RQTFSGGLSG  660
ELSGNASTAA KLKTARKISN VAFDGSSDIT LKASHVGAFA LGKTGSTVAN DKAVGWNWSS  720
GAYNATISGA STLIIHFYMG EGSCPAAQFR INYKNGGIFY RSARDGYGFE ADWSEFYTTT  780
RKPSAGDVGA LPLSGGQLNG ALGIGTSSAL GGNSIVLGDN DTGFKQNGDG NLDVYANNVH  840
VMRFVSGSIQ SNKTINITGR VNPSDYGNFD SRYVKDVRLG SQQYYGVNNW QTWNFQCPSG  900
HVLSGINVQD TGSNSADNIA GVYYRPVQKY INGTWYNVAS V                      941

SEQ ID NO: 16          moltype = AA  length = 177
FEATURE                Location/Qualifiers
REGION                 1..177
                       note = Synthetic: STF17-AP1
source                 1..177
                       mol_type = protein
                       organism = synthetic construct
SEQUENCE: 16
MMHLKNIKAG NAKTLEQYEL TKKHGVIWLY SEDGKNWYEE VKNFQPDTIK IVYDENNIIV  60
AITKDASTLN PEGYSVVEIP DITANRRADD SGKWMFKDGA VIKRVYTEEE LRLQTENQKK  120
ILLQQAREKT QFWQTQLTLG IITDSDRQQL MNWMRYVQQV ETTDTSVLPV TFPEPPE     177

SEQ ID NO: 17          moltype = AA  length = 791
FEATURE                Location/Qualifiers
REGION                 1..791
                       note = Synthetic: STF-13
```

```
source                1..791
                      mol_type = protein
                      organism = synthetic construct
SEQUENCE: 17
MAVKISGVLK DGTGKPVQNC TIQLKARRNS TTVVVNTVGS ENPDEAGRYS MDVEYGQYSV  60
ILQVDGFPPS HAGTITVYED SQPGTLNDFL CAMTEDDARP EVLRRLELMV EEVARNASVV  120
AQSTADAKKS AGDASASAAQ VAALVTDATD SARAASTSAG QAASSAQEAS SGAEAASAKA  180
TEAEKSAAAA ESSKNAAATS AGAAKTSETN AAASQQSAAT SASTAATKAS EAATSARDAV  240
ASKEAAKSSE TNASSSAGRA ASSATAAENS ARAAKTSETN ARSSETAAER SASAAASSAT  300
ASANSQKAAK TSETNAKASE TAAANSAKAS AASQTAAKAS EDAAREYASQ AAEPYKQVLQ  360
PLPDVWIPFN DSLDMLAGFS PGYKQITVGD DVIKMPSDKV VSFKRASGAT YINKSGVLTV  420
AEVDEPRFER EGLLIEGQRT NYHLNSLTPS KWGATTSVTI TESGVDEFGF TYGRFQIKDE  480
KIGTNTTMNI AAVSGGRGVD VTGTEKYVTT SCRVKSDSAN IQCRIRFERY DGSAYFYLAD  540
AYLNITDMSI RKTGGGAARI TARAEKESNG WIYFEVTYQS EAIDNMVGSQ IQIAPPVSPG  600
TYLGGEYLDV TTPQFEGGSC ASSFIISDTV ASTRASDIVT LPCKNNMASK PLTCMVEVNK  660
NWSIAPNSAP RIYDITGFKT KDDAFVFAFR NTAGSVGTPY VQFGNPISFP PGNYPRKIIA  720
VYRIKSDGKF QAGCNGVLST PASTTWKSVS GATGIRIGGQ TTAGLRHLFG YIRNFRIWHK  780
ELTDAQMGEI I                                                       791

SEQ ID NO: 18         moltype = AA  length = 93
FEATURE               Location/Qualifiers
REGION                1..93
                      note = Synthetic: STF13-AP1
source                1..93
                      mol_type = protein
                      organism = synthetic construct
SEQUENCE: 18
MRDLIIKFTD KADFSAFMKS AGYYDDESMQ DDILIDVIGN VYKETGELTE DGEPVCVKED  60
GYFVNVRIIN DAKKSSIFDK YAVVVEHQLR GWM                               93

SEQ ID NO: 19         moltype = AA  length = 234
FEATURE               Location/Qualifiers
REGION                1..234
                      note = Synthetic: STF13-AP2
source                1..234
                      mol_type = protein
                      organism = synthetic construct
SEQUENCE: 19
MATSTVIPGD ITKLKGDVSK AKEDISSISR KVSTLQTEMT SAKQDISSRY TKTEVDNKLK  60
NKVEVNDLES GRYGGDFYPL TGREAFYLWN LATTTAAANL YLNPDPAISS VLRSTSSIRY  120
KHSVETIDSE HADLIFRMRP VWYRSQCEND RRDWGFYGLI AEEVGEIAPQ FVHWRPANED  180
DAPEAISSNG LVAEGVMYER LVVPLIHHIQ KLTERVDELE SELKLLLTSR SDIR        234

SEQ ID NO: 20         moltype = AA  length = 781
FEATURE               Location/Qualifiers
REGION                1..781
                      note = Synthetic: STF-12
source                1..781
                      mol_type = protein
                      organism = synthetic construct
SEQUENCE: 20
MAVKISGVLK DGTGKPVQNC TIQLKARRNS TTVVVNTVGS ENPDEAGRYS MDVEYGQYSV  60
ILQVDGFPPS HAGTITVYED SQPGTLNDFL CAMTEDDARP EVLRRLELMV EEVARNASVV  120
AQSTADAKKS AGDASASAAQ VAALVTDATD SARAASTSAG QAASSAQEAS SGAEAASAKA  180
TEAEKSAAAA ESSKNAAATS AGAAKTSETN AAASQQSAAT SASTAATKAS EAATSARDAV  240
ASKEAAKSSE TNASSSAGRA ASSATAAENS ARAAKTSETN ARSSETAAER SASAAAASAT  300
ASANSQKAAK TSETNAKTSE TAAANSAQAS AASQTAAKAS EDAAREYASQ AAEPYKYVLQ  360
PLPDVWIPFN DSLDMLAGFS PGYKQITVGD DVIKMPSDKV VSFKRASGAT YINKSGVLTV  420
AEVDEPRFER EGLLIEGQRT NYFRNSNTPE AWNNTGSVSV ESFDSDKGFN YGRITVINEN  480
PTAQGYQAIA VNTNDAYTCP AGSYTTISCL TKSDNSRCRA RFGKMSDNGA FVFHSDAVLD  540
PVTGNVVHGN NVTVTAERVG EWWLFTATLF ADAEMIISSR FEILAMPGIS IIPNGSTLDI  600
AMPQAEIGSY RTSFIITEGA PGTRSSDMVT IPVRNNIHRL PFSALVEVNK NWDIPPSKSP  660
LIFNVKDYQE NGLFTHGFRG NNFSDAGSPF ISMGGCNKYV ATTQRKIISG FRCGADGDVQ  720
AVCNGELSVA AKTTWTSIVP RAVLRIGGQG TNGEYHLFGH IRNLRIWHKE LTDAQMGESI  780
K                                                                  781

SEQ ID NO: 21         moltype = AA  length = 93
FEATURE               Location/Qualifiers
REGION                1..93
                      note = Synthetic: STF12-AP1
source                1..93
                      mol_type = protein
                      organism = synthetic construct
SEQUENCE: 21
MKDLTLKFAD RADFSAFMES IGYYDDESMQ DDILIDVIGN VYKETGELTE DGEPVCVKED  60
GYFVNVRIIN DVKKSSIFDK YAVVVEHQLR GWM                               93

SEQ ID NO: 22         moltype = AA  length = 234
FEATURE               Location/Qualifiers
```

```
REGION                 1..234
                       note = Synthetic: STF12-AP2
source                 1..234
                       mol_type = protein
                       organism = synthetic construct
SEQUENCE: 22
MATSTVIPGD ITTLKGDVSK TKEDISSING KVSTLQTDMT SAKQDISTRY TKTEVDNKLK  60
NKLEVNDLES GRYGGDFYPL TGREAFYMWG LGTTTAAANL YLNPDPAISS VLRSTSSIRY  120
KHSVETIDSE HADLIFRMRP VWYRSQCEND RRDWGFYGLI AEEVGEIAPQ FVHWRPANED  180
DAPEAISSNG LVAEGVMYER LVVPLIHHIQ KLTERVDELE SELKLLSVSR SDIG        234

SEQ ID NO: 23          moltype = AA  length = 702
FEATURE                Location/Qualifiers
REGION                 1..702
                       note = Synthetic: STF-63
source                 1..702
                       mol_type = protein
                       organism = synthetic construct
SEQUENCE: 23
MAVKISGVLK DGTGKPVQNC TIQLKARRNS TTVVVNTVGS ENPDEAGRYS MDVEYGQYSV  60
ILQVDGFPPS HAGTITVYED SQPGTLNDFL CAMTEDDARP EVLRRLELMV EEVARNASVV  120
AQSTADAKKS AGDASASAAQ VAALVTDATD SARAASTSAG QAASSAQEAS SGAEAASAKA  180
TEAEKSAAAA ESSKNAAATS AGAAKTSETN AAASQQSAAT SASTAATKAS EAATSARDAV  240
ASKEAAKSSE TNASSSAGRA ASSATAAENS ARAAKTSETN ARSSETAAER SASAAANSAT  300
AAKKSETNAK NSESAAKVSE TNAKASENKA KEYLDKVGGL VSPMTQYDWP VVTGNESFYI  360
KIAKLSDPGS NNCHVTLMVT NGGDYGSPYG NIDFIEISAR GLPSSLTADN VSRYLSIRRL  420
GPTGLINSMQ MRYGLVKDDG FIEVWAFQRA FINGAKVAVL AQTARTELYI PDGFVKQTAA  480
PSGYVESPVV RIYDQLNKPT KADLGLSNAM LTGAFGLGGS GISTNGKMSD VEILKALRDK  540
GGHFWRGDKP TGSTATIYSH GSGIFSRCGD TWSAINIDYS TAKIKIYAGN DARLNNGTFS  600
INELYGSANK PSKSDVGLGN VTNDAQVKKT GDTMTGDLTI KKGTPSVFLR ADSGVTALRF  660
YTGDNTERGI IYAGPNTDSL GEVRIRAKTA GGTSGGDLVV RH                    702

SEQ ID NO: 24          moltype = AA  length = 1253
FEATURE                Location/Qualifiers
REGION                 1..1253
                       note = Synthetic: STF-62
source                 1..1253
                       mol_type = protein
                       organism = synthetic construct
SEQUENCE: 24
MAVKISGVLK DGTGKPVQNC TIQLKARRNS TTVVVNTVGS ENPDEAGRYS MDVEYGQYSV  60
ILQVDGFPPS HAGTITVYED SQPGTLNDFL CAMTEDDARP EVLRRLELMV EEVARNASVV  120
AQSTADAKKS AGDASASAAQ VAALVTDATD SARAASTSAG QAASSAQEAS SGAEAASAKA  180
TEAEKSAAAA ESSKNAAATS AGAAKTSETN AAASQQSAAT SASTAATKAS EAATSARDAV  240
ASKEAAKSSE TNASSSAGRA ASSATAAENS ARAAKTSETN ARSSETAAER SASAAANSAT  300
AAKKSETNAK NSEAAAKVSE TNAKASENKA KEYLDKVGGL VSPMTQYDWP VVTASESLYI  360
KIAKLSDPGT SRSHVTLMVT NAGNYGSPYG NIDFIEISAR GLPSLLSADN VSRHLSIRRL  420
GSTGLTDNNQ MRYGLVKGDG FIEVWAFQGA FINDAKVAVL AQTTLNTELY IPDGFVKQTA  480
APSGYIEGNV VRIYDQVNKP TKADLGLSNA MLTGAFGLGG SGISTNGKMS DVEILKALRD  540
KGGHFWRGDK PTGSTATIYS HGSGIFSRCG DTWSAINIDY STAKIKIYAG NDARLNNGTF  600
SVNELYGSAN KPSKSDVGLG NVTNDAQVKK SGDVMSGDLD ILKETPSIRL KSAKGTAHLW  660
FMNNDGSERG VVWSPENNES LGEIHIRAKN TKGESSGDFI VRHDGRVEAR NLKITYKISA  720
ATAEFANTST SSDNTTVSIK GSQHTPLVLT SNNTIKNLSI GFKVDDVDQK YLGIAGDGDL  780
YFGSYSDHTK NSKVITQAKL DSGVTVGGKT TFSDLATFNA GMAGSIEPET IDNKTIDLND  840
LIIANTVAGS VKYYQCKTVA GGAYITNKPD GVSGNFLLRV ESTRKTTGSD YAIMQTLIGS  900
DTKRIYVRFV VNGSWTEWSQ VVVSGWNQDV TVRSLTSTTP SKLGGGRVDV LGSTSDYSSM  960
NCAVRGVDST GTNSAWSVGT SKNTGKMLCL KNHRSSAQVL LNGDDGAVQL LSGTVNGATA  1020
QALTINKDEV NSTADLVIRK QTGTGNRFAL LNSGNSELPV GIRVWGSSTR QNVFEVGTST  1080
AYLFYAQKTS AGQLFDVNGA INCTTLNQSS DRDLKDDILV ISDATKAIRK MNGYTYTLRE  1140
NGMPYAGVIA QEVMEAIPEA VGSFTHYGEE LQGPTVDGNE LREETRYLNV DYAAVTGLLV  1200
QFARETDDRV TALEEENTTL RQNLATADTR ISTLENQVSE LVALVRQLTG SEH         1253

SEQ ID NO: 25          moltype = AA  length = 790
FEATURE                Location/Qualifiers
REGION                 1..790
                       note = Synthetic: STF-71
source                 1..790
                       mol_type = protein
                       organism = synthetic construct
SEQUENCE: 25
MAVKISGVLK DGTGKPVQNC TIQLKARRNS TTVVVNTVGS ENPDEAGRYS MDVEYGQYSV  60
ILQVDGFPPS HAGTITVYED SQPGTLNDFL CAMTEDDARP EVLRRLELMV EEVARNASVV  120
AQSTADAKKS AGDASASAAQ VAALVTDATD SARAASTSAG QAASSAQEAS SGAEAASAKA  180
TEAEKSAAAA ESSKNAAATS AGAAKTSETN AAASQQSAAT SASTAATKAS EAATSARDAV  240
ASKEAAKSSE TNASSSAGRA ASSATAAENS ARAAKTSETN ARSSETAAER SASAAASSAT  300
ASANSQKAAK TSETNAKASE TAAANSAKAS AASQTAAKAS EDAAREYASQ AAEPYKQVLQ  360
PLPDVWIPFN DSLDMITGFS PSYKKIVIGD DEITMSGDKV VKFKRASKAT YINKSGVLTE  420
AAIDEPRFER DGLLIEGQRT NYMLNSESPA SWGRSSNMDV PETGTDNFGF TYGKFVCNDS  480
LIGQTSAINM ASIAATKSVD VSGDNKHVTT SCRFKTELQV RLRIRFDKYD GSATTFLGDA  540
```

-continued

```
YIDTQTLEIN MTGGAASRIT ARVRKDEATG WIFAEATIQA IDGELKIGSQ IQYSPKQGGA  600
TVSGDYIYLA TPQVENGPCV SSFIISGTTA ATRASDIVTV PIKNNLYNLP FTVLCEVHKN  660
WYKTPNAAPR VFDTGGHQTG AAIILGFGSS ADYDGFPYCD IGGANRRVNE NALLEKMVMG  720
MRVKSDQSTC SVSNGRISSE TKTTWSYIQN TAIIRIGGQT TAGLRHLFGH VRNFRIWHKA  780
LTDAQVGESI                                                         790

SEQ ID NO: 26          moltype = AA  length = 93
FEATURE                Location/Qualifiers
REGION                 1..93
                       note = Synthetic: STF71-AP1
source                 1..93
                       mol_type = protein
                       organism = synthetic construct
SEQUENCE: 26
MKDLTLKLAD RADFSAFMES TGYYDDESMQ DDILIDVIGN VYKETGELNE DGEPVCVKED  60
GYFVNVRIIN DVKTPSIFDE YVVAVEHQLR GWM                               93

SEQ ID NO: 27          moltype = AA  length = 1098
FEATURE                Location/Qualifiers
REGION                 1..1098
                       note = Synthetic: STF-20
source                 1..1098
                       mol_type = protein
                       organism = synthetic construct
SEQUENCE: 27
MAVKISGVLK DGTGKPVQNC TIQLKARRNS TTVVVNTVGS ENPDEAGRYS MDVEYGQYSV  60
ILQVDGFPPS HAGTITVYED SQPGTLNDFL CAMTEDDARP EVLRRLELMV EEVARNASVV  120
AQSTADAKKS AGDASASAAQ VAALVTDATD SARAASTSAG QAASSAQEAS SGAEAASAKA  180
TEAEKSAAAA ESSKNAAATS AGAAKTSETN AAASQQSAAT SASTAATKAS EAATSARDAV  240
ASKEAAKSSE TNASSSAGRA ASSATAAENS ARAAKTSETN ARSSETAAER SASAAADAKT  300
AAAGSASTAS TKATEAAGSA VSASQSKSAA EAAAIRAKNS AKRAEDIASA VALEDADTTR  360
KGIVQLSSAT NSTSETLAAT PKAVKVVMDE TNRRLAKNQN GADIQDKSAF LDNIGVTSLT  420
FMKNNGEMPV DADLNTFGPV KAYVGVWYKS TSSNATLEKN FPEDGAVGVL EVFNGGNFSG  480
MQRYTTRTGN VYMRNLSGTW NGSDGPWIYW RQIQSATRPL STTIDLNTLG GAEHLGLWRN  540
SSGSIASFDR NYPEEGSYGQ GFLEVLEGGG YSRTQRYTTR RGNVYVRCLS AIWNAQNPQW  600
EPWSRVGHQS ECRYYEGDLN DLTSPGIYSV TGKASNGPMQ DTAGATLLGI LEVIRRFDGV  660
SVWQRYTTTG KSETTQGRTF ERVYAGSKWT EWREVYNSFS LPLNLGIGGA VAKLSSLDWQ  720
TYDFVPGSLI TVRLDNMTNI PDGMDWGVID GNLINISVGP SDDSGSGRSM HVWRSTVSKA  780
NYRFFMVRIS GNPGSRTITT RRVPIIDEAQ TWGAKQTFSA GLSGELSGNA ATATKLKTAR  840
KINNVSFDGT SDINLTPKNI GAFASGKTGD TVANDKAVGW NWSSGAYNAT IGGASTLILH  900
FNIGEGSCPA AQFRVNYKNG GIFYRSARDG YGFEADWSEF YTTTRKPTAG DVGALPLSGG  960
QLNGALGIGT SSALGGNSIV LGDNDTGFKQ NGDGNLDVYA NSVHVMRFVS GSVQSNKTIN  1020
ITGRVNPSDY GNFDSRYVRD VRLGTRVVQT MQKGVMYEKA GHVITGLGIV GEVDGDDPAV  1080
FRPIQKYING TWYNVAQV                                                1098

SEQ ID NO: 28          moltype = AA  length = 175
FEATURE                Location/Qualifiers
REGION                 1..175
                       note = Synthetic: STF20-AP1
source                 1..175
                       mol_type = protein
                       organism = synthetic construct
SEQUENCE: 28
MQHLKNITAG NPKTVAQYQL TKNFDVIWLW SEEGKNWYEE VSNFQEDTIK IVYDENNIIV  60
GITRDASTLN PEGFSVVEVP DITANRRADD SGKWMFKDGA VIKRIYTADE QLQLAELQKS  120
ALLSEAETII QPLERSVRLN MATDDERSRL EAWERYSVLV SRVDPANPEW PEMPQ       175

SEQ ID NO: 29          moltype = AA  length = 757
FEATURE                Location/Qualifiers
REGION                 1..757
                       note = Synthetic: STF-23
source                 1..757
                       mol_type = protein
                       organism = synthetic construct
SEQUENCE: 29
MAVKISGVLK DGTGKPVQNC TIQLKARRNS TTVVVNTVGS ENPDEAGRYS MDVEYGQYSV  60
ILQVDGFPPS HAGTITVYED SQPGTLNDFL CAMTEDDARP EVLRRLELMV EEVARNASVV  120
AQSTADAKKS AGDASASAAQ VAALVTDATD SARAASTSAG QAASSAQEAS SGAEAASAKA  180
TEAEKSAAAA ESSKNAAATS AGAAKTSETN AAASQQSAAT SASTAATKAS EAATSARDAV  240
ASKEAAKSSE TNASSSAGRA ASSATAAENS ARAAKTSETN ARSSETAAER SASAAADAKT  300
AAAGSASTAS TKATEAAGSA VSASQSKSAA EAAAIRAKNS AKRAEDIASA VALEDADTTR  360
KGIVQLSSAT NSTSETLAAT PKAVKVVMDE TNRKAPLNSP ALTGTPTTPT ARQGTNNTQI  420
ASTAFVMAAI AALVDSSPDA LNTLNELAAA LGNDPNFATT MTNALAGKQP KDATLTALAG  480
LATAADRFPY FTGNDVASLA TLTKVGRDIL AKSTVAAVIE YLGLRELGTS GEKIPLLSTA  540
NTWTNRQTFS GGLSGGLSGN AATATKLKTA RKIAGVGFDG SSDISISAKN VNAFALRQTG  600
NTVNGDTSVG WNWDSGAYNA LIGGASALIL HFNINAGSCP AVQFRVNYKN GGISYRSARD  660
GYGFELGWSD FYTTTRKPSA GDVGAYTRAE CNSRFITGIR LGGLSSVQTW NGPGWSDRSG  720
YVVTGSVNGN RDELIDTTQA RPIQYCINGT WYNAGSI                           757
```

```
SEQ ID NO: 30          moltype = AA  length = 177
FEATURE                Location/Qualifiers
REGION                 1..177
                       note = Synthetic: STF23-AP1
source                 1..177
                       mol_type = protein
                       organism = synthetic construct
SEQUENCE: 30
MMHLKNITAG NPKTKEQYQL TKQFNIKWLY SDDGKNWYEE QKNFQPDTLK MVYDHNGVII  60
CIEKDVSAIN PEGASVVELP DITANRRADI SGKWLFKDGV VIKRTYTEEE QRQQAENEKQ  120
SLLQLVRDKT QLWDSQLRLG IISDENKQKL TEWMLYAQKV ESTDTSSLPV TFPEQPE     177

SEQ ID NO: 31          moltype = AA  length = 712
FEATURE                Location/Qualifiers
REGION                 1..712
                       note = Synthetic: STF-24
source                 1..712
                       mol_type = protein
                       organism = synthetic construct
SEQUENCE: 31
MAVKISGVLK DGTGKPVQNC TIQLKARRNS TTVVVNTVGS ENPDEAGRYS MDVEYGQYSV  60
ILQVDGFPPS HAGTITVYED SQPGTLNDFL CAMTEDDARP EVLRRLELMV EEVARNASVV  120
AQSTADAKKS AGDASASAAQ VAALVTDATD SARAASTSAG QAASSAQEAS SGAEAASAKA  180
TEAEKSAAAA ESSKNAAATS AGAAKTSETN AAASQQSAAT SASTAATKAS EAATSARDAV  240
ASKEAAKSSE TNASSSAGRA ASSATAAENS ARAAKTSETN ARSSETAAER SASAAADAKT  300
AAAGSASTAS TKATEAAGSA VSASQSKSAA EAAAIRAKNS AKRAEDIASA VALEDADTTR  360
KGIVQLSSAT NSTSETLAAT PKAVKVVMDE TNRRLQKDQN GADIPDKRLF LRNIGATNST  420
TMSFSGGTGW FRLATVTMPQ ASSVVYISLI GGAGYNVNSP MQAGISELVL RAGNGNPKGL  480
TGALWRRTSV GFTNFAWVNT SGDTYDVYVE IGNYATGVNI QWDYTSNASV TIHTSPTYTA  540
NKPTGLTDGT VYVIYSSYIK PTAADVGALS LSGGQLNGAL GIGTSSALGG NSIVLGDNDT  600
GFKQNGDGNL DVYANSVHVM RFVSGSVQSN KTINITGRVN PSDYGNFDSR YVRDVRLGTR  660
VVQTMQKGVM YEKAGHVITG LGIVGEVDGD DPAVFRPIQK YINGTWYNVA QV          712

SEQ ID NO: 32          moltype = AA  length = 175
FEATURE                Location/Qualifiers
REGION                 1..175
                       note = Synthetic: STF24-AP1
source                 1..175
                       mol_type = protein
                       organism = synthetic construct
SEQUENCE: 32
MQHLKNITAG NPKTVAQYQL TKNFDVIWLW SEEGKNWYEE VSNFQEDTIK IVYDENNIIV  60
GITRDASTLN PEGFSVVEVP DITANRRADD SGKWMFKDGA VIKRIYTADE QLQLAELQKS  120
ALLSEAETII QPLERSVRLN MATDEERSRL EAWERYSVLV SRVDPANPEW PEMPQ       175

SEQ ID NO: 33          moltype = AA  length = 840
FEATURE                Location/Qualifiers
REGION                 1..840
                       note = Synthetic: O111-2.0
source                 1..840
                       mol_type = protein
                       organism = synthetic construct
SEQUENCE: 33
MAVKISGVLK DGTGKPVQNC TIQLKARRNS TTVVVNTVGS ENPDEAGRYS MDVEYGQYSV  60
ILQVDGFPPS HAGTITVYED SQPGTLNDFL CAMTEDDARP EVLRRLELMV EEVARNASVV  120
AQSTADAKKS AGDASASAAQ VAALVTDATD SARAASTSAG QAASSAQEAS SGAEAASAKA  180
TEAEKSAAAA ESSKNAAATS AGAAKTSETN AAASQQSAAT SASTAATKAS EAATSARDAV  240
ASKEAAKSSE TNASSSAGRA ASSATAAENS ARAAKTSETN ARSSETAAER SASAAADAKT  300
AAAGSASTAS TKATEAAGSA VSASQSKSAA EAAAIRAKNS AKRAEDIASA VALEDADTTR  360
KGIVQLSSAT NSTSETLAAT PKAVKVVMDE TNRKAPLNSP ALTGTPTTPT APQGTNSTQI  420
ASTAFVMAAI AALVDSSPDA LNTLSELAAA LGNDPNFATT MTNALAGKQP KDATLTALAG  480
LVTAADRFPY FTGNDVASLA TLTEVGRDIL AKSTVAAVIE YLGLQETVNQ ASGALQKNQN  540
GADIPGKDTF TKNIGACRAY SAWLNIGGDS QVWTTAQFIS WLESQGAFNH PYWMCKGSWA  600
YANNKVITDT GCGNICLAGA VVEVIGTRGA MTIRVTTPST SSGGGITNAQ FTYINHGDAY  660
APGWRRDYNT KNQQPAFALG QTGSRVANDK AVGWNWNSGV YNADISGAST LILHFNMNAG  720
SCPAVQFRVN YRNGGIFYRS ARDGYGFEAN WSEFYTTTRK PSAGDVGAYT QAECNSRFIT  780
GIRLGGLSSV QTWNGPGWSD RSGYVVTGSV NGNRDELIDT TQARPIQYCI NGTWYNAGSI  840

SEQ ID NO: 34          moltype = AA  length = 177
FEATURE                Location/Qualifiers
REGION                 1..177
                       note = Synthetic: O111 2.0-AP1
source                 1..177
                       mol_type = protein
                       organism = synthetic construct
SEQUENCE: 34
MMHLKNITAG NPKTKEQYQL TKQFNIKWLY SEDGKNWYEE QKNFQPDTLK MVYDHNGVII  60
CIEKDVSAIN PEGASVVELP DITANRRADI SGKWMFKDGV VVKRTYTEEE QRQQAENEKQ  120
SLLQLVRDKT QLWDSQLRLG IISDENKQKL TEWMLFAQKV ESTDTSSLPV TFPEQPE     177
```

```
SEQ ID NO: 35          moltype = AA  length = 754
FEATURE                Location/Qualifiers
REGION                 1..754
                       note = Synthetic: STF-74
source                 1..754
                       mol_type = protein
                       organism = synthetic construct
SEQUENCE: 35
MAVKISGVLK DGTGKPVQNC TIQLKARRNS TTVVVNTVGS ENPDEAGRYS MDVEYGQYSV  60
ILQVDGFPPS HAGTITVYED SQPGTLNDFL CAMTEDDARP EVLRRLELMV EEVARNASVV  120
AQSTADAKKS AGDASASAAQ VAALVTDATD SARAASTSAG QAASSAQEAS SGAEAASAKA  180
TEAEKSAAAA ESSKNAAATS AGAAKTSETN AAASQQSAAT SASTAATKAS EAATSARDAV  240
ASKEAAKSSE TNASSSAGRA ASSATAAENS ARAAKTSETN ARSSETAAER SASAAADAKT  300
AAAGSASTAS TKATEAAGSA VSASQSKSAA EAAAIRAKNS AKRAEDIASA VALEDADTTR  360
KGIVQLSSAT NSTSETLAAT PKAVKVVMDE TNRKYTAQDA STAQKGLVKL SSATDSTSET  420
LAATPKAVKA VNDNANGRVP SERKVNGHSL AGDISVTSQD IFDGQCVEIG PGQDLDNYQT  480
PGLYFQPANA NTSAALHYPE NNAGSLMVLR SAGITQVYRV YSGSRSYLRS KYSTQPWTTW  540
TPDDAFPVGA PIPWPSDIAP PAYALMQGQS FDKSAYPLLA VAYPSGVIPD MRGQTIKGKP  600
DGRAVLSYEQ DGIKSHAHTA SISDTDLGTK YTNSFDYGSK PTTSFDYGNK SSTEGGWHVH  660
NFRYCATSAY RDTPGSGLGM HSSNISWSAG DRIEGSGNHA HVTWIGPHDH WVGIGEHNHY  720
VVMGYHGHTA TVHATGNTEN TVKNIAFNYI VRLA                              754

SEQ ID NO: 36          moltype = AA  length = 192
FEATURE                Location/Qualifiers
REGION                 1..192
                       note = Synthetic: STF74-AP1
source                 1..192
                       mol_type = protein
                       organism = synthetic construct
SEQUENCE: 36
MAFEMTGENR TIILYNLRSD TNEFIGKSDG FIPANTGLPA YSTDIAPPKV TAGFVAVFDA  60
QTNKWSRVED YRGTTVYDIS TGKPAVIEKL GALPDNVVSV APDGEYVKWD GAKWIHDAEA  120
EKTFRQGQAA QEKSNLLMIA TSAIAPLQDA VDLDMATEDE ATALNEWKKY RVMLNRVKPE  180
DAPDITWPEL PA                                                      192

SEQ ID NO: 37          moltype = AA  length = 710
FEATURE                Location/Qualifiers
REGION                 1..710
                       note = Synthetic: STF-86
source                 1..710
                       mol_type = protein
                       organism = synthetic construct
SEQUENCE: 37
MAVKISGVLK DGTGKPVQNC TIQLKARRNS TTVVVNTVGS ENPDEAGRYS MDVEYGQYSV  60
ILQVDGFPPS HAGTITVYED SQPGTLNDFL CAMTEDDARP EVLRRLELMV EEVARNASVV  120
AQSTADAKKS AGDASASAAQ VAALVTDATD SARAASTSAG QAASSAQEAS SGAEAASAKA  180
TEAEKSAAAA ESSKNAAATS AGAAKTSETN AAASQQSAAT SASTAATKAS EAATSARDAV  240
ASKEAAKSSE TNASSSAGRA ASSATAAENS ARAAKTSETN ARSSETAAER SASAAADAKT  300
AAAGSASTAS TKATEAAGSA VSASQSKSAA EAAAIRAKNS AKRAEDIASA VALEDADTTR  360
KGIVQLSSAT NSTSETLAAT PKAVKVVMDE TNRRVPASRK VNGHALNGDI NVTSRDIFDG  420
QVIAIGANKN LDDYQVPGLY FQEANNNTSA AMNYPENSAG SLMVLRGAGV TQVYRVYNSS  480
RSYSRSKYST LAWTPWMPED SYPVGAPIPW PSDVTPTGYA LMQGQPFDKA VYPLLAIAYP  540
AGIIPDMRGQ TIKGKPNGRA VLSYEQDGVI SHTHGASISD TDLGTKYTSS FDYGSKPTTS  600
FDYGNKSSTE GGWHAHNFRY CATSAYRDTP GQGLGMHSSN VSWAAGDRIE GSGNHAHVTW  660
IGPHDHWVGI GAHNHYVVMG YHGHTATVHA AGNAENTVKN IAFNYIVRLA              710

SEQ ID NO: 38          moltype = AA  length = 195
FEATURE                Location/Qualifiers
REGION                 1..195
                       note = Synthetic: STF86-AP1
source                 1..195
                       mol_type = protein
                       organism = synthetic construct
SEQUENCE: 38
MTFEMTGENR TITIYNLRAD TNEFIGKSDG FIPANTGLPA NSTNIAPPPM KAGFVAVFNS  60
ASEKWSLVED HRGKIVYDIL TGKSITIDEL GQLPDDVVSV APEGHFVKWN GKKWVHDADA  120
EKTAQITQAT QQKDSLLALA ASKIAPLQDA VDLDIATEEE TALLLAWKKY RVLINRIKPE  180
DAPDIDWPEV PGDVA                                                   195

SEQ ID NO: 39          moltype = AA  length = 863
FEATURE                Location/Qualifiers
REGION                 1..863
                       note = Synthetic: STF-84
source                 1..863
                       mol_type = protein
                       organism = synthetic construct
SEQUENCE: 39
MAVKISGVLK DGTGKPVQNC TIQLKARRNS TTVVVNTVGS ENPDEAGRYS MDVEYGQYSV  60
```

```
ILQVDGFPPS HAGTITVYED SQPGTLNDFL CAMTEDDARP EVLRRLELMV EEVARNASVV  120
AQSTADAKKS AGDASASAAQ VAALVTDATD SARAASTSAG QAASSAQEAS SGAEAASAKA  180
TEAEKSAAAA ESSKNAAATS AGAAKTSETN AAASQQSAAT SASTAATKAS EAATSARDAV  240
ASKEAAKSSE TNASSSAGRA ASSATAAENS ARAAKTSETN ARSSETAAER SASAAADAKT  300
AAAGSASTAS TKATEAAGSA VSASQSKSAA EAAAIRAKNS AKRAEDIASA VALEDADTTR  360
KGIVQLSSAT NSTSETLAAT PKAVKVVMDE TNRKYTAQDA TTAQKGIVQL SNATNSTSEM  420
LAATPKSVKA AYDLANGKYT AQDATTAQKG IVQLSSATNS ASETLAATPK AANDNANGRV  480
PSARKVNGKA LSADITLTPK DIGTLNSTTM SFSGGAGWFK LATVTMPQAS SVVSITLIGG  540
AGFNVGSPQQ AGISELVLRA GNGNPKGITG ALWQRTSTGF TNFAWVNTSG DTYDIYVAIG  600
NYATGVNIQW DYTSNASVTI HTSPAYSANK PEGLTDGTVY SLYTPSGQFY PPGAPIPWPS  660
DTVPSGYALM QGQTFDKSAY PKLAAAYPSG VIPDMRGWTI KGKPASGRAV LSQEQDGIKS  720
HTHSASASST DLGTKTTSSF DYGTKSTNNT GAHTHSVSGT AASAGNHTHS VTGASAVSQW  780
SQNGSVHKVV SAASVNTSAA GAHTHSVSGT AASAGAHAHT VGIGAHTHSV AIGSHGHTIT  840
VNAAGNAENT VKNIAFNYIV RLA                                          863

SEQ ID NO: 40          moltype = AA  length = 194
FEATURE                Location/Qualifiers
REGION                 1..194
                       note = Synthetic: STF84-AP1
source                 1..194
                       mol_type = protein
                       organism = synthetic construct
SEQUENCE: 40
MAFRMSEQPR TIKIYNLLAG TNEFIGEGDA YIPPHTGLPA NSTYIAPPDI PAGFVAVFNS  60
DEGSWHLVED HRGKTVYDVA SGDALFISEL GPLPENVTWL SPEGEFQKWN GTAWVKDAEA  120
EKLFRIREAE ETKNSLMQVA SEHIAPLQDA VDLEIATEEE TSLLEAWKKY RVLLNRVDTS  180
TAPDIEWPTN PVRE                                                    194

SEQ ID NO: 41          moltype = AA  length = 1283
FEATURE                Location/Qualifiers
REGION                 1..1283
                       note = Synthetic: STF-93
source                 1..1283
                       mol_type = protein
                       organism = synthetic construct
SEQUENCE: 41
MAVKISGVLK DGTGKPVQNC TIQLKARRNS TTVVVNTVGS ENPDEAGRYS MDVEYGQYSV  60
ILQVDGFPPS HAGTITVYED SQPGTLNDFL CAMTEDDARP EVLRRLELMV EEVARNASVV  120
AQSTADAKKS AGDASASAAQ VAALVTDATD SARAASTSAG QAASSAQEAS SGAEAASAKA  180
TEAEKSAAAA ESSKNAAATS AGAAKTSETN AAASQQSAAT SASTAATKAS EAATSARDAV  240
ASKEAAKSSE TNASSSAGRA ASSATAAENS ARAAKTSETN ARSSETAAER SASAAADAKT  300
AAAGSASTAS TKATEAAGSA VSASQSKSAA EAAAIRAKNS AKRAEDIASA VALEDADTTR  360
KGIVQLSSAT NSTSETLAAT PKAVKVVMDE TNRRVPSNRK VNGKALTADI TLTPKDIGTL  420
NSVTMSFSGG AGWFKLATVT MPQASSIVYI ALIGGAGYNV GSPHQAGISE LVLRAGNGNP  480
KGITGALWKR TAVGLTNFAW INTSGDTYDI YVEIGNYATS VNIHWDCTAN ATVSIYTSPT  540
YSASKPSSVT DGVVYTMYST HQKPTPLDIG ALPTTGGTVS GPLSVTGGIT GTLNGNASTA  600
TKLQTARSIG GVGFDGSANI NLPGVNTTGN QNTTGNAATA TKLQTARTIG GVSFDGTANI  660
NLPGVNTTGN QNTTGNAATA TKLQTARTIN GVSFDGSANI SLSPANIGCP ASPTGWLTTG  720
SNGGAITTAQ LVTLLQNNGA FNTKSWIARC AWAYANSATI PNSETGCGVI PLAGAVIEVF  780
NNGSSSNNYT IRITTATTTS VSGALTNAEF IYVFNGTDYS PGWRRVYNTK NKPTASDVGA  840
LPLTGGTLSG GLTSSGEIIS KYANGFRIAY GSFGFFIRND GSNTYFMLTA SGDTLGSWNG  900
LRPITINNTS GAVSIGNGLN VTGGVNGSLN GNASTATKLQ TARNINGVKF DGSGDININT  960
LVSRGRVTAL SGSTQGTAGI QMYEAYNNSY PTTYGNVLHM KGASAAGEGE LLIGWSGTSG  1020
AHAPVFIRSR RDTTDAAWSA WAQLYTAKDS IPGVNTTGNQ NTTGNAATAT KLQTARKIAG  1080
VAFDGSADIT LTAANLNAYT KTEVTNLLSS YASRSSLTGY SGNLDIIAET LVVKSGGSGG  1140
FAIWDIGTTT SGANMYIDPN PGINTVWRST SSRRYKKDIE TLQDRYADEL LSLRPVWYRS  1200
ICRGDRKDWG YYGLIAEEVG EIAPQYVHWR EPTNNDSPED ISSNGMVAEG VMYERLVVPL  1260
IHHIQQLTKR VEELETKLNS PKE                                          1283

SEQ ID NO: 42          moltype = AA  length = 798
FEATURE                Location/Qualifiers
REGION                 1..798
                       note = Synthetic: STF-95
source                 1..798
                       mol_type = protein
                       organism = synthetic construct
SEQUENCE: 42
MAVKISGVLK DGTGKPVQNC TIQLKARRNS TTVVVNTVGS ENPDEAGRYS MDVEYGQYSV  60
ILQVDGFPPS HAGTITVYED SQPGTLNDFL CAMTEDDARP EVLRRLELMV EEVARNASVV  120
AQSTADAKKS AGDASASAAQ VAALVTDATD SARAASTSAG QAASSAQEAS SGAEAASAKA  180
TEAEKSAAAA ESSKNAAATS AGAAKTSETN AAASQQSAAT SASTAATKAS EAATSARDAV  240
ASKEAAKSSE TNASSSAGRA ASSATAAENS ARAAKTSETN ARSSETAAER SASAAADAKT  300
AAAGSASTAS TKATEAAGSA VSASQSKSAA EAAAIRAKNS AKRAEDIASA VALEDADTTR  360
KGIVQLSSAT NSTSETLAAT PKAVKVVMDE TNRRVPSARK VNGKALSADI TLTPKDIGTL  420
NSTTMSFSGG AGWFKLATVT MPQASSVVSI TLIGGAGFNV GSPQQAGISE LVLRAGNGNP  480
KGITGALWQR TSTGFTNFAW VNTSGDTYDI YVAIGNYATG VNIQWDYTSN ASVTIHTSPA  540
YSANKPEGLT DGTVYSLYTP SEQFYPPGAP IPWPSDTVPS GYALMQGQTF DKSAYPKLAA  600
AYPSGVIPDM RGWTIKGKPA SGRAVLSQEQ DGIKSHTHSA SASSTDLGTK NTSSFDYGTK  660
STNNTGAHTH SLSGSTGSAG DHTHGNGIRW PGGGGSALAF YDGGGFTYVQ DSQYQVSPGT  720
```

-continued

```
SSRRSYYQRI QTQSAGAHTH SLSGTAASSG AHAHTVGIGA HTHSVAIGSH GHTITVNAAG  780
NAENTVKNIA FNYIVRLA                                                798

SEQ ID NO: 43          moltype = AA  length = 194
FEATURE                Location/Qualifiers
REGION                 1..194
                       note = Synthetic: STF95-AP1
source                 1..194
                       mol_type = protein
                       organism = synthetic construct
SEQUENCE: 43
MAFRMSEQAR TIKIYNLLAG TNEFIGEGDA YIPPHTGLPA NSTDIAPPDI PAGFVAVFNS  60
DEASWHLVED HRGKTVYDVA SGDELFISEL GPLPENVTWL SPEGEFQKWN GTAWVKDTEA  120
EKMFRIREAE ETKNNLMQVA SEHIAPLQDA ADLEIATEEE TSLLEAWKKY RVLLNRVDTS  180
TAPDIEWPTN PVRE                                                    194

SEQ ID NO: 44          moltype = AA  length = 625
FEATURE                Location/Qualifiers
REGION                 1..625
                       note = Synthetic: STF-132
source                 1..625
                       mol_type = protein
                       organism = synthetic construct
SEQUENCE: 44
MAVKISGVLK DGTGKPVQNC TIQLKARRNS TTVVVNTVGS ENPDEAGRYS MDVEYGQYSV  60
ILQVDGFPPS HAGTITVYED SQPGTLNDFL CAMTEDDARP EVLRRLELMV EEVARNASVV  120
AQSTADAKKS AGDASASAAQ VAALVTDATD SARAASTSAG QAASSAQEAS SGAEAASAKA  180
TEAEKSAAAA ESSKNAAATS AGAAKTSETN AAASQQSAAT SASTAATKAS EAATSARDAV  240
ASKEAAKSSE TNASSSAGRA ASSATAAENS ARAAKTSETN ARSSETAAER SASAAADAKT  300
AAAGSASTAS TKATEAAGSA VSASQSKSAA EAAAIRAKNS AKRAEDIASA VALEDADTTR  360
KGIVQLSSAT NSTSETLAAT PKAVKVVMDE TNRAVQRDGD TMTGELKIRG VNALRIFNDA  420
FGLIFRRSEE CLHLIPTSEG QGENGDIGPL RPFTINLRTG EISMSHKVSV GGGSQVNGAL  480
GIGVQNALGG NSIAFGDNDT GIKQNGDGIL DVYANGQHVF RFQNGALQSH RAVNVSGRVT  540
PTDYGNFDER YQTKTGGVQN FQYTSEVFHK PAGNEVSWVF RAPSGCTLSG INVQETGSNS  600
ADNIGGVYYK QAQIYINGAW RSVSG                                        625

SEQ ID NO: 45          moltype = AA  length = 188
FEATURE                Location/Qualifiers
REGION                 1..188
                       note = Synthetic: STF132-AP1
source                 1..188
                       mol_type = protein
                       organism = synthetic construct
SEQUENCE: 45
MALSIRLIKA KIMELRNVTR YYPENMPYGE GVQYFRSEDG QDFYESLDKF AKKYKLCTHP  60
ETGVIYSMAE DVSRLYPAGF TIVEVDELPD GFCIEARWYY KDGEVLPVPV DYRLLAESER  120
ARLTAIAERE ISDKKTDLLL GIINNGEKEM LKLWRMYIRN LKNIDFNHIH DKSSFDSIKW  180
PCDPENSH                                                           188

SEQ ID NO: 46          moltype = AA  length = 1348
FEATURE                Location/Qualifiers
REGION                 1..1348
                       note = Synthetic: K1F
source                 1..1348
                       mol_type = protein
                       organism = synthetic construct
SEQUENCE: 46
MAVKISGVLK DGTGKPVQNC TIQLKARRNS TTVVVNTVGS ENPDEAGRYS MDVEYGQYSV  60
ILQVDGFPPS HAGTITVYED SQPGTLNDFL CAMTEDDARP EVLRRLELMV EEVARNASVV  120
AQSTADAKKS AGDASASAAQ VAALVTDATD SARAASTSAG QAASSAQEAS SGAEAASAKA  180
TEAEKSAAAA ESSKNAAATS AGAAKTSETN AAASQQSAAT SASTAATKAS EAATSARDAV  240
ASKEAAKSSE TNASSSAGRA ASSATAAENS ARAAKTSETN ARSSETAAER SASAAADAKT  300
AAAGSASTAS TKATEAAGSA VSASQSKSAA EAAAIRAKNS AKRAEDIASA VALEDADTTR  360
KGIVQLSSAT NSTSETLAAT PKAVKVVMDE TNRKAPLDSP ALTGTPTAPT ALRGTNNTQI  420
ANTAFVLAAI ADVIDASPDA LNTLNELAAA LGNDPDFATT MTNALAGKQP KNATLTALAG  480
LSTAKNKLPY FAENDAASLT ELTQVGRDIL AKNSVADVLE YLGAGENSGA KGDGVTDDTA  540
ALTSALNDTP VGQKINGNGK TYKVTSLPDI SRFINTRFVY ERIPGQPLYY ASEEFVQGEL  600
FKITDTPYYN AWPQDKAFVY ENVIYAPYMG SDRHGVSRLH VSWVKSGDDG QTWSTPEWLT  660
DLHPDYPTVN YHCMSMGVCR NRLFAMIETR TLAKNALTNC ALWDRPMSRS LHLTGGITKA  720
ANQRYATIHV PDHGLFVGDF VNFSNSAVTG VSGDMTVATV IDKDNFTVLT PNQQTSDLNN  780
AGKNWHMGTS FHKSPWRKTD LGLIPSVTEV HSFATIDNNG FAMGYHQGDV APREVGLFYF  840
PDAFNSPSNY VRRQIPSEYE PDASEPCIKY YDGVLYLITR GTRGDRLGSS LHRSRDIGQT  900
WESLRFPHNV HHTTLPFAKV GDDLIMFGSE RAENEWEAGA PDDRYKASYP RTFYARLNVN  960
NWNADDIEWV NITDQIYQGG IVNSGVGVGS VVVKDNYIYY MFGGEDHFNP WTYGDNSAKD  1020
PFKSDGHPSD LYCYKMKIGP DNRVSRDFRY GAVPNRAVPV FFDTNGVRTV PAPMEFTGDL  1080
GLGHVTIRAS TSSNIRSEVL MEGEYGFIGK SIPTDNPAGQ RIIFCGGEGT SSTTGAQITL  1140
YGANNTDSRR IVYNGDEHLF QSADVKPYND NVTALGGPSN RFTTAYLGSN PIVTSNGERK  1200
TEPVVFDDAF LDAWGDVHYI MYQWLDAVQL KGNDARIHFG VIAQQIRDVF IAHGLMDENS  1260
TNCRYAVLCY DKYPRMTDTV FSHNEIVEHT DEEGNVTTTE EPVYTEVVIH EEGEEWGVRP  1320
```

```
DGIFFAEAAY QRRKLERIEA RLSALEQK                              1348

SEQ ID NO: 47           moltype = AA  length = 1154
FEATURE                 Location/Qualifiers
REGION                  1..1154
                        note = Synthetic: K5
source                  1..1154
                        mol_type = protein
                        organism = synthetic construct
SEQUENCE: 47
MAVKISGVLK DGTGKPVQNC TIQLKARRNS TTVVVNTVGS ENPDEAGRYS MDVEYGQYSV  60
ILQVDGFPPS HAGTITVYED SQPGTLNDFL CAMTEDDARP EVLRRLELMV EEVARNASVV  120
AQSTADAKKS AGDASASAAQ VAALVTDATD SARAASTSAG QAASSAQEAS SGAEAASAKA  180
TEAEKSAAAA ESSKNAAATS AGAAKTSETN AAASQQSAAT SASTAATKAS EAATSARDAV  240
ASKEAAKSSE TNASSSAGRA ASSATAAENS ARAAKTSETN ARSSETAAER SASAAADAKT  300
AAAGSASTAS TKATEAAGSA VSASQSKSAA EAAAIRAKNS AKRAEDIASA VALEDADTTR  360
KGIVQLSSAT NSTSETLAAT PKAVKVVMDE TNRKAPLDSP ALTGTPTAPT ALRGTNNTQI  420
ANTAFVLAAI ADVIDASPDA LNTLNELAAA LGNDPDFATT MTNALAGKQP KNATLTALAG  480
LSTAKNKLPY FAENDAASLT ELTQVGRDIL AKNSVADVLE YLGAGENSPK TEGILHKGQS  540
LYEYLDARVL TSKPFGAAGD ATTDDTEVIA ASLNSQKAVT ISDGVFSSSG INSNYCNLDG  600
RGSGVLSHRS STGNYLVFNN PRTGRLSNIT VESNKATDTT QGQQVSLAGG SDVTVSDVNF  660
SNVKGTGFSL IAYPNDAPPD GLMIKGIRGS YSGYATNKAA GCVLADSSVN SLIDNVIAKN  720
YPQFGAVELK GTASYNIVSN VIGADCQHVT YNGTEGPIAP SNNLIKGVMA NNPKYAAVVA  780
GKGSTNLISD VLVDYSTSDA RQAHGVTVEG SDNVINNVLM SGCDGTNSLG QRQTATIARF  840
IGTANNNYAS VFPSYSATGV ITFESGSTRN FVEVKHPGRR NDLLSSASTI DGAATIDGTS  900
NSNVVHAPAL GQYIGSMSGR FEWRIKSMSL PSGVLTSADK YRMLGDGAVS LAVGGGTSSQ  960
VRLFTSDGTS RTVSLTNGNV RLSTSSTGYL QLGADAMTPD STGTYALGSA SRAWSGGFTQ  1020
AAFTVTSDAR CKTEPLTISD ALLDAWSEVD FVQFQYLDRV EEKGADSARW HFGIIAQRAK  1080
EAFERHGIDA HRYGFLCFDS WDDVYEEDAN GSRKLITPAG SRYGIRYEEV LILEAALMRR  1140
TIKRMQEALA ALPK                                             1154

SEQ ID NO: 48           moltype = AA  length = 1075
FEATURE                 Location/Qualifiers
REGION                  1..1075
                        note = Synthetic: STF-37
source                  1..1075
                        mol_type = protein
                        organism = synthetic construct
SEQUENCE: 48
MAVKISGVLK DGTGKPVQNC TIQLKARRNS TTVVVNTVGS ENPDEAGRYS MDVEYGQYSV  60
ILQVDGFPPS HAGTITVYED SQPGTLNDFL CAMTEDDARP EVLRRLELMV EEVARNASVV  120
AQSTADAKKS AGDASASAAQ VAALVTDATD SARAASTSAG QAASSAQEAS SGAEAASAKA  180
TEAEKSAAAA ESSKNAAATS AGAAKTSETN AAASQQSAAT SASTAATKAS EAATSARDAV  240
ASKEAAKSSE TNASSSAGRA ASSATAAENS ARAAKTSETN ARSSETAAER SASAAADAKT  300
AAAGSASTAS TKATEAAGSA VSASQSKSAA EAAAIRAKNS AKRAEDIASA VALEDADTTR  360
KGIVQLSSAT NSTSETLAAT PKAVKVVMDE TNRKAPLDSP ALTGTPTAPT ALRGTNNTQI  420
ANTAFVLAAI ADVIDASPDA LNTLNELAAA LGNDPDFATT MTNALAGKQP KNATLTALAG  480
LSTAKNKLPY FAENDAASLT ELTQVGRDIL AKNSVADVLE YLGAGENSEL SGEHGSFLIG  540
GVIDCYSTVS DLISSSPSVG RVCRTIGYYS PGDGGGADYI ISIGTPMQDF SDSGSIVIDE  600
CKFAKLIQQS QYDLKQFGVK PSDPSYAEKN DIFISQAITR SRVGRCKIII SDVIYHKKPL  660
IFDYYNHMEG SCIGSDPEFT PRFIKIDNTT SGLPDMGYPG VADVVSYDVD AGIIIKRQNS  720
GTSFARGFII KGFLLQSEKK SAWAIYAPHM ADFDIDIDSR GFNGGIRWFV NFLGRMAGRH  780
IGLGANSSDP TLSIGAWCSK FSTIPDCGNS VVFRLSFNGF NRGMQMEYFG NGVLDRVTLE  840
NISKPTPTSP TTHGIYATDT WLTGQVSCES SSTCIIRAGN NANFDITLSA VFHVTQDDPS  900
EGIVHVLNGG RLTLRSSTIL ADLADTKIIN ENGGYLDIAA NTRTGNIVYS NSDNYRFKDR  960
TIGFGQTAAT TKTSFSSGEE ITFSLLNGTP KANLSGGTIQ FNSPCLIKIT VQGRGITSGA  1020
LTFGINGESS ESVSQGQQVS MVVGVVSGDI LNLKATSSLT LGSAGGVRVL LEPVN       1075

SEQ ID NO: 49           moltype = AA  length = 955
FEATURE                 Location/Qualifiers
REGION                  1..955
                        note = Synthetic: 1JL
source                  1..955
                        mol_type = protein
                        organism = synthetic construct
SEQUENCE: 49
MAVKISGVLK DGTGKPVQNC TIQLKARRNS TTVVVNTVGS ENPDEAGRYS MDVEYGQYSV  60
ILQVDGFPPS HAGTITVYED SQPGTLNDFL CAMTEDDARP EVLRRLELMV EEVARNASVV  120
AQSTADAKKS AGDASASAAQ VAALVTDATD SARAASTSAG QAASSAQEAS SGAEAASAKA  180
TEAEKSAAAA ESSKNAAATS AGAAKTSETN AAASQQSAAT SASTAATKAS EAATSARDAV  240
ASKEAAKSSE TNASSSAGRA ASSATAAENS ARAAKTSETN ARSSETAAER SASAAADAKT  300
AAAGSASTAS TKATEAAGSA VSASQSKSAA EAAAIRAKNS AKRAEDIASA VALEDADTTR  360
KGIVQLSSAT NSTSETLAAT PKAVKVVMDE TNRKAPLDSP ALTGTPTAPT ALRGTNNTQI  420
ANTAFVLAAI ADVIDASPDA LNTLNELAAA LGNDPDFATT MTNALAGKQP KNATLTALAG  480
LSTAKNKLPY FAENDAASLT ELTQVGRDIL AKNSVADVLE YLGAGENSGY KVQSLAILSD  540
TQAVHDATNT IKTQTDKIKA DTQAIKTQTN QIKTETGVIR DKANTAKTDA QAASAAAQGF  600
RDQAKEWAQS VNADNLLTKT GNLAGLTDKS AARSNLGLGS VATENTVPIK KGGTAATTVA  660
AARSNLGLGS VATENTVPIE KGGTAATTAA KARSNLGLGS VATENTVPIE KGGTAATTAA  720
KARSNFGLGD NNKVKLGTLR LNGGESLVFN DVERNGLIIS NASFGIDSWV GQTMHKWYTD  780
```

```
WTRAGLVRAG DAHLSDYRVH VWKDGFTEAL FRFLPDGRLI SGNSGNPSVN EFQKAPLSDR  840
DLKKEIKYTD GEESYNRVRQ WLPAMFKYKE SDVQRYGLIA QDLARIDPEY VHLLPGYAIY  900
EDVKGVDEEG NEVVVDRKEI GYTDDVLSLD SNVLLMDLCA AFVHLLHKVE KLEGK       955

SEQ ID NO: 50          moltype = AA  length = 1051
FEATURE                Location/Qualifiers
REGION                 1..1051
                       note = Synthetic: STF-48
source                 1..1051
                       mol_type = protein
                       organism = synthetic construct
SEQUENCE: 50
MAVKISGVLK DGTGKPVQNC TIQLKARRNS TTVVVNTVGS ENPDEAGRYS MDVEYGQYSV  60
ILQVDGFPPS HAGTITVYED SQPGTLNDFL CAMTEDDARP EVLRRLELMV EEVARNASVV  120
AQSTADAKKS AGDASASAAQ VAALVTDATD SARAASTSAG QAASSAQEAS SGAEAASAKA  180
TEAEKSAAAA ESSKNAAATS AGAAKTSETN AAASQQSAAT SASTAATKAS EAATSARDAV  240
ASKEAAKSSE TNASSSAGRA ASSATAAENS ARAAKTSETN ARSSETAAER SASAAADAKT  300
AAAGSASTAS TKATEAAGSA VSASQSKSAA EAAAIRAKNS AKRAEDIASA VALEDADTTR  360
KGIVQLSSAT NSTSETLAAT PKAVKVVMDE TNRKAPLDSP ALTGTPTAPT ALRGTNNTQI  420
ANTAFVLAAI ADVIDASPDA LNTLNELAAA LGNDPDFATT MTNALAGKQP KNATLTALAG  480
LSTAKNKLPY FAENDAASLT ELTQVGRDIL AKNSVADVLE YLGAGENSQL ESDADGMGDA  540
LVAVKQPYIG SIALTQHDKN TNFISAKDFG ATADGTLHPL SEKFSTLSAA QAVYPFVTSL  600
TQSLDYAGIQ AAINTGRNVL LTSGTYFVNA TIEMNSNCTI NGETNSNINR PETFIAVIGN  660
IACFHYHAAF NTINIENVYI FYDGGRPTSP TGNDGKIGIL IDGGTTSPGV MHIKNVEVDG  720
AWWAIYDDSG NYLTKYTQVW ARRVAHGFYK ANGTTIQWDT CYVLDAAQAW YVVNCLSPQL  780
INCAGDQITV DGSQYTFDSS GLYFSGCKCL TITGYDGESN IIKNTNGITA SYIKLNDTIA  840
HISGLAGHGN SMQTTGSGTA AFIFATGTSI VNIKSSTDSF LDSESITYTG SGYPNTLLTD  900
STAKIIAEGC RFKAPTGGTP VISTYSTGNG VFTDCSLTGT QTSGSYVESR SSAGNQLPAV  960
YTAKGTQAVA ANVATTLFEL PNSQGMYLIS VWAESSGTNF SSLQLAMWDG TTLTLTPLKS  1020
GGLISFTVTG RIVTITSQGT TTFNWTYTKA G                                 1051

SEQ ID NO: 51          moltype = AA  length = 1365
FEATURE                Location/Qualifiers
REGION                 1..1365
                       note = Synthetic: STF-49
source                 1..1365
                       mol_type = protein
                       organism = synthetic construct
SEQUENCE: 51
MAVKISGVLK DGTGKPVQNC TIQLKARRNS TTVVVNTVGS ENPDEAGRYS MDVEYGQYSV  60
ILQVDGFPPS HAGTITVYED SQPGTLNDFL CAMTEDDARP EVLRRLELMV EEVARNASVV  120
AQSTADAKKS AGDASASAAQ VAALVTDATD SARAASTSAG QAASSAQEAS SGAEAASAKA  180
TEAEKSAAAA ESSKNAAATS AGAAKTSETN AAASQQSAAT SASTAATKAS EAATSARDAV  240
ASKEAAKSSE TNASSSAGRA ASSATAAENS ARAAKTSETN ARSSETAAER SASAAADAKT  300
AAAGSASTAS TKATEAAGSA VSASQSKSAA EAAAIRAKNS AKRAEDIASA VALEDADTTR  360
KGIVQLSSAT NSTSETLAAT PKAVKVVMDE TNRKAPLDSP ALTGTPTAPT ALRGTNNTQI  420
ANTAFVLAAI ADVIDASPDA LNTLNELAAA LGNDPDFATT MTNALAGKQP KNATLTALAG  480
LSTAKNKLPY FAENDAASLT ELTQVGRDIL AKNSVADVLE YLGAGENSGA IGDGVHDDTS  540
ALSELLSVAT GGEKIDGRGL TFKVSTLPDV SRFKNARFLF ERIPGQPLFY ASEDFIQGEL  600
FKITDTPWYN AWTQDKTFVY DNVIYAPFMA GDRHGVNNLH VAWVRSGDDG RTWTTPEWLT  660
DLHENYPTVN YHCMSMGVVR NRLFAVIETR TVSGNKLQVA ELWDRPMSRS LRAYGGITKA  720
ANQQVAYIRI TDHGLFAGDF VNFSNSGVTG VTGNMTVTTV IDKNTFTVTT QNTQDVDQNN  780
EGRYWSFGTS FHSSPWRKTS LGTIPSFVDG STPVTEIHSF ATISDNSFAV GYHNGDIGPR  840
ELGILYFSDA FGSPGSFVRR RIPAEYEANA SEPCVKYYDG ILYLTTRGTL STQPGSSLHR  900
SSDLGTSWNS LRFPNNVHHS NLPFAKVGDE LIIFGSERAF GEWEGGEPDN RYAGNYPRTF  960
MTRVNVNEWS LDNVEWVNVT DQIYQGGIVN SAVGVGSVCI KDNWLYYIFG GEDFLNPWSI  1020
GDNNRKYPYV HDGHPADLYC FRVKIKQEEF VSRDFVYGAT PNRTLPTFMS TSGVRTVPVP  1080
VDFTDDVAVQ SLTVHAGTSG QVRAEVKLEG NYAIIAKKVP SDDVTAQRLI VSGGETTSSA  1140
DGAMITLHGS GSSTPRRAVY NALEHLFENG DVKPYLDNVN ALGGPGNRFS TVYLGSNPVV  1200
TSDGTLKTEP VSPDEALLDA WGDVRYIAYK WLNAVAIKGE EGARIHHGVI AQQLRDVLIS  1260
HGLMEEESTT CRYAFLCYDD YPAVYDDVIT GQREMPLTDN DGSIIVDEDD NPVMVMEDII  1320
ERVEITPAGS RWGVRPDLLF YIEAAWQRRE IERIKARLDL IEGKH                  1365

SEQ ID NO: 52          moltype = AA  length = 1051
FEATURE                Location/Qualifiers
REGION                 1..1051
                       note = Synthetic: STF-52
source                 1..1051
                       mol_type = protein
                       organism = synthetic construct
SEQUENCE: 52
MAVKISGVLK DGTGKPVQNC TIQLKARRNS TTVVVNTVGS ENPDEAGRYS MDVEYGQYSV  60
ILQVDGFPPS HAGTITVYED SQPGTLNDFL CAMTEDDARP EVLRRLELMV EEVARNASVV  120
AQSTADAKKS AGDASASAAQ VAALVTDATD SARAASTSAG QAASSAQEAS SGAEAASAKA  180
TEAEKSAAAA ESSKNAAATS AGAAKTSETN AAASQQSAAT SASTAATKAS EAATSARDAV  240
ASKEAAKSSE TNASSSAGRA ASSATAAENS ARAAKTSETN ARSSETAAER SASAAADAKT  300
AAAGSASTAS TKATEAAGSA VSASQSKSAA EAAAIRAKNS AKRAEDIASA VALEDADTTR  360
KGIVQLSSAT NSTSETLAAT PKAVKVVMDE TNRKAPLDSP ALTGTPTAPT ALRGTNNTQI  420
ANTAFVLAAI ADVIDASPDA LNTLNELAAA LGNDPDFATT MTNALAGKQP KNATLTALAG  480
```

```
LSTAKNKLPY FAENDAASLT ELTQVGRDIL AKNSVADVLE YLGAGENSQL ASSEDGMGDA  540
LVAVKQPYIG SIALTQHDKN TNFISAKDFG ATADGTLHPL SEKFSTLSAA QAVYPFVTSL  600
TQSLDYAGIQ AAINTGRNVL LTSGTYFVNA TIEMNSNCTI NGETNSNINR PETFIAVIGN  660
IACFHYHAAF NTINIENVYI FYDGGRPTSP TGNDGKIGIL IDGGTTSPGV MHIKNVEVDG  720
AWWAIYDDSG NYLTKYTQVW ARRVAHGFYK ANGTTIQWDT CYVLDAAQAW YVVNCLSPQL  780
INCAGDQITV DGSQYTFDSS GLYFSGCKCL TITGYDGESN IIKNTNGITA SYIKLNDTIA  840
HISGLAGHGN SMQTTGSGTA AFIFATGTSI VNIKSSTDSF LDSESITYTG SGYPNTLLTD  900
STAKIIAEGC RFKAPTGGTP VISTYSTGNG VFTDCSLTGT QTSGSYVESR SSAGNQLPAV  960
YTAKGTQAVA ANVATTLFEL PNSQGMYLIS VWAESSGTNF SSLQLAMWDG TTLTLTPLKS  1020
GGLISFTVTG RIVTITSQGT TTFNWTYTKA G                                 1051

SEQ ID NO: 53          moltype = AA  length = 931
FEATURE                Location/Qualifiers
REGION                 1..931
                       note = Synthetic: 1AR
source                 1..931
                       mol_type = protein
                       organism = synthetic construct
SEQUENCE: 53
MAVKISGVLK DGTGKPVQNC TIQLKARRNS TTVVVNTVGS ENPDEAGRYS MDVEYGQYSV  60
ILQVDGFPPS HAGTITVYED SQPGTLNDFL CAMTEDDARP EVLRRLELMV EEVARNASVV  120
AQSTADAKKS AGDASASAAQ VAALVTDATD SARAASTSAG QAASSAQEAS SGAEAASAKA  180
TEAEKSAAAA ESSKNAAATS AGAAKTSETN AAASQQSAAT SASTAATKAS EAATSARDAV  240
ASKEAAKSSE TNASSSAGRA ASSATAAENS ARAAKTSETN ARSSETAAER SASAAADAKT  300
AAAGSASTAS TKATEAAGSA VSASQSKSAA EAAAIRAKNS AKRAEDIASA VALEDADTTR  360
KGIVQLSSAT NSTSETLAAT PKAVKVVMDE TNRKAPLDSP ALTGTPTAPT ALRGTNNTQI  420
ANTAFVLAAI ADVIDASPDA LNTLNELAAA LGNDPDFATT MTNALAGKQP KNATLTALAG  480
LSTAKNKLPY FAENDAASLT ELTQVGRDIL AKNSVADVLE YLGAGENSIA TRVSKEGDTM  540
TGKLTLSAGN DALVLTAGEG ASSHIRSDVG GTNNWYIGKG SGDNGLGFYS YITQGGVYIT  600
NNGEIALSPQ GQGTFNFNRD RLHINGTQWT AHQGGGWENQ WNQEAPIFID FGNVGNDSYY  660
PIIKGKSGIT NEGYISGVDF GMRRITNTWA QGIIRVGNQE NGSDPQAIYE FHHNGVLYVP  720
NMVKTGARLS AGGGDPVWQG ACVVIGDNDT GLVHGGDGRI NMVANGMHIA SWSSAYHLHE  780
GLWDTTGALW TEQGRAIISF GHLVQQSDAY STFVRDVYVR SDIRVKKDLV KFENASEKLS  840
KINGYTYMQK RGLDEEGNQK WEPNAGLIAQ EVQAILPELV EGDPDGEALL RLNYNGVIGL  900
NTAAINEHTA EIAELKSEIE ELKKIVKSLL K                                 931

SEQ ID NO: 54          moltype = AA  length = 259
FEATURE                Location/Qualifiers
REGION                 1..259
                       note = Synthetic: 1AR-AP1
source                 1..259
                       mol_type = protein
                       organism = synthetic construct
SEQUENCE: 54
MAVTGPWVGS SAVVNTGQNW MVGAAQRLRM GAPFWMSNMI GRSVEVIHTL GADHNFNGQW  60
FRDRCFEAGS APIVFNITGD LVSYSRDVPL FFMYGDTPNE YVQLNIHGVT MYGRGGNGWA  120
AGAIGASDGG VCIQNDIGGR LRINNGGAIA GGGGGGGGYS QANNWAGKYV CGGGGGRPFG  180
LGGNNGARWP GGNASLTSPG AGGNTGTRYY AGGGGEVGQP GQYANPGAGY STPPTSPGAA  240
VAGSAPTWQN VGAIYGPRV                                               259

SEQ ID NO: 55          moltype = AA  length = 80
FEATURE                Location/Qualifiers
REGION                 1..80
                       note = Synthetic: 1AR-AP2
source                 1..80
                       mol_type = protein
                       organism = synthetic construct
SEQUENCE: 55
MSEQTIEQKL SAEIVTLKSR ILDTQDQAAR LMEESKILQG TLAEIARAVG ITGDTIKVEE  60
IVEAVKNLTA ESTDEAKDEE                                              80

SEQ ID NO: 56          moltype = AA  length = 901
FEATURE                Location/Qualifiers
REGION                 1..901
                       note = Synthetic: 13-13.0
source                 1..901
                       mol_type = protein
                       organism = synthetic construct
SEQUENCE: 56
MAVKISGVLK DGTGKPVQNC TIQLKARRNS TTVVVNTVGS ENPDEAGRYS MDVEYGQYSV  60
ILQVDGFPPS HAGTITVYED SQPGTLNDFL CAMTEDDARP EVLRRLELMV EEVARNASVV  120
AQSTADAKKS AGDASASAAQ VAALVTDATD SARAASTSAG QAASSAQEAS SGAEAASAKA  180
TEAEKSAAAA ESSKNAAATS AGAAKTSETN AAASQQSAAT SASTAATKAS EAATSARDAV  240
ASKEAAKSSE TNASSSAGRA ASSATAAENS ARAAKTSETN ARSSETAAER SASAAADAKT  300
AAAGSASTAS TKATEAAGSA VSASQSKSAA EAAAIRAKNS AKRAEDIASA VALEDADTTR  360
KGIVQLSSAT NSTSETLAAT PKAVKVVMDE TNRKAPLDSP ALTGTPTAPT ALRGTNNTQI  420
ANTAFVLAAI ADVIDASPDA LNTLNELAAA LGNDPDFATT MTNALAGKQP KNATLTALAG  480
LSTAKNKLPY FAENDAASLT ELTQVGRDIL AKNSVADVLE YLGAGENSII QLEDSQGAHF  540
STERTLATGA IKTRFFGETF TDGTLYLNQM NNSSERFSIN NWGNSEVGRP AVLEVGDSKG  600
```

```
YHFYTERGTD NSLNFDVAGN FTVHGPSGIT IKTSTGARHI WFRDDSDAEK AVIWATDEGI  660
LHIRNNYGGS FSHHFQGAMI LAGERVPYNS EYALIRGNIS GGAWVDWRGR PAGLLVDCQD  720
SRNQAYNIWK ATHWGDQHLA AMGVHAGGGN PQVVLHVGGN DYAFASNGDF TAGAAVYCND  780
VYIRSDRRLK INVKDYEENA VDKVNKLKVK TYDKVKSLSD REVIGHEIGI IAQDLQEVLP  840
EAVSTSSVGS QDNPEEILTI SNSAVNALLI KAIQEMSEEI KELKTPLFTK IARKISKYFK  900
F                                                                  901

SEQ ID NO: 57           moltype = AA  length = 259
FEATURE                 Location/Qualifiers
REGION                  1..259
                        note = Synthetic: 13-13.0-AP1
source                  1..259
                        mol_type = protein
                        organism = synthetic construct
SEQUENCE: 57
MAVVGVPGWI GSSAVNETGQ RWMSQAAGQL RLGVPCWMSQ FAGRSREIIH TLGADHNFNG  60
QWFRDRCFEA GSTPIVFNIT GDLVSYSKDV PLFFMYGDTP NEYVQLNIHG VTMYGRGGNG  120
GSNSPGSAGG HCIQNDIGGR LRINNGGAIA GGGGGGGGGR YGRLSFGGGG GRPFGAGGSS  180
SHMSSGATAG TISAPGAGSV GEGSLWVYTG GSGGNVGAAG GRCNIQGNGT EYDGGAAGYA  240
VIGSAPTWIN VGAIYGPRV                                               259

SEQ ID NO: 58           moltype = AA  length = 80
FEATURE                 Location/Qualifiers
REGION                  1..80
                        note = Synthetic: 13-13.0-AP2
source                  1..80
                        mol_type = protein
                        organism = synthetic construct
SEQUENCE: 58
MSEQTIEQKL SAEIVTLKSR ILDTQDQAAR LMEESKILQG TLAEIARAVG ITGDTIKVEE  60
IVEAVKNLTA ESADEAKDEE                                              80

SEQ ID NO: 59           moltype = AA  length = 761
FEATURE                 Location/Qualifiers
REGION                  1..761
                        note = Synthetic: 13-14.3
source                  1..761
                        mol_type = protein
                        organism = synthetic construct
SEQUENCE: 59
MAVKISGVLK DGTGKPVQNC TIQLKARRNS TTVVVNTVGS ENPDEAGRYS MDVEYGQYSV  60
ILQVDGFPPS HAGTITVYED SQPGTLNDFL CAMTEDDARP EVLRRLELMV EEVARNASVV  120
AQSTADAKKS AGDASISDDI GWMHYIQRNK DNTVEAVLNG QQTINENIIA KKDIWVDRAV  180
HTLGEITTNA VNGLRIWNND YGVIFRRSEG SLHIIPTAFG EGETGDIGPL RPLSIALDTG  240
KVTIPDLQSS YNTFAANGYI KFVGHGAGAG GYDIQYAQAA PIFQEIDDDA VSKYYPIVKQ  300
KFLNGKSVWS LGTEIESGTF VIHHLKEDGS QGHASRFNQD GTVNFPDNVL VGGDINMKGM  360
MTFDAGRLGS RDYFKFNHWG DSNNGRDNII QLEDSQGAHF STERTLATGA IKTRFFGETF  420
TDGTLYLNQM NNSSERFSIN NWGNSEVGRP AVLEVGDSKG YHFYTERGTD NSLNFDVAGN  480
FTVHGPSGIT IKTSTGARHI WFRDDSDAEK AVIWATDEGI LHIRNNYGGS FSHHFQGAMI  540
LAGERVPYNS EYALIRGNIS GGAWVDWRGR PAGLLVDCQD SRNQAYNIWK ATHWGDQHLA  600
AMGVHAGGGN PQVVLHVGGN DYAFASNGDF TAGAAVYCND VYIRSDRRLK INVKDYEENA  660
VDKVNKLKVK TYDKVKSLSD REVIGHEIGI IAQDLQEVLP EAVSTSSVGS QDNPEEILTI  720
SNSAVNALLI KAIQEMSEEI KELKTPLFTK IARKISKYFK F                      761

SEQ ID NO: 60           moltype = AA  length = 259
FEATURE                 Location/Qualifiers
REGION                  1..259
                        note = Synthetic: 13-14.3-AP1
source                  1..259
                        mol_type = protein
                        organism = synthetic construct
SEQUENCE: 60
MAVVGVPGWI GSSAVNETGQ RWMSQAAGQL RLGVPCWMSQ FAGRSREIIH TLGADHNFNG  60
QWFRDRCFEA GSTPIVFNIT GDLVSYSKDV PLFFMYGDTP NEYVQLNIHG VTMYGRGGNG  120
GSNSPGSAGG HCIQNDIGGR LRINNGGAIA GGGGGGGGGR YGRLSFGGGG GRPFGAGGSS  180
SHMSSGATAG TISAPGAGSV GEGSLWVYTG GSGGNVGAAG GRCNIQGNGT EYDGGAAGYA  240
VIGSAPTWIN VGAIYGPRV                                               259

SEQ ID NO: 61           moltype = AA  length = 80
FEATURE                 Location/Qualifiers
REGION                  1..80
                        note = Synthetic: 13-14.3-AP2
source                  1..80
                        mol_type = protein
                        organism = synthetic construct
SEQUENCE: 61
MSEQTIEQKL SAEIVTLKSR ILDTQDQAAR LMEESKILQG TLAEIARAVG ITGDTIKVEE  60
IVEAVKNLTA ESADEAKDEE                                              80
```

```
SEQ ID NO: 62           moltype = DNA  length = 2058
FEATURE                 Location/Qualifiers
misc_feature            1..2058
                        note = Synthetic: STF-25
source                  1..2058
                        mol_type = other DNA
                        organism = synthetic construct
SEQUENCE: 62
atggcagtaa agatttcagg agtcctgaaa gacggcacag gaaaaccggt acagaactgc  60
accattcagc tgaaagccag acgtaacagc accacggtgg tggtgaacac ggtgggctca  120
gagaatccgg atgaagccgg gcgttacagc atggatgtgg agtacggtca gtacagtgtc  180
atcctgcagg ttgacggttt tccaccatcg cacgccggga ccatcaccgt gtatgaagat  240
tcacaaccgg ggacgctgaa tgattttctc tgtgccatga cggaggatga tgcccggccg  300
gaggtgctgc gtcgtcttga actgatggtg gaagaggtgg cgcgtaacgc gtccgtggtg  360
gcacagagta cggcagacgc gaagaaatca gaaacagcag cggcatcgtc caggaacgcg  420
gcgaaaacat cagagacgaa tgcaggtaac agcgcgaaag cggcagcttc ttcaaaaaca  480
gccgcacaaa acgcagcaac agcggcagaa cgttcagaga caaatgcccg tgcgtcagaa  540
gaagcctccg cagacagtga agaggcttcc cgccgtaatg cagagtcagc cgctgaaaat  600
gccggagtcg ccaccacaaa agcgcgggag gccgcagcag acgcaacaaa ggccgggcag  660
aaaaaggatg aggctctgtc ggcagcgaca cgagctgaaa aggcggcaga ccgcgcagaa  720
gccgcagcgg aagtgactgc agagccctgt gcgaatatag tgccgccgct gcctgatgtg  780
tggataccgt ttaacgattc actggatatg attgcgggtt tttctccggg ctataaaaaa  840
atagctattg gtgacgatgt ggttcaggtc gccagtgata aacaggttaa tttcagtcgc  900
gcatcaacgg caacatatat caacaaatct ggcgaactga aacggcgga aattaatgag  960
ccgcgatttg agtgtgatgg cctgcttatt gagggacaaa gaacgaacta catgctcaat  1020
tcggaaagtc cagccagctg gggaagtca tcaaacatgg atgtgcccga aaccgggacg  1080
gatagttttg gttttactta tggaaagttt gtctgcaacg attctctggt tgggcaaact  1140
tcggctatta atatggcatc aattgctgca acaaagtcag ttgatgtctc aggcgataac  1200
aagtacgtga caacctcatg ccgttttaaa acagaacgac aggtaaggtt acgtatacgg  1260
tttgataagt atgatggtag tgcaacaact tttcttggcg atgcgtacat tgatacgcaa  1320
acgcttgaaa ttagtatgac aggtggtgct gccggcagaa ttacggcacg agtcaggaag  1380
gataagacca cgggctggat ttttgcagag gcaacgattc aggcaattga tggtgagtta  1440
aaaataggct ctcagataca gtattctcct gggcagggtg gggcaacagt atctggtgac  1500
tatatttatc ttgccacccc acaagtagag aatgggccgt gtgtatcatc atttattatt  1560
tcaggaggca gcgcaacgac aagagccagt gatttggtta gtatccccac cagaaataat  1620
ctttataagt taccatttac ttttttactt gagattcata aaaactggga tattgcacca  1680
aacgccgcac cccgcgtgtg ggatatagca gcagccaata ccgggcaatc agcaattgca  1740
gcaatcaaca gaggtagtgg taagttatat atgagtctgt caaacccttc aggctcgtat  1800
gttaatagcg cagcgacaga tgtatttgca gagaaaacca catttggatg tattgcaaaa  1860
gctgatggtc actttcatgt ggtgacaaat ggtaaagcgg ttaatgaagt ttattgtgaa  1920
tataatggcg tgaccgctga taaaaatatc cgatttggag ggcagacgaa tactggagaa  1980
cgacatctgt ttggccatat tcgcaatttc cgcatatggc ataaagaatt aaatgacagg  2040
caattaaaag aggtcgta                                                2058

SEQ ID NO: 63           moltype = DNA  length = 276
FEATURE                 Location/Qualifiers
misc_feature            1..276
                        note = Synthetic: STF-25-AP1
source                  1..276
                        mol_type = other DNA
                        organism = synthetic construct
SEQUENCE: 63
atgaaagatt taactttgaa gtttcatgac aaactgcagt ttaaggcctt cctgtcatct  60
cttggctggg cggaagatga agacctccag aataaactgt tagttgatga aattggtttc  120
acctacacag aaacaggggt aacagaagag ggagaacctg tctgtatccg gaatgatggt  180
tattttgtca acattcgcat tcttgatgac ttgtttgatg tttctgtatt ctctgattat  240
gtcgtggagc tggaaacacc gcttcgggaa tggagc                            276

SEQ ID NO: 64           moltype = DNA  length = 2061
FEATURE                 Location/Qualifiers
misc_feature            1..2061
                        note = Synthetic: STF-27
source                  1..2061
                        mol_type = other DNA
                        organism = synthetic construct
SEQUENCE: 64
atggcagtaa agatttcagg agtcctgaaa gacggcacag gaaaaccggt acagaactgc  60
accattcagc tgaaagccag acgtaacagc accacggtgg tggtgaacac ggtgggctca  120
gagaatccgg atgaagccgg gcgttacagc atggatgtgg agtacggtca gtacagtgtc  180
atcctgcagg ttgacggttt tccaccatcg cacgccggga ccatcaccgt gtatgaagat  240
tcacaaccgg ggacgctgaa tgattttctc tgtgccatga cggaggatga tgcccggccg  300
gaggtgctgc gtcgtcttga actgatggtg gaagaggtgg cgcgtaacgc gtccgtggtg  360
gcacagagta cggcagacgc gaagaaatca gaaacggcag cagcctcatc gaagaatgcg  420
gcgaaaacct cagaaacgaa tgcagctaac agcgcacagg cggcagcggc ctcgcagact  480
gcatcggcaa actccgcgac agcagccaaa aaatcagaaa ccagcgcgaa aaatagcgag  540
acagccacaa aggccagcga aaaaaacgca aaatccagcc agacggcagc gaaaaccagt  600
gagacgaatg ccaaagacag tgaagccaac gcaaaggtga gcgaaacagc ggcggcgaac  660
tcggcgaaag catcggcagc aagccagacg gcagcaaaag caagtgaaga tgctgccaga  720
gaatacgcaa accagacagc agagccgtac agatatgttt tacagccgct gccggatgtg  780
```

```
tggataccct ttaatgattc gctggatatg attacgggct attctccggg ttataaaaaa  840
gtgaagattg gtgataatgt ggttcaggtt gccagtgata aacaggttaa tttcagtcgc  900
gcatcaacgg caacatatat caacaaatct ggcgaactga aacggcggaa aattaatgag  960
ccgcgatttg agtgtgatgg cctgcttatt gagggacaaa gaacgaactt cttccagaac  1020
agtacagacc cttcgaagtg gaataagtca acttcactgg acgttacaga aacaggcaca  1080
gatagtttcg ggtttaatta tggtcggttt gtcgtacagg attcgattgt tggtacaagt  1140
aaagcgcata ccattatcgg actgtattcg agtaccggag gggttgatac ttcaggggac  1200
gaaaagcatg taactatatc ctgtcgggta aaaagtgaag ttgataatat cgccgttcgt  1260
attttatttg aacattatga tggggaggta aggacatcaa taggagcagc aaacctgaac  1320
cttaccaccc gcataattag caagacaggt cagacaagcc gtgttacagc aaggtctgtt  1380
aaggatgatg caactggctg gatatttttt gaggctacat taaaagcaga tacaacagaa  1440
aatacggttg gtggtttgt ccagtattct ccggatacag ggcagatggt tacatcaggg  1500
gattatctcg atgtaaccac tccacagatt gaggctggta caggcgcatc atcttttatt  1560
gttacgggga cggcaccggc aacgcgggca agcgatatgg tgacagtccc aatcaagaat  1620
aacctttata atcttccttt tacggttctt tgtgaggtac ataagaactg gtataaaacg  1680
ccaaatgtag cgccgcgtgt ttttgatacc ggcggtcatc aaaccggagc ggggatcgta  1740
atggggtttg gttcatcagg tgggtacgac ggttttccgt attgcgatat aggtggttca  1800
gaccgacgaa taaatgaaaa tgccgggctg gaaaaaatgc ttattggtat gcgggtaaag  1860
tccgaacggt ccacatgtgt agtcagtaac ggtaagttaa gcagcgaaac taaaaccaaa  1920
tgggaatata tccggagtac agcaaccatt cgcattggtg gacaaactac agcaggatta  1980
cgccatttat ttgggcatgt gaggaatttt cgtctctggc ataaagagct aacagatgcg  2040
cagcttgggg aggttgtgga g                                           2061

SEQ ID NO: 65          moltype = DNA  length = 276
FEATURE                Location/Qualifiers
misc_feature           1..276
                       note = Synthetic: STF27-AP1
source                 1..276
                       mol_type = other DNA
                       organism = synthetic construct
SEQUENCE: 65
gtgagagatt tcacgttgcg tttcagtgat aaagcagatt tcagggcatt tctcaggaaa  60
cttaactggg aagaggacga agagctgcag aatgccgttc tggttgatga gattggtttt  120
acgttcaggg agacagatgt ttctgatgac ggagaaccag aatacacgcg aaacgaaggg  180
tactttgtta atatccgtct tcttgacgat ggatttgagg attccgtgtt ccgtgagtgg  240
gtggttacac cagagcgccc gctcagggag tggttt                           276

SEQ ID NO: 66          moltype = DNA  length = 264
FEATURE                Location/Qualifiers
misc_feature           1..264
                       note = Synthetic: STF27-AP2
source                 1..264
                       mol_type = other DNA
                       organism = synthetic construct
SEQUENCE: 66
atgctgccgc agcatagcga tattgaaata gcctggtatg cttcgataca gcaggagccg  60
aatggctgga agaccgtcac cacacagttc tacatccagg aattcagtga gtatattgcg  120
ccactgcagg atgctgtaga tctggaaatc gcaacggagg aagaaagatc gttgctggag  180
gcatggaata aatatcgggt attgttgaat cgtgttgata catcaactgc acctgatatt  240
gagtggccga cttcacctgc agag                                       264

SEQ ID NO: 67          moltype = DNA  length = 2019
FEATURE                Location/Qualifiers
misc_feature           1..2019
                       note = Synthetic: STF-28
source                 1..2019
                       mol_type = other DNA
                       organism = synthetic construct
SEQUENCE: 67
atggcagtaa agatttcagg agtcctgaaa gacggcacag gaaaaccggt acagaactgc  60
accattcagc tgaaagccag acgtaacagc accacggtgg tggtgaacac ggtgggctca  120
gagaatccgg atgaagccgg gcgttacagc atggatgtgg agtacggtca gtacagtgtc  180
atcctgcagg ttgacggttt tccaccatcg cacgccggga ccatcaccgt gtatgaagat  240
tcacaaccgg ggacgctgaa tgatttttctc tgtgccatga cggaggatga tgcccggccg  300
gaggtgctgc gtcgtcttga actgatggtg gaagaggtgg cgcgtaacgc gtccgtggtg  360
gcacagagta cggcagacgc gaagaaatca gaaacagcag cggcatcgtc caggaacgcg  420
gcgaaaacat cagagacgaa tgcaggtaac agcgcgaaag cggcagcttc ttcaaaaaca  480
gccgcacaaa acgcagcaac agcggcagaa cgttcagaga caaatgcccg tgcgtcagaa  540
gaagcctccg cagacagtga agaggcttcc cgccgtaatg cagagtcagc cgctgaaaat  600
gccggagtcg ccaccacaaa agcgcgggag gccgcagcag acgcaacaaa ggccgggcag  660
aaaaaggatg aggctctgtc ggcagcgaca cgagctgaaa aggcggcaga ccgcgcagaa  720
tccgcagcgg aagtgactgc agagccctgt gcgaatatag tgccgccgct gcctgatgtg  780
tggataccgt ttaacgattc gctggatatg attacgggtt tttcgccatc ttataaaaag  840
attgttattg gtgacgatga aataacaatg ccaggcgaca agattgttaa gtttaaacgt  900
gcttcaacag caacgtatat taataagtcc ggccaactca agcttgctga agttgacgaa  960
ccgcgatttg agcgcgatgg cttattgatt gaaggacaga ggacaaatta tctgaggaac  1020
tcaaataaac cagactcatg gactgttcat tccgcactga ataaaacatt tggcactgat  1080
aaacaggggt tcaattatgc cacggtgaca cccacggaaa gtatagtggg aacaacaggt  1140
ggctatactg tgcatggtgt ggttgcagca gacagattcc cgctggcaag tggtgaatgt  1200
```

```
ttcacttttt cgtgccgggt taaaggcgct aaagcacgat gcaggttaag agtttcagtt  1260
attattggtg gaacagatac attctctgct gactcttatc ttgatctgga tacccggatc  1320
gcaacagtaa gcggtaatac atcccttata acagccaaag ctgaacaaca gggcgagtgg  1380
acctactatg aggccactta tacagctaat acggacattg ataccgttaa ctgtgctttt  1440
tatatgacaa ataaaataag taatgagcca ttctatgatg actcaacatt aaccatgacg  1500
acgccgcaaa ttgaactggg caatacggca tcgtcattta ttgtaactac aatgccaaca  1560
acacgcgcaa gtgatgtggt tactatcccc tcggcgaata acctgtcaac acggcctttt  1620
acagtattgt gcgaagtaag gaggaactgg agtacaccgc ccaatgttgc gccaaggata  1680
tttgatgttg gagggcacag tattgatgat aattatttat cgctggggtt tgtttcaaca  1740
ggaaagataa gcgccaacgt aggaatggtt cagccacaaa tttcctcaga tggagaaagg  1800
ttcattgtgg gtgtgagagc taaatctgat ttatcagtaa atgcaatatg caatggtaat  1860
tatacaacaa accttaatgg taaaatattt ggagttacag caacatcgta ccggtttggt  1920
gggcagaccg cagcaggaac gcgtcatttg tttggacaca tcagaaattt cagagtctgg  1980
tttaaagaat taaatgacag gcaaatcaag gaggcagta                        2019
```

```
SEQ ID NO: 68          moltype = DNA  length = 276
FEATURE                Location/Qualifiers
misc_feature           1..276
                       note = Synthetic: STF28-AP1
source                 1..276
                       mol_type = other DNA
                       organism = synthetic construct
SEQUENCE: 68
atgaaagatt taactttgaa atttcctggt aacagagagt ttaaatcctt cctgtcatct  60
cttgactggg aggaagatga agacctccag aataaactgt tagtcgatga aattggtttc  120
acctacacag aaacaggggt aactgaagag ggagaacctg tctgtatccg gaataacggt  180
tattttgtca acattcgcat tcttgatgac ttgtttgatg tttctgtatt ctctgattat  240
gtcgtggagc tggaaacacc gcttcgggaa tggagc                           276
```

```
SEQ ID NO: 69          moltype = DNA  length = 2394
FEATURE                Location/Qualifiers
misc_feature           1..2394
                       note = Synthetic: STF-15
source                 1..2394
                       mol_type = other DNA
                       organism = synthetic construct
SEQUENCE: 69
atggcagtaa agatttcagg agtcctgaaa gacggcacag gaaaaccggt acagaactgc  60
accattcagc tgaaagccag acgtaacagc accacggtgg tggtgaacac ggtgggctca  120
gagaatccgg atgaagccgg gcgttacagc atggatgtgg agtacggtca gtacagtgtc  180
atcctgcagg ttgacggttt tccaccatcg cacgccggga ccatcaccgt gtatgaagat  240
tcacaaccgg ggacgctgaa tgattttctc tgtgccatga cggaggatga tgcccggccg  300
gaggtgctgc gtcgtcttga actgatggtg gaagaggtgg cgcgtaacgc gtccgtggtg  360
gcacagagta cggcagacgc gaagaaatca gccggcgatg ccagtgcatc agctgctcag  420
gtcgcggccc ttgtgactga tgcaactgac tcagcacgcg ccgccagcac gtccgccgga  480
caggctgcat cgtcagctca ggaagcgtcc tccggcgcag aagcggcatc agcaaaggcc  540
actgaagcgg aaaaaagtgc cgcagccgca gagtcctcaa aaacgcggc ggccaccagt  600
gccggtgcgg cgaaaacgtc agaaacgaat gctgcagcgt cacaacaatc agccgccacg  660
tctgcctcca ccgcggccac gaaagcgtca gaggccgcca cttcagcacg agatgcggtg  720
gcctcaaaag aggcagcaaa atcatcagaa acgaacgcat catcaagtgc cggtcgtgca  780
gcttcctcgg caacggcggc agaaaattct gccagggcgg caaaaacgtc cgagacgaat  840
gccaggtcat ctgaaacagc agcggaacgg agcgcctctg ccgcggcagc ttctgcaact  900
gcatcagcta acagtcaaaa agcagcaaaa accagtgaaa ccaacgcaaa ggtgagcgaa  960
acagcggctg cgaactcagc gaaagcatcg gcagcaagcc agacggcagc taaagcaagc  1020
gaagatgcag ccagagagta tgcaagtcag gcagcagagc cgtataaata tgtcttacag  1080
ccactgcctg atgtgtggat accgtttaac gattcactgg atatgattac gggcttttcg  1140
ccgtcatata aaaaaattgt tattggtgat gatgaaataa cgatgcctgg cgacaaggtt  1200
gttaagttta aacgcgcatc aactgccaca tatatcaata aatcaggcgt atttagtgtt  1260
gctaaaattg atgagccacg atttgaaaaa gaaggtttat tgattgaagg acagcgcact  1320
aactatttg ttaaatccaa tactcccgct gaatggacga gtaccagcaa tatcgataaa  1380
actaataatg gtgttgatga atttggtttt tcatatgcca aaatgcgaac aaaagataat  1440
atgacaggac aatcatctgc acttagtctg catagatgca gtgcatcccg ggggattgat  1500
gttagtggcg ataataagta ttgcactgtt tcatgcaggg ttaaagctcc tgatggtctt  1560
cgttgtcgtt tgcgttttga aaaatacgat gggtcggttt atacattttt aggagatgct  1620
tatttaactt tcggaactct gataatagaa aaaactggcg gggcagccaa tagaatagca  1680
gctactgcaa ctaaagatcc ggttacaggg tggattttct atgaggcaac tatagaagct  1740
gttgaaggtg aaaccttaat tggcgcaatg attcagtatg cgccgaaaaa aggtggtata  1800
actgaagcgg gagattatat ttaccttgca acaccacaat ttgaaaacgg cggatgtgct  1860
tcatcttttg ttattacgac aactgcaccc gcaacccgct ccagtgatat ggtgacgatt  1920
ccaactaaaa ataatatcta taatagaccg cttacgtgtc ttgtcgaggt taatagaatt  1980
tggggcgata ttcctcctaa tgtagcaccg cgtatttttg atttttctgg tgtgccacct  2040
attgagtcaa ttacatacgc ttttaacaca actgagaaat attacggtca gctttatatg  2100
caaacttata aagcgtcgac aagtacttac gtttctagtg tgtttgctgg tcgagctgat  2160
gttcgaaaat tcattggtgg ttttaatatt tattctgatg gtactaaacg agtagtttct  2220
aacggtgagg ctactaaaac tatgaaaacg gagtggacgg gcgtaaaaac acggaccttt  2280
attcgaattg gaggtcaagc cacatcggga actcgtcatc tattcggcca tttgagaaat  2340
cttcgtctct ggcataaaga attaactgat gcgcaaatgg gggagagtat taaa        2394
```

```
SEQ ID NO: 70          moltype = DNA  length = 279
```

```
FEATURE                 Location/Qualifiers
misc_feature            1..279
                        note = Synthetic: STF15-AP1
source                  1..279
                        mol_type = other DNA
                        organism = synthetic construct
SEQUENCE: 70
atgaaagatt taacactcaa atttgcagac agggccgact tttcggcctt tatggagagc  60
attggctatt atgatgacga gtcgatgcag gatgatattc ttattgacgt gataggtaat  120
gtgtacaaag aaaccggaga acttactgaa gatggcgagc cggcatgtgt taaggaggac  180
ggatattttg taaatgtgcg catcattaat gattcgcaaa tatcgtcatt attcgatgaa  240
cacgcggttg ctgttgagca tcaactccgt agctggatg                         279

SEQ ID NO: 71           moltype = DNA  length = 702
FEATURE                 Location/Qualifiers
misc_feature            1..702
                        note = Synthetic: STF15-AP2
source                  1..702
                        mol_type = other DNA
                        organism = synthetic construct
SEQUENCE: 71
atggctacat cgacagtaat tcctgatgac atcaaaacgc taaagggaga tgtcagtaag  60
gcaaaggaag atatttcctc aattaacgta aaagtatcaa cgcttcagac tgatatggac  120
agtgcaaagc aggatatcag taccagatac acaaaaacag aagtggataa taagctgaaa  180
aacaaagtgg aagtgaacga tctggaaagt ggtcgttatg gcggagattt ttacccgctg  240
actggccgtg aagcgtttta tttatgggga ttgggcacaa ctacagcggc ggcaaatctt  300
tatcttaatc ctgaccctgc aatttcgtct gtgctgcggt caacatcgtc tatccgctat  360
aaacattcag tagagacgat agattcagag cacgccgatc tcattttcag gatgcgccct  420
gtgtggtaca ggtcgcaatg cgaaaatgac aggcgtgact ggggattcta tggattgatt  480
gccgaggaag taggagaaat tgcccctcag tttgttcact ggcgaccagc caacgaagat  540
gatgcaccgg aaaccatttc cagcaatggc cttgttgccg aaggtgtaat gtacgaacgt  600
ctggttgttc cactgattca ccatatccag aaactgactg aaagagttga tgaacttgag  660
tcagaattga agttgttatc aacttcccaa agcgatatcg ga                     702

SEQ ID NO: 72           moltype = DNA  length = 2373
FEATURE                 Location/Qualifiers
misc_feature            1..2373
                        note = Synthetic: STF-16
source                  1..2373
                        mol_type = other DNA
                        organism = synthetic construct
SEQUENCE: 72
atggcagtaa agatttcagg agtcctgaaa gacggcacag gaaaaccggt acagaactgc  60
accattcagc tgaaagccag acgtaacagc accacggtgg tggtgaacac ggtgggctca  120
gagaatccgg atgaagccgg gcgttacagc atggatgtgg agtacggtca gtacagtgtc  180
atcctgcagg ttgacggttt tccaccatcg cacgccggga ccatcaccgt gtatgaagat  240
tcacaaccgg ggacgctgaa tgattttctc tgtgccatga cggaggatga tgcccggccg  300
gaggtgctgc gtcgtcttga actgatggtg gaagaggtgg cgcgtaacgc gtccgtggtg  360
gcacagagta cggcagacgc gaagaaatca gccggcgatg ccagtgcatc agctgctcag  420
gtcgcggccc ttgtgactga tgcaactgac tcagcacgcg ccgccagcac gtccgccgga  480
caggctgcat cgtcagctca ggaagcgtcc tccggcgcag aagcggcatc agcaaaggcc  540
actgaagcgg aaaaaagtgc cgcagccgca gagtcctcaa aaacgcggc ggccaccagt  600
gccggtgcgg cgaaaacgtc agaaacgaat gctgcagcgt cacaacaatc agccgccacg  660
tctgcctcca ccgcggccac gaaagcgtca gaggccgcca cttcagcacg agatgcggtg  720
gcctcaaaag aggcagcaaa atcatcagaa acgaacgcat catcaagtgc cggtcgtgca  780
gcttcctcgg caacggcggc agaaaattct gccagggcgg caaaaaacgtc cgagacgaat  840
gccaggtcat ctgaaacagc agcggaacgg agcgcctctg ccgcggcagc ttctgccact  900
gcatcagcca acagtcaaaa agcagcaaaa accagtgaaa ccaatgcaaa gacaagcgag  960
actgcagcgg cgaactcggc gaaagcatcc gctgcaagcc agaccgctgc aaaagcaagt  1020
gaagacgcag ccagagagta tgcaagccag gcagcagatc cgtataaata tgtcttacag  1080
ccgctgcctg atgtgtggat accgtttaac gattcactgg atatgattac gggctttttcg  1140
ccatcatata aaaagattgt tattggtgac gacgaaataa cgatgcctgg cgacaagatt  1200
gttaagttta aacgtgcatc gaaagcaacc tatattaaca aatctggtgt gctgacagag  1260
gctgccattg atgagccacg atttgaacgt gatggcctgc ttattgaggg gcaaagaact  1320
aatcttctgc ttaattcaac aaatccatct aaatggaata agtcaggcaa tctggaactc  1380
acagaaatat ccacggattc ttttaatttt acttatggga gatttactgt aaaagatact  1440
cttattggtc agacaagtgc tattaatatc gtaacgattt ctggcagtaa agggtttgat  1500
gtcacaggtg atgaaaaata tgtgaccatt tcatgccgtg taagaagtga tgttgaaaat  1560
ataaggtgtc gtttaagatt tgaacaccat gatggttata cttacacttt tttgggagat  1620
gcttacctca atttatcaac acttgtaatt gataaaactg gtactgctgc agaccgtatt  1680
attgcaaagg ctgtaaaaga tgaggttact ggttggattt tctatcaggc tacaattaat  1740
gcactagata cagagagcat gattggtgcg atggttcaat acgctcctgt aaaaggttca  1800
ggtacagcat ctggagacta tctggatatc gcaactccac aagtggaagg tggatcaagt  1860
gcttcgtcat ttattgtaac tgatataact gcaagcactc gcgcaagcga tatggtgaca  1920
gtcccaatca agaataacct ttataatctt ccttttacgg ttctttgtga ggtacataag  1980
aactggtata aaacgccaaa tgcagcaccg cgtgtttttg ataccggcgg tcatcaaacc  2040
ggagcggcta ttattcttgg cttcggtcgt tcaacagatt acgacggatt tccttattgt  2100
gatataggtt tggctaacag acgggtaaac gaaaacgcat cgcttgaaaa aatggttatg  2160
gggatgcgtg taaagtcaga tcagtctacg tgctcagtaa gtaacgggcg tatatccagc  2220
```

```
gaaaagaaag ccacatggtc ctatattcag aactccgcaa ttatccgtat tggaggccag  2280
actacagccg ggttgcgtca tttatttggt catgtcagga atttcagaat atggcacaag  2340
gcattgactg atgctcagat gggggagtca atc                               2373

SEQ ID NO: 73           moltype = DNA  length = 279
FEATURE                 Location/Qualifiers
misc_feature            1..279
                        note = Synthetic: STF16-AP1
source                  1..279
                        mol_type = other DNA
                        organism = synthetic construct
SEQUENCE: 73
atgaaagatt taacactcaa atttgcagac agggccgact tttcggcctt tatggatagc  60
attggctatt atgatgacga gtcgatgcag gatgatattc ttattgacgt gataggtaac  120
gtgtacaaag aaaccggaga actgactgaa gatggcgaac cggtatgtgt taaggaagat  180
ggatattatg taaacgtgcg catcattaat gatgcaaaaa aatcgtcaat attcgatgaa  240
tacgcggttg tagttgaaca tcaacttcgt ggctggatg                         279

SEQ ID NO: 74           moltype = DNA  length = 702
FEATURE                 Location/Qualifiers
misc_feature            1..702
                        note = Synthetic: STF16-AP2
source                  1..702
                        mol_type = other DNA
                        organism = synthetic construct
SEQUENCE: 74
atggctacat cgacagtaat tccaggagac atcaccacgt taaagggaga tgtcagtaaa  60
gccaaggaag atatttcctc aattaacgga aaagtatcaa cgcttcaggc tgatatgacc  120
agtgcaaagc aggatatcag caccagatac acaaaaactg aagttgataa taagctgaaa  180
aacaaactgg aagtgaacgc tctggaaagc ggtcgttatg gtggagattt ttacccgttg  240
actggccgtg aagcgtttta tttgtgggga ttgggcacga ctacagcggc ggcaaacctt  300
tatcttaatc ctgaccccgc aatttcgtct gtgctgcggt caacatcgtc tatccgctat  360
aaacattcag tagagacaat agattcagag cacgccgatc tcattttcag gatgcgccct  420
gtgtggtaca ggtcacaatg cgaaaatgac aggcgtgact ggggattcta cggattgatt  480
gccgaggaag taggagaaat tgcccctcag tttgtacact ggcgaccagc taacgaagat  540
gatgcaccgg aagctatttc cagcaatggc cttgttgccg aaggtgtaat gtacgaacgt  600
ctggttgttc cactgattca ccatatccag aagctgactg aaagagttga tgaacttgag  660
tcagaattaa agttgttatc cgtttcccga agcgatatcg ga                     702

SEQ ID NO: 75           moltype = DNA  length = 2373
FEATURE                 Location/Qualifiers
misc_feature            1..2373
                        note = Synthetic: STF-17
source                  1..2373
                        mol_type = other DNA
                        organism = synthetic construct
SEQUENCE: 75
atggcagtaa agatttcagg agtcctgaaa gacggcacag gaaaaccggt acagaactgc  60
accattcagc tgaaagccag acgtaacagc accacggtgg tggtgaacac ggtgggctca  120
gagaatccgg atgaagccgg gcgttacagc atggatgtgg agtacggtca gtacagtgtc  180
atcctgcagg ttgacggttt tccaccatcg cacgccggga ccatcaccgt gtatgaagat  240
tcacaaccgg ggacgctgaa tgattttctc tgtgccatga cggaggatga tgcccggccg  300
gaggtgctgc gtcgtcttga actgatggtg gaagaggtgg cgcgtaacgc gtccgtggtg  360
gcacagagta cggcagacgc gaagaaatca gccggcgatg ccagtgcatc agctgctcag  420
gtcgcggccc ttgtgactga tgcaactgac tcagcacgcg ccgccagcac gtccgccgga  480
caggctgcat cgtcagctca ggaagcgtcc tccggcgcag aagcggcatc agcaaaggcc  540
actgaagcgg aaaaaagtgc cgcagccgca gagtcctcaa aaaacgcggc ggccaccagt  600
gccggtgcgg cgaaaacgtc agaaacgaat gctgcagcgt cacaacaatc agccgccacg  660
tctgcctcca ccgcggccac gaaagcgtca gaggccgcca cttcagcacg agatgcggtg  720
gcctcaaaag aggcagcaaa atcatcagaa acgaacgcat catcaagtgc cggtcgtgca  780
gcttcctcgg caacggcggc agaaaattct gccagggcgg caaaaacgtc cgagacgaat  840
gccaggtcat ctgaaacagc agcggaacgg agcgcctctg ccgcggcagc ttctgccact  900
gcatcagcca acagtcaaaa agcagcaaaa accagtgaaa ccaatgcaaa gacaagcgag  960
actgcagcgg cgaactcggc gaaagcatcc gctgcaagcc agaccgctgc aaaagcaagt  1020
gaagacgcag ccagagagta tgcaagccag gcagcagatc cgtataaata tgtcttacag  1080
ccgctgcctg atgtgtggat accgtttaac gattcactgg atatgattac gggctttttcg  1140
ccatcatata aaaagattgt tattggtgac gacgaaataa cgatgcctgg cgacaagatt  1200
gttaagttta aacgtgcatc gaaagcaacc tatattaaca aatctggtgt gctgacagag  1260
gctgccattg atgagccacg atttgaactg gatgcctgc ttattgaggg gcaaagaact  1320
aatcttctgc ttaattcaac aaatccatct aaatggaata agtcaggcaa tctggaactc  1380
acagaaatat ccacggattc ttttaatttt acttatggga gatttactgt aaaagatact  1440
cttattggtc agacaagtgc tattaatatc gtaacgattt ctggcagtaa agggtttgat  1500
gtcacaggtg atgaaaaata tgtgaccatt tcatgccgtg taagaagtga tgttgaaaat  1560
ataaggtgtc gtttaagatt tgaacaccat gatggttata cttacacttt tttgggagat  1620
gcttacctca atttatcaac acttgtaatt gataaaactg gtactgctgc agaccgtatt  1680
attgcaaagg ctgtaaaaga tgaggttact ggttggattt tctatcaggc tacaattaat  1740
gcactagata cagagagcat gattggtgcg atggttcaat acgctcctgt aaaaggttca  1800
ggtacagcat ctggagacta tctggatatc gcaactccac aagtggaagg tggatcaagt  1860
gcttcgtcat ttattgtaac tgatataact gcaagcactc gcgcaagcga tatggtgaca  1920
```

```
gtcccaatca agaataacct ttataatctt ccttttacgg ttctttgtga ggtacataag  1980
aactggtata aaacgccaaa tgcagcaccg cgtgtttttg ataccggcgg tcatcaaacc  2040
ggagcggcta ttattcttgg cttcggtcgt tcaacagatt acgacggatt tccttattgt  2100
gatataggtt tggctaacag acgggtaaac gaaaacgcat cgcttgaaaa aatggttatg  2160
gggatgcgtg taaagtcaga tcagtctacg tgctcagtaa gtaacgggcg tatatccagc  2220
gaaaagaaag ccacatggtc ctatattcag aactccgcaa ttatccgtat tggaggccag  2280
actacagccg ggttgcgtca tttatttggt catgtcagga atttcagaat atggcacaag  2340
gcattgactg atgctcagat gggggagtca atc                               2373

SEQ ID NO: 76          moltype = DNA  length = 279
FEATURE                Location/Qualifiers
misc_feature           1..279
                       note = Synthetic: STF-17-AP1
source                 1..279
                       mol_type = other DNA
                       organism = synthetic construct
SEQUENCE: 76
atgaaagatt taacactcaa atttgcagac agggccgact tttcggcctt tatggatagc  60
attggctatt atgatgacga gtcgatgcag gatgatattc ttattgacgt gataggtaac  120
gtgtacaaag aaaccggaga actgactgaa gatggcgaac cggtatgtgt taaggaagat  180
ggatattatg taaacgtgcg catcattaat gatgcaaaaa aatcgtcaat attcgatgaa  240
tacgcggttg tagttgaaca tcaacttcgt ggctggatg                         279

SEQ ID NO: 77          moltype = DNA  length = 2374
FEATURE                Location/Qualifiers
misc_feature           1..2374
                       note = Synthetic: STF-13
source                 1..2374
                       mol_type = other DNA
                       organism = synthetic construct
SEQUENCE: 77
atggcagtaa agatttcagg agtcctgaaa gacggcacag gaaaaccggt acagaactgc  60
accattcagc tgaaagccag acgtaacagc accacggtgg tggtgaacac ggtgggctca  120
gagaatccgg atgaagccgg gcgttacagc atggatgtgg agtacggtca gtacagtgtc  180
atcctgcagg ttgacggttt tccaccatcg cacgccggga ccatcaccgt gtatgaagat  240
tcacaaccgg ggacgctgaa tgattttctc tgtgccatga cggaggatga tgcccggccg  300
gaggtgctgc gtcgtcttga actgatggtg gaagaggtgg cgcgtaacgc gtccgtggtg  360
gcacagagta cggcagacgc gaagaaatca gccggcgatg ccagtgcatc agctgctcag  420
gtcgcggccc ttgtgactga tgcaactgac tcagcacgcg ccgccagcac gtccgccgga  480
caggctgcat cgtcagctca ggaagcgtcc tccggcgcag aagcggcatc agcaaaggcc  540
actgaagcgg aaaaaagtgc cgcagccgca gagtcctcaa aaaacgcggc ggccaccagt  600
gccggtgcgg cgaaaacgtc agaaacgaat gctgcagcgt cacaacaatc agccgccacg  660
tctgcctcca ccgcggccac gaaagcgtca gaggccgcca cttcagcacg agatgcggtg  720
gcctcaaaag aggcagcaaa atcatcagaa acgaacgcat catcaagtgc cggtcgtgca  780
gcttcctcgg caacggcggc agaaaattct gccagggcgg caaaaacgtc cgagacgaat  840
gccaggtcat ctgaaacagc agcggaacgg agcgcctctg ccgcggcatc ttctgccact  900
gcatcagcca acagtcaaaa agctgcaaaa accagtgaaa ccaacgcaaa ggcgagcgag  960
actgcggcgg ctaactcggc gaaagcatcc gctgcaagcc agacggctgc aaaagcaagt  1020
gaagacgcag ccagagagta tgcaagccag gctgcggagc cgtataaaca agtttttgcag  1080
ccgcttcccg atgtgtggat accgtttaac gattcactgg atatgcttgc tggcttttcg  1140
cctggttata agcaaataac tgtaggtgat gatgttatta aaatgccatc cgataaggtt  1200
gttagcttca aacgcgcatc aggtgcaaca tacattaata aatcaggagt attaaccgtt  1260
gctgaagttg acgaaccgcg atttgaacga gaaggtttgc tgattgaagg acaaagaacc  1320
aactatcatc ttaattcact tacgccatct aagtggggag ctacaacaag tgtaactata  1380
acagaaagtg gtgttgatga gtttggcttt acttatgggc ggtttcaaat aaaggacgaa  1440
aaaattggga caaatacgac aatgaatatc gctgcggttt caggaggaag aggtgtcgat  1500
gttactggaa ctgaaaagta tgttacaaca tcatgtcgtg taaaaagcga tagtgctaat  1560
atacaatgtc gtataagatt tgaaagatat gacgggtccg catatttttta tctggcagat  1620
gcatatctta atataacaga tatgtccatt aggaaaacgg gaggaggggc tgcaagaata  1680
accgcccgag cggagaaaga atctaatgga tggatttatt tcgaggttac atatcaatct  1740
gaagctattg ataatatggt gtggctctca gatccaaatt gctccacctg tttcacctgg  1800
aacttatttg ggcggggaat atttggatgt tacgacacca caatttgaag gcggctcatg  1860
cgcatcatct tttatcattt ccgatacagt tgcatcaacg cgagcaagcg atattgttac  1920
attgccttgt aaaaataaca tggccagcaa acctttaacc tgcatggttg aagtgaataa  1980
aaattggtct atagcaccaa attccgcgcc tagaatttat gatataacag gatttaaaac  2040
aaaagacgac gcttttgttt ttgcattcag aaatacagca ggtagtgtag gaactccata  2100
tgttcaattt ggtaatccaa tatcatttcc acctggaaat tacccaagaa agattatcgc  2160
tgtatataga ataaaaagcg atggcaagtt tcaggctggc tgcaatgggg ttttatcaac  2220
accagcatca acaacgtgga agagtgttag tggtgctaca ggtataagga ttggaggcca  2280
gactacagcc ggcttacgtc atttatttgg ttatatcagg aattttagaa tatggcataa  2340
agaattaacc gatgcgcaaa tgggagagat aata                              2374

SEQ ID NO: 78          moltype = DNA  length = 279
FEATURE                Location/Qualifiers
misc_feature           1..279
                       note = Synthetic: STF-13-AP1
source                 1..279
                       mol_type = other DNA
                       organism = synthetic construct
```

```
SEQUENCE: 78
atgcgagatt taattatcaa attcacagac aaggccgact tttcggcctt tatgaagagt  60
gctggctatt atgatgacga gtcgatgcag gatgatattc ttattgacgt gataggtaac  120
gtgtacaaag aaaccggaga acttactgaa gatggcgagc cggtatgtgt taaggaagac  180
ggatattttg taaacgtgcg catcattaat gatgcaaaaa aatcgtcaat attcgataaa  240
tacgcggttg ttgttgagca tcaacttcgt ggctggatg                          279

SEQ ID NO: 79           moltype = DNA  length = 702
FEATURE                 Location/Qualifiers
misc_feature            1..702
                        note = Synthetic: STF-13-AP2
source                  1..702
                        mol_type = other DNA
                        organism = synthetic construct
SEQUENCE: 79
atggctacat cgacagtaat tccaggagat atcaccaagc taaaggggga tgtcagtaaa  60
gctaaggaag atatttcatc aattagcaga aaagtatcaa cgcttcagac tgagatgacc  120
agtgcaaagc aggatatcag ctccagatac acaaaaactg aagttgataa taagctgaaa  180
aacaaagtgg aagtgaacga tctggaaagt ggtcgttatg gcggagattt ttatccactg  240
acaggtcgtg aagcgtttta tttatggaat ttggccacga ctacagcggc ggcaaacctt  300
tatcttaatc ctgaccctgc aatttcgtct gtgctgcggt caacatcgtc tatccgctat  360
aaacattcag tagagacaat agattcagag cacgccgatc tcattttcag gatgcgccct  420
gtgtggtaca ggtcgcaatg cgaaaatgac aggcgtgact ggggattcta cggattgatt  480
gccgaggaag taggagaaat tgctcctcag tttgtacact ggcgaccagc taacgaagat  540
gatgctcctg aagctatttc cagcaatggc cttgttgccg aaggtgtaat gtacgaacgt  600
ctggttgttc cactgattca ccatatccag aaactgactg aaagagttga tgaacttgag  660
tcagaattaa agttgttatt aacttcccga agcgatatta ga                      702

SEQ ID NO: 80           moltype = DNA  length = 2343
FEATURE                 Location/Qualifiers
misc_feature            1..2343
                        note = Synthetic: STF-12
source                  1..2343
                        mol_type = other DNA
                        organism = synthetic construct
SEQUENCE: 80
atggcagtaa agatttcagg agtcctgaaa gacggcacag gaaaaccggt acagaactgc  60
accattcagc tgaaagccag acgtaacagc accacggtgg tggtgaacac ggtgggctca  120
gagaatccgg atgaagccgg gcgttacagc atggatgtgg agtacggtca gtacagtgtc  180
atcctgcagg ttgacggttt tccaccatcg cacgccggga ccatcaccgt gtatgaagat  240
tcacaaccgg ggacgctgaa tgattttctc tgtgccatga cggaggatga tgcccggccg  300
gaggtgctgc gtcgtcttga actgatggtg gaagaggtgg cgcgtaacgc gtccgtggtg  360
gcacagagta cggcagacgc gaagaaatca gccggcgatg ccagtgcatc agctgctcag  420
gtcgcggccc ttgtgactga tgcaactgac tcagcacgcg ccgccagcac gtccgccgga  480
caggctgcat cgtcagctca ggaagcgtcc tccggcgcag aagcggcatc agcaaaggcc  540
actgaagcgg aaaaaagtgc cgcagccgca gagtcctcaa aaacgcggc ggccaccagt  600
gccggtgcgg cgaaaacgtc agaaacgaat gctgcagcgt cacaacaatc agccgccacg  660
tctgcctcca ccgcggccac gaaagcgtca gaggccgcca cttcagcacg agatgcggtg  720
gcctcaaaag aggcagcaaa atcatcagaa acgaacgcat catcaagtgc cggtcgtgca  780
gcttcctcgg caacggcggc agaaaattct gccagggcgg caaaaacgtc cgagacgaat  840
gccaggtcat ctgaaacagc agcggaacgg agcgcctctg ccgcggcagc ttctgccact  900
gcatcagcaa acagtcaaaa agctgcaaaa accagtgaaa ccaatgcaaa gacaagcgag  960
actgcagcgg cgaactcggc gcaagcatcg gcagcaagcc agacagcagc taaagcaagt  1020
gaggatgcag ccagagagta tgcaagccag gcagcagagc cgtataaata tgtcttacag  1080
ccactgcctg atgtgtggat accgtttaac gattcactgg atatgcttgc tggcttttcg  1140
cctggttata agcaaataac cgtaggtgat gatgttatta aaatgccatc cgataaggtt  1200
gttagcttca aacgcgcatc aggtgcaaca tacattaata aatcaggtgt attaaccgtt  1260
gctgaagttg acgaaccgcg atttgaacga gaaggtttgc tgattgaagg acagagaaca  1320
aactatttca gaaattcaaa tacaccagaa gcatggaata acacgggtag tgtgtctgtt  1380
gagtcgttcg acagtgataa ggggtttaac tatggaagga taactgttat taatgaaaat  1440
ccgacagcac aaggatatca ggcaattgct gtaaacacga atgatgctta cacctgcccg  1500
gcaggttctt atacgacgat atcgtgtctg acgaaaagtg ataattcccg gtgtcgtgca  1560
aggttcggaa aaatgtctga taatggtgcg tttgtttttc attcagatgc agttctggat  1620
cctgttacgg gaaatgttgt tcatggaaat aatgtgacgg tgacggcaga aagagtcggt  1680
gaatggtggt tgtttaccgc cactcttttt gcagatgcgg aaatgataat cagctcaaga  1740
tttgaaatcc tggcgatgcc tggaatcagt attatcccca atggctctac gttagatatt  1800
gcgatgcctc aggcggagat tggtcgtac aggacgtcat ttatcattac tgaaggggct  1860
cctggcactc gctccagcga catggtgaca atacctgtaa gaaacaatat tcaccgatta  1920
ccattcagtg ctcttgttga agttaataaa aactgggata tccctcccag caaatcacca  1980
ttaatcttta atgttaaaga ttatcaggaa aatggtctgt tcacgcatgg attccgtggt  2040
aataatttct ctgatgccgg ttctcctttt atttctatgg gagggtgtaa taaatatgtg  2100
gcaacaaccc agaggaaaat catttcaggc ttccgttgtg gcgctgatgg agatgttcag  2160
gccgtatgta atggtgaatt atctgttgcg gcaaaaacaa catggacttc aattgttcca  2220
cgggcagtat tgcgaattgg agggcagggc actaatgggg agtatcatct tttggtcat  2280
atccgtaatc tgcgtatctg gcataaagaa ttaactgatg cgcaaatggg ggagagtatt  2340
aaa                                                                 2343

SEQ ID NO: 81           moltype = DNA  length = 279
FEATURE                 Location/Qualifiers
```

```
misc_feature           1..279
                       note = Synthetic: STF-12-AP1
source                 1..279
                       mol_type = other DNA
                       organism = synthetic construct
SEQUENCE: 81
atgaaagatt taacactcaa atttgcagac agggccgact tttcggcctt tatggagagt  60
attggctatt atgatgacga gtcgatgcag gatgatattc ttattgacgt gataggtaac  120
gtgtacaaag aaaccggaga actgactgaa gatggcgaac cggtatgtgt taaggaagac  180
ggatattttg taaacgtgcg catcattaat gatgtaaaaa aatcgtcaat attcgataaa  240
tacgcggttg ttgttgagca tcaacttcgt ggctggatg                         279

SEQ ID NO: 82          moltype = DNA  length = 702
FEATURE                Location/Qualifiers
misc_feature           1..702
                       note = Synthetic: STF-12-AP2
source                 1..702
                       mol_type = other DNA
                       organism = synthetic construct
SEQUENCE: 82
atggctacat cgacagtaat tccaggagat atcaccacgc taaagggaga tgtcagtaaa  60
actaaggaag atatttcctc aattaacgga aaagtatcaa cgcttcagac tgatatgacc  120
agtgcaaagc aggatatcag caccagatac acaaaaactg aagttgataa taagctgaaa  180
aacaaactgg aagtgaacga tctggaaagc ggtcgttatg gtggagattt ttacccgttg  240
actggccgtg aagcgtttta tatgtgggga ttgggcacga ctacagcggc ggcaaacctt  300
tatcttaatc ctgaccctgc aatttcgtct gtactgcggt caacatcgtc tattcgctat  360
aaacattcag tagagacgat agattcagag cacgccgatc tcattttcag gatgcgccct  420
gtgtggtaca ggtcgcaatg cgaaaatgac aggcgtgact ggggattcta cggattgatt  480
gccgaggaag taggagaaat tgcccctcag tttgtacact ggcgaccagc taacgaagat  540
gatgctcctg aagctatttc cagcaatggc cttgttgccg aaggtgtaat gtacgaacgt  600
ctggttgttc cactgattca ccatatccag aagctgactg aaagagttga tgaacttgag  660
tcagaattaa agttgttatc cgtttcccga agcgatatcg ga                     702

SEQ ID NO: 83          moltype = DNA  length = 3777
FEATURE                Location/Qualifiers
misc_feature           1..3777
                       note = Synthetic: STF-63
source                 1..3777
                       mol_type = other DNA
                       organism = synthetic construct
SEQUENCE: 83
atggcagtaa agatttcagg agtcctgaaa gacggcacag gaaaaccggt acagaactgc  60
accattcagc tgaaagccag acgtaacagc accacggtgg tggtgaacac ggtgggctca  120
gagaatccgg atgaagccgg gcgttacagc atggatgtgg agtacggtca gtacagtgtc  180
atcctgcagg ttgacggttt tccaccatcg cacgccggga ccatcaccgt gtatgaagat  240
tcacaaccgg ggacgctgaa tgattttctc tgtgccatga cggaggatga tgcccggccg  300
gaggtgctgc gtcgtcttga actgatggtg gaagaggtgg cgcgtaacgc gtccgtggtg  360
gcacagagta cggcagacgc gaagaaatca gccggcgatg ccagtgcatc agctgctcag  420
gtcgcggccc ttgtgactga tgcaactgac tcagcacgcg ccgccagcac gtccgccgga  480
caggctgcat cgtcagctca ggaagcgtcc tccggcgcag aagcggcatc agcaaaggcc  540
actgaagcgg aaaaaagtgc cgcagccgca gagtcctcaa aaaacgcggc ggccaccagt  600
gccggtgcgg cgaaaacgtc agaaacgaat gctgcagcgt cacaacaatc agccgccacg  660
tctgcctcca ccgcggccac gaaagcgtca gaggccgcca cttcagcacg agatgcggtg  720
gcctcaaaag aggcagcaaa atcatcagaa acgaacgcat catcaagtgc cggtcgtgca  780
gcttcctcgg caacggcggc agaaaattct gccagggcgg caaaaacgtc cgagacgaat  840
gccaggtcat ctgaaacagc agcggaacgg agcgcctctg ccgcggcaaa ttccgcgaca  900
gcagccaaaa aatcagaaac caacgcgaaa aatagtgagt cagcagcaaa ggtcagcgaa  960
accaacgcta aagcgtcaga gaacaaggcg aaagaatatc tcgacaaggt cgggggactc  1020
gtcagcccga tgacgcaata cgattggccc gttgttactg gtaatgagtc tttttacata  1080
aagatcgcga aactttccga tcccggaagc aacaattgcc atgtaacgct aatggttact  1140
aacggcggtg actacggctc cccttacgga aacattgact ttatcgagat ctcggcgcgc  1200
ggtctgcctt cttcgcttac tgctgataat gtatctcgtt acctgagtat acgccgttta  1260
gggccaaccg ggctaatcaa tagcatgcaa atgcgttacg gcctggttaa agatgatggc  1320
tttattgagg tttgggcctt ccagcgtgca tttatcaacg gcgcaaaggt tgcggtactg  1380
gcgcagacgg cacgcacgga attatacatt ccagacggat ttgttaagca aaccgccgcg  1440
ccttctggat atgttgaaag ccccgttgta aggatttacg accagttaaa caagccgact  1500
aaagcagatt tgggtctttc taatgctatg cttacaggcg ctttcggtct tggcggtagc  1560
gggatatcaa caaacggcaa gatgagcgat gtagagatct taaaagctct gcgtgacaaa  1620
ggtggtcatt tctggcgcgg tgataagccg accggaagca cggcgaccat ttatagccac  1680
ggttctggta tattctcgcg gtgcggcgat acgtggtcag cgatcaatat cgactactca  1740
accgcgaaga ttaagatcta tgccggcaac gatgcccggc ttaacaacgg gacttttagc  1800
atcaatgagc tatacggctc ggcaaacaag ccgtcgaaat cggatgttgg acttggcaac  1860
gtaacgaacg atgcgcaggt aaaaaaaacc ggcgatacaa tgaccggtga cttgacaatc  1920
aaaaaaggta caccgtcagt cttcctgcgg gcagacagtg gagtcaccgc tttgcggttt  1980
tatactggcg ataacacaga gcgcggcata atctatgctg gtcctaacac tgattcgctt  2040
ggcgaagttc gcatcagggc aaagacagca ggggggacat caggagggga tcttgttgtt  2100
cgtcacgacg ggagggttga agtccgtgat ctcacagtag cgtataaaat taaaagcaga  2160
acgattgaga ttgcaaatac cgatactgac tcatcggcaa ctacgctcag catctatgga  2220
gtacagcaca cgccgttggt tttaacgcgt tctggttctt ctgaaaatgt gtccattggg  2280
```

```
tttaagttag acaacatgaa cccaaagtat cttggaattg atactaatgg ggatctggct  2340
tttggtgaga gtcctgatca gaaacaaaac agcaaattga tcacgcaagc gaaactcgac  2400
aagggattaa cgattggtgg tcaactggct ttcaaaggta cgacagcgtt ttcagccgtt  2460
gctacgttca ttgccgggat agcaggagcc atcgagccgg aaaacattga cggccagacg  2520
gttaatctta acaacctgac catcatcaag tcagatgccg gggcagttaa atactatatt  2580
tgtccatcct ctgcaggtgg tgcaaatatt accaataagc ctgacggcat agccggtaac  2640
tttttgctcc gtgtagagtc gactcgtaag gttagggatt cagattatgc gaacatgcaa  2700
acgctgatta acagcgacac aaaacgtata tacgttcgct ttgttgttaa tggaaactgg  2760
acagcgtgga gtcaggttgt tgtttccgga tggaatcagg atataactgt caggtcgtta  2820
accacatcta gtccggtaaa atctggcgga gggcgaattg atgtccttgg aagcacgtca  2880
gactatagca aaatggattg ctttgtacgt gggtttgata gcaccggtaa ttctctcgcg  2940
tgggcgttgg gttcatcagc cggcgtaagt aagatgctgt cgctaaaaaa tttctttagc  3000
ggagctgaga tactgttaaa tggtaatgac ggcacggttc aactcaaaac aggtgctgtt  3060
aacggggcta cagcgcaggc gctcactatc aacaggaatg aggttaactc aactgttgat  3120
ttaaccctta caaaacaatc agggactggc aatcgttttg ttttacagaa ctcaggtaat  3180
gcagaactac cgttttctgt cagggtgtgg ggttccagta ctcgacaaaa cgtttttgag  3240
gttggcacgt ctgctgcgta tctgttttat gcgcaaaaaa cgtcagcagg ccagttgttt  3300
gatgtaaatg gcgctattaa ttgcacaacg ctgaatcagt catcagaccg cgaccttaaa  3360
gacgatattc tcgttatcag cgacgcgacg aaagcaatcc gtaaaatgaa cggatacacc  3420
tacacgctca gggaaaacgg gatgccttat gctggcgtta ttgcacagga agtaatggag  3480
gcgataccag aagctgtggg atcgtttact cattatggtg aagagttgca aggtccgacc  3540
gttgacggca acgagctacg cgaagaaacg cgctatctta atgttgacta cgccgccgtg  3600
acgggcttac ttgttcagtt cgcccgtgaa acagatgatc gcgttaccgc gctggaagag  3660
gaaaacacaa cgctacgtca aaatctggca acagcagaca cccggatcag cactctggaa  3720
aatcaggtaa gcgaactggt tgcacttgtc cggcagttaa caggaagcga acattga     3777

SEQ ID NO: 84          moltype = DNA  length = 3762
FEATURE                Location/Qualifiers
misc_feature           1..3762
                       note = Synthetic: STF-62
source                 1..3762
                       mol_type = other DNA
                       organism = synthetic construct
SEQUENCE: 84
atggcagtaa agatttcagg agtcctgaaa gacggcacag gaaaaccggt acagaactgc  60
accattcagc tgaaagccag acgtaacagc accacggtgg tggtgaacac ggtgggctca  120
gagaatccgg atgaagccgg gcgttacagc atggatgtgg agtacggtca gtacagtgtc  180
atcctgcagg ttgacggttt tccaccatcg cacgccggga ccatcaccgt gtatgaagat  240
tcacaaccgg ggacgctgaa tgatttttctc tgtgccatga cggaggatga tgcccggccg  300
gaggtgctgc gtcgtcttga actgatggtg gaagaggtgg cgcgtaacgc gtccgtggtg  360
gcacagagta cggcagacgc gaagaaatca gccggcgatg ccagtgcatc agctgctcag  420
gtcgcggccc ttgtgactga tgcaactgac tcagcacgcg ccgccagcac gtccgccgga  480
caggctgcat cgtcagctca ggaagcgtcc tccggcgcag aagcggcatc agcaaaggcc  540
actgaagcgg aaaaaagtgc cgcagccgca gagtcctcaa aaacgcggc ggccaccagt  600
gccggtgcgg cgaaaacgtc agaaacgaat gctgcagcgt cacaacaatc agccgccacg  660
tctgcctcca ccgcggccac gaaagcgtca gaggccgcca cttcagcacg agatgcggtg  720
gcctcaaaag aggcagcaaa atcatcagaa acgaacgcat catcaagtgc cggtcgtgca  780
gcttcctcgg caacggcggc agaaaattct gccagggcgg caaaaacgtc cgagacgaat  840
gccaggtcat ctgaaacagc agcggaacgg agcgcctctg ccgcggcaaa ctccgcgaca  900
gcagccaaaa aatcagaaac caacgcgaaa aatagtgagg cagcagcaaa ggtcagcgaa  960
accaacgcta aagcgtcaga gaacaaggcg aaagaatatc tcgacaaggt cgggggactc  1020
gtcagcccga tgacgcaata cgattggcct gttgttactg ctagtgagtc tctttacatc  1080
aagatcgcga aactttccga tcctggaacc agcagaagtc atgtaacgct aatggttact  1140
aacgctggta actacggctc cccttacgga aacattgact ttatcgagat ctcggcgcgc  1200
ggtctgcctt ctttgcttag tgcggataat gtttctcgtc atctgagtat acgccgctta  1260
gggtcaaccg ggctgaccga taacaaccag atgcgttacg gcctggttaa aggtgacggc  1320
tttattgagg tttgggcatt ccagggtgcg tttattaacg acgcaaaggt tgcggtgctg  1380
gcgcagacaa cactaaacac agaattatac attccagacg gatttgttaa gcaaaccgcc  1440
gcgccttctg gatatattga aggcaacgtt gtaaggattt acgaccaggt aaacaagccg  1500
actaaagcag atttgggtct ttctaatgct atgcttacag gcgctttcgg tcttggcggt  1560
agcgggatat caacaaacgg caagatgagc gatgtagaga tcttaaaagc tctgcgtgac  1620
aaaggtggtc atttctggcg cggtgataag ccgaccggaa gcacggcgac catttatagc  1680
cacggttctg gtatattctc gcggtgcggc gatacgtggt cagcgatcaa tatcgactac  1740
tcaaccgcga agattaagat ctatgccggc aacgatgccc ggcttaacaa cgggactttt  1800
agcgtcaatg agctatacgg ctcggcaaac aagccgtcga aatcggatgt tggacttggc  1860
aacgtaacga acgatgcgca ggtgaaaaaa tccggcgatg ttatgtctgg tgatcttgat  1920
atattgaaag aaacgccatc tatcaggcta aaatcagcaa aggaaccgc tcatctgtgg  1980
ttcatgaaca acgacggaag cgagcgcggc gttgtttggt cgcctgaaaa caacgaatca  2040
cttggcgaaa tccacatcag ggcgaaaaac acaaaaggtg aatcaagtgg tgattttatt  2100
gttcgccacg acgggagggt tgaggcccgc aatctaaaaa taacttacaa aatcagcgca  2160
gccaccgcag aatttgcaaa cacaagcacc agttccgata acactacggt aagcatcaaa  2220
ggatctcagc atacgccttt ggttttaacg agcaacaaca caattaaaaa cttgtccatt  2280
gggtttaagg ttgatgatgt tgatcaaaaa tacctaggta tagctggtga cggtgatttg  2340
tattttggta gttattctga ccacacaaaa aacagcaaag taatcacaca agcaaaactc  2400
gatagcgggg tgacggtagg cggtaaaaca accttttctg accttgccac atttaacgca  2460
ggtatggcgg gatctatcga gccggaaacc attgacaaca agactattga tttaaacgac  2520
ttgatcattg ctaatacagt ggctggatct gttaaatact atcaatgcaa aactgtcgca  2580
ggtggtgcat atattaccaa taagcctgac ggcgtaagcg gtaacttttt gctacgtgta  2640
gaatctactc gtaaaactac gggttcagat tatgcgatca tgcaaacgct gattggcagc  2700
```

```
gacacaaaac gcatatacgt tcgctttgtt gtcaatggaa gttggacgga gtggagtcag  2760
gtagttgttt caggatggaa tcaggatgta accgtcaggt cgttaacctc gacgactcca  2820
tcaaaattag gcggcgggcg tgttgatgtg ctggggagta cgtcagatta cagtagtatg  2880
aattgtgctg tgcgcggtgt tgatagcact ggaaccaatt cggcgtggtc agtaggtaca  2940
tcgaaaaaca cgggaaaaat gttgtgcctt aaaaaccaca gaagcagcgc tcaagtgctg  3000
ttaaatggcg atgatggcgc ggtgcaacta ctaagcggta ctgtcaacgg tgctacagca  3060
caggcgctaa ccatcaacaa agatgaggtt aactcaactg ccgatttagt aattagaaaa  3120
caaacaggga ctggcaatcg ttttgcttta cttaattcag gtaattcaga actaccagtt  3180
ggtatcaggg tgtggggttc cagtactcgt caaaacgttt ttgaggttgg aacgtctact  3240
gcgtatctgt tttatgcgca aaaaacgtca gcaggccagt tgtttgatgt aaatggcgct  3300
attaattgca caacgctgaa tcagtcatca gaccgcgacc ttaaagacga tattctcgtt  3360
atcagcgacg cgacgaaagc aatccgtaaa atgaacggat acacctacac gctcagggaa  3420
aacgggatgc cttatgctgg cgttattgca caggaagtaa tggaggcgat accagaagct  3480
gtgggatcgt ttactcatta tggtgaagag ttgcaaggtc cgaccgttga cggcaacgag  3540
ctacgcgaag aaacgcgcta tcttaatgtt gactacgccg ccgtgacggg cttacttgtt  3600
cagttcgccc gtgaaacaga tgatcgcgtt accgcgctgg aagaggaaaa cacaacgcta  3660
cgtcaaaatc tggcaacagc agacacccgg atcagcactc tggaaaatca ggtaagcgaa  3720
ctggttgcac ttgtccggca gttaacagga agcgaacatt ga                     3762
```

```
SEQ ID NO: 85           moltype = DNA  length = 2373
FEATURE                 Location/Qualifiers
misc_feature            1..2373
                        note = Synthetic: STF-71
source                  1..2373
                        mol_type = other DNA
                        organism = synthetic construct
SEQUENCE: 85
atggcagtaa agatttcagg agtcctgaaa gacggcacag gaaaaccggt acagaactgc  60
accattcagc tgaaagccag acgtaacagc accacggtgg tggtgaacac ggtgggctca  120
gagaatccgg atgaagccgg gcgttacagc atggatgtgg agtacggtca gtacagtgtc  180
atcctgcagg ttgacggttt tccaccatcg cacgccggga ccatcaccgt gtatgaagat  240
tcacaaccgg ggacgctgaa tgatttttctc tgtgccatga cggaggatga tgcccggccg  300
gaggtgctgc gtcgtcttga actgatggtg gaagaggtgg cgcgtaacgc gtccgtggtg  360
gcacagagta cggcagacgc gaagaaatca gccggcgatg ccagtgcatc agctgctcag  420
gtcgcggccc ttgtgactga tgcaactgac tcagcacgcg ccgccagcac gtccgccgga  480
caggctgcat cgtcagctca ggaagcgtcc tccggcgcag aagcggcatc agcaaaggcc  540
actgaagcgg aaaaaagtgc cgcagccgca gagtcctcaa aaacgcggc ggccaccagt  600
gccggtgcgg cgaaaacgtc agaaacgaat gctgcagcgt cacaacaatc agccgccacg  660
tctgcctcca ccgcggccac gaaagcgtca gaggccgcca cttcagcacg agatgcggtg  720
gcctcaaaag aggcagcaaa atcatcagaa acgaacgcat catcaagtgc cggtcgtgca  780
gcttcctcgg caacggcggc agaaaattct gccagggcgg caaaaacgtc cgagacgaat  840
gccaggtcat ctgaaacagc agcggaacgg agcgcctctg ccgcggcatc ttctgccact  900
gcatcagcca acagtcaaaa agctgcaaaa accagtgaaa ccaacgcaaa ggcgagcgag  960
actgcggcgg ctaactcggc gaaagcatcc gctgcaagcc agacggcagc taaagcaagt  1020
gaagatgcag ccagagagta cgcaagccag gctgcggagc cgtataaaca agttttgcag  1080
ccgcttcccg atgtgtggat accgtttaac gattcactgg atatgattac gggcttttcg  1140
ccgtcatata aaaagattgt tattggtgat gatgaaataa cgatgtctgg cgataaggtt  1200
gtaaagttta aacgcgcatc gaaagcaacc tatattaata aatctggtgt gctgacagag  1260
gctgccattg acgagccacg atttgaacgt gatggcctgc ttattgaggg gcaaagaaca  1320
aactacatgc tcaattcgga aagccctgcc agttgggggc gatcgtcaaa tatggatgtg  1380
cccgaaacag ggacggataa ttttggtttt acctatggaa agtttgtctg caacgattct  1440
ctgattgggc aaacctcagc cattaaatatg gcatcaattg ctgcaacaaa gtcagttgat  1500
gtctcaggcg ataataaaca cgtgacaacc tcatgtcgtt ttaaaacaga actgcaggta  1560
aggttgcgta tccggtttga taaatatgac ggtagcgcaa caacttttct tggtgatgcg  1620
tatattgata cacaaacgct tgaaattaat atgacaggcg gtgctgcctc aaggattaca  1680
gcgagagtca gaaaggacga agctaccgga tggatttttg cagaggcaac aattcaggca  1740
attgatgggg agttaaaaat aggttctcag atacagtatt ctcctaagca gggcggggca  1800
accgtatctg gtgactatat ttatctggcc accccacaag tagaaaatgg gccttgtgta  1860
tcatctttta ttatatcagg aacgacggcg gcgacccgcg caagcgatat agtcacagtt  1920
cccattaaga ataatcttta taatcttcct tttacggttc tttgtgaggt acataagaac  1980
tggtataaaa cgccaaatgc agcgccgcgt gtttttgaca ccggcggtca tcaaaccgga  2040
gcggcaatta ttcttggatt cggttcttca gcagattacg acggatttcc ttattgcgat  2100
attggaggag ctaacagacg ggtaaacgaa aacgcattgc ttgaaaaaat ggttatgggg  2160
atgcgtgtaa agtcagatca gtctacgtgc tcagtaagta acgggcgtat atccagcgaa  2220
acaaaaacca catggtccta tattcagaac accgcaatta tccgtattgg aggccaaact  2280
acagccgggt tacgtcattt atttggtcat gtcaggaatt tcagaatatg gcacaaggca  2340
ttgactgatg ctcaggtggg ggagtcaatc taa                                2373
```

```
SEQ ID NO: 86           moltype = DNA  length = 282
FEATURE                 Location/Qualifiers
misc_feature            1..282
                        note = Synthetic: STF-71-AP1
source                  1..282
                        mol_type = other DNA
                        organism = synthetic construct
SEQUENCE: 86
atgaaagatt taacactcaa attagccgac agggccgact tttcggcctt tatggagagt  60
actggctatt atgatgacga gtcgatgcag gatgatattc ttattgacgt gataggtaac  120
gtgtacaaag aaaccggaga actgaatgaa gatggcgaac cggtatgtgt taaggaagac  180
```

```
ggatattttg taaacgtgcg catcattaat gatgtgaaaa caccgtcaat attcgatgaa  240
tacgtggttg ctgttgagca tcaacttcgt ggctggatgt ga                     282

SEQ ID NO: 87          moltype = DNA  length = 3294
FEATURE                Location/Qualifiers
misc_feature           1..3294
                       note = Synthetic: STF-20
source                 1..3294
                       mol_type = other DNA
                       organism = synthetic construct
SEQUENCE: 87
atggcagtaa agatttcagg agtcctgaaa gacggcacag gaaaaccggt acagaactgc  60
accattcagc tgaaagccag acgtaacagc accacggtgg tggtgaacac ggtgggctca  120
gagaatccgg atgaagccgg gcgttacagc atggatgtgg agtacggtca gtacagtgtc  180
atcctgcagg ttgacggttt tccaccatcg cacgccggga ccatcaccgt gtatgaagat  240
tcacaaccgg ggacgctgaa tgattttctc tgtgccatga cggaggatga tgcccggccg  300
gaggtgctgc gtcgtcttga actgatggtg gaagaggtgg cgcgtaacgc gtccgtggtg  360
gcacagagta cggcagacgc gaagaaatca gccggcgatg ccagtgcatc agctgctcag  420
gtcgcggccc ttgtgactga tgcaactgac tcagcacgcg ccgccagcac gtccgccgga  480
caggctgcat cgtcagctca ggaagcgtcc tccggcgcag aagcggcatc agcaaaggcc  540
actgaagcgg aaaaaagtgc cgcagccgca gagtcctcaa aaaacgcggc ggccaccagt  600
gccggtgcgg cgaaaacgtc agaaacgaat gctgcagcgt cacaacaatc agccgccacg  660
tctgcctcca ccgcggccac gaaagcgtca gaggccgcca cttcagcacg agatgcggtg  720
gcctcaaaag aggcagcaaa atcatcagaa acgaacgcat catcaagtgc cggtcgtgca  780
gcttcctcgg caacggcggc agaaaattct gccagggcgg caaaaacgtc cgagacgaat  840
gccaggtcat ctgaaacagc agcggaacgg agcgcctctg ccgcggcaga cgcaaaaaca  900
gcggcggcgg ggagtgcgtc aacggcatcc acgaaggcga cagaggctgc gggaagtgcg  960
gtatcagcat cgcagagcaa aagtgcggca gaagcggcgg caatacgtgc aaaaaattcg  1020
gcaaaacgtg cagaagatat agcttcagct gtcgcgcttg aggatgcgga cacaacgaga  1080
aaggggatag tgcagctcag cagtgcaacc aacagcacgt ctgaaacgct tgctgcaacg  1140
ccaaaggcgg ttaaggtggt aatggatgag actaatcgtc gtctggcgaa aaatcagaac  1200
ggtgcagata tccaggataa atcagctttt ctggacaata ttggtgttac cagcctgacg  1260
tttatgaaaa acaacggcga aatgccggtt gatgctgatc tcaatacatt tggtccagtt  1320
aaggcttatg tgggtgtctg gtataaatcc acatcctcca acgcaacact ggagaaaaat  1380
ttccctgaag acggtgcagt cggtgttctt gaggtattca atggcggtaa tttttccgga  1440
atgcagcgtt ataccaccag aactggcaat gtttatatgc gtaatctttc tggcacctgg  1500
aatggctcag acggtccgtg gatctactgg cgtcagattc agtctgcaac acgcccccctg  1560
agcacaacta ttgacctgaa cacgctagga ggcgcagagc atcttggttt atggcgaaac  1620
agtagtggct ctatcgcttc atttgaccgc aactatccgg aagaaggaag ttatggtcag  1680
ggattccttg aagttcttga gggtggtggg tactcacgca cgcaacgcta tacgacccgc  1740
cgtgggaacg tatatgttcg ctgcctttct gctatatgga atgcacagaa cccacagtgg  1800
gagccgtggt caagagtagg ccatcagtca gaatgtcgtt attacgaagg tgatttgaat  1860
gatctgactt cgccaggcat ttacagcgtt acagggaagg cgtcaaacgg tccaatgcag  1920
gataccgctg gagcgacact gcttggaata ctggaagtaa tcaggcgttt tgatggtgta  1980
tctgtctggc agcgttacac aaccacaggg aaatcagaaa ccacacaggg gcgcactttt  2040
gagcgcgtct atgccgggag caaatggacc gaatggcgag aagtatataa ctccttttcg  2100
ttgcctctga atctgggcat cggtggcgca gtggcaaaac tatccagtct ggactggcag  2160
acctacgatt ttgtgccggg cagtctgata accgttcggc ttgataatat gaccaacatt  2220
cccgacggta tggactgggg cgtcattgat ggcaacctga taaacatctc agtcggtccg  2280
agtgatgatt ctggttcggg gcgctcaatg catgtatggc gcagcactgt aagtaaagcc  2340
aactaccgct tttttatggt gcgcatttca ggaaatccgg gaagccgcac gatcacaaca  2400
agacgagtac caatcattga cgaagcccag acatggggcg cgaaacagac attcagtgct  2460
ggcctttctg gtgaactgtc cggcaatgcg gcgacagcaa caaagctgaa aacagcccgt  2520
aaaattaata acgtttcgtt tgatggaaca tcagatatta acctgacgcc gaaaaatatt  2580
ggtgcatttg cttcaggaaa aacaggagac accgttgcga atgataaagc cgttggatgg  2640
aactggagta gcggagccta taacgcaact attggtgggg catcaacgtt aattcttcat  2700
tttaatatcg gggaaggaag ttgtcccgcc gcccagtttc gcgttaatta taagaacggt  2760
ggtatttttt atcgttctgc tcgtgacggt tacggattcg aggctgactg gtctgagttt  2820
tataccacaa cgcgaaaacc tacagcggga gatgtcggtg cactgccgtt atctggtggt  2880
caattgaatg gtgctctggg tataggaaca tccagtgctc ttggcggtaa ttcgattgtt  2940
ttgggtgata atgacacggg ctttaaacaa aatggtgatg gtaatctgga tgtttatgct  3000
aatagcgtcc atgttatgcg ctttgtctcc ggaagcgttc aaagtaataa aaccataaat  3060
attacggggc gtgttaatcc ctcggattac ggtaactttg attcccgcta tgtgagagat  3120
gtcagacttg gcacacgtgt tgtccagacc atgcagaaag gggtgatgta tgagaaagca  3180
gggcacgtaa ttaccgggct tggtattgtc ggtgaagtcg atggtgatga ccccgcagta  3240
ttcagaccaa tacaaaaata catcaatggc acatggtata acgtcgcaca ggtg        3294

SEQ ID NO: 88          moltype = DNA  length = 525
FEATURE                Location/Qualifiers
misc_feature           1..525
                       note = Synthetic: STF-20-AP1
source                 1..525
                       mol_type = other DNA
                       organism = synthetic construct
SEQUENCE: 88
atgcagcatt taaaaaatat tactgcgggt aatccaaaaa ctgttgccca atatcaactg  60
acaaaaaatt ttgatgttat ctggttatgg tccgaagagg gaaaaaactg gtatgaggaa  120
gtaagtaatt ttcaggaaga cacgataaag attgtttacg atgagaataa tataattgtc  180
ggcatcacca gagatgcttc aacgctcaac cctgaaggtt ttagcgttgt cgaggttcct  240
```

```
gatattaccg ccaaccgacg tgctgatgac tcaggtaaat ggatgtttaa ggatggtgcc  300
gtgattaagc ggatttatac ggcagacgaa cagctgcaac tggcggaatt acagaagtca  360
gctttgcttt ccgaagctga aactatcatt cagccactgg aacgctctgt cagactgaat  420
atggcaacag atgatgagcg tagccgactg gaagcatggg aacgctacag tgttctggtc  480
agccgtgtgg atcctgcaaa tcctgaatgg ccggaaatgc cgcaa                   525
```

```
SEQ ID NO: 89          moltype = DNA  length = 2274
FEATURE                Location/Qualifiers
misc_feature           1..2274
                       note = Synthetic: STF-23
source                 1..2274
                       mol_type = other DNA
                       organism = synthetic construct
SEQUENCE: 89
atggcagtaa agatttcagg agtcctgaaa gacggcacag gaaaaccggt acagaactgc  60
accattcagc tgaaagccag acgtaacagc accacggtgg tggtgaacac ggtgggctca  120
gagaatccgg atgaagccgg gcgttacagc atggatgtgg agtacggtca gtacagtgtc  180
atcctgcagg ttgacggttt tccaccatcg cacgccggga ccatcaccgt gtatgaagat  240
tcacaaccgg ggacgctgaa tgattttctc tgtgccatga cggaggatga tgcccggccg  300
gaggtgctgc gtcgtcttga actgatggtg gaagaggtgg cgcgtaacgc gtccgtggtg  360
gcacagagta cggcagacgc gaagaaatca gccggcgatg ccagtgcatc agctgctcag  420
gtcgcggccc ttgtgactga tgcaactgac tcagcacgcg ccgccagcac gtccgccgga  480
caggctgcat cgtcagctca ggaagcgtcc tccggcgcag aagcggcatc agcaaaggcc  540
actgaagcgg aaaaaagtgc cgcagccgca gagtcctcaa aaacgcggc ggccaccagt  600
gccggtgcgg cgaaaacgtc agaaacgaat gctgcagcgt cacaacaatc agccgccacg  660
tctgcctcca ccgcggccac gaaagcgtca gaggccgcca cttcagcacg agatgcggtg  720
gcctcaaaag aggcagcaaa atcatcagaa acgaacgcat catcaagtgc cggtcgtgca  780
gcttcctcgg caacggcggc agaaaattct gccagggcgg caaaaacgtc cgagacgaat  840
gccaggtcat ctgaaacagc agcggaacgg agcgcctctg ccgcggcaga cgcaaaaaca  900
gcggcggcgg ggagtgcgtc aacggcatcc acgaaggcga cagaggctgc gggaagtgcg  960
gtatcagcat cgcagagcaa aagtgcggca gaagcggcgg caatacgtgc aaaaaattcg  1020
gcaaaacgtg cagaagatat agcttcagct gtcgcgcttg aggatgcgga cacaacgaga  1080
aaggggatag tgcagctcag cagtgcaacc aacagcacgt ctgaaacgct tgctgcaacg  1140
ccaaaggcgg ttaaggtggt aatggatgag actaatcgta aagcccccatt aaacagcccg  1200
gcgctgaccg gaacgccaac aacaccaact gcgcgacagg gaacgaataa tacccaaatc  1260
gcaagcacgg ctttcgttat ggctgcgatt gccgcccttg tagattcgtc acctgatgca  1320
ctgaacacgc tgaacgagct ggctgcggcg ttgggcaacg acccgaattt tgcgaccacc  1380
atgactaacg cgcttgcggg taagcaaccg aaagatgcca ccctgacggc gctggccggg  1440
cttgctactg cggcagacag gtttccgtat tttacgggga atgatgtcgc cagcctggca  1500
accctgacaa aagtcgggcg ggatattctt gcgaaatcga ccgttgctgc cgttatcgaa  1560
tacctcggtt tacgagaact cggcacaagc ggggagaaaa taccgttact cagtacagcg  1620
aatacctgga ccaatcgaca aacattcagc ggtggccttt ctgggggact gtccggcaat  1680
gccgctactg caacaaagct gaaaacagca cgaaaaattg ctggagttgg ttttgatggt  1740
tctagcgata tttcaattag tgccaaaaat gtcaatgcat ttgcactccg acaaacaggt  1800
aatactgtta atggtgatac atccgttgga tggaattggg atagtggtgc atataacgcc  1860
ctgattggtg gtgcatctgc attaattctt cactttaata taaatgctgg tagctgtcct  1920
gccgtacaat tccgtgtgaa ttataaaaat ggtggcattt cctacaggtc ggctcgtgat  1980
ggttatgggt ttgaattagg ttggtcagat ttctatacca cgacacgaaa accttcagcg  2040
ggagatgttg gtgcatatac gcgggcagaa tgtaactcaa ggtttattac aggtattcgc  2100
cttggcggtc tgtcatctgt tcagacatgg aatggtcccg gctggtctga caggtcaggt  2160
tatgtcgtta cgggttcagt taacggaaac cgtgatgaat taattgatac aacacaggca  2220
aggccaattc agtattgcat taatgggacg tggtataacg cggggagtat ttaa        2274
```

```
SEQ ID NO: 90          moltype = DNA  length = 531
FEATURE                Location/Qualifiers
misc_feature           1..531
                       note = Synthetic: STF-23-AP1
source                 1..531
                       mol_type = other DNA
                       organism = synthetic construct
SEQUENCE: 90
atgatgcact taaaaaacat tactgctggc aaccctaaaa caaaagagca ataccagcta  60
acaaagcaat ttaacatcaa atggctttat tcagatgatg gaaaaaactg gtatgaggaa  120
caaaagaatt tccagccaga cactttgaaa atggtctatg accataacgg cgttattatt  180
tgtattgaaa aggatgtttc agcaattaat ccggaaggcg caagcgtcgt tgaattacct  240
gatattacag caaatcgccg ggctgatatt tcggggaaat ggttgttcaa agatggcgta  300
gtgataaagc gaacttatac cgaggaagag cagaggcaac aagcggaaaa tgaaaagcaa  360
agcctgttgc aacttgtcag ggataaaacc cagctatggg actcacagct acggctgggc  420
atcatttccg acgagaataa acaaaaatta accgagtgga tgctctatgc gcagaaagtc  480
gaatctacag acacctccag cctgccagta acgtttcccg aacaaccaga a            531
```

```
SEQ ID NO: 91          moltype = DNA  length = 2136
FEATURE                Location/Qualifiers
misc_feature           1..2136
                       note = Synthetic: STF-24
source                 1..2136
                       mol_type = other DNA
                       organism = synthetic construct
SEQUENCE: 91
```

```
atggcagtaa agatttcagg agtcctgaaa gacggcacag gaaaaccggt acagaactgc  60
accattcagc tgaaagccag acgtaacagc accacggtgg tggtgaacac ggtgggctca  120
gagaatccgg atgaagccgg gcgttacagc atggatgtgg agtacggtca gtacagtgtc  180
atcctgcagg ttgacggttt tccaccatcg cacgccggga ccatcaccgt gtatgaagat  240
tcacaaccgg ggacgctgaa tgattttctc tgtgccatga cggaggatga tgcccggccg  300
gaggtgctgc gtcgtcttga actgatggtg gaagaggtgg cgcgtaacgc gtccgtggtg  360
gcacagagta cggcagacgc gaagaaatca gccggcgatg ccagtgcatc agctgctcag  420
gtcgcggccc ttgtgactga tgcaactgac tcagcacgcg ccgccagcac gtccgccgga  480
caggctgcat cgtcagctca ggaagcgtcc tccggcgcag aagcggcatc agcaaaggcc  540
actgaagcgg aaaaaagtgc cgcagccgca gagtcctcaa aaacgcggc ggccaccagt  600
gccggtgcgg cgaaaacgtc agaaacgaat gctgcagcgt cacaacaatc agccgccacg  660
tctgcctcca ccgcggccac gaaagcgtca gaggccgcca cttcagcacg agatgcggtg  720
gcctcaaaag aggcagcaaa atcatcagaa acgaacgcat catcaagtgc cggtcgtgca  780
gcttcctcgg caacggcggc agaaaattct gccagggcgg caaaaacgtc cgagacgaat  840
gccaggtcat ctgaaacagc agcggaacgg agcgcctctg ccgcggcaga cgcaaaaaca  900
gcggcggcgg ggagtgcgtc aacggcatcc acgaaggcga cagaggctgc gggaagtgcg  960
gtatcagcat cgcagagcaa aagtgcggca gaagcggcgg caatacgtgc aaaaaattcg  1020
gcaaaacgtg cagaagatat agcttcagct gtcgcgcttg aggatgcgga cacaacgaga  1080
aaggggatag tgcagctcag cagtgcaacc aacagcacgt ctgaaacgct tgctgcaacg  1140
ccaaaggcgg ttaaggtggt aatggatgag actaatcgtc gtcttcagaa agatcagaac  1200
ggtgcggata ttcctgataa aagattattc ctgcgcaata ttggagcaac aaattcaaca  1260
accatgtctt ttagtggtgg tacaggatgg ttcaggctgg caactgtaac catgccccag  1320
gccagttccg tggtttacat aagcctgatt ggtggtgccg gatataatgt taactcccct  1380
atgcaggctg gtatatctga acttgttctt cgtgcgggaa atggaaatcc aaaaggtctt  1440
actggtgcgt tatggcgacg gacatcggtt ggatttacta attttgcatg ggtgaataca  1500
tccggtgata cctatgatgt ttatgttgaa ataggtaatt acgccacagg tgttaatatt  1560
cagtgggatt ataccagtaa cgccagcgta acgattcata catcaccaac ttatacagcg  1620
aataaaccaa caggcctgac agatggaact gtatatgtaa tttacagttc gtacattaaa  1680
ccgactgctg ctgatgttgg ggcgttatca ttatctggtg gtcaattgaa tggtgctctg  1740
ggtataggaa catccagtgc tcttggcggt aattcgattg ttttgggtga taatgacacg  1800
ggctttaaac aaaatggtga tggtaatctg gatgtttatg ctaatagcgt ccatgttatg  1860
cgctttgtct ccggaagcgt tcaaagtaat aaaaccataa atattacggg gcgtgttaat  1920
ccctcggatt acggtaactt tgattcccgc tatgtgagag atgtcagact tggcacacgt  1980
gttgtccaga ccatgcagaa aggggtgatg tatgagaaag cagggcacgt aattaccggg  2040
cttggtattg tcggtgaagt cgatggtgat gaccccgcag tattcagacc aatacaaaaa  2100
tacatcaatg gcacatggta taacgtcgca caggtg                           2136
```

```
SEQ ID NO: 92          moltype = DNA  length = 528
FEATURE                Location/Qualifiers
misc_feature           1..528
                       note = Synthetic: STF-24-AP1
source                 1..528
                       mol_type = other DNA
                       organism = synthetic construct
SEQUENCE: 92
atgcagcatt taaaaaatat tactgcgggt aatccaaaaa ctgttgccca atatcaactg  60
acaaaaaatt ttgatgttat ctggttatgg tccgaagagg gaaaaaactg gtatgaggaa  120
gtaagtaatt ttcaggaaga cacgataaag attgtttacg atgagaataa tataattgtc  180
ggcatcacca gagatgcttc aacgctcaac cctgaaggtt ttagcgttgt cgaggttcct  240
gatattaccg ccaaccgacg tgctgatgac tcaggtaaat ggatgtttaa ggatggtgcc  300
gtgattaagc ggatttatac ggcagacgaa cagctgcaac tggcggaatt acagaagtca  360
gctttgcttt ccgaagctga aactatcatt cagccactgg aacgctctgt cagactgaat  420
atggcaacag atgaggagcg tagccgactg gaagcatggg aacgctacag tgttctggtc  480
agccgtgtgg atcctgcaaa tcctgaatgg ccggaaatgc cgcaataa                528
```

```
SEQ ID NO: 93          moltype = DNA  length = 2523
FEATURE                Location/Qualifiers
misc_feature           1..2523
                       note = Synthetic: O111-2.0
source                 1..2523
                       mol_type = other DNA
                       organism = synthetic construct
SEQUENCE: 93
atggcagtaa agatttcagg agtcctgaaa gacggcacag gaaaaccggt acagaactgc  60
accattcagc tgaaagccag acgtaacagc accacggtgg tggtgaacac ggtgggctca  120
gagaatccgg atgaagccgg gcgttacagc atggatgtgg agtacggtca gtacagtgtc  180
atcctgcagg ttgacggttt tccaccatcg cacgccggga ccatcaccgt gtatgaagat  240
tcacaaccgg ggacgctgaa tgattttctc tgtgccatga cggaggatga tgcccggccg  300
gaggtgctgc gtcgtcttga actgatggtg gaagaggtgg cgcgtaacgc gtccgtggtg  360
gcacagagta cggcagacgc gaagaaatca gccggcgatg ccagtgcatc agctgctcag  420
gtcgcggccc ttgtgactga tgcaactgac tcagcacgcg ccgccagcac gtccgccgga  480
caggctgcat cgtcagctca ggaagcgtcc tccggcgcag aagcggcatc agcaaaggcc  540
actgaagcgg aaaaaagtgc cgcagccgca gagtcctcaa aaacgcggc ggccaccagt  600
gccggtgcgg cgaaaacgtc agaaacgaat gctgcagcgt cacaacaatc agccgccacg  660
tctgcctcca ccgcggccac gaaagcgtca gaggccgcca cttcagcacg agatgcggtg  720
gcctcaaaag aggcagcaaa atcatcagaa acgaacgcat catcaagtgc cggtcgtgca  780
gcttcctcgg caacggcggc agaaaattct gccagggcgg caaaaacgtc cgagacgaat  840
gccaggtcat ctgaaacagc agcggaacgg agcgcctctg ccgcggcaga cgcaaaaaca  900
gcggcggcgg ggagtgcgtc aacggcatcc acgaaggcga cagaggctgc gggaagtgcg  960
```

```
gtatcagcat cgcagagcaa aagtgcggca gaagcggcgg caatacgtgc aaaaaattcg  1020
gcaaaacgtg cagaagatat agcttcagct gtcgcgcttg aggatgcgga cacaacgaga  1080
aaggggatag tgcagctcag cagtgcaacc aacagcacgt ctgaaacgct tgctgcaacg  1140
ccaaaggcgg ttaaggtggt aatggatgag actaatcgta aggctcctct gaactctccg  1200
gccctgactg gcacgcctac tactccgact gcgccgcaag ggaccaactc tacccagatt  1260
gcgtccacgg cattcgttat ggctgctatt gcagcactgg tagattcctc gccggacgct  1320
ctgaacactc tgtcggaact ggcggctgca ctcggaaatg atccgaactt cgccaccacc  1380
atgactaacg ctctggccgg caaacagccg aaagatgcta ccctgaccgc cctggcaggt  1440
ctcgtgaccg ctgcggaccg cttcccgtat ttcacaggca atgacgttgc ctccctggct  1500
accctgaccg aggttggtcg tgacatcctg gcgaagtcta ccgttgcggc cgtgattgaa  1560
tatctgggtc tgcaggaaac tgttaaccag gcatcaggtg cattacagaa gaatcaaaac  1620
ggtgcagaca ttccgggcaa agataccttt accaagaata tcggtgcttg tcgtgcttat  1680
tcggcatggc ttaatatcgg aggtgattct caggtatgga ctacggctca gtttatctct  1740
tggctcgaga gtcagggtgc gtttaatcat ccgtactgga tgtgcaaagg ctcttgggcg  1800
tacgcgaaca acaaagtcat caccgacact ggttgtggta acatctgtct ggcgggtgca  1860
gtagtggaag ttatcggtac gcgcggtgcg atgacgatcc gtgtaactac tccatctacc  1920
tcctccggtg gcggtatcac caacgcccag ttcacttaca ttaaccacgg cgatgcctat  1980
gctccgggct ggcgccgtga ttacaacact aaaaaccaac aacctgcgtt tgcactgggt  2040
cagacgggta gtcgtgtggc gaacgataaa gcggtcggtt ggaattggaa ctctggtgtg  2100
tacaacgctg atattagtgg agcttctact ctgatccttc attttaacat gaatgctgga  2160
agttgtccgg cagtgcagtt tcgtgttaac tatcgtaatg gaggaatctt ttaccgctct  2220
gcacgtgacg gctacggctt cgaagcgaac tggagtgaat tttacacgac cactcgtaag  2280
ccgagtgctg gagatgtggg agcttatact caggcagaat gcaattcgcg tttcattact  2340
ggtattcgtc tgggaggttt aagttccgtg cagacttgga acggtccagg ttggagtgat  2400
cgtagtggct atgttgtgac aggcagtgtt aacggcaacc gtgacgaact gatcgacact  2460
actcaagcgc gtccgatcca gtactgcatt aacggaactt ggtataacgc gggaagtatc  2520
taa                                                                2523
```

```
SEQ ID NO: 94           moltype = DNA  length = 534
FEATURE                 Location/Qualifiers
misc_feature            1..534
                        note = Synthetic: O111-2.0-AP1
source                  1..534
                        mol_type = other DNA
                        organism = synthetic construct
SEQUENCE: 94
atgatgcact taaaaaacat tactgctggc aaccctaaaa caaaagagca ataccagcta  60
acgaaacaat ttaacatcaa atggctttat tcagaggatg gaaaaaactg gtatgaggaa  120
caaaagaatt tccagccaga cactttgaaa atggtttatg accataacgg cgttattatt  180
tgtattgaaa aggatgtttc agcaattaat ccggaaggcg caagcgtcgt tgaattacct  240
gatattacag caaatcgccg tgctgacatt tcgggtaaat ggatgttcaa agatggcgta  300
gtggtaaagc gtacttacac agaagaagag caacgtcaac aggcggaaaa tgaaaagcaa  360
agcctgctac agctcgtcag ggataaaacc cagctatggg acagtcagct acggctgggc  420
atcatttccg acgagaataa acaaaaatta acagagtgga tgctctttgc gcagaaagtc  480
gaatctacag acacttccag cctgccagta acgtttcccg aacaaccaga atga        534
```

```
SEQ ID NO: 95           moltype = DNA  length = 2265
FEATURE                 Location/Qualifiers
misc_feature            1..2265
                        note = Synthetic: STF-74
source                  1..2265
                        mol_type = other DNA
                        organism = synthetic construct
SEQUENCE: 95
atggcagtaa agatttcagg agtcctgaaa gacggcacag gaaaaccggt acagaactgc  60
accattcagc tgaaagccag acgtaacagc accacggtgg tggtgaacac ggtgggctca  120
gagaatccgg atgaagccgg gcgttacagc atggatgtgg agtacggtca gtacagtgtc  180
atcctgcagg ttgacggttt tccaccatcg cacgccggga ccatcaccgt gtatgaagat  240
tcacaaccgg ggacgctgaa tgattttctc tgtgccatga cggaggatga tgcccggccg  300
gaggtgctgc gtcgtcttga actgatggtg gaagaggtgg cgcgtaacgc gtccgtggtg  360
gcacagagta cggcagacgc gaagaaatca gccggcgatg ccagtgcatc agctgctcag  420
gtcgcggccc ttgtgactga tgcaactgac tcagcacgcg ccgccagcac gtccgccgga  480
caggctgcat cgtcagctca ggaagcgtcc tccggcgcag aagcggcatc agcaaaggcc  540
actgaagcgg aaaaaagtgc cgcagccgca gagtcctcaa aaaacgcggc ggccaccagt  600
gccggtgcgg cgaaaacgtc agaaacgaat gctgcagcgt cacaacaatc agccgccacg  660
tctgcctcca ccgcggccac gaaagcgtca gaggccgcca cttcagcacg agatgcggtg  720
gcctcaaaag aggcagcaaa atcatcagaa acgaacgcat catcaagtgc cggtcgtgca  780
gcttcctcgg caacggcggc agaaaattct gccagggcgg caaaaacgtc cgagacgaat  840
gccaggtcat ctgaaacagc agcggaacgg agcgcctctg ccgcggcaga cgcaaaaaca  900
gcggcggcgg ggagtgcgtc aacggcatcc acgaaggcga cagaggctgc gggaagtgcg  960
gtatcagcat cgcagagcaa aagtgcggca gaagcggcgg caatacgtgc aaaaaattcg  1020
gcaaaacgtg cagaagatat agcttcagct gtcgcgcttg aggatgcgga cacaacgaga  1080
aaggggatag tgcagctcag cagtgcaacc aacagcacgt ctgaaacgct tgctgcaacg  1140
ccaaaggcgg ttaaggtggt aatggatgag actaatcgta aatatacggc tcaggacgcg  1200
agcacggcgc agaaaggtct ggtgaaactg agcagcgcca ccgacagcac atctgagacc  1260
ctcgccgcga caccgaaagc ggttaaggcg gtgaatgata atgcgaatgg tcgcgtcccg  1320
tctgagcgaa aagttaacgg acattcgctg gccggtgata tcagtgtcac ctcacaggat  1380
atttttgacg gtcagtgtgt tgaaattggt ccgggtcagg atctggataa ttaccagacg  1440
ccgggtctgt attttcagcc cgcaaatgcc aataccagtg ctgctctgca ttacccggaa  1500
```

```
aataatgccg gttccctgat ggttttaaga agcgcaggga taacgcaggt ttatcgcgtg  1560
tacagcggtt cgcgaagtta tttgcggagc aaatattcca cgcagccatg gacgacgtgg  1620
acacccgatg atgcttttcc tgtcggcgcg ccgattccgt ggccatctga catcgccccg  1680
cccgcttacg ccttaatgca ggggcagtca tttgataaat ctgcatatcc attgcttgct  1740
gtagcgtatc cctctggtgt tatcccggat atgcgtggtc agacgataaa gggcaagccg  1800
gacggacgag cggtactctc gtatgaacag gacggtatta aatcgcacgc tcatacagcc  1860
agtatttccg ataccgattt gggaacgaaa tataccaact cttttgatta tggttcaaaa  1920
ccaacaacca gttttgacta cggcaataag tcctccactg aggggggatg gcacgtacat  1980
aactttcgtt attgtgctac gtctgcatac cgggatactc ctggctcagg gctggggatg  2040
cactcgtcga atatttcgtg gtcagccggg gatcgcattg aggggagtgg taatcatgca  2100
catgttacgt ggattggtcc ccatgatcac tgggttggta tcggtgagca taaccattat  2160
gtggttatgg ggtatcacgg acatacagcg accgttcatg caaccgggaa tacagaaaac  2220
accgttaaaa atattgcgtt taactacatt gtgaggcttg cataa                   2265
```

```
SEQ ID NO: 96          moltype = DNA  length = 579
FEATURE                Location/Qualifiers
misc_feature           1..579
                       note = Synthetic: STF-74-AP1
source                 1..579
                       mol_type = other DNA
                       organism = synthetic construct
SEQUENCE: 96
atggctttg  aaatgaccgg agaaaaccgg acaattattc tttataacct tcgttcagat  60
acaaatgaat ttattgggaa atctgatggg tttatccctg ctaatacggg cttgcctgct  120
tacagtaccg atatcgcgcc cccaaaagtg acggcaggtt ttgtggctgt tttcgatgca  180
cagacgaata aatggtcgcg ggtggaggac taccgcggga caaccgtcta tgacatcagc  240
accggtaagc ccgctgttat tgaaaaactt ggcgctctgc ctgataacgt tgtgtcggtt  300
gctcctgacg gggagtatgt aaaatgggat ggcgctaagt ggatccacga tgccgaagcg  360
gaaaaaacat ttcgtcaggg gcaggcggcg caggaaaaat caaacctgct gatgattgca  420
acatcggcta ttgccccccct gcaggatgcc gttgatctgg atatggcaac ggaagacgaa  480
gcgaccgcgc ttaatgaatg gaaaaaatac cgggtcatgc tcaacagagt caaacccgaa  540
gatgcccccg atatcacatg gccggaactg cccgcataa                        579
```

```
SEQ ID NO: 97          moltype = DNA  length = 2133
FEATURE                Location/Qualifiers
misc_feature           1..2133
                       note = Synthetic: STF86
source                 1..2133
                       mol_type = other DNA
                       organism = synthetic construct
SEQUENCE: 97
atggcagtaa agatttcagg agtcctgaaa gacggcacag gaaaaccggt acagaactgc  60
accattcagc tgaaagccag acgtaacagc accacggtgg tggtgaacac ggtgggctca  120
gagaatccgg atgaagccgg gcgttacagc atggatgtgg agtacggtca gtacagtgtc  180
atcctgcagg ttgacggttt tccaccatcg cacgccggga ccatcaccgt gtatgaagat  240
tcacaaccgg ggacgctgaa tgattttctc tgtgccatga cggaggatga tgcccggccg  300
gaggtgctgc gtcgtcttga actgatggtg gaagaggtgg cgcgtaacgc gtccgtggtg  360
gcacagagta cggcagacgc gaagaaatca gccggcgatg ccagtgcatc agctgctcag  420
gtcgcggccc ttgtgactga tgcaactgac tcagcacgcg ccgccagcac gtccgccgga  480
caggctgcat cgtcagctca ggaagcgtcc tccggcgcag aagcggcatc agcaaaggcc  540
actgaagcgg aaaaaagtgc cgcagccgca gagtcctcaa aaacgcggc ggccaccagt  600
gccggtgcgg cgaaaacgtc agaaacgaat gctgcagcgt cacaacaatc agccgccacg  660
tctgcctcca ccgcggccac gaaagcgtca gaggccgcca cttcagcacg agatgcggtg  720
gcctcaaaag aggcagcaaa atcatcagaa acgaacgcat catcaagtgc cggtcgtgca  780
gcttcctcgg caacggcggc agaaaattct gccagggcgg caaaaacgtc cgagacgaat  840
gccaggtcat ctgaaacagc agcggaacgg agcgcctctg ccgcggcaga cgcaaaaaca  900
gcggcggcgg ggagtgcgtc aacggcatcc acgaaggcga cagaggctgc gggaagtgcg  960
gtatcagcat cgcagagcaa aagtgcggca gaagcggcgg caatacgtgc aaaaaattcg  1020
gcaaaacgtg cagaagatat agcttcagct gtcgcgcttg aggatgcgga cacaacgaga  1080
aaggggatag tgcagctcag cagtgcaacc aacagcacgt ctgaaacgct tgctgcaacg  1140
ccaaaggcgg ttaaggtggt aatggatgag actaatcgtc gcgttccggc atcacgaaaa  1200
gtgaacggcc atgccctgaa tggagatatc aatgtcactt cacgggatat ttttgacggc  1260
caggttatag cgattggtgc aaataagaat ctggatgatt accaggtacc ggggctttat  1320
tttcaggaag cgaacaacaa taccagtgca gcaatgaatt acccggagaa tagcgcgggt  1380
tctctgatgg tactgagagg tgccggagtc actcaggttt atcgtgtgta caacagctcg  1440
cgcagttatt cgcgcagcaa gtattcaacg ctggcatgga cgccgtggat gccagaagat  1500
tcttaccctg tcggcgcacc tatcccctgg ccatcggatg ttaccccgac agggtacgcc  1560
ttaatgcagg ggcagccctt tgataaagcg gtctatccat tgctagcgat tgcctatcct  1620
gcggggatta tcccggacat gcgaggccag acgattaagg gtaaaccgaa cggtcgcgcg  1680
gtactctcgt atgaacagga tggtgttata tcgcataccc acggagccag tatttccgat  1740
accgatttgg ggacgaaata caccagctct tttgattatg gttcaaaacc aacaaccagt  1800
tttgactacg gcaataaatc ctccactgag ggtgggtggc acgcacataa ctttcgttat  1860
tgcgcaacgt ctgcataccg ggataccccc ggtcaggggc tggggatgca ttcgtctaat  1920
gtttcatggg cggcgggaga tcgcattgag ggaagcggta atcatgctca tgtgacatgg  1980
atcggccctc atgatcactg ggtgggtatt ggtgcgcata accattatgt ggttatgggc  2040
tatcacggac atacagcgac cgttcatgcc gcaggaaatg cggaaaatac cgttaaaaat  2100
attgcgttta actacattgt gaggcttgcc tga                               2133
```

```
SEQ ID NO: 98          moltype = DNA  length = 588
```

```
FEATURE                Location/Qualifiers
misc_feature           1..588
                       note = Synthetic: STF86-AP1
source                 1..588
                       mol_type = other DNA
                       organism = synthetic construct
SEQUENCE: 98
atgacttttg aaatgaccgg agaaaaccgg acaattacca tctataacct gcgtgctgat  60
acaaatgaat ttatcgggaa aagtgatggg tttatccctg ctaataccgg tttgcctgct  120
aacagtacca atattgcgcc accgccgatg aaagccggtt ttgtcgctgt atttaattct  180
gcgtcagaaa aatggtcact tgttgaagac catcgcggga aaattgttta cgacattctc  240
accgggaaat ccatcacgat tgatgaatta ggtcagttac ctgacgacgt tgtttccgtt  300
gcgccggaag gccattttgt taaatggaat ggtaaaaaat gggtgcatga tgctgacgca  360
gaaaaaacgg cacagattac acaggctaca cagcaaaaag acagtcttct ggcgctggct  420
gcatcaaaaa ttgccccatt acaggatgct gttgatctgg atattgcaac ggaagaggaa  480
acagcgcttt tgctggcgtg gaaaaaatac agggttttga ttaatcgtat taagccagaa  540
gatgcgccag atattgactg gccggaggtt ccgggcgatg tggcgtga              588

SEQ ID NO: 99          moltype = DNA  length = 2592
FEATURE                Location/Qualifiers
misc_feature           1..2592
                       note = Synthetic: STF84
source                 1..2592
                       mol_type = other DNA
                       organism = synthetic construct
SEQUENCE: 99
atggcagtaa agatttcagg agtcctgaaa gacggcacag gaaaaccggt acagaactgc  60
accattcagc tgaaagccag acgtaacagc accacggtgg tggtgaacac ggtgggctca  120
gagaatccgg atgaagccgg gcgttacagc atggatgtgg agtacggtca gtacagtgtc  180
atcctgcagg ttgacggttt tccaccatcg cacgccggga ccatcaccgt gtatgaagat  240
tcacaaccgg ggacgctgaa tgattttctc tgtgccatga cggaggatga tgcccggccg  300
gaggtgctgc gtcgtcttga actgatggtg gaagaggtgg cgcgtaacgc gtccgtggtg  360
gcacagagta cggcagacgc gaagaaatca gccggcgatg ccagtgcatc agctgctcag  420
gtcgcggccc ttgtgactga tgcaactgac tcagcacgcg ccgccagcac gtccgccgga  480
caggctgcat cgtcagctca ggaagcgtcc tccggcgcag aagcggcatc agcaaaggcc  540
actgaagcgg aaaaaagtgc cgcagccgca gagtcctcaa aaaacgcggc ggccaccagt  600
gccggtgcgg cgaaaacgtc agaaacgaat gctgcagcgt cacaacaatc agccgccacg  660
tctgcctcca ccgcggccac gaaagcgtca gaggccgcca cttcagcacg agatgcggtg  720
gcctcaaaag aggcagcaaa atcatcagaa acgaacgcat catcaagtgc cggtcgtgca  780
gcttcctcgg caacggcggc agaaaattct gccagggcgg caaaaacgtc cgagacgaat  840
gccaggtcat ctgaaacagc agcggaacgg agcgcctctg ccgcggcaga cgcaaaaaca  900
gcggcggcgg ggagtgcgtc aacggcatcc acgaaggcga cagaggctgc gggaagtgcg  960
gtatcagcat cgcagagcaa aagtgcggca gaagcggcgg caatacgtgc aaaaaattcg  1020
gcaaaacgtg cagaagatat agcttcagct gtcgcgcttg aggatgcgga cacaacgaga  1080
aaggggatag tgcagctcag cagtgcaacc aacagcacgt ctgaaacgct tgctgcaacg  1140
ccaaaggcgg ttaaggtggt aatggatgag actaatcgta aatacaccgc acaggatgca  1200
acgacagcac agaaagggat agttcagctt agcaacgcga ccaacagcac atctgaaatg  1260
ctggcggcaa cgccaaagtc ggtaaaggca gcctatgacc ttgctaacgg gaaatatact  1320
gctcaggacg ctacgacagc acaaaaagga attgtccagc tcagtagtgc aaccaacagc  1380
gcatctgaaa cgcttgccgc gacaccgaaa gcagctaatg ataatgcgaa tggtcgggta  1440
ccttctgccc gtaaggtgaa tggtaaggcg ctttcagcgg atataacact gacgccgaaa  1500
gatattggta cgcttaactc aacaacaatg tcattcagcg gtggtgctgg ttggttcaaa  1560
ttagcaacgg taaccatgcc acaggcgagt tctgttgttt caattacgtt gattggtggc  1620
gcgggattta acgtggggtc acctcaacag gcaggtatat ctgaacttgt tttgcgtgca  1680
ggtaatggta atccgaaggg gattactggt gctttatggc agcgcacatc gacagggttt  1740
acaaattttg cctgggtcaa tacatctggt gatacttacg atatttacgt tgcaatcgga  1800
aattatgcga ctggtgtaaa tattcaatgg gattatacca gtaatgccag cgtgacgatt  1860
catacgtcac cagcatattc tgctaataag ccggaagggt taacggacgg tacagtttat  1920
tcactctata cgccatcagg gcagttttat ccgcctggcg caccaatccc gtggccatca  1980
gataccgttc cgtctggtta tgccctgatg caggggcaga cttttgacaa atctgcttac  2040
ccgaaactcg cagccgctta tccgtcaggc gtgatccctg atatgcgtgg ctggacgatt  2100
aagggcaaac ctgccagtgg tcgtgccgta ttgtctcagg aacaggacgg cattaaatcg  2160
cacacccaca gcgccagcgc atccagtacg gatttgggga cgaaaaccac atcgtcgttt  2220
gattacggca ctaaatccac gaataacacc ggggcgcata cgcacagtgt gagcggtaca  2280
gccgcaagtg ccggaaacca tactcatagt gtcacaggcg catcagcagt cagccagtgg  2340
tcacaaaatg ggtcagtaca taaggtagtg tctgcggcca gtgtgaatac aagtgctgca  2400
ggagcgcaca ctcatagtgt cagcggcaca gccgcatctg caggtgctca cgcacatact  2460
gtcggtattg gtgctcatac gcactctgtt gcgattggct cacatggaca caccatcacc  2520
gttaacgctg ctggtaacgc ggaaaacacc gtcaaaaaca tcgcatttaa ctacattgtg  2580
aggcttgcat aa                                                     2592

SEQ ID NO: 100         moltype = DNA  length = 585
FEATURE                Location/Qualifiers
misc_feature           1..585
                       note = Synthetic: STF84-AP1
source                 1..585
                       mol_type = other DNA
                       organism = synthetic construct
SEQUENCE: 100
```

```
atggcattca gaatgagtga acaaccacgg accataaaaa tttataatct gctggccgga  60
actaatgaat ttattggtga aggtgacgca tatattccgc ctcatacagg tctgccagca  120
aacagtacct atattgcacc gccagatatt cctgctggct ttgtggccgt tttcaacagt  180
gatgagggat cgtggcatct cgttgaagac catcggggaa aaaccgtcta tgacgtggct  240
tccggcgacg cgttatttat ttctgaactt ggcccattac cggaaaatgt cacctggtta  300
tccccggaag gggagtttca gaagtggaac ggcacagcct gggtgaaaga tgcagaagca  360
gaaaaactgt tccggatccg ggaggcggaa gaaacaaaaa acagcctgat gcaggtagcc  420
agtgagcata ttgcgccact tcaggatgct gtagatctgg aaatcgcaac ggaggaagaa  480
acctcattgc tggaagcctg gaaaaagtat cgggtgttgc tgaaccgtgt tgatacatca  540
actgcacctg atattgagtg gcctacgaac cctgtcaggg agtaa                 585

SEQ ID NO: 101          moltype = DNA  length = 3849
FEATURE                 Location/Qualifiers
misc_feature            1..3849
                        note = Synthetic: STF-93
source                  1..3849
                        mol_type = other DNA
                        organism = synthetic construct
SEQUENCE: 101
atggcagtaa agatttcagg agtcctgaaa gacggcacag gaaaaccggt acagaactgc  60
accattcagc tgaaagccag acgtaacagc accacggtgg tggtgaacac ggtgggctca  120
gagaatccgg atgaagccgg gcgttacagc atggatgtgg agtacggtca gtacagtgtc  180
atcctgcagg ttgacggttt tccaccatcg cacgccggga ccatcaccgt gtatgaagat  240
tcacaaccgg ggacgctgaa tgatttctc tgtgccatga cggaggatga tgcccggccg  300
gaggtgctgc gtcgtcttga actgatggtg gaagaggtgg cgcgtaacgc gtccgtggtg  360
gcacagagta cggcagacgc gaagaaatca gccggcgatg ccagtgcatc agctgctcag  420
gtcgcggccc ttgtgactga tgcaactgac tcagcacgcg ccgccagcac gtccgccgga  480
caggctgcat cgtcagctca ggaagcgtcc tccggcgcag aagcggcatc agcaaaggcc  540
actgaagcgg aaaaaagtgc cgcagccgca gagtcctcaa aaacgcggc ggccaccagt  600
gccggtgcgg cgaaaacgtc agaaacgaat gctgcagcgt cacaacaatc agccgccacg  660
tctgcctcca ccgcggccac gaaagcgtca gaggccgcca cttcagcacg agatgcggtg  720
gcctcaaaag aggcagcaaa atcatcagaa acgaacgcat catcaagtgc cggtcgtgca  780
gcttcctcgg caacggcggc agaaaattct gccagggcgg caaaaacgtc cgagacgaat  840
gccaggtcat ctgaaacagc agcggaacgg agcgcctctg ccgcggcaga cgcaaaaaca  900
gcggcggcgg ggagtgcgtc aacggcatcc acgaaggcga cagaggctgc gggaagtgcg  960
gtatcagcat cgcagagcaa aagtgcggca gaagcggcgg caatacgtgc aaaaaattcg  1020
gcaaaacgtg cagaagatat agcttcagct gtcgcgcttg aggatgcgga cacaacgaga  1080
aaggggatag tgcagctcag cagtgcaacc aacagcacgt ctgaaacgct tgctgcaacg  1140
ccaaaggcgg ttaaggtggt aatggatgag actaatcgta gggtgccatc taaccgaaaa  1200
gttaacggta aagcactgac tgcggatatc acattaacgc cgaaagatat tggtacttta  1260
aattcagtaa cgatgtcttt ctctggcggg gctgggtggt tcaaactggc tacggttacc  1320
atgccacaag cgagttccat cgtttacatc gcattgattg gtggcgctgg ttacaacgtc  1380
ggctccccac atcaggcagg catttcagaa ctggttctac gagcaggcaa tggaaacccc  1440
aaagggatta ccggtgcttt gtggaagcgt acagccgtcg gattaacgaa tttcgcctgg  1500
atcaacacat ccggcgatac atatgatatt tacgttgaga ttggcaatta tgcgactagt  1560
gtaaatatcc attgggattg tactgcaaat gcgacagttt ctatttatac atcgccaaca  1620
tattcagcga gtaagccttc cagcgttacc gatggtgttg tttatacgat gtatagcaca  1680
catcagaaac cgacgccgtt agatattgga gcactgccaa caaccggagg aacagtttca  1740
ggtccgttgt ctgttactgg tgggatcacc ggaacattaa atggtaatgc aagtacagca  1800
acgaaattgc agacggcaag atctatcggt ggagttggtt tcgacggttc tgcaaatatc  1860
aaccttccag gtgtaaatac tacgggtaat cagaacacca ctggtaatgc tgcaactgct  1920
acaaaacttc agacggcaag aactatcggc ggcgtgagct ttgatggtac tgcgaatatt  1980
aatttgccag gtgttaatac gactggtaat cagaatacaa cgggcaacgc ggctactgct  2040
acgaagttgc agactgcgcg tactatcaat ggggtgtcgt ttgacggctc ggcaaatatt  2100
tccttgtcgc cagcaaatat aggttgcccg gcatctccta ctggttggtt aactacagga  2160
agtaatggcg gagcaataac aacagcacag ttagtgacgt tattgcaaaa taatggagca  2220
tttaacacaa agtcatggat tgctcgatgt gcgtgggcct atgccaatag tgcaaccata  2280
ccaaatagtg aaactggttg tggcgttatt ccattggcag gagctgttat agaggtattt  2340
aataacggta gtagctcaaa caattatacg atccgtataa caacggccac aacgacgagt  2400
gtctctggtg ctctcactaa tgcggagttt atctatgtat ttaatggcac agattattct  2460
ccgggatggc gaagagtata taacacgaaa aacaaaccaa cagcctctga tgtcggtgca  2520
ttacctctta ccggtggtac attatctgga ggtttgacat cttctggcga gatcatttca  2580
aaatatgcaa atggtttccg cattgcttac ggtagctttg ggttctttat ccgtaatgat  2640
ggatcgaaca catatttcat gctaacagca tcaggagaca cattaggttc atggaacggt  2700
ttgcgaccta ttacaattaa taataccagc ggtgcggtat caattggtaa tggactaaat  2760
gtgactggtg gcgtaaatgg tagtttgaac ggtaatgctt caacagctac gaagttgcaa  2820
acagcgagaa acatcaatgg tgttaagttt gatggctcag gcgatatcaa cattaataca  2880
ctggtatctc gtggccgagt tacggcatta agcggctcta ctcaaggcac tgctggcatt  2940
caaatgtacg aggcgtacaa caatagctac ccgaccacgt atggcaacgt attgcacatg  3000
aaaggtgcga gtgctgctgg tgagggcgag ttgcttattg gctggagtgg tacgagcggt  3060
gcacatgcgc cagttttcat tcgctcacga agagatacca cagatgcggc atggtcagcg  3120
tgggcgcagc tatatactgc taaggattca atccctggtg tgaatacaac cggtaatcag  3180
aatactactg gtaatgccgc aacagccaca aaattgcaga cagcaaggaa aattgctggt  3240
gtggcgtttg atggctctgc cgatattact ttgactgcgg ctaaccttaa tgcttatacg  3300
aaaacagagg taacaaacct tctaagttcc tatgcaagca gatcatcact gacaggctat  3360
agtggcaacc tggatattat tgctgaaaca ctggttgtca aatcaggcgg tagtggaggg  3420
tttgctatat gggatattgg cacaactact agcggtgcca atatgtacat tgatccaaac  3480
cctggtatca atacagtttg gcgttcaaca tcttcaaggc gctataaaaa ggatattgaa  3540
acattacaag atcgatatgc tgatgaactt ttgtcattaa gacctgtttg gtatcgttca  3600
```

```
atttgtcgag gtgaccgaaa ggattggggg tattacggcc ttattgctga agaggttggt  3660
gagattgccc cgcaatatgt ccattggcgt gaaccaacaa ataatgattc tccagaagat  3720
atttcctcaa atggtatggt cgctgaaggg gtgatgtatg agcgtttggt tgtaccactc  3780
attcatcata ttcagcaatt gaccaaaagg gttgaggagc ttgaaacgaa gttaaattca  3840
cctaaagaa                                                          3849

SEQ ID NO: 102         moltype = DNA  length = 2397
FEATURE                Location/Qualifiers
misc_feature           1..2397
                       note = Synthetic: STF-95
source                 1..2397
                       mol_type = other DNA
                       organism = synthetic construct
SEQUENCE: 102
atggcagtaa agatttcagg agtcctgaaa gacggcacag gaaaaccggt acagaactgc  60
accattcagc tgaaagccag acgtaacagc accacggtgg tggtgaacac ggtgggctca  120
gagaatccgg atgaagccgg gcgttacagc atggatgtgg agtacggtca gtacagtgtc  180
atcctgcagg ttgacggttt tccaccatcg cacgccggga ccatcaccgt gtatgaagat  240
tcacaaccgg ggacgctgaa tgattttctc tgtgccatga cggaggatga tgcccggccg  300
gaggtgctgc gtcgtcttga actgatggtg gaagaggtgg cgcgtaacgc gtccgtggtg  360
gcacagagta cggcagacgc gaagaaatca gccggcgatg ccagtgcatc agctgctcag  420
gtcgcggccc ttgtgactga tgcaactgac tcagcacgcg ccgccagcac gtccgccgga  480
caggctgcat cgtcagctca ggaagcgtcc tccggcgcag aagcggcatc agcaaaggcc  540
actgaagcgg aaaaaagtgc cgcagccgca gagtcctcaa aaacgcggc ggccaccagt  600
gccggtgcgg cgaaaacgtc agaaacgaat gctgcagcgt cacaacaatc agccgccacg  660
tctgcctcca ccgcggccac gaaagcgtca gaggccgcca cttcagcacg agatgcggtg  720
gcctcaaaag aggcagcaaa atcatcagaa acgaacgcat catcaagtgc cggtcgtgca  780
gcttcctcgg caacggcggc agaaaattct gccagggcgg caaaaacgtc cgagacgaat  840
gccaggtcat ctgaaacagc agcggaacgg agcgcctctg ccgcggcaga cgcaaaaaca  900
gcggcggcgg ggagtgcgtc aacggcatcc acgaaggcga cagaggctgc gggaagtgcg  960
gtatcagcat cgcagagcaa aagtgcggca gaagcggcgg caatacgtgc aaaaaattcg  1020
gcaaaacgtg cagaagatat agcttcagct gtcgcgcttg aggatgcgga cacaacgaga  1080
aaggggatag tgcagctcag cagtgcaacc aacagcacgt ctgaaacgct tgctgcaacg  1140
ccaaaggcgg ttaaggtggt aatggatgag actaatcgtc gggtaccttc tgcccgtaag  1200
gtgaatggta aggcgctttc agcggatata acactgacgc cgaaagatat tggtacgctt  1260
aactcaacaa caatgtcatt cagcggtggt gctggttggt tcaaattagc aacggtaacc  1320
atgccacagg cgagttctgt tgtttcaatt acgttgattg gtggtgcggg atttaacgtg  1380
gggtcacctc aacaggcagg tatatctgaa cttgttttgc gtgcaggtaa tggtaatccg  1440
aaggggatta ctggtgcttt atggcagcgc acatcgacag ggtttacaaa ttttgcctgg  1500
gtcaatacat ctggtgatac ttacgatatt tacgttgcaa tcggaaatta tgcgactggt  1560
gtaaatattc aatgggatta taccagtaat gccagcgtga cgattcatac gtcaccagca  1620
tattctgcta ataagccgga agggttaacg gacggtacag tttattcact ctatacgcca  1680
tcagagcagt tttatccgcc tggcgcacca atcccgtggc catcagatac cgttccgtct  1740
ggctatgccc tgatgcaggg gcagactttt gacaaatctg catacccgaa acttgcagcc  1800
gcttatccgt caggcgtgat ccctgatatg cgtggctgga cgattaaggg caaacccgcc  1860
agtggtcgtg ccgtattgtc tcaggaacag gacggcatta aatcgcacac ccacagcgcc  1920
agcgcatcca gtacggattt ggggacgaaa aacacatcgt cgtttgatta cggaaccaaa  1980
tccacgaata acaccggggc gcatacgcac agtctgagtg gctctacggg gtctgccggt  2040
gatcatactc atggtaatgg tattcgttgg ccaggaggcg gcggttctgc gttagcattt  2100
tatgatggcg gtgggttcac ttatgtccag gattcacagt atcaagtaag cccggggact  2160
tcttcccgta gatcgtatta tcaacgtatt cagacacagt cagcaggtgc tcatacccac  2220
tcgctgtctg gtactgcagc aagttctggc gcacatgcac atactgtagg tattggtgcg  2280
catacgcact ccgttgcgat tggttcacat ggacacacca tcaccgttaa cgctgctggt  2340
aacgcggaaa acaccgtcaa aaacatcgca tttaactata ttgtgaggct tgcataa     2397

SEQ ID NO: 103         moltype = DNA  length = 585
FEATURE                Location/Qualifiers
misc_feature           1..585
                       note = Synthetic: STF-95-AP1
source                 1..585
                       mol_type = other DNA
                       organism = synthetic construct
SEQUENCE: 103
atggcattca gaatgagtga acaagcacgg accataaaaa tttataatct gctggccgga  60
actaatgaat ttattggtga aggtgacgca tatattccgc ctcatacagg tctgccagca  120
aacagtaccg atattgcacc accagatatt cctgctggct ttgtggctgt tttcaacagt  180
gatgaggcat cgtggcatct cgttgaagac catcggggta aaacggttta tgacgtagcg  240
tcaggggacg agttatttat ttctgaactc ggtccgttac cggaaaatgt tacctggtta  300
tcgccggaag gggagtttca gaagtggaac ggcacagcct gggtgaagga tacggaagca  360
gaaaaaatgt tccggatccg ggaggcggaa gaaacaaaaa acaacctgat gcaggtagcc  420
agtgagcata ttgcgccgct tcaggatgct gcagatctgg aaattgcaac ggaggaagaa  480
acctcattgc tggaagcctg gaaaaagtat cgggtgttgc tgaaccgtgt tgatacatca  540
actgcacctg atattgagtg gcctacgaac cctgtcaggg agtaa                  585

SEQ ID NO: 104         moltype = DNA  length = 1878
FEATURE                Location/Qualifiers
misc_feature           1..1878
                       note = Synthetic: STF-132
source                 1..1878
```

```
                        mol_type = other DNA
                        organism = synthetic construct
SEQUENCE: 104
atggcagtaa agatttcagg agtcctgaaa gacggcacag gaaaaccggt acagaactgc  60
accattcagc tgaaagccag acgtaacagc accacggtgg tggtgaacac ggtgggctca  120
gagaatccgg atgaagccgg gcgttacagc atggatgtgg agtacggtca gtacagtgtc  180
atcctgcagg ttgacggttt tccaccatcg cacgccggga ccatcaccgt gtatgaagat  240
tcacaaccgg ggacgctgaa tgattttctc tgtgccatga cggaggatga tgcccggccg  300
gaggtgctgc gtcgtcttga actgatggtg gaagaggtgg cgcgtaacgc gtccgtggtg  360
gcacagagta cggcagacgc gaagaaatca gccggcgatg ccagtgcatc agctgctcag  420
gtcgcggccc ttgtgactga tgcaactgac tcagcacgcg ccgccagcac gtccgccgga  480
caggctgcat cgtcagctca ggaagcgtcc tccggcgcag aagcggcatc agcaaaggcc  540
actgaagcgg aaaaaagtgc cgcagccgca gagtcctcaa aaacgcggc ggccaccagt  600
gccggtgcgg cgaaaacgtc agaaacgaat gctgcagcgt cacaacaatc agccgccacg  660
tctgcctcca ccgcggccac gaaagcgtca gaggccgcca cttcagcacg agatgcggtg  720
gcctcaaaag aggcagcaaa atcatcagaa acgaacgcat catcaagtgc cggtcgtgca  780
gcttcctcgg caacggcggc agaaaattct gccagggcgg caaaaacgtc cgagacgaat  840
gccaggtcat ctgaaacagc agcggaacgg agcgcctctg ccgcggcaga cgcaaaaaca  900
gcggcggcgg ggagtgcgtc aacggcatcc acgaaggcga cagaggctgc gggaagtgcg  960
gtatcagcat cgcagagcaa aagtgcggca gaagcggcgg caatacgtgc aaaaaattcg  1020
gcaaaacgtg cagaagatat agcttcagct gtcgcgcttg aggatgcgga cacaacgaga  1080
aaggggatag tgcagctcag cagtgcaacc aacagcacgt ctgaaacgct tgctgcaacg  1140
ccaaaggcgg ttaaggtggt aatggatgag actaatcgtg ccgttcagcg tgatggtgac  1200
accatgaccg gggaactgaa aatccgtggt gttaatgcgc tgaggatttt caacgacgcc  1260
tttggtctga tttttcgtcg ttcagaagag tgcctgcacc ttatccctac cagtgaaggt  1320
cagggcgaga atggcgatat tggtccactt cgcccgttca ctattaatct gcggacgggt  1380
gaaatatcca tgtcgcataa agtgtctgtt ggcggcggtt ctcaggtcaa tggtgcgctg  1440
ggtatcggcg ttcagaacgc gctgggcgga aactcaattg ctttcgggga taacgataca  1500
ggtataaaac aaaacggcga cggcattctg gatgtttatg cgaatggaca gcacgtattc  1560
cgttttcaga atggcgcgtt acaaagtcac cgggcagtga atgtttcagg gcgggtaaca  1620
ccaactgatt atggcaattt cgatgaacgc taccagacca aaacaggcgg cgtgcagaat  1680
tttcagtaca ccagtgaggt gtttcacaag ccagccggta atgaggtttc ctgggttttt  1740
cgggcgccgt caggttgcac tctttctggg attaatgtgc aggagaccgg tagtaactct  1800
gcggataata tcggtggtgt gtattacaaa caggcccaga tttatataaa tggcgcatgg  1860
cgctcagtat caggttaa                                               1878

SEQ ID NO: 105          moltype = DNA  length = 567
FEATURE                 Location/Qualifiers
misc_feature            1..567
                        note = Synthetic: STF-132-AP1
source                  1..567
                        mol_type = other DNA
                        organism = synthetic construct
SEQUENCE: 105
atggcgctca gtatcaggtt aattaaggca aaaataatgg aactcagaaa tgtcacgcgt  60
tattacccgg aaaacatgcc ttatggtgaa ggtgttcagt atttccgtag tgaagacggg  120
caggattttt atgaatcact ggataaattc gcgaagaaat acaagctgtg cacgcatcct  180
gaaaccggtg ttatttattc aatggcggaa gacgtatccc ggctttatcc ggcaggtttc  240
accattgtgg aagtggatga actaccggat ggcttttgta tagaggcgcg ctggtattat  300
aaagacggtg aagtactgcc ggttcctgtt gattacagac tgctggctga gtcggaacga  360
gcacgtctta cggcgattgc tgaacgggaa atatccgaca agaaaacaga tttacttctg  420
ggaataatta ataatgggga aaaagaaatg ctgaaattat ggcggatgta catcagaaat  480
ttaaagaata ttgattttaa tcacattcat gataaatcgt catttgatag tattaaatgg  540
ccttgtgatc ctgagaattc acattaa                                     567

SEQ ID NO: 106          moltype = DNA  length = 4023
FEATURE                 Location/Qualifiers
misc_feature            1..4023
                        note = Synthetic: K1F
source                  1..4023
                        mol_type = other DNA
                        organism = synthetic construct
SEQUENCE: 106
atggcagtaa agatttcagg agtcctgaaa gacggcacag gaaaaccggt acagaactgc  60
accattcagc tgaaagccag acgtaacagc accacggtgg tggtgaacac ggtgggctca  120
gagaatccgg atgaagccgg gcgttacagc atggatgtgg agtacggtca gtacagtgtc  180
atcctgcagg ttgacggttt tccaccatcg cacgccggga ccatcaccgt gtatgaagat  240
tcacaaccgg ggacgctgaa tgattttctc tgtgccatga cggaggatga tgcccggccg  300
gaggtgctgc gtcgtcttga actgatggtg gaagaggtgg cgcgtaacgc gtccgtggtg  360
gcacagagta cggcagacgc gaagaaatca gccggcgatg ccagtgcatc agctgctcag  420
gtcgcggccc ttgtgactga tgcaactgac tcagcacgcg ccgccagcac gtccgccgga  480
caggctgcat cgtcagctca ggaagcgtcc tccggcgcag aagcggcatc agcaaaggcc  540
actgaagcgg aaaaaagtgc cgcagccgca gagtcctcaa aaacgcggc ggccaccagt  600
gccggtgcgg cgaaaacgtc agaaacgaat gctgcagcgt cacaacaatc agccgccacg  660
tctgcctcca ccgcggccac gaaagcgtca gaggccgcca cttcagcacg agatgcggtg  720
gcctcaaaag aggcagcaaa atcatcagaa acgaacgcat catcaagtgc cggtcgtgca  780
gcttcctcgg caacggcggc agaaaattct gccagggcgg caaaaacgtc cgagacgaat  840
gccaggtcat ctgaaacagc agcggaacgg agcgcctctg ccgcggcaga cgcaaaaaca  900
gcggcggcgg ggagtgcgtc aacggcatcc acgaaggcga cagaggctgc gggaagtgcg  960
```

```
gtatcagcat cgcagagcaa aagtgcggca gaagcggcgg caatacgtgc aaaaaattcg  1020
gcaaaacgtg cagaagatat agcttcagct gtcgcgcttg aggatgcgga cacaacgaga  1080
aaggggatag tgcagctcag cagtgcaacc aacagcacgt ctgaaacgct tgctgcaacg  1140
ccaaaggcgg ttaaggtggt aatggatctg gacagtccgg cactgaccgg aacgccaaca  1200
gcaccaaccg cgctcagggg aacaaacaat acccagattg cgaacaccgc ttttgtactg  1260
gccgcgattg cagatgttat cgacgcgtca cctgacgcac tgaatacgct gaatgaactg  1320
gccgcagcgc tcgggaatga tccagatttt gctaccacca tgactaacgc gcttgcgggt  1380
aaacaaccga agaatgcgac actgacggcg ctggcagggc tttccacggc gaaaaataaa  1440
ttaccgtatt ttgcggaaaa tgatgccgcc agcctgactg aactgactca ggttggcagg  1500
gatattctgg caaaaaattc cgttgcagat gttcttgaat accttggggc cggtgagaat  1560
tcgggtgcga agggcgatgg cgttaccgac gacactgcag cgctgacttc cgccctgaac  1620
gatactccgg tgggtcagaa aatcaacggt aacggtaaaa cttataaagt tacgtccctg  1680
ccggacatct cccgctttat caacacccgt ttcgtgtatg aacgtatccc aggccagccg  1740
ctgtactacg catcggaaga gttcgttcag ggtgagcttt ttaaaatcac cgacactccg  1800
tattataacg cctggccaca ggataaggct ttcgtgtacg aaaacgttat ctatgctccg  1860
tacatgggtt ccgaccgtca cggtgtcagc cgactgcacg taagctgggt gaaatcgggc  1920
gacgatggtc agacctggag cacgcctgag tggctgaccg accttcatcc ggactatccg  1980
accgttaact atcactgcat gagcatgggc gtctgtcgca accgtctgtt cgcaatgatc  2040
gaaacccgta cgctggcaaa aaacgctctg actaactgcg ccctgtggga tcgtccaatg  2100
agccgctctc tgcacctgac gggtggtatt accaaagcag cgaaccagcg ttacgccacc  2160
attcacgtac cggatcatgg tctgttcgtt ggtgactttg taaatttctc taattctgca  2220
gttaccggtg tgtctggcga catgaccgtt gcgaccgtaa tcgataagga caatttcacc  2280
gtcctgaccc cgaaccagca aacctctgat cttaacaacg ctggcaagaa ctggcacatg  2340
ggcactagct ttcacaaatc tccgtggcgt aaaaccgatc tgggcctgat cccgtctgta  2400
actgaagtgc actccttcgc gaccattgat aacaacggtt tcgctatggg ttatcaccaa  2460
ggtgatgttg caccgcgtga agtcggcctc ttttattttc cggacgcatt caacagcccg  2520
tccaactacg tgcgccgtca gattccgtct gaatatgaac cggacgcctc cgagccgtgc  2580
attaagtact atgacggtgt gctgtacctg attacccgtg gcacccgtgg tgatcgtctg  2640
ggttcatctc tgcatcgctc ccgcgacatt ggtcagacgt gggaaagtct gcgcttcccg  2700
cacaatgttc atcacaccac cctgccgttc gcgaaagtcg gcgatgacct gatcatgttt  2760
ggctccgaac gtgctgaaaa cgaatgggaa gcgggcgccc cagacgatcg ctacaaggca  2820
tcttacccgc gcaccttcta cgcgcgtctg aacgtgaaca actggaacgc agacgatatc  2880
gaatgggtaa acatcaccga ccagatctac cagggtggta tcgtgaactc tggtgtgggc  2940
gttggttccg ttgtagttaa agataactac atctattata tgttcggcgg cgaagaccac  3000
ttcaacccgt ggacttacgg cgataactcc gcgaaagacc cgttcaaatc cgatggtcac  3060
ccttctgacc tctattgtta caaaatgaaa atcggtccgg acaaccgtgt ttcccgcgat  3120
tttcgctacg gcgctgttcc aaaccgtgca gttccggtat tcttcgacac gaacggcgtg  3180
cgtaccgttc cggctccgat ggaattcacc ggcgacctgg gtctgggcca cgtaaccatt  3240
cgtgcctcca ccagctctaa catccgttcc gaagtactca tggaaggtga atacggcttt  3300
atcggtaagt ctatcccgac ggacaacccg gcaggtcagc gtatcatctt ctgcggcggt  3360
gagggtacct ctagcaccac cggcgcgcaa atcaccctgt acggcgctaa caacaccgac  3420
tctcgtcgta tcgtatacaa cggtgatgaa catctgttcc agtccgcaga cgtgaaaccg  3480
tacaacgaca acgtcaccgc actgggtggt ccatccaacc gtttcaccac tgcgtacctg  3540
ggttccaacc cgatcgttac tagcaatggt gaacgcaaaa ctgaaccggt agtgtttgac  3600
gacgcttttc tggacgcatg gggcgatgtt cattacatca tgtatcagtg gctggatgcc  3660
gtgcagctga aggtaacgca cgcgcgtatc cactttggtg tgatcgcaca gcagattcgc  3720
gatgtcttca tcgcacacgg tctgatggat gaaaatagta ctaactgtcg ctatgcggtg  3780
ctgtgctatg acaaataccc gcgtatgacc gacaccgtgt tctcgcacaa tgagattgtt  3840
gaacataccg atgaagaagg taacgtgact actaccgaag aaccggttta taccgaagtg  3900
gttattcacg aagaaggtga agaatggggc gtgcgtcctg atggtatctt tttcgcggag  3960
gcagcgtacc agcgtcgcaa actggaacgc atcgaagctc gtctgtcggc actggaacag  4020
aaa                                                                4023
```

```
SEQ ID NO: 107          moltype = DNA  length = 3462
FEATURE                 Location/Qualifiers
misc_feature            1..3462
                        note = Synthetic: K5
source                  1..3462
                        mol_type = other DNA
                        organism = synthetic construct
SEQUENCE: 107
atggcagtaa agatttcagg agtcctgaaa gacggcacag gaaaaccggt acagaactgc  60
accattcagc tgaaagccag acgtaacagc accacggtgg tggtgaacac ggtgggctca  120
gagaatccgg atgaagccgg gcgttacagc atggatgtgg agtacggtca gtacagtgtc  180
atcctgcagg ttgacggttt tccaccatcg cacgccggga ccatcaccgt gtatgaagat  240
tcacaaccgg ggacgctgaa tgatttctc tgtgccatga cggaggatga tgcccggccg  300
gaggtgctgc gtcgtcttga actgatggtg gaagaggtgg cgcgtaacgc gtccgtggtg  360
gcacagagta cggcagacgc gaagaaatca gccggcgatg ccagtgcatc agctgctcag  420
gtcgcggccc ttgtgactga tgcaactgac tcagcacgcg ccgccagcac gtccgccgga  480
caggctgcat cgtcagctca ggaagcgtcc tccggcgcag aagcggcatc agcaaaggcc  540
actgaagcgg aaaaaagtgc cgcagccgca gagtcctcaa aaacgcggc ggccaccagt  600
gccggtgcgg cgaaaacgtc agaaacgaat gctgcagcgt cacaacaatc agccgccacg  660
tctgcctcca ccgcggccac gaaagcgtca gaggccgcca cttcagcacg agatgcggtg  720
gcctcaaaag aggcagcaaa atcatcagaa acgaacgcat catcaagtgc cggtcgtgca  780
gcttcctcgg caacggcggc agaaaattct gccagggcgg caaaaacgtc cgagacgaat  840
gccaggtcat ctgaaacagc agcggaacgg agcgcctctg ccgcggcaga cgcaaaaaca  900
gcggcggcgg ggagtgcgtc aacggcatcc acgaaggcga cagaggctgc gggaagtgcg  960
gtatcagcat cgcagagcaa aagtgcggca gaagcggcgg caatacgtgc aaaaaattcg  1020
gcaaaacgtg cagaagatat agcttcagct gtcgcgcttg aggatgcgga cacaacgaga  1080
```

```
aaggggatag tgcagctcag cagtgcaacc aacagcacgt ctgaaacgct tgctgcaacg  1140
ccaaaggcgg ttaaggtggt aatggatgag actaatcgta aggcacctct ggacagtccg  1200
gcactgaccg gaacgccaac agcaccaacc gcgctcaggg gaacaaacaa tacccagatt  1260
gcgaacaccg cttttgtact ggccgcgatt gcagatgtta tcgacgcgtc acctgacgca  1320
ctgaatacgc tgaatgaact ggccgcagcg ctcgggaatg atccagattt tgctaccacc  1380
atgactaacg cgcttgcggg taaacaaccg aagaatgcga cactgacggc gctggcaggg  1440
ctttccacgg cgaaaaataa attaccgtat tttgcggaaa atgatgccgc cagcctgact  1500
gaactgactc aggttggcag ggatattctg gcaaaaaatt ccgttgcaga tgttcttgaa  1560
taccttgggg ccggtgagaa ttcgcctaaa accgaaggta tcctccataa aggtcagagc  1620
ttatacgaat atctggatgc ccgtgttctt acttctaagc cattcggtgc agcgggtgat  1680
gcaacgaccg acgacacgga ggttatcgct gcgagcctga acagccagaa agctgttacc  1740
atctctgacg gcgttttcag ttcttctggc atcaactcca actactgtaa cctggatggt  1800
cgcggatccg gtgtgctcag ccaccgtagc tctactggta attacctggt gtttaacaat  1860
ccgcgtactg gtcgtctgag caatatcact gttgaatcta acaaagcgac cgataccact  1920
cagggccaac aggtgtccct ggcaggtggc agtgacgtga ccgtgtcaga tgtcaacttc  1980
tccaacgtga aggcactggg ttttagcctg attgcctacc caaacgatgc tccgccggat  2040
ggcctgatga tcaaaggcat tcgcggatct tacagcggtt acgcgaccaa caaagcagct  2100
ggttgcgtcc tggcggatag ctccgttaac agcctgatcg acaatgtgat cgctaagaat  2160
tacccgcaat tcggtgctgt tgaattaaag ggcactgcaa gctacaacat tgtatcgaac  2220
gttatcggtg cggattgtca gcacgtgact tacaacggca ctgagggacc gatcgctcct  2280
agtaacaatc tgatcaaggg cgttatggcg aacaacccga aatacgcggc agttgtggcg  2340
ggtaaaggct cgacgaatct gatctctgat gtactggtag actattctac cagcgatgct  2400
cgtcaggcgc atggtgttac cgtcgaagga tctgataacg tgattaacaa cgtactgatg  2460
tccggttgcg acggaactaa ttccctgggt cagcgtcaaa ccgcaactat cgcgcgtttc  2520
atcggtactg caaataacaa ctatgctagc gtgttcccat cctattctgc cactggtgtg  2580
atcacgtttg agtctggcag tacccgtaac ttcgtcgagg ttaagcatcc gggccgtcgc  2640
aacgatcttc tgtcatcggc aagcacgatt gacggcgctg cgaccatcga cgggacttct  2700
aactctaacg tagtacacgc gcctgctctg ggccaataca ttggctccat gagtggtcgc  2760
tttgaatggc gtattaagtc aatgagcctg ccgtccggcg tactcactag cgcggataaa  2820
taccgtatgc tgggtgacgg tgctgttagc cttgctgttg gcggaggaac tagcagtcag  2880
gtgcgcttgt tcacctcaga cggtacttct cgcactgttt ctctgaccaa tggtaacgtg  2940
cgcctgagca cgtcctctac tggctattta cagctgggtg cagacgcaat gactccggac  3000
tccactggta cttacgcgtt aggctccgca tctcgtgctt ggagtggcgg attcactcag  3060
gcagcattca ccgttacttc tgacgcacgt tgcaaaactg agcctttaac catctctgac  3120
gctttactgg atgcttggag tgaagtggac tttgtccagt tccagtatct ggatcgtgtt  3180
gaagagaaag gtgctgactc cgcgcgttgg catttcggaa tcatcgccca gcgtgctaaa  3240
gaggcattcg aacgtcacgg catcgatgcg catcgttacg gtttcttatg ctttgactct  3300
tgggacgatg tgtacgaaga ggatgcaaat ggatctcgca aactgatcac tccggcgggt  3360
agtcgctatg gtattcgcta tgaggaagtt ctgatcctcg aagcagcgct gatgcgtcgc  3420
acgatcaagc gcatgcagga agcactggct gcgttaccga ag                    3462

SEQ ID NO: 108          moltype = DNA  length = 3225
FEATURE                 Location/Qualifiers
misc_feature            1..3225
                        note = Synthetic: STF-37
source                  1..3225
                        mol_type = other DNA
                        organism = synthetic construct
SEQUENCE: 108
atggcagtaa agatttcagg agtcctgaaa gacggcacag gaaaaccggt acagaactgc  60
accattcagc tgaaagccag acgtaacagc accacggtgg tggtgaacac ggtgggctca  120
gagaatccgg atgaagccgg gcgttacagc atggatgtgg agtacggtca gtacagtgtc  180
atcctgcagg ttgacggttt tccaccatcg cacgccggga ccatcaccgt gtatgaagat  240
tcacaaccgg ggacgctgaa tgatttttctc tgtgccatga cggaggatga tgcccggccg  300
gaggtgctgc gtcgtcttga actgatggtg gaagaggtgg cgcgtaacgc gtccgtggtg  360
gcacagagta cggcagacgc gaagaaatca gccggcgatg ccagtgcatc agctgctcag  420
gtcgcggccc ttgtgactga tgcaactgac tcagcacgcg ccgccagcac gtccgccgga  480
caggctgcat cgtcagctca ggaagcgtcc tccggcgcag aagcggcatc agcaaaggcc  540
actgaagcgg aaaaaagtgc cgcagccgca gagtcctcaa aaaacgcggc ggccaccagt  600
gccggtgcgg cgaaaacgtc agaaacgaat gctgcagcgt cacaacaatc agccgccacg  660
tctgcctcca ccgcggccac gaaagcgtca gaggccgcca cttcagcacg agatgcggtg  720
gcctcaaaag aggcagcaaa atcatcagaa acgaacgcat catcaagtgc cggtcgtgca  780
gcttcctcgg caacggcggc agaaaattct gccagggcgg caaaaacgtc cgagacgaat  840
gccaggtcat ctgaaacagc agcggaacgg agcgcctctg ccgcggcaga cgcaaaaaca  900
gcggcggcgg ggagtgcgtc aacggcatcc acgaaggcga cagaggctgc gggaagtgcg  960
gtatcagcat cgcagagcaa aagtgcggca gaagcggcgg caatacgtgc aaaaaattcg  1020
gcaaaacgtg cagaagatat agcttcagct gtcgcgcttg aggatgcgga cacaacgaga  1080
aaggggatag tgcagctcag cagtgcaacc aacagcacgt ctgaaacgct tgctgcaacg  1140
ccaaaggcgg ttaaggtggt aatggatgag actaatcgta aggcacctct ggacagtccg  1200
gcactgaccg gaacgccaac agcaccaacc gcgctcaggg gaacaaacaa tacccagatt  1260
gcgaacaccg cttttgtact ggccgcgatt gcagatgtta tcgacgcgtc acctgacgca  1320
ctgaatacgc tgaatgaact ggccgcagcg ctcgggaatg atccagattt tgctaccacc  1380
atgactaacg cgcttgcggg taaacaaccg aagaatgcga cactgacggc gctggcaggg  1440
ctttccacgg cgaaaaataa attaccgtat tttgcggaaa atgatgccgc cagcctgact  1500
gaactgactc aggttggcag ggatattctg gcaaaaaatt ccgttgcaga tgttcttgaa  1560
taccttgggg ccggtgagaa ttcggagtta tctggagagc acgggtcgtt tttgattggc  1620
ggagtaattg attgttactc aaccgtttca gatcttattt cttcctcccc atccgttggt  1680
agagtatgca ggactatagg gtattacagc ccaggtgatg gaggtggggc agattacata  1740
attagtattg gaactccgat gcaagatttt agcgattctg gttctatagt tatagatgaa  1800
```

```
tgcaagttcg ctaaattaat ccagcaaagc caatatgatt taaagcagtt tggagtaaaa  1860
ccatctgacc cgtcttatgc agaaaaaaac gacatattta tctcgcaagc cattactagg  1920
tctagagttg gaagatgcaa gattattata agcgatgtta tatatcataa aaaacccttta 1980
atttttgatt attacaatca tatggaagga agttgtattg gtagtgaccc ggaatttact  2040
cctaggttta taaaaataga taatacaact agcggtttgc cagatatggg ataccctggt  2100
gttgctgatg ttgtatctta cgatgttgat gcaggaataa taattaaaag acagaattct  2160
ggcacaagtt ttgccagagg tttcataatt aaggggtttc ttcttcagtc ggagaagaaa  2220
tcagcatggg caatttacgc gccgcatatg gcggatttg atatagacat tgatagtcgt   2280
gggtttaatg gaggaatcag atggtttgtt aatttttcttg gaagaatggc aggaagacat 2340
ataggtcttg gtgcaaactc atcagatcca acattatcta taggtgcgtg gtgttcgaaa  2400
ttctctacaa tacctgattg tggtaattcc gttgtattca gattgtcatt caatggattt  2460
aacagaggta tgcaaatgga gtattttggt aatggggttt tagatagagt aactcttgaa  2520
aatatttcaa aaccaacacc tacgtcgcca acaacacatg gaatatagc aactgataca   2580
tggttaactg gccaggtgtc atgtgaaagt tcttcaacct gcatcatccg tgctggcaat  2640
aacgcgaact tcgatattac ccttagtgcg gtattccatg ttacgcaaga tgatccttcc  2700
gagggtattg ttcatgtatt aaatggaggc cgcctaactc tgcgttcatc tacaattctt  2760
gctgatttgg cagatacaaa aatcattaat gagaatggag gttatctcga tattgccgca  2820
aataccagaa caggaaatat tgtttattcc aatagtgata attacagatt caaagacaga  2880
accattggtt ttggtcagac tgcggcaact acaaaaacaa gcttctcttc tggtgaagag  2940
attacatttt cactactaaa cggaacgcca aaagcgaatc tatctggcgg aacgatccag  3000
tttaactctc catgcctgat taaaatcact gtgcagggga ggggtataac atcaggagca  3060
cttacttttg ggataaatgg agaatcttca gagagcgtga gtcagggaca gcaggtttct  3120
atggttgtcg gagtggtatc cggtgacatt cttaacctga aggcaacctc atcactgacg  3180
ctgggtagtg caggaggggt gcgggtactt cttgagcctg taaac                  3225
```

```
SEQ ID NO: 109          moltype = DNA  length = 2865
FEATURE                 Location/Qualifiers
misc_feature            1..2865
                        note = Synthetic: 1JL
source                  1..2865
                        mol_type = other DNA
                        organism = synthetic construct
SEQUENCE: 109
atggcagtaa agatttcagg agtcctgaaa gacggcacag gaaaaccggt acagaactgc  60
accattcagc tgaaagccag acgtaacagc accacggtgg tggtgaacac ggtgggctca  120
gagaatccgg atgaagccgg gcgttacagc atggatgtgg agtacggtca gtacagtgtc  180
atcctgcagg ttgacggttt tccaccatcg cacgccggga ccatcaccgt gtatgaagat  240
tcacaaccgg ggacgctgaa tgatttctc tgtgccatga cggaggatga tgcccggccg   300
gaggtgctgc gtcgtcttga actgatggtg gaagaggtgg cgcgtaacgc gtccgtggtg  360
gcacagagta cggcagacgc gaagaaatca gccggcgatg ccagtgcatc agctgctcag  420
gtcgcggccc ttgtgactga tgcaactgac tcagcacgcg ccgccagcac gtccgccgga  480
caggctgcat cgtcagctca ggaagcgtcc tccggcgcag aagcggcatc agcaaaggcc  540
actgaagcgg aaaaaagtgc cgcagccgca gagtcctcaa aaacgcggc ggccaccagt   600
gccggtgcgg cgaaaacgtc agaaacgaat gctgcagcgt cacaacaatc agccgccacg  660
tctgcctcca ccgcggccac gaaagcgtca gaggccgcca cttcagcacg agatgcggtg  720
gcctcaaaag aggcagcaaa atcatcagaa acgaacgcat catcaagtgc cggtcgtgca  780
gcttcctcgg caacggcggc agaaaattct gccagggcgg caaaaacgtc cgagacgaat  840
gccaggtcat ctgaaacagc agcggaacgg agcgcctctg ccgcggcaga cgcaaaaaca  900
gcggcggcgg ggagtgcgtc aacggcatcc acgaaggcga cagaggctgc gggaagtgcg  960
gtatcagcat cgcagagcaa aagtgcggca gaagcggcgg caatacgtgc aaaaaattcg  1020
gcaaaacgtg cagaagatat agcttcagct gtcgcgcttg aggatgcgga cacaacgaga  1080
aaggggatag tgcagctcag cagtgcaacc aacagcacgt ctgaaacgct tgctgcaacg  1140
ccaaaggcgg ttaaggtggt aatggatgag actaatcgta aggcacctct ggacagtccg  1200
gcactgaccg gaacgccaac agcaccaacc gcgctcaggg gaacaaacaa tacccagatt  1260
gcgaacaccg cttttgtact ggccgcgatt gcagatgtta tcgacgcgtc acctgacgca  1320
ctgaatacgc tgaatgaact ggccgcagcg ctcgggaatg atccagattt tgctaccacc  1380
atgactaacg cgcttgcggg taaacaaccg aagaatgcga cactgacggc gctggcaggg  1440
ctttccacgg cgaaaaataa attaccgtat tttgcggaaa atgatgccgc cagcctgact  1500
gaactgactc aggttggcag ggatattctg gcaaaaaatt ccgttgcaga tgttcttgaa  1560
taccttgggg ccggtgagaa ttcgggctac aaagttcaga gcttagcaat tctgtccgac  1620
acccaagctg tccacgatgc tactaacacc attaaaaccc agacggacaa gatcaaggca  1680
gacacgcagg caatcaaaac tcaaacaaat caaattaaaa ccgaaacggg cgtaattcgt  1740
gataaagcga acactgcgaa aactgatgcg caggccgcga gcgccgccgc acaaggcttc  1800
cgtgatcagg cgaaggagtg ggcacaaagt gtaaacgctg ataacttatt aaccaaaacg  1860
ggcaacttag ctggcctgac tgacaagagc gcggcacgtt ctaatttagg gctaggaagc  1920
gtagcaacgg aaaacaccgt tccaattaag aaaggcggca ctgcggcaac gaccgtcgcg  1980
gcggcacgct ccaatttagg gctgggtagc gttgcaacgg agaacactgt cccaattgaa  2040
aaggggggga ctgcggcgac aaccgccgcg aaagcgcgta gcaatctggg tttaggtagc  2100
gtagctacgg agaataccgt gccgattgaa aagggcggca cggcggcgac cactgccgct  2160
aaagcccgtt cgaacttcgg cttaggcgat aacaacaaag taaaacttgg tacactgcgc  2220
ctgaacgggg gtgaatctct ggttttcaac gatgtggaac gcaatggcct gattatcagc  2280
aacgccagct tcggtatcga tagctgggtt ggtcaaacca tgcacaaatg gtataccgat  2340
tggacgcgtg ctggcttagt gcgtgcaggt gacgcgcatc tgagcgatta tcgtgtgcat  2400
gtttggaaag acggtttcac cgaagccctg tttcgtttcc tgccggacgg gcgcttgatt  2460
tccggcaact ccggtaatcc gtctgttaac gaatttcaaa aagccccgct gtctgatcgt  2520
gacctgaaaa aagaaatcaa gtacactgat ggcgaagaat cctataaccg tgttcgccaa  2580
tggcttccgg ctatgttcaa atacaaagag agcgacgttc agcgttacgg cctgattgca  2640
caagatctgg cacgtattga tccggaatac gttcacttat taccgggcta tgcaatctac  2700
gaagacgtta agggtgtaga cgaagagggc aatgaggttg ttgtggatcg taaagagatc  2760
```

```
ggctataccg acgatgtgtt atctctggat tctaacgtct tattaatgga tttatgcgcg  2820
gcattcgtgc atttattaca taaagttgaa aaattggaag gcaaa                  2865

SEQ ID NO: 110          moltype = DNA  length = 3153
FEATURE                 Location/Qualifiers
misc_feature            1..3153
                        note = Synthetic: STF-48
source                  1..3153
                        mol_type = other DNA
                        organism = synthetic construct
SEQUENCE: 110
atggcagtaa agatttcagg agtcctgaaa gacggcacag gaaaaccggt acagaactgc  60
accattcagc tgaaagccag acgtaacagc accacggtgg tggtgaacac ggtgggctca  120
gagaatccgg atgaagccgg gcgttacagc atggatgtgg agtacggtca gtacagtgtc  180
atcctgcagg ttgacggttt tccaccatcg cacgccggga ccatcaccgt gtatgaagat  240
tcacaaccgg ggacgctgaa tgattttctc tgtgccatga cggaggatga tgcccggccg  300
gaggtgctgc gtcgtcttga actgatggtg gaagaggtgg cgcgtaacgc gtccgtggtg  360
gcacagagta cggcagacgc gaagaaatca gccggcgatg ccagtgcatc agctgctcag  420
gtcgcggccc ttgtgactga tgcaactgac tcagcacgcg ccgccagcac gtccgccgga  480
caggctgcat cgtcagctca ggaagcgtcc tccggcgcag aagcggcatc agcaaaggcc  540
actgaagcgg aaaaaagtgc cgcagccgca gagtcctcaa aaaacgcggc ggccaccagt  600
gccggtgcgg cgaaaacgtc agaaacgaat gctgcagcgt cacaacaatc agccgccacg  660
tctgcctcca ccgcggccac gaaagcgtca gaggccgcca cttcagcacg agatgcggtg  720
gcctcaaaag aggcagcaaa atcatcagaa acgaacgcat catcaagtgc cggtcgtgca  780
gcttcctcgg caacggcggc agaaaattct gccagggcgg caaaaacgtc cgagacgaat  840
gccaggtcat ctgaaacagc agcggaacgg agcgcctctg ccgcggcaga cgcaaaaaca  900
gcggcggcgg ggagtgcgtc aacggcatcc acgaaggcga cagaggctgc gggaagtgcg  960
gtatcagcat cgcagagcaa aagtgcggca gaagcggcgg caatacgtgc aaaaaattcg  1020
gcaaaacgtg cagaagatat agcttcagct gtcgcgcttg aggatgcgga cacaacgaga  1080
aaggggatag tgcagctcag cagtgcaacc aacagcacgt ctgaaacgct tgctgcaacg  1140
ccaaaggcgg ttaaggtggt aatggatgag actaatcgta aggcacctct ggacagtccg  1200
gcactgaccg gaacgccaac agcaccaacc gcgctcaggg gaacaaacaa tacccagatt  1260
gcgaacaccg cttttgtact ggccgcgatt gcagatgtta tcgacgcgtc acctgacgca  1320
ctgaatacgc tgaatgaact ggccgcagcg ctcgggaatg atccagattt tgctaccacc  1380
atgactaacg cgcttgcggg taaacaaccg aagaatgcga cactgacggc gctggcaggg  1440
ctttccacgg cgaaaaataa attaccgtat tttgcggaaa atgatgccgc cagcctgact  1500
gaactgactc aggttggcag ggatattctg gcaaaaaatt ccgttgcaga tgttcttgaa  1560
taccttgggg ccggtgagaa ttcgcagtta gaaagcgatg ctgatggaat gggagatgca  1620
ctagttgcag ttaagcagcc atatatcggc tcaatagctt taactcaaca tgataaaaat  1680
accaacttca tttcagccaa ggatttcggt gcaacagctg acggaactct gcatccactc  1740
agcgagaaat tctccacact atcagcggcg caggctgttt atccattcgt aacatcacta  1800
actcagtctc ttgactatgc aggcatacag gccgcaatta atacagggcg gaatgtatta  1860
ttgacatctg gaacttactt cgtaaatgca acgatagaga tgaattcaaa ctgcacaata  1920
aatggcgaaa caaacagcaa cataaatagg ccggaaactt tcatagcagt aataggaaat  1980
atagcttgtt tccattacca cgcagcgttt aatacaataa atattgaaaa tgtctatatt  2040
ttttacgatg gaggacgccc tacatcacct actggcaatg atggtaaaat tggcattcta  2100
attgatggag gaactacttc accaggcgtt atgcacatta aaatgttga ggttgatggt  2160
gcatggtggg ccatatatga tgactctgga aattacctaa caaagtatac ccaggtatgg  2220
gcgaggagag ttgcgcatgg tttctataag gcgaacggaa cgacaataca gtgggataca  2280
tgttatgtgc tggatgcagc acaggcatgg tatgttgtaa attgcctgtc tcctcagcta  2340
ataaactgtg caggagacca gatcacagtt gacgggtcgc aatatacatt tgattcctca  2400
gggttatatt tttctggatg taagtgtctt actattacag ggtatgatgg tgagtctaat  2460
ataataaaaa atacaaatgg aattactgcg tcgtatataa aacttaatga tactattgcc  2520
catatatcag gattggccgg gcatggaaac tcaatgcaaa caacggggag tgggacagca  2580
gcatttatct ttgcaacagg cacaagcatt gttaacataa aatcaagtac cgatagcttc  2640
cttgatagcg aatcaataac ctacactggc tctggatacc caaacacatt gctgacagac  2700
tcaacagcaa aaataattgc tgagggatgc cggtttaagg ctccgactgg tgggactcct  2760
gtaatatcaa cttacagcac agggaatgga gtatttactg actgctcatt aactgggacg  2820
caaacttcag gctcatatgt tgaatcacga agctctgcag gtaatcagtt gccagcagtg  2880
tacacagcga aaggaactca ggctgttgca gctaacgtag caactacgtt gtttgaactg  2940
ccaaatagcc aagggatgta cctgataagc gtttgggcag aaagcagtgg aacaaatttc  3000
tcttcgcttc agcttgccat gtgggacgga acaacactta ctttaactcc gcttaagtca  3060
ggagggttga tatcatttac agtgacagga aggattgtaa ccatcacaag ccagggaaca  3120
acaacattta actggacata caccaaggca ggg                               3153

SEQ ID NO: 111          moltype = DNA  length = 4095
FEATURE                 Location/Qualifiers
misc_feature            1..4095
                        note = Synthetic: STF-49
source                  1..4095
                        mol_type = other DNA
                        organism = synthetic construct
SEQUENCE: 111
atggcagtaa agatttcagg agtcctgaaa gacggcacag gaaaaccggt acagaactgc  60
accattcagc tgaaagccag acgtaacagc accacggtgg tggtgaacac ggtgggctca  120
gagaatccgg atgaagccgg gcgttacagc atggatgtgg agtacggtca gtacagtgtc  180
atcctgcagg ttgacggttt tccaccatcg cacgccggga ccatcaccgt gtatgaagat  240
tcacaaccgg ggacgctgaa tgattttctc tgtgccatga cggaggatga tgcccggccg  300
gaggtgctgc gtcgtcttga actgatggtg gaagaggtgg cgcgtaacgc gtccgtggtg  360
```

```
gcacagagta cggcagacgc gaagaaatca gccggcgatg ccagtgcatc agctgctcag  420
gtcgcggccc ttgtgactga tgcaactgac tcagcacgcg ccgccagcac gtccgccgga  480
caggctgcat cgtcagctca ggaagcgtcc tccggcgcag aagcggcatc agcaaaggcc  540
actgaagcgg aaaaaagtgc cgcagccgca gagtcctcaa aaaacgcggc ggccaccagt  600
gccggtgcgg cgaaaacgtc agaaacgaat gctgcagcgt cacaacaatc agccgccacg  660
tctgcctcca ccgcggccac gaaagcgtca gaggccgcca cttcagcacg agatgcggtg  720
gcctcaaaag aggcagcaaa atcatcagaa acgaacgcat catcaagtgc cggtcgtgca  780
gcttcctcgg caacggcggc agaaaattct gccagggcgg caaaaacgtc cgagacgaat  840
gccaggtcat ctgaaacagc agcggaacgg agcgcctctg ccgcggcaga cgcaaaaaca  900
gcggcggcgg ggagtgcgtc aacggcatcc acgaaggcga cagaggctgc gggaagtgcg  960
gtatcagcat cgcagagcaa aagtgcggca gaagcggcgg caatacgtgc aaaaaattcg  1020
gcaaaacgtg cagaagatat agcttcagct gtcgcgcttg aggatgcgga cacaacgaga  1080
aaggggatag tgcagctcag cagtgcaacc aacagcacgt ctgaaacgct tgctgcaacg  1140
ccaaaggcgg ttaaggtggt aatggatgag actaatcgta aggcacctct ggacagtccg  1200
gcactgaccg gaacgccaac agcaccaacc gcgctcaggg gaacaaacaa tacccagatt  1260
gcgaacaccg cttttgtact ggccgcgatt gcagatgtta tcgacgcgtc acctgacgca  1320
ctgaatacgc tgaatgaact ggccgcagcg ctcgggaatg atccagattt tgctaccacc  1380
atgactaacg cgcttgcggg taaacaaccg aagaatgcga cactgacggc gctggcaggg  1440
ctttccacgg cgaaaaataa attaccgtat tttgcggaaa atgatgccgc cagcctgact  1500
gaactgactc aggttggcag ggatattctg gcaaaaaatt ccgttgcaga tgttcttgaa  1560
taccttgggg ccggtgagaa ttcgggggct attggtgatg gtgttcatga tgatacatca  1620
gctctatcag aattactttc tgttgcaaca ggtggtgaaa agatagatgg gcgagggctt  1680
acttttaaag tatcaactct tccagatgtc agtcgattta aaaatgctcg tttttttattt  1740
gagagaatac cgggtcagcc tctttttat gcttctgaag attttatcca gggagagtta  1800
tttaaaatta cagatacacc gtggtacaac gcctggacgc aggataaaac gtttgtatat  1860
gacaatgtca tctatgcgcc ttttatggct ggagaccgcc atggtgtaaa taacctccat  1920
gttgcatggg ttcgctcagg agatgacggg aggacctgga caacgccgga atggcttaca  1980
gatttacatg aaaactatcc cacagttaac tatcactgca tgagtatggg ggttgtcaga  2040
aatcgccttt ttgctgtaat tgagacgcgg accgtgagcg gaaataaact gcaggttgca  2100
gagttgtggg atcgcccaat gagtcgcagc cttcgcgctt atggtggtat aacgaaagca  2160
gcaaatcagc aagtcgctta tattcgcatt actgatcacg gattatttgc tggtgatttt  2220
gtcaacttct caaactctgg tgttacaggt gttaccggga atatgacggt gactactgtt  2280
attgataaaa atactttttac agttacgacg caaaataccc aggatgtgga tcagaataac  2340
gagggtagat actggagttt tggtacatca tttcactcgt caccatggag aaaaaccagt  2400
cttggaacta ttccttcttt tgttgacgga agcactcctg ttactgagat tcacagtttt  2460
gcgacgatta gcgataacag ttttgctgtt ggctaccata atggtgatat tggtccacgc  2520
gagcttggga tactctattt ctctgatgct ttcggttctc ctggtagctt tgttcgcaga  2580
cgcatacctg cagaatatga ggcgaatgca tctgagccat gtgtaaaata ttatgatggc  2640
attctgtatc tgacgaccag ggggacatta agtactcaac ccggtagttc attgcacaga  2700
agctctgatt taggtacatc atggaattct cttcgcttcc caaataatgt tcatcactca  2760
aaccttcctt ttgccaaagt tggcgatgag ctgattattt ttggcagtga gcgcgcattt  2820
ggtgagtggg aaggaggaga acctgataac cgttatgcag gaaactatcc aagaacattt  2880
atgaccagag ttaacgtcaa tgagtggagt ctggataatg tagagtgggt taatgttact  2940
gatcagattt atcagggcgg aatagttaac tctgcggttg gtgttggttc agtttgtatc  3000
aaagacaact ggctgtacta cattttcggt ggggaagact ttctaaaccc atggagcata  3060
ggggataaca acagaaaata tccttatgtt cacgatggtc acccggctga tttgtattgt  3120
ttcagggtga aaattaaaca ggaagaattt gtttcaaggg attttgtcta cggagccact  3180
cctaacagaa cgcttcctac ttttatgtcg acgtcaggcg tgaggacggt tcctgtaccc  3240
gttgatttca cagatgatgt tgccgtccag tcactgactg tccatgcagg tacatcagga  3300
caagttcgcg cggaagtcaa acttgagggt aattacgcca ttattgcgaa gaaagtaccg  3360
tctgatgatg ttaccgctca gagattaatc gttagcggcg gtgaaacaac gtcttcagca  3420
gatggtgcaa tgataacgtt gcatggttcc ggaagcagta ctcctcgtcg cgcggtatat  3480
aacgcactcg aacatctttt tgagaacgga gatgttaaac cttatcttga taatgtaaat  3540
gctcttggtg gtccgggaaa caggttctcg acagtttatc ttggctccaa tcctgtggtt  3600
accagtgacg gaacattaaa gacagagccg gtctctcctg acgaagcatt gctggatgcc  3660
tggggtgacg tcaggtatat cgcttataaa tggctgaacg ctgtcgctat aaagggggaa  3720
gaaggggcga ggatacatca tggtgtaatc gcgcagcaac ttcgtgatgt tcttatttct  3780
cacggactca tggaagaaga aagcacaaca tgccgctatg cgtttctttg ctatgacgat  3840
tatcccgcag tatatgatga cgtcattact ggccaaaggg aaatgccgct gactgataat  3900
gacgggagca tcattgttga tgaggatgat aatccagtga tggtaatgga agacatcatt  3960
gagcgcgttg aaataacgcc agcaggatct agatgggggg tcagacctga tctcttattc  4020
tatatcgagg cggcatggca gcgcagagaa atagaaagaa taaaagctag gttagactta  4080
atagaaggga agcac                                                   4095
```

```
SEQ ID NO: 112          moltype = DNA  length = 3153
FEATURE                 Location/Qualifiers
misc_feature            1..3153
                        note = Synthetic: STF-52
source                  1..3153
                        mol_type = other DNA
                        organism = synthetic construct
SEQUENCE: 112
atggcagtaa agatttcagg agtcctgaaa gacggcacag gaaaaccggt acagaactgc  60
accattcagc tgaaagccag acgtaacagc accacggtgg tggtgaacac ggtgggctca  120
gagaatccgg atgaagccgg gcgttacagc atggatgtgg agtacggtca gtacagtgtc  180
atcctgcagg ttgacggttt tccaccatcg cacgccggga ccatcaccgt gtatgaagat  240
tcacaaccgg ggacgctgaa tgattttctc tgtgccatga cggaggatga tgcccggccg  300
gaggtgctgc gtcgtcttga actgatggtg gaagaggtgg cgcgtaacgc gtccgtggtg  360
gcacagagta cggcagacgc gaagaaatca gccggcgatg ccagtgcatc agctgctcag  420
```

```
gtcgcggccc ttgtgactga tgcaactgac tcagcacgcg ccgccagcac gtccgccgga  480
caggctgcat cgtcagctca ggaagcgtcc tccggcgcag aagcggcatc agcaaaggcc  540
actgaagcgg aaaaaagtgc cgcagccgca gagtcctcaa aaaacgcggc ggccaccagt  600
gccggtgcgg cgaaaacgtc agaaacgaat gctgcagcgt cacaacaatc agccgccacg  660
tctgcctcca ccgcggccac gaaagcgtca gaggccgcca cttcagcacg agatgcggtg  720
gcctcaaaag aggcagcaaa atcatcagaa acgaacgcat catcaagtgc cggtcgtgca  780
gcttcctcgg caacggcggc agaaaattct gccagggcgg caaaaacgtc cgagacgaat  840
gccaggtcat ctgaaacagc agcggaacgg agcgcctctg ccgcggcaga cgcaaaaaca  900
gcggcggcgg ggagtgcgtc aacggcatcc acgaaggcga cagaggctgc gggaagtgcg  960
gtatcagcat cgcagagcaa aagtgcggca gaagcggcgg caatacgtgc aaaaaattcg  1020
gcaaaacgtg cagaagatat agcttcagct gtcgcgcttg aggatgcgga cacaacgaga  1080
aaggggatag tgcagctcag cagtgcaacc aacagcacgt ctgaaacgct tgctgcaacg  1140
ccaaaggcgg ttaaggtggt aatggatgag actaatcgta aggcacctct ggacagtccg  1200
gcactgaccg gaacgccaac agcaccaacc gcgctcaggg gaacaaacaa tacccagatt  1260
gcgaacaccg cttttgtact ggccgcgatt gcagatgtta tcgacgcgtc acctgacgca  1320
ctgaatacgc tgaatgaact ggccgcagcg ctcgggaatg atccagattt tgctaccacc  1380
atgactaacg cgcttgcggg taaacaaccg aagaatgcga cactgacggc gctggcaggg  1440
ctttccacgg cgaaaaataa attaccgtat tttgcggaaa atgatgccgc cagcctgact  1500
gaactgactc aggttggcag ggatattctg gcaaaaaatt ccgttgcaga tgttcttgaa  1560
taccttgggg ccggtgagaa ttcgcagcta gcaagctcag aagatggaat gggtgacgca  1620
ctagttgcag ttaagcagcc atatatcggc tcaatagctt taactcaaca tgataaaaat  1680
accaacttca tttcagccaa ggatttcggt gcaacagctg acggaactct gcatccactc  1740
agcgagaaat tctccacact atcagcggcg caggctgttt atccattcgt aacatcacta  1800
actcagtctc ttgactatgc aggcatacag gccgcaatta atacagggcg gaatgtatta  1860
ttgacatctg gaacttactt cgtaaatgca acgatagaga tgaattcaaa ctgcacaata  1920
aatggcgaaa caaacagcaa cataaatagg ccggaaactt tcatagcagt aataggaaat  1980
atagcttgtt tccattacca cgcagcgttt aatacaataa atattgaaaa tgtctatatt  2040
ttttacgatg gaggacgccc tacatcacct actggcaatg atggtaaaat tggcattcta  2100
attgatggag gaactacttc accaggcgtt atgcacatta aaaatgttga ggttgatggt  2160
gcatggtggg ccatatatga tgactctgga aattacctaa caaagtatac ccaggtatgg  2220
gcgaggagag ttgcgcatgg tttctataag gcgaacggaa cgacaataca gtgggataca  2280
tgttatgtgc tggatgcagc acaggcatgg tatgttgtaa attgcctgtc tcctcagcta  2340
ataaactgtg caggagacca gatcacagtt gacgggtcgc aatatacatt tgattcctca  2400
gggttatatt tttctggatg taagtgtctt actattacag ggtatgatgg tgagtctaat  2460
ataataaaaa atacaaatgg aattactgcg tcgtatataa aacttaatga tactattgcc  2520
catatatcag gattggccgg gcatggaaac tcaatgcaaa caacggggag tgggacagca  2580
gcatttatct ttgcaacagg cacaagcatt gttaacataa aatcaagtac cgatagcttc  2640
cttgatagcg aatcaataac ctacactggc tctggatacc caaacacatt gctgacagac  2700
tcaacagcaa aaataattgc tgagggatgc cggtttaagg ctccgactgg tgggactcct  2760
gtaatatcaa cttacagcac agggaatgga gtatttactg actgctcatt aactgggacg  2820
caaacttcag gctcatatgt tgaatcacga agctctgcag gtaatcagtt gccagcagtg  2880
tacacagcga aaggaactca ggctgttgca gctaacgtag caactacgtt gtttgaactg  2940
ccaaatagcc aagggatgta cctgataagc gtttgggcag aaagcagtgg aacaaatttc  3000
tcttcgcttc agcttgccat gtgggacgga acaacactta ctttaactcc gcttaagtca  3060
ggagggttga tatcatttac agtgacagga aggattgtaa ccatcacaag ccagggaaca  3120
acaacattta actggacata caccaaggca ggg                                3153
```

```
SEQ ID NO: 113          moltype = DNA  length = 2793
FEATURE                 Location/Qualifiers
misc_feature            1..2793
                        note = Synthetic: 1AR
source                  1..2793
                        mol_type = other DNA
                        organism = synthetic construct
SEQUENCE: 113
atggcagtaa agatttcagg agtcctgaaa gacggcacag gaaaaccggt acagaactgc  60
accattcagc tgaaagccag acgtaacagc accacggtgg tggtgaacac ggtgggctca  120
gagaatccgg atgaagccgg gcgttacagc atggatgtgg agtacggtca gtacagtgtc  180
atcctgcagg ttgacggttt tccaccatcg cacgccggga ccatcaccgt gtatgaagat  240
tcacaaccgg ggacgctgaa tgattttctc tgtgccatga cggaggatga tgcccggccg  300
gaggtgctgc gtcgtcttga actgatggtg gaagaggtgg cgcgtaacgc gtccgtggtg  360
gcacagagta cggcagacgc gaagaaatca gccggcgatg ccagtgcatc agctgctcag  420
gtcgcggccc ttgtgactga tgcaactgac tcagcacgcg ccgccagcac gtccgccgga  480
caggctgcat cgtcagctca ggaagcgtcc tccggcgcag aagcggcatc agcaaaggcc  540
actgaagcgg aaaaaagtgc cgcagccgca gagtcctcaa aaaacgcggc ggccaccagt  600
gccggtgcgg cgaaaacgtc agaaacgaat gctgcagcgt cacaacaatc agccgccacg  660
tctgcctcca ccgcggccac gaaagcgtca gaggccgcca cttcagcacg agatgcggtg  720
gcctcaaaag aggcagcaaa atcatcagaa acgaacgcat catcaagtgc cggtcgtgca  780
gcttcctcgg caacggcggc agaaaattct gccagggcgg caaaaacgtc cgagacgaat  840
gccaggtcat ctgaaacagc agcggaacgg agcgcctctg ccgcggcaga cgcaaaaaca  900
gcggcggcgg ggagtgcgtc aacggcatcc acgaaggcga cagaggctgc gggaagtgcg  960
gtatcagcat cgcagagcaa aagtgcggca gaagcggcgg caatacgtgc aaaaaattcg  1020
gcaaaacgtg cagaagatat agcttcagct gtcgcgcttg aggatgcgga cacaacgaga  1080
aaggggatag tgcagctcag cagtgcaacc aacagcacgt ctgaaacgct tgctgcaacg  1140
ccaaaggcgg ttaaggtggt aatggatgag actaatcgta aggcacctct ggacagtccg  1200
gcactgaccg gaacgccaac agcaccaacc gcgctcaggg gaacaaacaa tacccagatt  1260
gcgaacaccg cttttgtact ggccgcgatt gcagatgtta tcgacgcgtc acctgacgca  1320
ctgaatacgc tgaatgaact ggccgcagcg ctcgggaatg atccagattt tgctaccacc  1380
atgactaacg cgcttgcggg taaacaaccg aagaatgcga cactgacggc gctggcaggg  1440
```

```
ctttccacgg cgaaaaataa attaccgtat tttgcggaaa atgatgccgc cagcctgact  1500
gaactgactc aggttggcag ggatattctg gcaaaaaatt ccgttgcaga tgttcttgaa  1560
taccttgggg ccggtgagaa ttcgatcgct acccgcgtgt ccaaagaagg tgacactatg  1620
actggtaagc tgactctgtc tgcgggtaac gatgcgctgg tgctgactgc gggcgagggc  1680
gcgtcctcgc acattcgctc tgacgtgggc gggacgaaca actggtatat cggtaaaggc  1740
agtggggata acggtttagg cttctactca tacatcactc agggcggggt gtatattacc  1800
aacaacgggg aaatcgcttt aagcccgcag ggtcagggta cgtttaactt caaccgtgat  1860
cgtctgcaca tcaacggcac gcaatggacg gcacatcaag gcggtggctg ggaaaaccag  1920
tggaatcagg aagcgccgat ttttattgat ttcggcaacg tgggcaatga tagctactac  1980
ccgattatca aggtaagtc cggcattacc aacgaaggtt atatttctgg cgtggacttc  2040
ggtatgcgtc ggattactaa cacgtgggcg cagggtatta tccgcgtagg caatcaggaa  2100
aacggtagcg atccgcaggc catctacgag ttccatcata atggcgtact gtacgttcct  2160
aatatggtaa aaacgggtgc gcgtctgagc gcaggtgggg gggatccggt atggcagggt  2220
gcatgtgttg ttatcggtga caatgacacg ggcttagtgc atggtggcga tggtcgcatc  2280
aatatggttg caaacggtat gcacattgcg tcttggagtt ccgcgtatca tttacatgag  2340
ggtttatggg atactacggg cgcgttatgg acggagcaag ggcgtgcaat tatcagcttc  2400
ggtcatctgg tacaacaaag cgatgcctat tccacctttg tccgtgatgt atacgttcgt  2460
tcggatattc gcgttaaaaa agatctggtg aaattcgaaa acgctagcga aaaactgtcc  2520
aaaatcaacg gttatactta tatgcagaaa cgcgggttag acgaagaagg taatcagaaa  2580
tgggagccta acgccggatt aatcgcgcag gaagtgcagg cgattctgcc ggaactggta  2640
gaaggcgatc cggacggtga agcattatta cgtctgaact acaatggcgt gatcggcctg  2700
aatactgcgg cgattaatga acatacggca gagatcgcgg agctgaaaag cgagattgaa  2760
gaactgaaaa aaattgtcaa aagcctgtta aag                              2793
```

```
SEQ ID NO: 114          moltype = DNA  length = 780
FEATURE                 Location/Qualifiers
misc_feature            1..780
                        note = Synthetic: 1AR-AP1
source                  1..780
                        mol_type = other DNA
                        organism = synthetic construct
SEQUENCE: 114
atggcagtaa caggaccgtg ggtaggatcg tctgcagtag ttaatacagg acaaaattgg  60
atggtcggcg cggcccaacg attaagaatg ggtgctccgt tctggatgag caacatgatt  120
gggcgctctg ttgaagtgat tcatacgtta ggcgcagatc ataattttaa tggtcaatgg  180
tttcgtgacc gttgctttga ggcgggcagt gcgccgatcg tgtttaacat cactggcgat  240
ttagtttctt actcccgtga cgttccgctg tttttcatgt atggtgacac gccgaacgag  300
tatgtacaat taaacattca cggtgtcacg atgtacgggc gcgggggcaa cggttgggcg  360
gcgggtgcaa tcggtgcgag cgatggcggg gtgtgcatcc agaatgatat tggaggccga  420
ctgcgtatca acaatggtgg ggcaatcgcg ggcggtggcg gtggtggggg tggttattct  480
caggctaaca attgggcagg taagtacgtt tgcggtggcg gtggcggtcg tccgttcggc  540
ttaggtggca acaacggtgc gcgttggcct gggggcaacg ctagcctgac ctcgccgggc  600
gcaggtggga acactggcac gcgttattac gctggcgggg gaggtgaggt tggtcagccg  660
ggtcagtatg caaaccccgg cgcgggttac tccaccccac caacgtcgcc gggcgcggca  720
gttgcaggta gtgcgccaac ttggcaaaac gtgggcgcta tttatggccc gcgtgtttaa  780
```

```
SEQ ID NO: 115          moltype = DNA  length = 243
FEATURE                 Location/Qualifiers
misc_feature            1..243
                        note = Synthetic: 1AR-AP2
source                  1..243
                        mol_type = other DNA
                        organism = synthetic construct
SEQUENCE: 115
atgagtgaac agaccatcga acaaaaaatta agcgcggaaa tcgtgactct gaaaagtcgc  60
attctggata ctcaggacca ggcagcacgt ctgatggaag agtctaaaat cttgcagggc  120
actctggcag aaattgcccg tgcggtgggt atcacaggcg acacgatcaa agtagaagaa  180
attgtggagg ccgtaaagaa tctcacagcg gagagcaccg atgaagcaaa agacgaagaa  240
taa                                                               243
```

```
SEQ ID NO: 116          moltype = DNA  length = 2706
FEATURE                 Location/Qualifiers
misc_feature            1..2706
                        note = Synthetic: 13-13.0
source                  1..2706
                        mol_type = other DNA
                        organism = synthetic construct
SEQUENCE: 116
atggcagtaa agatttcagg agtcctgaaa gacggcacag gaaaaccggt acagaactgc  60
accattcagc tgaaagccag acgtaacagc accacggtgg tggtgaacac ggtgggctca  120
gagaatccgg atgaagccgg gcgttacagc atggatgtgg agtacggtca gtacagtgtc  180
atcctgcagg ttgacggttt tccaccatcg cacgccggga ccatcaccgt gtatgaagat  240
tcacaaccgg ggacgctgaa tgattttctc tgtgccatga cggaggatga tgcccggccg  300
gaggtgctgc gtcgtcttga actgatggtg gaagaggtgg cgcgtaacgc gtccgtggtg  360
gcacagagta cggcagacgc gaagaaatca gccggcgatg ccagtgcatc agctgctcag  420
gtcgcggccc ttgtgactga tgcaactgac tcagcacgcg ccgccagcac gtccgccgga  480
caggctgcat cgtcagctca ggaagcgtcc tccggcgcag aagcggcatc agcaaaggcc  540
actgaagcgg aaaaaagtgc cgcagccgca gagtcctcaa aaaacgcggc ggccaccagt  600
gccggtgcgg cgaaaacgtc agaaacgaat gctgcagcgt cacaacaatc agccgccacg  660
```

-continued

```
tctgcctcca ccgcggccac gaaagcgtca gaggccgcca cttcagcacg agatgcggtg  720
gcctcaaaag aggcagcaaa atcatcagaa acgaacgcat catcaagtgc cggtcgtgca  780
gcttcctcgg caacggcggc agaaaattct gccagggcgg caaaaacgtc cgagacgaat  840
gccaggtcat ctgaaacagc agcggaacgg agcgcctctg ccgcggcaga cgcaaaaaca  900
gcggcggcgg ggagtgcgtc aacggcatcc acgaaggcga cagaggctgc gggaagtgcg  960
gtatcagcat cgcagagcaa aagtgcggca gaagcggcgg caatacgtgc aaaaaattcg  1020
gcaaaacgtg cagaagatat agcttcagct gtcgcgcttg aggatgcgga cacaacgaga  1080
aaggggatag tgcagctcag cagtgcaacc aacagcacgt ctgaaacgct tgctgcaacg  1140
ccaaaggcgg ttaaggtggt aatggatgag actaatcgta aggcacctct ggacagtccg  1200
gcactgaccg gaacgccaac agcaccaacc gcgctcaggg gaacaaacaa tacccagatt  1260
gcgaacaccg cttttgtact ggccgcgatt gcagatgtta tcgacgcgtc acctgacgca  1320
ctgaatacgc tgaatgaact ggccgcagcg ctcgggaatg atccagattt tgctaccacc  1380
atgactaacg cgcttgcggg taaacaaccg aagaatgcga cactgacggc gctggcaggg  1440
ctttccacgg cgaaaaataa attaccgtat tttgcggaaa atgatgccgc cagcctgact  1500
gaactgactc aggttggcag ggatattctg gcaaaaaatt ccgttgcaga tgttcttgaa  1560
taccttgggg ccggtgagaa ttcgatcatc cagttagaag atagtcaagg cgcccatttt  1620
tccactgaac gtactttagc gacaggtgca attaaaactc gtttctttgg cgaaacattt  1680
actgatggta cattatacct aaatcagatg aataatagtt ctgaacgatt ctctattaat  1740
aattggggaa attcagaagt tggtcgcccg gcagtgttgg aagtcggtga ttccaaaggt  1800
tatcacttct atacggaacg cgggacagat aacagtttga attttgatgt tgctggcaat  1860
tttactgtgc atggaccttc cgggattact atcaaaacct ctactggtgc tcgccatatc  1920
tggtttagag atgatagcga tgcagaaaag gctgttatct gggctacaga tgagggtatt  1980
ttacatatac gaaataatta tgggggttca tttagtcatc acttccaggg tgcaatgatt  2040
ctagcgggag agcgtgttcc atataatagt gaatacgctc ttatccgtgg taatatttcc  2100
ggtggtgcat gggtagactg gcgaggtcgt ccggctggat tgttggtaga ctgtcaggac  2160
tcacgaaatc aagcatataa catttggaaa gctactcatt ggggcgacca gcaccttgcg  2220
gcgatgggtg ttcatgctgg cggtggtaat cctcaggttg tattgcatgt gggtgggaat  2280
gattatgcat ttgcatctaa cggtgatttt actgctggtg ctgctgtata ttgtaacgac  2340
gtttatattc gttctgaccg tcgtctgaaa attaatgtta aagactacga agagaatgcg  2400
gtggataagg taaataaact caaagttaaa acctatgata aagttaaatc tctttctgac  2460
cgcgaagtta tcggccatga gattggtatt atcgcacagg atttgcaaga agtattaccg  2520
gaagctgtta gcacttctag tgtcggatct caggataacc cagaagaaat tttaacaatt  2580
tctaactctg ctgtgaacgc gcttttaatt aaggctattc aggaaatgag tgaagaaatt  2640
aaagaattga aaacgcctct ctttactaaa attgctcgca aaattagtaa atattttaaa  2700
ttctaa                                                             2706

SEQ ID NO: 117          moltype = DNA  length = 780
FEATURE                 Location/Qualifiers
misc_feature            1..780
                        note = Synthetic: 13-13.0-AP1
source                  1..780
                        mol_type = other DNA
                        organism = synthetic construct
SEQUENCE: 117
atggcagtag ttggagttcc tggctggatt ggaagttcag ccgtaaatga aacgggtcag  60
cgctggatga gtcaagcagc tggtcaatta agattgggtg ttccttgctg gatgagtcaa  120
tttgcaggtc gctcaagaga aattattcat acacttggag cagaccataa cttcaatggt  180
caatggttcc gagatagatg ttttgaggca ggtagtacac ctatagtgtt taatatcact  240
ggagatttag tatcatattc taaagatgtt cctttattct tcatgtacgg agatacaccg  300
aatgaatatg ttcaactgaa tatacacggc gtaacgatgt atggacgtgg cggtaatggc  360
ggtagcaata gtcctggttc agctggaggt cattgtattc aaaacgatat tggtgggaga  420
ctaagaatta ataacggtgg agctattgcc ggcggcggcg gtggcggcgg tggcggtaga  480
tatggcagac tatcatttgg tggtggcggt ggtcgcccat tcggtgctgg cgggtcttcc  540
tctcatatga gttccggtgc aactgctggc accatttccg ctccgggtgc aggatctgtc  600
ggtgagggat ctctttgggt atatacaggc ggttcgggtg gtaatgtcgg tgctgctgga  660
ggaagatgta atattcaagg taacggtaca gaatatgatg gcggtgctgc tggttatgct  720
gttatagggt ctgctccaac ttggataaat gttggagcaa tatatggtcc aagagtataa  780

SEQ ID NO: 118          moltype = DNA  length = 243
FEATURE                 Location/Qualifiers
misc_feature            1..243
                        note = Synthetic: 13-13.0-AP2
source                  1..243
                        mol_type = other DNA
                        organism = synthetic construct
SEQUENCE: 118
atgtctgaac aaactattga acaaaaactg tctgctgaaa tcgtaactct gaagtctcgt  60
atccttgata cgcaggacca agcggctcgt ctgatggaag aatccaaaat tctgcaagga  120
actttggctg aaattgctcg tgcagtaggt atcactggcg atactatcaa agttgaagaa  180
atcgttgaag ctgtcaagaa tcttactgct gaatctgcag atgaagcaaa agatgaagaa  240
tga                                                             243

SEQ ID NO: 119          moltype = DNA  length = 2283
FEATURE                 Location/Qualifiers
misc_feature            1..2283
                        note = Synthetic: 13-14.3
source                  1..2283
                        mol_type = other DNA
                        organism = synthetic construct
```

-continued

SEQUENCE: 119
atggcagtaa agatttcagg agtcctgaaa gacggcacag gaaaaccggt acagaactgc 60
accattcagc tgaaagccag acgtaacagc accacggtgg tggtgaacac ggtgggctca 120
gagaatccgg atgaagccgg gcgttacagc atggatgtgg agtacggtca gtacagtgtc 180
atcctgcagg ttgacggttt tccaccatcg cacgccggga ccatcaccgt gtatgaagat 240
tcacaaccgg ggacgctgaa tgatttttctc tgtgccatga cggaggatga tgcccggccg 300
gaggtgctgc gtcgtcttga actgatggtg gaagaggtgg cgcgtaacgc gtccgtggtg 360
gcacagagta cggcagacgc gaagaaatca gccggcgatg ccagtatttc tgatgatatt 420
ggatggatgc attatattca acgaaataaa gataatacag ttgaagccgt attaaatggt 480
caacagacaa ttaacgaaaa tattattgcg aaaaaggata tttgggttga ccgagcagtt 540
cacacccttg gcgaaatcac tacaaatgct gttaatggtc ttcgtatttg gaataatgat 600
tatggagtca tttttagacg ttcagaagga agtcttcata ttattcctac cgcatttggt 660
gaaggagaaa ccggtgatat tggaccttta cgtcctctca gtatagcttt agataccggt 720
aaagttacta ttccggattt acaatcaagt tacaatacgt tcgctgctaa cggttatatt 780
aaatttgttg gtcatggagc gggggccggc ggttatgaca ttcaatatgc tcaagcggct 840
cctattttcc aggaaatcga tgatgatgct gtaagcaaat attatcctat tgttaaacag 900
aagtttttaa acggtaaatc cgtttggtct ttaggtaccg aaattgaatc aggtacattc 960
gttattcatc atctgaaaga agatggttca caaggccatg cgtctcgttt taatcaagac 1020
ggtactgtta acttcccgga taacgttctg gtcggcggtg atattaacat gaaaggcatg 1080
atgacttttg acgccggacg tttaggatca cgagattatt ttaaatttaa ccattggggt 1140
gatagtaata atggtcgtga taacatcatc cagttagaag atagtcaagg cgcccatttt 1200
tccactgaac gtactttagc gacaggtgca attaaaactc gtttctttgg cgaaacattt 1260
actgatggta cattatacct aaatcagatg aataatagtt ctgaacgatt ctctattaat 1320
aattggggaa attcagaagt tggtcgcccg gcagtgttgg aagtcggtga ttccaaaggt 1380
tatcacttct atacggaacg cgggacagat aacagtttga attttgatgt tgctggcaat 1440
tttactgtgc atggaccttc cgggattact atcaaaacct ctactggtgc tcgccatatc 1500
tggtttagag atgatagcga tgcagaaaag gctgttatct gggctacaga tgagggtatt 1560
ttacatatac gaaataatta tgggggttca tttagtcatc acttccaggg tgcaatgatt 1620
ctagcgggag agcgtgttcc atataatagt gaatacgctc ttatccgtgg taatatttcc 1680
ggtggtgcat gggtagactg gcgaggtcgt ccggctggat tgttggtaga ctgtcaggac 1740
tcacgaaatc aagcatataa catttggaaa gctactcatt ggggcgacca gcaccttgcg 1800
gcgatgggtg ttcatgctgg cggtggtaat cctcaggttg tattgcatgt gggtgggaat 1860
gattatgcat ttgcatctaa cggtgatttt actgctggtg ctgctgtata ttgtaacgac 1920
gtttatattc gttctgaccg tcgtctgaaa attaatgtta aagactacga agagaatgcg 1980
gtggataagg taaataaact caaagttaaa acctatgata aagttaaatc tctttctgac 2040
cgcgaagtta tcggccatga gattggtatt atcgcacagg atttgcaaga agtattaccg 2100
gaagctgtta gcacttctag tgtcggatct caggataacc cagaagaaat tttaacaatt 2160
tctaactctg ctgtgaacgc gcttttaatt aaggctattc aggaaatgag tgaagaaatt 2220
aaagaattga aaacgcctct ctttactaaa attgctcgca aaattagtaa atattttaaa 2280
ttc 2283

SEQ ID NO: 120 moltype = DNA length = 777
FEATURE Location/Qualifiers
misc_feature 1..777
note = Synthetic: 13-14.3-AP1
source 1..777
mol_type = other DNA
organism = synthetic construct
SEQUENCE: 120
atggcagtag ttggagttcc tggctggatt ggaagttcag ccgtaaatga aacgggtcag 60
cgctggatga gtcaagcagc tggtcaatta agattgggtg ttccttgctg gatgagtcaa 120
tttgcaggtc gctcaagaga aattattcat acacttggag cagaccataa cttcaatggt 180
caatggttcc gagatagatg ttttgaggca ggtagtacac ctatagtgtt taatatcact 240
ggagatttag tatcatattc taaagatgtt cctttattct tcatgtacgg agatacaccg 300
aatgaatatg ttcaactgaa tatacacggc gtaacgatgt atggacgtgg cggtaatggc 360
ggtagcaata gtcctggttc agctggaggt cattgtattc aaaacgatat tggtgggaga 420
ctaagaatta ataacggtgg agctattgcc ggcggcggcg gtggcggcgg tggcggtaga 480
tatggcagac tatcatttgg tggtggcggt ggtcgcccat tcggtgctgg cgggtcttcc 540
tctcatatga gttccggtgc aactgctggc accatttccg ctccgggtgc aggatctgtc 600
ggtgagggat ctctttgggt atatacaggc ggttcgggtg gtaatgtcgg tgctgctgga 660
ggaagatgta atattcaagg taacggtaca gaatatgatg gcggtgctgc tggttatgct 720
gttatagggt ctgctccaac ttggataaat gttggagcaa tatatggtcc aagagta 777

SEQ ID NO: 121 moltype = AA length = 1064
FEATURE Location/Qualifiers
REGION 1..1064
note = Synthetic: K1F tail fiber
source 1..1064
mol_type = protein
organism = synthetic construct
SEQUENCE: 121
MSTITQFPSG NTQYRIEFDY LARTFVVVTL VNSSNPTLNR VLEVGRDYRF LNPTMIEMLV 60
DQSGFDIVRI HRQTGTDLVV DFRNGSVLTA SDLTTAELQA IHIAEEGRDQ TVDLAKEYAD 120
AAGSSAGNAK DSEDEARRIA ESIRAAGLIG YMTRRSFEKG YNVTTWSEVL LWEEDGDYYR 180
WDGTLPKNVP AGSTPETSGG IGLGAWVSVG DAALRSQISN PEGAILYPEL HRARWLDEKD 240
ARGWGAKGDG VTDDTAALTS ALNDTPVGQK INGNGKTYKV TSLPDISRFI NTRFVYERIP 300
GQPLYYASEE FVQGELFKIT DTPYYNAWPQ DKAFVYENVI YAPYMGSDRH GVSRLHVSWV 360
KSGDDGQTWS TPEWLTDLHP DYPTVNYHCM SMGVCRNRLF AMIETRTLAK NALTNCALWD 420
RPMSRSLHLT GGITKAANQR YATIHVPDHG LFVGDFVNFS NSAVTGVSGD MTVATVIDKD 480

```
NFTVLTPNQQ TSDLNNAGKN WHMGTSFHKS PWRKTDLGLI PSVTEVHSFA TIDNNGFAMG  540
YHQGDVAPRE VGLFYFPDAF NSPSNYVRRQ IPSEYEPDAS EPCIKYYDGV LYLITRGTRG  600
DRLGSSLHRS RDIGQTWESL RFPHNVHHTT LPFAKVGDDL IMFGSERAEN EWEAGAPDDR  660
YKASYPRTFY ARLNVNNWNA DDIEWVNITD QIYQGGIVNS GVGVGSVVVK DNYIYYMFGG  720
EDHFNPWTYG DNSAKDPFKS DGHPSDLYCY KMKIGPDNRV SRDFRYGAVP NRAVPVFFDT  780
NGVRTVPAPM EFTGDLGLGH VTIRASTSSN IRSEVLMEGE YGFIGKSIPT DNPAGQRIIF  840
CGGEGTSSTT GAQITLYGAN NTDSRRIVYN GDEHLFQSAD VKPYNDNVTA LGGPSNRFTT  900
AYLGSNPIVT SNGERKTEPV VFDDAFLDAW GDVHYIMYQW LDAVQLKGND ARIHFGVIAQ  960
QIRDVFIAHG LMDENSTNCR YAVLCYDKYP RMTDTVFSHN EIVEHTDEEG NVTTTEEPVY  1020
TEVVIHEEGE EWGVRPDGIF FAEAAYQRRK LERIEARLSA LEQK                  1064

SEQ ID NO: 122         moltype = DNA  length = 240
FEATURE                Location/Qualifiers
misc_feature           1..240
                       note = Synthetic: 13-14.3-AP2
source                 1..240
                       mol_type = other DNA
                       organism = synthetic construct
SEQUENCE: 122
atgtctgaac aaactattga acaaaaactg tctgctgaaa tcgtaactct gaagtctcgt  60
atccttgata cgcaggacca agcggctcgt ctgatggaag aatccaaaat tctgcaagga  120
actttggctg aaattgctcg tgcagtaggt atcactggcg atactatcaa agttgaagaa  180
atcgttgaag ctgtcaagaa tcttactgct gaatctgcag atgaagcaaa agatgaagaa  240

SEQ ID NO: 123         moltype = AA  length = 1083
FEATURE                Location/Qualifiers
REGION                 1..1083
                       note = Synthetic: WW13
source                 1..1083
                       mol_type = protein
                       organism = synthetic construct
SEQUENCE: 123
MATLKQIQFK RSKTAGARPA ASVLAEGELA INLKDRVLFT KDDQGNIIDL GFAKGGSIDG  60
NVIHIGNYNQ TGDYTLNGTF TQTGNFNLTG IARVTRDIIA AGQIMTEGGE LITKSSGTAH  120
VRFFDGNSRE RGIIYAPAND GLTTQVLNIR VQDYAAGSES TYAFSGSGLF TSPEVSAWKS  180
MSTPQILTDK VITNGKKTGD YDIYSLSNNT PLAESETAIN HLRVMRNAVG AGIFHEVNVN  240
DGITWYSGDG LDTYLWSFNW AGGLKAGHSI SVGLPGGSKG YSELGTASIA LGDNDTGFKW  300
HQDGYFHTVN NGTRTFIYGP AETQSLRKMV MGYSPDGILM TTPPTENYAL ATVVTYHDNN  360
AFGDGQTLLG YYQGGNYHHY FRGKGTTNIN THGGLLVTPG NIDVIGGSVN IDGRNNNSTL  420
MFKGYTMGQS SVDNMYIAVW GNTFTNPSEG TRKNVMEISD DIGWMHYIQR NKDNTVEAVL  480
NGQQTINENI IAKKDIWVDR AVHTLGEITT NAVNGLRIWN NDYGVIFRRS EGSLHIIPTA  540
FGEGETGDIG PLRPLSIALD TGKVTIPDLQ SSYNTFAANG YIKFVGHGAG AGGYDIQYAQ  600
AAPIFQEIDD DAVSKYYPIV KQKFLNGKSV WSLGTEIESG TFVIHHLKED GSQGHASRFN  660
QDGTVNFPDN VLVGGDINMK GMMTFDAGRL GSRDYFKFNH WGDSNNGRDN IIQLEDSQGA  720
HFSTERTLAT GAIKTRFFGE TFTDGTLYLN QMNNSSERFS INNWGNSEVG RPAVLEVGDS  780
KGYHFYTERG TDNSLNFDVA GNFTVHGPSG ITIKTSTGAR HIWFRDDSDA EKAVIWATDE  840
GILHIRNNYG GSFSHHFQGA MILAGERVPY NSEYALIRGN ISGGAWVDWR GRPAGLLVDC  900
QDSRNQAYNI WKATHWGDQH LAAMGVHAGG GNPQVVLHVG GNDYAFASNG DFTAGAAVYC  960
NDVYIRSDRR LKINVKDYEE NAVDKVNKLK VKTYDKVKSL SDREVIGHEI GIIAQDLQEV  1020
LPEAVSTSSV GSQDNPEEIL TISNSAVNAL LIKAIQEMSE EIKELKTPLF TKIARKISKY  1080
FKF                                                               1083

SEQ ID NO: 124         moltype = AA  length = 1103
FEATURE                Location/Qualifiers
REGION                 1..1103
                       note = Synthetic: PP-1
source                 1..1103
                       mol_type = protein
                       organism = synthetic construct
SEQUENCE: 124
MATLKQIQFK RSKTAGQRPA ASVLAEGELA INLKDRVLFT KDDQGNIIDL GFAKGGSIDG  60
NVIHKGNYNQ TGDYTLNGTF TQTGNFNLTG IARVTRDIIA AGQIMTEGGE LITKSSGTAH  120
VRFHDSADRE RGIIFSPAND GLTTQVVNIR VQDYKASSES TFAFNGNGLF SSPEVFGWKS  180
VSTPVIYTNK VITNKKVKDD YDIYSMADNV PLSEITTAIN HLRVMRNAVG SGIFHEVKDN  240
DGITWYSGDG LDAYLWSFTW SGGIKSSHSI SIGLTPGPKD YSILGPSSIA LGDNDTGFKW  300
HQDGYYFSVN NGTKTFLFSP SETTSLRKFV AGYSTNGTDL TTPPTENYAL ATVVTYHDNN  360
AFGDGQTLLG YYQGGNYHHY FRGKGTTNIN THGGLLVTPG NIDVIGGSVN IDGRNNASTA  420
MFKGNTTGSS SVDNMTISVW GNTFTNPSEG NRKNVMEISD ATSWMSYIQR LTTGEVEMNV  480
NGSFESSGVT AGNRGVHTTG EISSGAVNAL RIWNADYGVI FRRSEGSLHI IPTAYGEGKN  540
GDIGPLRPFS IALDTGKVVI PDLESSYNTF AANGYIKFAG HGAGAGGYDI QYSQAAPIFQ  600
EIDDAAVSKY YPIVKQKFLN GKAVWSLGTE INSGTFVLHH LKEDGSQGHT SRFNADGTVN  660
FPDNVQVGGG EATIARNGNI FSDIWKTFTS AGETTNIRDA IATRVSKEGD TMTGKLTLSA  720
GNDALVLTAG EGASSHIRSD VGGTNNWYIG KGSGDNGLGF YSYITQGGVY ITNNGEIALS  780
PQGQGTFNFN RDRLHINGTQ WTAHQGGGWE NQWNQEAPIF IDFGNVGNDS YYPIIKGKSG  840
ITNEGYISGV DFGMRRITNT WAQGIIRVGN QENGSDPQAI YEFHHNGVLY VPNMVKTGAR  900
LSAGGGDPVW QGACVVIGDN DTGLVHGGDG RINMVANGMH IASWSSAYHL HEGLWDTTGA  960
LWTEQGRAII SFGHLVQQSD AYSTFVRDVY VRSDIRVKKD LVKFENASEK LSKINGYTYM  1020
QKRGLDEEGN QKWEPNAGLI AQEVQAILPE LVEGDPDGEA LLRLNYNGVI GLNTAAINEH  1080
TAEIAELKSE IEELKKIVKS LLK                                         1103
```

```
SEQ ID NO: 125          moltype = AA  length = 980
FEATURE                 Location/Qualifiers
REGION                  1..980
                        note = Synthetic: WW55
source                  1..980
                        mol_type = protein
                        organism = synthetic construct
SEQUENCE: 125
MADLSRIQFK RTSTKGRRPD ASTMNPGELA INLADQYLLT KNDSGAIINL SCPPVYDRDV  60
TMAGKVKGNN YILSKTANYL EDQTARDLNY FGAFRTNGLD GLLELTLNVP HSSGVQHGRG  120
FTFQYGHTGS RVETYGYNKE GQKAFSYKMY HEGDKPTPGE LNVYSKQEID RMFVKNVKMV  180
VPSGGATRGY FKIASAMIPQ SGRMAFLRIY GGNGYNVNSY DQVDFLEIVI RSGNNNPKGV  240
SIAAYRRNSL NVHEVFAINT SGDNYDIYVN YGRFTDNVIV EFGKTVDVAL TVHDVPEFSA  300
TKPETGTKFD ARVITMFNTE NKAGTLMFDN NNQLTYDIVS LSNGPDDVRN YLRKFRSKAG  360
EMIWHETVQG AVYRLATGTT DSTEVLRVDS NSALPGSYKG YVITGKMELH GSGSAMNLHR  420
QTGQAAYMAW WDRRDGKNQR SGYIGHADGT TDGFVWRNDV GANSFDLESS GQVNLTTGKT  480
KIVYTNGQYY SANSDAFRMI YGNYGAFWRN DGGKVYLLST AENDRFGGWN GNRPFIYDLS  540
TGKVTLGGDG NEGALVLERD SRAARFSNSV FLEKGLLTFS AGGNQSMDSF TINHWGNSNA  600
GRYNVLQFED TKGTHFTTER NADGGLLAHF RGDLTTEGKL TWGKGTATSS FNIRAWGNSD  660
SRKQVFECVD ESGWHWYTQR PGGPGTSAIE FAINGTVKPQ AIHTGGNILL NGADIEFRRT  720
GNKHLWFRDP NGLELGLIYC DDNGVIRFRG QKQGQDWVFA NKMIQLGTAS TVGGSGNGLI  780
RGQVQGGAWA QWRDRAAGIL VDCQQSTDSA HNIWKATHWG KYHIAAMGVH VPSGTIGNAM  840
ARLNVNDANF DFSASGDMSA GRNGSFNDVY IRSDARLKIN KEEYKENATD KVNRLTVYTY  900
DKVKSLTDRT VIAHEVGIIA QDLEKELPEA VTTSKIGDPD KPEEILTISN SAVNALLIKA  960
FQEMSEELKA VKAELAELKK                                            980

SEQ ID NO: 126          moltype = AA  length = 980
FEATURE                 Location/Qualifiers
REGION                  1..980
                        note = Synthetic: WW34
source                  1..980
                        mol_type = protein
                        organism = synthetic construct
SEQUENCE: 126
MADLSRIQFK RTSTKGRRPD AGTMNPGELA INLADQYLLT KNDSGAIINL SCPPVYDSDV  60
TMAGKVKGNN YILSKTANYF EDQTARDLNY FGAFRPNNAD DWSNLILNIP HPSGKAHGRG  120
FEFQYGSSSS QVKTYGFDKD GNKRFSFRMY HEGDKPTPGE LNVYSKQEID RMFVKNVKMS  180
TPSGEATRGY FKIASAMIPQ SGRMAFLRIY GGNGFNVNSY DQVDFLEIVI RSGNNNPKGV  240
SIAAYRRNSL NVHEVFAINT SGDNYDIYVN YGRFTDNVIV EFGKTVDVAL TVHDVPEFSA  300
TKPETGTKFD ARVITMFNTE NKAGTLMFDN NNQLTYDIVS LSNGPDDVRN YLRKFRSKAG  360
EMIWHETVQG AVYRLATGTT DSTEVLRVDS NSAIPGSYKG YVITGKMELH GSGNSMILHR  420
QTAQAAYMSW WDRRDGKNQR SGYIGHADGT SDAIVWNNDI GQNSAVLETS GQISFRTGAT  480
KIVYTNGQYY SANSDAYRMI FGNYGAFWRN DGTKVYLLST AENDKYGGWN AYRPFIYDLT  540
SGNVQLGGDG NEDALTLECA SRAARFSNDV YIKKGLLTFD AGRAGSRDYI RFNHWGDSNN  600
ARDNVLCIED SQGRHFSTER AMGTGALKAY FLGDLEVGGK FTWGKNTATS SFNIRAWGND  660
SRKQVLECAD ESGWHWYTQR TGGPDTSAID FAINGTVRPQ AIHTGGNITI NGADIEFKRT  720
GNKHIWFRDP NGLELGLMYC DDAGAIRFRG QKQAQAWKFA DKMIQLESGT VSGGGNGLIR  780
GEVAGGSWAS WRDRAAGLMV GCPQSTNSAH NVWKATHWGK YHIAAMAVHV PDGTITNALA  840
RLNVHDANFD FSASGDLSAG RNGSFNDVYI RSDARLKINK EEYKENATDK VNRLTVYTYD  900
KVKSLTDRTV IAHEVGIIAQ DLEKELPEAV TTSKIGDPDK PEEILTISNS AVNALLIKAF  960
QEMSEELKAV KAELAELKKN                                            980

SEQ ID NO: 127          moltype = AA  length = 1302
FEATURE                 Location/Qualifiers
REGION                  1..1302
                        note = Synthetic: WW14
source                  1..1302
                        mol_type = protein
                        organism = synthetic construct
SEQUENCE: 127
MATLKAIQFK RSKTPGAKPT VDQLVEGELA INLRDRTIFT KSDQNQIIDL GFAKGGQVDG  60
DVTINGTLNL NGPEIVASGG YIEFNYRTTG SGSWAGQHAA KAPIFVDLSA ALSTSEYNPL  120
FKQRYKDGTF SAGTLVTEGS FKFHYINEAG DSKYWTFNRN GNFQVDTGSL FVSGGNISAS  180
GNINSASGFV SAPQINTKNI ILDTKAFGQY DSQSLVNYVY PGTGETNGVN YLRKVRAKSG  240
GTMWHELCTA QLGQADEMSW WTGNTPQSKQ YGVRNDGRLI GRNSLALGTM TTDFPSSDYG  300
NTGAMGDKYL VLGDTATGLK YIKQGNFDLV GGGYSVASIT TDGFRGTSKT LFGRSNDQGL  360
TWLLPGQNSA MVSIRTEIDG NNSGDGQTHL GYNSNGKLYH YFRGTGRVAI SMAEGMIIEP  420
GILNIKTGVN ELNLRADGTV STTQRLMVNN GLVLNANNNT SALALTAPTG VDGTKTINWD  480
AGTRNGQNKN TVTMKAWGNS FNAGGGNRET VFEVSDSQGY YFYGQRTNPA SGETVGPINF  540
KFNGSVETGH FSSLGNISAS GTGSFGGNVT MTNGLFVQGG ASINGQVKMG GTADALRIWN  600
AEYGMIFRRS ETGSSASFHL IPTLQNAGEN GGISDLRPLS INLASGTVIM GNKSTGGPLF  660
TVDNVSKFVQ TDCRLRVNMD SDGIVLNASS QAASNFIQGR KADVTKWYLG IGDGGNVVRM  720
HNYTYSHGIA LNSDTVDITK PLKIGSDIRI GTDGNIIGSA TLDNFKNLNT TLDHKVNMGG  780
WSGGATTGWY KFATVEIPQA TGTASFKIFG GSGFNFKSYG QASIAEIILR TGNNNPKGLN  840
ATLWNRTSEA ISQIASVNTS EDIYDIYVYL GGYSNSLVVE YTCSSNSKVT VVGMDGGVQP  900
LVETLPEGHV VGKSVRMLNN LDGMFAAGES DIVTRGEYVT NNQKGMRIKS KGNDLDSNAA  960
LLRNDGGSFY ILATDKNTTE KPDAANGDWN GLRPFSINMA DGRVGMNHGL NITGGGLNVT  1020
GGNTNLGNIT SRVVSSARAG SGWGDNSDAM KSKITFMADH GDLSNSGSYY PIVGAYSNYG  1080
```

-continued

```
SAGYRQTFEF GWVGSGSTAN WREGIIRIRG DNANGQQARW RFTMDGILGC PGKVEMPETS  1140
AFGINTTNGF GGNSIVIGDS DTGFRQVGDG LLEVWTNASR RMRFQGGDTY SDMNINAPNV  1200
YIRSDIRLKS NFKPIENALD KVEQLDGLIY DKADYIGGEV VHTEAGVIAQ SLEKVLPEAV  1260
REVDDIKGNK VLTVSTQAQV ALLIEAVKTL SAKVKELEAK LN                    1302

SEQ ID NO: 128         moltype = AA  length = 976
FEATURE                Location/Qualifiers
REGION                 1..976
                       note = Synthetic: WW170
source                 1..976
                       mol_type = protein
                       organism = synthetic construct
SEQUENCE: 128
MADLSRIQFK RTSTKGRRPD ASTMNPGELA INLADQYLLT KNDSGAIINL SCPPVYDRDV  60
TMAGKVKGNN YILSKTANYL EDQTARDLNY FGAFRTNGQD GLLDLTLNVP HSAGVNHGRG  120
FTFRYATGGS RVETYGYNAQ GQKAFSYKMY HEGDKPTPSE LNVYSKQEVD RMFVKTVKLA  180
TVPVDIVDGY FKLATAMIPQ NGRSVFFRIH GGNGYNVTAY DQVDIVEIVI RSGNNRPKGV  240
NVIAYRRNTN KAFDVLAVNT SGDNYDIYVK YQRYTDNVIV EFGKSVDVDL VVHDVPDFVV  300
DRPVGDNVIG GRAVTLFNTE NKRGVLSFDD NTQNSYDIVH LSNDRGTGRK YIRKFRSNYN  360
EMIWHETVQG STYRLATGST DAQEILSVES SSSIAGTHKG NILSGRMMLG GGSNVITLRR  420
PAGQSNHIAF QDNRTGSITR QGWIGYGNAD TNVFEWYSDV GGTSIRHHID GQIELATGNT  480
KRVYTNAQFI SMNSDAYRMI FGNYGAFWRN DGTKVYLLST AEDDKFGGWN GNRPFIYDLT  540
NGKVTLGGDG NEGALVLERD SRAARFAGDV YVEKGFLHFS SGRQGASGFM KINHLGDIAS  600
GRHNILQIED PTGIHFSTER NDETGNITAR FKGFVRVEAG EIAFDANRGS QSQFTLHTWG  660
NEQRKQVFEC KDATGYHWYT ERTQGGTGNV LFSMAGSLNV TSNITTTGAD ITFKRAGNKH  720
IWFRDPDGLE LGLMYCDDAG AIRFRGQKQA QAWKFADKMI QLESGTVSGG GNGLIRGEVA  780
GGSWSSWRDR AAGLMVGCPQ STNSAHNVWK ATHWGKYHIA AMGIHVPDGT IGNALARLHV  840
HDTNFDFSAS GDMTAGRNGS FNDVYIRSDA RLKINKEEYK ENATDKINRL TVYTYDKVKS  900
LTDRTVIAHE VGIIAQDLEK ELPEAVTTSK VGDPDKPEEI LTISNSAVNA LLIKAFQEMS  960
EELKAVKAEL AELKKN                                                 976

SEQ ID NO: 129         moltype = AA  length = 966
FEATURE                Location/Qualifiers
REGION                 1..966
                       note = Synthetic: WW202
source                 1..966
                       mol_type = protein
                       organism = synthetic construct
SEQUENCE: 129
MADLNRIQFK RTSTAGRKPD AGTMNPGELA INLADQYLLT KNDDGQIVNL SCPPVYDKGF  60
DVRGRVVVDD LVWSNTANYF DDPTARNLDK FGAFRTNDMD GHLAFALHIP HPSGINHARG  120
FDFTYGSNVV PTVKTYGYNA DGVLAYSYRM YHEGDKPSPS ELNVYSKQEV DRMFQKTINF  180
GVETGWFKIA TAFIPQNDGR SLKIRLVGGN GWNVGQTGQC NIIELVIRTS NGSPKGINFV  240
AYHHVSGYEN QFCAINTGDD TYDIYAYYYE FTNMVMAEYQ ASSDVNLTVF DRPEYVGEKP  300
VAEHIFDAYT IHSFNSFSNR GTLNFAGNHQ GQYDIEHMNE QPTNAKKMLR RFRSSASATI  360
WHETVDDQNY RLATGGTDSV QQLLLSSGTG LHIRRLTIDG GLGSGSNAGI DIRRGPNESS  420
HFNFMDYRTG QDVRNGWFGF GDLTTKDFIW WNDNGQNSIN LIENGELHIT GGRGQKIVMN  480
SEVALSENAR LAVKGGNYGL ILRNDGTGFH ILTTDLKDSF GSWNNRRPFS YNFADGGLYL  540
GGTETARCLH LGIDGSTRLE DNLFFKAGSR QSMDYMELVH WGASNTGRNN VLSLRDSKGF  600
LAEFERVGGT DGVKTRFFGE TFTDGTLYLN QMNNSSERFS INNWGNSEVG RAAVMEVGDS  660
KGYHFYAERR TDDTVLFDVS GALTVHGPNG ITVKNSTGAR HIWFRDDSDT EKAVIWATDD  720
GMLHIRNNHE GSFAHHFQGA MIKLEGRVPY GAAKGLIRGE VDGGAYVAWR DRPAGLLVDC  780
QKSIDSAHAV WKAVDWGRQY IAAMDVHCPG DGNNTAAAVL HVQAADYQFH ASGEFHASGN  840
GNFNDVYIRS DRRLKDNIED YTGNALSLIG KLKVKTYDKV KSLKDREIIG HEIGIIAQDL  900
QEILPEAVKS SKVGNLDNPD DVLTISNSAV NALLIKAIQE MSEEIKELKT PFFTKIARKI  960
SKYFKF                                                            966

SEQ ID NO: 130         moltype = AA  length = 901
FEATURE                Location/Qualifiers
REGION                 1..901
                       note = Synthetic: WW13 13.0 (FIG. 8)
source                 1..901
                       mol_type = protein
                       organism = synthetic construct
SEQUENCE: 130
MAVKISGVLK DGTGKPVQNC TIQLKARRNS TTVVVNTVGS ENPDEAGRYS MDVEYGQYSV  60
ILQVDGFPPS HAGTITVYED SQPGTLNDFL CAMTEDDARP EVLRRLELMV EEVARNASVV  120
AQSTADAKKS AGDASASAAQ VAALVTDATD SARAASTSAG QAASSAQEAS SGAEAASAKA  180
TEAEKSAAAA ESSKNAAATS AGAAKTSETN AAASQQSAAT SASTAATKAS EAATSARDAV  240
ASKEAAKSSE TNASSSAGRA ASSATAAENS ARAAKTSETN ARSSETAAER SASAAADAKT  300
AAAGSASTAS TKATEAAGSA VSASQSKSAA EAAAIRAKNS AKRAEDIASA VALEDADTTR  360
KGIVQLSSAT NSTSETLAAT PKAVKVVMDE TNRKAPLDSP ALTGTPTAPT ALRGTNNTQI  420
ANTAFVLAAI ADVIDASPDA LNTLNELAAA LGNDPDFATT MTNALAGKQP KNATLTALAG  480
LSTAKNKLPY FAENDAASLT ELTQVGRDIL AKNSVADVLE YLGAGENSII QLEDSQGAHF  540
STERTLATGA IKTRFFGETF TDGTLYLNQM NNSSERFSIN NWGNSEVGRP AVLEVGDSKG  600
YHFYTERGTD NSLNFDVAGN FTVHGPSGIT IKTSTGARHI WFRDDSDAEK AVIWATDEGI  660
LHIRNNYGGS FSHHFQGAMI LAGERVPYNS EYALIRGNIS GGAWVDWRGR PAGLLVDCQD  720
SRNQAYNIWK ATHWGDQHLA AMGVHAGGGN PQVVLHVGGN DYAFASNGDF TAGAAVYCND  780
VYIRSDRRLK INVKDYEENA VDKVNKLKVK TYDKVKSLSD REVIGHEIGI IAQDLQEVLP  840
```

```
EAVSTSSVGS QDNPEEILTI SNSAVNALLI KAIQEMSEEI KELKTPLFTK IARKISKYFK  900
F                                                                  901

SEQ ID NO: 131          moltype = AA  length = 979
FEATURE                 Location/Qualifiers
REGION                  1..979
                        note = Synthetic: WW13 10.0
source                  1..979
                        mol_type = protein
                        organism = synthetic construct
SEQUENCE: 131
MAVKISGVLK DGTGKPVQNC TIQLKARRNS TTVVVNTVGS ENPDEAGRYS MDVEYGQYSV  60
ILQVDGFPPS HAGTITVYED SQPGTLNDFL CAMTEDDARP EVLRRLELMV EEVARNASVV  120
AQSTADAKKS AGDASASAAQ VAALVTDATD SARAASTSAG QAASSAQEAS SGAEAASAKA  180
TEAEKSAAAA ESSKNAAATS AGAAKTSETN AAASQQSAAT SASTAATKAS EAATSARDAV  240
ASKEAAKSSE TNASSSAGRA ASSATAAENS ARAAKTSETN ARSSETAAER SASAAADAKT  300
AAAGSASTAS TKATEAAGSA VSASQSKSAA EAAAIRAKNS AKRAEDIASA VALEDADTTR  360
KGIVQLSSAT NSTSETLAAT PKAVKVVMDE TNRVDRAVHT LGEITTNAVN GLRIWNNDYG  420
VIFRRSEGSL HIIPTAFGEG ETGDIGPLRP LSIALDTGKV TIPDLQSSYN TFAANGYIKF  480
VGHGAGAGGY DIQYAQAAPI FQEIDDDAVS KYYPIVKQKF LNGKSVWSLG TEIESGTFVI  540
HHLKEDGSQG HASRFNQDGT VNFPDNVLVG GDINMKGMMT FDAGRLGSRD YFKFNHWGDS  600
NNGRDNIIQL EDSQGAHFST ERTLATGAIK TRFFGETFTD GTLYLNQMNN SSERFSINNW  660
GNSEVGRPAV LEVGDSKGYH FYTERGTDNS LNFDVAGNFT VHGPSGITIK TSTGARHIWF  720
RDDSDAEKAV IWATDEGILH IRNNYGGSFS HHFQGAMILA GERVPYNSEY ALIRGNISGG  780
AWVDWRGRPA GLLVDCQDSR NQAYNIWKAT HWGDQHLAAM GVHAGGGNPQ VVLHVGGNDY  840
AFASNGDFTA GAAVYCNDVY IRSDRRLKIN VKDYEENAVD KVNKLKVKTY DKVKSLSDRE  900
VIGHEIGIIA QDLQEVLPEA VSTSSVGSQD NPEEILTISN SAVNALLIKA IQEMSEEIKE  960
LKTPLFTKIA RKISKYFKF                                               979

SEQ ID NO: 132          moltype = AA  length = 1432
FEATURE                 Location/Qualifiers
REGION                  1..1432
                        note = Synthetic: WW13-G8 (FIG.10)
source                  1..1432
                        mol_type = protein
                        organism = synthetic construct
SEQUENCE: 132
MAVKISGVLK DGTGKPVQNC TIQLKARRNS TTVVVNTVGS ENPDEAGRYS MDVEYGQYSV  60
ILQVDGFPPS HAGTITVYED SQPGTLNDFL CAMTEDDARP EVLRRLELMV EEVARNASVV  120
AQSTADAKKS AGDASASAAQ VAALVTDATD SARAASTSAG QAASSAQEAS SGAEAASAKA  180
TEAEKSAAAA ESSKNAAATS AGAAKTSETN AAASQQSAAT SASTAATKAS EAATSARDAV  240
ASKEAAKSSE TNASSSAGRA ASSATAAENS ARAAKTSETN ARSSETAAER SASAAADAKT  300
AAAGSASTAS TKATEAAGSA VSASQSKSAA EAAAIRAKNS AKRAEDIASA VALEDADTTR  360
KGIVQLSSAT NSTSETLAAT PKAVKVVMDE TNRGNIIDLG FAKGGSIDGN VIHIGNYNQT  420
GDYTLNGTFT QTGNFNLTGI ARVTRDIIAA GQIMTEGGEL ITKSSGTAHV RFFDGNSRER  480
GIIYAPANDG LTTQVLNIRV QDYAAGSEST YAFSGSGLFT SPEVSAWKSM STPQILTDKV  540
ITNGKKTGDY DIYSLSNNTP LAESETAINH LRVMRNAVGA GIFHEVNVND GITWYSGDGL  600
DTYLWSFNWA GGLKAGHSIS VGLPGGSKGY SELGTASIAL GDNDTGFKWH QDGYFHTVNN  660
GTRTFIYGPA ETQSLRKMVM GYSPDGILMT TPPTENYALA TVVTYHDNNA FGDGQTLLGY  720
YQGGNYHHYF RGKGTTNINT HGGLLVTPGN IDVIGGSVNI DGRNNNSTLM FKGYTMGQSS  780
VDNMYIAVWG NTFTNPSEGT RKNVMEISDD IGWMHYIQRN KDNTVEAVLN GQQTINENII  840
AKKDIWVDRA VHTLGEITTN AVNGLRIWNN DYGVIFRRSE GSLHIIPTAF GEGETGDIGP  900
LRPLSIALDT GKVTIPDLQS SYNTFAANGY IKFVGHGAGA GGYDIQYAQA APIFQEIDDD  960
AVSKYYPIVK QKFLNGKSVW SLGTEIESGT FVIHHLKEDG SQGHASRFNQ DGTVNFPDNV  1020
LVGGDINMKG MMTFDAGRLG SRDYFKFNHW GDSNNGRDNI IQLEDSQGAH FSTERTLATG  1080
AIKTRFFGET FTDGTLYLNQ MNNSSERFSI NNWGNSEVGR PAVLEVGDSK GYHFYTERGT  1140
DNSLNFDVAG NFTVHGPSGI TIKTSTGARH IWFRDDSDAE KAVIWATDEG ILHIRNNYGG  1200
SFSHHFQGAM ILAGERVPYN SEYALIRGNI SGGAWVDWRG RPAGLLVDCQ DSRNQAYNIW  1260
KATHWGDQHL AAMGVHAGGG NPQVVLHVGG NDYAFASNGD FTAGAAVYCN DVYIRSDRRL  1320
KINVKDYEEN AVDKVNKLKV KTYDKVKSLS DREVIGHEIG IIAQDLQEVL PEAVSTSSVG  1380
SQDNPEEILT ISNSAVNALL IKAIQEMSEE IKELKTPLFT KIARKISKYF KF          1432

SEQ ID NO: 133          moltype = AA  length = 259
FEATURE                 Location/Qualifiers
REGION                  1..259
                        note = Synthetic: WW13 gp38
source                  1..259
                        mol_type = protein
                        organism = synthetic construct
SEQUENCE: 133
MAVVGVPGWI GSSAVNETGQ RWMSQAAGQL RLGVPCWMSQ FAGRSREIIH TLGADHNFNG  60
QWFRDRCFEA GSTPIVFNIT GDLVSYSKDV PLFFMYGDTP NEYVQLNIHG VTMYGRGGNG  120
GSNSPGSAGG HCIQNDIGGR LRINNGGAIA GGGGGGGGGR YGRLSFGGGG GRPFGAGGSS  180
SHMSSGATAG TISAPGAGSV GEGSLWVYTG GSGGNVGAAG GRCNIQGNGT EYDGGAAGYA  240
VIGSAPTWIN VGAIYGPRV                                               259

SEQ ID NO: 134          moltype = AA  length = 80
FEATURE                 Location/Qualifiers
REGION                  1..80
```

```
                       note = Synthetic: WW13 gp57A
source                 1..80
                       mol_type = protein
                       organism = synthetic construct
SEQUENCE: 134
MSEQTIEQKL SAEIVTLKSR ILDTQDQAAR LMEESKILQG TLAEIARAVG ITGDTIKVEE  60
IVEAVKNLTA ESADEAKDEE                                              80

SEQ ID NO: 135         moltype = AA  length = 931
FEATURE                Location/Qualifiers
REGION                 1..931
                       note = Synthetic: PP-1 (FIG. 8)
source                 1..931
                       mol_type = protein
                       organism = synthetic construct
SEQUENCE: 135
MAVKISGVLK DGTGKPVQNC TIQLKARRNS TTVVVNTVGS ENPDEAGRYS MDVEYGQYSV  60
ILQVDGFPPS HAGTITVYED SQPGTLNDFL CAMTEDDARP EVLRRLELMV EEVARNASVV  120
AQSTADAKKS AGDASASAAQ VAALVTDATD SARAASTSAG QAASSAQEAS SGAEAASAKA  180
TEAEKSAAAA ESSKNAAATS AGAAKTSETN AAASQQSAAT SASTAATKAS EAATSARDAV  240
ASKEAAKSSE TNASSSAGRA ASSATAAENS ARAAKTSETN ARSSETAAER SASAAADAKT  300
AAAGSASTAS TKATEAAGSA VSASQSKSAA EAAAIRAKNS AKRAEDIASA VALEDADTTR  360
KGIVQLSSAT NSTSETLAAT PKAVKVVMDE TNRKAPLDSP ALTGTPTAPT ALRGTNNTQI  420
ANTAFVLAAI ADVIDASPDA LNTLNELAAA LGNDPDFATT MTNALAGKQP KNATLTALAG  480
LSTAKNKLPY FAENDAASLT ELTQVGRDIL AKNSVADVLE YLGAGENSIA TRVSKEGDTM  540
TGKLTLSAGN DALVLTAGEG ASSHIRSDVG GTNNWYIGKG SGDNGLGFYS YITQGGVYIT  600
NNGEIALSPQ GQGTFNFNRD RLHINGTQWT AHQGGGWENQ WNQEAPIFID FGNVGNDSYY  660
PIIKGKSGIT NEGYISGVDF GMRRITNTWA QGIIRVGNQE NGSDPQAIYE FHHNGVLYVP  720
NMVKTGARLS AGGGDPVWQG ACVVIGDNDT GLVHGGDGRI NMVANGMHIA SWSSAYHLHE  780
GLWDTTGALW TEQGRAIISF GHLVQQSDAY STFVRDVYVR SDIRVKKDLV KFENASEKLS  840
KINGYTYMQK RGLDEEGNQK WEPNAGLIAQ EVQAILPELV EGDPDGEALL RLNYNGVIGL  900
NTAAINEHTA EIAELKSEIE ELKKIVKSLL K                                 931

SEQ ID NO: 136         moltype = AA  length = 259
FEATURE                Location/Qualifiers
REGION                 1..259
                       note = Synthetic: PP-1 gp38
source                 1..259
                       mol_type = protein
                       organism = synthetic construct
SEQUENCE: 136
MAVTGPWVGS SAVVNTGQNW MVGAAQRLRM GAPFWMSNMI GRSVEVIHTL GADHNFNGQW  60
FRDRCFEAGS APIVFNITGD LVSYSRDVPL FFMYGDTPNE YVQLNIHGVT MYGRGGNGWA  120
AGAIGASDGG VCIQNDIGGR LRINNGGAIA GGGGGGGGYS QANNWAGKYV CGGGGGRPFG  180
LGGNNGARWP GGNASLTSPG AGGNTGTRYY AGGGGEVGQP GQYANPGAGY STPPTSPGAA  240
VAGSAPTWQN VGAIYGPRV                                               259

SEQ ID NO: 137         moltype = AA  length = 80
FEATURE                Location/Qualifiers
REGION                 1..80
                       note = Synthetic: PP-1 gp57A
source                 1..80
                       mol_type = protein
                       organism = synthetic construct
SEQUENCE: 137
MSEQTIEQKL SAEIVTLKSR ILDTQDQAAR LMEESKILQG TLAEIARAVG ITGDTIKVEE  60
IVEAVKNLTA ESTDEAKDEE                                              80

SEQ ID NO: 138         moltype = AA  length = 1217
FEATURE                Location/Qualifiers
REGION                 1..1217
                       note = Synthetic: WW55 3.0 (FIG. 9)
source                 1..1217
                       mol_type = protein
                       organism = synthetic construct
SEQUENCE: 138
MAVKISGVLK DGTGKPVQNC TIQLKARRNS TTVVVNTVGS ENPDEAGRYS MDVEYGQYSV  60
ILQVDGFPPS HAGTITVYED SQPGTLNDFL CAMTEDDARP EVLRRLELMV EEVARNASVV  120
AQSTADAKKS AGDASASAAQ VAALVTDATD SARAASTSAG QAASSAQEAS SGAEAASAKA  180
TEAEKSAAAA ESSKNAAATS AGAAKTSETN AAASQQSAAT SASTAATKAS EAATSARDAV  240
ASKEAAKSSE TNASSSAGRA ASSATAAENS ARAAKTSETN ARSSETAAER SASAAADAKT  300
AAAGSASTAS TKATEAAGSA VSASQSKSAA EAAAIRAKNS AKRAEDIASA VALEDADTTR  360
KGIVQLSSAT NSTSETLAAT PKAVKVVMDE TNRTPGELNV YSKQEIDRMF VKNVKMVVPS  420
GGATRGYFKI ASAMIPQSGR MAFLRIYGGN GYNVNSYDQV DFLEIVIRSG NNNPKGVSIA  480
AYRRNSLNVH EVFAINTSGD NYDIYVNYGR FTDNVIVEFG KTVDVALTVH DVPEFSATKP  540
ETGTKFDARV ITMFNTENKA GTLMFDNNNQ LTYDIVSLSN GPDDVRNYLR KFRSKAGEMI  600
WHETVQGAVY RLATGTTDST EVLRVDSNSA LPGSYKGYVI TGKMELHGSG SAMNLHRQTG  660
QAAYMAWWDR RDGKNQRSGY IGHADGTTDG FVWRNDVGAN SFDLESSGQV NLTTGKTKIV  720
YTNGQYYSAN SDAFRMIYGN YGAFWRNDGG KVYLLSTAEN DRFGGWNGNR PFIYDLSTGK  780
```

```
VTLGGDGNEG ALVLERDSRA ARFSNSVFLE KGLLTFSAGG NQSMDSFTIN HWGNSNAGRY  840
NVLQFEDTKG THFTTERNAD GGLLAHFRGD LTTEGKLTWG KGTATSSFNI RAWGNSDSRK  900
QVFECVDESG WHWYTQRPGG PGTSAIEFAI NGTVKPQAIH TGGNILLNGA DIEFRRTGNK  960
HLWFRDPNGL ELGLIYCDDN GVIRFRGQKQ GQDWVFANKM IQLGTASTVG GSGNGLIRGQ  1020
VQGGAWAQWR DRAAGILVDC QQSTDSAHNI WKATHWGKYH IAAMGVHVPS GTIGNAMARL  1080
NVNDANFDFS ASGDMSAGRN GSFNDVYIRS DARLKINKEE YKENATDKVN RLTVYTYDKV  1140
KSLTDRTVIA HEVGIIAQDL EKELPEAVTT SKIGDPDKPE EILTISNSAV NALLIKAFQE  1200
MSEELKAVKA ELAELKK                                                 1217

SEQ ID NO: 139          moltype = AA  length = 1330
FEATURE                 Location/Qualifiers
REGION                  1..1330
                        note = Synthetic: WW55-G8 (FIG. 10)
source                  1..1330
                        mol_type = protein
                        organism = synthetic construct
SEQUENCE: 139
MAVKISGVLK DGTGKPVQNC TIQLKARRNS TTVVVNTVGS ENPDEAGRYS MDVEYGQYSV  60
ILQVDGFPPS HAGTITVYED SQPGTLNDFL CAMTEDDARP EVLRRLELMV EEVARNASVV  120
AQSTADAKKS AGDASASAAQ VAALVTDATD SARAASTSAG QAASSAQEAS SGAEAASAKA  180
TEAEKSAAAA ESSKNAAATS AGAAKTSETN AAASQQSAAT SASTAATKAS EAATSARDAV  240
ASKEAAKSSE TNASSSAGRA ASSATAAENS ARAAKTSETN ARSSETAAER SASAAADAKT  300
AAAGSASTAS TKATEAAGSA VSASQSKSAA EAAAIRAKNS AKRAEDIASA VALEDADTTR  360
KGIVQLSSAT NSTSETLAAT PKAVKVVMDE TNRGAIINLS CPPVYDRDVT MAGKVKGNNY  420
ILSKTANYLE DQTARDLNYF GAFRTNGLDG LLELTLNVPH SSGVQHGRGF TFQYGHTGSR  480
VETYGYNKEG QKAFSYKMYH EGDKPTPGEL NVYSKQEIDR MFVKNVKMVV PSGGATRGYF  540
KIASAMIPQS GRMAFLRIYG GNGYNVNSYD QVDFLEIVIR SGNNNPKGVS IAAYRRNSLN  600
VHEVFAINTS GDNYDIYVNY GRFTDNVIVE FGKTVDVALT VHDVPEFSAT KPETGTKFDA  660
RVITMFNTEN KAGTLMFDNN NQLTYDIVSL SNGPDDVRNY LRKFRSKAGE MIWHETVQGA  720
VYRLATGTTD STEVLRVDSN SALPGSYKGY VITGKMELHG SGSAMNLHRQ TGQAAYMAWW  780
DRRDGKNQRS GYIGHADGTT DGFVWRNDVG ANSFDLESSG QVNLTTGKTK IVYTNGQYYS  840
ANSDAFRMIY GNYGAFWRND GGKVYLLSTA ENDRFGGWNG NRPFIYDLST GKVTLGGDGN  900
EGALVLERDS RAARFSNSVF LEKGLLTFSA GGNQSMDSFT INHWGNSNAG RYNVLQFEDT  960
KGTHFTTERN ADGGLLAHFR GDLTTEGKLT WGKGTATSSF NIRAWGNSDS RKQVFECVDE  1020
SGWHWYTQRP GGPGTSAIEF AINGTVKPQA IHTGGNILLN GADIEFRRTG NKHLWFRDPN  1080
GLELGLIYCD DNGVIRFRGQ KQGQDWVFAN KMIQLGTAST VGGSGNGLIR GQVQGGAWAQ  1140
WRDRAAGILV DCQQSTDSAH NIWKATHWGK YHIAAMGVHV PSGTIGNAMA RLNVNDANFD  1200
FSASGDMSAG RNGSFNDVYI RSDARLKINK EEYKENATDK VNRLTVYTYD KVKSLTDRTV  1260
IAHEVGIIAQ DLEKELPEAV TTSKIGDPDK PEEILTISNS AVNALLIKAF QEMSEELKAV  1320
KAELAELKKN                                                         1330

SEQ ID NO: 140          moltype = AA  length = 261
FEATURE                 Location/Qualifiers
REGION                  1..261
                        note = Synthetic: WW55 gp38
source                  1..261
                        mol_type = protein
                        organism = synthetic construct
SEQUENCE: 140
MAISSGWVGS SAVSETGQRW MSAAMQAVRL GRPAYMSAMV GRSKEIHYSI GASNSYNKDT  60
LINWMKAQGS TPVVITITGN IVSQSTGVPC LDFPSSLTNE YVTLIINSGV HVLGRGGNGG  120
SNSAGGAGGN AINNGIGTRL RINNNGIIGG GGGGGAGARY NPFPQMDMKF GGGGGRPFGA  180
AGAAGGGAAA ASAGTISAPG KGTVSGVHYG GDGGDLGAAG KSSYIKGGTG GTVHSGGAAG  240
KAVTGNAPRW DKVGTIYGAR V                                            261

SEQ ID NO: 141          moltype = AA  length = 86
FEATURE                 Location/Qualifiers
REGION                  1..86
                        note = Synthetic: WW55 gp57A
source                  1..86
                        mol_type = protein
                        organism = synthetic construct
SEQUENCE: 141
MSNQHEQMIN VLKVRLFDTQ EKAAFLEGQL KDRERVLMEL VRILGIQPDE NGTVSLDAIV  60
EEVKALLPKD EAAEDAEEEV ELITEA                                       86

SEQ ID NO: 142          moltype = AA  length = 1217
FEATURE                 Location/Qualifiers
REGION                  1..1217
                        note = Synthetic: WW34 3.0
source                  1..1217
                        mol_type = protein
                        organism = synthetic construct
SEQUENCE: 142
MAVKISGVLK DGTGKPVQNC TIQLKARRNS TTVVVNTVGS ENPDEAGRYS MDVEYGQYSV  60
ILQVDGFPPS HAGTITVYED SQPGTLNDFL CAMTEDDARP EVLRRLELMV EEVARNASVV  120
AQSTADAKKS AGDASASAAQ VAALVTDATD SARAASTSAG QAASSAQEAS SGAEAASAKA  180
TEAEKSAAAA ESSKNAAATS AGAAKTSETN AAASQQSAAT SASTAATKAS EAATSARDAV  240
ASKEAAKSSE TNASSSAGRA ASSATAAENS ARAAKTSETN ARSSETAAER SASAAADAKT  300
```

```
AAAGSASTAS TKATEAAGSA VSASQSKSAA EAAAIRAKNS AKRAEDIASA VALEDADTTR  360
KGIVQLSSAT NSTSETLAAT PKAVKVVMDE TNRTPGELNV YSKQEIDRMF VKNVKMSTPS  420
GEATRGYFKI ASAMIPQSGR MAFLRIYGGN GFNVNSYDQV DFLEIVIRSG NNNPKGVSIA  480
AYRRNSLNVH EVFAINTSGD NYDIYVNYGR FTDNVIVEFG KTVDVALTVH DVPEFSATKP  540
ETGTKFDARV ITMFNTENKA GTLMFDNNNQ LTYDIVSLSN GPDDVRNYLR KFRSKAGEMI  600
WHETVQGAVY RLATGTTDST EVLRVDSNSA IPGSYKGYVI TGKMELHGSG NSMILHRQTA  660
QAAYMSWWDR RDGKNQRSGY IGHADGTSDA IVWNNDIGQN SAVLETSGQI SFRTGATKIV  720
YTNGQYYSAN SDAYRMIFGN YGAFWRNDGT KVYLLSTAEN DKYGGWNAYR PFIYDLTSGN  780
VQLGGDGNED ALTLECASRA ARFSNDVYIK KGLLTFDAGR AGSRDYIRFN HWGDSNNARD  840
NVLCIEDSQG RHFSTERAMG TGALKAYFLG DLEVGGKFTW GKNTATSSFN IRAWGNDSRK  900
QVLECADESG WHWYTQRTGG PDTSAIDFAI NGTVRPQAIH TGGNITINGA DIEFKRTGNK  960
HIWFRDPNGL ELGLMYCDDA GAIRFRGQKQ AQAWKFADKM IQLESGTVSG GGNGLIRGEV  1020
AGGSWASWRD RAAGLMVGCP QSTNSAHNVW KATHWGKYHI AAMAVHVPDG TITNALARLN  1080
VHDANFDFSA SGDLSAGRNG SFNDVYIRSD ARLKINKEEY KENATDKVNR LTVYTYDKVK  1140
SLTDRTVIAH EVGIIAQDLE KELPEAVTTS KIGDPDKPEE ILTISNSAVN ALLIKAFQEM  1200
SEELKAVKAE LAELKKN                                                 1217

SEQ ID NO: 143          moltype = AA  length = 259
FEATURE                 Location/Qualifiers
REGION                  1..259
                        note = Synthetic: WW34 gp38
source                  1..259
                        mol_type = protein
                        organism = synthetic construct
SEQUENCE: 143
MAISSGWVGS SAVSETGQRW MSAAMQAVRL GRPAYMSAMV GRSKEIHYSI GASNSYNKDT  60
LINWMKAQGS TPVVITITGN IVSQSTGVPC LDFPSSLTNE YVTLIINPGV HVWGRGGNGG  120
NNSAGGAGGN AINNGIGTRL RITNNGAICG GGGGGGGGYY SPFSQMRLTF GGGGGRPFGA  180
AGGSANMEQG ATAGTISAPG KGSVNGVYNG GNGGDAGGAG GKCNIRGQGS EYNGGAAGKA  240
VTGNAPRWDK VGTIYGARV                                               259

SEQ ID NO: 144          moltype = AA  length = 86
FEATURE                 Location/Qualifiers
REGION                  1..86
                        note = Synthetic: WW34 gp57A
source                  1..86
                        mol_type = protein
                        organism = synthetic construct
SEQUENCE: 144
MSNQHEQMIN VLKVRLFDTQ EKAAFLEGQL KDRERVLMEL VRILGIQPDE NGTVSLDAIV  60
EEVKALLPKD EAAEDAEEEV ELITEA                                       86

SEQ ID NO: 145          moltype = AA  length = 1651
FEATURE                 Location/Qualifiers
REGION                  1..1651
                        note = Synthetic: WW14-G8
source                  1..1651
                        mol_type = protein
                        organism = synthetic construct
SEQUENCE: 145
MAVKISGVLK DGTGKPVQNC TIQLKARRNS TTVVVNTVGS ENPDEAGRYS MDVEYGQYSV  60
ILQVDGFPPS HAGTITVYED SQPGTLNDFL CAMTEDDARP EVLRRLELMV EEVARNASVV  120
AQSTADAKKS AGDASASAAQ VAALVTDATD SARAASTSAG QAASSAQEAS SGAEAASAKA  180
TEAEKSAAAA ESSKNAAATS AGAAKTSETN AAASQQSAAT SASTAATKAS EAATSARDAV  240
ASKEAAKSSE TNASSSAGRA ASSATAAENS ARAAKTSETN ARSSETAAER SASAAADAKT  300
AAAGSASTAS TKATEAAGSA VSASQSKSAA EAAAIRAKNS AKRAEDIASA VALEDADTTR  360
KGIVQLSSAT NSTSETLAAT PKAVKVVMDE TNRNQIIDLG FAKGGQVDGD VTINGTLNLN  420
GPEIVASGGY IEFNYRTTGS GSWAGQHAAK APIFVDLSAA LSTSEYNPLF KQRYKDGTFS  480
AGTLVTEGSF KFHYINEAGD SKYWTFNRNG NFQVDTGSLF VSGGNISASG NINSASGFVS  540
APQINTKNII LDTKAFGQYD SQSLVNYVYP GTGETNGVNY LRKVRAKSGG TMWHELCTAQ  600
LGQADEMSWW TGNTPQSKQY GVRNDGRLIG RNSLALGTMT TDFPSSDYGN TGAMGDKYLV  660
LGDTATGLKY IKQGNFDLVG GGYSVASITT DGFRGTSKTL FGRSNDQGLT WLLPGQNSAM  720
VSIRTEIDGN NSGDGQTHLG YNSNGKLYHY FRGTGRVAIS MAEGMIIEPG ILNIKTGVNE  780
LNLRADGTVS TTQRLMVNNG LVLNANNNTS ALALTAPTGV DGTKTINWDA GTRNGQNKNT  840
VTMKAWGNSF NAGGGNRETV FEVSDSQGYY FYGQRTNPAS GETVGPINFK FNGSVETGHF  900
SSLGNISASG TGSFGGNVTM TNGLFVQGGA SINGQVKMGG TADALRIWNA EYGMIFRRSE  960
TGSSASFHLI PTLQNAGENG GISDLRPLSI NLASGTVIMG NKSTGGPLFT VDNVSKFVQT  1020
DCRLRVNMDS DGIVLNASSQ AASNFIQGRK ADVTKWYLGI GDGGNVVRMH NYTYSHGIAL  1080
NSDTVDITKP LKIGSDIRIG TDGNIIGSAT LDNFKNLNTT LDHKVNMGGW SGGATTGWYK  1140
FATVEIPQAT GTASFKIFGG SGFNFKSYGQ ASIAEIILRT GNNNPKGLNA TLWNRTSEAI  1200
SQIASVNTSE DIYDIYVYLG GYSNSLVVEY TCSSNSKVTV VGMDGGVQPL VETLPEGHVV  1260
GKSVRMLNNL DGMFAAGESD IVTRGEYVTN NQKGMRIKSK GNDLDSNAAL LRNDGGSFYI  1320
LATDKNTTEK PDAANGDWNG LRPFSINMAD GRVGMNHGLN ITGGGLNVTG GNTNLGNITS  1380
RVVSSARAGS GWGDNSDAMK SKITFMADHG DLSNSGSYYP IVGAYSNYGS AGYRQTFEFG  1440
WVGSGSTANW REGIIRIRGD NANGQQARWR FTMDGILGCP GKVEMPETSA FGINTTNGFG  1500
GNSIVIGDSD TGFRQVGDGL LEVWTNASRR MRFQGGDTYS DMNINAPNVY IRSDIRLKSN  1560
FKPIENALDK VEQLDGLIYD KADYIGGEVV HTEAGVIAQS LEKVLPEAVR EVDDIKGNKV  1620
LTVSTQAQVA LLIEAVKTLS AKVKELEAKL N                                 1651
```

```
SEQ ID NO: 146          moltype = AA  length = 262
FEATURE                 Location/Qualifiers
REGION                  1..262
                        note = Synthetic: WW14 gp38
source                  1..262
                        mol_type = protein
                        organism = synthetic construct
SEQUENCE: 146
MAIVGVPGWI GQSAVDETGQ RWMDAAMRDV RVAVPGWMGS MAGQSKEIYL SIGANNSYDR  60
NSLINWMRAQ GGAPVVITIT GNLVSNSTGN ACLEFPSNLP NAYIQLIINS GVTVYGRGGN  120
GSTNGSAGGN GGTAIHNAAG TKLRIRNNGA IAGGGGGGGA VSLQNSYPTN GTCGGGGGRP  180
FGVGGKIGSD AILSGSNASL TAAGTGGATV QYGGGNGGNV GAGGGRGWGK NVYTSAGGSA  240
GAAVTGNAPN WQNVGTIYGS RV                                            262

SEQ ID NO: 147          moltype = AA  length = 76
FEATURE                 Location/Qualifiers
REGION                  1..76
                        note = Synthetic: WW14 gp57A
source                  1..76
                        mol_type = protein
                        organism = synthetic construct
SEQUENCE: 147
MSEQTIEQKL QAEIVALKSR ILDTQDVAAQ AQQESRILQD ALSKIAARLG ITGDQIQIED  60
LIAAVPDLTA ESADEE                                                   76

SEQ ID NO: 148          moltype = AA  length = 1325
FEATURE                 Location/Qualifiers
REGION                  1..1325
                        note = Synthetic: WW170-G8
source                  1..1325
                        mol_type = protein
                        organism = synthetic construct
SEQUENCE: 148
MAVKISGVLK DGTGKPVQNC TIQLKARRNS TTVVVNTVGS ENPDEAGRYS MDVEYGQYSV  60
ILQVDGFPPS HAGTITVYED SQPGTLNDFL CAMTEDDARP EVLRRLELMV EEVARNASVV  120
AQSTADAKKS AGDASASAAQ VAALVTDATD SARAASTSAG QAASSAQEAS SGAEAASAKA  180
TEAEKSAAAA ESSKNAAATS AGAAKTSETN AAASQQSAAT SASTAATKAS EAATSARDAV  240
ASKEAAKSSE TNASSSAGRA ASSATAAENS ARAAKTSETN ARSSETAAER SASAAADAKT  300
AAAGSASTAS TKATEAAGSA VSASQSKSAA EAAAIRAKNS AKRAEDIASA VALEDADTTR  360
KGIVQLSSAT NSTSETLAAT PKAVKVVMDE TNRGAIINLS CPPVYDRDVT MAGKVKGNNY  420
ILSKTANYLE DQTARDLNYF GAFRTNGQDG LLDLTLNVPH SAGVNHGRGF TFRYATGGSR  480
VETYGYNAQG QKAFSYKMYH EGDKPTPSEL NVYSKQEVDR MFVKTVKLAT VPVDIVDGYF  540
KLATAMIPQN GRSVFFRIHG GNGYNVTAYD QVDIVEIVIR SGNNRPKGVN VIAYRRNTNK  600
AFDVLAVNTS GDNYDIYVKY QRYTDNVIVE FGKSVDVDLV VHDVPDFVVD RPVGDNVIGG  660
RAVTLFNTEN KRGVLSFDDN TQNSYDIVHL SNDRGTGRKY IRKFRSNYNE MIWHETVQGS  720
TYRLATGSTD AQEILSVESS SSIAGTHKGN ILSGRMMLGG GSNVITLRRP AGQSNHIAFQ  780
DNRTGSITRQ GWIGYGNADT NVFEWYSDVG GTSIRHHIDG QIELATGNTK RVYTNAQFIS  840
MNSDAYRMIF GNYGAFWRND GTKVYLLSTA EDDKFGGWNG NRPFIYDLTN GKVTLGGDGN  900
EGALVLERDS RAARFAGDVY VEKGFLHFSS GRQGASGFMK INHLGDIASG RHNILQIEDP  960
TGIHFSTERN DETGNITARF KGFVRVEAGE IAFDANRGSQ SQFTLHTWGN EQRKQVFECK  1020
DATGYHWYTE RTQGGTGNVL FSMAGSLNVT SNITTTGADI TFKRAGNKHI WFRDPDGLEL  1080
GLMYCDDAGA IRFRGQKQAQ AWKFADKMIQ LESGTVSGGG NGLIRGEVAG GSWSSWRDRA  1140
AGLMVGCPQS TNSAHNVWKA THWGKYHIAA MGIHVPDGTI GNALARLHVH DTNFDFSASG  1200
DMTAGRNGSF NDVYIRSDAR LKINKEEYKE NATDKINRLT VYTYDKVKSL TDRTVIAHEV  1260
GIIAQDLEKE LPEAVTTSKV GDPDKPEEIL TISNSAVNAL LIKAFQEMSE ELKAVKAELA  1320
ELKKN                                                               1325

SEQ ID NO: 149          moltype = AA  length = 259
FEATURE                 Location/Qualifiers
REGION                  1..259
                        note = Synthetic: WW170 gp38
source                  1..259
                        mol_type = protein
                        organism = synthetic construct
SEQUENCE: 149
MAISSGWVGS SAVSETGQRW MSAAMQAVRL GRPAYMSAMV GRSKEIHYSI GASNSYNKDT  60
LINWMKAQGS TPVVITITGN IVSQSTGVPC LDFPSSLTNE YVTLIINPGV HVWGRGGNGG  120
NNSAGGAGGN AINNGIGTRL RITNNGAICG GGGGGGGGYY SPFSQMRLTF GGGGGRPFGA  180
AGGSANMEQG ATAGTISAPG KGSVNGVYNG GNGGDAGGAG GKCNIRGQGS EYNGGAAGKA  240
VTGNAPRWDK VGTIYGARV                                                259

SEQ ID NO: 150          moltype = AA  length = 86
FEATURE                 Location/Qualifiers
REGION                  1..86
                        note = Synthetic: WW170 gp57A
source                  1..86
                        mol_type = protein
                        organism = synthetic construct
SEQUENCE: 150
```

```
MSNQHEQMIN VLKVRLFDTQ EKAAFLEGQL KDRERVLMEL VRILGIQPDE NGTVSLDAIV  60
EEVKALLPKD EAAEDAKEEV ELITEA                                       86

SEQ ID NO: 151          moltype = AA  length = 1315
FEATURE                 Location/Qualifiers
REGION                  1..1315
                        note = Synthetic: WW202-G8
source                  1..1315
                        mol_type = protein
                        organism = synthetic construct
SEQUENCE: 151
MAVKISGVLK DGTGKPVQNC TIQLKARRNS TTVVVNTVGS ENPDEAGRYS MDVEYGQYSV  60
ILQVDGFPPS HAGTITVYED SQPGTLNDFL CAMTEDDARP EVLRRLELMV EEVARNASVV  120
AQSTADAKKS AGDASASAAQ VAALVTDATD SARAASTSAG QAASSAQEAS SGAEAASAKA  180
TEAEKSAAAA ESSKNAAATS AGAAKTSETN AAASQQSAAT SASTAATKAS EAATSARDAV  240
ASKEAAKSSE TNASSSAGRA ASSATAAENS ARAAKTSETN ARSSETAAER SASAAADAKT  300
AAAGSASTAS TKATEAAGSA VSASQSKSAA EAAAIRAKNS AKRAEDIASA VALEDADTTR  360
KGIVQLSSAT NSTSETLAAT PKAVKVVMDE TNRGQIVNLS CPPVYDKGFD VRGRVVVDDL  420
VWSNTANYFD DPTARNLDKF GAFRTNDMDG HLAFALHIPH PSGINHARGF DFTYGSNVVP  480
TVKTYGYNAD GVLAYSYRMY HEGDKPSPSE LNVYSKQEVD RMFQKTINFG VETGWFKIAT  540
AFIPQNDGRS LKIRLVGGNG WNVGQTGQCN IIELVIRTSN GSPKGINFVA YHHVSGYENQ  600
FCAINTGDDT YDIYAYYYEF TNMVMAEYQA SSDVNLTVFD RPEYVGEKPV AEHIFDAYTI  660
HSFNSFSNRG TLNFAGNHQG QYDIEHMNEQ PTNAKKMLRR FRSSASATIW HETVDDQNYR  720
LATGGTDSVQ QLLLSSGTGL HIRRLTIDGG LGSGSNAGID IRRGPNESSH FNFMDYRTGQ  780
DVRNGWFGFG DLTTKDFIWW NDNGQNSINL IENGELHITG GRGQKIVMNS EVALSENARL  840
AVKGGNYGLI LRNDGTGFHI LTTDLKDSFG SWNNRRPFSY NFADGGLYLG GTETARCLHL  900
GIDGSTRLED NLFFKAGSRQ SMDYMELVHW GASNTGRNNV LSLRDSKGFL AEFERVGGTD  960
GVKTRFFGET FTDGTLYLNQ MNNSSERFSI NNWGNSEVGR AAVMEVGDSK GYHFYAERRT  1020
DDTVLFDVSG ALTVHGPNGI TVKNSTGARH IWFRDDSDTE KAVIWATDDG MLHIRNNHEG  1080
SFAHHFQGAM IKLEGRVPYG AAKGLIRGEV DGGAYVAWRD RPAGLLVDCQ KSIDSAHAVW  1140
KAVDWGRQYI AAMDVHCPGD GNNTAAAVLH VQAADYQFHA SGEFHASGNG NFNDVYIRSD  1200
RRLKDNIEDY TGNALSLIGK LKVKTYDKVK SLKDREIIGH EIGIIAQDLQ EILPEAVKSS  1260
KVGNLDNPDD VLTISNSAVN ALLIKAIQEM SEEIKELKTP FFTKIARKIS KYFKF       1315

SEQ ID NO: 152          moltype = AA  length = 260
FEATURE                 Location/Qualifiers
REGION                  1..260
                        note = Synthetic: WW202 gp38
source                  1..260
                        mol_type = protein
                        organism = synthetic construct
SEQUENCE: 152
MAVVGVPGWI GSSAANETGQ RWMSQAAGQL RLGVPCWMSQ FSGRSREIIH TLGADHNFNG  60
QWFRDRCFEA GSTPIVFNIT GDLVSYSKDV PLFFMYGDTP NEYVQLNIHG VTMYGRGGNG  120
GSNSPGSAGG HCIQNDIGGR LRINNGGAIA GGGGGGGGGY YSPFSQMRLT FGGGGGRPFG  180
APGGSIDMQS GATAGTLYAP GSGSVNGIYN GGSGGEVGAA GGRCNIRGQG YEYNGGDAGY  240
AVIGSSPTWQ NRGAIYGPAV                                              260

SEQ ID NO: 153          moltype = AA  length = 86
FEATURE                 Location/Qualifiers
REGION                  1..86
                        note = Synthetic: WW202 gp57A
source                  1..86
                        mol_type = protein
                        organism = synthetic construct
SEQUENCE: 153
MSNQHEQMIN VLKVRLFDTQ EKAAFLEGQL KDRERVLMEL VRVLGIQPDE NGTVSLDAIV  60
EEVKALLPKD EAAEDAKEEV ELITEA                                       86

SEQ ID NO: 154          moltype = DNA  length = 2706
FEATURE                 Location/Qualifiers
misc_feature            1..2706
                        note = Synthetic: WW13 13.0
source                  1..2706
                        mol_type = other DNA
                        organism = synthetic construct
SEQUENCE: 154
atggcagtaa agatttcagg agtcctgaaa gacggcacag gaaaaccggt acagaactgc  60
accattcagc tgaaagccag acgtaacagc accacggtgg tggtgaacac ggtgggctca  120
gagaatccgg atgaagccgg gcgttacagc atggatgtgg agtacggtca gtacagtgtc  180
atcctgcagg ttgacggttt tccaccatcg cacgccggga ccatcaccgt gtatgaagat  240
tcacaaccgg ggacgctgaa tgatttctc tgtgccatga cggaggatga tgcccggccg  300
gaggtgctgc gtcgtcttga actgatggtg gaagaggtgg cgcgtaacgc gtccgtggtg  360
gcacagagta cggcagacgc gaagaaatca gccggcgatg ccagtgcatc agctgctcag  420
gtcgcggccc ttgtgactga tgcaactgac tcagcacgcg ccgccagcac gtccgccgga  480
caggctgcat cgtcagctca ggaagcgtcc tccggcgcag aagcggcatc agcaaaggcc  540
actgaagcgg aaaaaagtgc cgcagccgca gagtcctcaa aaacgcggc ggccaccagt  600
gccggtgcgg cgaaaacgtc agaaacgaat gctgcagcgt cacaacaatc agccgccacg  660
tctgcctcca ccgcggccac gaaagcgtca gaggccgcca cttcagcacg agatgcggtg  720
```

```
gcctcaaaag aggcagcaaa atcatcagaa acgaacgcat catcaagtgc cggtcgtgca  780
gcttcctcgg caacggcggc agaaaattct gccagggcgg caaaaacgtc cgagacgaat  840
gccaggtcat ctgaaacagc agcggaacgg agcgcctctg ccgcggcaga cgcaaaaaca  900
gcggcggcgg ggagtgcgtc aacggcatcc acgaaggcga cagaggctgc gggaagtgcg  960
gtatcagcat cgcagagcaa aagtgcggca gaagcggcgg caatacgtgc aaaaaattcg  1020
gcaaaacgtg cagaagatat agcttcagct gtcgcgcttg aggatgcgga cacaacgaga  1080
aaggggatag tgcagctcag cagtgcaacc aacagcacgt ctgaaacgct tgctgcaacg  1140
ccaaaggcgg ttaaggtggt aatggatgag actaatcgta aggcacctct ggacagtccg  1200
gcactgaccg gaacgccaac agcaccaacc gcgctcaggg gaacaaacaa tacccagatt  1260
gcgaacaccg cttttgtact ggccgcgatt gcagatgtta tcgacgcgtc acctgacgca  1320
ctgaatacgc tgaatgaact ggccgcagcg ctcgggaatg atccagattt tgctaccacc  1380
atgactaacg cgcttgcggg taaacaaccg aagaatgcga cactgacggc gctggcaggg  1440
ctttccacgg cgaaaaataa attaccgtat tttgcggaaa atgatgccgc cagcctgact  1500
gaactgactc aggttggcag ggatattctg gcaaaaaatt ccgttgcaga tgttcttgaa  1560
taccttgggg ccggtgagaa ttcgatcatc cagttagaag atagtcaagg cgcccatttt  1620
tccactgaac gtactttagc gacaggtgca attaaaactc gtttctttgg cgaaacattt  1680
actgatggta cattatacct aaatcagatg aataatagtt ctgaacgatt ctctattaat  1740
aattggggaa attcagaagt tggtcgcccg gcagtgttgg aagtcggtga ttccaaaggt  1800
tatcacttct atacggaacg cgggacagat aacagtttga attttgatgt tgctggcaat  1860
tttactgtgc atggaccttc cgggattact atcaaaacct ctactggtgc tcgccatatc  1920
tggtttagag atgatagcga tgcagaaaag gctgttatct gggctacaga tgagggtatt  1980
ttacatatac gaaataatta tgggggttca tttagtcatc acttccaggg tgcaatgatt  2040
ctagcgggag agcgtgttcc atataatagt gaatacgctc ttatccgtgg taatatttcc  2100
ggtggtgcat gggtagactg gcgaggtcgt ccggctggat tgttggtaga ctgtcaggac  2160
tcacgaaatc aagcatataa catttggaaa gctactcatt ggggcgacca gcaccttgcg  2220
gcgatgggtg ttcatgctgg cggtggtaat cctcaggttg tattgcatgt gggtgggaat  2280
gattatgcat ttgcatctaa cggtgatttt actgctggtg ctgctgtata ttgtaacgac  2340
gtttatattc gttctgaccg tcgtctgaaa attaatgtta aagactacga agagaatgcg  2400
gtggataagg taaataaact caaagttaaa acctatgata aagttaaatc tctttctgac  2460
cgcgaagtta tcggccatga gattggtatt atcgcacagg atttgcaaga agtattaccg  2520
gaagctgtta gcacttctag tgtcggatct caggataacc cagaagaaat tttaacaatt  2580
tctaactctg ctgtgaacgc gcttttaatt aaggctattc aggaaatgag tgaagaaatt  2640
aaagaattga aacgcctctc ctttactaaa attgctcgca aaattagtaa atattttaaa  2700
ttctaa                                                             2706

SEQ ID NO: 155         moltype = DNA  length = 2940
FEATURE                Location/Qualifiers
misc_feature           1..2940
                       note = Synthetic: WW13 10.0
source                 1..2940
                       mol_type = other DNA
                       organism = synthetic construct
SEQUENCE: 155
atggcagtaa agatttcagg agtcctgaaa gacggcacag gaaaaccggt acagaactgc  60
accattcagc tgaaagccag acgtaacagc accacggtgg tggtgaacac ggtgggctca  120
gagaatccgg atgaagccgg gcgttacagc atggatgtgg agtacggtca gtacagtgtc  180
atcctgcagg ttgacggttt tccaccatcg cacgccggga ccatcaccgt gtatgaagat  240
tcacaaccgg ggacgctgaa tgatttctc tgtgccatga cggaggatga tgcccggccg  300
gaggtgctgc gtcgtcttga actgatggtg gaagaggtgg cgcgtaacgc gtccgtggtg  360
gcacagagta cggcagacgc gaagaaatca gccggcgatg ccagtgcatc agctgctcag  420
gtcgcggccc ttgtgactga tgcaactgac tcagcacgcg ccgccagcac gtccgccgga  480
caggctgcat cgtcagctca ggaagcgtcc tccggcgcag aagcggcatc agcaaaggcc  540
actgaagcgg aaaaaagtgc cgcagccgca gagtcctcaa aaacgcggc ggccaccagt  600
gccggtgcgg cgaaaacgtc agaaacgaat gctgcagcgt cacaacaatc agccgccacg  660
tctgcctcca ccgcggccac gaaagcgtca gaggccgcca cttcagcacg agatgcggtg  720
gcctcaaaag aggcagcaaa atcatcagaa acgaacgcat catcaagtgc cggtcgtgca  780
gcttcctcgg caacggcggc agaaaattct gccagggcgg caaaaacgtc cgagacgaat  840
gccaggtcat ctgaaacagc agcggaacgg agcgcctctg ccgcggcaga cgcaaaaaca  900
gcggcggcgg ggagtgcgtc aacggcatcc acgaaggcga cagaggctgc gggaagtgcg  960
gtatcagcat cgcagagcaa aagtgcggca gaagcggcgg caatacgtgc aaaaaattcg  1020
gcaaaacgtg cagaagatat agcttcagct gtcgcgcttg aggatgcgga cacaacgaga  1080
aaggggatag tgcagctcag cagtgcaacc aacagcacgt ctgaaacgct tgctgcaacg  1140
ccaaaggcgg ttaaggtggt aatggatgag actaatcgtg ttgaccgagc agttcacacc  1200
cttggcgaaa tcactacaaa tgctgttaat ggtcttcgta tttggaataa tgattatgga  1260
gtcattttta gacgttcaga aggaagtctt catattattc ctaccgcatt tggtgaagga  1320
gaaaccggtg atattggacc tttacgtcct ctcagtatag ctttagatac cggtaaagtt  1380
actattccgg atttacaatc aagttacaat acgttcgctg ctaacggtta tattaaattt  1440
gttggtcatg gagcgggggc cggcggttat gacattcaat atgctcaagc ggctcctatt  1500
ttccaggaaa tcgatgatga tgctgtaagc aaatattatc ctattgttaa acagaagttt  1560
ttaaacggta aatccgtttg gtctttaggt accgaaattg aatcaggtac attcgttatt  1620
catcatctga aagaagatgg ttcacaaggc catgcgtctc gttttaatca agacggtact  1680
gttaacttcc cggataacgt tctggtcggc ggtgatatta acatgaaagg catgatgact  1740
tttgacgccg gacgtttagg atcacgagat tattttaaat ttaaccattg gggtgatagt  1800
aataatggtc gtgataacat catccagtta gaagatagtc aaggcgccca tttttccact  1860
gaacgtactt tagcgacagg tgcaattaaa actcgtttct ttggcgaaac atttactgat  1920
ggtacattat acctaaatca gatgaataat agttctgaac gattctctat taataattgg  1980
ggaaattcag aagttggtcg cccggcagtg ttggaagtcg gtgattccaa aggttatcac  2040
ttctatacgg aacgcgggac agataacagt ttgaattttg atgttgctgg caattttact  2100
gtgcatggac cttccgggat tactatcaaa acctctactg gtgctcgcca tatctggttt  2160
```

```
agagatgata gcgatgcaga aaaggctgtt atctgggcta cagatgaggg tattttacat  2220
atacgaaata attatggggg ttcatttagt catcacttcc agggtgcaat gattctagcg  2280
ggagagcgtg ttccatataa tagtgaatac gctcttatcc gtggtaatat ttccggtggt  2340
gcatgggtag actggcgagg tcgtccggct ggattgttgg tagactgtca ggactcacga  2400
aatcaagcat ataacatttg gaaagctact cattggggcg accagcacct tgcggcgatg  2460
ggtgttcatg ctggcggtgg taatcctcag gttgtattgc atgtgggtgg gaatgattat  2520
gcatttgcat ctaacggtga ttttactgct ggtgctgctg tatattgtaa cgacgtttat  2580
attcgttctg accgtcgtct gaaaattaat gttaaagact acgaagagaa tgcggtggat  2640
aaggtaaata aactcaaagt taaaacctat gataaagtta aatctctttc tgaccgcgaa  2700
gttatcggcc atgagattgg tattatcgca caggatttgc aagaagtatt accggaagct  2760
gttagcactt ctagtgtcgg atctcaggat aacccagaag aaattttaac aatttctaac  2820
tctgctgtga acgcgctttt aattaaggct attcaggaaa tgagtgaaga aattaaagaa  2880
ttgaaaacgc ctctctttac taaaattgct cgcaaaatta gtaaatattt taaattctaa  2940
```

```
SEQ ID NO: 156          moltype = DNA  length = 4299
FEATURE                 Location/Qualifiers
misc_feature            1..4299
                        note = Synthetic: WW13-G8
source                  1..4299
                        mol_type = other DNA
                        organism = synthetic construct
SEQUENCE: 156
atggcagtaa agatttcagg agtcctgaaa gacggcacag gaaaaccggt acagaactgc  60
accattcagc tgaaagccag acgtaacagc accacggtgg tggtgaacac ggtgggctca  120
gagaatccgg atgaagccgg gcgttacagc atggatgtgg agtacggtca gtacagtgtc  180
atcctgcagg ttgacggttt tccaccatcg cacgccggga ccatcaccgt gtatgaagat  240
tcacaaccgg ggacgctgaa tgatttttctc tgtgccatga cggaggatga tgcccggccg  300
gaggtgctgc gtcgtcttga actgatggtg gaagaggtgg cgcgtaacgc gtccgtggtg  360
gcacagagta cggcagacgc gaagaaatca gccggcgatg ccagtgcatc agctgctcag  420
gtcgcggccc ttgtgactga tgcaactgac tcagcacgcg ccgccagcac gtccgccgga  480
caggctgcat cgtcagctca ggaagcgtcc tccggcgcag aagcggcatc agcaaaggcc  540
actgaagcgg aaaaaagtgc cgcagccgca gagtcctcaa aaaacgcggc ggccaccagt  600
gccggtgcgg cgaaaacgtc agaaacgaat gctgcagcgt cacaacaatc agccgccacg  660
tctgcctcca ccgcggccac gaaagcgtca gaggccgcca cttcagcacg agatgcggtg  720
gcctcaaaag aggcagcaaa atcatcagaa acgaacgcat catcaagtgc cggtcgtgca  780
gcttcctcgg caacggcggc agaaaattct gccagggcgg caaaaacgtc cgagacgaat  840
gccaggtcat ctgaaacagc agcggaacgg agcgcctctg ccgcggcaga cgcaaaaaca  900
gcggcggcgg ggagtgcgtc aacggcatcc acgaaggcga cagaggctgc gggaagtgcg  960
gtatcagcat cgcagagcaa aagtgcggca gaagcggcgg caatacgtgc aaaaaattcg  1020
gcaaaacgtg cagaagatat agcttcagct gtcgcgcttg aggatgcgga cacaacgaga  1080
aaggggatag tgcagctcag cagtgcaacc aacagcacgt ctgaaacgct tgctgcaacg  1140
ccaaaggcgg ttaaggtggt aatggatgag actaatcgtg gaaatattat tgatctgggt  1200
tttgctaaag gcggtagtat tgacggaaat gttattcata taggaaatta taatcaaact  1260
ggtgattata ctttaaatgg caccttcact cagacaggta attttaattt aactggtatt  1320
gctcgagtaa ctcgcgatat tattgccgcc gggcaaatta tgactgaggg cggagaactt  1380
attacaaaaa gttcaggtac agcacatgtt cgtttttttcg atggcaatag ccgcgaacgt  1440
ggaatcattt atgccccggc caatgatggt ttaactacgc aagttcttaa tatcagggtt  1500
caagactacg ccgctggtag cgaaagcact tatgcatttt caggcagtgg cctatttact  1560
tcacctgaag tatcggcatg gaaatctatg tcaactcctc agattttgac cgataaagtt  1620
attacaaatg ggaagaagac aggcgattat gatatctatt cattatcaaa taacactcca  1680
ttggcagaaa gcgaaacggc tattaaccac ctccgtgtta tgcgaaatgc tgtaggagca  1740
ggtattttcc acgaagttaa tgttaatgac ggaataacct ggtattccgg agatggctta  1800
gacacttatc tttggtcgtt taactgggcc ggtggattga aagctggtca ttctatttct  1860
gtaggtcttc cgggtggctc taaaggatat tctgaattag gaacggcctc aattgctctt  1920
ggtgataatg acaccggatt taaatggcat caggacggat attttcatac agtaaacaat  1980
ggaacaagaa ctttcatcta cggccctgcg gaaacacaaa gccttagaaa aatggttatg  2040
ggttattctc cggacgggat tcttatgaca acgccaccga cagaaaacta tgctcttgct  2100
actgtagtga catacccacga taataacgcg tttggagatg gtcaaactct tttaggatat  2160
tatcaaggcg gtaactatca tcactatttc cgcggtaagg gtactacaaa cattaatact  2220
catggcggtt tgttagttac tccaggcaat attgacgtta ttggtggttc tgttaatatc  2280
gatggtagaa ataataattc aactttaatg tttaaaggct ataccatggg tcaaagctcc  2340
gttgataaca tgtatatagc tgtttgggga aatacattta ctaatcctag tgaaggcacc  2400
cgtaaaaatg tcatggaaat ttctgatgat attggatgga tgcattatat tcaacgaaat  2460
aaagataata cagttgaagc cgtattaaat ggtcaacaga caattaacga aaatattatt  2520
gcgaaaaagg atatttgggt tgaccgagca gttcacaccc ttggcgaaat cactacaaat  2580
gctgttaatg gtcttcgtat ttggaataat gattatggag tcatttttag acgttcagaa  2640
ggaagtcttc atattattcc taccgcattt ggtgaaggag aaaccggtga tattggacct  2700
ttacgtcctc tcagtatagc tttagatacc ggtaaagtta ctattccgga tttacaatca  2760
agttacaata cgttcgctgc taacggttat attaaatttg ttggtcatgg agcgggggcc  2820
ggcggttatg acattcaata tgctcaagcg gctcctattt tccaggaaat cgatgatgat  2880
gctgtaagca aatattatcc tattgttaaa cagaagtttt taaacggtaa atccgtttgg  2940
tctttaggta ccgaaattga atcaggtaca ttcgttattc atcatctgaa agaagatggt  3000
tcacaaggcc atgcgtctcg ttttaatcaa gacggtactg ttaacttccc ggataacgtt  3060
ctggtcggcg gtgatattaa catgaaaggc atgatgactt ttgacgccgg acgtttagga  3120
tcacgagatt attttaaatt taaccattgg ggtgatagta ataatggtcg tgataacatc  3180
atccagttag aagatagtca aggcgcccat ttttccactg aacgtacttt agcgacaggt  3240
gcaattaaaa ctcgtttctt tggcgaaaca tttactgatg gtacattata cctaaatcag  3300
atgaataata gttctgaacg attctctatt aataattggg gaaattcaga agttggtcgc  3360
ccggcagtgt tggaagtcgg tgattccaaa ggttatcact tctatacgga acgcgggaca  3420
```

```
gataacagtt tgaattttga tgttgctggc aattttactg tgcatggacc ttccgggatt  3480
actatcaaaa cctctactgg tgctcgccat atctggttta gagatgatag cgatgcagaa  3540
aaggctgtta tctgggctac agatgagggt attttacata tacgaaataa ttatgggggt  3600
tcatttagtc atcacttcca gggtgcaatg attctagcgg gagagcgtgt tccatataat  3660
agtgaatacg ctcttatccg tggtaatatt tccggtggtg catgggtaga ctggcgaggt  3720
cgtccggctg gattgttggt agactgtcag gactcacgaa atcaagcata taacatttgg  3780
aaagctactc attggggcga ccagcacctt gcggcgatgg gtgttcatgc tggcggtggt  3840
aatcctcagg ttgtattgca tgtgggtggg aatgattatg catttgcatc taacggtgat  3900
tttactgctg gtgctgctgt atattgtaac gacgtttata ttcgttctga ccgtcgtctg  3960
aaaattaatg ttaaagacta cgaagagaat gcggtggata aggtaaataa actcaaagtt  4020
aaaacctatg ataaagttaa atctctttct gaccgcgaag ttatcggcca tgagattggt  4080
attatcgcac aggatttgca agaagtatta ccggaagctg ttagcacttc tagtgtcgga  4140
tctcaggata acccagaaga aattttaaca atttctaact ctgctgtgaa cgcgctttta  4200
attaaggcta ttcaggaaat gagtgaagaa attaaagaat tgaaaacgcc tctctttact  4260
aaaattgctc gcaaaattag taaatatttt aaattctaa                        4299
```

```
SEQ ID NO: 157          moltype = DNA  length = 780
FEATURE                 Location/Qualifiers
misc_feature            1..780
                        note = Synthetic: WW13 GP38
source                  1..780
                        mol_type = other DNA
                        organism = synthetic construct
SEQUENCE: 157
atggcagtag ttggagttcc tggctggatt ggaagttcag ccgtaaatga aacgggtcag  60
cgctggatga gtcaagcagc tggtcaatta agattgggtg ttccttgctg gatgagtcaa  120
tttgcaggtc gctcaagaga aattattcat acacttggag cagaccataa cttcaatggt  180
caatggttcc gagatagatg ttttgaggca ggtagtacac ctatagtgtt taatatcact  240
ggagatttag tatcatattc taaagatgtt cctttattct tcatgtacgg agatacaccg  300
aatgaatatg ttcaactgaa tatacacggc gtaacgatgt atggacgtgg cggtaatggc  360
ggtagcaata gtcctggttc agctggaggt cattgtattc aaaacgatat tggtgggaga  420
ctaagaatta ataacggtgg agctattgcc ggcggcggcg gtggcggcgg tggcggtaga  480
tatggcagac tatcatttgg tggtggcggt ggtcgcccat tcggtgctgg cgggtcttcc  540
tctcatatga gttccggtgc aactgctggc accatttccg ctccgggtgc aggatctgtc  600
ggtgagggat ctctttgggt atatacaggc ggttcgggtg gtaatgtcgg tgctgctgga  660
ggaagatgta atattcaagg taacggtaca gaatatgatg gcggtgctgc tggttatgct  720
gttatagggt ctgctccaac ttggataaat gttggagcaa tatatggtcc aagagtataa  780
```

```
SEQ ID NO: 158          moltype = DNA  length = 243
FEATURE                 Location/Qualifiers
misc_feature            1..243
                        note = Synthetic: WW13 GP57A
source                  1..243
                        mol_type = other DNA
                        organism = synthetic construct
SEQUENCE: 158
atgtctgaac aaactattga acaaaaaactg tctgctgaaa tcgtaactct gaagtctcgt  60
atccttgata cgcaggacca agcggctcgt ctgatggaag aatccaaaat tctgcaagga  120
actttggctg aaattgctcg tgcagtaggt atcactggcg atactatcaa agttgaagaa  180
atcgttgaag ctgtcaagaa tcttactgct gaatctgcag atgaagcaaa agatgaagaa  240
tga                                                               243
```

```
SEQ ID NO: 159          moltype = DNA  length = 2796
FEATURE                 Location/Qualifiers
misc_feature            1..2796
                        note = Synthetic: PP-1
source                  1..2796
                        mol_type = other DNA
                        organism = synthetic construct
SEQUENCE: 159
atggcagtaa agatttcagg agtcctgaaa gacggcacag gaaaaccggt acagaactgc  60
accattcagc tgaaagccag acgtaacagc accacggtgg tggtgaacac ggtgggctca  120
gagaatccgg atgaagccgg gcgttacagc atggatgtgg agtacggtca gtacagtgtc  180
atcctgcagg ttgacggttt tccaccatcg cacgccggga ccatcaccgt gtatgaagat  240
tcacaaccgg ggacgctgaa tgattttctc tgtgccatga cggaggatga tgcccggccg  300
gaggtgctgc gtcgtcttga actgatggtg gaagaggtgg cgcgtaacgc gtccgtggtg  360
gcacagagta cggcagacgc gaagaaatca gccggcgatg ccagtgcatc agctgctcag  420
gtcgcggccc ttgtgactga tgcaactgac tcagcacgcg ccgccagcac gtccgccgga  480
caggctgcat cgtcagctca ggaagcgtcc tccggcgcag aagcggcatc agcaaaggcc  540
actgaagcgg aaaaaagtgc cgcagccgca gagtcctcaa aaacgcggc ggccaccagt  600
gccggtgcgg cgaaaacgtc agaaacgaat gctgcagcgt cacaacaatc agccgccacg  660
tctgcctcca ccgcggccac gaaagcgtca gaggccgcca cttcagcacg agatgcggtg  720
gcctcaaaag aggcagcaaa atcatcagaa acgaacgcat catcaagtgc cggtcgtgca  780
gcttcctcgg caacggcggc agaaaattct gccagggcgg caaaaacgtc cgagacgaat  840
gccaggtcat ctgaaacagc agcggaacgg agcgcctctg ccgcggcaga cgcaaaaaca  900
gcggcggcgg ggagtgcgtc aacggcatcc acgaaggcga cagaggctgc gggaagtgcg  960
gtatcagcat cgcagagcaa aagtgcggca gaagcggcgg caatacgtgc aaaaaattcg  1020
gcaaaacgtg cagaagatat agcttcagct gtcgcgcttg aggatgcgga cacaacgaga  1080
aaggggatag tgcagctcag cagtgcaacc aacagcacgt ctgaaacgct tgctgcaacg  1140
```

```
ccaaaggcgg ttaaggtggt aatggatgag actaatcgta aggcacctct ggacagtccg  1200
gcactgaccg gaacgccaac agcaccaacc gcgctcaggg gaacaaacaa tacccagatt  1260
gcgaacaccg cttttgtact ggccgcgatt gcagatgtta tcgacgcgtc acctgacgca  1320
ctgaatacgc tgaatgaact ggccgcagcg ctcgggaatg atccagattt tgctaccacc  1380
atgactaacg cgcttgcggg taaacaaccg aagaatgcga cactgacggc gctggcaggg  1440
ctttccacgg cgaaaaataa attaccgtat tttgcggaaa atgatgccgc cagcctgact  1500
gaactgactc aggttggcag ggatattctg gcaaaaaatt ccgttgcaga tgttcttgaa  1560
taccttgggg ccggtgagaa ttcgatcgct acccgcgtgt ccaaagaagg tgacactatg  1620
actggtaagc tgactctgtc tgcgggtaac gatgcgctgg tgctgactgc gggcgagggc  1680
gcgtcctcgc acattcgctc tgacgtgggc gggacgaaca actggtatat cggtaaaggc  1740
agtggggata acggtttagg cttctactca tacatcactc agggcggggt gtatattacc  1800
aacaacgggg aaatcgcttt aagcccgcag ggtcagggta cgtttaactt caaccgtgat  1860
cgtctgcaca tcaacggcac gcaatggacg gcacatcaag gcggtggctg ggaaaaccag  1920
tggaatcagg aagcgccgat ttttattgat ttcggcaacg tgggcaatga tagctactac  1980
ccgattatca aggtaagtc cggcattacc aacgaaggtt atatttctgg cgtggacttc  2040
ggtatgcgtc ggattactaa cacgtgggcg cagggtatta tccgcgtagg caatcaggaa  2100
aacggtagcg atccgcaggc catctacgag ttccatcata atggcgtact gtacgttcct  2160
aatatggtaa aaacgggtgc gcgtctgagc gcaggtgggg gggatccggt atggcagggt  2220
gcatgtgttg ttatcggtga caatgacacg ggcttagtgc atggtggcga tggtcgcatc  2280
aatatggttg caaacggtat gcacattgcg tcttggagtt ccgcgtatca tttacatgag  2340
ggtttatggg atactacggg cgcgttatgg acggagcaag ggcgtgcaat tatcagcttc  2400
ggtcatctgg tacaacaaag cgatgcctat tccacctttg tccgtgatgt atacgttcgt  2460
tcggatattc gcgttaaaaa agatctggtg aaattcgaaa acgctagcga aaaactgtcc  2520
aaaatcaacg gttatactta tatgcagaaa cgcgggttag acgaagaagg taatcagaaa  2580
tgggagccta acgccggatt aatcgcgcag gaagtgcagg cgattctgcc ggaactggta  2640
gaaggcgatc cggacggtga agcattatta cgtctgaact acaatggcgt gatcggcctg  2700
aatactgcgg cgattaatga acatacggca gagatcgcgg agctgaaaag cgagattgaa  2760
gaactgaaaa aaattgtcaa aagcctgtta aagtaa                            2796

SEQ ID NO: 160          moltype = DNA  length = 780
FEATURE                 Location/Qualifiers
misc_feature            1..780
                        note = Synthetic: PP-1 GP38
source                  1..780
                        mol_type = other DNA
                        organism = synthetic construct
SEQUENCE: 160
atggcagtaa caggaccgtg ggtaggatcg tctgcagtag ttaatacagg acaaaattgg  60
atggtcggcg cggcccaacg attaagaatg ggtgctccgt tctggatgag caacatgatt  120
gggcgctctg ttgaagtgat tcatacgtta ggcgcagatc ataattttaa tggtcaatgg  180
tttcgtgacc gttgctttga ggcgggcagt gcgccgatcg tgtttaacat cactggcgat  240
ttagtttctt actcccgtga cgttccgctg tttttcatgt atggtgacac gccgaacgag  300
tatgtacaat taaacattca cggtgtcacg atgtacgggc gcgggggcaa cggttgggcg  360
gcgggtgcaa tcggtgcgag cgatggcggg gtgtgcatcc agaatgatat tggaggccga  420
ctgcgtatca acaatggtgg ggcaatcgcg ggcggtggcg gtggtggggg tggttattct  480
caggctaaca attgggcagg taagtacgtt tgcggtggcg gtggcggtcg tccgttcggc  540
ttaggtggca acaacggtgc gcgttggcct gggggcaacg ctagcctgac ctcgccgggc  600
gcaggtggga acactggcac gcgttattac gctggcgggg gaggtgaggt tggtcagccg  660
ggtcagtatg caaaccccgg cgcgggttac tccaccccac caacgtcgcc gggcgcggca  720
gttgcaggta gtgcgccaac ttggcaaaac gtgggcgcta tttatggccc gcgtgtttaa  780

SEQ ID NO: 161          moltype = DNA  length = 243
FEATURE                 Location/Qualifiers
misc_feature            1..243
                        note = Synthetic: PP-1 GP57A
source                  1..243
                        mol_type = other DNA
                        organism = synthetic construct
SEQUENCE: 161
atgagtgaac agaccatcga acaaaaatta agcgcggaaa tcgtgactct gaaaagtcgc  60
attctggata ctcaggacca ggcagcacgt ctgatggaag agtctaaaat cttgcagggc  120
actctggcag aaattgcccg tgcggtgggt atcacaggcg acacgatcaa agtagaagaa  180
attgtggagg ccgtaaagaa tctcacagcg gagagcaccg atgaagcaaa agacgaagaa  240
taa                                                                243

SEQ ID NO: 162          moltype = DNA  length = 3654
FEATURE                 Location/Qualifiers
misc_feature            1..3654
                        note = Synthetic: WW55 3.0
source                  1..3654
                        mol_type = other DNA
                        organism = synthetic construct
SEQUENCE: 162
atggcagtaa agatttcagg agtcctgaaa gacggcacag gaaaaccggt acagaactgc  60
accattcagc tgaaagccag acgtaacagc accacggtgg tggtgaacac ggtgggctca  120
gagaatccgg atgaagccgg gcgttacagc atggatgtgg agtacggtca gtacagtgtc  180
atcctgcagg ttgacggttt tccaccatcg cacgccggga ccatcaccgt gtatgaagat  240
tcacaaccgg ggacgctgaa tgattttctc tgtgccatga cggaggatga tgcccggccg  300
gaggtgctgc gtcgtcttga actgatggtg gaagaggtgg cgcgtaacgc gtccgtggtg  360
```

```
gcacagagta cggcagacgc gaagaaatca gccggcgatg ccagtgcatc agctgctcag  420
gtcgcggccc ttgtgactga tgcaactgac tcagcacgcg ccgccagcac gtccgccgga  480
caggctgcat cgtcagctca ggaagcgtcc tccggcgcag aagcggcatc agcaaaggcc  540
actgaagcgg aaaaaagtgc cgcagccgca gagtcctcaa aaaacgcggc ggccaccagt  600
gccggtgcgg cgaaaacgtc agaaacgaat gctgcagcgt cacaacaatc agccgccacg  660
tctgcctcca ccgcggccac gaaagcgtca gaggccgcca cttcagcacg agatgcggtg  720
gcctcaaaag aggcagcaaa atcatcagaa acgaacgcat catcaagtgc cggtcgtgca  780
gcttcctcgg caacggcggc agaaaattct gccagggcgg caaaaacgtc cgagacgaat  840
gccaggtcat ctgaaacagc agcggaacgg agcgcctctg ccgcggcaga cgcaaaaaca  900
gcggcggcgg ggagtgcgtc aacggcatcc acgaaggcga cagaggctgc gggaagtgcg  960
gtatcagcat cgcagagcaa aagtgcggca gaagcggcgg caatacgtgc aaaaaattcg  1020
gcaaaaacgtg cagaagatat agcttcagct gtcgcgcttg aggatgcgga cacaacgaga  1080
aaggggatag tgcagctcag cagtgcaacc aacagcacgt ctgaaacgct tgctgcaacg  1140
ccaaaggcgg ttaaggtggt aatggatgag actaatcgta ctccaggaga attgaacgtc  1200
tatagcaaac aagaaattga ccgtatgttt gttaagaacg ttaaaatggt tgttccttct  1260
ggtggtgcaa cccgtggtta ttttaaaatt gcatccgcaa tgatcccgca gagtggtcgg  1320
atggcgtttc tgcgaatcta tggtggtaat ggatataatg taaactcata tgatcaagtt  1380
gattttcttg aaattgtgat tcgtagtggt aataataacc ctaaaggcgt tagtattgct  1440
gcatatcgtc gaaattcttt gaacgtccat gaagtatttg caattaatac ttccggtgat  1500
aactatgaca tttatgttaa ctatggtcgc ttcaccgata acgttattgt agagtttgga  1560
aaaactgttg acgtcgcatt gactgttcat gatgttcctg aattttcggc gactaaacca  1620
gaaaccggaa ctaaatttga tgctcgtgtt attacgatgt tcaacaccga aaacaaagcc  1680
ggaacattga tgtttgataa taacaatcag ttaacctatg atattgttag ccttagcaat  1740
ggtcctgatg atgttagaaa ttatctgcgt aaattccgaa gtaaagcggg tgaaatgatt  1800
tggcatgaaa ccgttcaggg tgctgtatat cgtcttgcta ctggaactac tgattctacg  1860
gaagttctta gagttgattc taacagtgct ctcccgggta gctataaagg atatgtaatt  1920
actggtaaaa tggaattgca cggtagcggt agtgcgatga atttacaccg ccagactggt  1980
caagctgcat atatggcgtg gtgggatcgt cgtgatggta aaaaccaacg tagcggttat  2040
atcggtcatg cggatggtac tactgatggt tttgtgtggc gtaatgatgt tggtgcgaac  2100
tcatttgatt tggaaagtag tggacaagta aatttgacta caggaaaaac aaaaattgta  2160
tataccaacg gacaatatta ttccgctaac tctgatgcat tccgtatgat ttacggcaat  2220
tatggcgcat tctggcgaaa tgatggtggt aaagtttatc tgttgtctac tgccgaaaat  2280
gatagatttg gtggatggaa cggcaaccga ccattcattt acgacctgtc aactggtaaa  2340
gttactttag gtggcgacgg taacgaaggc gcattagttc tcgaaagaga tagccgtgcg  2400
gctagattta gcaacagcgt attcttagaa aaaggattgc ttactttctc tgcgggtggg  2460
aatcagtcaa tggattcttt cacgattaac cattggggga atagtaacgc tggacgatat  2520
aatgttttac aatttgaaga cacgaaagga acacatttta caaccgaacg taatgctgat  2580
ggtggattgc ttgctcactt ccgaggggat ttaaccacag aagggaaatt aacgtggggt  2640
aagggtacag ccacatctag ctttaacatt cgtgcatggg gtaatagtga ttcccgtaaa  2700
caggttttcg agtgtgtaga tgaaagtggt tggcattggt atacccagcg accgggcggt  2760
cctggtactt ctgcaattga gtttgccatc aatggtactg ttaagcctca agcaattcac  2820
actggcggta atattctttt gaacggtgct gatattgagt ttcgtcgcac tggtaataag  2880
catttgtggt ttagagatcc aaacggatta gaattgggtt tgatttattg tgatgacaac  2940
ggtgtcattc gttttcgtgg tcagaaacaa ggtcaagatt gggtatttgc caataagatg  3000
atccaattag ggaccgcttc tactgttggt ggatctggta acggtttgat tcgcggacaa  3060
gttcaaggtg gtgcttgggc acaatggaga gaccgtgctg ctggaatcct tgtagactgt  3120
cagcaatcta ctgattccgc tcataacatc tggaaagcga ctcattgggg aaaatatcat  3180
attgcggcaa tgggtgtaca cgttcctagc ggcactatag gtaatgctat ggcacgtcta  3240
aacgtaaatg acgccaactt tgactttagc gcctccggtg acatgtcggc agggcgtaac  3300
ggttcgttta acgatgttta tattcgttct gatgctcgcc ttaaaatcaa taaggaagag  3360
tataaagaga atgccaccga taaagttaat cgcttaactg tatacaccta tgacaaggtt  3420
aaatctttaa ccgaccgtac tgtcattgct catgaagttg gcattatcgc acaggatctt  3480
gagaaagaat tgccggaagc agtaacaacc tcgaagatcg gcgatccaga taaaccagaa  3540
gagatcttaa caatttctaa ctctgctgtc aacgctcttt taattaaggc gtttcaggaa  3600
atgagcgaag aattgaaagc cgttaaagct gaactagcgg aacttaaaaa gtaa        3654
```

```
SEQ ID NO: 163          moltype = DNA  length = 3993
FEATURE                 Location/Qualifiers
misc_feature            1..3993
                        note = Synthetic: WW55-G8
source                  1..3993
                        mol_type = other DNA
                        organism = synthetic construct
SEQUENCE: 163
atggcagtaa agatttcagg agtcctgaaa gacggcacag gaaaaccggt acagaactgc  60
accattcagc tgaaagccag acgtaacagc accacggtgg tggtgaacac ggtgggctca  120
gagaatccgg atgaagccgg gcgttacagc atggatgtgg agtacggtca gtacagtgtc  180
atcctgcagg ttgacggttt tccaccatcg cacgccggga ccatcaccgt gtatgaagat  240
tcacaaccgg ggacgctgaa tgattttctc tgtgccatga cggaggatga tgcccggccg  300
gaggtgctgc gtcgtcttga actgatggtg gaagaggtgg cgcgtaacgc gtccgtggtg  360
gcacagagta cggcagacgc gaagaaatca gccggcgatg ccagtgcatc agctgctcag  420
gtcgcggccc ttgtgactga tgcaactgac tcagcacgcg ccgccagcac gtccgccgga  480
caggctgcat cgtcagctca ggaagcgtcc tccggcgcag aagcggcatc agcaaaggcc  540
actgaagcgg aaaaaagtgc cgcagccgca gagtcctcaa aaaacgcggc ggccaccagt  600
gccggtgcgg cgaaaacgtc agaaacgaat gctgcagcgt cacaacaatc agccgccacg  660
tctgcctcca ccgcggccac gaaagcgtca gaggccgcca cttcagcacg agatgcggtg  720
gcctcaaaag aggcagcaaa atcatcagaa acgaacgcat catcaagtgc cggtcgtgca  780
gcttcctcgg caacggcggc agaaaattct gccagggcgg caaaaacgtc cgagacgaat  840
gccaggtcat ctgaaacagc agcggaacgg agcgcctctg ccgcggcaga cgcaaaaaca  900
```

```
gcggcggcgg ggagtgcgtc aacggcatcc acgaaggcga cagaggctgc gggaagtgcg  960
gtatcagcat cgcagagcaa aagtgcggca gaagcggcgg caatacgtgc aaaaaattcg  1020
gcaaaacgtg cagaagatat agcttcagct gtcgcgcttg aggatgcgga cacaacgaga  1080
aaggggatag tgcagctcag cagtgcaacc aacagcacgt ctgaaacgct tgctgcaacg  1140
ccaaaggcgg ttaaggtggt aatggatgag actaatcgtg gtgctattat caatttaagt  1200
tgtcctcctg tttatgaccg cgatgttaca atggcgggta aggttaaagg taataattat  1260
atcttaagta aaaccgctaa ctatctggaa gatcagacag cgagagatct taactacttt  1320
ggcgctttcc gtaccaatgg tcttgatggt cttctcgaac tcacgctaaa cgttcctcac  1380
tcttccggtg tccaacatgg tcgaggattt actttccagt atgggcacac tggatcgcgt  1440
gtagaaactt atggctataa taaagaaggt caaaaagcat ttagttataa aatgtatcac  1500
gaaggtgata aaccaactcc aggagaattg aacgtctata gcaaacaaga aattgaccgt  1560
atgtttgtta agaacgttaa aatggttgtt ccttctggtg gtgcaacccg tggttatttt  1620
aaaattgcat ccgcaatgat cccgcagagt ggtcggatgg cgtttctgcg aatctatggt  1680
ggtaatggat ataatgtaaa ctcatatgat caagttgatt ttcttgaaat tgtgattcgt  1740
agtggtaata ataaccctaa aggcgttagt attgctgcat atcgtcgaaa ttctttgaac  1800
gtccatgaag tatttgcaat taatacttcc ggtgataact atgacattta tgttaactat  1860
ggtcgcttca ccgataacgt tattgtagag tttggaaaaa ctgttgacgt cgcattgact  1920
gttcatgatg ttcctgaatt ttcggcgact aaaccagaaa ccggaactaa atttgatgct  1980
cgtgttatta cgatgttcaa caccgaaaac aaagccggaa cattgatgtt tgataataac  2040
aatcagttaa cctatgatat tgttagcctt agcaatggtc ctgatgatgt tagaaattat  2100
ctgcgtaaat tccgaagtaa agcgggtgaa atgatttggc atgaaaccgt tcagggtgct  2160
gtatatcgtc ttgctactgg aactactgat tctacggaag ttcttagagt tgattctaac  2220
agtgctctcc cgggtagcta taaaggatat gtaattactg gtaaaatgga attgcacggt  2280
agcggtagtg cgatgaattt acaccgccag actggtcaag ctgcatatat ggcgtggtgg  2340
gatcgtcgtg atggtaaaaa ccaacgtagc ggttatatcg gtcatgcgga tggtactact  2400
gatggttttg tgtggcgtaa tgatgttggt gcgaactcat ttgatttgga aagtagtgga  2460
caagtaaatt tgactacagg aaaaacaaaa attgtatata ccaacggaca atattattcc  2520
gctaactctg atgcattccg tatgatttac ggcaattatg gcgcattctg gcgaaatgat  2580
ggtggtaaag tttatctgtt gtctactgcc gaaaatgata gatttggtgg atggaacggc  2640
aaccgaccat tcatttacga cctgtcaact ggtaaagtta ctttaggtgg cgacggtaac  2700
gaaggcgcat tagttctcga aagagatagc cgtgcggcta gatttagcaa cagcgtattc  2760
ttagaaaaag gattgcttac tttctctgcg ggtgggaatc agtcaatgga ttctttcacg  2820
attaaccatt gggggaatag taacgctgga cgatataatg ttttacaatt tgaagacacg  2880
aaaggaacac attttacaac cgaacgtaat gctgatggtg gattgcttgc tcacttccga  2940
ggggatttaa ccacagaagg gaaattaacg tggggtaagg gtacagccac atctagcttt  3000
aacattcgtg catggggtaa tagtgattcc cgtaaacagg ttttcgagtg tgtagatgaa  3060
agtggttggc attggtatac ccagcgaccg ggcggtcctg gtacttctgc aattgagttt  3120
gccatcaatg gtactgttaa gcctcaagca attcacactg gcggtaatat tcttttgaac  3180
ggtgctgata ttgagtttcg tcgcactggt aataagcatt tgtggtttag agatccaaac  3240
ggattagaat tgggtttgat ttattgtgat gacaacggtg tcattcgttt tcgtggtcag  3300
aaacaaggtc aagattgggt atttgccaat aagatgatcc aattagggac cgcttctact  3360
gttggtggat ctggtaacgg tttgattcgc ggacaagttc aaggtggtgc ttgggcacaa  3420
tggagagacc gtgctgctgg aatccttgta gactgtcagc aatctactga ttccgctcat  3480
aacatctgga aagcgactca ttggggaaaa tatcatattg cggcaatggg tgtacacgtt  3540
cctagcggca ctataggtaa tgctatggca cgtctaaacg taaatgacgc caactttgac  3600
tttagcgcct ccggtgacat gtcggcaggg cgtaacggtt cgtttaacga tgtttatatt  3660
cgttctgatg ctcgccttaa aatcaataag gaagagtata aagagaatgc caccgataaa  3720
gttaatcgct taactgtata cacctatgac aaggttaaat ctttaaccga ccgtactgtc  3780
attgctcatg aagttggcat tatcgcacag gatcttgaga aagaattgcc ggaagcagta  3840
acaacctcga agatcggcga tccagataaa ccagaagaga tcttaacaat ttctaactct  3900
gctgtcaacg ctcttttaat taaggcgttt caggaaatga gcgaagaatt gaaagccgtt  3960
aaagctgaac tagcggaact taaaaagaat taa                              3993
```

```
SEQ ID NO: 164          moltype = DNA  length = 783
FEATURE                 Location/Qualifiers
misc_feature            1..783
                        note = Synthetic: WW55 GP38
source                  1..783
                        mol_type = other DNA
                        organism = synthetic construct
SEQUENCE: 164
atggcaatat cttctggatg ggtaggatca tctgctgtgt ccgagactgg tcaacggtgg  60
atgagcgccg caatgcaagc tgttcgctta ggtcgtccgg cgtatatgtc ggcaatggtc  120
ggacgctcta aagagattca ttatagcatt ggtgctagta actcttacaa taaagacact  180
cttattaact ggatgaaagc acaaggatct actccggtag taattactat cacgggtaat  240
attgtttccc aatctactgg cgttccttgt cttgatttcc ctagctcact gacaaacgaa  300
tatgtaacac tcattattaa ctctggtgtt catgtattag gtcgtggagg aaatggcgga  360
agtaactctg ctggtggagc aggaggaaat gcaataaata acggaattgg aactcgttta  420
agaataaaca ataatggtat tattggtggt ggcggtggtg gcggtgctgg tgctagatac  480
aatcctttcc ctcaaatgga tatgaaattt ggcggcggtg gaggccgtcc atttggtgct  540
gcgggtgcgg caggaggcgg cgcagcggca gcatctgctg gtacaatttc tgccccaggt  600
aaaggcactg tttctggggt tcattatgga ggagatggtg gagatttggg agctgctggc  660
aaatcttcat atattaaagg tggtactggt ggaactgttc actcgggtgg tgctgcgggt  720
aaagctgtta ctggtaatgc ccctcgctgg gataaagtag gcacgatcta cggtgctcgc  780
gtg                                                               783
```

```
SEQ ID NO: 165          moltype = DNA  length = 261
FEATURE                 Location/Qualifiers
misc_feature            1..261
```

```
                        note = Synthetic: WW55 GP57A
source                  1..261
                        mol_type = other DNA
                        organism = synthetic construct
SEQUENCE: 165
atgtccaatc agcatgaaca aatgattaat gtcctgaaag tacgtctgtt tgacactcaa  60
gaaaaggccg cattcttaga aggccaactg aaagatcgtg agcgtgtatt gatggaactg  120
gtacgcattc tgggtattca gccagacgaa aacggcactg tttcccttga tgctattgtc  180
gaagaagtga aagcacttct ccctaaagac gaagcagcgg aagacgcaga agaggaagta  240
gaactgatca cggaggcttg a                                             261

SEQ ID NO: 166          moltype = DNA  length = 3654
FEATURE                 Location/Qualifiers
misc_feature            1..3654
                        note = Synthetic: WW34 3.0
source                  1..3654
                        mol_type = other DNA
                        organism = synthetic construct
SEQUENCE: 166
atggcagtaa agatttcagg agtcctgaaa gacggcacag gaaaaccggt acagaactgc  60
accattcagc tgaaagccag acgtaacagc accacggtgg tggtgaacac ggtgggctca  120
gagaatccgg atgaagccgg gcgttacagc atggatgtgg agtacggtca gtacagtgtc  180
atcctgcagg ttgacggttt tccaccatcg cacgccggga ccatcaccgt gtatgaagat  240
tcacaaccgg ggacgctgaa tgattttctc tgtgccatga cggaggatga tgcccggccg  300
gaggtgctgc gtcgtcttga actgatggtg gaagaggtgg cgcgtaacgc gtccgtggtg  360
gcacagagta cggcagacgc gaagaaatca gccggcgatg ccagtgcatc agctgctcag  420
gtcgcggccc ttgtgactga tgcaactgac tcagcacgcg ccgccagcac gtccgccgga  480
caggctgcat cgtcagctca ggaagcgtcc tccggcgcag aagcggcatc agcaaaggcc  540
actgaagcgg aaaaaagtgc cgcagccgca gagtcctcaa aaaacgcggc ggccaccagt  600
gccggtgcgg cgaaaacgtc agaaacgaat gctgcagcgt cacaacaatc agccgccacg  660
tctgcctcca ccgcggccac gaaagcgtca gaggccgcca cttcagcacg agatgcggtg  720
gcctcaaaag aggcagcaaa atcatcagaa acgaacgcat catcaagtgc cggtcgtgca  780
gcttcctcgg caacggcggc agaaaattct gccagggcgg caaaaacgtc cgagacgaat  840
gccaggtcat ctgaaacagc agcggaacgg agcgcctctg ccgcggcaga cgcaaaaaca  900
gcggcggcgg ggagtgcgtc aacggcatcc acgaaggcga cagaggctgc gggaagtgcg  960
gtatcagcat cgcagagcaa aagtgcggca gaagcggcgg caatacgtgc aaaaaattcg  1020
gcaaaacgtg cagaagatat agcttcagct gtcgcgcttg aggatgcgga cacaacgaga  1080
aaggggatag tgcagctcag cagtgcaacc aacagcacgt ctgaaacgct tgctgcaacg  1140
ccaaaggcgg ttaaggtggt aatggatgag actaatcgta ctccaggaga attgaacgtc  1200
tatagcaaac aagaaattga ccgtatgttt gttaagaacg ttaaaatgtc tactccttct  1260
ggtgaagcaa cccgtggtta ttttaaaatt gcatccgcaa tgatcccgca gagtggtcgg  1320
atggcgtttc tgcgaatcta tggtgggaac ggatttaatg ttaactccta cgatcaggtg  1380
gatttccttg aaattgtgat tcgtagtggt aataataacc ctaaaggcgt tagtattgct  1440
gcatatcgtc gaaattcttt gaacgtccat gaagtatttg caattaatac ttccggtgat  1500
aactatgaca tttatgttaa ctatggtcgc ttcaccgata acgttattgt agagtttgga  1560
aaaactgttg atgttgcatt gactgttcac gatgttcctg aattttcggc gactaaacca  1620
gaaaccggaa ctaaatttga tgctcgtgtt attacgatgt tcaacaccga aaacaaagcc  1680
ggaacgttga tgtttgataa taacaatcag ttaacctatg atattgttag ccttagcaat  1740
ggtcctgatg atgttagaaa ttatctgcgt aaattccgaa gtaaagcggg tgaaatgatt  1800
tggcatgaaa cagttcaggg tgctgtatat cgtcttgcta ctggaactac tgattctacg  1860
gaagttctta gagttgattc taatagtgct ataccaggta gctataaagg atatgtaatt  1920
actggtaaaa tggaattgca tggtagtggt aattcgatga ttttacatcg ccagactgct  1980
caagccgcgt acatgtcgtg gtgggatcgt cgtgatggca aaaaccaacg tagcggttat  2040
atcggtcatg cagatgggac tagtgatgct attgtgtgga ataatgatat tggacaaaac  2100
agtgctgttc tagaaacatc tggtcaaata tctttcagaa caggtgcaac caaaattgta  2160
tataccaacg gacaatatta ttccgctaac tctgatgcat accgtatgat ctttggtaat  2220
tacggtgcat tctggcgtaa tgacggcact aaagtttatc ttctttctac tgctgaaaat  2280
gataagtatg gtggatggaa tgcctatcgt ccattcattt atgatttaac ttccggtaac  2340
gttcaattag gcggtgatgg taacgaagat gcattaacgt tagaatgtgc ttctcgtgcc  2400
gctcgcttta gtaatgacgt ttacattaag aaagggcttt tgactttcga cgctgggcgc  2460
gctggatctc gcgattatat tcgatttaat cattggggtg atagtaataa tgcccgtgat  2520
aacgttttgt gcatagaaga tagtcaaggc cgacatttta gcacagaacg tgcgatgggt  2580
actggtgctc ttaaagcata cttcttaggc gatcttgaag tcggtggtaa gtttacttgg  2640
ggtaaaaata cagctacatc tagctttaat attcgtgcat ggggtaatga ttcccgtaaa  2700
caagtattag aatgcgcgga tgaaagtggg tggcattggt acacacaacg aacgggcggt  2760
cctgatactt ctgcaattga ttttgccatc aatggtactg ttaggcctca agcaattcac  2820
actggcggta atatcactat caacggtgct gatattgagt ttaaacgcac tggcaataag  2880
cacatctggt ttagagatcc gaacggttta gagttaggct tgatgtactg cgatgatgct  2940
ggtgctattc gcttccgtgg tcagaaacaa gcccaggcgt ggaaatttgc agataaaatg  3000
atccagttgg aatctggcac tgtatccggt ggcggtaatg gcctgattcg tggtgaagtt  3060
gctggcggta gttgggctag ctggcgtgac cgtgctgctg gtcttatggt tgggtgtcct  3120
caatccacca actcggcaca taacgtatgg aaagcgacgc attggggtaa atatcacatt  3180
gcagcaatgg ctgtacatgt tcctgatggt actattacca atgctttagc tcgcctaaac  3240
gttcatgacg ccaactttga ctttagcgcc tccggtgacc tgtcggcagg gcgtaatggt  3300
tcgtttaacg atgtttatat tcgttctgat gctcgcctta aatcaacaa ggaagagtat  3360
aaggagaatg ccaccgataa agttaatcgc ttgacggtat acacctatga caaggttaaa  3420
tctttaaccg accgtactgt cattgctcat gaagttggta ttattgctca ggatcttgag  3480
aaagaattgc cggaagcagt aacaacttct aagatcggcg atcctgataa gccagaagag  3540
atcttaacaa tttctaactc tgctgtcaac gctcttttaa ttaaggcgtt tcaggaaatg  3600
```

```
agcgaagaat tgaaagccgt taaagctgaa ctagcggaac ttaaaaagaa ttaa        3654

SEQ ID NO: 167         moltype = DNA  length = 777
FEATURE                Location/Qualifiers
misc_feature           1..777
                       note = Synthetic: WW34 GP38
source                 1..777
                       mol_type = other DNA
                       organism = synthetic construct
SEQUENCE: 167
atggcaatat cttctggatg ggtaggatca tctgcggtgt ccgagactgg tcaacggtgg  60
atgagcgccg caatgcaagc tgttcgctta ggtcgtccgg cgtatatgtc ggcaatggtc  120
ggacgctcta aagagattca ttatagcatt ggtgctagta actcttacaa taaagacact  180
cttattaact ggatgaaagc acagggatct actccggtag taattactat cacgggtaat  240
attgtttccc aatctactgg agttccttgt cttgacttcc ctagctcgtt aacaaacgaa  300
tatgtaacat tgatcattaa cccaggtgtt catgtttggg ggcgtggtgg taatggtggc  360
aataactccg ctggtggcgc tggtggtaat gcaattaaca acggtatagg cacacgctta  420
cgcatcacaa ataacggcgc tatttgcggt ggtggcggcg gcggcggcgg cgggtattat  480
tctccttttt cacaaatgag attaaccttt ggtggtggcg gtgggcgtcc gtttggtgct  540
gccggtgggt ctgctaatat ggaacagggt gctactgctg gtactatttc cgcgccaggt  600
aaagggtctg taaacggtgt atataatggc ggtaacggtg gtgatgctgg tggtgctggt  660
ggtaaatgta atatccgtgg acagggatcg gaatataacg gtggtgcggc tggtaaggct  720
gttactggca atgcccctcg ctgggataaa gtaggcacga tctacggtgc tcgcgtg     777

SEQ ID NO: 168         moltype = DNA  length = 261
FEATURE                Location/Qualifiers
misc_feature           1..261
                       note = Synthetic: WW34 GP57A
source                 1..261
                       mol_type = other DNA
                       organism = synthetic construct
SEQUENCE: 168
atgtccaatc agcatgaaca aatgattaat gtcctgaaag tacgtctgtt tgacactcaa  60
gaaaaggccg cattcttaga aggccaactg aaagatcgtg agcgtgtatt gatggaactg  120
gtacgcattc tgggtattca gccagacgaa aacggcactg tttcccttga tgctattgtc  180
gaagaagtga aagcacttct ccctaaagac gaagcagcgg aagacgcaga agaggaagta  240
gaactgatca cggaggcttg a                                            261

SEQ ID NO: 169         moltype = DNA  length = 4956
FEATURE                Location/Qualifiers
misc_feature           1..4956
                       note = Synthetic: WW14-G8
source                 1..4956
                       mol_type = other DNA
                       organism = synthetic construct
SEQUENCE: 169
atggcagtaa agatttcagg agtcctgaaa gacggcacag gaaaaccggt acagaactgc  60
accattcagc tgaaagccag acgtaacagc accacggtgg tggtgaacac ggtgggctca  120
gagaatccgg atgaagccgg gcgttacagc atggatgtgg agtacggtca gtacagtgtc  180
atcctgcagg ttgacggttt tccaccatcg cacgccggga ccatcaccgt gtatgaagat  240
tcacaaccgg ggacgctgaa tgattttctc tgtgccatga cggaggatga tgcccggccg  300
gaggtgctgc gtcgtcttga actgatggtg gaagaggtgg cgcgtaacgc gtccgtggtg  360
gcacagagta cggcagacgc gaagaaatca gccggcgatg ccagtgcatc agctgctcag  420
gtcgcggccc ttgtgactga tgcaactgac tcagcacgcg ccgccagcac gtccgccgga  480
caggctgcat cgtcagctca ggaagcgtcc tccggcgcag aagcggcatc agcaaaggcc  540
actgaagcgg aaaaaagtgc cgcagccgca gagtcctcaa aaaacgcggc ggccaccagt  600
gccggtgcgg cgaaaacgtc agaaacgaat gctgcagcgt cacaacaatc agccgccacg  660
tctgcctcca ccgcggccac gaaagcgtca gaggccgcca cttcagcacg agatgcggtg  720
gcctcaaaag aggcagcaaa atcatcagaa acgaacgcat catcaagtgc cggtcgtgca  780
gcttcctcgg caacggcggc agaaaattct gccagggcgg caaaaaacgtc cgagacgaat  840
gccaggtcat ctgaaacagc agcggaacgg agcgcctctg ccgcggcaga cgcaaaaaca  900
gcggcggcgg ggagtgcgtc aacggcatcc acgaaggcga cagaggctgc gggaagtgcg  960
gtatcagcat cgcagagcaa aagtgcggca gaagcggcgg caatacgtgc aaaaaattcg  1020
gcaaaacgtg cagaagatat agcttcagct gtcgcgcttg aggatgcgga cacaacgaga  1080
aaggggatag tgcagctcag cagtgcaacc aacagcacgt ctgaaacgct tgctgcaacg  1140
ccaaaggcgg ttaaggtggt aatggatgag actaatcgta accagattat tgatttaggc  1200
tttgcaaagg gtggacaagt tgacggtgat gtaactatta acggaactct gaatttaaac  1260
ggccctgaaa ttgttgcctc cggtggttat atagaattta actatcgtac gacaggtagt  1320
ggctcttggg cgggtcagca cgcggccaaa gctcctattt ttgttgattt aagtgcggcg  1380
ttatctactt cagaatacaa cccactgttt aagcagcgtt acaaagatgg aacattttca  1440
gcaggtacat tagttactga aggtagtttt aaatttcact atattaatga agctggtgat  1500
tcgaaatatt ggaccttttaa tcgtaatggt aattttcaag ttgataccgg tagtttattt  1560
gtatcgggtg gtaatatttc cgcttcaggc aatatcaact ctgcctcagg gtttgtgtct  1620
gcgcctcaga ttaatactaa aaatattatt ttagatacaa aagcatttgg acaatacgac  1680
agtcagtctt tagttaatta cgtataccca ggcaccggcg aaacaaatgg tgtaaactat  1740
cttcgtaaag ttcgtgctaa atccggcggc actatgtggc atgagctttg cactgcccaa  1800
ttaggccaag ccgatgaaat gtcttggtgg acaggtaata cccctcagtc taaacaatac  1860
ggtgttcgta acgacggccg tttgattggt agaaatagcc ttgcattagg tactatgact  1920
accgatttcc catctagcga ttatggtaat accggagcta tgggtgacaa atacctagtt  1980
```

```
ttaggtgata ctgcaaccgg tttaaaatat atcaaacaag gcaattttga tttagttggt  2040
ggtggatatt ctgttgcgtc aattaccaca gacggtttcc gtggcacaag taaaacctta  2100
tttggtcgta gtaatgacca aggtttaaca tggcttcttc ctggtcaaaa ctctgcaatg  2160
gtttctatca gaaccgaaat agatggtaat aactctggcg atggccaaac ccatttaggt  2220
tataattcta atggtaaact ttatcattat ttccgtggta ccggtcgtgt agccatttct  2280
atggcagaag gtatgattat tgaacctggt attttaaata ttaagaccgg ggttaacgaa  2340
ttaaatctta gagcagacgg cacagtttct actacacagc gtttaatggt taataacggc  2400
ttagttctta acgcaaacaa taatacttct gcattggcat taactgctcc taccggtgtt  2460
gatggtacaa aaaccattaa ctgggacgct ggtacccgaa atggccagaa caaaaatacc  2520
gttaccatga aagcatgggg taactcattt aacgcgggtg gtggtaatag agaaactgta  2580
ttcgaagtat cagattcaca aggatattat ttctatggcc aacgtactaa tccggcttcc  2640
ggtgaaactg taggccctat taacttcaag ttcaacggtt ctgttgaaac aggtcatttt  2700
tctagtctcg gaaatataag tgcatctggt accggttctt ttggtggcaa tgttaccatg  2760
actaatggcc tgtttgtcca aggcggcgct tcaattaatg gccaagttaa aatgggtggt  2820
actgctgacg cattaagaat ttggaacgct gaatatggta tgattttccg tcgttcagaa  2880
acgggttctt ctgcttcatt ccatcttatt cctacccttc aaaacgccgg tgaaaatggc  2940
ggaataagtg accttcgtcc actatctatc aatttagcta gcggcacggt tataatgggt  3000
aataaaagca caggtggccc acttttcaca gtagacaacg taagtaaatt tgttcaaacc  3060
gactgtagat tgcgtgttaa tatggattct gatggtattg ttttgaatgc ttcatctcaa  3120
gcagcatcca actttattca aggacgtaaa gcagatgtta caaaatggta tctaggtatt  3180
ggcgatggtg gcaacgtcgt tcgtatgcac aactatactt attcacatgg tattgcatta  3240
aactctgata ccgttgatat aaccaagcct cttaaaatag gttctgatat tcgtatcggt  3300
actgatggga atattatagg cagtgctact ttagataact ttaaaaacct gaatacaaca  3360
ttagaccata aagttaatat gggcggttgg tccggcggtg ctactacagg ttggtataaa  3420
tttgctactg tagaaattcc acaggcaaca ggcacggcat cttttaaaat atttggcggt  3480
tccgggttta attttaaaag ttacggtcag gcttcaatag ctgaaataat tcttagaacc  3540
ggtaataata accctaaagg ccttaatgcc acgttgtgga ataggacttc tgaagctatt  3600
tcccagattg cttcggttaa tacaagcgaa gatatctatg atatttacgt ttacttaggt  3660
gggtattcta attctttggt ggtagaatat acctgcagca gcaatagtaa agtaaccgta  3720
gtaggtatgg atggtggtgt ccagcctttg gtagaaacat tacctgaagg tcatgttgta  3780
ggtaaatctg taagaatgct gaacaacctt gacggaatgt ttgccgctgg cgaatcggat  3840
attgttactc gtggtgaata tgttaccaat aaccaaaaag gtatgcgtat taaatctaaa  3900
ggtaatgatt tagattctaa tgctgcttta cttagaaacg acggtggaag tttttatatt  3960
ttagctacag ataaaaatac gacagaaaaa cccgatgcgg ctaatggtga ttggaatggc  4020
ttaagacctt tctcgattaa tatggctgat ggtcgcgttg gtatgaacca cggattgaat  4080
attactggcg gtggtctgaa cgttaccggc ggtaatacta accttggtaa tattacatct  4140
cgtgtagttt cttcggcacg cgccgggtcc ggttggggtg ataactctga tgctatgaaa  4200
tccaaaatta cctttatggc tgaccacggt gatttatcta attcaggcag ttattatcct  4260
atcgtaggcg catacagcaa ctatggttca gcgggttatc gtcaaacctt tgaatttgga  4320
tgggtcggct ctggtagcac cgcaaattgg cgagaaggta ttattcgtat tcgcggtgat  4380
aatgctaacg gccagcaagc aagatggcgc tttacaatgg acggtatttt aggttgccct  4440
ggtaaagtag agatgccaga aacaagcgca tttggtatca acacaacaaa tggatttggt  4500
ggtaactcga ttgtaattgg tgatagcgat actggtttta gacaagtcgg tgatgggctt  4560
ttagaagttt ggactaacgc ctcacgccga atgagattcc aaggcggtga tacctattca  4620
gatatgaata ttaacgcccc gaacgtttat attcgttctg atattcgttt gaaatctaac  4680
ttcaaaccga ttgaaaatgc tcttgataag gttgaacagc tagacggttt aatctatgat  4740
aaagctgatt atattggcgg cgaagttgtt cataccgagg ccggtgttat tgctcagagt  4800
ttggaaaaag tattgcctga agctgtccgt gaagttgacg acattaaagg taacaaagtt  4860
cttaccgttt caacccaggc acaagttgct ctgttaattg aagcagttaa aactctgtcg  4920
gctaaagtta aagaacttga agcaaaactt aattaa                           4956

SEQ ID NO: 170          moltype = DNA  length = 789
FEATURE                 Location/Qualifiers
misc_feature            1..789
                        note = Synthetic: WW14 GP38
source                  1..789
                        mol_type = other DNA
                        organism = synthetic construct
SEQUENCE: 170
atggcaattg taggtgttcc tggttggatt ggacaatctg ccgtagatga aacgggacaa  60
cgttggatgg atgccgctat gcgcgatgtg cgagttgcag tacccggttg gatggggtcg  120
atggcaggac aatcaaaaga aatttatcta tctatagggg ctaataactc ttatgataga  180
aactccctta ttaactggat gagggctcaa ggtggcgcgc ctgtagttat tacaatcacc  240
ggtaacttag tatccaatag caccggtaac gcttgtttgg aatttcctag caatcttcct  300
aacgcgtata ttcaacttat cattaatagc ggtgtgactg tttatggccg aggaggtaat  360
ggttctacta atggttcggc aggtggaaac ggtggtacag ctatccataa cgcagccgga  420
actaaactcc gtattcgtaa taacggcgct attgccggtg gtggtggtgg cggtggcgca  480
gtatcattgc aaaatagcta cccgactaat ggtacatgcg gtggtggtgg tggtagacca  540
tttggcgtag gtggtaaaat aggctctgac gctatattgt ccggttcgaa tgcgtcttta  600
acagctgccg gtacaggtgg tgctacagtc caatatggtg gaggtaatgg cggtaacgtt  660
ggagctggcg gtggacgagg atggggcaaa aatgtttata cctctgcagg tggctcagct  720
ggtgctgctg tcactggcaa tgctcctaac tggcaaaacg taggaactat ttacggctca  780
agagtctag                                                          789

SEQ ID NO: 171          moltype = DNA  length = 231
FEATURE                 Location/Qualifiers
misc_feature            1..231
                        note = Synthetic: WW14 GP57A
source                  1..231
```

```
                        mol_type = other DNA
                        organism = synthetic construct
SEQUENCE: 171
atgtctgaac aaactattga acaaaaactg caagccgaaa tcgtagctct taaatcccgc  60
attctggaca cccaggatgt tgcagctcaa gctcaacagg aatcacgtat tctgcaggat  120
gcgctgagta aaatcgctgc tcgcttaggc atcaccggtg accagattca gattgaagac  180
ctgattgccg ctgttcctga tttgaccgct gaaagtgctg acgaagaata a          231

SEQ ID NO: 172          moltype = DNA  length = 3978
FEATURE                 Location/Qualifiers
misc_feature            1..3978
                        note = Synthetic: WW170-G8
source                  1..3978
                        mol_type = other DNA
                        organism = synthetic construct
SEQUENCE: 172
atggcagtaa agatttcagg agtcctgaaa gacggcacag gaaaaccggt acagaactgc  60
accattcagc tgaaagccag acgtaacagc accacggtgg tggtgaacac ggtgggctca  120
gagaatccgg atgaagccgg gcgttacagc atggatgtgg agtacggtca gtacagtgtc  180
atcctgcagg ttgacggttt tccaccatcg cacgccggga ccatcaccgt gtatgaagat  240
tcacaaccgg ggacgctgaa tgattttctc tgtgccatga cggaggatga tgcccggccg  300
gaggtgctgc gtcgtcttga actgatggtg gaagaggtgg cgcgtaacgc gtccgtggtg  360
gcacagagta cggcagacgc gaagaaatca gccggcgatg ccagtgcatc agctgctcag  420
gtcgcggccc ttgtgactga tgcaactgac tcagcacgcg ccgccagcac gtccgccgga  480
caggctgcat cgtcagctca ggaagcgtcc tccggcgcag aagcggcatc agcaaaggcc  540
actgaagcgg aaaaaagtgc cgcagccgca gagtcctcaa aaaacgcggc ggccaccagt  600
gccggtgcgg cgaaaacgtc agaaacgaat gctgcagcgt cacaacaatc agccgccacg  660
tctgcctcca ccgcggccac gaaagcgtca gaggccgcca cttcagcacg agatgcggtg  720
gcctcaaaag aggcagcaaa atcatcagaa acgaacgcat catcaagtgc cggtcgtgca  780
gcttcctcgg caacggcggc agaaaattct gccagggcgg caaaaacgtc cgagacgaat  840
gccaggtcat ctgaaacagc agcggaacgg agcgcctctg ccgcggcaga cgcaaaaaca  900
gcggcggcgg ggagtgcgtc aacggcatcc acgaaggcga cagaggctgc gggaagtgcg  960
gtatcagcat cgcagagcaa aagtgcggca gaagcggcgg caatacgtgc aaaaaattcg  1020
gcaaaacgtg cagaagatat agcttcagct gtcgcgcttg aggatgcgga cacaacgaga  1080
aaggggatag tgcagctcag cagtgcaacc aacagcacgt ctgaaacgct tgctgcaacg  1140
ccaaaggcgg ttaaggtggt aatggatgag actaatcgtg gtgctattat caatttaagt  1200
tgccctccgg tgtatgaccg cgatgttaca atggcgggta aggttaaagg aaataattat  1260
attttaagta aaaccgccaa ctatctggaa gatcagacag cgcgagatct taattacttt  1320
ggtgctttcc gaactaatgg acaagatggt cttttagatc taactcttaa tgttcctcat  1380
tctgctggcg ttaatcatgg tcgaggattt actttccgtt atgcgactgg cggatctcgt  1440
gttgaaacct atgggtataa tgcacaggga caaaaagcat ttagctataa aatgtatcat  1500
gaaggtgata aacctacccc atcggaattg aacgtttata gcaaacaaga agttgaccgt  1560
atgtttgtta aaaccgttaa acttgctaca gttcctgttg atatcgttga cggttatttt  1620
aaattagcaa ctgcgatgat tccgcaaaac ggtcgtagcg tatttttccg tattcatggt  1680
ggtaacggat ataacgttac tgcatacgat caagttgata ttgtagaaat tgttattcgc  1740
agtggaaata atcgtcctaa aggtgttaac gttattgcat accgccgaaa tacaaacaaa  1800
gcatttgatg ttttggctgt taatacttct ggtgataact atgatatcta cgtgaaatat  1860
cagcgttaca ctgataacgt tattgttgaa tttggtaaaa gtgttgatgt tgatctggta  1920
gtccatgacg ttccagactt tgttgttgat cgtcctgttg gcgataatgt tattggcggt  1980
cgcgcggtaa ctcttttcaa caccgaaaac aaacgaggtg tgttgagttt tgacgataac  2040
acacaaaata gttatgatat tgttcacttg agtaatgata ggggtactgg acgaaaatat  2100
attcgtaaat tccgtagcaa ctataacgaa atgatctggc atgagacggt tcaaggttct  2160
acttatcgac tcgccacggg tagcacagat gcccaggaga ttctatccgt tgaatctagt  2220
agctctattg ctggaactca taaaggtaat attctttctg gtcgaatgat gttgggtggc  2280
ggtagtaatg ttattacctt gcggcgtcct gctggtcaat ccaaccatat tgcgtttcaa  2340
gataatcgta ctggatctat tacccgtcaa gggtggatcg gttatggtaa tgctgatact  2400
aacgtttttg aatggtatag tgatgtaggt ggtacttcta ttcgtcacca catcgacgga  2460
cagatcgaac ttgcaaccgg taacacaaaa cgcgtttata ctaacgctca attcatctca  2520
atgaatagcg acgcctaccg tatgatcttt ggtaattacg gtgcattctg gcgtaatgac  2580
ggcactaaag tttatcttct ttctactgcc gaagatgata aatttggcgg gtggaatgga  2640
aacagaccgt tcatttacga tttgaccaac ggtaaagtta ctttaggtgg tgatggtaac  2700
gaaggtgcat tagttctcga aagagatagc cgtgctgctc gatttgctgg tgatgtttat  2760
gtagaaaaag gatttcttca tttttctagt gggcgtcagg gtgctagcgg tttcatgaaa  2820
ataaaccatt tgggtgatat tgccagtgga cgacacaaca ttcttcaaat agaagaccct  2880
acaggtatac atttctctac tgaacgcaat gatgaaaccg gaaatattac tgcacgtttt  2940
aaaggctttg tacgtgtaga agctggtgaa attgcatttg atgctaatcg gggtcgcag  3000
tctcaattta ccttacacac atggggtaac gagcaacgca aacaggtttt tgaatgtaag  3060
gatgctacag gttatcactg gtatactgaa cgtactcagg gtggcactgg aaatgttctg  3120
ttctctatgg ctggtagtct aaacgttact agcaatatca caacaactgg tgctgatatt  3180
acgtttaaac gcgctggcaa taagcacatc tggtttagag atccagacgg tttagagttg  3240
ggcttgatgt attgcgatga tgctggtgct attcgcttcc gtggtcagaa acaagcccag  3300
gcgtggaaat ttgcagataa aatgatccag ttggaatctg gtactgtatc tggtggcggt  3360
aatggcctga ttcgtggtga agttgctggc ggtagttggt ctagctggcg tgaccgtgct  3420
gctggcctta tggttgggtg tcctcaatcc accaactcgg cacataacgt atggaaagcg  3480
acgcattggg gtaaatatca cattgcagca atgggtatac atgttcctga cggtactatc  3540
ggtaacgctc ttgctcgtct ccatgttcat gatactaact ttgactttag cgcctccggt  3600
gatatgacgg caggtcgtaa cggttcgttt aacgatgtgt atattcgttc tgatgctcgc  3660
cttaaaatca ataaggaaga gtataaagag aatgccaccg ataaaattaa tcgcttgacg  3720
gtatacacct atgacaaggt taaatcttta accgaccgta ctgtcattgc tcatgaagtt  3780
```

```
ggtattattg ctcaggatct tgaaaaagaa ttgccggaag cagtaacaac ttctaaggtc  3840
ggcgatcctg ataagccaga agagatctta acaatttcta actctgctgt caacgctctt  3900
ttaattaagg cgtttcagga aatgagcgaa gaattgaaag ccgttaaagc tgaactagcg  3960
gaacttaaaa agaattaa                                                3978

SEQ ID NO: 173          moltype = DNA  length = 780
FEATURE                 Location/Qualifiers
misc_feature            1..780
                        note = Synthetic: WW170 GP38
source                  1..780
                        mol_type = other DNA
                        organism = synthetic construct
SEQUENCE: 173
atggcaatat cttctggatg ggtaggatca tctgcggtgt ccgagactgg tcaacggtgg  60
atgagcgccg caatgcaagc tgtacgctta ggtcgtccgg cgtatatgtc ggcaatggtc  120
ggacgctcta aagagattca ttatagcatt ggtgctagta actcttacaa taaagacact  180
cttattaact ggatgaaagc acaaggatct actccggtag taattactat cactggtaat  240
attgtttccc aatctactgg cgttccttgt cttgacttcc ctagctcgtt aacaaacgaa  300
tatgtaacat tgatcattaa ccccggtgtt catgtttggg ggcgtggtgg taatggtggc  360
aataactccg ctggtggtgc tggtggtaat gcaattaaca acggtatagg cacacgctta  420
cgcatcacaa ataacggcgc tatttgcggt ggcggtggcg gtggcggcgg tgggtattat  480
tctccttttt cacaaatgag attaaccttc ggcggtggtg gtgggcgtcc gtttggtgct  540
gccggtgggt ctgctaatat ggaacagggt gctactgctg gtactatttc cgcgccaggt  600
aaagggtctg tcaacggtgt atataatggc ggtaacggtg gtgatgctgg tggtgctggt  660
ggtaaatgta atatccgtgg acagggatcg gaatataacg gtggtgcggc tggtaaggct  720
gttactggca atgcccctcg ctgggataaa gtaggcacga tctacggtgc tcgtgtgtaa  780

SEQ ID NO: 174          moltype = DNA  length = 261
FEATURE                 Location/Qualifiers
misc_feature            1..261
                        note = Synthetic: WW170 GP57A
source                  1..261
                        mol_type = other DNA
                        organism = synthetic construct
SEQUENCE: 174
atgtccaatc agcatgaaca aatgattaat gtcctgaaag tacgtctgtt tgacactcaa  60
gaaaaggccg cattcttaga aggccaactg aaagatcgtg agcgtgtatt gatggaactg  120
gtacgcattc tgggtattca gccagacgaa aacggcactg tttcccttga tgctatcgtc  180
gaagaagtga aagcacttct ccctaaagac gaagcagcgg aagacgctaa agaggaagta  240
gaactgatca cggaggcttg a                                            261

SEQ ID NO: 175          moltype = DNA  length = 3948
FEATURE                 Location/Qualifiers
misc_feature            1..3948
                        note = Synthetic: WW202-G8
source                  1..3948
                        mol_type = other DNA
                        organism = synthetic construct
SEQUENCE: 175
atggcagtaa agatttcagg agtcctgaaa gacggcacag gaaaaccggt acagaactgc  60
accattcagc tgaaagccag acgtaacagc accacggtgg tggtgaacac ggtgggctca  120
gagaatccgg atgaagccgg gcgttacagc atggatgtgg agtacggtca gtacagtgtc  180
atcctgcagg ttgacggttt tccaccatcg cacgccggga ccatcaccgt gtatgaagat  240
tcacaaccgg ggacgctgaa tgatttctc tgtgccatga cggaggatga tgcccggccg  300
gaggtgctgc gtcgtcttga actgatggtg gaagaggtgg cgcgtaacgc gtccgtggtg  360
gcacagagta cggcagacgc gaagaaatca gccggcgatg ccagtgcatc agctgctcag  420
gtcgcggccc ttgtgactga tgcaactgac tcagcacgcg ccgccagcac gtccgccgga  480
caggctgcat cgtcagctca ggaagcgtcc tccggcgcag aagcggcatc agcaaaggcc  540
actgaagcgg aaaaaagtgc cgcagccgca gagtcctcaa aaaacgcggc ggccaccagt  600
gccggtgcgg cgaaaacgtc agaaacgaat gctgcagcgt cacaacaatc agccgccacg  660
tctgcctcca ccgcggccac gaaagcgtca gaggccgcca cttcagcacg agatgcggtg  720
gcctcaaaag aggcagcaaa atcatcagaa acgaacgcat catcaagtgc cggtcgtgca  780
gcttcctcgg caacggcggc agaaaattct gccagggcgg caaaaacgtc cgagacgaat  840
gccaggtcat ctgaaacagc agcggaacgg agcgcctctg ccgcggcaga cgcaaaaaca  900
gcggcggcgg ggagtgcgtc aacggcatcc acgaaggcga cagaggctgc gggaagtgcg  960
gtatcagcat cgcagagcaa aagtgcggca gaagcggcgg caatacgtgc aaaaaattcg  1020
gcaaaacgtg cagaagatat agcttcagct gtcgcgcttg aggatgcgga cacaacgaga  1080
aaggggatag tgcagctcag cagtgcaacc aacagcacgt ctgaaacgct tgctgcaacg  1140
ccaaaggcgg ttaaggtggt aatggatgag actaatcgtg ggcaaattgt taatttaagt  1200
tgccctcctg tttatgacaa aggctttgat gtaagaggcc gcgtggttgt ggatgacctt  1260
gtgtggagta ataccgcaaa ctatttcgat gacccgaccg cacgaaatct tgataaattt  1320
ggggcatttc gtactaatga tatggatggt catctagcat ttgctttgca tattccccat  1380
cctagcggta taaatcatgc tcgtgggttt gattttactt atggttctaa cgttgttcct  1440
actgtaaaaa cctatggtta taacgctgat ggtgtattgg catattcata tcgcatgtat  1500
cacgaaggtg ataagcctag tccgtcagaa ttaaatgtat acagcaaaca agaagtagat  1560
cggatgttcc aaaaaaccat caactttggt gtagaaactg gatggtttaa aattgctaca  1620
gcatttattc cgcaaaatga tggacgtagc ttgaaaatta gattggttgg tggaaatggg  1680
tggaacgtag gccaaacggg acaatgtaat attattgaac ttgttataag gactagcaac  1740
ggttccccta aggaattaa ctttgttgca tatcatcatg tttctggtta cgaaaatcaa  1800
```

```
ttttgtgcca ttaatacagg tgatgacact tatgatatct atgcatacta ctacgaattt  1860
actaatatgg taatggctga atatcaagcg tccagcgatg ttaatttaac tgtatttgat  1920
cgacctgaat atgtaggcga aaaacctgta gccgaacata tattcgatgc atatacaata  1980
cactccttta acagtttcag taaccgtgga acattaaatt ttgctggcaa ccatcaagga  2040
caatatgaca ttgagcatat gaacgaacaa ccgacaaatg ctaaaaagat gttgcgtcgg  2100
tttcgaagct ctgccagcgc gacaatctgg catgaaaccg ttgatgacca gaattatcgt  2160
cttgccactg gaggtacaga ctcagttcaa caattattgt tgtcttctgg gactggtttg  2220
catattcgta gattgaccat cgatggtggc ttaggttccg gttctaatgc tggtattgat  2280
attcgtcgag gaccaaacga atcaagccat tttaatttta tggattatcg cactggtcaa  2340
gatgttcgta atggttggtt tggttttggt gatttgacga ccaaagattt tatttggtgg  2400
aacgataacg gtcaaaactc gataaacttg atcgaaaacg gtgaattaca tattactggc  2460
ggtagaggcc agaaaattgt aatgaatagc gaagttgcat tatctgaaaa tgctcgtttg  2520
gctgtcaaag gtggtaacta tggtttaatc cttcgtaatg atgggactgg tttccatata  2580
ctgactaccg atttaaaaga ttcttttggt agttggaata atcgcagacc attcagctat  2640
aattttgcgg acggtggatt atatttaggt ggtactgaaa ctgctcgttg tttgcatctt  2700
ggaattgatg gtagcactcg tctagaagac aacctttttct ttaaagctgg ttctcgtcaa  2760
tctatggact atatggaact cgtccattgg ggggcaagca atacaggtcg aaataacgtt  2820
ttaagtcttc gtgactcaaa aggattttta gcagaatttg aacgcgtggg ggggactgac  2880
ggcgttaaaa ccagattctt tggcgaaaca ttcactgacg gtacattata cctaaatcag  2940
atgaataata gctctgaacg attctctatc aataactggg gaaattcaga agttggtcgc  3000
gcggcagtaa tggaagttgg cgattccaaa ggttatcact tctatgcgga acgtagaaca  3060
gatgacaccg ttttatttga tgtatctggt gctttgaccg tgcatggacc taacggaata  3120
accgtcaaaa actcaactgg tgcacgccat atctggttta gagatgatag cgatacggaa  3180
aaggctgtta tctgggctac agatgatggt atgttacata tacgaaataa tcatgagggt  3240
tcatttgctc atcacttcca gggcgcaatg attaaactgg aagggcgtgt tccttatggt  3300
gcagcaaaag ggcttattcg aggcgaggta gacggtggtg catatgttgc atggagagat  3360
cgccctgctg gtttgttggt tgactgccag aaaagtattg acagtgctca tgctgtttgg  3420
aaagcggttg attgggggcg tcaatatatc gctgctatgg acgttcattg tccgggtgat  3480
ggtaataata ctgcggcagc ggttcttcat gttcaggctg ctgattatca attccatgca  3540
agcggagaat ttcatgcctc tggtaacggg aactttaacg atgtgtatat tcgttcagac  3600
cgtcgcctta aagacaatat agaagattat acaggaaatg cgttaagttt gatcggcaaa  3660
ctgaaagtga aaacttacga taaagttaaa tctcttaaag accgtgaaat tatcggtcac  3720
gagatcggca ttatcgcaca ggatttacaa gaaatattac cggaagctgt aaaatcttca  3780
aaagttggca atcttgataa tccagacgat gttctgacaa tttctaactc tgctgtgaat  3840
gctcttttaa ttaaggctat tcaggaaatg agtgaagaaa ttaaagaatt gaaaactcct  3900
ttctttacta aaattgctcg caaaattagt aaatatttta aattctaa              3948
```

```
SEQ ID NO: 176          moltype = DNA  length = 783
FEATURE                 Location/Qualifiers
misc_feature            1..783
                        note = Synthetic: WW202 GP38
source                  1..783
                        mol_type = other DNA
                        organism = synthetic construct
SEQUENCE: 176
atggcagtag ttggtgttcc tggttggatt ggaagttcag ccgcaaatga aacagggcaa  60
cgatggatga gtcaagcggc tggtcaatta agattgggtg ttccttgctg gatgagccaa  120
ttctccggtc gttcaagaga aattattcat acacttggag cagaccataa cttcaatggt  180
cagtggttcc gtgatagatg ctttgaagca ggtagtacac ctatagtgtt taatatcacc  240
ggagatttag tatcatattc taaagatgtt cctttattct ttatgtacgg agatacacct  300
aatgaatatg ttcagttgaa tatacatggc gtaacgatgt atggtcgtgg cgggaatggc  360
ggtagcaata gtcctggatc agctgggggt cattgtattc aaaatgatat tggtgggaga  420
ctaagaatta ataatggtgg agctattgca ggtggcggtg gcggtggcgg tggcgggtat  480
tattctcctt tttcacaaat gagattaacc tttggcggtg gcggtgggcg tccgtttggt  540
gcacccggcg gatctattga tatgcaatca ggcgcaactg ctggtactct ttatgctcct  600
ggatcggggt ccgtgaacgg tatctataat ggcggaagcg gtggtgaggt aggcgccgca  660
ggaggtagat gtaatattcg tggtcaagga tatgaataca atggcggcga tgctggttat  720
gctgttatag gttcttctcc aacgtggcaa aatcgcggag ctatttacgg acctgctgtt  780
taa                                                                783
```

```
SEQ ID NO: 177          moltype = DNA  length = 261
FEATURE                 Location/Qualifiers
misc_feature            1..261
                        note = Synthetic: WW202 GP57A
source                  1..261
                        mol_type = other DNA
                        organism = synthetic construct
SEQUENCE: 177
atgtccaatc agcatgaaca aatgattaat gtcctgaaag tccgtctgtt tgacactcaa  60
gaaaaagccg cattcttaga aggccaactg aaagatcgtg agcgtgtatt gatggaactg  120
gtgcgtgttc tgggtattca gccagatgaa aatggcactg tttcccttga tgctatcgtc  180
gaagaagtaa aagcacttct ccctaaagac gaagcagcgg aagacgctaa agaggaagta  240
gaactgatca cggaggcttg a                                            261
```

```
SEQ ID NO: 178          moltype = DNA  length = 7300
FEATURE                 Location/Qualifiers
misc_feature            1..7300
                        note = Synthetic: p7.3 (p513)
source                  1..7300
```

```
                        mol_type = other DNA
                        organism = synthetic construct
SEQUENCE: 178
cctttaggga aatatgctaa gttttcaccg taacacgcca catcttgact atatatgtgt  60
agaaactgcc ggaaatcgtc gtggtattct gaccagagcg atgaaaacgt ttcagtttgc  120
tcatggaaaa cggtgtaaca agggtgaaca ctatcccata tcaccagctc accgtctttc  180
attgccatac gaaactccgg atgtgcattc atcaggcggg caagaatgtg aataaaggcc  240
ggataaaact tgtgcttatt tttctttacg gtttttaaaa aggccgtaat atccagctga  300
acggtttggt tataggtgca ctgagcaact gactggaatg cctcaaaatg ttctttacga  360
tgccattgac ttatatcaac tgtagtatat ccagtgattt ttttctccat tttagcttcc  420
ttagcttgcg aaatctcgat aactcaaaaa atagtagtga tcttatttca ttatggtgaa  480
agttgtctta cgtgcaacat ttcgcaaaa agttggcgct ttatcaacac tgtccctcct  540
gttcagctac tgacggtact gcggaactga ctaaagtagt gcgtaacggc aaaagcaccg  600
ccggacatct gcgctagcgg agtgtatact ggcttactat gttggcactg atgagggtgt  660
aagtgaagtg cttcatgtgg caggagaaaa aaggctgcat cggtgcgtca gcagaatatg  720
tgatacagga tatattccgc ttcctcgctc actgactcgc tacgctcggt cgttcgactg  780
tggcgagcgg aaatggctta cgaacggggc ggagatttcc tggaagatgc caggaagata  840
cttaacaggg aagtgagagg gtcgcggcaa agccgttttt ccataggctc cgcccccctg  900
acaagcatca cgaaatctga cgctcaaatc agtggtggcg aaacctgaca ggactataaa  960
gataccaggc gtttccccct ggcggctccc tcgtgcgctc tcctgttcct gcctttcggt  1020
ttgccggtgt cattcctctg ttacggccga gtttgtctca ttccacgcct gacactcagt  1080
tccgggtagg cagttcgctc caagctggac tgtatgcacg aaccccccgt tcagtccgac  1140
cgctgcgcct tatccggtaa ctatcgtctt gagtccaacc cggaaagaca tgcaaaagca  1200
ccactggcag cagccactgg taattgattt agaggagtta gtcttgaagt catgcgccgg  1260
ataaggctaa actgaaagga caagttttgg cgactgcgct cctccaagcc agttacctcg  1320
gttcaaagag ttggtagctc agagaacctt cgaaaaaccg ccctgcaagg cggttttttc  1380
gttttcagag caagagatta cgcgcagacc aaaacgatct caagaagatc atcttattaa  1440
tcagataaaa tatttctaga tttcagtgca atttatctct tcaaatgtag cactttatag  1500
ctagctcagc ccttggtaca atgctagcgt tttcattaaa gaggagaaag gaagccatga  1560
gtaaaggtga ggaattattt actggtgttg ttccgatctt agttgaactg gacggcgatg  1620
ttaacggtca taaattcagt gttcgtggtg aaggtgaagg tgatgcaacc aacggtaagc  1680
tgaccctgaa attcatctgc actactggaa aattaccagt accgtggcct actctggtga  1740
ctaccctgac ctatggtgtt cagtgttttt ctcgttaccc tgaccacatg aagcaacatg  1800
atttcttcaa atctgcaatg ccggaaggtt atgtacagga gcgcaccatt tctttcaaag  1860
acgatggcac gtataaaacc cgtgcagagg ttaaatttga aggtgacact ctggtgaatc  1920
gtattgaact gaaaggcatt gatttcaaag aggacggcaa tattttaggc cacaaactgg  1980
aatataactt caactcccat aacgtttaca tcaccgcaga caaacaaaag aacggtatca  2040
aagctaactt caaaattcgc cataacgttg aagacggtag cgtacagctg gcggatcatt  2100
accaacagaa cactccgatt ggagatgctc ctgttttact gccggataac cactacctgt  2160
ccacccagtc taaactgtcg aaggatccga acgaaaagcg cgaccacatg gtgttattag  2220
agttcgttac cgctagtggt atcacgcacg gtatggatga actctacaaa taagtcagtt  2280
tcacctgttt tacgttaaaa cccgcttcgg cgggtttttta cttttgggtt tagccgaacg  2340
ccccaaaaag cctcgctttc agcacctgtc gtttcctttc ttttcagagg gtattttaaa  2400
taaaaacatt aagttatgac gaagaagaac ggaaacgcct taaaccggaa aattttcata  2460
aatagcgaaa acccgcgagg tcgccgcccc gtaacctgtc ggatcaccgg aaagaacctg  2520
taaagtgata atgattatca tctacatatc acaacgtgcg taaagggact ataacaagac  2580
gcaaacggag gtaggctcac tcctacttcg gaaacttaac cgaagaacta ggacggtatt  2640
gtttgcgctt ggaattggcc ttgaagtaag tcaggttttg acggaacgat tagttacagg  2700
gggggaacag tcgttggtcg ccaccaagtc gatttttggc ttacctctta tctcgtagtt  2760
ggtgagggtt gggattcacg ggacgagatc cagcctaagt atattgtcac ttctgattcg  2820
ttcgatcact tactcccctt acttatcctg cggctactgt ttccgctggc tcgtaagctc  2880
tacgttcggc aatctacccg cgaggtcaga cgtgacactc ttaaactaaa aattggtagc  2940
ttctttggct gaattgctgg atcttattcg ttcacccaat aaaacggtac agcttcaagc  3000
aatatcctca gtaagttaat acccgttgta ctattacttt cacgaccgtt cgacgttccc  3060
gctctattta ttaagagctg tcacttcgag tctttagctc acttaggaat tagctgagtt  3120
taggctcagc cctcttgggt tgcttgtact ttcagagtta ttcgcacggc tggttttgtc  3180
gagtggggaa ttgtggttga ccgaaagtcc gctatccttc aacgccgaat cagctcttgc  3240
cctttactat cttcaatctc ttggaggcta ttacgggcgg gggcaagaga ttagaactgc  3300
aagacacccg ttgataatcg agtcgctcga tagattgtcg agagccggag agattagtac  3360
gttattcaag gcaatacgtg cagggttaat ctgggcgcgt tgtagtctac gctggcgtaa  3420
gtccccaata acacgctcgt ccggcgagtc acgatcctct aggcggtgtt caacgcgtac  3480
gccagctatt tgggatactt agctacgtta cacgtaagaa tatcttagcg gaggatcgcc  3540
ctgcttccgc ttggacggat aaacgggaga gtgggcgcgt atagcgcagg cggtgtgaag  3600
gcttttaagt aattctagcc ctctttgaac ggtatttccc aatttggaga ttaccggata  3660
gcgcgtttaa atgagtgtca gagaaacgga agccgaagtc tttccattcc ggatgtttgg  3720
aaatgctctg tttatagaag tcgatgaact tacggcagtc ctctatatta aattcgaatt  3780
tttcataccc tttctgcggg ctaccgtttt tagtgtgcgt gctatgattg cggatgcgca  3840
gaatatcctc agacgggttg tagaatttga tgcttttcgc ggaaaagaac actttcggta  3900
acattttatt cgcacccggc aggagcttgt acacgatttt cttatagcct tcacccttgt  3960
tttctttgat cgctttatcg tcgaagatct tgttgttctt cttgttcatt acgcccagat  4020
agtatttgtc gtctttgatg aacaggattg cggtgttgtc cggctctttg ttcttatccc  4080
agccgttcgc cagcgtgctg ttttcgaagt tcagtttgaa tttctcgtca gagtaaggct  4140
tctgcgtgat gtagttgcgg attttattgt agagagggac gatgtttgcc agttcgaagt  4200
aacattcttc gaacaccaga tagaagtgtt catctttatc cagaatgttc gccttgtcct  4260
cgctctggct gatgtggaag attttgagct tgtgtaataa gttattcgtc tgatctaata  4320
agtctttaat tgctttcaca tcgtcctccg cagatgcttg aagcagatct ttcttaccct  4380
gattctggta cttgatagag atctgcgcca gattgtcttt gttttgagca atttcgtcga  4440
agatcatcgg gattgccgca aagttcgcca gaatttcctc aaaacgacac tgtttatcaa  4500
tatcacgatg tttattaaat tcctcaagtg ccagtttgat agtttctaag ctcaggtatt  4560
```

```
tagctttttc tgtttcttt gcaatcagtt cctgttcctt cttggacggg ttgtccagat  4620
ttttcggcgc gatttgttgg gtgatgtatt ccaaaactgc cgtgccgatc acgctatagt  4680
catcgaaaac ttgttgactg agatcggtca gagatttgtc gtttttaaag taaatcttag  4740
acagatctag tttctgcgct ttgaggtcgt caaagagcag ggacagagtt tctttaatag  4800
atttctcttc cacggtttg aacgccgcaa tctgctcata aaagctctgc atcgtggtga  4860
caacgtcgct atcatcttcc agtttatcaa ttacgaagga tttagattcg gtgtccgata  4920
aaatctgttt aaacagaacg gacattttat actttttcag ggttttgtcg ttgatttgtt  4980
ggctatacag gttaatgtat tcgttgatgc ccttacgctt ggtgttttcg ccgttaacaa  5040
atttgccacc aataatggtg ttgaatttgg tgatgccaga ttgattcagg taattgttga  5100
aattagcgat ttcgaaaacc tcgtccagtg agaaaacacg ctggttaact tcggaggttt  5160
tatagtcgat gtcgaaggtc agttcttccg ccagatcttt cttgatctgt tcatagttaa  5220
tagcttccgg tgctttgtct ttcagagatt catatttcgc tttgttttcc agaaacttcg  5280
gcaggttgtc gtccacgata cgataaataa tagaggtcgg aatatcgttg ctcgaatata  5340
cattcttacg gttttcatga aaacctttga aatacgtcgt ccagcctttg aaagacttga  5400
tgatttcggt attcgaatat gacctgatca aagataaacg tttcaccgaa gataagttct  5460
ttttccactg tccgattacc atcaacttca aatctagcgg tgcgaacaag ttcaacgatg  5520
aaattaactt attactgaaa gagaaagcta atgacgtaca catcttatct attgatcgcg  5580
gtgaacgtca tttagcatac tatacactgg tagatggtaa aggtaatatt attaaacagg  5640
atactttcaa tattatcggt aatgaccgta tgaaaaccaa ctatcacgat aagctggcgg  5700
cgatcgaaaa agatcgtgat tctgcgcgta aagattggaa gaaaattaac aatatcaaag  5760
aaatgaaaga aggctatctg agccaagtgg tgcacgagat cgcaaaactg gtgattgaat  5820
ataacgctat cgtggtttc gaagatctga actttggttt taaacgtggt cgcttcaaag  5880
tagaaaaaca ggtgtaccaa aaactggaaa aaatgctgat tgaaaaactg aactatctgg  5940
tttttaaaga caacgaattt gacaaaacgg gtggcgtact ccgtgcctat cagctgaccg  6000
ctccgttcga aacgttcaag aaaatgggta aacaaacggg gattatctat tatgtgccag  6060
ctggtttcac ctccaagatt tgtccagtta cgggcttcgt taaccagctg tacccgaaat  6120
acgagagcgt tagcaaatct caagaatttt tcagcaaatt cgacaagatc tgctataatc  6180
tggataaagg ctatttcgag ttcagcttcg attacaaaaa cttcggcgat aaagcggcta  6240
aaggtaagtg gactattgct agctttggta gccgtctgat taactttcgc aactccgaca  6300
aaaaccataa ttgggacacg cgtgaagtgt atccgaccaa agaactggaa aaattactga  6360
aagactattc cggacactca gaagggttat aggaatagtc actactgggg taagcacttc  6420
ggaaattata ttattctcgc ttcttattgc ggtaacgtga tcctgaacga tacttattac  6480
tttgtaattt acttaacgtc ggagtccctg caatcttcta gtacccgctt cccgaataca  6540
ggagataact ttttaacact caagagttgc ttcgtgctta gccagtcttg gatttgattg  6600
ctctaatcct tcaacgtgtc aaagacagtg tatctggtca agtaaagtct agagaaaggc  6660
gtagtcagtt acggagttat cccaccttag tgttactccg atttaatttc tgctttcttt  6720
gatttctacc cgactttcgc cgtgacttca atagagaggc aggctcttgc tatttctttc  6780
aagggcttgt ccaactacct aattaagata aagatacggc agttgacgca ctgccgataa  6840
tttctttacg tcagcgaaat taaatcgagc accagtcgta gagtcgcggt tgcctagcag  6900
tttatctcgc gtacgggcct tcgctactta cacgatacct agtacgtgga ttcgggtagc  6960
accagaagtc tatagcatgt gcatacottt ggtcgaaaaa aaaagcccgc actgtcaggt  7020
gcgggctttt ttcagtgttt ccttgccgga ttacgccccg ccctgccact catcgcagta  7080
ttgttgtaat tcattaagca ttctgccgac atggaagcca tcacaaacgg catgatgaac  7140
ttggatcgcc agtggcatta acaccttgtc gccttgcgta taatattttc ccatagtgaa  7200
aacgggggcg aagaagttgt ccatatttgc tacgtttaaa tcaaaactgg tgaaactcac  7260
ccagggattg gcactgacga aaaacatatt ttcgataaac                        7300
```

```
SEQ ID NO: 179          moltype = DNA  length = 3396
FEATURE                 Location/Qualifiers
misc_feature            1..3396
                        note = Synthetic: 1A2
source                  1..3396
                        mol_type = other DNA
                        organism = synthetic construct
SEQUENCE: 179
atgggtaaag gaagcagtaa ggggcatacc ccgcgcgaag cgaaggacaa cctgaagtcc  60
acgcagttgc tgagtgtgat cgatgccatc agcgaagggc cgattgaagg tccggtggat  120
ggcttaaaaa gcgtgctgct gaacagtacg ccggtgctgg acactgaggg gaataccaac  180
atatccggtg tcacggtggt gttccgggct ggtgagcagg agcagactcc gccggaggga  240
tttgaatcct ccggctccga gacggtgctg ggtacggaag tgaaatatga cacgccgatc  300
acccgcacca ttacgtctgc aaacatcgac cgtctgcgct ttaccttcgg tgtacaggca  360
ctggtggaaa ccacctcaaa gggtgacagg aatccgtcgg aagtccgcct gctggttcag  420
atacaacgta acggtggctg ggtgacggaa aaagacatca ccattaaggg caaaaccacc  480
tcgcagtatc tggcctcggt ggtgatgggt aacctgccgc cgcgcccgtt taatatccgg  540
atgcgcagga tgacgccgga cagcaccaca gaccagctgc agaacaaaac gctctggtcg  600
tcatacactg aaatcatcga tgtgaaacag tgctacccga acacggcact ggtcggcgtg  660
caggtggact cggagcagtt cggcagccag caggtgagcc gtaattatca tctgcgcggg  720
cgtattctgc aggtgccgtc gaactataac ccgcagacgc ggcaatacag cggtatctgg  780
gacggaacgt ttaaaccggc atacagcaac aacatggcct ggtgtctgtg ggatatgctg  840
acccatccgc gctacggcat ggggaaacgt cttggtgcgg cggatgtgga taaatgggcg  900
ctgtatgtca tcggccagta ctgcgaccag tcagtgccgg acggctttgg cggcacggag  960
ccgcgcatca cctgtaatgc gtacctgacc acacagcgta aggcgtggga tgtgctcagc  1020
gatttctgct cggcgatgcg ctgtatgccg gtatggaacg ggcagacgct gacgttcgtg  1080
caggaccgac cgtcggataa gacgtggacc tataaccgca gtaatgtggt gatgccggat  1140
gatggcgcgc cgttccgcta cagcttcagc gccctgaagg accgccataa tgccgttgag  1200
gtgaactgga ttgacccgaa caacggctgg gagacggcga cagagcttgt tgaagatacg  1260
caggccattg cccgttacgg tcgtaatgtt acgaagatgg atgcctttgg ctgtaccagc  1320
cgggggcagg cacaccgcgc cgggctgtgg ctgattaaaa cagaactgct ggaaacgcag  1380
accgtggatt tcagcgtcgg cgcagaaggg cttcgccatg taccgggcga tgttattgaa  1440
```

```
atctgcgatg atgactatgc cggtatcagc accggtggtc gtgtgctggc ggtgaacagc  1500
cagacccgga cgctgacgct cgaccgtgaa atcacgctgc catcctccgg taccgcgctg  1560
ataagcctgg ttgacggaag tggcaatccg gtcagcgtgg aggttcagtc cgtcaccgac  1620
ggcgtgaagg taaaagtgag ccgtgttcct gacggtgttg ctgaatacag cgtatgggag  1680
ctgaagctgc cgacgctgcg ccagcgactg ttccgctgcg tgagtatccg tgagaacgac  1740
gacggcacgt atgccatcac cgccgtgcag catgtgccgg aaaaagaggc catcgtggat  1800
aacggggcgc actttgacgg cgaacagagt ggcacggtga atggtgtcac gccgccagcg  1860
gtgcagcacc tgaccgcaga agtcactgca gacagcgggg aatatcaggt gctggcgcga  1920
tgggacacac cgaaggtggt gaagggcgtg agtttcctgc tccgtctgac cgtaacagcg  1980
gacgacggca gtgagcggct ggtcagcacg gcccggacga cggaaaccac ataccgcttc  2040
acgcaactgg cgctggggaa ctacaggctg acagtccggg cggtaaatgc gtgggggcag  2100
cagggcgatc cggcgtcggt atcgttccgg attgccgcac cggcagcacc gtcgaggatt  2160
gagctgacgc cgggctattt tcagataacc gccacgccgc atcttgccgt ttatgacccg  2220
acggtacagt ttgagttctg gttctcggaa aagcagattg cggatatcag acaggttgaa  2280
accagcacgc gttatcttgg tacggcgctg tactggatag ccgccagtat caatatcaaa  2340
ccgggccatg attattactt ttatatccgc agtgtgaaca ccgttggcaa atcggcattc  2400
gtggaggccg tcggtcgggc gagcgatgat gcggaaggtt acctggattt tttcaaaggc  2460
aagataaccg aatcccatct cggcaaggag ctgctggaaa aagtcgagct gacggaggat  2520
aacgccagca gactggagga gttttcgaaa gagtggaagg atgccagtga taagtggaat  2580
gccatgtggg ctgtcaaaat tgagcagacc aaagacggca aacattatgt cgcgggtatt  2640
ggcctcagca tggaggacac ggaggaaggc aaactgagcc agtttctggt tgccgccaat  2700
cgtatcgcat ttattgaccc ggcaaacggg aatgaaacgc cgatgtttgt ggcgcagggc  2760
aaccagatat tcatgaacga cgtgttcctg aagcgcctga cggcccccac cattaccagc  2820
ggcggcaatc ctccggcctt ttccctgaca ccggacggaa agctgaccgc taaaaatgcg  2880
gatatcagcg gtaacgtgaa tgcgaactcc gggacgctca acaacgtcac gattaacgag  2940
aactgtcggg ttctgggaaa attgtccgcg aaccagattg aaggcgatct cgttaaaaca  3000
gtgggcaaag ctttcccccg ggactcccgt gcaccggagc ggtggccatc aggaaccatt  3060
accgtcaggg tttatgacga tcagccgttt gaccggcaga ttgttattcc ggcggtggca  3120
ttcagcggcg ctaaacatga gaaagagcat actgatattt actcctcatg ccgtctgata  3180
gtgcggaaaa acggtgctga aatttataac cgtaccgcgc tggataatac gctgatttac  3240
agtggcgtta ttgatatgcc tgccggtcac ggtcacatga cactggagtt ttcggtgtca  3300
gcatggctgg taaataactg gtatcccaca gcaagtatca gcgatttgct ggttgtggtg  3360
atgaagaaag ccactgcagg catcacgatt agctga                            3396

SEQ ID NO: 180          moltype = DNA  length = 2325
FEATURE                 Location/Qualifiers
misc_feature            1..2325
                        note = Synthetic: WT STF
source                  1..2325
                        mol_type = other DNA
                        organism = synthetic construct
SEQUENCE: 180
atggcagtaa agatttcagg agtcctgaaa gacggcacag gaaaaccggt acagaactgc  60
accattcagc tgaaagccag acgtaacagc accacggtgg tggtgaacac ggtgggctca  120
gagaatccgg atgaagccgg gcgttacagc atggatgtgg agtacggtca gtacagtgtc  180
atcctgcagg ttgacggttt tccaccatcg cacgccggga ccatcaccgt gtatgaagat  240
tcacaaccgg ggacgctgaa tgattttctc tgtgccatga cggaggatga tgcccggccg  300
gaggtgctgc gtcgtcttga actgatggtg gaagaggtgg cgcgtaacgc gtccgtggtg  360
gcacagagta cggcagacgc gaagaaatca gccggcgatg ccagtgcatc agctgctcag  420
gtcgcggccc ttgtgactga tgcaactgac tcagcacgcg ccgccagcac gtccgccgga  480
caggctgcat cgtcagctca ggaagcgtcc tccggcgcag aagcggcatc agcaaaggcc  540
actgaagcgg aaaaaagtgc cgcagccgca gagtcctcaa aaacgcggc ggccaccagt  600
gccggtgcgg cgaaaacgtc agaaacgaat gctgcagcgt cacaacaatc agccgccacg  660
tctgcctcca ccgcggccac gaaagcgtca gaggccgcca cttcagcacg agatgcggtg  720
gcctcaaaag aggcagcaaa atcatcagaa acgaacgcat catcaagtgc cggtcgtgca  780
gcttcctcgg caacggcggc agaaaattct gccagggcgg caaaaacgtc cgagacgaat  840
gccaggtcat ctgaaacagc agcggaacgg agcgcctctg ccgcggcaga cgcaaaaaca  900
gcggcggcgg ggagtgcgtc aacggcatcc acgaaggcga cagaggctgc gggaagtgcg  960
gtatcagcat cgcagagcaa aagtgcggca gaagcggcgg caatacgtgc aaaaaattcg  1020
gcaaaacgtg cagaagatat agcttcagct gtcgcgcttg aggatgcgga cacaacgaga  1080
aaggggatag tgcagctcag cagtgcaacc aacagcacgt ctgaaacgct tgctgcaacg  1140
ccaaaggcgg ttaaggtggt aatggatgag actaatcgta aggcacctct ggacagtccg  1200
gcactgaccg gaacgccaac agcaccaacc gcgctcaggg gaacaaacaa tacccagatt  1260
gcgaacaccg cttttgtact ggccgcgatt gcagatgtta tcgacgcgtc acctgacgca  1320
ctgaatacgc tgaatgaact ggccgcagcg ctcgggaatg atccagattt tgctaccacc  1380
atgactaacg cgcttgcggg taaacaaccg aagaatgcga cactgacggc gctggcaggg  1440
ctttccacgg cgaaaaataa attaccgtat tttgcggaaa atgatgccgc cagcctgact  1500
gaactgactc aggttggcag ggatattctg gcaaaaaatt ccgttgcaga tgttcttgaa  1560
taccttgggg ccggtgagaa ttcggccttt ccggcaggtg cgccgatccc gtggccatca  1620
gatatcgttc cgtctggcta cgtcctgatg caggggcagg cgtttgacaa atcagcctac  1680
ccaaaacttg ctgtcgcgta tccatcgggt gtgcttcctg atatgcgagg ctggacaatc  1740
aaggggaaac ccgccagcgg tcgtgctgta ttgtctcagg aacaggatgg aattaagtcg  1800
cacacccaca gtgccagtgc atccggtacg gatttgggga cgaaaaccac atcgtcgttt  1860
gattacggga cgaaaacaac aggcagtttc gattacggca ccaaatcgac gaataacacg  1920
ggggctcatg ctcacagtct gagcggttca acaggggccg cgggtgctca tgcccacaca  1980
agtggtttaa ggatgaacag ttctggctgg agtcagtatg gaacagcaac cattacagga  2040
agtttatcca cagttaaagg aaccagcaca cagggtattg cttatttatc gaaaacggac  2100
agtcagggca gccacagtca ctcattgtcc ggtacagccg tgagtgccgg tgcacatgcg  2160
catacagttg gtattggtgc gcaccagcat ccggttgtta tcggtgctca tgcccattct  2220
```

```
ttcagtattg gttcacacgg acacaccatc accgttaacg ctgcgggtaa cgcggaaaac  2280
accgtcaaaa acattgcatt taactatatt gtgaggcttg cataa                  2325

SEQ ID NO: 181          moltype = DNA  length = 585
FEATURE                 Location/Qualifiers
misc_feature            1..585
                        note = Synthetic: WT STF accessory protein 1
source                  1..585
                        mol_type = other DNA
                        organism = synthetic construct
SEQUENCE: 181
atggcattca gaatgagtga acaaccacgg accataaaaa tttataatct gctggccgga  60
actaatgaat ttattggtga aggtgacgca tatattccgc ctcataccgg tctgcctgca  120
aacagtaccg atattgcacc gccagatatt ccggctggct ttgtggctgt tttcaacagt  180
gatgaggcat cgtggcatct cgttgaagac catcggggta aaaccgtcta tgacgtggct  240
tccggcgacg cgttatttat ttctgaactc ggtccgttac cggaaaattt tacctggtta  300
tcgccgggag gggaatatca gaagtggaac ggcacagcct gggtgaagga tacggaagca  360
gaaaaactgt tccggatccg ggaggcggaa gaaacaaaaa aaagcctgat gcaggtagcc  420
agtgagcata ttgcgccgct tcaggatgct gcagatctgg aaattgcaac gaaggaagaa  480
acctcgttgc tggaagcctg gaagaagtat cgggtgttgc tgaaccgtgt tgatacatca  540
actgcacctg atattgagtg gcctgctgtc cctgttatgg agtaa                  585

SEQ ID NO: 182          moltype = DNA  length = 2376
FEATURE                 Location/Qualifiers
misc_feature            1..2376
                        note = Synthetic: SIED6
source                  1..2376
                        mol_type = other DNA
                        organism = synthetic construct
SEQUENCE: 182
atggcagtaa agatttcagg agtcctgaaa gacggcacag gaaaaccggt acagaactgc  60
accattcagc tgaaagccag acgtaacagc accacggtgg tggtgaacac ggtgggctca  120
gagaatccgg atgaagccgg gcgttacagc atggatgtgg agtacggtca gtacagtgtc  180
atcctgcagg ttgacggttt tccaccatcg cacgccggga ccatcaccgt gtatgaagat  240
tcacaaccgg ggacgctgaa tgattttctc tgtgccatga cggaggatga tgcccggccg  300
gaggtgctgc gtcgtcttga actgatggtg gaagaggtgg cgcgtaacgc gtccgtggtg  360
gcacagagta cggcagacgc gaagaaatca gccggcgatg ccagtgcatc agctgctcag  420
gtcgcggccc ttgtgactga tgcaactgac tcagcacgcg ccgccagcac gtccgccgga  480
caggctgcat cgtcagctca ggaagcgtcc tccggcgcag aagcggcatc agcaaaggcc  540
actgaagcgg aaaaaagtgc cgcagccgca gagtcctcaa aaaacgcggc ggccaccagt  600
gccggtgcgg cgaaaacgtc agaaacgaat gctgcagcgt cacaacaatc agccgccacg  660
tctgcctcca ccgcggccac gaaagcgtca gaggccgcca cttcagcacg agatgcggtg  720
gcctcaaaag aggcagcaaa atcatcagaa acgaacgcat catcaagtgc cggtcgtgca  780
gcttcctcgg caacggcggc agaaaattct gccagggcgg caaaaacgtc cgagacgaat  840
gccaggtcat ctgaaacagc agcggaacgg agcgcctctg ccgcggcaga cgcaaaaaca  900
gcggcggcgg ggagtgcgtc aacggcatcc acgaaggcga cagaggctgc gggaagtgcg  960
gtatcagcat cgcagagcaa aagtgcggca gaagcggcgg caatacgtgc aaaaaattcg  1020
gcaaaacgtg cagaagatat agctgatcct gcttctgtcc ctccgcttcc tgatatctgg  1080
ctacccttga atgattctct ggaagcgata acagggtatg cgccggggta taaaacaata  1140
accatcggca gcgatgaaat cactgtgcca gttaatggca tatgccaatt tagccgggct  1200
tcatctgcaa cgtatattga taagtccggg catattaccg tggcagggaa taacgttcct  1260
cgttttgaaa aatatggttt gctgatagag aatcagcgaa caaacatgtt cgtaaatagt  1320
tttaatcctg atgcgtggaa taaaagcggt ggtatatctg taacatcatc aacagatgaa  1380
tttgagttta aatatggacg tttcacagta ggaagcgaca tagcaggaac gacaacaggg  1440
agaaatatat gcacagttgc tggtaataga ggcatagatg tgactggcga tgatcagtac  1500
agtaaaggtc cgtatgttac cgcgtcgttc agggtaagaa gtgatctcaa tgttcgcgca  1560
cgtatccgtt ttgaacggta taactcggaa ggatacactt tcctttgtga cgcctatttg  1620
tcattacaga cccatgaact acaaattacg ggtgataatg cccagctatt aacagcaaac  1680
tttgaaatcg atccaggtag tggatggata tattttcagg caaccctgaa atgtctgcca  1740
gaatggggaa tggttggtac gcagttgcaa attgcagccg acagagctgt ggggtctttt  1800
gcaacaggtg actggataga agtaaccacc ccgcaatttg agtatggtgc ttgtgcaact  1860
tcctttatca taacgacaac agagccagcg actcgtgcat cagatttatg taaatttccg  1920
ctgatgaaaa atatgtatac catgcctttt acgttcatgg tggaagtcca taaaaactgg  1980
tttattgctc ataatgctgc accgcgagta attgatacag aaaaccatca gtcaggtgct  2040
ccatttatca tgggatttgg ctcttctgga actatcagtc aggacggtta tccctattgt  2100
gatataggcg gggctaaccg acgtgtatat gagtcatgcg gagtaagaga tcttgttatg  2160
ggattcaggg ttaaggctga cggcatgaca tgctcatttg caaataagca tataagcaca  2220
gaaacaaaaa cagtatggaa atatattcgt gaagctgctg tgattcgtat cgggggacaa  2280
acgacgacag gattacgaca ccttaatggt catataaaaa acctccgttt ctggaacaga  2340
gcattgtcag atacgcagct taaggaatac gtataa                            2376

SEQ ID NO: 183          moltype = DNA  length = 270
FEATURE                 Location/Qualifiers
misc_feature            1..270
                        note = Synthetic: SIED6 accessory protein 1
source                  1..270
                        mol_type = other DNA
                        organism = synthetic construct
SEQUENCE: 183
```

```
atgcgggata taacattacg attcgataac agagaacagt ttaacgcaat tgtatatgac  60
agtggcctgt tcagtcttga agaagaaaac gggattcttg ttgatgttat tggccgcgtt  120
atcgattacg aggagccaga aaacgaaaga tgtacaggca ttgatcgcgg cggttttttc  180
gtaaacatga ggattgttga tagcagtaaa aacatatctt ctttaatgcc tttcattacg  240
acagatcagc atgtaaggac atgggcttaa                                   270

SEQ ID NO: 184          moltype = DNA  length = 885
FEATURE                 Location/Qualifiers
misc_feature            1..885
                        note = Synthetic: SIED6 accessory protein 2
source                  1..885
                        mol_type = other DNA
                        organism = synthetic construct
SEQUENCE: 184
atggttacaa aaacagtaat tcctgatgac atcaaaacgc taaaatccga tgttagtaaa  60
ctaaaaaacg atcaaggaag ctacgcaaca aaatcatatg tagacagcaa agatgaaacc  120
gttggtgact ggtctgcttc atggtatcag caggtattgc caactagcgg agctatattt  180
gggagaaaac tccgctcaac tcaccggacg gcaggtgttg aggatgcgta ttgcgaacta  240
taccttaaaa aatggataga cagcccaggg aacgcaatgg cgcgccttaa cctgaacgat  300
aacggtgaaa atatttgctg ggattttacc aacctttacg gcggaacaat gatcttccct  360
ggaacttcag gctatctgaa aatggggaac tgtctcatgt cgtatggtgt gcggggaagt  420
aacgcgctta ttaagtttga taatacagac tcattgcaga tcaaatatgc taatcacggg  480
tcgaccatga cactaaacac gcaaggcacg gcgtattctg gtgtgtcgac gttattatgg  540
ggaaattcca gtcgtccagt tgtttatgag attagggatg atggcgggct ttttttgttt  600
tatgcacaaa ggaacccaga taaaacctat cagcttgaga taaacgggcc atgtaaggct  660
acatcattcg accaggtgtc ggacagagat cttaaagaaa acattcgggt tattgataat  720
gccactgaac gcatcagatt aatgaatggg tatacttacc gtctcaagtc taatggtatg  780
ccttatgctg gcgttattgc gcaagaggca cttaatgcaa tccctgaatc agttggtagc  840
acaataaagt acaagagcgg ggacaatggg tctgatggag aatag                  885

SEQ ID NO: 185          moltype = DNA  length = 3291
FEATURE                 Location/Qualifiers
misc_feature            1..3291
                        note = Synthetic: SIEA11
source                  1..3291
                        mol_type = other DNA
                        organism = synthetic construct
SEQUENCE: 185
atggcagtaa agatttcagg agtcctgaaa gacggcacag gaaaaccggt acagaactgc  60
accattcagc tgaaagccag acgtaacagc accacggtgg tggtgaacac ggtgggctca  120
gagaatccgg atgaagccgg gcgttacagc atggatgtgg agtacggtca gtacagtgtc  180
atcctgcagg ttgacggttt tccaccatcg cacgccggga ccatcaccgt gtatgaagat  240
tcacaaccgg ggacgctgaa tgatttttctc tgtgccatga cggaggatga tgcccggccg  300
gaggtgctgc gtcgtcttga actgatggtg gaagaggtgg cgcgtaacgc gtccgtggtg  360
gcacagagta cggcagacgc gaagaaatca gccggcgatg ccagtgcatc agctgctcag  420
gtcgcggccc ttgtgactga tgcaactgac tcagcacgcg ccgccagcac gtccgccgga  480
caggctgcat cgtcagctca ggaagcgtcc tccggcgcag aagcggcatc agcaaaggcc  540
actgaagcgg aaaaaagtgc cgcagccgca gagtcctcaa aaacgcggc ggccaccagt  600
gccggtgcgg cgaaaacgtc agaaacgaat gctgcagcgt cacaacaatc agccgccacg  660
tctgcctcca ccgcggccac gaaagcgtca gaggccgcca cttcagcacg agatgcggtg  720
gcctcaaaag aggcagcaaa atcatcagaa acgaacgcat catcaagtgc cggtcgtgca  780
gcttcctcgg caacggcggc agaaaattct gccagggcgg caaaaacgtc cgagacgaat  840
gccaggtcat ctgaaacagc agcggaacgg agcgcctctg ccgcggcaga cgcaaaaaca  900
gcggcggcgg ggagtgcgtc aacggcatcc acgaaggcga cagaggctgc gggaagtgcg  960
gtatcagcat cgcagagcaa aagtgcggca gaagcggcgg caatacgtgc aaaaaattcg  1020
gcaaaacgtg cagaagatat agcttcagct gtcgcgcttg aggatgcgga cacaacgaga  1080
aaggggatag tgcagctcag cagtgcaacc aacagcacgt ctgaaacgct tgctgcaacg  1140
ccaaaggcgg ttaaggcagc aaatgacaac gcaaattcac gtctggcgaa aaatcagaat  1200
ggtgcagata tccaggataa atcagctttt ctggacaatg ttggcgttac cagcctgacg  1260
tttatgaaaa acaatggcga aatgccggtt gatgctgatc tgaatacgtt tggttctgtt  1320
aaggcttatt caggtatctg gtctaaagca acgtccacca acgcaacact ggagaaaaac  1380
ttccctgaag ataatgctgt cggtgtgctt gaggttttta ctggcggcaa ttttgcaggc  1440
acgcaacgct ataccacacg tgacggaaat ttgtatatcc gcaaactcat tggaacatgg  1500
aatggtaatg atggaccatg gggagcatgg cgccatgttc aggctgtaac gcgagctcta  1560
agtacgacca ttgaccttaa ctctctcggt ggcgcagaac atttaggtct atggagaaac  1620
agcagttcag caatagcttc ttttgaacga cattaccccg agcagggagg agacgcgcag  1680
ggcattctgg aaattttcga aggtgggcta tatggacgca cacagcgtta tacaacccgt  1740
aacgggacta tgtatattcg cggcctgaca gccaaatggg atgcagaaaa tccacagtgg  1800
gaagactgga accaaattgg ttatcagacc agtagtacct tctatgagga tgacctggat  1860
gatttgatgt ctccaggtat ttacagtgtg acaggcaaag cgacccacac cccaatccag  1920
gggcagtctg gttttctgga agtcatcagg cgcaaggatg gtgtctatgt tttgcaacgt  1980
tacacgacca caggaaccag cgcagctaca aaagaccgtt tatatgagcg agtgtttctt  2040
ggtggctcat ttaacgcgtg gggggagtgg cgacagattt ataactcaaa ctctttgccg  2100
ttagagttgg gtatcggtgg cgcagtggca aaactcacca gcctggactg gcagacatac  2160
gattttgtgc cgggcagtct gataaccgtt cggctggata acatgaccaa tattcccgac  2220
ggtatggact ggggcgtcat tgatggcaac ctgataaaca tctcagtcgg tccgagtgat  2280
gattctggtt cgggacgctc aatgcatgta tggcgcagca ctgtaagtaa agccaactac  2340
cgctttttta tggtgcgtat ttcaggaaat ccgggaagcc gcacgatcac gacaagacgt  2400
gtgccaatta tcgacgaagc ccagacatgg ggcgcgaaac agacattcag tgctggcctt  2460
```

```
tctggtgaac tgtccggcaa tgcggcgaca gcaacaaagc tgaaaacagc ccgtaaaatt  2520
aataacgttt cgtttgatgg aacatcagat attaacctga cgccgaaaaa tattggtgca  2580
tttgcttcag gaaaaacagg agacaccgtt gcgaatgata aagccgttgg atggaactgg  2640
agtagcggag cctataacgc aactattggt ggggcatcaa cgttaattct tcattttaat  2700
atcggggaag gaagttgtcc cgccgcccag tttcgcgtta attataagaa cggtggtatt  2760
ttttatcgtt ctgctcgtga cggttacgga ttcgaggctg actggtctga gttttatacc  2820
acaacgcgaa aacctacagc gggagatgtc ggtgcactgc cgttatctgg tggtcaattg  2880
aatggtgctc tgggtatagg aacatccagt gctcttggcg gtaattcgat tgttttgggt  2940
gataatgaca cgggctttaa acaaaatggt gatggtaatc tggatgttta tgctaatagc  3000
gtccatgtta tgcgctttgt ctccggaagc gttcaaagta ataaaaccat aaatattacg  3060
gggcgtgtta atccctcgga ttacggtaac tttgattccc gctatgtgag agatgtcaga  3120
cttggcacac gtgttgtcca gaccatgcag aaaggggtga tgtatgagaa agcagggcac  3180
gtaattaccg ggcttggtat tgtcggtgaa gtcgatggtg atgaccccgc agtattcaga  3240
ccaatacaaa aatacatcaa tggcacatgg tataacgtcg cacaggtgta a           3291
```

```
SEQ ID NO: 186          moltype = DNA  length = 528
FEATURE                 Location/Qualifiers
misc_feature            1..528
                        note = Synthetic: SIEA11 accessory protein 1
source                  1..528
                        mol_type = other DNA
                        organism = synthetic construct
SEQUENCE: 186
atgcagcatt taaaaaatat tactgcgggt aatccaaaaa ctgttgccca atatcaactg  60
acaaaaaatt ttgatgttat ctggttatgg tccgaagagg gaaaaaactg gtatgaggaa  120
gtaagtaatt ttcaggaaga cacgataaag attgtttacg atgagaataa tataattgtc  180
ggcatcacca gagatgcttc aacgctcaac cctgaaggtt ttagcgttgt cgaggttcct  240
gatattaccg ccaaccgacg tgctgatgac tcaggtaaat ggatgtttaa ggatggtgcc  300
gtgattaagc ggatttatac ggcagacgaa cagctgcaac tggcggaatt acagaagtca  360
gctttgcttt ccgaagctga aactatcatt cagccactgg aacgctctgt cagactgaat  420
atggcaacag atgaggagcg tagccgactg gaagcatggg aacgctacag tgttctggtc  480
agccgtgtgg atcctgcaaa tcctgaatgg ccggaaatgc cgcaataa               528
```

```
SEQ ID NO: 187          moltype = DNA  length = 2238
FEATURE                 Location/Qualifiers
misc_feature            1..2238
                        note = Synthetic: EB6
source                  1..2238
                        mol_type = other DNA
                        organism = synthetic construct
SEQUENCE: 187
atggcagtaa agatttcagg agtcctgaaa gacggcacag gaaaaccggt acagaactgc  60
accattcagc tgaaagccag acgtaacagc accacggtgg tggtgaacac ggtgggctca  120
gagaatccgg atgaagccgg gcgttacagc atggatgtgg agtacggtca gtacagtgtc  180
atcctgcagg ttgacggttt tccaccatcg cacgccggga ccatcaccgt gtatgaagat  240
tcacaaccgg ggacgctgaa tgattttctc tgtgccatga cggaggatga tgcccggccg  300
gaggtgctgc gtcgtcttga actgatggtg gaagaggtgg cgcgtaacgc gtccgtggtg  360
gcacagagta cggcagacgc gaagaaatca gccggcgatg ccagtgcatc agctgctcag  420
gtcgcggccc ttgtgactga tgcaactgac tcagcacgcg ccgccagcac gtccgccgga  480
caggctgcat cgtcagctca ggaagcgtcc tccggcgcag aagcggcatc agcaaaggcc  540
actgaagcgg aaaaaagtgc cgcagccgca gagtcctcaa aaacgcggc ggccaccagt  600
gccggtgcgg cgaaaacgtc agaaacgaat gctgcagcgt cacaacaatc agccgccacg  660
tctgcctcca ccgcggccac gaaagcgtca gaggccgcca cttcagcacg agatgcggtg  720
gcctcaaaag aggcagcaaa atcatcagaa acgaacgcat catcaagtgc cggtcgtgca  780
gcttcctcgg caacggcggc agaaaattct gccagggcgg caaaaacgtc cgagacgaat  840
gccaggtcat ctgaaacagc agcggaacgg agcgcctctg ccgcggcaga cgcaaaaaca  900
gcggcggcgg ggagtgcgtc aacggcatcc acgaaggcga cagaggctgc gggaagtgcg  960
gtatcagcat cgcagagcaa aagtgcggca gaagcggcgg caatacgtgc aaaaaattcg  1020
gcaaaacgtg cagaagatat agcttcagct gtcgcgcttg aggatgcgga cacaacgaga  1080
aaggggatag tgcagctcag cagtgcaacc aacagcacgt ctgaaacgct tgctgcaacg  1140
ccaaaggcgg ttaagattgc gatggataat gccaatgccc gtctggcaaa agaccggaac  1200
ggagcagata ttcccaataa gccgctgttt atccaaaacc tcggtttaca ggaaacggta  1260
aacaaggctg gtaacgccgt tcaaaagaca ggcgatacct tgtccggcgg acttactttt  1320
gaaaacgact caatccttgc ctggattcgg aatactgact gggcaaagat tggatttaaa  1380
aatgatgccg acagcgacac tgattcatac atgtggtttg aaacaggcga caacggcaat  1440
gaatatttca aatggagaag ccgccagagc accacaacaa aagacctgat gaatcttaaa  1500
tgggatgctt tgtatgttct tgtcaatgcc attgtaaatg gcgaagtcat atcaaaatca  1560
gcaaacggcc tacgtattgc ttatggtaat tacggattct ttattcgtaa tgatggttca  1620
aatacatact tcatgttgac aaactccggt gacaacatgg ggacttataa cggattaagg  1680
ccattatgga ttaataacgc tactggcgct gtttcgatgg ggcgtggtct taatgtttca  1740
ggggagacac tttcagaccg ttttgctatt aacagcagta atggtatgtg gattcagatg  1800
cgcgataaca acgctatctt tgggaaaaat atagttaaca ctgatagcgc tcaggcgtta  1860
cttcgccaga atcacgccga ccgaaagttc atgataggtg gactggggaa caagcaattt  1920
ggcatctaca tgattaataa ctcaaggaca gccaatggca ccgatggtca ggcgtacatg  1980
gataataacg gtaactggct ttgtggtgcg caagttattc ccggcaatta tggcaatttt  2040
gactcacgct atgtgagaga tgtccgactt ggcacacgtg ttgttcaatt gatggcgcgt  2100
ggtggtcgtt atgaaaaagc cggacacgca attaccggat taagaatcat tggtgaagta  2160
gatggcgatg atgaagccat cttcaggcca atacaaaaat acatcaatgg cacatggtat  2220
aacgtcgcac aggtgtaa                                                2238
```

```
SEQ ID NO: 188         moltype = DNA  length = 528
FEATURE                Location/Qualifiers
misc_feature           1..528
                       note = Synthetic: EB6 accessory protein 1
source                 1..528
                       mol_type = other DNA
                       organism = synthetic construct
SEQUENCE: 188
atgcagcatt taaaaaatat taagtctgga aatcctaaaa cgaaagaaca atatcagcta  60
acaaagaatt ttgatgttat ctggttatgg tccgaagacg gtaaaaactg gtatgaagaa  120
gtaaataact ttcaggacga caccataaag attgtatacg acgaaaataa tattattgtt  180
gccataacca aagatgcctc aacgcttaat cccgaaggct ttagcgtcgt tgagattcca  240
gatataacag ccaatcgtcg tgccgatgat tcagggaagt ggatgtttaa ggacggagct  300
gtggttaaac ggatttatac ggcagacgag caacaacaac aggccgaatc acaaaaggcc  360
gcgttacttt ccgaagcaga aaacgttatt cagccactgg aacgcgctgt cagactgaat  420
atggcgacgg atgaggaacg cgcacgactg gagtcatggg aacgctacag tgttctggtc  480
agccgtgtgg atacggcaaa gccagaatgg ccacaaaagc ctgaataa               528

SEQ ID NO: 189         moltype = DNA  length = 3321
FEATURE                Location/Qualifiers
misc_feature           1..3321
                       note = Synthetic: AH11L
source                 1..3321
                       mol_type = other DNA
                       organism = synthetic construct
SEQUENCE: 189
atggcagtaa agatttcagg agtcctgaaa gacggcacag gaaaaccggt acagaactgc  60
accattcagc tgaaagccag acgtaacagc accacggtgg tggtgaacac ggtgggctca  120
gagaatccgg atgaagccgg gcgttacagc atggatgtgg agtacggtca gtacagtgtc  180
atcctgcagg ttgacggttt tccaccatcg cacgccggga ccatcaccgt gtatgaagat  240
tcacaaccgg ggacgctgaa tgattttctc tgtgccatga cggaggatga tgcccggccg  300
gaggtgctgc gtcgtcttga actgatggtg gaagaggtgg cgcgtaacgc gtccgtggtg  360
gcacagagta cggcagacgc gaagaaatca gccggcgatg ccagtgcatc agctgctcag  420
gtcgcggccc ttgtgactga tgcaactgac tcagcacgcg ccgccagcac gtccgccgga  480
caggctgcat cgtcagctca ggaagcgtcc tccggcgcag aagcggcatc agcaaaggcc  540
actgaagcgg aaaaaagtgc cgcagccgca gagtcctcaa aaacgcggc ggccaccagt  600
gccggtgcgg cgaaaacgtc agaaacgaat gctgcagcgt cacaacaatc agccgccacg  660
tctgcctcca ccgcggccac gaaagcgtca gaggccgcca cttcagcacg agatgcggtg  720
gcctcaaaag aggcagcaaa atcatcagaa acgaacgcat catcaagtgc cggtcgtgca  780
gcttcctcgg caacggcggc agaaaattct gccagggcgg caaaaacgtc cgagacgaat  840
gccaggtcat ctgaaacagc agcggaacgg agcgcctctg ccgcggcaga cgcaaaaaca  900
gcggcggcgg ggagtgcgtc aacggcatcc acgaaggcga cagaggctgc gggaagtgcg  960
gtatcagcat cgcagagcaa aagtgcggca gaagcggcgg caatacgtgc aaaaaattcg  1020
gcaaaacgtg cagaagatat agcttcagct gtcgcgcttg aggatgcgga cacaacgaga  1080
aaggggatag tgcagctcag cagtgcaacc aacagcacgt ctgaaacgct tgctgcaacg  1140
ccaaaggcgg ttaaggcagc aaatgacaac gcaaattcac gtctggcgaa aaatcagaac  1200
ggtgcagata tccaggataa atcagttttt ctggacaatg ttggcgttac cagcctgacg  1260
tttatgaaaa acaatggcga aatgccgctt gatgctgatc tgaatacatt tggtcccgtt  1320
aaggcttatc tggggatctg gtctaaagct acctcaacta acgcaacact ggagaaaaat  1380
ttcccggaag ataatgctgt cggtgtgctt gaggtttttg ctgccggcaa ttttgcaggt  1440
acgcaacgct ttaccacaag agacggcaat gtatacatgc gtaaactcgc caataagtgg  1500
aatggcactg atggtccgtg gggcgtatgg cgtcacactc aatcagctac ccgccccttg  1560
agtacgacta tagacctgaa tacgcttgga gccgccgaac atcttggttt atggcgtaac  1620
agtagctcgg ctatagcttc atatgaacgc aattatccag aggaaggcgg ctttgctcag  1680
gggacgcttg agatcctcga aggcgggaat tatggaagaa cgcaacgtta taccactcgc  1740
cgtggaaata tgtatgtccg ctgccttgcg gcaagctggg atgcatcaaa tccgcagtgg  1800
gaaccgtggt taagagtcgg tcatcagtca gagagtcgtt attacgaagg tgatttgaat  1860
gatgtaacct caccaggtat ttacagcgtt acaggtaaag cgaccaacgg tccagtactg  1920
gacggaaacg gcgtgactgt actcggcatt ctggaagtgt tgaggcggtt tgatggtgtt  1980
aatgtatggc agcgttatac aactgccgga acaggtacaa cccttaaagg ccgcaccttt  2040
gagcgcgtct ttaccggcag ctcatggagc gaatggcggg aagtctacac ctcgtattca  2100
cttcccctga atctgggtat cggcggtgct gtggcaaagc tcaccagcct ggactggcag  2160
acctacgatt ttgtgccggg cagtctgata accgttaggc tggataatat gaccaatatt  2220
cccgacggta tggactgggg cgtcattgat ggcaacctga taaacatcgc agttggtccg  2280
agtgatgatt ccggtacggg gcgctcaatg catgtatggc gcagcactgt aagtaaagcg  2340
aactaccgat tttttatggt gcgtatttca ggaaatccgg gaagccgcac gatcacagca  2400
agacgagtac caatcattga cgaagcccag acatggggcg cgaaacagac attcagtgct  2460
ggcctttctg gtgaactgtc cggcaatgcg gcgacagcaa caaagctgaa aacagcccgt  2520
aaaattaata acgtttcgtt tgatggaaca tcagatatta acctgacgcc gaaaaatatt  2580
ggtgcatttg cttcaggaaa aacaggagac accgttgcga atgataaagc cgttgggtgg  2640
aactggagta gcggagccta taacgcaact actggtgggg catcaacgtt aattcttcat  2700
tttaatatcg gtgaaggaag ttgtcccgcc gcccagttcc gcgttaatta taagaacggc  2760
ggtatttttt atcgttctgc tcgtgacggt tacggattcg aggctgactg gtctgagttt  2820
tataccacaa cgcgaaaacc tacagcggga gatgtcggtg cactgccgtt atctggtggt  2880
caattgaatg gtgctctggg tataggaaca tccagtgctc ttggcggtaa ttcgattgtt  2940
ttgggtgata atgacacggg ctttaaacaa aatggtgatg gtaatctgga tgtttatgct  3000
aatagcgtcc atattatgcg ctttgtctcg ggaagtattc aaagtaataa aaccataaat  3060
attacggggc gtgttaatcc ctcggattac ggtaactttg attcccgcta tgtccgggat  3120
```

```
atccggcttg gtggtgctgc cacatacaaa cctgcgaaca atggcatgac atggacacat  3180
caggcaccgt ccgggtgtgt atattccggc attattgttc aggataccgg ctcaaactct  3240
gccgataaca ttggtggtgt atattacagg ccggttcaga aatacattaa cgggacatgg  3300
tataacgtgg cgcaggtata a                                            3321

SEQ ID NO: 190         moltype = DNA  length = 528
FEATURE                Location/Qualifiers
misc_feature           1..528
                       note = Synthetic: AH11L accessory protein 1
source                 1..528
                       mol_type = other DNA
                       organism = synthetic construct
SEQUENCE: 190
atgcagcatt tgaaaaatat tacggcgggt aatccaaaaa cggttgaaca atatcaattg  60
acaaagggtt ttgatgttgt ctggtttttt tcagaagatg gtaagaactg gtacgaagaa  120
caaaagtatt ttgctgatga cacgataaaa atagcgtacg acaaagataa tattatccgc  180
tatgtggaaa aggatgtgac agctatcaga ccggatggat taagtgttgt tgaagtggcg  240
gatattactg ctaaccgacg ggcggacatt tcagggggct ggatgtttaa ggacggcaaa  300
gtgattaaac gcatttatac ggcagaggaa ttgctgcagc aggcagaaaa ccggaaagcc  360
agacttcttg cagatgctga atccgtgatt ttgccgctgg agcgcgcggt cagactgaac  420
atggcaacag atgaggagcg tagccgactg gatgcatggg agcgttacag cgttctggtc  480
agtcgtgtgg atcctgcaaa tcctgaatgg ccggaaatgc cgcaataa             528

SEQ ID NO: 191         moltype = DNA  length = 786
FEATURE                Location/Qualifiers
misc_feature           1..786
                       note = Synthetic: WW55 3.0 accessory protein 1
source                 1..786
                       mol_type = other DNA
                       organism = synthetic construct
SEQUENCE: 191
atggcaatat cttctggatg ggtaggatca tctgctgtgt ccgagactgg tcaacggtgg  60
atgagcgccg caatgcaagc tgttcgctta ggtcgtccgg cgtatatgtc ggcaatggtc  120
ggacgctcta aagagattca ttatagcatt ggtgctagta actcttacaa taaagacact  180
cttattaact ggatgaaagc acaaggatct actccggtag taattactat cacgggtaat  240
attgtttccc aatctactgg cgttccttgt cttgatttcc ctagctcact gacaaacgaa  300
tatgtaacac tcattattaa ctctggtgtt catgtattag gtcgtggagg aaatggcgga  360
agtaactctg ctggtggagc aggaggaaat gcaataaata acggaattgg aactcgttta  420
agaataaaca ataatggtat tattggtggt ggcggtggtg gcggtgctgg tgctagatac  480
aatcctttcc ctcaaatgga tatgaaattt ggcggcggtg gaggccgtcc atttggtgct  540
gcgggtgcgg caggaggcgg cgcagcggca gcatctgctg gtacaatttc tgccccaggt  600
aaaggcactg tttctggggt tcattatgga ggagatggtg gagatttggg agctgctggc  660
aaatcttcat atattaaagg tggtactggt ggaactgttc actcgggtgg tgctgcgggt  720
aaagctgtta ctggtaatgc ccctcgctgg gataaagtag gcacgatcta cggtgctcgc  780
gtgtaa                                                           786

SEQ ID NO: 192         moltype = DNA  length = 261
FEATURE                Location/Qualifiers
misc_feature           1..261
                       note = Synthetic: WW55 3.0 accessory protein 2
source                 1..261
                       mol_type = other DNA
                       organism = synthetic construct
SEQUENCE: 192
atgtccaatc agcatgaaca aatgattaat gtcctgaaag tacgtctgtt tgacactcaa  60
gaaaaggccg cattcttaga aggccaactg aaagatcgtg agcgtgtatt gatggaactg  120
gtacgcattc tgggtattca gccagacgaa aacggcactg tttcccttga tgctattgtc  180
gaagaagtga aagcacttct ccctaaagac gaagcagcgg aagacgcaga agaggaagta  240
gaactgatca cggaggcttg a                                          261

SEQ ID NO: 193         moltype = DNA  length = 2394
FEATURE                Location/Qualifiers
misc_feature           1..2394
                       note = Synthetic: STF68B
source                 1..2394
                       mol_type = other DNA
                       organism = synthetic construct
SEQUENCE: 193
atggcagtaa agatttcagg agtcctgaaa gacggcacag gaaaaccggt acagaactgc  60
accattcagc tgaaagccag acgtaacagc accacggtgg tggtgaacac ggtgggctca  120
gagaatccgg atgaagccgg gcgttacagc atggatgtgg agtacggtca gtacagtgtc  180
atcctgcagg ttgacggttt tccaccatcg cacgccggga ccatcaccgt gtatgaagat  240
tcacaaccgg ggacgctgaa tgatttttctc tgtgccatga cggaggatga tgcccggccg  300
gaggtgctgc gtcgtcttga actgatggtg gaagaggtgg cgcgtaacgc gtccgtggtg  360
gcacagagta cggcagacgc gaagaaatca gccggcgatg ccagtgcatc agctgctcag  420
gtcgcggccc ttgtgactga tgcaactgac tcagcacgcg ccgccagcac gtccgccgga  480
caggctgcat cgtcagctca ggaagcgtcc tccggcgcag aagcggcatc agcaaaggcc  540
actgaagcgg aaaaaagtgc cgcagccgca gagtcctcaa aaaacgcggc ggccaccagt  600
gccggtgcgg cgaaaacgtc agaaacgaat gctgcagcgt cacaacaatc agccgccacg  660
```

```
tctgcctcca ccgcggccac gaaagcgtca gaggccgcca cttcagcacg agatgcggtg  720
gcctcaaaag aggcagcaaa atcatcagaa acgaacgcat catcaagtgc cggtcgtgca  780
gcttcctcgg caacggcggc agaaaattct gccagggcgg caaaaacgtc cgagacgaat  840
gccaggtcat ctgaaacagc agcggaacgg agcgcctctg ccgcggcagc ttctgccact  900
gcatctgcca acagtcaaaa agctgcaaag acgagcgaaa ccaacgcaaa gacaagcgag  960
actgcggcgg ctaactcggc gaaagcatca gctgcaagcc agacggctgc aaaagcgagt  1020
gaagacgcag ccagagagta tgcaagccag gctgcggagc cgtataaaca agttttgcag  1080
ccgcttcccg atgtgtggat accgtttaac gattcactgg aaatgattac tggtttcgct  1140
cctggttata aaaaagtaac tatcggtgat gatgttatta cttttccatc agagaaggtt  1200
gtatctttca ctcgctccac ttctgcaacg tatataaaca aatcaggttc atttgctttt  1260
gcagaaatta acgagccgcg ctttgaaaag gaaggtttat taattgaagg tcagaggaca  1320
aatacattta ctaatagtaa caatccttca ttatggaatt atgacgacaa gaatatagaa  1380
ataaccacat cggttgatga atatggtttt aaatatggtt tgttcgatgt aaaggaaaca  1440
tcaactactg aaagggcgac gataatatct actggataca gtagggttat tgatgttgct  1500
gcaaatgaat ctgttacttt gtcctgtagg gttaagaaga taaatggaga aggtattata  1560
acgttaagac ccagaatatc tttcgttaac gatgacggta caagcaacac gctggtagct  1620
ggttcctaca tagattgcga aactggtgat gttttaggtt tttctggtgg ggatgctgta  1680
aatcatgtca tatacagaga agctaacgga tggttacgcg tcgaatttac atataaatca  1740
ccagaagcaa aaagcatgta tggcgcttt gaaatgggag cagataaaag ggcgatcaaa  1800
aaaggcgatc agataatgtt tactacgccg caatttgaaa aggatcgtg tgcatcatca  1860
tttatcgtta catcagatgt ggcagttaca cgggctagtg acgtggtaat aatgccaata  1920
agactgaact ggtcaacacc tccgttaagc gttcttatgg aagttaatat caactgggac  1980
aaaatgccaa acagtgaagg ttcagcaagg cttcttaacg tgtcaataac tggcgcaaca  2040
acggatgttg ctgatgaaag ttatatgtat tttggtttta cctctggagg cgcgcgctca  2100
attataacta acggaaaagg aacaaagacc gagtataaag cctactgtaa caggacaacc  2160
cgcaggttta ttgctgggtt taagtttaca gagcagaaag aattgcgtgc tgttataaac  2220
ggtaactttg gcgctgttga tgtatcacaa cacacaagac aacgttatac agaagggcca  2280
ataaatatag gcggtcaatc aatatcaggt aacaggcatt tatttggaca cgtgcgcaat  2340
ttacgtatct ggcataagga actgacagat gcacaaatgg gagaaagaat ataa        2394
```

```
SEQ ID NO: 194         moltype = DNA  length = 282
FEATURE                Location/Qualifiers
misc_feature           1..282
                       note = Synthetic: STF68B accessory protein 1
source                 1..282
                       mol_type = other DNA
                       organism = synthetic construct
SEQUENCE: 194
atgcgagact taaccctcaa attcataaac aaggccgact tttcggcctt tatggatagc  60
attggttatg aagatgacga ggtaatgcag aacaatgttc tcattgatgt gataggtaac  120
gtgtacaaag aaaccggaga acttactgaa gatggcgagc cggtatgtgt taaggaagac  180
ggatattttg taaacgtgcg catcattaat gatgcaaaaa aatcgtcaat attcgataaa  240
tacgcggttg ttgttgagca tcaacttcgt ggctggatgt ga                    282
```

```
SEQ ID NO: 195         moltype = DNA  length = 1041
FEATURE                Location/Qualifiers
misc_feature           1..1041
                       note = Synthetic: STF68B accessory protein 2
source                 1..1041
                       mol_type = other DNA
                       organism = synthetic construct
SEQUENCE: 195
atggctacat cgacagtaat tcctgatgac atcaaaacgc taaaatccga cgttagcaaa  60
ttaaaaaacg atcaaggaag ctacgcaaca aaatcatatg tagacagcaa agatgaaacc  120
gttggtgact ggtctgcttc atggtatcag caagtattgc caactagcgg agctatattt  180
gggagaaaac tccgctcaac tcacaggacg gcaggtgttg aggatgcgta ttgcgaacta  240
tacctcaaaa aatggataga cagtccaggt aacgcaatgg cgcgccttaa cctgaacgat  300
aacgggacaa acatttgctg ggactttacc aacctttatg gcggtacgat gatttttccc  360
ggtgacagcg gatacctcaa aatgggtaac tgccttatgt catacagcaa gcgtggaagt  420
aacgcgctta ttaaatttga ttacaccgac acattacaga tcaaatatgc taatcatggg  480
tcaaccatga cattaaacac acagggaacc gctcacgctg gcgtaacaac tagactatgg  540
ggtaattcta gccgtccggt tgtttatgaa gttggcgtag atgaggctct gtatatgttc  600
tacgcacaga aaactaccag caatacctac gaattaacgg ttaacggcgc gtgcaatgca  660
agtgcattta atcaaggctc tgaccgggat ctgaaagaca atattcaggt gatcgataat  720
gcaaccgacc gcattcgtaa aatgaacggc tatacataca cgcttaaaga aaacggtatg  780
ccttacgctg gtgttattgc acaagaaacc ctggaagcca tccccgaagc cgtaggggct  840
atgatgaaat atccagacgg cgggagtgga ttagatggag aagaaggtga acggtattac  900
actgtagatt attctggtgt tactggcttg cttgttcagg tagccagaga gtcagacgac  960
aggataacag cactggaaga agaaaacgca gaattaagac aaagattatc tgcaattgag  1020
gcggcgcttg cgtctaaata a                                           1041
```

```
SEQ ID NO: 196         moltype = DNA  length = 2640
FEATURE                Location/Qualifiers
misc_feature           1..2640
                       note = Synthetic: STF90B
source                 1..2640
                       mol_type = other DNA
                       organism = synthetic construct
SEQUENCE: 196
```

```
atggcagtaa agatttcagg agtcctgaaa gacggcacag gaaaaccggt acagaactgc  60
accattcagc tgaaagccag acgtaacagc accacggtgg tggtgaacac ggtgggctca  120
gagaatccgg atgaagccgg gcgttacagc atggatgtgg agtacggtca gtacagtgtc  180
atcctgcagg ttgacggttt tccaccatcg cacgccggga ccatcaccgt gtatgaagat  240
tcacaaccgg ggacgctgaa tgattttctc tgtgccatga cggaggatga tgcccggccg  300
gaggtgctgc gtcgtcttga actgatggtg gaagaggtgg cgcgtaacgc gtccgtggtg  360
gcacagagta cggcagacgc gaagaaatca gccggcgatg ccagtgcatc agctgctcag  420
gtcgcggccc ttgtgactga tgcaactgac tcagcacgcg ccgccagcac gtccgccgga  480
caggctgcat cgtcagctca ggaagcgtcc tccggcgcag aagcggcatc agcaaaggcc  540
actgaagcgg aaaaaagtgc cgcagccgca gagtcctcaa aaacgcggc ggccaccagt  600
gccggtgcgg cgaaaacgtc agaaacgaat gctgcagcgt cacaacaatc agccgccacg  660
tctgcctcca ccgcggccac gaaagcgtca gaggccgcca cttcagcacg agatgcggtg  720
gcctcaaaag aggcagcaaa atcatcagaa acgaacgcat catcaagtgc cggtcgtgca  780
gcttcctcgg caacggcggc agaaaattct gccagggcgg caaaaacgtc cgagacgaat  840
gccaggtcat ctgaaacagc agcggaacgg agcgcctctg ccgcggcaga cgcaaaaaca  900
gcggcggcgg ggagtgcgtc aacggcatcc acgaaggcga cagaggctgc gggaagtgcg  960
gtatcagcat cgcagagcaa aagtgcggca gaagcggcgg caatacgtgc aaaaaattcg  1020
gcaaaacgtg cagaagatat agcttcagct gtcgcgcttg aggatgcgga cacaacgaga  1080
aaggggatag tgcagctcag cagtgcaacc aacagcacgt ctgaaacgct tgctgcaacg  1140
ccaaaggcgg ttaaggtggt aatggatgag actaatcgta aatataccgc acaggacgcc  1200
accaccgcgc gaaaaggcct tgtccagcta agtagcgtca ccaacagcga ttctgaaacg  1260
cttgcggcaa cgccaaaggc ggttaagaca gcgtatgacc ttgctaacgg gaaatacact  1320
gcacaggatg ccaccacagc gcgaaaaggt cttgtccagc tcagtagcgc caccaacagc  1380
gattctgaaa cgcttgcggc aacaccaaaa gcggtgaagt ctgcctatga caatgctgaa  1440
aaacgtcttc agaaagatca gaacggtgcg gatattccgg gaaaggatac tttcacgaaa  1500
aatatcggtg cctgtcgtgc ttatagcggt gctttgagca ctgacgccgg aaactggaca  1560
accgctcagt ttattgactg gctagagtct cagggagcct ttaatcatcc ctactggatg  1620
tgcaagtgtt cctggtcata cggtaataac aaaattatta ccgatactga ctgtgggact  1680
attcatcttg caggttgcgt gattgaggtt atgggcgtta aagctgcaat gaccattcgt  1740
gtgaccactc cgagtacatc aagcggtggt ggtaccacca gtgcgcaatt cacgtatatc  1800
aatcacggag ctgattatgc gccgggctgg cgacgcgact acaatacgaa aaataagcaa  1860
ccggcttttg cattagggaa aacaggaaat acggttgcaa ataataaagc ggtaggatgg  1920
aactgggaca gtggtgctta ttgtgcacag gatggcggag catcaaaaat ggtgctgcat  1980
ttttacacgg gtgagggaag ttgtccggca atgcagtttc ttgtggatta taaaaacagg  2040
gggatttttt acaggtcggc acgtgatggg tatggatttg aggctgactg gtcagagttt  2100
tataccacat cacgaaagcc aacacctgcg gatattcttg ctctggcatt atcaggcgga  2160
agcatgtcag gcagcataaa atttatcaat gatgccttcc tgatttggga aagaaacact  2220
gactgggcga aaattggatt taaaaatgat tcagatgctg attctgactc atacatgtgg  2280
tttgaaactg gtgataatgg caatgaatat tttaaatggc gcatcaggtc tggcagcaca  2340
acaaaagacc tgatgacgct taagtctgat gcactacggg ttaccgggca ggtgatacca  2400
tcaaatttca gcaattttga ctcccgctat gtccgggata tccggcttgg tggtgccgcc  2460
acatacaaac ctgcgaacaa tggcatgaca tggacacatc aggcaccgtc cgggtgtgta  2520
tataccggca ttattgttca ggataccggc tcaaactctg ccgataacat tggtggcgta  2580
tattacagac cggtgcagaa atacattaac gggacatggt ataacgtggc gcaggtataa  2640

SEQ ID NO: 197          moltype = DNA  length = 528
FEATURE                 Location/Qualifiers
misc_feature            1..528
                        note = Synthetic: STF90B accessory protein
source                  1..528
                        mol_type = other DNA
                        organism = synthetic construct
SEQUENCE: 197
atgcagcatt taaaaaatat tacggcgggt aatccaaaaa cggttgaaca atatcaattg  60
acaaaggact ttgatgttgt ctggtttttt tcagaagatg gtaagaactg gtacgaagaa  120
caaaagtatt ttgctgatga cacgataaaa atagcgtacg acaaagataa tatcatccgc  180
tatgtggaaa aggatgtgac agctatcaga ccggatggat taagtgttgt tgaagtggcg  240
gatattactg ctaaccgacg ggcggatatt tcagggaact ggatgtttaa ggatggcaca  300
gtgatcaaac gaatttatac ggcagaggaa ttgcaacagc aggcagaaaa caggaaagcc  360
agacttcttg cagatgctga atccgtgatt ttgccgctgg agcgcgctgt caggctgaat  420
atggcaacag aggaggagcg tagcagactg gaaagatggg aacgctacag cgttctggtc  480
agtcgtgtgg atcctgcaaa tcccgaatgg ccggaaatgc cgcaataa              528

SEQ ID NO: 198          moltype = DNA  length = 2616
FEATURE                 Location/Qualifiers
misc_feature            1..2616
                        note = Synthetic: STF117
source                  1..2616
                        mol_type = other DNA
                        organism = synthetic construct
SEQUENCE: 198
atggcagtaa agatttcagg agtcctgaaa gacggcacag gaaaaccggt acagaactgc  60
accattcagc tgaaagccag acgtaacagc accacggtgg tggtgaacac ggtgggctca  120
gagaatccgg atgaagccgg gcgttacagc atggatgtgg agtacggtca gtacagtgtc  180
atcctgcagg ttgacggttt tccaccatcg cacgccggga ccatcaccgt gtatgaagat  240
tcacaaccgg ggacgctgaa tgattttctc tgtgccatga cggaggatga tgcccggccg  300
gaggtgctgc gtcgtcttga actgatggtg gaagaggtgg cgcgtaacgc gtccgtggtg  360
gcacagagta cggcagacgc gaagaaatca gccggcgatg ccagtgcatc agctgctcag  420
gtcgcggccc ttgtgactga tgcaactgac tcagcacgcg ccgccagcac gtccgccgga  480
```

```
caggctgcat cgtcagctca ggaagcgtcc tccggcgcag aagcggcatc agcaaaggcc  540
actgaagcgg aaaaaagtgc cgcagccgca gagtcctcaa aaaacgcggc ggccaccagt  600
gccggtgcgg cgaaaacgtc agaaacgaat gctgcagcgt cacaacaatc agccgccacg  660
tctgcctcca ccgcggccac gaaagcgtca gaggccgcca cttcagcacg agatgcggtg  720
gcctcaaaag aggcagcaaa atcatcagaa acgaacgcat catcaagtgc cggtcgtgca  780
gcttcctcgg caacggcggc agaaaattct gccagggcgg caaaaacgtc cgagacgaat  840
gccaggtcat ctgaaacagc agcggaacgg agcgcctctg ccgcggcaga cgcaaaaaca  900
gcggcggcgg ggagtgcgtc aacggcatcc acgaaggcga cagaggctgc gggaagtgcg  960
gtatcagcat cgcagagcaa aagtgcggca gaagcggcgg caatacgtgc aaaaaattcg  1020
gcaaaacgtg cagaagatat agcttcagct gtcgcgcttg aggatgcgga cacaacgaga  1080
aaggggatag tgcagctcag cagtgcaacc aacagcacgt ctgaaacgct tgctgcaacg  1140
ccaaaggcgg ttaaggtggt aatggatgag actaatcgta aatatactgc gcaggatgcc  1200
accacagcgc gaaaagggct tgtccagctc agtagcgcca ccaacagtga ttctgaaacc  1260
ctcgcggcaa cgccaaaagc agtgaagtct gcctatgaca atgctgaaaa acgtcttcag  1320
aaagatcaga acggtgcgga tattccggga aaggatacct tcacgaaaaa tatcggtgcc  1380
tgtcgtgctt atagcggcgc tttgagcact gaagccggaa actggacaac cgctcagttt  1440
attgaatggc tggattcccg tggtgcattt aatcatccgt actggatgtg caaaggctcc  1500
tggtcatatg caaataacaa aatcattacg gataccggat gtggtgatat ccacctggct  1560
ggttgtgtcg tcgaggtcat gggaactaaa tctgcaatca ctatccgagt gaccacgccg  1620
acaacatcaa gcggtggcgg tacaaccagc gcgcaattca cttacattaa tcatggggac  1680
ggctactccc ccggctggcg tcgtgactgg aatcgtcagg gcgacgcaat gaccggaacg  1740
attaatcagg atggcggaag ccagaatgcc tatatgtcta cggccttatg ttcaggcacc  1800
agaggcggca aaaaatatct cagaaagttt cgtggtggag aaggagacac tatctggcat  1860
gaaacagtac agggcggggt agttcgctgg gcgactggta atactgatgc tcaggaagaa  1920
ttatcactca gctccgctta tggtctccgt tcaagaggtg agattacatc aagcagtgct  1980
aatggtctgc gcattgctta tggcaattat ggattcttta tcaggaatga tggcagcagc  2040
acttatttta tgttgactaa atcaggtgac agattaggca cttataataa tttaagacca  2100
ctgattataa atgatgccac gggtgctgta tcaatggggc atggcctgag tgttactggt  2160
gatattgcct caagtaccaa agtacgtgcc ggtagcggga aaaaattcac ggtcagcagc  2220
agtaatacat ccacgaagga agccgcattc aatttgtggg gaaactcaag tcgtccggtg  2280
gtggctgaat taggtgatga tgcaggctgg cctttttaca gtcagagaaa tacagataac  2340
agcatcactt ttgctgttaa cgggcaggta tcaccatcta actatagtaa ttttgattca  2400
cgctatgtcc gggatatccg gcttggtggt gctgccacat acaaacctgc gaacaatggc  2460
atgacatgga cacatcaggc accgtccggg tgtgtatatt ccggcattat tgttcaggat  2520
accggctcaa actctgccga taacattggt ggcgtatatt acagaccggt gcagaaatac  2580
attaacggga catggtataa cgtggcacag gtataa                           2616
```

```
SEQ ID NO: 199          moltype = DNA  length = 528
FEATURE                 Location/Qualifiers
misc_feature            1..528
                        note = Synthetic: STF117 accessory protein 1
source                  1..528
                        mol_type = other DNA
                        organism = synthetic construct
SEQUENCE: 199
atgcagcatt tgataaatat aaccgcgggt aatccaaaaa cggttgaaca atatcaattg  60
acaaaggact ttgatgttgt ctggtttttt acagaagatg gtaagaactg gtacgaagaa  120
caaaagtatt ttgctgatga cacgataaaa atagcgtacg acaaggataa tattatccgc  180
tatgtggaaa aagatgtgac agctatcaga ccagatggat taagtgtggt tgaagtggcg  240
gatattactg ctaaccgacg ggcggacatt tcagggaact ggatgtttaa ggacggcaaa  300
gtgattaaac gcatttatac ggcagaggaa ttgcagcagc aggcagaaaa ccggaaagcc  360
agacttcttg cagatgctga atccgtgatt ttgccactgg agcgcgctgt caggctgaac  420
atggcaacag atgaggagcg tagccgactg gaagcatggg aacgctacag tgttctggtc  480
agccgtgtgg atcctgcaaa tcctgaatgg ccggaaatgc cgcaataa            528
```

```
SEQ ID NO: 200          moltype = DNA  length = 2517
FEATURE                 Location/Qualifiers
misc_feature            1..2517
                        note = Synthetic: O111
source                  1..2517
                        mol_type = other DNA
                        organism = synthetic construct
SEQUENCE: 200
atggcagtaa agatttcagg agtcctgaaa gacggcacag gaaaaccggt acagaactgc  60
accattcagc tgaaagccag acgtaacagc accacggtgg tggtgaacac ggtgggctca  120
gagaatccgg atgaagccgg gcgttacagc atggatgtgg agtacggtca gtacagtgtc  180
atcctgcagg ttgacggttt tccaccatcg cacgccggga ccatcaccgt gtatgaagat  240
tcacaaccgg ggacgctgaa tgattttctc tgtgccatga cggaggatga tgcccggccg  300
gaggtgctgc gtcgtcttga actgatggtg gaagaggtgg cgcgtaacgc gtccgtggtg  360
gcacagagta cggcagacgc gaagaaatca gccggcgatg ccagtgcatc agctgctcag  420
gtcgcggccc ttgtgactga tgcaactgac tcagcacgcg ccgccagcac gtccgccgga  480
caggctgcat cgtcagctca ggaagcgtcc tccggcgcag aagcggcatc agcaaaggcc  540
actgaagcgg aaaaaagtgc cgcagccgca gagtcctcaa aaaacgcggc ggccaccagt  600
gccggtgcgg cgaaaacgtc agaaacgaat gctgcagcgt cacaacaatc agccgccacg  660
tctgcctcca ccgcggccac gaaagcgtca gaggccgcca cttcagcacg agatgcggtg  720
gcctcaaaag aggcagcaaa atcatcagaa acgaacgcat catcaagtgc cggtcgtgca  780
gcttcctcgg caacggcggc agaaaattct gccagggcgg caaaaacgtc cgagacgaat  840
gccaggtcat ctgaaacagc agcggaacgg agcgcctctg ccgcggcaga cgcaaaaaca  900
gcggcggcgg ggagtgcgtc aacggcatcc acgaaggcga cagaggctgc gggaagtgcg  960
```

```
gtatcagcat cgcagagcaa aagtgcggca gaagcggcgg caatacgtgc aaaaaattcg  1020
gcaaaacgtg cagaagatat agcttcagct gtcgcgcttg aggatgcgga cacaacgaga  1080
aaggggatag tgcagctcag cagtgcaacc aacagcacgt ctgaaacgct tgctgcaacg  1140
ccaaaggcgg ttaaggtggt aatggatgag actaatcgta aggcacctct ggacagtccg  1200
gcactgaccg gaacgccaac agcaccaacc gcgctcaggg gaacaaacaa tacccagatt  1260
gcgaacaccg cttttgtact ggccgcgatt gcagatgtta tcgacgcgtc acctgacgca  1320
ctgaatacgc tgaatgaact ggccgcagcg ctcgggaatg atccagattt tgctaccacc  1380
atgactaacg cgcttgcggg taaacaaccg aagaatgcga cactgacggc gctggcaggg  1440
ctttccacgg cgaaaaataa attaccgtat tttgcggaaa atgatgccgc cagcctgact  1500
gaactgactc aggttggcag ggatattctg gcaaaaaatt ccgttgcaga tgttcttgaa  1560
taccttgggg ccggtgagaa ttcggcatca ggtgcattac agaagaatca aaacggtgca  1620
gacattccgg gcaaagatac ctttaccaag aatatcggtg cttgtcgtgc ttattcggca  1680
tggcttaata tcggaggtga ttctcaggta tggactacgg ctcagtttat ctcttggctc  1740
gagagtcagg gtgcgtttaa tcatccgtac tggatgtgca aaggctcttg ggcgtacgcg  1800
aacaacaaag tcatcaccga cactggttgt ggtaacatct gtctggcggg tgcagtagtg  1860
gaagttatcg gtacgcgcgg tgcgatgacg atccgtgtaa ctactccatc tacctcctcc  1920
ggtggcggta tcaccaacgc ccagttcact tacattaacc acggcgatgc ctatgctccg  1980
ggctggcgcc gtgattacaa cactaaaaac caacaacctg cgtttgcact gggtcagacg  2040
ggtagtcgtg tggcgaacga taaagcggtc ggttggaatt ggaactctgg tgtgtacaac  2100
gctgatatta gtggagcttc tactctgatc cttcatttta acatgaatgc tggaagttgt  2160
ccggcagtgc agtttcgtgt taactatcgt aatggaggaa tcttttaccg ctctgcacgt  2220
gacggctacg gcttcgaagc gaactggagt gaattttaca cgaccactcg taagccgagt  2280
gctggagatg tgggagctta tactcaggca gaatgcaatt cgcgtttcat tactggtatt  2340
cgtctgggag gtttaagttc cgtgcagact tggaacggtc caggttggag tgatcgtagt  2400
ggctatgttg tgacaggcag tgttaacggc aaccgtgacg aactgatcga cactactcaa  2460
gcgcgtccga tccagtactg cattaacgga acttggtata acgcgggaag tatctaa     2517
```

```
SEQ ID NO: 201          moltype = DNA  length = 534
FEATURE                 Location/Qualifiers
misc_feature            1..534
                        note = Synthetic: O111 accessory protein
source                  1..534
                        mol_type = other DNA
                        organism = synthetic construct
SEQUENCE: 201
atgatgcact taaaaaacat tactgctggc aaccctaaaa caaaagagca ataccagcta  60
acgaaacaat ttaacatcaa atggctttat tcagaggatg gaaaaaactg gtatgaggaa  120
caaaagaatt tccagccaga cactttgaaa atggtttatg accataacgg cgttattatt  180
tgtattgaaa aggatgtttc agcaattaat ccggaaggcg caagcgtcgt tgaattacct  240
gatattacag caaatcgccg tgctgacatt tcgggtaaat ggatgttcaa agatggcgta  300
gtggtaaagc gtacttacac agaagaagag caacgtcaac aggcggaaaa tgaaaagcaa  360
agcctgctac agctcgtcag ggataaaacc cagctatggg acagtcagct acggctgggc  420
atcatttccg acgagaataa acaaaaatta acagagtgga tgctctttgc gcagaaagtc  480
gaatctacag acacttccag cctgccagta acgtttcccg aacaaccaga atga        534
```

```
SEQ ID NO: 202          moltype = DNA  length = 2505
FEATURE                 Location/Qualifiers
misc_feature            1..2505
                        note = Synthetic: DC1
source                  1..2505
                        mol_type = other DNA
                        organism = synthetic construct
SEQUENCE: 202
atggcagtaa agatttcagg agtcctgaaa gacggcacag gaaaaccggt acagaactgc  60
accattcagc tgaaagccag acgtaacagc accacggtgg tggtgaacac ggtgggctca  120
gagaatccgg atgaagccgg gcgttacagc atggatgtgg agtacggtca gtacagtgtc  180
atcctgcagg ttgacggttt tccaccatcg cacgccggga ccatcaccgt gtatgaagat  240
tcacaaccgg ggacgctgaa tgattttctc tgtgccatga cggaggatga tgcccggccg  300
gaggtgctgc gtcgtcttga actgatggtg gaagaggtgg cgcgtaacgc gtccgtggtg  360
gcacagagta cggcagacgc gaagaaatca gccggcgatg ccagtgcatc agctgctcag  420
gtcgcggccc ttgtgactga tgcaactgac tcagcacgcg ccgccagcac gtccgccgga  480
caggctgcat cgtcagctca ggaagcgtcc tccggcgcag aagcggcatc agcaaaggcc  540
actgaagcgg aaaaaagtgc cgcagccgca gagtcctcaa aaaacgcggc ggccaccagt  600
gccggtgcgg cgaaaacgtc agaaacgaat gctgcagcgt cacaacaatc agccgccacg  660
tctgcctcca ccgcggccac gaaagcgtca gaggccgcca cttcagcacg agatgcggtg  720
gcctcaaaag aggcagcaaa atcatcagaa acgaacgcat catcaagtgc cggtcgtgca  780
gcttcctcgg caacggcggc agaaaattct gccagggcgg caaaaacgtc cgagacgaat  840
gccaggtcat ctgaaacagc agcggaacgg agcgcctctg ccgcggcaga cgcaaaaaca  900
gcggcggcgg ggagtgcgtc aacggcatcc acgaaggcga cagaggctgc gggaagtgcg  960
gtatcagcat cgcagagcaa aagtgcggca gaagcggcgg caatacgtgc aaaaaattcg  1020
gcaaaacgtg cagaagatat agcttcagct gtcgcgcttg aggatgcgga cacaacgaga  1080
aaggggatag tgcagctcag cagtgcaacc aacagcacgt ctgaaacgct tgctgcaacg  1140
ccaaaggcgg ttaaggcagc atatgacctt gctaacggga aatacactgc acaggacgcc  1200
accacagcgc gaaaaggtct tgtccagctc agtagcgtca ccaacagtga ttctgaaacc  1260
ctcgcggcaa cgccaaaagc agtgaagtct gcctatgaca atgctgaaaa acgtcttcag  1320
aaagatcaga acggtgcgga tattccggga aaggatacct tcacgaaaaa tatcggtgcc  1380
tgtcgtgctt atagcggcgc tttgagcact gaagccggaa actggacaac cgcgcagttt  1440
attgactggc tagagtctca gggagccttt aatcatccct actggatgtg caagtgttcc  1500
tggtcatacg gtaataacaa aattattacc gatactgact gtgggacgat tcatcttgca  1560
```

```
ggttgcgtga ttgaggttat gggtgttaaa gcagcaatga ccattcgtgt gaccactccg  1620
agtacatcaa gcagtggtgg taccaccagt gcgcaattca cgtatatcaa tcacggagct  1680
gattatgcgc cgggctggcg acgcgactac aatacgaaaa ataagcaacc ggcttttgca  1740
ttagggaaaa caggaaatac ggttgcaaat aataaagcag taggatggaa ctgggacagt  1800
ggtgcttatt gtgcacagga tggcggagca tcaaaaatgg tgctgcattt ttacacgggt  1860
gagggaagtt gtccggcaat gcagtttctt gtggattata aaaacagggg gattttttac  1920
aggtcggcac gtgatgggta tggatttgag gctgactggt cagagtttta taccacatca  1980
cgaaagccaa cacctgcgga tattcttgct ctggcattat caggcggaag catgtcaggc  2040
agcataaaat ttatcaatga tgccttcctg atttgggaaa gaaacactga ctgggcgaaa  2100
attggattta aaaatgattc agatgctgat tctgactcat acatgtggtt tgaaactggt  2160
gataatggca atgaatattt taaatggcgc atcaggtctg gcagcacaac aaaagacctg  2220
atgacgctta agtctgatgc actacgggtt accgggcagg tgataccatc aaatttcagc  2280
aattttgact cccgctatgt ccgggatatc cggcttggtg gtgccgccac atacaaacct  2340
gcgaacaatg gcatgacatg gacacatcag gcaccgtccg ggtgtgtata taccggcatt  2400
attgttcagg ataccggctc aaactctgcc gataacattg gtggcgtata ttacagaccg  2460
gttcagaaat acattaacgg gacgtggtac aacgtggcgc aggta                    2505
```

```
SEQ ID NO: 203          moltype = DNA  length = 528
FEATURE                 Location/Qualifiers
misc_feature            1..528
                        note = Synthetic: DC1 accessory protein 1
source                  1..528
                        mol_type = other DNA
                        organism = synthetic construct
SEQUENCE: 203
atgcagcatt tgataaatat aacggcaggt aatccaaaaa cggttgaaca atatcaattg  60
acaaaggact ttgatgttgt ctggtttttt tcagaagatg gtaagaactg gtacgaagaa  120
caaaagtatt ttgctgatga cacgataaaa atagcgtacg acaaagataa tattatccgc  180
tatgtggaaa aggatgtgac agctatcaga ccagatggat taagtgttgt tgaagtgccg  240
gatattactg ctaatcgacg ggcggacatt tcagggggct ggatgtttaa ggacggcaaa  300
gtgattaaac gcatttatac ggcagaggaa ttgcagcagc aggcagaaaa ccggaaagcc  360
agacttcttg cagatgctga atccgtgatt ttgccgctgg agcgcgcggt cagactgaac  420
atggcaacag atgaggagcg tagccgactg gatgcatggg agcgttacag cgttctggtc  480
agtcgtgtgg atcctgcaaa tcctgaatgg ccggaaatgc cgcaataa                528
```

```
SEQ ID NO: 204          moltype = DNA  length = 2748
FEATURE                 Location/Qualifiers
misc_feature            1..2748
                        note = Synthetic: STF94A
source                  1..2748
                        mol_type = other DNA
                        organism = synthetic construct
SEQUENCE: 204
atggcagtaa agatttcagg agtcctgaaa gacggcacag gaaaaccggt acagaactgc  60
accattcagc tgaaagccag acgtaacagc accacggtgg tggtgaacac ggtgggctca  120
gagaatccgg atgaagccgg gcgttacagc atggatgtgg agtacggtca gtacagtgtc  180
atcctgcagg ttgacggttt tccaccatcg cacgccggga ccatcaccgt gtatgaagat  240
tcacaaccgg ggacgctgaa tgatttctc tgtgccatga cggaggatga tgcccggccg  300
gaggtgctgc gtcgtcttga actgatggtg gaagaggtgg cgcgtaacgc gtccgtggtg  360
gcacagagta cggcagacgc gaagaaatca gccggcgatg ccagtgcatc agctgctcag  420
gtcgcggccc ttgtgactga tgcaactgac tcagcacgcg ccgccagcac gtccgccgga  480
caggctgcat cgtcagctca ggaagcgtcc tccggcgcag aagcggcatc agcaaaggcc  540
actgaagcgg aaaaaagtgc cgcagccgca gagtcctcaa aaacgcggc ggccaccagt  600
gccggtgcgg cgaaaacgtc agaaacgaat gctgcagcgt cacaacaatc agccgccacg  660
tctgcctcca ccgcggccac gaaagcgtca gaggccgcca cttcagcacg agatgcggtg  720
gcctcaaaag aggcagcaaa atcatcagaa acgaacgcat catcaagtgc cggtcgtgca  780
gcttcctcgg caacggcggc agaaaattct gccagggcgg caaaaacgtc cgagacgaat  840
gccaggtcat ctgaaacagc agcggaacgg agcgcctctg ccgcggcaga cgcaaaaaca  900
gcggcggcgg ggagtgcgtc aacggcatcc acgaaggcga cagaggctgc gggaagtgcg  960
gtatcagcat cgcagagcaa aagtgcggca gaagcggcgg caatacgtgc aaaaaattcg  1020
gcaaaacgtg cagaagatat agcttcagct gtcgcgcttg aggatgcgga cacaacgaga  1080
aaggggatag tgcagctcag cagtgcaacc aacagcacgt ctgaaacgct tgctgcaacg  1140
ccaaaggcgg ttaaggtggt aatggatgag actaatcgta aatataccgc acaggacgcc  1200
accacagcgc gaaaaggcct tgttcagctg agtagcgcca tcaacagcga ttctgaaacg  1260
cttgcggcaa cgccaaaggc ggttaagaca gcgtatgacc ttgctaacag gaaatacact  1320
gcacaggatg ccaccacagc gcgaaaaggt cttgtccagc taagtagcgc caccaacagt  1380
gattctgaaa cgctggccgc aacatcaaaa gcggtgaagt ctgcctatga caatgctgaa  1440
aaacgtcttc agaaagatca gaatggtgcg gatattccgg gaaaggatac cttcacgaaa  1500
aatatcggtg cctgtcgtgc ttatagcggc gctttgagca ctgaagccgg aaactggaca  1560
accgctcagt ttattgaatg gctggattcc cgtggtgcat ttaatcatcc gtactggatg  1620
tgcaaaggct cctggtcata tgcaaataac aaaatcatta cggataccgg atgtggtgat  1680
atccacctgg ctggttgtgt cgtcgaggtc atgggaacta aatctgcaat cactatccga  1740
gtgaccacac cgacaacatc aagcggtggc ggtacaacca gcgcacaatt cacttacatt  1800
aatcatgggg acggctactc ccccggctgg cgtcgtgact ggaatcgtca gggcgacgca  1860
atgaccggaa cgattaatca ggacggtgga agccagaatg cctatatgtc tacggcctta  1920
tgttcaggca caagaggcgg caaaaaatat ctcagaaagt ttcgtggtgg agaaggagac  1980
actatctggc atgaaacagt acagggcggg gtagttcgtt gggcgactgg taatactgat  2040
gctcaggaag aattatcact cagctccgct tatggtctcc gttcaagagg tgagattaca  2100
tcactcagtg ctaatggtct gcgcattgct tatggcaatt atggtttctt tatcaggaat  2160
```

```
gatggcagca gcacttattt tatgttgact aaatcaggtg acagattagg aacttataat  2220
aatttaagac cgctgattat aaatgatgcc actggtgctg tatcaatggg gcatggcctg  2280
aatgttactg gtgatattgt ctcaagtacc aaagtacgtg ccggtagcgg gaaaaaattc  2340
acggtcagca gcagtaatac atccacgaag gaagccgcat tcaatttgtg ggaaactca  2400
agtcgtccgg tggtggctga attaggtgat gatgcaggct ggcatttttta cagtcagaga  2460
aatacagata acagcatcac ttttgctgtt aacgggcagg tatcaccatc taactatggc  2520
aactttgatt cacgctatgt ccgggatatc cggcttggtg gtgctgccac atacaaacct  2580
gcgaacaatg gcatgacatg gacacatcag gcaccgtccg ggtgtgtata ttccggcatt  2640
attgttcagg ataccggctc aaactctgcc gataacattg gtggcatata ttacagaccg  2700
gtgcagaaat acattaacgg gacatggtat aacgtagcgc aggtataa                2748
```

```
SEQ ID NO: 205         moltype = DNA  length = 528
FEATURE                Location/Qualifiers
misc_feature           1..528
                       note = Synthetic: STF94A accessory protein
source                 1..528
                       mol_type = other DNA
                       organism = synthetic construct
SEQUENCE: 205
atgcagcatt tgataaatat aatggcgggt aatccaaaaa cagttgaaca atatcaattg  60
acaaagggct ttgatgttgt ctggtttttt acagaagatg gtaagaactg gtacgaagaa  120
caaaagtatt ttgctgatga cacgataaaa atagcgtacg acaaagataa tatcatccgc  180
tatgtggaaa aggatgtgac agctatcaga ccggatggat taagtgtggt tgaagtggcg  240
gatattactg ctaaccgacg ggcggatatt tcagggggct ggatgtttaa ggacggcaaa  300
gtgattaaac gcatttatac ggcggaggaa ttacagcagc aggcagaaat tcggaaagcc  360
agacttcttg cagatgctga atccgtgatt ttgccgctgg agcgcgcggt cagactgaac  420
atggcaacag aggaggagcg cacacggctg gaggcttggg aacgctacag cgttctggtc  480
agtcgtgtgg atcctgcaaa tcctgaatgg ccggaaatgc cgcaataa                528
```

```
SEQ ID NO: 206         moltype = DNA  length = 1509
FEATURE                Location/Qualifiers
misc_feature           1..1509
                       note = Synthetic: STF69A
source                 1..1509
                       mol_type = other DNA
                       organism = synthetic construct
SEQUENCE: 206
gcttctgcca ctgcatcagc taacagtcaa aaagcagcaa aaaccagtga aaccaacgca  60
aaggcgagcg aaacagcggc tgcgaactca gcgaaagcat cggcagcaag ccagacggca  120
gctaaagcaa gcgaagatgc agccagagag tacgcaagcc aggctgcgga gccgtataaa  180
tatgtcttac agccgttacc tgaggtgtgg ataccgttta acgattcact ggatatgatt  240
accgggtttg ctcctggata taagagcatc acagttggtg acgatgttat tgcattgccg  300
tctgaaaagg ttgtttcatt taccagggcg tcaactgcaa cgtatataga taagtctggg  360
tgttttgctg aatcagcgat aaatgaacca cgttttgaaa aagatggtct gctcattgaa  420
ggtcagagaa cgaatacttt ttcttatacg aatacaccag tatcgtggaa ctatgacact  480
gctaacttaa ctattaccac gggagttgat gagtatggtt tcagttatgg tttgtttggc  540
gttaaagaaa catccacaac tgaaagggcg acattaattt ctactggata taccagggtt  600
atttcagttt cggcaaatga atcagttact ttatcctgca gagttaaaaa agtaagtggg  660
gatggtatta tcacgttgcg tccaagaata tcatatgtta acgacgatgg ctcaagtaac  720
acactgaccg ctggcgcata tattgattgc gagactggcg atatgttgag ttattctgga  780
ggtgaggcgg caacttataa catattcaga gagtctaatg gatggattcg tgttgagttt  840
acctacaaat caccagaagc aaaaaatatg tatgggcgtt ttgagtttgg agcacatcaa  900
cgatcaatca agtctggcga taaattaatg ttaacaaccc ctcaattcga aaagggacta  960
aacgcgtcat cttttatcat cacaacagag gtcggtgcca cgagagcaag tgaccaggta  1020
atcataccta tacctttcaa ttgggcaact ccaccagtta gtgttctcat ggaagttaat  1080
gttaattggg attctgaaat gcctaattta gaaggctctg cgcgtttgct taatatctca  1140
attacagggg cgacgactga agtttctgat gaaagttata tgtattttgg ttttaccact  1200
cgtggtaaaa ggctaattat caccaatggc aaaggaacaa aaacagaata taaagcatat  1260
gggaatagag agaaaaggaa atttgttact ggctttaagt ttacagaaga taaacagttg  1320
caggttgttg ttgatggaat tttaggtggc agctccccgt ctctgcatac attgcaacgt  1380
tatactgccg gtaatattaa tatcggtgga caatcatcca gtggcaacag acacctgttc  1440
ggtcatgtga aaaatttacg catttggcat aaagaattaa ctgaggcaca aatgggggag  1500
tcaatctaa                                                           1509
```

```
SEQ ID NO: 207         moltype = DNA  length = 282
FEATURE                Location/Qualifiers
misc_feature           1..282
                       note = Synthetic: STF69A accessory protein 1
source                 1..282
                       mol_type = other DNA
                       organism = synthetic construct
SEQUENCE: 207
atgaaagatt taacactcaa atttgaagac agggccgact tttcggcctt tatggagagt  60
attggctatt atgatgacga gtcgatgcag gatgatattc ttatcgacgt gataggtaac  120
gtgtacaaag aaaccggaga actgactgaa gatggcgaac cggtatgtgt taaggaagac  180
ggatattttg taaacgtgcg catcattaat gattcgcaaa tatcgtcatt attcgatgaa  240
tacgtggttg ctgttgagca tcaacttcgt ggctggatgt ga                      282
```

```
SEQ ID NO: 208         moltype = DNA  length = 1041
```

```
FEATURE                 Location/Qualifiers
misc_feature            1..1041
                        note = Synthetic: STF69A accessory protein 2
source                  1..1041
                        mol_type = other DNA
                        organism = synthetic construct
SEQUENCE: 208
atggctacat cgacagtaat tcctgatgac atcaaaacgc taaaatccga cgttagcaaa  60
ttaaaaaacg atcaaggaag ctacgcaaca aaattatatg tagacagcaa agatgaaatc  120
gttggtgact ggtctgcttc atggtatcag caggtattgc caactagcgg agctatattt  180
gggagaaaac tccgctcaac tcacaggacg gcaggtgttg aggatgcgta ttgcgaacta  240
tacctcaaaa aatggataga cagtccaggt aacgcaatgg cgcgccttaa cctgaacgat  300
aacgggacaa acatttgctg ggactttacc aacctttatg gcggtacgat gatttttccc  360
ggtgacagcg gatacctcaa aatgggtaac tgccttatgt catacagcaa gcgtggaagt  420
aacgcgctta ttaaatttga ttacaccgac acattacaga tcaaatatgc caatcatggg  480
tcaaccatga cattaaacac acagggaacc gcttatgctg gtgttactgc tcaattgtgg  540
ggcaactcca gccgtcctgt tgtttatgaa gtcggtgttg atggtggcgc ttatatgttc  600
tatgcgcaga aaaataccga taacacctat atgttaagcg ttaatggtgc atgtcatgcc  660
accgcattta accagcattc cgaccgggat ctgaaagaca acattcaggt gatcgataat  720
gcaaccgacc gcatccgtaa aatgaacggc tatacataca cgcttaaaga aaacggtatg  780
ccctatgctg gtgtcattgc acaggaagct ctggaagcaa tcccagaagt tgtaggttcc  840
gcaatgaaat atcaggacgg tgcgagcgga tcggaaggtg aagaaggtga acgttattac  900
acagtagatt attctggtgt tactggcttg cttgttcagg tagccagaga gtcagacgac  960
agaataacag cactggaaga agaaaacgca gaattaagac aaagattatc tgcaattgag  1020
gcggcgcttg cgtctaaata a                                           1041

SEQ ID NO: 209          moltype = DNA  length = 2475
FEATURE                 Location/Qualifiers
misc_feature            1..2475
                        note = Synthetic: STF118
source                  1..2475
                        mol_type = other DNA
                        organism = synthetic construct
SEQUENCE: 209
atggcagtaa agatttcagg agtcctgaaa gacggcacag gaaaaccggt acagaactgc  60
accattcagc tgaaagccag acgtaacagc accacggtgg tggtgaacac ggtgggctca  120
gagaatccgg atgaagccgg gcgttacagc atggatgtgg agtacggtca gtacagtgtc  180
atcctgcagg ttgacggttt tccaccatcg cacgccggga ccatcaccgt gtatgaagat  240
tcacaaccgg ggacgctgaa tgattttctc tgtgccatga cggaggatga tgcccggccg  300
gaggtgctgc gtcgtcttga actgatggtg gaagaggtgg cgcgtaacgc gtccgtggtg  360
gcacagagta cggcagacgc gaagaaatca gccggcgatg ccagtgcatc agctgctcag  420
gtcgcggccc ttgtgactga tgcaactgac tcagcacgcg ccgccagcac gtccgccgga  480
caggctgcat cgtcagctca ggaagcgtcc tccggcgcag aagcggcatc agcaaaggcc  540
actgaagcgg aaaaaagtgc cgcagccgca gagtcctcaa aaacgcggc ggccaccagt  600
gccggtgcgg cgaaaacgtc agaaacgaat gctgcagcgt cacaacaatc agccgccacg  660
tctgcctcca ccgcggccac gaaagcgtca gaggccgcca cttcagcacg agatgcggtg  720
gcctcaaaag aggcagcaaa atcatcagaa acgaacgcat catcaagtgc cggtcgtgca  780
gcttcctcgg caacggcggc agaaaattct gccagggcgg caaaaacgtc cgagacgaat  840
gccaggtcat ctgaaacagc agcggaacgg agcgcctctg ccgcggcaga cgcaaaaaca  900
gcggcggcgg ggagtgcgtc aacggcatcc acgaaggcga cagaggctgc gggaagtgcg  960
gtatcagcat cgcagagcaa aagtgcggca gaagcggcgg caatacgtgc aaaaaattcg  1020
gcaaaacgtg cagaagatat agcttcagct gtcgcgcttg aggatgcgga cacaacgaga  1080
aaggggatag tgcagctcag cagtgcaacc aacagcacgt ctgaaacgct tgctgcaacg  1140
ccaaaggcgg ttaaggtggt aatggatgag actaatcgta aagcgccatt aaacagccct  1200
gcactgaccg gaacgccaac gacgccaact gcgcgacagg gaacgaataa tactcagatc  1260
gcaaacacgg ctttcgttat ggccgcgatt gccgcccttg tagactcgtc gcctgacgca  1320
ctgaatacgc tgaacgagct ggcagcggcg ctgggcaacg acccgaattt tgctaccact  1380
atgactaatg cgcttgcggg taagcaaccg aaagatgcta ccctggcggc gctggcgggg  1440
cttgctactg cggcagacag gtttccgtat tttacgggga atgatgttgc cagtctggca  1500
actctgacaa aagtcgggcg ggatattctt gcgaaatcga ccgtttccgc cgttatcgaa  1560
tatctcggtt tacaggaaac ggtaaaccga gccgggaacg ccgtgcaaaa aaatggcgat  1620
accttgtccg gtggacttac ttttgaaaac gactcaatcc ttgcctggat tcgaaatact  1680
gactgggcga agattggatt taaaaatgat gccgatggtg acactgattc atatatgtgg  1740
tttgaaacag gtgacaacgg caatgaatac ttcaaatgga gaagtcgcca gagcaccaca  1800
acaaaagacc tgatgaatct taaatgggat gctctgtatg ttcttgttaa agccctttc  1860
agcagtgaag taaaaatatc tacagtcaat gcactgagga tatttaattc atcttttggt  1920
gctatttttc gccgttctga agaaaacctg tatatcatcc ctacacgaga aaatgagggt  1980
gaaaatggag atattgggcc attaaggcca ttcggcatca acttaagaac aggagttgtg  2040
tctgttggta atggtgccag gattgatggc gggctggcac ttggcacgaa taacgcgttg  2100
ggtgggaact ctattgttct tggtgataac gacaccggat ttaaacaaaa tggcgatggt  2160
aatctggatg tttatgctaa taacgtccat gttatgcgct ttgtttccgg aagcattcaa  2220
agtaataaga ccataaatat tacggggcgt gttaatccct cggattacgg taactttgat  2280
tcccgctatg tgagagatat cagacttggc acacgtgttg tccagaccat gcagaaaggg  2340
gtgatgtatg agaaagcagg gcacgtaatt accgggcttg gtattgtcgg tgaagtcgat  2400
ggtgatgacc ccgcagtatt caggccaata caaaaaataca tcaatggcac atggtataac  2460
gtcgcacagg tgtaa                                                  2475

SEQ ID NO: 210          moltype = DNA  length = 528
FEATURE                 Location/Qualifiers
```

```
misc_feature           1..528
                       note = Synthetic: STF118 accessory protein
source                 1..528
                       mol_type = other DNA
                       organism = synthetic construct
SEQUENCE: 210
atgcagcatt taaaaaatat tactgcgggt aatccaaaaa ctgttgccca atatcaactg  60
acaaaaaatt ttgatgttat ctggttatgg tccgaagagg gaaaaaactg gtatgaggaa  120
gtaagtaatt ttcaggaaga cacgataaag attgtttacg acgagaataa tataattgtc  180
ggcatcacca gagatgcttc aacgcttaac cctgaaggtt tcagcgttgt cgaggttcct  240
gatattacct ccaaccgacg tgctgatgac tcaggtaaat ggatgtttaa ggatggtgcc  300
gtgattaagc ggatttatac ggcagatgaa caggagcaac aggcagaatc acaaaaggca  360
gctttacttt ccgaagctga atccgtgatt ttgccgctgg aacgcgctgt caggctgaat  420
atggcgacgg atgaggaacg cagccgactg gaagcatggg aacgctacag cgttctggtc  480
agtcgtgtgg atcctgcaaa tcccgaatgg ccggaaatgc cgcaataa              528

SEQ ID NO: 211         moltype = DNA  length = 4044
FEATURE                Location/Qualifiers
misc_feature           1..4044
                       note = Synthetic: K1F
source                 1..4044
                       mol_type = other DNA
                       organism = synthetic construct
SEQUENCE: 211
atggcagtaa agatttcagg agtcctgaaa gacggcacag gaaaaccggt acagaactgc  60
accattcagc tgaaagccag acgtaacagc accacggtgg tggtgaacac ggtgggctca  120
gagaatccgg atgaagccgg gcgttacagc atggatgtgg agtacggtca gtacagtgtc  180
atcctgcagg ttgacggttt tccaccatcg cacgccggga ccatcaccgt gtatgaagat  240
tcacaaccgg ggacgctgaa tgattttctc tgtgccatga cggaggatga tgcccggccg  300
gaggtgctgc gtcgtcttga actgatggtg gaagaggtgg cgcgtaacgc gtccgtggtg  360
gcacagagta cggcagacgc gaagaaatca gccggcgatg ccagtgcatc agctgctcag  420
gtcgcggccc ttgtgactga tgcaactgac tcagcacgcg ccgccagcac gtccgccgga  480
caggctgcat cgtcagctca ggaagcgtcc tccggcgcag aagcggcatc agcaaaggcc  540
actgaagcgg aaaaaagtgc cgcagccgca gagtcctcaa aaacgcggc ggccaccagt  600
gccggtgcgg cgaaaacgtc agaaacgaat gctgcagcgt cacaacaatc agccgccacg  660
tctgcctcca ccgcggccac gaaagcgtca gaggccgcca cttcagcacg agatgcggtg  720
gcctcaaaag aggcagcaaa atcatcagaa acgaacgcat catcaagtgc cggtcgtgca  780
gcttcctcgg caacggcggc agaaaattct gccagggcgg caaaaacgtc cgagacgaat  840
gccaggtcat ctgaaacagc agcggaacgg agcgcctctg ccgcggcaga cgcaaaaaca  900
gcggcggcgg ggagtgcgtc aacggcatcc acgaaggcga cagaggctgc gggaagtgcg  960
gtatcagcat cgcagagcaa aagtgcggca gaagcggcgg caatacgtgc aaaaaattcg  1020
gcaaaacgtg cagaagatat agcttcagct gtcgcgcttg aggatgcgga cacaacgaga  1080
aaggggatag tgcagctcag cagtgcaacc aacagcacgt ctgaaacgct tgctgcaacg  1140
ccaaaggcgg ttaaggtggt aatggatgag actaatcgta aggcacctct ggacagtccg  1200
gcactgaccg gaacgccaac agcaccaacc gcgctcaggg gaacaaacaa tacccagatt  1260
gcgaacaccg cttttgtact ggccgcgatt gcagatgtta tcgacgcgtc acctgacgca  1320
ctgaatacgc tgaatgaact ggccgcagcg ctcgggaatg atccagattt tgctaccacc  1380
atgactaacg cgcttgcggg taaacaaccg aagaatgcga cactgacggc gctggcaggg  1440
ctttccacgg cgaaaaataa attaccgtat tttgcggaaa atgatgccgc cagcctgact  1500
gaactgactc aggttggcag ggatattctg gcaaaaaatt ccgttgcaga tgttcttgaa  1560
taccttgggg ccggtgagaa ttcgggtgcg aagggcgatg gcgttaccga cgacactgca  1620
gcgctgactt ccgccctgaa cgatactccg gtgggtcaga aaatcaacgg taacggtaaa  1680
acttataaag ttacgtccct gccggacatc tcccgcttta tcaacacccg tttcgtgtat  1740
gaacgtatcc caggccagcc gctgtactac gcatcggaag agttcgttca gggtgagctt  1800
tttaaaatca ccgacactcc gtattataac gcctggccac aggataaggc tttcgtgtac  1860
gaaaacgtta tctatgctcc gtacatgggt tccgaccgtc acggtgtcag ccgactgcac  1920
gtaagctggg tgaaatcggg cgacgatggt cagacctgga gcacgcctga gtggctgacc  1980
gaccttcatc cggactatcc gaccgttaac tatcactgca tgagcatggg cgtctgtcgc  2040
aaccgtctgt tcgcaatgat cgaaacccgt acgctggcaa aaaacgctct gactaactgc  2100
gccctgtggg atcgtccaat gagccgctct ctgcacctga cgggtggtat taccaaagca  2160
gcgaaccagc gttacgccac cattcacgta ccggatcatg gtctgttcgt tggtgacttt  2220
gtaaatttct ctaattctgc agttaccggt gtgtctggcg acatgaccgt tgcgaccgta  2280
atcgataagg acaatttcac cgtcctgacc ccgaaccagc aaacctctga tcttaacaac  2340
gctggcaaga actggcacat gggcactagc tttcacaaat ctccgtggcg taaaaccgat  2400
ctgggcctga tcccgtctgt aactgaagtg cactccttcg cgaccattga taacaacggt  2460
ttcgctatgg gttatcacca aggtgatgtt gcaccgcgtg aagtcggcct cttttatttt  2520
ccggacgcat tcaacagccc gtccaactac gtgcgccgtc agattccgtc tgaatatgaa  2580
ccggacgcct ccgagccgtg cattaagtac tatgacggtg tgctgtacct gattacccgt  2640
ggcacccgtg gtgatcgtct gggttcatct ctgcatcgct cccgcgacat tggtcagacg  2700
tgggaaagtc tgcgcttccc gcacaatgtt catcacacca ccctgccgtt cgcgaaagtc  2760
ggcgatgacc tgatcatgtt tggctccgaa cgtgctgaaa acgaatggga agcgggcgcc  2820
ccagacgatc gctacaaggc atcttacccg cgcaccttct acgcgcgtct gaacgtgaac  2880
aactggaacg cagacgatat cgaatgggta aacatcaccg accagatcta ccagggtggt  2940
atcgtgaact ctggtgtggg cgttggttcc gttgtagtta aagataacta catctattat  3000
atgttcggcg gcgaagacca cttcaacccg tggacttacg gcgataactc cgcgaaagac  3060
ccgttcaaat ccgatggtca cccttctgac ctctattgtt acaaaaatgaa aatcggtccg  3120
gacaaccgtg tttcccgcga ttttcgctac ggcgctgttc caaaccgtgc agttccggta  3180
ttcttcgaca cgaacggcgt gcgtaccgtt ccggctccga tggaattcac cggcgacctg  3240
ggtctgggcc acgtaaccat tcgtgcctcc accagctcta acatccgttc cgaagtactc  3300
```

```
atggaaggtg aatacggctt tatcggtaag tctatcccga cggacaaccc ggcaggtcag  3360
cgtatcatct tctgcggcgg tgagggtacc tctagcacca ccggcgcgca aatcaccctg  3420
tacggcgcta acaacaccga ctctcgtcgt atcgtataca acggtgatga acatctgttc  3480
cagtccgcag acgtgaaacc gtacaacgac aacgtcaccg cactgggtgg tccatccaac  3540
cgtttcacca ctgcgtacct gggttccaac ccgatcgtta ctagcaatgg tgaacgcaaa  3600
actgaaccgg tagtgtttga cgacgctttt ctggacgcat ggggcgatgt tcattacatc  3660
atgtatcagt ggctggatgc cgtgcagctg aaaggtaacg acgcgcgtat ccactttggt  3720
gtgatcgcac agcagattcg cgatgtcttc atcgcacacg gtctgatgga tgaaaatagt  3780
actaactgtc gctatgcggt gctgtgctat gacaaatacc cgcgtatgac cgacaccgtg  3840
ttctcgcaca atgagattgt tgaacatacc gatgaagaag gtaacgtgac tactaccgaa  3900
gaaccggttt ataccgaagt ggttattcac gaagaaggtg aagaatgggg cgtgcgtcct  3960
gatggtatct tttcgcggga ggcagcgtac cagcgtcgca aactggaacg catcgaagct  4020
cgtctgtcgg cactggaaca gaaa                                        4044

SEQ ID NO: 212          moltype = DNA  length = 2397
FEATURE                 Location/Qualifiers
misc_feature            1..2397
                        note = Synthetic: STF66
source                  1..2397
                        mol_type = other DNA
                        organism = synthetic construct
SEQUENCE: 212
atggcagtaa agatttcagg agtcctgaaa gacggcacag gaaaaccggt acagaactgc  60
accattcagc tgaaagccag acgtaacagc accacggtgg tggtgaacac ggtgggctca  120
gagaatccgg atgaagccgg gcgttacagc atggatgtgg agtacggtca gtacagtgtc  180
atcctgcagg ttgacggttt tccaccatcg cacgccggga ccatcaccgt gtatgaagat  240
tcacaaccgg ggacgctgaa tgatttttctc tgtgccatga cggaggatga tgcccggccg  300
gaggtgctgc gtcgtcttga actgatggtg gaagaggtgg cgcgtaacgc gtccgtggtg  360
gcacagagta cggcagacgc gaagaaatca gccggcgatg ccagtgcatc agctgctcag  420
gtcgcggccc ttgtgactga tgcaactgac tcagcacgcg ccgccagcac gtccgccgga  480
caggctgcat cgtcagctca ggaagcgtcc tccggcgcag aagcggcatc agcaaaggcc  540
actgaagcgg aaaaaagtgc cgcagccgca gagtcctcaa aaaacgcggc ggccaccagt  600
gccggtgcgg cgaaaacgtc agaaacgaat gctgcagcgt cacaacaatc agccgccacg  660
tctgcctcca ccgcggccac gaaagcgtca gaggccgcca cttcagcacg agatgcggtg  720
gcctcaaaag aggcagcaaa atcatcagaa acgaacgcat catcaagtgc cggtcgtgca  780
gcttcctcgg caacggcggc agaaaattct gccagggcgg caaaaacgtc cgagacgaat  840
gccaggtcat ctgaaacagc agcggaacgg agcgcctctg ccgcggcagc ttctgccact  900
gcagcagcca acagtcaaaa agctgcaaaa accagtgaaa ccaactcaaa ggcgagcgaa  960
acagcggctg cgaactcagc gaaagcatcg gcagcaagcc agacggctgc aaaagcaagt  1020
gaggatgcag ccagagagta tgcaagccag gctgcggagc cgtataaaca agttttgcag  1080
ccgcttcccg atgtgtggat accgtttaac gattcactgg atatgattac gggcttttcg  1140
ccgtcatata aaaagattgt tattggtgat gatgaaataa cgatgcctgg cgataaggtt  1200
gtaaagttta aacgcgcatc gaaagcaacc tatattaata aatctggtgt gctgacagag  1260
gctgccattg acgagccacg atttgaacgt gatggcctgc ttattgaggg gcaaagaaca  1320
aactacatgc tcaattcgga aaaccctgcc agttgggggc gatcgtcaaa tatggatgtt  1380
cccgaaaccg ggacggatag ttttggtttt acctatggaa agtttgtctg caacgattct  1440
ctgattgggc aaacctcagc cattaatatg gcatcaattg ctgcaacaaa gtcagttgat  1500
gtctcaggcg ataataaata cgtgacaacc tcatgtcgtt ttaaaacaga actgcaggta  1560
aggttgcgta tccgatttga taaatatgac ggtagcgcaa caacttttct tggtgatgcg  1620
tatattgata cacaaacgct tgaaattaat atgacaggtg gtgcttccgg tagaattacg  1680
gcacgagtca ggaaggatga aactacagga tggatttttg ctgaggcaac aattcaggca  1740
attgatggtg agttaaaaat aggctctcag atacagtatt cacctaagca gggaggggca  1800
accgtatcag gtgactatat ttatctggct accccacaag tagagaatgg ggcttgtgta  1860
tcatctttta ttatatcagg aacgacggcg gcgactcgtg cgagtgatat ggttacgatc  1920
ccgaccgaaa acaacattta taacagaccg cttacttgtt tggtcgaggt taacaggaat  1980
tggggcgata ttcctcctaa tgtagcaccg cgtatttttg atttttctgg tgtgccgcct  2040
attgagtcaa tcacatacgc ttttaacaca accgagaaat attacggtca gctttatatg  2100
caaacttata aagcgtcgac aagtagttac gtttctagtt tgtttactgg tcgaacggat  2160
gttcgaaaac tcattggtgg ttttaatatt tattctgatg gtactaaacg agtagtttct  2220
aacggtgagg ctactaaaac catgaaaacg gaatggacgg gcgtaaaaac gcggaccttt  2280
attcgaatag gaggtcaagc cacatcaggg acacgtcatc tattcggcca tttgagaaat  2340
cttcgtctct ggcataaaga attaactgat gcgcaaatgg gggagagtat taaatga     2397

SEQ ID NO: 213          moltype = DNA  length = 282
FEATURE                 Location/Qualifiers
misc_feature            1..282
                        note = Synthetic: STF66 accessory protein
source                  1..282
                        mol_type = other DNA
                        organism = synthetic construct
SEQUENCE: 213
atgaaagatt taacactcaa atttgccgac agggccgact tttcggcctt tatggagagt  60
attggctatt atgatgacga gtcgatgcag gatgatattc ttattgacgt gataggtaac  120
gtgtacaaag aaaccggaga actgactgaa gatggcgaac cggtatgtgt taaggaagac  180
ggatattttg taaacgtgcg catcattaat gattcgcaaa tatcgtcatt attcgatgaa  240
tacgtggttg ctgttgagca tcaacttcgt ggctggatgt ga                    282

SEQ ID NO: 214          moltype = AA  length = 1131
FEATURE                 Location/Qualifiers
```

```
REGION                  1..1131
                        note = Synthetic: 1A2
source                  1..1131
                        mol_type = protein
                        organism = synthetic construct
SEQUENCE: 214
MGKGSSKGHT PREAKDNLKS TQLLSVIDAI SEGPIEGPVD GLKSVLLNST PVLDTEGNTN  60
ISGVTVVFRA GEQEQTPPEG FESSGSETVL GTEVKYDTPI TRTITSANID RLRFTFGVQA  120
LVETTSKGDR NPSEVRLLVQ IQRNGGWVTE KDITIKGKTT SQYLASVVMG NLPPRPFNIR  180
MRRMTPDSTT DQLQNKTLWS SYTEIIDVKQ CYPNTALVGV QVDSEQFGSQ QVSRNYHLRG  240
RILQVPSNYN PQTRQYSGIW DGTFKPAYSN NMAWCLWDML THPRYGMGKR LGAADVDKWA  300
LYVIGQYCDQ SVPDGFGGTE PRITCNAYLT TQRKAWDVLS DFCSAMRCMP VWNGQTLTFV  360
QDRPSDKTWT YNRSNVVMPD DGAPFRYSFS ALKDRHNAVE VNWIDPNNGW ETATELVEDT  420
QAIARYGRNV TKMDAFGCTS RGQAHRAGLW LIKTELLETQ TVDFSVGAEG LRHVPGDVIE  480
ICDDDYAGIS TGGRVLAVNS QTRTLTLDRE ITLPSSGTAL ISLVDGSGNP VSVEVQSVTD  540
GVKVKVSRVP DGVAEYSVWE LKLPTLRQRL FRCVSIREND DGTYAITAVQ HVPEKEAIVD  600
NGAHFDGEQS GTVNGVTPPA VQHLTAEVTA DSGEYQVLAR WDTPKVVKGV SFLLRLTVTA  660
DDGSERLVST ARTTETTYRF TQLALGNYRL TVRAVNAWGQ QGDPASVSFR IAAPAAPSRI  720
ELTPGYFQIT ATPHLAVYDP TVQFEFWFSE KQIADIRQVE TSTRYLGTAL YWIAASINIK  780
PGHDYYFYIR SVNTVGKSAF VEAVGRASDD AEGYLDFFKG KITESHLGKE LLEKVELTED  840
NASRLEEFSK EWKDASDKWN AMWAVKIEQT KDGKHYVAGI GLSMEDTEEG KLSQFLVAAN  900
RIAFIDPANG NETPMFVAQG NQIFMNDVFL KRLTAPTITS GGNPPAFSLT PDGKLTAKNA  960
DISGNVNANS GTLNNVTINE NCRVLGKLSA NQIEGDLVKT VGKAFPRDSR APERWPSGTI  1020
TVRVYDDQPF DRQIVIPAVA FSGAKHEKEH TDIYSSCRLI VRKNGAEIYN RTALDNTLIY  1080
SGVIDMPAGH GHMTLEFSVS AWLVNNWYPT ASISDLLVVV MKKATAGITI S          1131

SEQ ID NO: 215          moltype = AA  length = 194
FEATURE                 Location/Qualifiers
REGION                  1..194
                        note = Synthetic: WT STF accessory protein 1
source                  1..194
                        mol_type = protein
                        organism = synthetic construct
SEQUENCE: 215
MAFRMSEQPR TIKIYNLLAG TNEFIGEGDA YIPPHTGLPA NSTDIAPPDI PAGFVAVFNS  60
DEASWHLVED HRGKTVYDVA SGDALFISEL GPLPENFTWL SPGGEYQKWN GTAWVKDTEA  120
EKLFRIREAE ETKKSLMQVA SEHIAPLQDA ADLEIATKEE TSLLEAWKKY RVLLNRVDTS  180
TAPDIEWPAV PVME                                                    194

SEQ ID NO: 216          moltype = AA  length = 791
FEATURE                 Location/Qualifiers
REGION                  1..791
                        note = Synthetic: SIED6
source                  1..791
                        mol_type = protein
                        organism = synthetic construct
SEQUENCE: 216
MAVKISGVLK DGTGKPVQNC TIQLKARRNS TTVVVNTVGS ENPDEAGRYS MDVEYGQYSV  60
ILQVDGFPPS HAGTITVYED SQPGTLNDFL CAMTEDDARP EVLRRLELMV EEVARNASVV  120
AQSTADAKKS AGDASASAAQ VAALVTDATD SARAASTSAG QAASSAQEAS SGAEAASAKA  180
TEAEKSAAAA ESSKNAAATS AGAAKTSETN AAASQQSAAT SASTAATKAS EAATSARDAV  240
ASKEAAKSSE TNASSSAGRA ASSATAAENS ARAAKTSETN ARSSETAAER SASAAADAKT  300
AAAGSASTAS TKATEAAGSA VSASQSKSAA EAAAIRAKNS AKRAEDIADP ASVPPLPDIW  360
LPLNDSLEAI TGYAPGYKTI TIGSDEITVP VNGICQFSRA SSATYIDKSG HITVAGNNVP  420
RFEKYGLLIE NQRTNMFVNS FNPDAWNKSG GISVTSSTDE FEFKYGRFTV GSDIAGTTTG  480
RNICTVAGNR GIDVTGDDQY SKGPYVTASF RVRSDLNVRA RIRFERYNSE GYTFLCDAYL  540
SLQTHELQIT GDNAQLLTAN FEIDPGSGWI YFQATLKCLP EWGMVGTQLQ IAADRAVGSF  600
ATGDWIEVTT PQFEYGACAT SFIITTTEPA TRASDLCKFP LMKNMYTMPF TFMVEVHKNW  660
FIAHNAAPRV IDTENHQSGA PFIMGFGSSG TISQDGYPYC DIGGANRRVY ESCGVRDLVM  720
GFRVKADGMT CSFANKHIST ETKTVWKYIR EAAVIRIGGQ TTTGLRHLNG HIKNLRFWNR  780
ALSDTQLKEY V                                                       791

SEQ ID NO: 217          moltype = AA  length = 89
FEATURE                 Location/Qualifiers
REGION                  1..89
                        note = Synthetic: SIED6 accessory protein 1
source                  1..89
                        mol_type = protein
                        organism = synthetic construct
SEQUENCE: 217
MRDITLRFDN REQFNAIVYD SGLFSLEEEN GILVDVIGRV IDYEEPENER CTGIDRGGFF  60
VNMRIVDSSK NISSLMPFIT TDQHVRTWA                                    89

SEQ ID NO: 218          moltype = AA  length = 294
FEATURE                 Location/Qualifiers
REGION                  1..294
                        note = Synthetic: SIED6 accessory protein 2
source                  1..294
                        mol_type = protein
```

```
                        organism = synthetic construct
SEQUENCE: 218
MVTKTVIPDD IKTLKSDVSK LKNDQGSYAT KSYVDSKDET VGDWSASWYQ QVLPTSGAIF  60
GRKLRSTHRT AGVEDAYCEL YLKKWIDSPG NAMARLNLND NGENICWDFT NLYGGTMIFP  120
GTSGYLKMGN CLMSYGVRGS NALIKFDNTD SLQIKYANHG STMTLNTQGT AYSGVSTLLW  180
GNSSRPVVYE IRDDGGLFLF YAQRNPDKTY QLEINGPCKA TSFDQVSDRD LKENIRVIDN  240
ATERIRLMNG YTYRLKSNGM PYAGVIAQEA LNAIPESVGS TIKYKSGDNG SDGE        294

SEQ ID NO: 219          moltype = AA  length = 1096
FEATURE                 Location/Qualifiers
REGION                  1..1096
                        note = Synthetic: SIEA11
source                  1..1096
                        mol_type = protein
                        organism = synthetic construct
SEQUENCE: 219
MAVKISGVLK DGTGKPVQNC TIQLKARRNS TTVVVNTVGS ENPDEAGRYS MDVEYGQYSV  60
ILQVDGFPPS HAGTITVYED SQPGTLNDFL CAMTEDDARP EVLRRLELMV EEVARNASVV  120
AQSTADAKKS AGDASASAAQ VAALVTDATD SARAASTSAG QAASSAQEAS SGAEAASAKA  180
TEAEKSAAAA ESSKNAAATS AGAAKTSETN AAASQQSAAT SASTAATKAS EAATSARDAV  240
ASKEAAKSSE TNASSSAGRA ASSATAAENS ARAAKTSETN ARSSETAAER SASAAADAKT  300
AAAGSASTAS TKATEAAGSA VSASQSKSAA EAAAIRAKNS AKRAEDIASA VALEDADTTR  360
KGIVQLSSAT NSTSETLAAT PKAVKAANDN ANSRLAKNQN GADIQDKSAF LDNVGVTSLT  420
FMKNNGEMPV DADLNTFGSV KAYSGIWSKA TSTNATLEKN FPEDNAVGVL EVFTGGNFAG  480
TQRYTTRDGN LYIRKLIGTW NGNDGPWGAW RHVQAVTRAL STTIDLNSLG GAEHLGLWRN  540
SSSAIASFER HYPEQGGDAQ GILEIFEGGL YGRTQRYTTR NGTMYIRGLT AKWDAENPQW  600
EDWNQIGYQT SSTFYEDDLD DLMSPGIYSV TGKATHTPIQ GQSGFLEVIR RKDGVYVLQR  660
YTTTGTSAAT KDRLYERVFL GGSFNAWGEW RQIYNSNSLP LELGIGGAVA KLTSLDWQTY  720
DFVPGSLITV RLDNMTNIPD GMDWGVIDGN LINISVGPSD DSGSGRSMHV WRSTVSKANY  780
RFFMVRISGN PGSRTITTRR VPIIDEAQTW GAKQTFSAGL SGELSGNAAT ATKLKTARKI  840
NNVSFDGTSD INLTPKNIGA FASGKTGDTV ANDKAVGWNW SSGAYNATIG GASTLILHFN  900
IGEGSCPAAQ FRVNYKNGGI FYRSARDGYG FEADWSEFYT TTRKPTAGDV GALPLSGGQL  960
NGALGIGTSS ALGGNSIVLG DNDTGFKQNG DGNLDVYANS VHVMRFVSGS VQSNKTINIT  1020
GRVNPSDYGN FDSRYVRDVR LGTRVVQTMQ KGVMYEKAGH VITGLGIVGE VDGDDPAVFR  1080
PIQKYINGTW YNVAQV                                                  1096

SEQ ID NO: 220          moltype = AA  length = 175
FEATURE                 Location/Qualifiers
REGION                  1..175
                        note = Synthetic: SIEA11 accessory protein 1
source                  1..175
                        mol_type = protein
                        organism = synthetic construct
SEQUENCE: 220
MQHLKNITAG NPKTVAQYQL TKNFDVIWLW SEEGKNWYEE VSNFQEDTIK IVYDENNIIV  60
GITRDASTLN PEGFSVVEVP DITANRRADD SGKWMFKDGA VIKRIYTADE QLQLAELQKS  120
ALLSEAETII QPLERSVRLN MATDEERSRL EAWERYSVLV SRVDPANPEW PEMPQ       175

SEQ ID NO: 221          moltype = AA  length = 745
FEATURE                 Location/Qualifiers
REGION                  1..745
                        note = Synthetic: EB6
source                  1..745
                        mol_type = protein
                        organism = synthetic construct
SEQUENCE: 221
MAVKISGVLK DGTGKPVQNC TIQLKARRNS TTVVVNTVGS ENPDEAGRYS MDVEYGQYSV  60
ILQVDGFPPS HAGTITVYED SQPGTLNDFL CAMTEDDARP EVLRRLELMV EEVARNASVV  120
AQSTADAKKS AGDASASAAQ VAALVTDATD SARAASTSAG QAASSAQEAS SGAEAASAKA  180
TEAEKSAAAA ESSKNAAATS AGAAKTSETN AAASQQSAAT SASTAATKAS EAATSARDAV  240
ASKEAAKSSE TNASSSAGRA ASSATAAENS ARAAKTSETN ARSSETAAER SASAAADAKT  300
AAAGSASTAS TKATEAAGSA VSASQSKSAA EAAAIRAKNS AKRAEDIASA VALEDADTTR  360
KGIVQLSSAT NSTSETLAAT PKAVKIAMDN ANARLAKDRN GADIPNKPLF IQNLGLQETV  420
NKAGNAVQKT GDTLSGGLTF ENDSILAWIR NTDWAKIGFK NDADSDTDSY MWFETGDNGN  480
EYFKWRSRQS TTTKDLMNLK WDALYVLVNA IVNGEVISKS ANGLRIAYGN YGFFIRNDGS  540
NTYFMLTNSG DNMGTYNGLR PLWINNATGA VSMGRGLNVS GETLSDRFAI NSSNGMWIQM  600
RDNNAIFGKN IVNTDSAQAL LRQNHADRKF MIGGLGNKQF GIYMINNSRT ANGTDGQAYM  660
DNNGNWLCGA QVIPGNYGNF DSRYVRDVRL GTRVVQLMAR GGRYEKAGHA ITGLRIIGEV  720
DGDDEAIFRP IQKYINGTWY NVAQV                                        745

SEQ ID NO: 222          moltype = AA  length = 175
FEATURE                 Location/Qualifiers
REGION                  1..175
                        note = Synthetic: EB6 accessory protein 1
source                  1..175
                        mol_type = protein
                        organism = synthetic construct
SEQUENCE: 222
MQHLKNIKSG NPKTKEQYQL TKNFDVIWLW SEDGKNWYEE VNNFQDDTIK IVYDENNIIV  60
```

```
AITKDASTLN PEGFSVVEIP DITANRRADD SGKWMFKDGA VVKRIYTADE QQQQAESQKA  120
ALLSEAENVI QPLERAVRLN MATDEERARL ESWERYSVLV SRVDTAKPEW PQKPE       175

SEQ ID NO: 223          moltype = AA  length = 1106
FEATURE                 Location/Qualifiers
REGION                  1..1106
                        note = Synthetic: AH11L
source                  1..1106
                        mol_type = protein
                        organism = synthetic construct
SEQUENCE: 223
MAVKISGVLK DGTGKPVQNC TIQLKARRNS TTVVVNTVGS ENPDEAGRYS MDVEYGQYSV  60
ILQVDGFPPS HAGTITVYED SQPGTLNDFL CAMTEDDARP EVLRRLELMV EEVARNASVV  120
AQSTADAKKS AGDASASAAQ VAALVTDATD SARAASTSAG QAASSAQEAS SGAEAASAKA  180
TEAEKSAAAA ESSKNAAATS AGAAKTSETN AAASQQSAAT SASTAATKAS EAATSARDAV  240
ASKEAAKSSE TNASSSAGRA ASSATAAENS ARAAKTSETN ARSSETAAER SASAAADAKT  300
AAAGSASTAS TKATEAAGSA VSASQSKSAA EAAAIRAKNS AKRAEDIASA VALEDADTTR  360
KGIVQLSSAT NSTSETLAAT PKAVKAANDN ANSRLAKNQN GADIQDKSVF LDNVGVTSLT  420
FMKNNGEMPL DADLNTFGPV KAYLGIWSKA TSTNATLEKN FPEDNAVGVL EVFAAGNFAG  480
TQRFTTRDGN VYMRKLANKW NGTDGPWGVW RHTQSATRPL STTIDLNTLG AAEHLGLWRN  540
SSSAIASYER NYPEEGGFAQ GTLEILEGGN YGRTQRYTTR RGNMYVRCLA ASWDASNPQW  600
EPWLRVGHQS ESRYYEGDLN DVTSPGIYSV TGKATNGPVL DGNGVTVLGI LEVLRRFDGV  660
NVWQRYTTAG TGTTLKGRTF ERVFTGSSWS EWREVYTSYS LPLNLGIGGA VAKLTSLDWQ  720
TYDFVPGSLI TVRLDNMTNI PDGMDWGVID GNLINIAVGP SDDSGTGRSM HVWRSTVSKA  780
NYRFFMVRIS GNPGSRTITA RRVPIIDEAQ TWGAKQTFSA GLSGELSGNA ATATKLKTAR  840
KINNVSFDGT SDINLTPKNI GAFASGKTGD TVANDKAVGW NWSSGAYNAT TGGASTLILH  900
FNIGEGSCPA AQFRVNYKNG GIFYRSARDG YGFEADWSEF YTTTRKPTAG DVGALPLSGG  960
QLNGALGIGT SSALGGNSIV LGDNDTGFKQ NGDGNLDVYA NSVHIMRFVS GSIQSNKTIN  1020
ITGRVNPSDY GNFDSRYVRD IRLGGAATYK PANNGMTWTH QAPSGCVYSG IIVQDTGSNS  1080
ADNIGGVYYR PVQKYINGTW YNVAQV                                       1106

SEQ ID NO: 224          moltype = AA  length = 175
FEATURE                 Location/Qualifiers
REGION                  1..175
                        note = Synthetic: AH11L accessory protein 1
source                  1..175
                        mol_type = protein
                        organism = synthetic construct
SEQUENCE: 224
MQHLKNITAG NPKTVEQYQL TKGFDVVWFF SEDGKNWYEE QKYFADDTIK IAYDKDNIIR  60
YVEKDVTAIR PDGLSVVEVA DITANRRADI SGGWMFKDGK VIKRIYTAEE LLQQAENRKA  120
RLLADAESVI LPLERAVRLN MATDEERSRL DAWERYSVLV SRVDPANPEW PEMPQ       175

SEQ ID NO: 225          moltype = AA  length = 261
FEATURE                 Location/Qualifiers
REGION                  1..261
                        note = Synthetic: WW55 3.0 accessory protein 1
source                  1..261
                        mol_type = protein
                        organism = synthetic construct
SEQUENCE: 225
MAISSGWVGS SAVSETGQRW MSAAMQAVRL GRPAYMSAMV GRSKEIHYSI GASNSYNKDT  60
LINWMKAQGS TPVVITITGN IVSQSTGVPC LDFPSSLTNE YVTLIINSGV HVLGRGGNGG  120
SNSAGGAGGN AINNGIGTRL RINNNGIIGG GGGGGAGARY NPFPQMDMKF GGGGGRPFGA  180
AGAAGGGAAA ASAGTISAPG KGTVSGVHYG GDGGDLGAAG KSSYIKGGTG GTVHSGGAAG  240
KAVTGNAPRW DKVGTIYGAR V                                            261

SEQ ID NO: 226          moltype = AA  length = 86
FEATURE                 Location/Qualifiers
REGION                  1..86
                        note = Synthetic: WW55 3.0 accessory protein 2
source                  1..86
                        mol_type = protein
                        organism = synthetic construct
SEQUENCE: 226
MSNQHEQMIN VLKVRLFDTQ EKAAFLEGQL KDRERVLMEL VRILGIQPDE NGTVSLDAIV  60
EEVKALLPKD EAAEDAEEEV ELITEA                                       86

SEQ ID NO: 227          moltype = AA  length = 797
FEATURE                 Location/Qualifiers
REGION                  1..797
                        note = Synthetic: STF68B
source                  1..797
                        mol_type = protein
                        organism = synthetic construct
SEQUENCE: 227
MAVKISGVLK DGTGKPVQNC TIQLKARRNS TTVVVNTVGS ENPDEAGRYS MDVEYGQYSV  60
ILQVDGFPPS HAGTITVYED SQPGTLNDFL CAMTEDDARP EVLRRLELMV EEVARNASVV  120
AQSTADAKKS AGDASASAAQ VAALVTDATD SARAASTSAG QAASSAQEAS SGAEAASAKA  180
```

```
TEAEKSAAAA ESSKNAAATS AGAAKTSETN AAASQQSAAT SASTAATKAS EAATSARDAV  240
ASKEAAKSSE TNASSSAGRA ASSATAAENS ARAAKTSETN ARSSETAAER SASAAAASAT  300
ASANSQKAAK TSETNAKTSE TAAANSAKAS AASQTAAKAS EDAAREYASQ AAEPYKQVLQ  360
PLPDVWIPFN DSLEMITGFA PGYKKVTIGD DVITFPSEKV VSFTRSTSAT YINKSGSFAF  420
AEINEPRFEK EGLLIEGQRT NTFTNSNNPS LWNYDDKNIE ITTSVDEYGF KYGLFDVKET  480
STTERATIIS TGYSRVIDVA ANESVTLSCR VKKINGEGII TLRPRISFVN DDGTSNTLVA  540
GSYIDCETGD VLGFSGGDAV NHVIYREANG WLRVEFTYKS PEAKSMYGRF EMGADKRAIK  600
KGDQIMFTTP QFEKGSCASS FIVTSDVAVT RASDVVIMPI RLNWSTPPLS VLMEVNINWD  660
KMPNSEGSAR LLNVSITGAT TDVADESYMY FGFTSGGARS IITNGKGTKT EYKAYCNRTT  720
RRFIAGFKFT EQKELRAVIN GNFGAVDVSQ HTRQRYTEGP INIGGQSISG NRHLFGHVRN  780
LRIWHKELTD AQMGERI                                                 797

SEQ ID NO: 228          moltype = AA  length = 93
FEATURE                 Location/Qualifiers
REGION                  1..93
                        note = Synthetic: STF68B accessory protein 1
source                  1..93
                        mol_type = protein
                        organism = synthetic construct
SEQUENCE: 228
MRDLTLKFIN KADFSAFMDS IGYEDDEVMQ NNVLIDVIGN VYKETGELTE DGEPVCVKED  60
GYFVNVRIIN DAKKSSIFDK YAVVVEHQLR GWM                               93

SEQ ID NO: 229          moltype = AA  length = 346
FEATURE                 Location/Qualifiers
REGION                  1..346
                        note = Synthetic: STF68B accessory protein 2
source                  1..346
                        mol_type = protein
                        organism = synthetic construct
SEQUENCE: 229
MATSTVIPDD IKTLKSDVSK LKNDQGSYAT KSYVDSKDET VGDWSASWYQ QVLPTSGAIF  60
GRKLRSTHRT AGVEDAYCEL YLKKWIDSPG NAMARLNLND NGTNICWDFT NLYGGTMIFP  120
GDSGYLKMGN CLMSYSKRGS NALIKFDYTD TLQIKYANHG STMTLNTQGT AHAGVTTRLW  180
GNSSRPVVYE VGVDEALYMF YAQKTTSNTY ELTVNGACNA SAFNQGSDRD LKDNIQVIDN  240
ATDRIRKMNG YTYTLKENGM PYAGVIAQET LEAIPEAVGA MMKYPDGGSG LDGEEGERYY  300
TVDYSGVTGL LVQVARESDD RITALEEENA ELRQRLSAIE AALASK                 346

SEQ ID NO: 230          moltype = AA  length = 879
FEATURE                 Location/Qualifiers
REGION                  1..879
                        note = Synthetic: STF90B
source                  1..879
                        mol_type = protein
                        organism = synthetic construct
SEQUENCE: 230
MAVKISGVLK DGTGKPVQNC TIQLKARRNS TTVVVNTVGS ENPDEAGRYS MDVEYGQYSV  60
ILQVDGFPPS HAGTITVYED SQPGTLNDFL CAMTEDDARP EVLRRLELMV EEVARNASVV  120
AQSTADAKKS AGDASASAAQ VAALVTDATD SARAASTSAG QAASSAQEAS SGAEAASAKA  180
TEAEKSAAAA ESSKNAAATS AGAAKTSETN AAASQQSAAT SASTAATKAS EAATSARDAV  240
ASKEAAKSSE TNASSSAGRA ASSATAAENS ARAAKTSETN ARSSETAAER SASAAADAKT  300
AAAGSASTAS TKATEAAGSA VSASQSKSAA EAAAIRAKNS AKRAEDIASA VALEDADTTR  360
KGIVQLSSAT NSTSETLAAT PKAVKVVMDE TNRKYTAQDA TTARKGLVQL SSVTNSDSET  420
LAATPKAVKT AYDLANGKYT AQDATTARKG LVQLSSATNS DSETLAATPK AVKSAYDNAE  480
KRLQKDQNGA DIPGKDTFTK NIGACRAYSG ALSTDAGNWT TAQFIDWLES QGAFNHPYWM  540
CKCSWSYGNN KIITDTDCGT IHLAGCVIEV MGVKAAMTIR VTTPSTSSGG GTTSAQFTYI  600
NHGADYAPGW RRDYNTKNKQ PAFALGKTGN TVANNKAVGW NWDSGAYCAQ DGGASKMVLH  660
FYTGEGSCPA MQFLVDYKNR GIFYRSARDG YGFEADWSEF YTTSRKPTPA DILALALSGG  720
SMSGSIKFIN DAFLIWERNT DWAKIGFKND SDADSDSYMW FETGDNGNEY FKWRIRSGST  780
TKDLMTLKSD ALRVTGQVIP SNFSNFDSRY VRDIRLGGAA TYKPANNGMT WTHQAPSGCV  840
YTGIIVQDTG SNSADNIGGV YYRPVQKYIN GTWYNVAQV                          879

SEQ ID NO: 231          moltype = AA  length = 175
FEATURE                 Location/Qualifiers
REGION                  1..175
                        note = Synthetic: STF90B accessory protein
source                  1..175
                        mol_type = protein
                        organism = synthetic construct
SEQUENCE: 231
MQHLKNITAG NPKTVEQYQL TKDFDVVWFF SEDGKNWYEE QKYFADDTIK IAYDKDNIIR  60
YVEKDVTAIR PDGLSVVEVA DITANRRADI SGNWMFKDGT VIKRIYTAEE LQQQAENRKA  120
RLLADAESVI LPLERAVRLN MATEEERSRL ERWERYSVLV SRVDPANPEW PEMPQ       175

SEQ ID NO: 232          moltype = AA  length = 871
FEATURE                 Location/Qualifiers
REGION                  1..871
                        note = Synthetic: STF117
source                  1..871
```

```
                         mol_type = protein
                         organism = synthetic construct
SEQUENCE: 232
MAVKISGVLK DGTGKPVQNC TIQLKARRNS TTVVVNTVGS ENPDEAGRYS MDVEYGQYSV  60
ILQVDGFPPS HAGTITVYED SQPGTLNDFL CAMTEDDARP EVLRRLELMV EEVARNASVV  120
AQSTADAKKS AGDASASAAQ VAALVTDATD SARAASTSAG QAASSAQEAS SGAEAASAKA  180
TEAEKSAAAA ESSKNAAATS AGAAKTSETN AAASQQSAAT SASTAATKAS EAATSARDAV  240
ASKEAAKSSE TNASSSAGRA ASSATAAENS ARAAKTSETN ARSSETAAER SASAAADAKT  300
AAAGSASTAS TKATEAAGSA VSASQSKSAA EAAAIRAKNS AKRAEDIASA VALEDADTTR  360
KGIVQLSSAT NSTSETLAAT PKAVKVVMDE TNRKYTAQDA TTARKGLVQL SSATNSDSET  420
LAATPKAVKS AYDNAEKRLQ KDQNGADIPG KDTFTKNIGA CRAYSGALST EAGNWTTAQF  480
IEWLDSRGAF NHPYWMCKGS WSYANNKIIT DTGCGDIHLA GCVVEVMGTK SAITIRVTTP  540
TTSSGGGTTS AQFTYINHGD GYSPGWRRDW NRQGDAMTGT INQDGGSQNA YMSTALCSGT  600
RGGKKYLRKF RGGEGDTIWH ETVQGGVRW  ATGNTDAQEE LSLSSAYGLR SRGEITSSSA  660
NGLRIAYGNY GFFIRNDGSS TYFMLTKSGD RLGTYNNLRP LIINDATGAV SMGHGLSVTG  720
DIASSTKVRA GSGKKFTVSS SNTSTKEAAF NLWGNSSRPV VAELGDDAGW HFYSQRNTDN  780
SITFAVNGQV SPSNYSNFDS RYVRDIRLGG AATYKPANNG MTWTHQAPSG CVYSGIIVQD  840
TGSNSADNIG GVYYRPVQKY INGTWYNVAQ V                                871

SEQ ID NO: 233           moltype = AA  length = 175
FEATURE                  Location/Qualifiers
REGION                   1..175
                         note = Synthetic: STF117 accessory protein 1
source                   1..175
                         mol_type = protein
                         organism = synthetic construct
SEQUENCE: 233
MQHLINITAG NPKTVEQYQL TKDFDVVWFF TEDGKNWYEE QKYFADDTIK IAYDKDNIIR  60
YVEKDVTAIR PDGLSVVEVA DITANRRADI SGNWMFKDGK VIKRIYTAEE LQQQAENRKA  120
RLLADAESVI LPLERAVRLN MATDEERSRL EAWERYSVLV SRVDPANPEW PEMPQ        175

SEQ ID NO: 234           moltype = AA  length = 838
FEATURE                  Location/Qualifiers
REGION                   1..838
                         note = Synthetic: O111
source                   1..838
                         mol_type = protein
                         organism = synthetic construct
SEQUENCE: 234
MAVKISGVLK DGTGKPVQNC TIQLKARRNS TTVVVNTVGS ENPDEAGRYS MDVEYGQYSV  60
ILQVDGFPPS HAGTITVYED SQPGTLNDFL CAMTEDDARP EVLRRLELMV EEVARNASVV  120
AQSTADAKKS AGDASASAAQ VAALVTDATD SARAASTSAG QAASSAQEAS SGAEAASAKA  180
TEAEKSAAAA ESSKNAAATS AGAAKTSETN AAASQQSAAT SASTAATKAS EAATSARDAV  240
ASKEAAKSSE TNASSSAGRA ASSATAAENS ARAAKTSETN ARSSETAAER SASAAADAKT  300
AAAGSASTAS TKATEAAGSA VSASQSKSAA EAAAIRAKNS AKRAEDIASA VALEDADTTR  360
KGIVQLSSAT NSTSETLAAT PKAVKVVMDE TNRKAPLDSP ALTGTPTAPT ALRGTNNTQI  420
ANTAFVLAAI ADVIDASPDA LNTLNELAAA LGNDPDFATT MTNALAGKQP KNATLTALAG  480
LSTAKNKLPY FAENDAASLT ELTQVGRDIL AKNSVADVLE YLGAGENSAS GALQKNQNGA  540
DIPGKDTFTK NIGACRAYSA WLNIGGDSQV WTTAQFISWL ESQGAFNHPY WMCKGSWAYA  600
NNKVITDTGC GNICLAGAVV EVIGTRGAMT IRVTTPSTSS GGGITNAQFT YINHGDAYAP  660
GWRRDYNTKN QQPAFALGQT GSRVANDKAV GWNWNSGVYN ADISGASTLI LHFNMNAGSC  720
PAVQFRVNYR NGGIFYRSAR DGYGFEANWS EFYTTTRKPS AGDVGAYTQA ECNSRFITGI  780
RLGGLSSVQT WNGPGWSDRS GYVVTGSVNG NRDELIDTTQ ARPIQYCING TWYNAGSI   838

SEQ ID NO: 235           moltype = AA  length = 177
FEATURE                  Location/Qualifiers
REGION                   1..177
                         note = Synthetic: O111 accessory protein
source                   1..177
                         mol_type = protein
                         organism = synthetic construct
SEQUENCE: 235
MMHLKNITAG NPKTKEQYQL TKQFNIKWLY SEDGKNWYEE QKNFQPDTLK MVYDHNGVII  60
CIEKDVSAIN PEGASVVELP DITANRRADI SGKWMFKDGV VVKRTYTEEE QRQQAENEKQ  120
SLLQLVRDKT QLWDSQLRLG IISDENKQKL TEWMLFAQKV ESTDTSSLPV TFPEQPE     177

SEQ ID NO: 236           moltype = AA  length = 835
FEATURE                  Location/Qualifiers
REGION                   1..835
                         note = Synthetic: DC1
source                   1..835
                         mol_type = protein
                         organism = synthetic construct
SEQUENCE: 236
MAVKISGVLK DGTGKPVQNC TIQLKARRNS TTVVVNTVGS ENPDEAGRYS MDVEYGQYSV  60
ILQVDGFPPS HAGTITVYED SQPGTLNDFL CAMTEDDARP EVLRRLELMV EEVARNASVV  120
AQSTADAKKS AGDASASAAQ VAALVTDATD SARAASTSAG QAASSAQEAS SGAEAASAKA  180
TEAEKSAAAA ESSKNAAATS AGAAKTSETN AAASQQSAAT SASTAATKAS EAATSARDAV  240
ASKEAAKSSE TNASSSAGRA ASSATAAENS ARAAKTSETN ARSSETAAER SASAAADAKT  300
```

```
AAAGSASTAS TKATEAAGSA VSASQSKSAA EAAAIRAKNS AKRAEDIASA VALEDADTTR  360
KGIVQLSSAT NSTSETLAAT PKAVKAAYDL ANGKYTAQDA TTARKGLVQL SSVTNSDSET  420
LAATPKAVKS AYDNAEKRLQ KDQNGADIPG KDTFTKNIGA CRAYSGALST EAGNWTTAQF  480
IDWLESQGAF NHPYWMCKCS WSYGNNKIIT DTDCGTIHLA GCVIEVMGVK AAMTIRVTTP  540
STSSSGGTTS AQFTYINHGA DYAPGWRRDY NTKNKQPAFA LGKTGNTVAN NKAVGWNWDS  600
GAYCAQDGGA SKMVLHFYTG EGSCPAMQFL VDYKNRGIFY RSARDGYGFE ADWSEFYTTS  660
RKPTPADILA LALSGGSMSG SIKFINDAFL IWERNTDWAK IGFKNDSDAD SDSYMWFETG  720
DNGNEYFKWR IRSGSTTKDL MTLKSDALRV TGQVIPSNFS NFDSRYVRDI RLGGAATYKP  780
ANNGMTWTHQ APSGCVYTGI IVQDTGSNSA DNIGGVYYRP VQKYINGTWY NVAQV       835

SEQ ID NO: 237         moltype = AA  length = 175
FEATURE                Location/Qualifiers
REGION                 1..175
                       note = Synthetic: DC1 accessory protein 1
source                 1..175
                       mol_type = protein
                       organism = synthetic construct
SEQUENCE: 237
MQHLINITAG NPKTVEQYQL TKDFDVVWFF SEDGKNWYEE QKYFADDTIK IAYDKDNIIR  60
YVEKDVTAIR PDGLSVVEVP DITANRRADI SGGWMFKDGK VIKRIYTAEE LQQQAENRKA  120
RLLADAESVI LPLERAVRLN MATDEERSRL DAWERYSVLV SRVDPANPEW PEMPQ       175

SEQ ID NO: 238         moltype = AA  length = 915
FEATURE                Location/Qualifiers
REGION                 1..915
                       note = Synthetic: STF94A
source                 1..915
                       mol_type = protein
                       organism = synthetic construct
SEQUENCE: 238
MAVKISGVLK DGTGKPVQNC TIQLKARRNS TTVVVNTVGS ENPDEAGRYS MDVEYGQYSV  60
ILQVDGFPPS HAGTITVYED SQPGTLNDFL CAMTEDDARP EVLRRLELMV EEVARNASVV  120
AQSTADAKKS AGDASASAAQ VAALVTDATD SARAASTSAG QAASSAQEAS SGAEAASAKA  180
TEAEKSAAAA ESSKNAAATS AGAAKTSETN AAASQQSAAT SASTAATKAS EAATSARDAV  240
ASKEAAKSSE TNASSSAGRA ASSATAAENS ARAAKTSETN ARSSETAAER SASAAADAKT  300
AAAGSASTAS TKATEAAGSA VSASQSKSAA EAAAIRAKNS AKRAEDIASA VALEDADTTR  360
KGIVQLSSAT NSTSETLAAT PKAVKVVMDE TNRKYTAQDA TTARKGLVQL SSAINSDSET  420
LAATPKAVKT AYDLANRKYT AQDATTARKG LVQLSSATNS DSETLAATSK AVKSAYDNAE  480
KRLQKDQNGA DIPGKDTFTK NIGACRAYSG ALSTEAGNWT TAQFIEWLDS RGAFNHPYWM  540
CKGSWSYANN KIITDTGCGD IHLAGCVVEV MGTKSAITIR VTTPTTSSGG GTTSAQFTYI  600
NHGDGYSPGW RRDWNRQGDA MTGTINQDGG SQNAYMSTAL CSGTRGGKKY LRKFRGGEGD  660
TIWHETVQGG VVRWATGNTD AQEELSLSSA YGLRSRGEIT SLSANGLRIA YGNYGFFIRN  720
DGSSTYFMLT KSGDRLGTYN NLRPLIINDA TGAVSMGHGL NVTGDIVSST KVRAGSGKKF  780
TVSSSNTSTK EAAFNLWGNS SRPVVAELGD DAGWHFYSQR NTDNSITFAV NGQVSPSNYG  840
NFDSRYVRDI RLGGAATYKP ANNGMTWTHQ APSGCVYSGI IVQDTGSNSA DNIGGIYYRP  900
VQKYINGTWY NVAQV                                                   915

SEQ ID NO: 239         moltype = AA  length = 175
FEATURE                Location/Qualifiers
REGION                 1..175
                       note = Synthetic: STF94A accessory protein
source                 1..175
                       mol_type = protein
                       organism = synthetic construct
SEQUENCE: 239
MQHLINIMAG NPKTVEQYQL TKGFDVVWFF TEDGKNWYEE QKYFADDTIK IAYDKDNIIR  60
YVEKDVTAIR PDGLSVVEVA DITANRRADI SGGWMFKDGK VIKRIYTAEE LQQQAEIRKA  120
RLLADAESVI LPLERAVRLN MATEEERTRL EAWERYSVLV SRVDPANPEW PEMPQ       175

SEQ ID NO: 240         moltype = AA  length = 502
FEATURE                Location/Qualifiers
REGION                 1..502
                       note = Synthetic: STF69A
source                 1..502
                       mol_type = protein
                       organism = synthetic construct
SEQUENCE: 240
ASATASANSQ KAAKTSETNA KASETAAANS AKASAASQTA AKASEDAARE YASQAAEPYK  60
YVLQPLPEVW IPFNDSLDMI TGFAPGYKSI TVGDDVIALP SEKVVSFTRA STATYIDKSG  120
CFAESAINEP RFEKDGLLIE GQRTNTFSYT NTPVSWNYDT ANLTITTGVD EYGFSYGLFG  180
VKETSTTERA TLISTGYTRV ISVSANESVT LSCRVKKVSG DGIITLRPRI SYVNDDGSSN  240
TLTAGAYIDC ETGDMLSYSG GEAATYNIFR ESNGWIRVEF TYKSPEAKNM YGRFEFGAHQ  300
RSIKSGDKLM LTTPQFEKGL NASSFIITTE VGATRASDQV IIPIPFNWAT PPVSVLMEVN  360
VNWDSEMPNL EGSARLLNIS ITGATTEVSD ESYMYFGFTT RGKRLIITNG KGTKTEYKAY  420
GNREKRKFVT GFKFTEDKQL QVVVDGILGG SSPSLHTLQR YTAGNINIGG QSSSGNRHLF  480
GHVKNLRIWH KELTEAQMGE SI                                           502

SEQ ID NO: 241         moltype = AA  length = 93
FEATURE                Location/Qualifiers
```

```
REGION                  1..93
                        note = Synthetic: STF69A accessory protein 1
source                  1..93
                        mol_type = protein
                        organism = synthetic construct
SEQUENCE: 241
MKDLTLKFED RADFSAFMES IGYYDDESMQ DDILIDVIGN VYKETGELTE DGEPVCVKED  60
GYFVNVRIIN DSQISSLFDE YVVAVEHQLR GWM                              93

SEQ ID NO: 242          moltype = AA  length = 346
FEATURE                 Location/Qualifiers
REGION                  1..346
                        note = Synthetic: STF69A accessory protein 2
source                  1..346
                        mol_type = protein
                        organism = synthetic construct
SEQUENCE: 242
MATSTVIPDD IKTLKSDVSK LKNDQGSYAT KLYVDSKDEI VGDWSASWYQ QVLPTSGAIF  60
GRKLRSTHRT AGVEDAYCEL YLKKWIDSPG NAMARLNLND NGTNICWDFT NLYGGTMIFP  120
GDSGYLKMGN CLMSYSKRGS NALIKFDYTD TLQIKYANHG STMTLNTQGT AYAGVTAQLW  180
GNSSRPVVYE VGVDGGAYMF YAQKNTDNTY MLSVNGACHA TAFNQHSDRD LKDNIQVIDN  240
ATDRIRKMNG YTYTLKENGM PYAGVIAQEA LEAIPEVVGS AMKYQDGASG SEGEEGERYY  300
TVDYSGVTGL LVQVARESDD RITALEEENA ELRQRLSAIE AALASK                346

SEQ ID NO: 243          moltype = AA  length = 824
FEATURE                 Location/Qualifiers
REGION                  1..824
                        note = Synthetic: STF118
source                  1..824
                        mol_type = protein
                        organism = synthetic construct
SEQUENCE: 243
MAVKISGVLK DGTGKPVQNC TIQLKARRNS TTVVVNTVGS ENPDEAGRYS MDVEYGQYSV  60
VMYEKAGHVI TGLGIVGEVD GDDPAVFRPI QKYINGTWYN VAQVILQVDG FPPSHAGTIT  120
VYEDSQPGTL NDFLCAMTED DARPEVLRRL ELMVEEVARN ASVVAQSTAD AKKSAGDASA  180
SAAQVAALVT DATDSARAAS TSAGQAASSA QEASSGAEAA SAKATEAEKS AAAAESSKNA  240
AATSAGAAKT SETNAAASQQ SAATSASTAA TKASEAATSA RDAVASKEAA KSSETNASSS  300
AGRAASSATA AENSARAAKT SETNARSSET AAERSASAAA DAKTAAAGSA STASTKATEA  360
AGSAVSASQS KSAAEAAAIR AKNSAKRAED IASAVALEDA DTTRKGIVQL SSATNSTSET  420
LAATPKAVKV VMDETNRKAP LNSPALTGTP TTPTARQGTN NTQIANTAFV MAAIAALVDS  480
SPDALNTLNE LAAALGNDPN FATTMTNALA GKQPKDATLA ALAGLATAAD RFPYFTGNDV  540
ASLATLTKVG RDILAKSTVS AVIEYLGLQE TVNRAGNAVQ KNGDTLSGGL TFENDSILAW  600
IRNTDWAKIG FKNDADGDTD SYMWFETGDN GNEYFKWRSR QSTTTKDLMN LKWDALYVLV  660
KALFSSEVKI STVNALRIFN SSFGAIFRRS EENLYIIPTR ENEGENGDIG PLRPFGINLR  720
TGVVSVGNGA RIDGGLALGT NNALGGNSIV LGDNDTGFKQ NGDGNLDVYA NNVHVMRFVS  780
GSIQSNKTIN ITGRVNPSDY GNFDSRYVRD IRLGTRVVQT MQKG                  824

SEQ ID NO: 244          moltype = AA  length = 175
FEATURE                 Location/Qualifiers
REGION                  1..175
                        note = Synthetic: STF118 accessory protein
source                  1..175
                        mol_type = protein
                        organism = synthetic construct
SEQUENCE: 244
MQHLKNITAG NPKTVAQYQL TKNFDVIWLW SEEGKNWYEE VSNFQEDTIK IVYDENNIIV  60
GITRDASTLN PEGFSVVEVP DITSNRRADD SGKWMFKDGA VIKRIYTADE QEQQAESQKA  120
ALLSEAESVI LPLERAVRLN MATDEERSRL EAWERYSVLV SRVDPANPEW PEMPQ       175

SEQ ID NO: 245          moltype = AA  length = 1348
FEATURE                 Location/Qualifiers
REGION                  1..1348
                        note = Synthetic: K1
source                  1..1348
                        mol_type = protein
                        organism = synthetic construct
SEQUENCE: 245
MAVKISGVLK DGTGKPVQNC TIQLKARRNS TTVVVNTVGS ENPDEAGRYS MDVEYGQYSV  60
ILQVDGFPPS HAGTITVYED SQPGTLNDFL CAMTEDDARP EVLRRLELMV EEVARNASVV  120
AQSTADAKKS AGDASASAAQ VAALVTDATD SARAASTSAG QAASSAQEAS SGAEAASAKA  180
TEAEKSAAAA ESSKNAAATS AGAAKTSETN AAASQQSAAT SASTAATKAS EAATSARDAV  240
ASKEAAKSSE TNASSSAGRA ASSATAAENS ARAAKTSETN ARSSETAAER SASAAADAKT  300
AAAGSASTAS TKATEAAGSA VSASQSKSAA EAAAIRAKNS AKRAEDIASA VALEDADTTR  360
KGIVQLSSAT NSTSETLAAT PKAVKVVMDE TNRKAPLDSP ALTGTPTAPT ALRGTNNTQI  420
ANTAFVLAAI ADVIDASPDA LNTLNELAAA LGNDPDFATT MTNALAGKQP KNATLTALAG  480
LSTAKNKLPY FAENDAASLT ELTQVGRDIL AKNSVADVLE YLGAGENSGA KGDGVTDDTA  540
ALTSALNDTP VGQKINGNGK TYKVTSLPDI SRFINTRFVY ERIPGQPLYY ASEEFVQGEL  600
FKITDTPYYN AWPQDKAFVY ENVIYAPYMG SDRHGVSRLH VSWVKSGDDG QTWSTPEWLT  660
DLHPDYPTVN YHCMSMGVCR NRLFAMIETR TLAKNALTNC ALWDRPMSRS LHLTGGITKA  720
```

```
ANQRYATIHV PDHGLFVGDF VNFSNSAVTG VSGDMTVATV IDKDNFTVLT PNQQTSDLNN  780
AGKNWHMGTS FHKSPWRKTD LGLIPSVTEV HSFATIDNNG FAMGYHQGDV APREVGLFYF  840
PDAFNSPSNY VRRQIPSEYE PDASEPCIKY YDGVLYLITR GTRGDRLGSS LHRSRDIGQT  900
WESLRFPHNV HHTTLPFAKV GDDLIMFGSE RAENEWEAGA PDDRYKASYP RTFYARLNVN  960
NWNADDIEWV NITDQIYQGG IVNSGVGVGS VVVKDNYIYY MFGGEDHFNP WTYGDNSAKD  1020
PFKSDGHPSD LYCYKMKIGP DNRVSRDFRY GAVPNRAVPV FFDTNGVRTV PAPMEFTGDL  1080
GLGHVTIRAS TSSNIRSEVL MEGEYGFIGK SIPTDNPAGQ RIIFCGGEGT SSTTGAQITL  1140
YGANNTDSRR IVYNGDEHLF QSADVKPYND NVTALGGPSN RFTTAYLGSN PIVTSNGERK  1200
TEPVVFDDAF LDAWGDVHYI MYQWLDAVQL KGNDARIHFG VIAQQIRDVF IAHGLMDENS  1260
TNCRYAVLCY DKYPRMTDTV FSHNEIVEHT DEEGNVTTTE EPVYTEVVIH EEGEEWGVRP  1320
DGIFFAEAAY QRRKLERIEA RLSALEQK                                    1348

SEQ ID NO: 246         moltype = AA  length = 798
FEATURE                Location/Qualifiers
REGION                 1..798
                       note = Synthetic: STF66
source                 1..798
                       mol_type = protein
                       organism = synthetic construct
SEQUENCE: 246
MAVKISGVLK DGTGKPVQNC TIQLKARRNS TTVVVNTVGS ENPDEAGRYS MDVEYGQYSV  60
ILQVDGFPPS HAGTITVYED SQPGTLNDFL CAMTEDDARP EVLRRLELMV EEVARNASVV  120
AQSTADAKKS AGDASASAAQ VAALVTDATD SARAASTSAG QAASSAQEAS SGAEAASAKA  180
TEAEKSAAAA ESSKNAAATS AGAAKTSETN AAASQQSAAT SASTAATKAS EAATSARDAV  240
ASKEAAKSSE TNASSSAGRA ASSATAAENS ARAAKTSETN ARSSETAAER SASAAAASAT  300
AAANSQKAAK TSETNSKASE TAAANSAKAS AASQTAAKAS EDAAREYASQ AAEPYKQVLQ  360
PLPDVWIPFN DSLDMITGFS PSYKKIVIGD DEITMPGDKV VKFKRASKAT YINKSGVLTE  420
AAIDEPRFER DGLLIEGQRT NYMLNSENPA SWGRSSNMDV PETGTDSFGF TYGKFVCNDS  480
LIGQTSAINM ASIAATKSVD VSGDNKYVTT SCRFKTELQV RLRIRFDKYD GSATTFLGDA  540
YIDTQTLEIN MTGGASGRIT ARVRKDETTG WIFAEATIQA IDGELKIGSQ IQYSPKQGGA  600
TVSGDYIYLA TPQVENGACV SSFIISGTTA ATRASDMVTI PTENNIYNRP LTCLVEVNRN  660
WGDIPPNVAP RIFDFSGVPP IESITYAFNT TEKYYGQLYM QTYKASTSSY VSSLFTGRTD  720
VRKLIGGFNI YSDGTKRVVS NGEATKTMKT EWTGVKTRTF IRIGGQATSG TRHLFGHLRN  780
LRLWHKELTD AQMGESIK                                               798

SEQ ID NO: 247         moltype = AA  length = 93
FEATURE                Location/Qualifiers
REGION                 1..93
                       note = Synthetic: STF66 accessory protein
source                 1..93
                       mol_type = protein
                       organism = synthetic construct
SEQUENCE: 247
MKDLTLKFAD RADFSAFMES IGYYDDESMQ DDILIDVIGN VYKETGELTE DGEPVCVKED  60
GYFVNVRIIN DSQISSLFDE YVVAVEHQLR GWM                              93

SEQ ID NO: 248         moltype = AA  length = 6
FEATURE                Location/Qualifiers
REGION                 1..6
                       note = Synthetic
source                 1..6
                       mol_type = protein
                       organism = synthetic construct
SEQUENCE: 248
SAGDAS                                                            6

SEQ ID NO: 249         moltype = AA  length = 6
FEATURE                Location/Qualifiers
REGION                 1..6
                       note = Synthetic
source                 1..6
                       mol_type = protein
                       organism = synthetic construct
SEQUENCE: 249
ADAKKS                                                            6

SEQ ID NO: 250         moltype = AA  length = 6
FEATURE                Location/Qualifiers
REGION                 1..6
                       note = Synthetic
source                 1..6
                       mol_type = protein
                       organism = synthetic construct
SEQUENCE: 250
MDETNR                                                            6

SEQ ID NO: 251         moltype = AA  length = 6
FEATURE                Location/Qualifiers
REGION                 1..6
```

```
                        note = Synthetic
source                  1..6
                        mol_type = protein
                        organism = synthetic construct
SEQUENCE: 251
SASAAA                                                                      6

SEQ ID NO: 252          moltype = AA  length = 6
FEATURE                 Location/Qualifiers
REGION                  1..6
                        note = Synthetic
source                  1..6
                        mol_type = protein
                        organism = synthetic construct
SEQUENCE: 252
GAGENS                                                                      6

SEQ ID NO: 253          moltype = AA  length = 6
FEATURE                 Location/Qualifiers
REGION                  1..6
                        note = Synthetic
source                  1..6
                        mol_type = protein
                        organism = synthetic construct
SEQUENCE: 253
ATLKQI                                                                      6

SEQ ID NO: 254          moltype = AA  length = 6
FEATURE                 Location/Qualifiers
REGION                  1..6
                        note = Synthetic
source                  1..6
                        mol_type = protein
                        organism = synthetic construct
SEQUENCE: 254
IIQLED                                                                      6

SEQ ID NO: 255          moltype = AA  length = 6
FEATURE                 Location/Qualifiers
REGION                  1..6
                        note = Synthetic
source                  1..6
                        mol_type = protein
                        organism = synthetic construct
SEQUENCE: 255
GNIIDL                                                                      6

SEQ ID NO: 256          moltype = AA  length = 5
FEATURE                 Location/Qualifiers
REGION                  1..5
                        note = Synthetic
source                  1..5
                        mol_type = protein
                        organism = synthetic construct
SEQUENCE: 256
IATRV                                                                       5

SEQ ID NO: 257          moltype = AA  length = 5
FEATURE                 Location/Qualifiers
REGION                  1..5
                        note = Synthetic
source                  1..5
                        mol_type = protein
                        organism = synthetic construct
SEQUENCE: 257
TPGEL                                                                       5

SEQ ID NO: 258          moltype = AA  length = 5
FEATURE                 Location/Qualifiers
REGION                  1..5
                        note = Synthetic
source                  1..5
                        mol_type = protein
                        organism = synthetic construct
SEQUENCE: 258
GAIIN                                                                       5

SEQ ID NO: 259          moltype = AA  length = 5
FEATURE                 Location/Qualifiers
```

```
REGION                  1..5
                        note = Synthetic
source                  1..5
                        mol_type = protein
                        organism = synthetic construct
SEQUENCE: 259
NQIID                                                                5

SEQ ID NO: 260          moltype = AA  length = 5
FEATURE                 Location/Qualifiers
REGION                  1..5
                        note = Synthetic
source                  1..5
                        mol_type = protein
                        organism = synthetic construct
SEQUENCE: 260
GQIVN                                                                5

SEQ ID NO: 261          moltype = AA  length = 5
FEATURE                 Location/Qualifiers
REGION                  1..5
                        note = Synthetic
source                  1..5
                        mol_type = protein
                        organism = synthetic construct
SEQUENCE: 261
VDRAV                                                                5

SEQ ID NO: 262          moltype = AA  length = 659
FEATURE                 Location/Qualifiers
REGION                  1..659
                        note = Synthetic: Phage AG22 stf
source                  1..659
                        mol_type = protein
                        organism = synthetic construct
SEQUENCE: 262
MAIYRQGQAS MDAQGYVTGY GTKWREQLTL IRPGATIFFL AQPLQAAVIT EVISDTSIRA  60
ITTGGAVVQK TNYLILLHDS LTVDGLAQDV AETLRYYQGK ESEFAGFIEI IKDFDWDKLQ  120
KIQEDVKTNA DAAAASQQAA KTSENNAKTS ATNAANSKKG ADTAKAAAES ARDAANTAKT  180
GAEAAKSGAE SARDAANTAK AGAESARDQA EEYAKQAAEP YKDLLQPLPD VWIPFNDSLD  240
MITGFSPSYK KIVIGDDEIT MPGDKIVKFK RASTATYINK SGVLTNAAID EPRFEKDGLL  300
IEGQRTNLLI NSTNPSKWNK SSNMILDRSG VDDFGFQYAK FTLKPEMVGQ TSSINIVTVS  360
GSRGFDVTGN EKYVTISCRA QSGTPNLRCR LRFENYDGSA YASLGDAYVN LTDLSIEKTG  420
GAANRITARA VKDEASKWIF FEATIKALDT ENMIGAMVQY APAKDGGGTG ADDYIYIATP  480
QVEGGVCASS FIITEATPVT RASDMVTIPI KNNLYNLPFT VLCEVHKNWY ITPNAAPRVF  540
DTGGHQSGAA IILAFGSADG DNDGFPYCDI GKSNRRVNEN AKLKKMIIGM RVKSDYNTCC  600
VSNARISSET KTEWRYIVST ATIRIGGQTS TGERHLFGHV RNFRIWHKAL TDHQLGEIV   659

SEQ ID NO: 263          moltype = AA  length = 909
FEATURE                 Location/Qualifiers
REGION                  1..909
                        note = Synthetic: Phage SIEA11 stf
source                  1..909
                        mol_type = protein
                        organism = synthetic construct
SEQUENCE: 263
MSTKFKTVIT TAGAAKLAAA TVPGGKKVTL SAMAVGDGNG KLPVPDAGQT KLVHEVWRHA  60
LNKVSVDNKN KNYIVAELVV PPEVGGFWMR ELGLYDDAGT LIAVSNMAES YKPELAEGSG  120
RAQTCRMVII VSNVASVELS IDASTVMATQ DYVDDKIAEH EQSRRHPDAT LTEKGFTQLS  180
SATNSTSESL AATPKAVKAA NDNANSRLAK NQNGADIQDK SAFLDNVGVT SLTFMKNNGE  240
MPVDADLNTF GSVKAYSGIW SKATSTNATL EKNFPEDNAV GVLEVFTGGN FAGTQRYTTR  300
DGNLYIRKLI GTWNGNDGPW GAWRHVQAVT RALSTTIDLN SLGGAEHLGL WRNSSSAIAS  360
FERHYPEQGG DAQGILEIFE GGLYGRTQRY TTRNGTMYIR GLTAKWDAEN PQWEDWNQIG  420
YQTSSTFYED DLDDLMSPGI YSVTGKATHT PIQGQSGFLE VIRRKDGVYV LQRYTTTGTS  480
AATKDRLYER VFLGGSFNAW GEWRQIYNSN SLPLELGIGG AVAKLTSLDW QTYDFVPGSL  540
ITVRLDNMTN IPDGMDWGVI DGNLINISVG PSDDSGSGRS MHVWRSTVSK ANYRFFMVRI  600
SGNPGSRTIT TRRVPIIDEA QTWGAKQTFS AGLSGELSGN AATATKLKTA RKINNVSFDG  660
TSDINLTPKN IGAFASGKTG DTVANDKAVG WNWSSGAYNA TIGGASTLIL HFNIGEGSCP  720
AAQFRVNYKN GGIFYRSARD GYGFEADWSE FYTTTRKPTA GDVGALPLSG GQLNGALGIG  780
TSSALGGNSI VLGDNDTGFK QNGDGNLDVY ANSVHVMRFV SGSVQSNKTI NITGRVNPSD  840
YGNFDSRYVR DVRLGTRVVQ TMQKGVMYEK AGHVITGLGI VGEVDGDDPA VFRPIQKYIN  900
GTWYNVAQV                                                            909
```

What is claimed is:

1. A method for delivering a nucleic acid payload of interest into a target bacterial cell, said method comprising contacting said target bacterial cell with one or more bacterial delivery vehicles comprising a chimeric receptor binding protein (RBP) and said payload of interest, wherein the chimeric RBP comprises a fusion between the N-terminal domain of a RBP from a lambda-like or lambda bacteriophage, wherein said lambda-like bacteriophage comprises amino acid sequence homology of around 35% identity for 45 amino acids or more, around 50% identity for 30 amino acids or more, or around 90% identity for 18 amino acids or more in one or more of three amino acid regions ranging from positions 1-150, 320-460, and 495-560 with reference to the lambda bacteriophage stf sequence of SEQ ID NO: 1, and the C-terminal domain of a different RBP, and wherein said N-terminal domain is fused to said C-terminal domain within one of the amino acids acid regions selected from positions 1-150, 320-460 or 495-560 of the N-terminal RBP with reference to the lambda stf sequence (SEQ ID NO: 1), wherein said region of fusion within the N-terminal RBP from positions 1-150, 320-460 or 495-560 comprises amino acid sequence homology of around 35% identity for 45 amino acids or more, around 50% identity for 30 amino acids or more, or around 90% identity for 18 amino acids or more with reference to the lambda bacteriophage stf sequence of SEQ ID NO: 1.

2. The method of claim 1, wherein said different RBP is derived from any bacteriophage or bacteriocin.

3. The method of claim 1, wherein said N-terminal domain of the chimeric RBP is fused to said C-terminal domain within one of the amino acid regions selected from positions 80-150, 320-460, or 495-560 of the N-terminal RBP.

4. The method of claim 1, wherein the N-terminal domain and the C-terminal domain are fused within said region at an insertion site having at least 80% identity with insertion site selected from the group consisting of amino acids SAGDAS (SEQ ID NO:248), ADAKKS (SEQ ID NO: 249), MDETNR (SEQ ID NO: 250), SASAAA (SEQ ID NO: 251), and GAGENS (SEQ ID NO: 252).

5. The method of claim 1, wherein the chimeric RBP comprises the amino acid sequence of SEQ ID NO: 2, 4, 7, 9, 12, 15, 17, 20, 23, 24, 25, 27, 29, 31, 33, 35, 37, 39, 41, 42, 44, 46, 47, 48, 49, 50, 51, 52, 53, 56, 59, 123-129, 130, 131, 132, 135, 138, 139, 142, 145, 148, 151, 216, 219, 221, 223, 227, 230, 232, 234, 236, 238, 240, 243, 245 or 246.

6. The method of claim 1, wherein the C-terminal domain of the different RBP has a depolymerase activity against an encapsulated bacterial strain.

7. The method of claim 1, wherein said nucleic acid payload of interest encodes a protein of interest or a nucleic acid of interest.

8. The method of claim 7, wherein the nucleic acid of interest is selected from the group consisting of Cas nuclease gene, a Cas9 nuclease gene, a guide RNA, a CRISPR locus, a toxin gene, a gene expressing an enzyme, a TALEN, a ZFN, a meganuclease, a recombinase, a bacterial receptor gene, a membrane protein gene, a structural protein gene, a secreted protein gene, a gene expressing resistance to an antibiotic or to a drug in general, a gene expressing a toxic protein or a toxic factor, and a gene expressing a virulence protein or a virulence factor, or any combination thereof.

9. The method of claim 8, wherein the enzyme is a nuclease or a kinase.

10. The method of claim 7, wherein the protein of interest is a nuclease that targets cleavage of the target bacterial cell genome or a plasmid of the target bacterial cell.

11. The method of claim 7, wherein the nucleic acid payload encodes a therapeutic protein.

12. The method of claim 7, wherein the nucleic acid payload encodes an anti-sense nucleic acid molecule.

13. The method of claim 1, wherein said target bacterial cell is a commensal, symbiotic or pathogenic bacterial cell of the microbiota or microbiome of a subject.

14. The method of claim 13, said method comprising administering said bacterial delivery vehicle to said subject.

* * * * *